(12) United States Patent
Bouchard et al.

(10) Patent No.: US 11,007,275 B2
(45) Date of Patent: May 18, 2021

(54) CRYPTOPHYCIN ANTIBODY CONJUGATES FOR THE TREATMENT OF CANCER

(71) Applicant: SANOFI, Paris (FR)

(72) Inventors: Hervé Bouchard, Thiais (FR);
Marie-Priscille Brun, Paris (FR);
Philippe Hubert, Maisons-Alfort (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 16/673,367

(22) Filed: Nov. 4, 2019

(65) Prior Publication Data

US 2020/0054760 A1    Feb. 20, 2020

Related U.S. Application Data

(62) Division of application No. 15/975,423, filed on May 9, 2018, now abandoned.

(30) Foreign Application Priority Data

May 10, 2017   (EP) .................................... 17305531

(51) Int. Cl.
| | | |
|---|---|---|
| *A61K 31/336* | (2006.01) | |
| *C07D 303/02* | (2006.01) | |
| *A61K 47/65* | (2017.01) | |
| *C07D 405/14* | (2006.01) | |
| *A61K 47/68* | (2017.01) | |
| *C07D 405/06* | (2006.01) | |
| *C07K 11/00* | (2006.01) | |
| *A61K 47/64* | (2017.01) | |
| *A61P 35/00* | (2006.01) | |
| *A61K 38/15* | (2006.01) | |
| *A61K 47/10* | (2017.01) | |
| *A61K 47/22* | (2006.01) | |

(52) U.S. Cl.
CPC .............. *A61K 47/65* (2017.08); *A61K 38/15* (2013.01); *A61K 47/10* (2013.01); *A61K 47/22* (2013.01); *A61K 47/64* (2017.08); *A61K 47/6829* (2017.08); *A61K 47/6889* (2017.08); *A61P 35/00* (2018.01); *C07D 405/06* (2013.01); *C07D 405/14* (2013.01); *C07K 11/00* (2013.01)

(58) Field of Classification Search
CPC .......................... A61K 31/336; C07D 303/02
USPC ........................................... 514/475; 549/512
See application file for complete search history.

(56) References Cited

FOREIGN PATENT DOCUMENTS

| WO | WO 2011/001052 A1 | 1/2011 |
|---|---|---|
| WO | WO 2015/057699 A2 | 4/2015 |
| WO | WO 2015/057876 A1 | 4/2015 |
| WO | WO 2016/065145 A1 | 4/2016 |
| WO | WO 2016/172273 A1 | 10/2016 |

OTHER PUBLICATIONS

Verma, et al. Bioorganic & Medicinal Chemistry Letters, 25(4), 2015, 864-868.*
Dubowchik et al., 2002, "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", Bioconjugate Chem., American Chemical Society, pp. 855-869.
Aug. 13, 2018, International Search Report and Written Opinion for International Patent Application No. PCT/EP2018/061989, 20 pages.
Steinfeld, et al. Journal of Medicinal Chemistry, 22(9), 1979, 1104-1109.
U.S. Appl. No. 15/975,423 2018/0369401, filed May 9, 2018 Dec. 27, 2018, Hervé Bouchard.
U.S. Appl. No. 16/612,090, filed Nov. 8, 2019, Hervé Bouchard.
Jain et al., "Current ADC Linker Chemistry", Pharmaceutical Research, 2015, vol. 32, pp. 3526-3540.

* cited by examiner

*Primary Examiner* — Douglas M Willis
(74) *Attorney, Agent, or Firm* — Lathrop GPM LLP; James H. Velema, Esq.

(57) ABSTRACT

The present disclosure relates to compounds of formula (V):

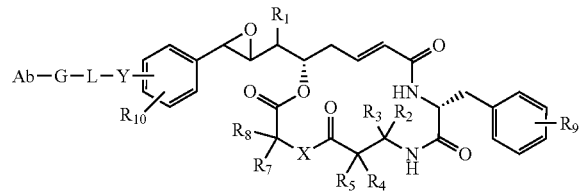

(V)

wherein Ab represents an antibody. The disclosure also relates to cryptophycin payloads, as well as to cryptophycin conjugates, to compositions containing them and to their therapeutic use, especially as anticancer agents. The disclosure also relates to the process for preparing these conjugates.

20 Claims, 7 Drawing Sheets

Specification includes a Sequence Listing.

Figure 1: *In vivo* efficacy of Ex.6 against MDA-MB-231 xenograft in SCID mice
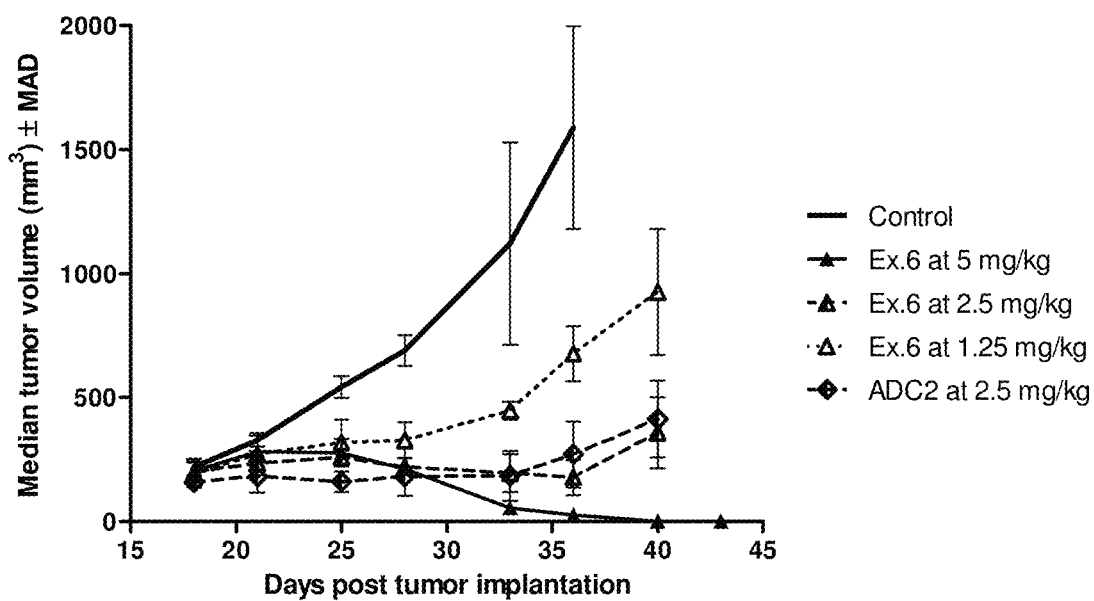

Figure 2: *In vivo* efficacy of Ex.16, Ex.19, Ex.23 and Ex.32 against MDA-MB-231 xenograft in SCID mice at 2.5 mg/kg
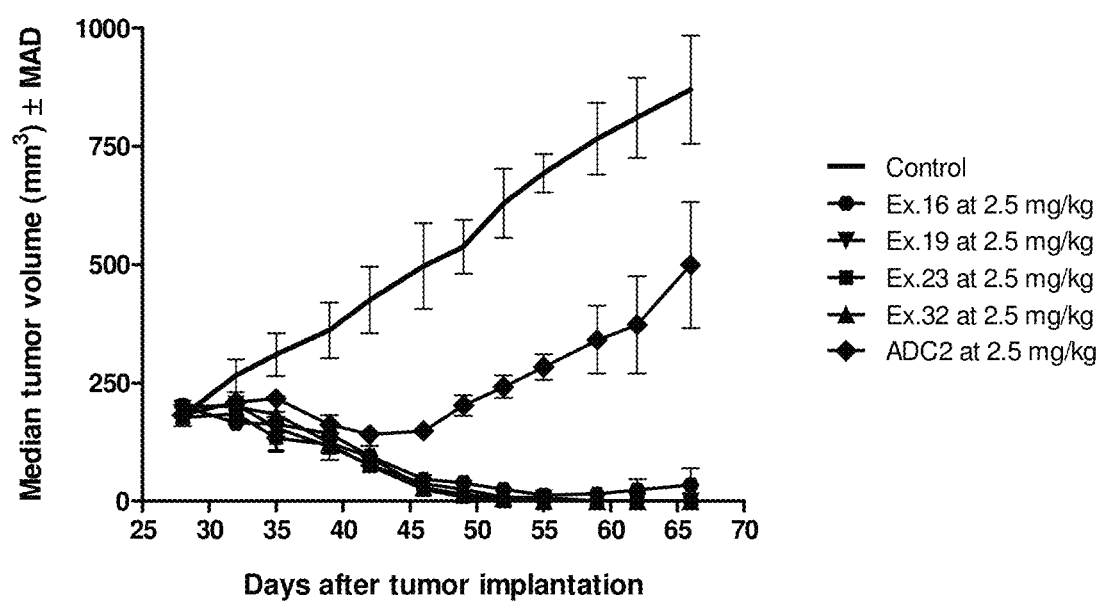

Figure 3: *In vivo* efficacy of Ex.16, Ex.19, Ex.23 and Ex.32 against MDA-MB-231 xenograft in SCID mice at 1.25 mg/kg
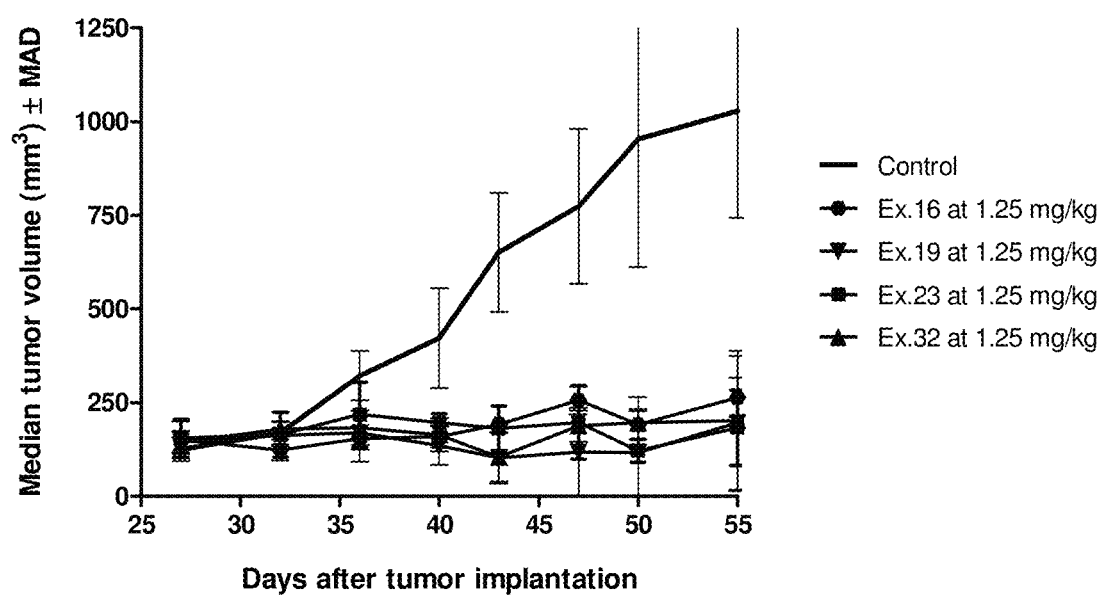

Figure 4: *In vivo* efficacy of Ex.26 against MDA-MB-231 xenograft in SCID mice
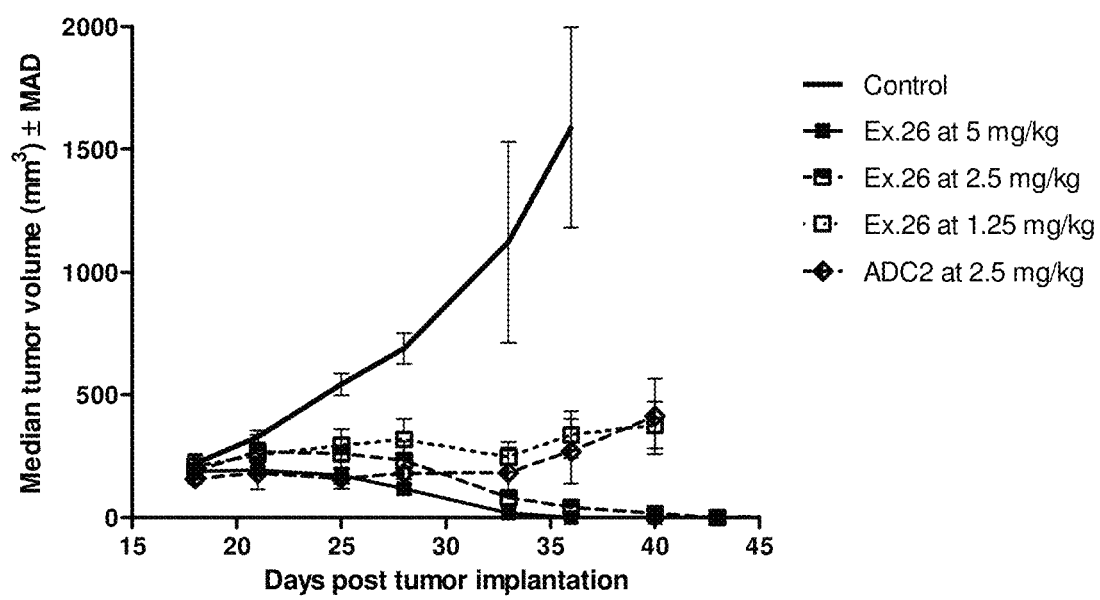

Figure 5: *In vivo* efficacy of Ex.29 against MDA-MB-231 xenograft in SCID mice
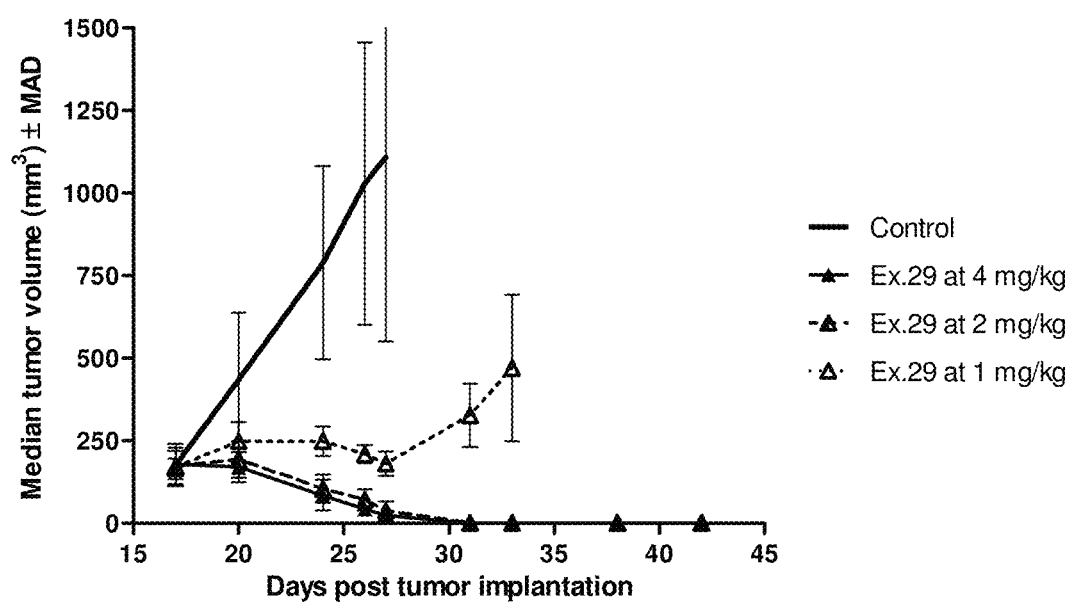

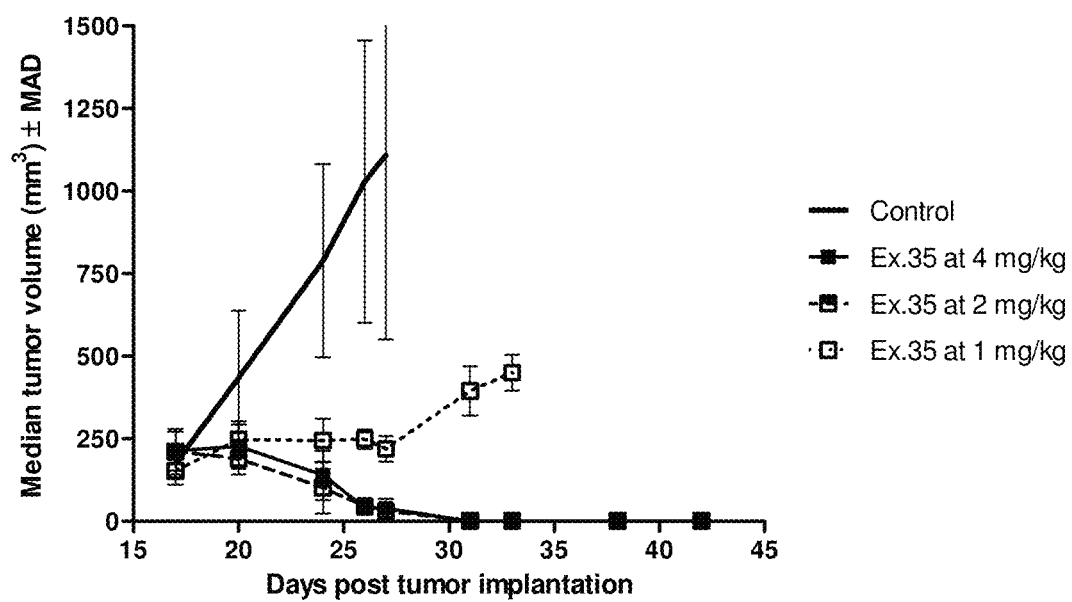
Figure 6: *In vivo* efficacy of Ex.35 against MDA-MB-231 xenograft in SCID mice

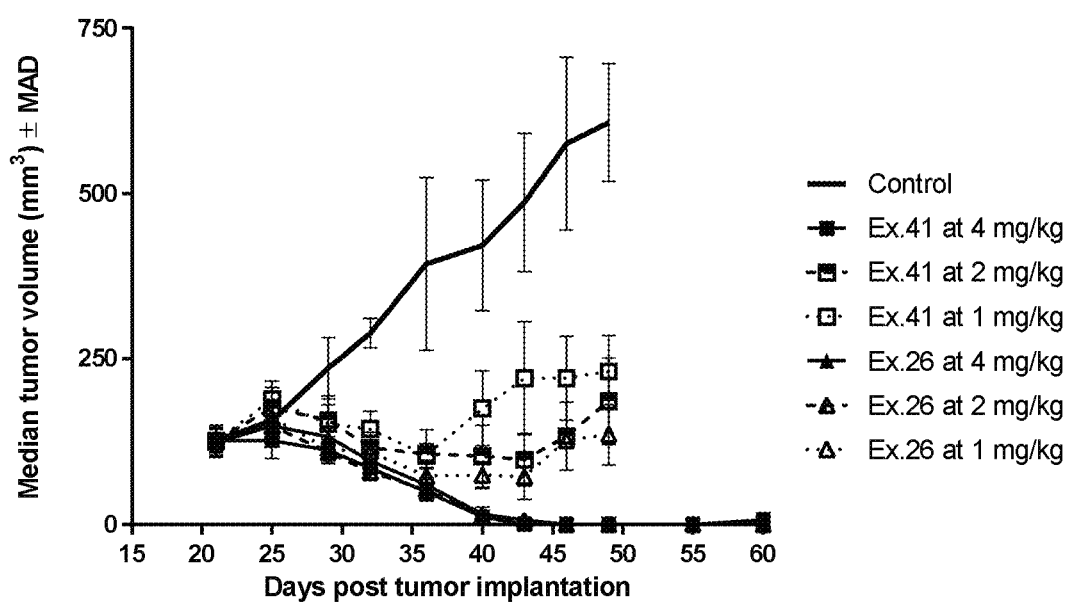
Figure 7: *In vivo* efficacy of Ex.41 against MDA-MB-231 xenograft in SCID mice

CRYPTOPHYCIN ANTIBODY CONJUGATES FOR THE TREATMENT OF CANCER

CROSS REFERENCE TO RELATED APPLICATIONS

This application is a divisional of U.S. patent application Ser. No. 15/975,423, filed May 9, 2018, which claims priority to European Patent Application No. 17305531.0, filed May 10, 2017, the entirety of which is hereby incorporated herein by reference.

The present disclosure relates to new peptidic linkers, to new cryptophycin payloads, to new cryptophycin conjugates, to compositions containing them and to their therapeutic use, such as for use as anticancer agents. The present disclosure also relates to the process for preparing these conjugates.

These linkers are enzymatically cleaved in the lysosome of cells, by enzymes such as Cathepsin B for example. Cathepsin B is a cysteine proteinase belonging to the papain family and one of the main lysosomal proteinases among mammals. It is involved in protein turnover and in the maintenance of cellular metabolism as well as in several other physiological or pathological processes, like for example tumoral progression. Its over-expression, both at the genetic and proteic levels, has been demonstrated in tumors, the increase of protein leading also to an increase of enzymatic activity. This was the basis of several prodrug approaches of chemotherapeutic agents (*Int J Oncology* 2013, 42, 373-383) but also of the conception of cleavable linkers for antibody-drug conjugates (ADC) (*Bioconj Chem* 2002, 13, 855-869). For ADC, one commonly used peptidic linker consists of the sequence Valine-Citrulline (ValCit) joined to the p-aminobenzylic alcohol self-immolative moeity (*J Org Chem* 2002, 67, 1866-1872), as exemplified in WO2011/001052 with example 23. Associated to a cytotoxic drug, the subsequent construct is quite hydrophobic which can be challenging for achieving certain drug-to-antibody ratio (DAR), monomeric purity and ADC stability. Actually, despite extensive conjugation optimization, example 23 of WO2011/00152 couldn't be successfully conjugated to provide an ADC with satisfactory DAR and monomeric purity, namely DAR>2 and >95% of monomers.

Since drugs used for ADC—like tubulin or DNA binders—are essentially hydrophobic, there was a need for more hydrophilic peptidic linkers to improve the solubility of the payload—a payload is a compound comprising the cytotoxic drug conjugated to a linker—and thus potentially its reactivity towards antibody conjugation and the stability of the subsequent ADC. Increasing payload solubility should allow to increase the DAR, the monomeric purity and ADC stability, especially in terms of aggregation propensity.

SUMMARY OF THE DISCLOSURE

The disclosure relates to new peptidic compounds, chosen from compounds of formula (I):

$$RCG1-L-P \quad (I)$$

wherein
RCG1 represents a reactive chemical group that is reactive towards a chemical group present on a polypeptide such as an antibody;
P represents a hydrogen atom, —OH or an activated O wherein an activated O is defined below.

L represents a linker of formula (II):

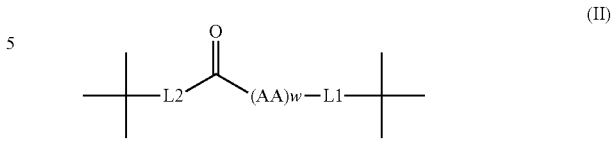

wherein:
L1 is of formula (III):

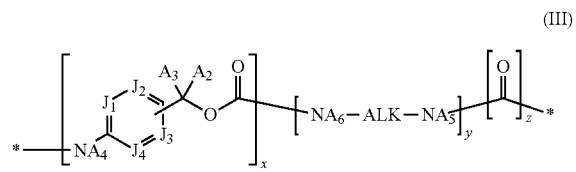

wherein:
when P represents a hydrogen atom, then x=0 or 1 and y=1 and z=0;
when P represents —OH, then x=y=z=0;
when P represents an activated O, then x=1 and y=z=0, or x=y=z=1;
$J_1$, $J_2$, $J_3$ and $J_4$ are chosen, independently of each other, from $CA_1$ and N;
ALK represents a $(C_1-C_{12})$alkylene group, for instance $(C_1-C_6)$alkylene, such as of the form —$(CH_2)_n$—, n being an integer ranging from 1 to 12 and for example ranging from 1 to 6;
$A_1$, $A_2$, $A_3$, $A_4$, $A_5$, and $A_6$ represent, independently of each other, a hydrogen atom or a $(C_1-C_6)$alkyl group, such as a hydrogen atom or a methyl group.
(AA)w represents a sequence of w substituted $AA_s$ or non-substituted amino acids $AA_{ns}$ connected together via peptide bonds wherein substituted $AA_s$ or non-substituted $AA_{ns}$ is defined below;
w represents an integer ranging from 1 to 12, for instance from 1 to 6, such as 2 or 3;
if (AA)w contains at least one substituted amino acid $AA_s$, then L2 represents a single bond, a $(C_1-C_6)$alkyl group, a $(C_1-C_6)$alkyl-$(OCH_2CH_2)_i$ group, a $(C_1-C_6)$alkyl-$(OCH_2CH_2)_i$—$O(C_1-C_6)$alkyl group, a $(CH_2CH_2O)_i(C_1-C_6)$alkyl group, a $CH(SO_3H)$—$(C_1-C_6)$alkyl group, a $(C_1-C_6)$alkyl-$CH(SO_3H)$ group, a $(C_1-C_6)$alkyl-cyclohexyl group, a $C(=O)$—$(C_1-C_6)$alkyl group, a $C(=O)$—$(C_1-C_6)$alkyl-$(OCH_2CH_2)_i$ group, a $C(=O)$—$(C_1-C_6)$alkyl-$(OCH_2CH_2)_i$—$O(C_1-C_6)$alkyl group, a $C(=O)$—$(CH_2CH_2O)_i(C_1-C_6)$alkyl group, a $C(=O)$—$CH(SO_3H)$—$(C_1-C_6)$alkyl group, a $C(=O)$—$(C_1-C_6)$alkyl-$CH(SO_3H)$ group, a $C(=O)$—$(C_1-C_6)$alkyl-cyclohexyl group, a $NA_8$-$(C_1-C_6)$alkyl group, a $NA_8$-$(C_1-C_6)$alkyl-$(OCH_2CH_2)_i$ group, a $NA_8$-$(C_1-C_6)$alkyl-$(OCH_2CH_2)_i$—$O(C_1-C_6)$alkyl group, a $NA_8$-$(CH_2CH_2O)(C_1-C_6)$alkyl group, a $NA_8$-$(C_1-C_6)$alkyl-$CH(SO_3H)$ group, a $C(=O)$—$NA_8$-$(C_1-C_6)$alkyl group, a $C(=O)$—$NA_8$-$(C_1-C_6)$alkyl-$(OCH_2CH_2)_i$ group, a $C(=O)$—$NA_8$-$(C_1-C_6)$alkyl-$(OCH_2CH_2)_i$—$O(C_1-C_6)$alkyl group, a $C(=O)$—$NA_8$-$(CH_2CH_2O)_i(C_1-C_6)$alkyl group, a $C(=O)$—$NA_8$-$(C_1-C_6)$alkyl-$CH(SO_3H)$ group, a $NA_7$-$(C_1-C_6)$alkyl group, a $(C_1-C_6)$alkyl-$NA_7$ group, a $NA_7$-$(CH_2CH_2O)_i(C_1-C_6)$alkyl group, a $NA_7$-aryl group, a $NA_7$-heteroaryl group, a $(C_1-C_6)$alkyl-$NA_7C(=O)$—$(C_1-C_6)$alkyl group, a $(C_1-C_6)$alkyl-$NA_7C(=O)$—$(C_1-C_6)$alkyl- (OCH₂CH₂)ᵢ group, a (C₁-C₆)alkyl-C(=O)NA₇-(C₁-C₆)alkyl group, a (C₁-C₆)alkyl-C(=O)NA₇-(C₁-C₆)alkyl-(OCH₂CH₂)ᵢ group, a (C₁-C₆)alkyl-NA₇-(C₁-C₆)alkyl group, a (C₁-C₆)alkyl-NA₇-(C₁-C₆)alkyl-(OCH₂CH₂)ᵢ group, a (C₁-C₆)alkyl-(OCH₂CH₂)ᵢ—NA₇-(C₁-C₆)alkyl group, a C(=O)—NA₇-(C₁-C₆)alkyl group, a C(=O)—(C₁-C₆)alkyl-NA₇ group, a C(=O)—NA₇-(CH₂CH₂O)ᵢ(C₁-C₆)alkyl group, a C(=O)—NA₇-aryl group, a C(=O)—NA₇-heteroaryl group, a C(=O)—(C₁-C₆)alkyl-NA₇C(=O)—(C₁-C₆)alkyl group, a C(=O)—(C₁-C₆)alkyl-NA₇C(=O)—(C₁-C₆)alkyl-(OCH₂CH₂)ᵢ group, a C(=O)—(C₁-C₆)alkyl-C(=O)NA₇-(C₁-C₆)alkyl group, a C(=O)—(C₁-C₆)alkyl-C(=O)NA₇-(C₁-C₆)alkyl-(OCH₂CH₂)ᵢ group, a C(=O)—(C₁-C₆)alkyl-NA₇-(C₁-C₆)alkyl group, a C(=O)—(C₁-C₆)alkyl-NA₇-(C₁-C₆)alkyl-(OCH₂CH₂)ᵢ group, a C(=O)—(C₁-C₆)alkyl-(OCH₂CH₂)ᵢ—NA₇-(C₁-C₆)alkyl group, a NA₈-(C₁-C₆)alkyl-NA₇ group, a NA₈-(C₁-C₆)alkyl-NA₇C(=O)—(C₁-C₆)alkyl group, a NA₈-(C₁-C₆)alkyl-NA₇C(=O)—(C₁-C₆)alkyl-(OCH₂CH₂)ᵢ group, a NA₈-(C₁-C₆)alkyl-C(=O)NA₇-(C₁-C₆)alkyl group, a NA₈-(C₁-C₆)alkyl-C(=O)NA₇-(C₁-C₆)alkyl-(OCH₂CH₂)ᵢ group, a NA₈-(C₁-C₆)alkyl-NA₇-(C₁-C₆)alkyl group, a NA₈-(C₁-C₆)alkyl-NA₇-(C₁-C₆)alkyl-(OCH₂CH₂)ᵢ group, a NA₈-(C₁-C₆)alkyl-(OCH₂CH₂)ᵢ—NA₇-(C₁-C₆)alkyl group, a C(=O)—NA₈-(C₁-C₆)alkyl-NA₇ group, a C(=O)—NA₈-(C₁-C₆)alkyl-NA₇C(=O)—(C₁-C₆)alkyl group, a C(=O)—NA₈-(C₁-C₆)alkyl-NA₇C(=O)—(C₁-C₆)alky-(OCH₂CH₂)ᵢ group, a C(=O)—NA₈-(C₁-C₆)alkyl-C(=O)NA₇-(C₁-C₆)alkyl group, a C(=O)—NA₆-(C₁-C₆)alkyl-C(=O)NA₇-(C₁-C₆)alkyl-(OCH₂CH₂)ᵢ group, a C(=O)—NA₈-(C₁-C₆)alkyl-NA₇-(C₁-C₆)alkyl group, a C(=O)—NA₈-(C₁-C₆)alkyl-NA₇-(C₁-C₆)alkyl-(OCH₂CH₂)ᵢ group or a C(=O)—NA₈-(C₁-C₆)alkyl-(OCH₂CH₂)ᵢ—NA₇-(C₁-C₆)alkyl group;

if (AA)w represents a sequence of w non-substituted amino acids AAₙₛ, L2 represents a NA₇-(C₁-C₆)alkyl group, a (C₁-C₆)alkyl-NA₇ group, a NA₇-(CH₂CH₂O)(C₁-C₆)alkyl group, a NA₇-aryl group, a NA₇-heteroaryl group, a (C₁-C₆)alkyl-NA₇C(=O)—(C₁-C₆)alkyl group, a (C₁-C₆)alkyl-NA₇C(=O)—(C₁-C₆)alkyl-(OCH₂CH₂)ᵢ group, a (C₁-C₆)alkyl-C(=O)NA₇-(C₁-C₆)alkyl group, a (C₁-C₆)alkyl-C(=O)NA₇-(C₁-C₆)alkyl-(OCH₂CH₂)ᵢ group, a (C₁-C₆)alkyl-NA₇-(C₁-C₆)alkyl group, a (C₁-C₆)alkyl-NA₇-(C₁-C₆)alkyl-(OCH₂CH₂)ᵢ group, a (C₁-C₆)alkyl-(OCH₂CH₂)ᵢ—NA₇-(C₁-C₆)alkyl group, a C(=O)—NA₇-(C₁-C₆)alkyl group, a C(=O)—(C₁-C₆)alkyl-NA₇ group, a C(=O)—NA₇-(CH₂CH₂O)ᵢ(C₁-C₆)alkyl group, a C(=O)—NA₇-aryl group, a C(=O)—NA₇-heteroaryl group, a C(=O)—(C₁-C₆)alkyl-NA₇C(=O)—(C₁-C₆)alkyl group, a C(=O)—(C₁-C₆)alkyl-NA₇C(=O)—(C₁-C₆)alkyl-(OCH₂CH₂)ᵢ group, a C(=O)—(C₁-C₆)alkyl-C(=O)NA₇-(C₁-C₆)alkyl group, a C(=O)—(C₁-C₆)alkyl-C(=O)NA₇-(C₁-C₆)alkyl-(OCH₂CH₂)ᵢ group, a C(=O)—(C₁-C₆)alkyl-NA₇-(C₁-C₆)alkyl group, a C(=O)—(C₁-C₆)alkyl-NA₇-(C₁-C₆)alkyl-(OCH₂CH₂)ᵢ group, a C(=O)—(C₁-C₆)alkyl-(OCH₂CH₂)ᵢ—NA₇-(C₁-C₆)alkyl group, a NA₈-(C₁-C₆)alkyl-NA₇ group, a NA₈-(C₁-C₆)alkyl-NA₇C(=O)—(C₁-C₆)alkyl group, a NA₈-(C₁-C₆)alkyl-NA₇C(=O)—(C₁-C₆)alkyl-(OCH₂CH₂)ᵢ group, a NA₈-(C₁-C₆)alkyl-C(=O)NA₇-(C₁-C₆)alkyl group, a NA₈-(C₁-C₆)alkyl-C(=O)NA₇-(C₁-C₆)alkyl-(OCH₂CH₂)ᵢ group, a NA₈-(C₁-C₆)alkyl-NA₇-(C₁-C₆)alkyl group, a NA₈-(C₁-C₆)alkyl-NA₇-(C₁-C₆)alkyl-(OCH₂CH₂)ᵢ group, a NA₈-(C₁-C₆)alkyl-(OCH₂CH₂)ᵢ—NA₇-(C₁-C₆)alkyl group, a C(=O)—NA₈-(C₁-C₆)alkyl-NA₇ group, a C(=O)—NA₈-(C₁-C₆)alkyl-NA₇C(=O)—(C₁-C₆)alkyl group, a C(=O)-NA₈-(C₁-C₆)alkyl-NA₇C(=O)—(C₁-C₆)alkyl-(OCH₂CH₂)ᵢ group, a C(=O)—NA₈-(C₁-C₆)alkyl-C(=O)NA₇-(C₁-C₆)alkyl group, a C(=O)—NA₈-(C₁-C₆)alkyl-C(=O)NA₇-(C₁-C₆)alkyl-(OCH₂CH₂)ᵢ group, a C(=O)—NA₈-(C₁-C₆)alkyl-NA₇-(C₁-C₆)alkyl group, a C(=O)—NA₈-(C₁-C₆)alkyl-NA₇-(C₁-C₆)alkyl-(OCH₂CH₂)ᵢ group or a C(=O)—NA₈-(C₁-C₆)alkyl-(OCH₂CH₂)ᵢ—NA₇-(C₁-C₆)alkyl group;

A₇ representing a straight or branched, saturated or unsaturated, optionally substituted C₁-C₁₆₀ hydrocarbon chain wherein at least one methylene unit is independently replaced by —NHC(=O)—, —N(alkyl)C(=O)—, —C(=O)NH—, —C(=O)N(alkyl)-, —OC(=O)—, —C(=O)O—, —OC(=O)O—, —CH(OH)—, —CH(SO₃H)—, —O—, —C(=O)—, —S(=O)—, —S(=O)₂—, —NHS(=O)₂—, —N(alkyl)S(=O)₂—, —S(=O)₂NH—, —SO₂N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —NH₂, —NHalkyl, and —N(alkyl)₂;

being understood that each A₇ comprising a SO₃H function can be under salt forms such as alkali metal salts, for instance sodium salts (SO₃⁻ ⁺Na);

A₈ representing a hydrogen atom or a (C₁-C₆)alkyl group, for instance a hydrogen atom or a methyl group;

i representing an integer ranging from 1 to 50, for instance ranging from 1 to 35.

The disclosure further relates to cryptophycin payloads of formula (IV):

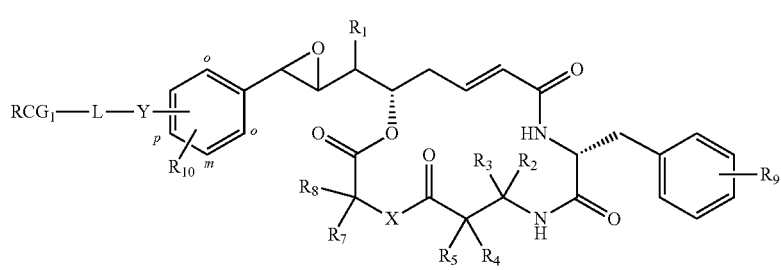

(IV)

wherein:

R₁ represents a (C₁-C₆)alkyl group;

R₂ and R₃ represent, independently of each other, a hydrogen atom or a (C₁-C₆)alkyl group;

or alternatively R₂ and R₃ form together with the carbon atom to which they are attached a (C₃-C₆)cycloalkyl or a (C₃-C₆)heterocycloalkyl group;

$R_4$ and $R_5$ represent, independently of each other, a hydrogen atom or a $(C_1-C_6)$alkyl group or a $(C_1-C_6)$alkyl-NH$(R_{12})$ group or a $(C_1-C_6)$alkyl-OH group or a $(C_1-C_6)$alkyl-SH group or a $(C_1-C_6)$alkyl-CO$_2$H group; or alternatively $R_4$ and $R_5$ form together with the carbon atom to which they are attached a $(C_3-C_6)$cycloalkyl or a $(C_3-C_6)$heterocycloalkyl group;

X represents O or N($R_6$);
$R_6$ represents a hydrogen atom or a $(C_1-C_6)$alkyl group;
$R_7$ and $R_8$ represent, independently of each other, a hydrogen atom or a $(C_1-C_6)$alkyl group or a $(C_1-C_6)$alkyl-CO$_2$H group or a $(C_1-C_6)$alkyl-N$(C_1-C_6)$alkyl$_2$ group; or alternatively $R_7$ and $R_8$ form together with the carbon atom to which they are attached a $(C_3-C_6)$cycloalkyl group or a $(C_3-C_6)$heterocycloalkyl group;

$R_9$ represents at least one substituent of the phenyl nucleus chosen, independently of each other, from: a hydrogen atom, —OH, $(C_1-C_4)$alkoxy, a halogen atom, —NH$_2$, —NH$(C_1-C_6)$alkyl, —N$(C_1-C_6)$alkyl$_2$, —NH$(C_1-C_6)$cycloalkyl or $(C_3-C_6)$heterocycloalkyl;

$R_{10}$ represents at least one substituent of the phenyl nucleus chosen from a hydrogen atom and a $(C_1-C_4)$alkyl group;

Y represents
—NR$_{11}$—$(C_1-C_6)$alkyl-, such as —NR$_{11}$—$(CH_2)_n$— like

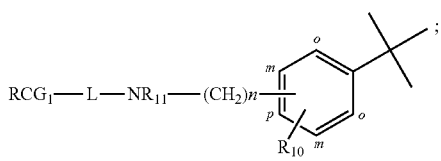

—O—$(C_1-C_6)$alkyl-, such as —O—$(CH_2)_n$— like

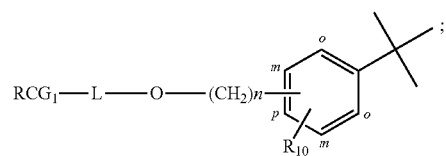

—S—$(C_1-C_6)$alkyl-, such as —S—$(CH_2)_n$— like

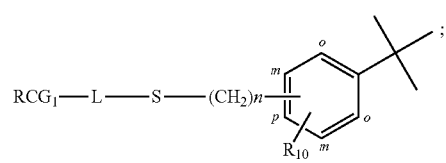

Y being positioned in an ortho (o), meta (m) or para (p) position of the phenyl nucleus;
$R_{11}$ and $R_{12}$ represent, independently of each other, a hydrogen atom or $(C_1-C_6)$alkyl, such as a hydrogen atom or a methyl group;
n represents an integer ranging from 1 to 6.
L is defined as in formula (I) and represents a linker of formula (II);
RCG1 represents a reactive chemical group present at the end of the linker, RCG1 being reactive towards a chemical group present on a polypeptide such as an antibody.

The present disclosure further relates to conjugates of formula (V):

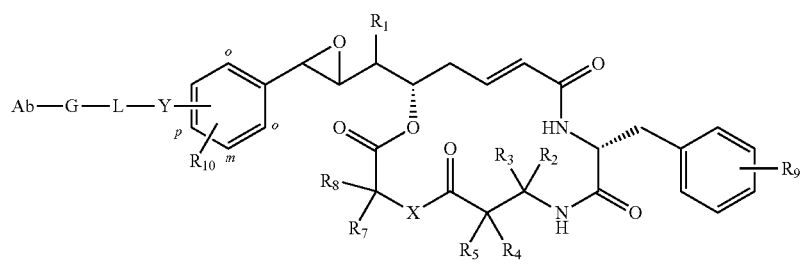

wherein:
R₁, R₂, R₃, R₄, R₅, R₆, R₇, R₈, R₉, R₁₀, R₁₁ and R₁₂ are as defined in formula (IV);
X, Y and L are as defined as in formula (IV);
G represents the product of reaction between RCG1, a reactive chemical group present at the end of the linker and RCG2, an orthogonal reactive chemical group present on the antibody (Ab);
Ab represents an antibody.

Each substituent R₁ to R₁₂ may also adopt one of the spatial configurations (e.g. R or S or alternatively Z or E) as described in the examples.

The compounds of formula (I), (II), (III), (IV) and (V) may contain at least one asymmetric carbon atoms. They may therefore exist in the form of enantiomers or diastereoisomers. These enantiomers and diastereoisomers, and also mixtures thereof, including racemic mixtures, form part of this disclosure.

The compounds of formula (I), (II), (IV), including those that are illustrated, may exist in the form of bases or of acid-addition salts, for instance of pharmaceutically acceptable acids. For example, if these compounds comprise a SO₃H function, they may exist in the form of SO₃⁻ alkali metal salts, such as of SO₃⁻ sodium salts (SO₃⁻ ⁺Na).

Definitions

In the context of the present disclosure, certain terms have the following definitions:
alkenyl group: a hydrocarbon group obtained by removing one hydrogen atom from an alkene. The alkenyl group may be linear or branched. Examples that may be mentioned include ethenyl (—CH═CH₂, also named vinyl) and propenyl (—CH₂—CH═CH₂, also named allyl).
alkoxy group: a group —O-alkyl, in which the alkyl group is as defined below;
alkyl group: a linear or branched saturated aliphatic hydrocarbon-based group obtained by removing a hydrogen atom from an alkane. Examples that may be mentioned include methyl, ethyl, propyl, isopropyl, butyl, isobutyl, tert-butyl, pentyl, neopentyl, 2,2-dimethylpropyl and hexyl groups;
alkylene group: a saturated divalent group of empirical formula —CₙH₂ₙ—, obtained by removing two hydrogen atoms from an alkane. The alkylene group may be linear or branched. Examples that may be mentioned include methylene (—CH₂—), ethylene (—CH₂CH₂—), propylene (—CH₂CH₂CH₂—), butylene (—CH₂CH₂CH₂CH₂—) and hexylene (—CH₂CH₂CH₂CH₂CH₂CH₂—) groups or the following branched groups

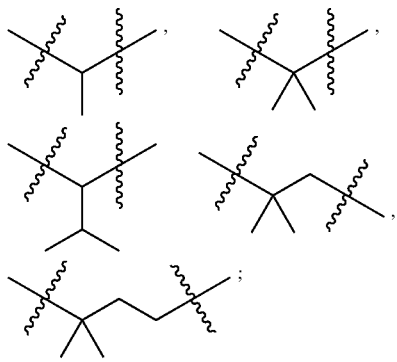

for instance, the alkylene group is of the formula —(CH₂)ₙ—, n representing an integer; in the ranges of values, the limits are included (e.g. a range of the type "n ranging from 1 to 6" or "ranging from 1 to 6" includes limits 1 and 6);
antibody: an antibody with affinity for a biological target, such as a monoclonal antibody. The function of the antibody is to direct the biologically active compound as a cytotoxic compound towards the biological target. The antibody may be monoclonal, polyclonal or multispecific; it may also be an antibody fragment; it may also be a murine, chimeric, humanized or human antibody. An "antibody" may be a natural or conventional antibody in which two heavy chains are linked to each other by disulfide bonds and each heavy chain is linked to a light chain by a disulfide bond (also referred to as a "full-length antibody"). The terms "conventional (or full-length) antibody" refers both to an antibody comprising the signal peptide (or pro-peptide, if any), and to the mature form obtained upon secretion and proteolytic processing of the chain(s). There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains or regions, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. CDRs refer to amino acid sequences which together define the binding affinity and specificity of the natural Fv region of a native immunoglobulin binding site. The light and heavy chains of an immunoglobulin each have three CDRs, designated CDR1-L, CDR2-L, CDR3-L and CDR1-H, CDR2-H, CDR3-H, respectively. A conventional antibody antigen-binding site, therefore, includes six CDRs, comprising the CDR set from each of a heavy and a light chain V region.

As used herein, the term "antibody" denotes both conventional (full-length) antibodies and fragments thereof, as well as single domain antibodies and fragments thereof, such as variable heavy chain of single domain antibodies. Fragments of (conventional) antibodies typically comprise a portion of an intact antibody, such as the antigen binding region or variable region of the intact antibody, and retain the biological function of the conventional antibody. Examples of such fragments include Fv, Fab, F(ab')2, Fab', dsFv, (dsFv)2, scFv, sc(Fv)2, nanobodies and diabodies.

The function of the antibody is to direct the biologically active compound as a cytotoxic compound towards the biological target.

aryl group: a cyclic aromatic group containing ranging from 5 to 10 carbon atoms. Examples of aryl groups include phenyl, tolyl, xylyl, naphthyl;

biological target: an antigen (or group of antigens) for instance located at the surface of cancer cells or stromal cells associated with this tumour; these antigens may be, for example, a growth factor receptor, an oncogene product or a mutated "tumor suppressant" gene product, an angiogenesis-related molecule or an adhesion molecule;

conjugate: an antibody-drug conjugate or ADC, i.e. a polypeptide such as an antibody to which is covalently attached via a linker at least one molecule of a cytotoxic compound;

cycloalkyl group: a cyclic alkyl group comprising carbon atoms ranging from 3 and 6 engaged in the cyclic structure. Examples that may be mentioned include cyclopropyl, cyclobutyl, cyclopentyl and cyclohexyl groups;

DAR (drug-to-antibody ratio): an average number of cytotoxic molecules attached via a linker to an antibody;

halogen: any of the four elements fluorine, chlorine, bromine and iodine;

heteroaryl group: an aryl group containing carbon atoms ranging from 2 to 10 and heteroatoms ranging from 1 to 5 such as nitrogen, oxygen or sulphur engaged in the ring and connected to the carbon atoms forming the ring. Examples of heteroaryl groups include pyridyl, pyrimidyl, thienyl, imidazolyl, triazolyl, indolyl, imidazo-pyridyl, pyrazolyl;

heterocycloalkyl group: a cycloalkyl group containing carbon atoms ranging from 2 to 8 and heteroatoms ranging from 1 to 3, such as nitrogen, oxygen or sulphur engaged in the ring and connected to the carbon atoms forming the ring. Examples include aziridinyl, pyrrolidinyl, piperidinyl, piperazinyl, morpholinyl, thiomorpholinyl, tetrahydrofuranyl, tetrahydrothiofuranyl, tetrahydropyranyl, azetidinyl, oxetanyl and pyranyl;

linker: a group of atoms or a single bond that can covalently attach a cytotoxic compound to a polypeptide such as an antibody in order to form a conjugate;

payload: a cytotoxic compound to which is covalently attached a linker;

reactive chemical group: a group of atoms that can promote or undergo a chemical reaction;

Further, as stated throughout the present disclosure, a $SO_3H$ function can be under salt forms such as alkali metal salts, for instance sodium salts ($SO_3^-$ $^+Na$).

Abbreviations

ADC: antibody-drug conjugate; ALK: $(C_1-C_{12})$alkylene group, for instance $(C_1-C_6)$alkylene, such as of the form $—(CH_2)_n—$, n being an integer ranging from 1 to 12 and for example ranging from 1 to 6; aq.: aqueous; Ar: argon; AUC: area under the curve; BCN: (1α,8α,9β)-bicyclo[6.1.0]non-4-yne-9-methanol; $CHCl_3$: chloroform; $CH_3CN$: acetonitrile; $CO_2$: carbon dioxide; CR: complete response; crypto denotes the unit of formula

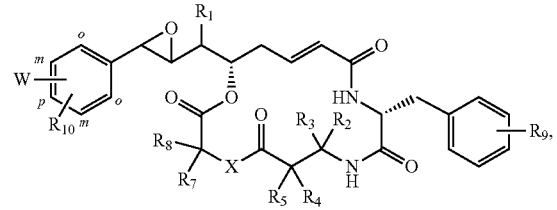

crypto for instance denoting a cryptophycin compound of an example, one of the $D_1$-$D_8$ cryptophycin compounds described in WO2011/001052 or one of the $D_1$-$D_{19}$ cryptophycin compounds below as described in PCT/EP2016/076603:

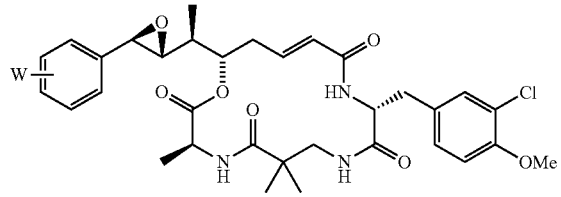

$D_1$

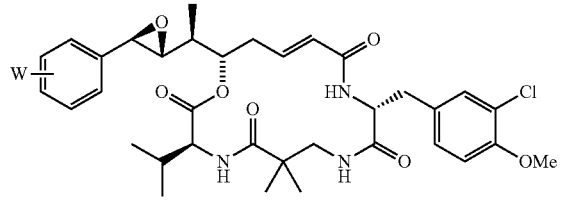

$D_2$

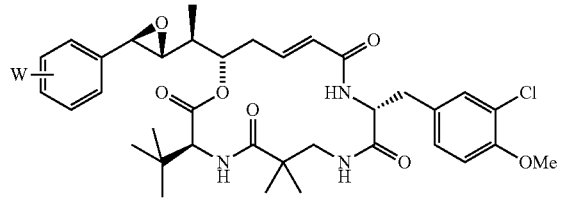

$D_3$

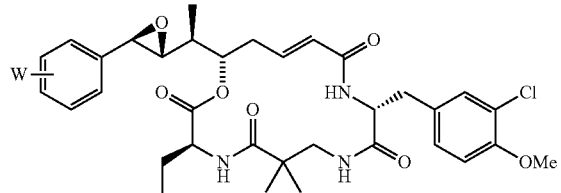

$D_4$

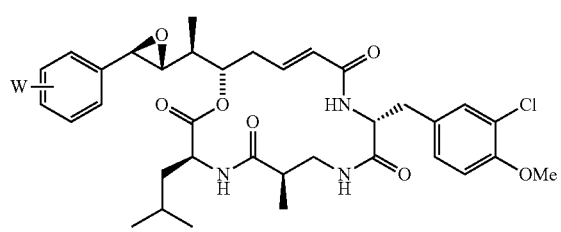

$D_5$

D6
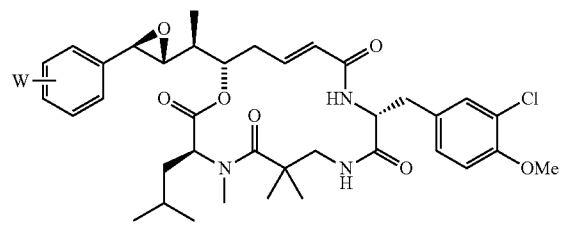
D7
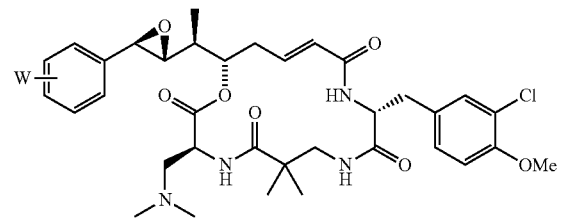
D8
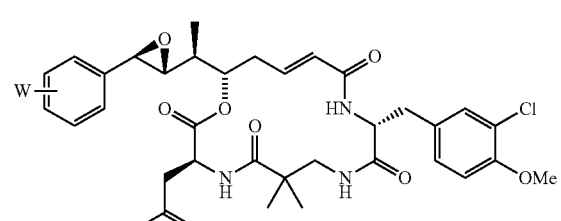
D9
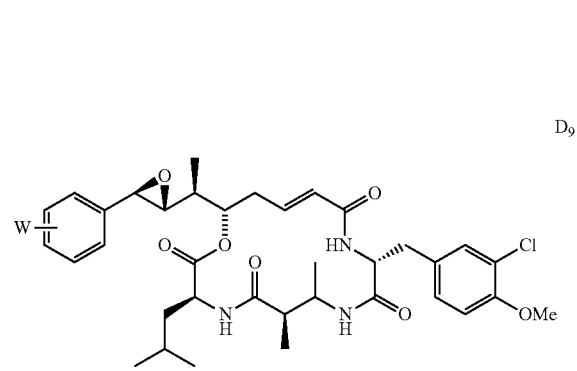
D10
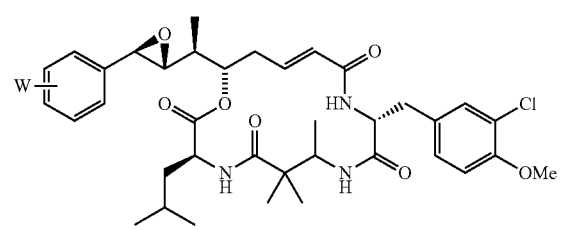
D11
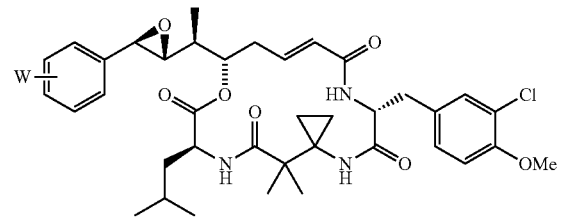
D12
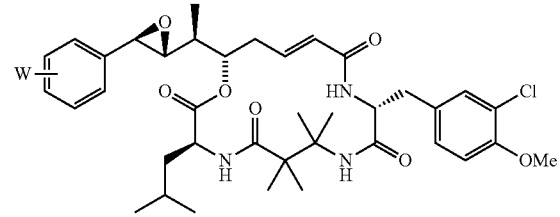
D13
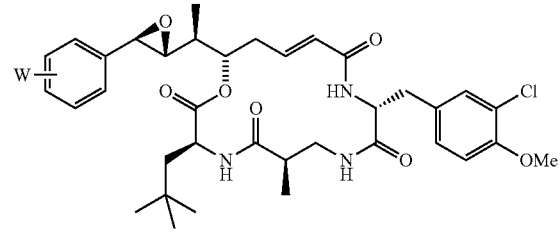
D14
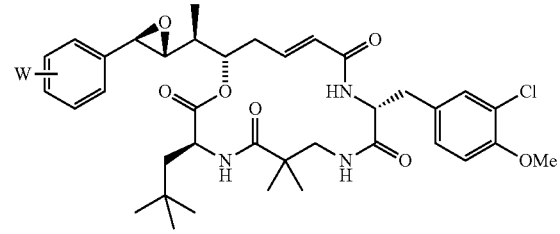
D15
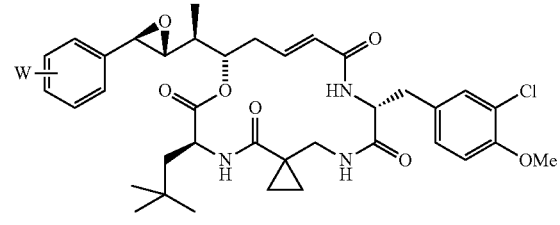
D16
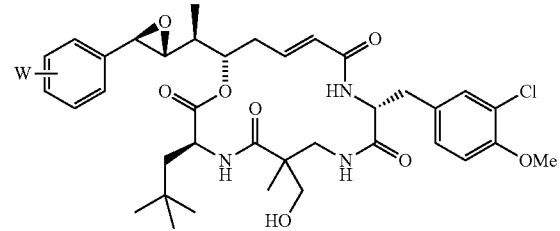
D17
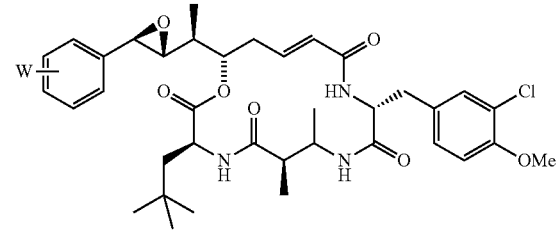

-continued

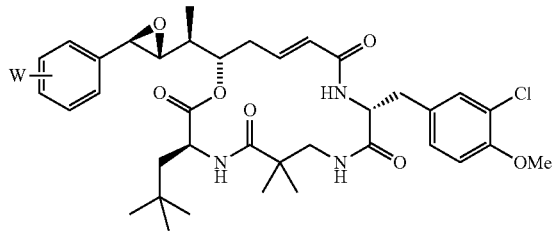

D18

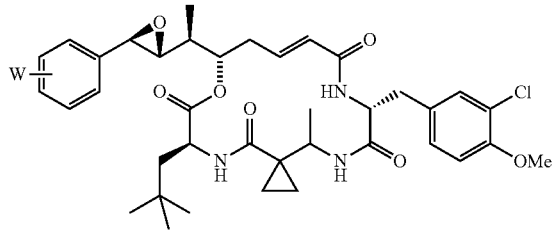

D19 wherein W represents
- $(C_1\text{-}C_6)$alkyl-$NH(R_{11})$, such as $(CH_2)_nNHR_{11}$;
- $(C_1\text{-}C_6)$alkyl-OH, such as $(CH_2)_n$OH;
- $(C_1\text{-}C_6)$alkyl-SH, such as $(CH_2)_n$SH;
- $CO_2H$ or $C(=O)NH_2$;
- $(C_1\text{-}C_6)$alkyl-$CO_2H$ or $(C_1\text{-}C_6)$alkyl-$C(=O)NH_2$; or
- $(C_1\text{-}C_6)$alkyl-$N_3$.

W is positioned in an ortho (o), meta (m) or para (p) position of the phenyl nucleus;

$R_{11}$ represents, independently of each other, a hydrogen atom or a group $(C_1\text{-}C_6)$alkyl, for instance a hydrogen atom or a methyl group;

n represents an integer ranging from 1 to 6;

d: day; DAR: drug-to-antibody ratio (D1 refers to an ADC with a DAR of 1, D2 to an ADC with a DAR of 2, etc.); DBCO: dibenzylcyclooctyne; DCC: N,N'-dicyclohexylcarbodiimide; DCM: dichloromethane; DIEA: N,N-diisopropylethylamine; DMA: dimethylacetamide; DMAP: 4-(dimethylamino)pyridine; DMEM: Dulbecco's Modified Eagle Medium; DMEM/F12: Dulbecco's Modified Eagle Medium Nutrient Mixture F-12; DMF: dimethylformamide; DMSO: dimethylsulfoxide; DPBS: Dulbecco's phosphate-buffered saline; DSC: N,N'-disuccinimidyl carbonate; EDC: 1-(3-dimethylaminopropyl)-3-ethylcarbodiimide; EDTA: ethylenediaminetetraacetic acid; EEDQ: N-ethoxycarbonyl-2-ethoxy-1,2-dihydroquinoline; ELSD: evaporating light scattering detector; eq.: equivalent; ES: electrospray; EtOAc: ethyl acetate; $Et_2O$: diethyl ether; Ex.: example; FCS: foetal calf serum; Fmoc: 9-fluorenylmethoxycarbonyl; GI: electroinductive group; h: hour; $H_2O$: water; Hal: halogen; HATU: 1-[bis(dimethylamino)methylene]-1H-1,2,3-triazolo[4,5-b]pyridinium 3-oxid hexafluorophosphate; HCl: chlorohydric acid; HEPES: 4-(2-hydroxyethyl)-1-piperazineethanesulfonic acid; HIC: hydrophobic interaction chromatography; HOAt: 1-hydroxy-7-azabenzotriazole; HOBt: 1-hydroxy-benzotriazole; HPLC: high performance liquid chromtography; HRMS: high resolution mass spectrometry; $IC_{50}$: median inhibitory concentration; i.e.: id est meaning that is; IEC: ion exchange chromatography; iPrOH: 2-propanol; $iPr_2O$: diisopropyl ether; i.v.: intravenous; MeCN: acetonitrile; MeOH: methanol; MeTHF: 2-methyltetrahydrofuran; MFCO: 1-fluoro-2-cyclooctyne-1-carboxylic acid; $MgSO_4$: magnesium sulfate; min: minute; MsCI: methanesulfonyl chloride; MTBE: methyl tert-butyl ether; MTD: maximum tolerated dose; NaH: sodium hydride; NaCl: sodium chloride; $NaHCO_3$: sodium hydrogen carbonate; n.d.: not determined; NHS: N-hydroxysuccinimide; NMP: 1-methyl-2-pyrrolidone; NMR: nuclear magnetic resonance; PABA: para-aminobenzyl alcohol; PBS: phosphate-buffered saline; PEG: polyethylene glycol; PNGase F: Peptide-N-Glycosidase F; ppm: parts per million; PR: partial response; QS: quantum satis meaning the amount what is needed; Q-Tof: quadrupole time-of-flight; quant.: quantitative yield; RCG: reactive chemical group; RT: room temperature; sat.: saturated; s.c.: subcutaneously; SCID: severe combined immunodeficiency; SEC: size exclusion chromatography; T3P: propylphosphonic anhydride; TBAF: tetrabutylammonium fluoride; TFA: trifluoroacetic acid; TFS: tumor-free survivor; THF: tetrahydrofuran; TLC: thin layer chromatography; $t_{1/2}$: half-life; $t_R$: retention time; UPLC: Ultra Performance Liquid Chromatography; UV: ultra-violet.

FIGURES

FIG. 1: In vivo efficacy of Ex. 6 against MDA-MB-231 xenograft in SCID mice

FIG. 2: In vivo efficacy of Ex. 16, Ex. 19, Ex. 23 and Ex. 32 against MDA-MB-231 xenograft in SCID mice at 2.5 mg/kg FIG. 3: In vivo efficacy of Ex. 16, Ex. 19, Ex. 23 and Ex. 32 against MDA-MB-231 xenograft in SCID mice at 1.25 mg/kg FIG. 4: In vivo efficacy of Ex. 26 against MDA-MB-231 xenograft in SCID mice FIG. 5: In vivo efficacy of Ex. 29 against MDA-MB-231 xenograft in SCID mice FIG. 6: In vivo efficacy of Ex. 35 against MDA-MB-231 xenograft in SCID mice FIG. 7: In vivo efficacy of Ex. 41 against MDA-MB-231 xenograft in SCID mice

DETAILED DESCRIPTION OF THE PRESENT DISCLOSURE

The disclosure relates to new peptidic compounds, chosen from compounds of formula (I):

$$\text{RCG1-L-P} \qquad (I)$$

wherein
RCG1 represents a reactive chemical group that is reactive towards a chemical group present on a polypeptide such as an antibody;
L represents a linker of formula (II) as defined below;
P represents a hydrogen atom, —OH or an activated O. Examples of activated O that may be mentioned include

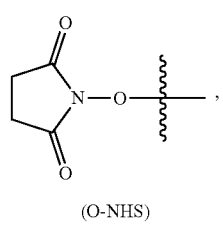

(O-NHS)

-continued

M = H or cation where cation represents for example sodium, potassium or cesium;
or, group in which Gl represents at least one electroinductive group such as —NO$_2$ or a halogen atom (-Hal), for instance a fluorine atom (—F). They may be, for example, the following groups:

The linker L which is present in formula (I) is of formula (II):

$$\text{(II)}$$

wherein:
L1 is of formula (III):

$$\text{(III)}$$

wherein:
when P represents a hydrogen atom, then x=0 or 1 and y=1 and z=0;
when P represents —OH, then x=y=z=0;
when P represents an activated O, then x=1 and y=z=0, or x=y=z=1;
$J_1$, $J_2$, $J_3$ and $J_4$ are chosen, independently of each other, from $CA_1$ and N;
ALK represents a ($C_1$-$C_{12}$)alkylene group, for instance ($C_1$-$C_6$)alkylene, such as of the form —(CH$_2$)$_n$—, n being an integer ranging from 1 to 12 and for example ranging from 1 to 6;
$A_1$, $A_2$, $A_3$, $A_4$, $A_5$, and $A_6$ represent, independently of each other, a hydrogen atom or a ($C_1$-$C_6$)alkyl group, such as a hydrogen atom or a methyl group.
(AA)w represents a sequence of w substituted $AA_s$ or non-substituted amino acids $AA_{ns}$ connected together via peptide bonds wherein substituted $AA_s$ or non-substituted $AA_{ns}$ is defined below;
w represents an integer ranging from 1 to 12, for instance from 1 to 6, such as 2 or 3;
if (AA)w contains at least one substituted amino acid $AA_s$, then L2 represents:
a single bond, a ($C_1$-$C_6$)alkyl group, a ($C_1$-$C_6$)alkyl-(OCH$_2$CH$_2$)$_i$ group, a ($C_1$-$C_6$)alkyl-(OCH$_2$CH$_2$)$_i$—O($C_1$-$C_6$)alkyl group, a (CH$_2$CH$_2$O)$_i$($C_1$-$C_6$)alkyl group, a CH(SO$_3$H)—($C_1$-$C_6$)alkyl group, a ($C_1$-$C_6$)alkyl-CH(SO$_3$H) group, a ($C_1$-$C_6$)alkyl-cyclohexyl group, a C(=O)—($C_1$-$C_6$)alkyl group, a C(=O)—($C_1$-$C_6$)alkyl-(OCH$_2$CH$_2$)$_i$ group, a C(=O)—($C_1$-$C_6$)alkyl-(OCH$_2$CH$_2$)$_i$—O($C_1$-$C_6$)alkyl group, a C(=O)—(CH$_2$CH$_2$O)$_i$($C_1$-$C_6$)alkyl group, a C(=O)—CH(SO$_3$H)—($C_1$-$C_6$)alkyl group, a C(=O)—($C_1$-$C_6$)alkyl-CH(SO$_3$H) group, a C(=O)—($C_1$-$C_6$)alkyl-cyclohexyl group, a $NA_8$-($C_1$-$C_6$)alkyl group, a $NA_8$-($C_1$-$C_6$)alkyl-(OCH$_2$CH$_2$)$_i$ group, a $NA_8$-($C_1$-$C_6$)alkyl-(OCH$_2$CH$_2$)$_i$—O($C_1$-$C_6$)alkyl group, a $NA_8$-(CH$_2$CH$_2$O)$_i$($C_1$-$C_6$)alkyl group, a $NA_8$-($C_1$-$C_6$)alkyl-CH(SO$_3$H) group, a C(=O)—$NA_8$-($C_1$-$C_6$)alkyl group, a C(=O)—$NA_8$-($C_1$-$C_6$)alkyl-(OCH$_2$CH$_2$)$_i$ group, a C(=O)—$NA_8$-($C_1$-$C_6$)alkyl-(OCH$_2$CH$_2$)$_i$—O($C_1$-$C_6$)alkyl group, a C(=O)—$NA_8$-(CH$_2$CH$_2$O)$_i$($C_1$-$C_6$)alkyl group, a C(=O)—$NA_8$-($C_1$-$C_6$)alkyl-CH(SO$_3$H) group, a $NA_7$-($C_1$-$C_6$)alkyl group, a ($C_1$-$C_6$)alkyl-$NA_7$ group, a $NA_7$-(CH$_2$CH$_2$O)$_i$($C_1$-$C_6$)alkyl group, a $NA_7$-aryl group, a $NA_7$-heteroaryl group, a ($C_1$-$C_6$)alkyl-$NA_7$C(=O)—($C_1$-$C_6$)alkyl group, a ($C_1$-$C_6$)alkyl-$NA_7$C(=O)—($C_1$-$C_6$)alkyl-(OCH$_2$CH$_2$)$_i$ group, a ($C_1$-$C_6$)alkyl-C(=O)$NA_7$-($C_1$-$C_6$)alkyl group, a ($C_1$-$C_6$)alkyl-C(=O)$NA_7$-($C_1$-$C_6$)alkyl-(OCH$_2$CH$_2$)$_i$ group, a ($C_1$-$C_6$)alkyl-$NA_7$-($C_1$-$C_6$)alkyl group, a ($C_1$-$C_6$)alkyl-$NA_7$-($C_1$-$C_6$)alkyl-(OCH$_2$CH$_2$)$_i$ group, a ($C_1$-$C_6$)alkyl-(OCH$_2$CH$_2$)$_i$—$NA_7$-($C_1$-$C_6$)alkyl group, a C(=O)—$NA_7$-($C_1$-$C_6$)alkyl group, a C(=O)—($C_1$-$C_6$)alkyl-$NA_7$ group, a C(=O)—$NA_7$-(CH$_2$CH$_2$O)$_i$($C_1$-$C_6$)alkyl group, a C(=O)—$NA_7$-aryl group, a C(=O)—$NA_7$-heteroaryl group, a C(=O)—($C_1$-$C_6$)alkyl-$NA_7$C(=O)—($C_1$-$C_6$)alkyl group, a C(=O)—($C_1$-$C_6$)alkyl-$NA_7$C(=O)—($C_1$-$C_6$)alkyl-(OCH$_2$CH$_2$)$_i$ group, a C(=O)—($C_1$-$C_6$)alkyl-C(=O)$NA_7$-($C_1$-$C_6$)alkyl group, a C(=O)—($C_1$-$C_6$)alkyl-C(=O)$NA_7$-($C_1$-$C_6$)alkyl-(OCH$_2$CH$_2$)$_i$ group, a C(=O)—($C_1$-$C_6$)alkyl-$NA_7$-($C_1$-$C_6$)alkyl group, a C(=O)—($C_1$-$C_6$)alkyl-$NA_7$-($C_1$-$C_6$)alkyl-(OCH$_2$CH$_2$)$_i$ group, a C(=O)—($C_1$-$C_6$)alkyl-(OCH$_2$CH$_2$)$_i$—$NA_7$-($C_1$-$C_6$)alkyl group, a $NA_8$-($C_1$-$C_6$)alkyl-$NA_7$ group, a $NA_8$-($C_1$-$C_6$)alkyl-$NA_7$C(=O)—($C_1$-$C_6$)alkyl group, a $NA_8$-($C_1$-$C_6$)alkyl-$NA_7$C(=O)—($C_1$-$C_6$)alkyl-(OCH$_2$CH$_2$)$_i$ group, a $NA_8$-($C_1$-$C_6$)alkyl-C(=O)$NA_7$-($C_1$-$C_6$)alkyl group, a $NA_8$-($C_1$-$C_6$)alkyl-C(=O)$NA_7$-($C_1$-$C_6$)alkyl-(OCH$_2$CH$_2$)$_i$ group, a $NA_8$-($C_1$-$C_6$)alkyl-$NA_7$-($C_1$-$C_6$)alkyl group, a $NA_8$-($C_1$-$C_6$)alkyl-$NA_7$-($C_1$-$C_6$)alkyl- (OCH$_2$CH$_2$)$_i$ group, a NA$_8$-(C$_1$-C$_6$)alkyl-(OCH$_2$CH$_2$)$_i$—NA$_7$-(C$_1$-C$_6$)alky group, a C(=O)—NA$_8$-(C$_1$-C$_6$)alkyl-NA$_7$ group, a C(=O)—NA$_8$-(C$_1$-C$_6$)alkyl-NA$_7$C(=O)—(C$_1$-C$_6$)alkyl group, a C(=O)—NA$_8$-(C$_1$-C$_6$)alkyl-NA$_7$C(=O)—(C$_1$-C$_6$)alky-(OCH$_2$CH$_2$)$_i$ group, a C(=O)—NA$_8$-(C$_1$-C$_6$)alkyl-C(=O)NA$_7$-(C$_1$-C$_6$)alkyl group, a C(=O)—NA$_8$-(C$_1$-C$_6$)alkyl-C(=O)NA$_7$-(C$_1$-C$_6$)alkyl-(OCH$_2$CH$_2$)$_i$ group, a C(=O)—NA$_8$-(C$_1$-C$_6$)alkyl-NA$_7$-(C$_1$-C$_6$)alkyl group, a C(=O)—NA$_8$-(C$_1$-C$_6$)alkyl-NA$_7$-(C$_1$-C$_6$)alkyl-(OCH$_2$CH$_2$)$_i$ group or a C(=O)—NA$_8$-(C$_1$-C$_6$)alkyl-(OCH$_2$CH$_2$)$_i$—NA$_7$-(C$_1$-C$_6$)alkyl group;

if (AA)w represents a sequence of w non-substituted amino acids AA$_{ns}$, then L2 represents:

a NA$_7$-(C$_1$-C$_6$)alkyl group, a (C$_1$-C$_6$)alkyl-NA$_7$ group, a NA$_7$-(CH$_2$CH$_2$O)$_i$(C$_1$-C$_6$)alkyl group, a NA$_7$-aryl group, a NA$_7$-heteroaryl group, a (C$_1$-C$_6$)alkyl-NA$_7$C(=O)—(C$_1$-C$_6$)alkyl group, a (C$_1$-C$_6$)alkyl-NA$_7$C(=O)—(C$_1$-C$_6$)alkyl-(OCH$_2$CH$_2$)$_i$ group, a (C$_1$-C$_6$)alkyl-C(=O)NA$_7$-(C$_1$-C$_6$)alkyl group, a (C$_1$-C$_6$)alkyl-C(=O)NA$_7$-(C$_1$-C$_6$)alkyl-(OCH$_2$CH$_2$)$_i$ group, a (C$_1$-C$_6$)alkyl-NA$_7$-(C$_1$-C$_6$)alkyl group, a (C$_1$-C$_6$)alkyl-NA$_7$-(C$_1$-C$_6$)alkyl-(OCH$_2$CH$_2$)$_i$ group, a (C$_1$-C$_6$)alkyl-(OCH$_2$CH$_2$)$_i$—NA$_7$-(C$_1$-C$_6$)alkyl group, a C(=O)—NA$_7$-(C$_1$-C$_6$)alkyl group, a C(=O)—(C$_1$-C$_6$)alkyl-NA$_7$ group, a C(=O)—NA$_7$-(CH$_2$CH$_2$O)(C$_1$-C$_6$)alkyl group, a C(=O)—NA$_7$-aryl group, a C(=O)—NA$_7$-heteroaryl group, a C(=O)—(C$_1$-C$_6$)alkyl-NA$_7$C(=O)—(C$_1$-C$_6$)alkyl group, a C(=O)—(C$_1$-C$_6$)alkyl-NA$_7$C(=O)—(C$_1$-C$_6$)alkyl-(OCH$_2$CH$_2$)$_i$ group, a C(=O)—(C$_1$-C$_6$)alkyl-C(=O)NA$_7$-(C$_1$-C$_6$)alkyl group, a C(=O)—(C$_1$-C$_6$)alkyl-C(=O)NA$_7$-(C$_1$-C$_6$)alkyl-(OCH$_2$CH$_2$)$_i$ group, a C(=O)—(C$_1$-C$_6$)alkyl-NA$_7$-(C$_1$-C$_6$)alkyl group, a C(=O)—(C$_1$-C$_6$)alkyl-NA$_7$-(C$_1$-C$_6$)alkyl-(OCH$_2$CH$_2$)$_i$ group, a C(=O)—(C$_1$-C$_6$)alkyl-(OCH$_2$CH$_2$)$_i$—NA$_7$-(C$_1$-C$_6$)alkyl group, a NA$_8$-(C$_1$-C$_6$)alkyl-NA$_7$ group, a NA$_8$-(C$_1$-C$_6$)alkyl-NA$_7$C(=O)—(C$_1$-C$_6$)alkyl group, a NA$_8$-(C$_1$-C$_6$)alkyl-NA$_7$C(=O)—(C$_1$-C$_6$)alkyl-(OCH$_2$CH$_2$)$_i$ group, a NA$_8$-(C$_1$-C$_6$)alkyl-C(=O)NA$_7$-(C$_1$-C$_6$)alkyl group, a NA$_8$-(C$_1$-C$_6$)alkyl-C(=O)NA$_7$-(C$_1$-C$_6$)alkyl-(OCH$_2$CH$_2$)$_i$ group, a NA$_8$-(C$_1$-C$_6$)alkyl-NA$_7$-(C$_1$-C$_6$)alkyl group, a NA$_8$-(C$_1$-C$_6$)alkyl-NA$_7$-(C$_1$-C$_6$)alkyl-(OCH$_2$CH$_2$)$_i$ group, a NA$_8$-(C$_1$-C$_6$)alkyl-(OCH$_2$CH$_2$)$_i$—NA$_7$-(C$_1$-C$_6$)alky group, a C(=O)—NA$_8$-(C$_1$-C$_6$)alkyl-NA$_7$ group, a C(=O)—NA$_8$-(C$_1$-C$_6$)alkyl-NA$_7$C(=O)—(C$_1$-C$_6$)alkyl group, a C(=O)—NA$_8$-(C$_1$-C$_6$)alkyl-NA$_7$C(=O)—(C$_1$-C$_6$)alkyl-(OCH$_2$CH$_2$)$_i$ group, a C(=O)—NA$_8$-(C$_1$-C$_6$)alkyl-C(=O)NA$_7$-(C$_1$-C$_6$)alkyl group, a C(=O)—NA$_8$-(C$_1$-C$_6$)alkyl-C(=O)NA$_7$-(C$_1$-C$_6$)alkyl-(OCH$_2$CH$_2$)$_i$ group, a C(=O)—NA$_8$-(C$_1$-C$_6$)alkyl-NA$_7$-(C$_1$-C$_6$)alkyl group, a C(=O)—NA$_8$-(C$_1$-C$_6$)alkyl-NA$_7$-(C$_1$-C$_6$)alkyl-(OCH$_2$CH$_2$)$_i$ group or a C(=O)—NA$_8$-(C$_1$-C$_6$)alkyl-(OCH$_2$CH$_2$)$_i$—NA$_7$-(C$_1$-C$_6$)alkyl group;

A$_7$ representing a straight or branched, saturated or unsaturated, optionally substituted C$_1$-C$_{160}$ hydrocarbon chain wherein optionally at least one methylene unit is independently replaced by —NHCO—, —N(alkyl)C(=O)—, —C(=O)NH—, —C(=O)N(alkyl)-, —OC(=O)—, —C(=O)O—, —OC(=O)O—, —CH(OH)—, —CH(SO$_3$H)—, —O—, —C(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —NH$_2$, —NHalkyl, and —N(alkyl)$_2$; being understood that each A$_7$ comprising a SO$_3$H function can be under salt forms such as alkali metal salts, for instance sodium salts (SO$_3^-$ $^+$Na).

A$_8$ representing a hydrogen atom or a (C$_1$-C$_6$)alkyl group, for instance a hydrogen atom or a methyl group;

i representing an integer ranging from 1 to 50, such as ranging from 1 to 35.

According to a particular embodiment, the disclosure relates to compounds of formula (I):

RCG1-L-P  (I)

wherein
RCG1 represents a reactive chemical group that is reactive towards a chemical group present on a polypeptide such as an antibody;
P represents a hydrogen atom, —OH or an activated O;
L represents a linker of formula (II):

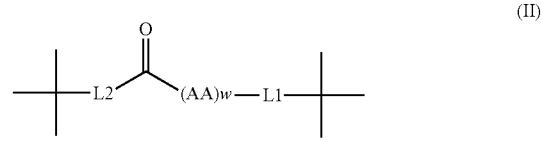

wherein:
L1 is of formula (III):

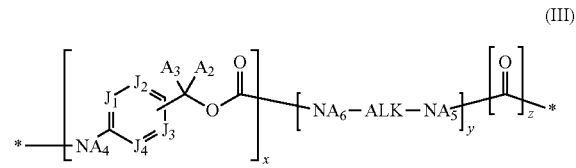

wherein:
when P represents a hydrogen atom, then x=0 or 1 and y=1 and z=0;
when P represents —OH, then x=y=z=0;
when P represents an activated O, then x=1 and y=z=0, or x=y=z=1;
J$_1$, J$_2$, J$_3$ and J$_4$ are chosen, independently of each other, from CA$_1$ and N;
ALK represents a (C$_1$-C$_{12}$)alkylene group, for instance (C$_1$-C$_6$)alkylene, such as of the form —(CH$_2$)$_n$—, n being an integer ranging from 1 to 12 and for example ranging from 1 to 6;
A$_1$, A$_2$, A$_3$, A$_4$, A$_5$, and A$_6$ represent, independently of each other, a hydrogen atom or a (C$_1$-C$_6$)alkyl group, such as a hydrogen atom or a methyl group.

(AA)w represents a sequence of w substituted AA$_s$ or non-substituted amino acids AA$_{ns}$ connected together via peptide bonds;
w represents an integer ranging from 1 to 12, for instance from 1 to 6, such as 2 or 3;
if (AA)w contains at least one substituted amino acid AA$_s$, then L2 represents a single bond, a (C$_1$-C$_6$)alkyl group, a (C$_1$-C$_6$)alkyl-(OCH$_2$CH$_2$)$_i$ group, a (C$_1$-C$_6$)alkyl-(OCH$_2$CH$_2$)$_i$—O(C$_1$-C$_6$)alkyl group, a (CH$_2$CH$_2$O)$_i$(C$_1$-C$_6$)alkyl group, a CH(SO$_3$H)—(C$_1$-C$_6$)alkyl group, a (C$_1$-C$_6$)alkyl-CH(SO$_3$H) group, a (C$_1$-C$_6$)alkyl-cyclohexyl group, a C(=O)—(C$_1$-C$_6$)alkyl group, a C(=O)—(C$_1$-C$_6$)alkyl-(OCH$_2$CH$_2$)$_i$ group, a C(=O)—(C$_1$-C$_6$)alkyl-(OCH$_2$CH$_2$)$_i$—O(C$_1$-C$_6$)alkyl group, a C(=O)—(CH$_2$CH$_2$O)$_i$(C$_1$-

$C_6$)alkyl group, a C(=O)—CH($SO_3H$)—($C_1$-$C_6$)alkyl group, a C(=O)—($C_1$-$C_6$)alkyl-CH($SO_3H$) group, a C(=O)—($C_1$-$C_6$)alkyl-cyclohexyl group, a $NA_8$-($C_1$-$C_6$)alkyl group, a $NA_8$-($C_1$-$C_6$)alkyl-(OCH$_2$CH$_2$)$_i$ group, a $NA_8$-($C_1$-$C_6$)alkyl-(OCH$_2$CH$_2$)$_i$—O($C_1$-$C_6$)alkyl group, a $NA_8$-(CH$_2$CH$_2$O)$_i$($C_1$-$C_6$)alkyl group, a $NA_8$-($C_1$-$C_6$)alkyl-CH(SO$_3$H) group, a C(=O)—$NA_8$-($C_1$-$C_6$)alkyl group, a C(=O)—$NA_8$-($C_1$-$C_6$)alkyl-(OCH$_2$CH$_2$)$_i$ group, a C(=O)—$NA_8$-($C_1$-$C_6$)alkyl-(OCH$_2$CH$_2$)$_i$—O($C_1$-$C_6$)alkyl group, a C(=O)—$NA_8$-(CH$_2$CH$_2$O)$_i$($C_1$-$C_6$)alkyl group, a C(=O)—$NA_8$-($C_1$-$C_6$)alkyl-CH(SO$_3$H) group, a $NA_7$-($C_1$-$C_6$)alkyl group, a ($C_1$-$C_6$)alkyl-$NA_7$ group, a $NA_7$-(CH$_2$CH$_2$O)$_i$($C_1$-$C_6$)alkyl group, a $NA_7$-aryl group, a $NA_7$-heteroaryl group, a ($C_1$-$C_6$)alkyl-$NA_7$C(=O)—($C_1$-$C_6$) alkyl group, a ($C_1$-$C_6$)alkyl-$NA_7$C(=O)—($C_1$-$C_6$)alkyl-(OCH$_2$CH$_2$)$_i$ group, a ($C_1$-$C_6$)alkyl-C(=O)$NA_7$-($C_1$-$C_6$) alkyl group, a ($C_1$-$C_6$)alkyl-C(=O)$NA_7$-($C_1$-$C_6$)alkyl-(OCH$_2$CH$_2$)$_i$ group, a ($C_1$-$C_6$)alkyl-$NA_7$-($C_1$-$C_6$)alkyl group, a ($C_1$-$C_6$)alkyl-$NA_7$-($C_1$-$C_6$)alkyl-(OCH$_2$CH$_2$)$_i$ group, a ($C_1$-$C_6$)alkyl-(OCH$_2$CH$_2$)$_i$—$NA_7$-($C_1$-$C_6$)alkyl group, a C(=O)—$NA_7$-($C_1$-$C_6$)alkyl group, a C(=O)—($C_1$-$C_6$)alkyl-$NA_7$ group, a C(=O)—$NA_7$-(CH$_2$CH$_2$O)$_i$($C_1$-$C_6$)alkyl group, a C(=O)—$NA_7$-aryl group, a C(=O)—$NA_7$-heteroaryl group, a C(=O)—($C_1$-$C_6$)alkyl-$NA_7$C(=O)—($C_1$-$C_6$)alkyl group, a C(=O)—($C_1$-$C_6$)alkyl-$NA_7$C(=O)—($C_1$-$C_6$)alkyl-(OCH$_2$CH$_2$)$_i$ group, a C(=O)—($C_1$-$C_6$)alkyl-C(=O)$NA_7$-($C_1$-$C_6$)alkyl group, a C(=O)—($C_1$-$C_6$)alkyl-C(=O)$NA_7$-($C_1$-$C_6$)alkyl-(OCH$_2$CH$_2$)$_i$ group, a C(=O)—($C_1$-$C_6$)alkyl-$NA_7$-($C_1$-$C_6$) alkyl group, a C(=O)—($C_1$-$C_6$)alkyl-$NA_7$-($C_1$-$C_6$)alkyl-(OCH$_2$CH$_2$)$_i$ group, a C(=O)—($C_1$-$C_6$)alkyl-(OCH$_2$CH$_2$)$_i$—$NA_7$-($C_1$-$C_6$)alkyl group, a $NA_8$-($C_1$-$C_6$)alkyl-$NA_7$ group, a $NA_8$-($C_1$-$C_6$)alkyl-$NA_7$C(=O)—($C_1$-$C_6$)alkyl group, a $NA_8$-($C_1$-$C_6$)alkyl-$NA_7$C(=O)—($C_1$-$C_6$)alkyl-(OCH$_2$CH$_2$)$_i$ group, a $NA_8$-($C_1$-$C_6$)alkyl-C(=O)$NA_7$-($C_1$-$C_6$)alkyl group, a $NA_8$-($C_1$-$C_6$)alkyl-C(=O)$NA_7$-($C_1$-$C_6$)alkyl-(OCH$_2$CH$_2$)$_i$ group, a $NA_8$-($C_1$-$C_6$)alkyl-$NA_7$-($C_1$-$C_6$) alkyl group, a $NA_8$-($C_1$-$C_6$)alkyl-$NA_7$-($C_1$-$C_6$)alkyl-(OCH$_2$CH$_2$)$_i$ group, a $NA_8$-($C_1$-$C_6$)alkyl-(OCH$_2$CH$_2$)$_i$—$NA_7$-($C_1$-$C_6$)alkyl group, a C(=O)—$NA_8$-($C_1$-$C_6$)alkyl-$NA_7$ group, a C(=O)—$NA_8$-($C_1$-$C_6$)alkyl-$NA_7$C(=O)—($C_1$-$C_6$)alkyl group, a C(=O)—$NA_8$-($C_1$-$C_6$)alkyl-$NA_7$C(=O)—($C_1$-$C_6$)alky-(OCH$_2$CH$_2$)$_i$ group, a C(=O)—$NA_8$-($C_1$-$C_6$)alkyl-C(=O)$NA_7$-($C_1$-$C_6$)alkyl group, a C(=O)—$NA_8$-($C_1$-$C_6$)alkyl-C(=O)$NA_7$-($C_1$-$C_6$)alkyl-(OCH$_2$CH$_2$)$_i$ group, a C(=O)—$NA_8$-($C_1$-$C_6$)alkyl-$NA_7$-($C_1$-$C_6$)alkyl group, a C(=O)—$NA_8$-($C_1$-$C_6$)alkyl-$NA_7$-($C_1$-$C_6$)alkyl-(OCH$_2$CH$_2$)$_i$ group or a C(=O)—$NA_8$-($C_1$-$C_6$)alkyl-(OCH$_2$CH$_2$)$_i$—$NA_7$-($C_1$-$C_6$)alkyl group;

if (AA)w represents a sequence of w non-substituted amino acids AA$_{ns}$, then L2 represents a $NA_7$-($C_1$-$C_6$)alkyl group, a ($C_1$-$C_6$)alkyl-$NA_7$ group, a $NA_7$-(CH$_2$CH$_2$O)$_i$($C_1$-$C_6$)alkyl group, a $NA_7$-aryl group, a $NA_7$-heteroaryl group, a ($C_1$-$C_6$)alkyl-$NA_7$C(=O)—($C_1$-$C_6$)alkyl group, a ($C_1$-$C_6$) alkyl-$NA_7$C(=O)—($C_1$-$C_6$)alkyl-(OCH$_2$CH$_2$)$_i$ group, a ($C_1$-$C_6$)alkyl-C(=O)$NA_7$-($C_1$-$C_6$)alkyl group, a ($C_1$-$C_6$)alkyl-C(=O)$NA_7$-($C_1$-$C_6$)alkyl-(OCH$_2$CH$_2$)$_i$ group, a ($C_1$-$C_6$)alkyl-$NA_7$-($C_1$-$C_6$)alkyl group, a ($C_1$-$C_6$)alkyl-$NA_7$-($C_1$-$C_6$)alkyl-(OCH$_2$CH$_2$)$_i$ group, a ($C_1$-$C_6$)alkyl-(OCH$_2$CH$_2$)$_i$—$NA_7$-($C_1$-$C_6$)alkyl group, a C(=O)—$NA_7$-($C_1$-$C_6$) alkyl group, a C(=O)—($C_1$-$C_6$)alkyl-$NA_7$ group, a C(=O)—$NA_7$-(CH$_2$CH$_2$O)$_i$($C_1$-$C_6$)alkyl group, a C(=O)—$NA_7$-aryl group, a C(=O)—$NA_7$-heteroaryl group, a C(=O)—($C_1$-$C_6$)alkyl-$NA_7$C(=O)—($C_1$-$C_6$)alkyl group, a C(=O)—($C_1$-$C_6$)alkyl-$NA_7$C(=O)—($C_1$-$C_6$)alkyl-(OCH$_2$CH$_2$)$_i$ group, a C(=O)—($C_1$-$C_6$)alkyl-C(=O)$NA_7$-($C_1$-$C_6$)alkyl group, a C(=O)—($C_1$-$C_6$)alkyl-C(=O) $NA_7$-($C_1$-$C_6$)alkyl-(OCH$_2$CH$_2$)$_i$ group, a C(=O)—($C_1$-$C_6$) alkyl-$NA_7$-($C_1$-$C_6$)alkyl group, a C(=O)—($C_1$-$C_6$)alkyl-$NA_7$-($C_1$-$C_6$)alkyl-(OCH$_2$CH$_2$)$_i$ group, a C(=O)—($C_1$-$C_6$)alkyl-(OCH$_2$CH$_2$)$_i$—$NA_7$-($C_1$-$C_6$)alkyl group, a $NA_8$-($C_1$-$C_6$)alkyl-$NA_7$ group, a $NA_8$-($C_1$-$C_6$)alkyl-$NA_7$C(=O)—($C_1$-$C_6$)alkyl group, a $NA_8$-($C_1$-$C_6$)alkyl-$NA_7$C(=O)—($C_1$-$C_6$)alkyl-(OCH$_2$CH$_2$)$_i$ group, a $NA_8$-($C_1$-$C_6$)alkyl-C(=O) $NA_7$-($C_1$-$C_6$)alkyl group, a $NA_8$-($C_1$-$C_6$)alkyl-C(=O)$NA_7$-($C_1$-$C_6$)alkyl-(OCH$_2$CH$_2$)$_i$ group, a $NA_8$-($C_1$-$C_6$)alkyl-$NA_7$-($C_1$-$C_6$)alkyl group, a $NA_8$-($C_1$-$C_6$)alkyl-$NA_7$-($C_1$-$C_6$)alkyl-(OCH$_2$CH$_2$)$_i$ group, a $NA_8$-($C_1$-$C_6$)alkyl-(OCH$_2$CH$_2$)$_i$—$NA_7$-($C_1$-$C_6$)alky group, a C(=O)—$NA_8$-($C_1$-$C_6$)alkyl-$NA_7$ group, a C(=O)—$NA_8$-($C_1$-$C_6$)alkyl-$NA_7$C(=O)—($C_1$-$C_6$)alkyl group, a C(=O)—$NA_8$-($C_1$-$C_6$)alkyl-$NA_7$C(=O)—($C_1$-$C_6$)alkyl-(OCH$_2$CH$_2$)$_i$ group, a C(=O)—$NA_8$-($C_1$-$C_6$)alkyl-C(=O)$NA_7$-($C_1$-$C_6$)alkyl group, a C(=O)—$NA_8$-($C_1$-$C_6$)alkyl-C(=O)$NA_7$-($C_1$-$C_6$)alkyl-(OCH$_2$CH$_2$)$_i$ group, a C(=O)—$NA_8$-($C_1$-$C_6$)alkyl-$NA_7$-($C_1$-$C_6$)alkyl group, a C(=O)—$NA_8$-($C_1$-$C_6$)alkyl-$NA_7$-($C_1$-$C_6$)alkyl-(OCH$_2$CH$_2$)$_i$ group or a C(=O)—$NA_8$-($C_1$-$C_6$)alkyl-(OCH$_2$CH$_2$)$_i$—$NA_7$-($C_1$-$C_6$)alkyl group;

- $A_7$ representing a straight or branched, saturated or unsaturated, optionally substituted $C_1$-$C_{160}$ hydrocarbon chain wherein optionally at least one methylene unit is independently replaced by —NHC(=O)—, —N(alkyl)C(=O)—, —C(=O)NH—, —C(=O)N(alkyl)-, —OC(=O)—, —C(=O)O—, —OC(=O)O—, —CH(OH)—, —CH(SO$_3$H)—, —O—, —C(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —NH$_2$, —NHalkyl, and —N(alkyl)$_2$, being understood that each $A_7$ comprising a SO$_3$H function can be under salt forms such as alkali metal salts, for instance sodium salts (SO$_3^-$ $^+$Na);
- $A_8$ representing a hydrogen atom or a ($C_1$-$C_6$)alkyl group, for instance a hydrogen atom or a methyl group;
- i representing an integer ranging from 1 to 50, for instance ranging from 1 to 35,
- a non-substituted amino acid AA$_{ns}$ denoting natural or non-natural amino acid, of configuration D or L, identical to or derived from: alanine (Ala), β-alanine, γ-aminobutyric acid, 2-amino-2-cyclohexylacetic acid, 2-amino-2-phenylacetic acid, arginine (Arg), asparagine (Asn), aspartic acid (Asp), citrulline (Cit), cysteine (Cys), α,α-dimethyl-γ-aminobutyric acid, β,β-dimethyl-γ-aminobutyric acid, glutamine (Gln), glutamic acid (Glu), glycine (Gly), homo-cysteine, selenocysteine, homo-selenocysteine, histidine (His), isoleucine (Ile), leucine (Leu), lysine (Lys), ε-acetyl-lysine (AcLys), methionine (Met), ornithine (Orn), phenylalanine (Phe), proline (Pro), serine (Ser), threonine (Thr), tryptophan (Trp), tyrosine (Tyr), and valine (Val).

According to another particular embodiment, the disclosure relates to compounds of formula (I):

$$RCG1-L-P \qquad (I)$$

wherein
- RCG1 represents a reactive chemical group that is reactive towards a chemical group present on a polypeptide such as an antibody;
- P represents a hydrogen atom, —OH or an activated O;

L represents a linker of formula (II):

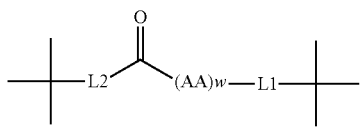

wherein:
L1 is of formula (III):

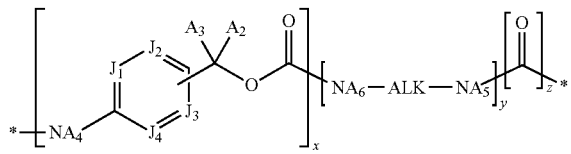

wherein:
- when P represents a hydrogen atom, then x=0 or 1 and y=1 and z=0;
- when P represents —OH, then x=y=z=0;
- when P represents an activated O, then x=1 and y=z=0, or x=y=z=1;
- $J_1$, $J_2$, $J_3$ and $J_4$ are chosen, independently of each other, from $CA_1$ and N;
- ALK represents a $(C_1-C_{12})$alkylene group, for instance $(C_1-C_6)$alkylene, such as of the form —$(CH_2)_n$—, n being an integer ranging from 1 to 12 and for example ranging from 1 to 6;
- $A_1$, $A_2$, $A_3$, $A_4$, $A_5$, and $A_6$ represent, independently of each other, a hydrogen atom or a $(C_1-C_6)$alkyl group, such as a hydrogen atom or a methyl group.

(AA)w represents a sequence of w substituted $AA_s$ or non-substituted amino acids $AA_{ns}$ connected together via peptide bonds;

w represents an integer ranging from 1 to 12, for instance from 1 to 6, such as 2 or 3;

if (AA)w contains at least one substituted amino acid $AA_s$, then L2 represents a single bond, a $(C_1-C_6)$alkyl group, a $(C_1-C_6)$alkyl-$(OCH_2CH_2)_i$ group, a $(C_1-C_6)$alkyl-$(OCH_2CH_2)_i$—O$(C_1-C_6)$alkyl group, a $(CH_2CH_2O)_i(C_1-C_6)$alkyl group, a $CH(SO_3H)$—$(C_1-C_6)$alkyl group, a $(C_1-C_6)$alkyl-$CH(SO_3H)$ group, a $(C_1-C_6)$alkyl-cyclohexyl group, a C(=O)—$(C_1-C_6)$alkyl group, a C(=O)—$(C_1-C_6)$alkyl-$(OCH_2CH_2)_i$ group, a C(=O)—$(C_1-C_6)$alkyl-$(OCH_2CH_2)_i$—O$(C_1-C_6)$alkyl group, a C(=O)—$(CH_2CH_2O)_i(C_1-C_6)$alkyl group, a C(=O)—$CH(SO_3H)$—$(C_1-C_6)$alkyl group, a C(=O)—$(C_1-C_6)$alkyl-$CH(SO_3H)$ group, a C(=O)—$(C_1-C_6)$alkyl-cyclohexyl group, a $NA_8$-$(C_1-C_6)$alkyl group, a $NA_8$-$(C_1-C_6)$alkyl-$(OCH_2CH_2)_i$ group, a $NA_8$-$(C_1-C_6)$alkyl-$(OCH_2CH_2)_i$—O$(C_1-C_6)$alkyl group, a $NA_8$-$(CH_2CH_2O)_i(C_1-C_6)$alkyl group, a $NA_8$-$(C_1-C_6)$alkyl-$CH(SO_3H)$ group, a C(=O)—$NA_8$-$(C_1-C_6)$alkyl group, a C(=O)—$NA_8$-$(C_1-C_6)$alkyl-$(OCH_2CH_2)_i$ group, a C(=O)—$NA_8$-$(C_1-C_6)$alkyl-$(OCH_2CH_2)_i$—O$(C_1-C_6)$alkyl group, a C(=O)—$NA_8$-$(CH_2CH_2O)_i(C_1-C_6)$alkyl group, a C(=O)—$NA_8$-$(C_1-C_6)$alkyl-$CH(SO_3H)$ group, a $NA_7$-$(C_1-C_6)$alkyl group, a $(C_1-C_6)$alkyl-$NA_7$ group, a $NA_7$-$(CH_2CH_2O)_i(C_1-C_6)$alkyl group, a $NA_7$-aryl group, a $NA_7$-heteroaryl group, a $(C_1-C_6)$alkyl-$NA_7C(=O)$—$(C_1-C_6)$alkyl group, a $(C_1-C_6)$alkyl-$NA_7C(=O)$—$(C_1-C_6)$alkyl-$(OCH_2CH_2)_i$ group, a $(C_1-C_6)$alkyl-C(=O)$NA_7$-$(C_1-C_6)$alkyl group, a $(C_1-C_6)$alkyl-C(=O)$NA_7$-$(C_1-C_6)$alkyl-$(OCH_2CH_2)_i$ group, a $(C_1-C_6)$alkyl-$NA_7$-$(C_1-C_6)$alkyl group, a $(C_1-C_6)$alkyl-$NA_7$-$(C_1-C_6)$alkyl-$(OCH_2CH_2)_i$ group, a $(C_1-C_6)$alkyl-$(OCH_2CH_2)_i$—$NA_7$-$(C_1-C_6)$alkyl group, a C(=O)—$NA_7$-$(C_1-C_6)$alkyl group, a C(=O)—$(C_1-C_6)$alkyl-$NA_7$ group, a C(=O)—$NA_7$-$(CH_2CH_2O)_i(C_1-C_6)$alkyl group, a C(=O)—$NA_7$-aryl group, a C(=O)—$NA_7$-heteroaryl group, a C(=O)—$(C_1-C_6)$alkyl-$NA_7C(=O)$—$(C_1-C_6)$alkyl group, a C(=O)—$(C_1-C_6)$alkyl-$NA_7C(=O)$—$(C_1-C_6)$alkyl-$(OCH_2CH_2)_i$ group, a C(=O)—$(C_1-C_6)$alkyl-C(=O)$NA_7$-$(C_1-C_6)$alkyl group, a C(=O)—$(C_1-C_6)$alkyl-C(=O)$NA_7$-$(C_1-C_6)$alkyl-$(OCH_2CH_2)_i$ group, a C(=O)—$(C_1-C_6)$alkyl-$NA_7$-$(C_1-C_6)$alkyl group, a C(=O)—$(C_1-C_6)$alkyl-$NA_7$-$(C_1-C_6)$alkyl-$(OCH_2CH_2)_i$ group, a C(=O)—$(C_1-C_6)$alkyl-$(OCH_2CH_2)_i$—$NA_7$-$(C_1-C_6)$alkyl group, a $NA_8$-$(C_1-C_6)$alkyl-$NA_7$ group, a $NA_8$-$(C_1-C_6)$alkyl-$NA_7C(=O)$—$(C_1-C_6)$alkyl group, a $NA_8$-$(C_1-C_6)$alkyl-$NA_7C(=O)$—$(C_1-C_6)$alkyl-$(OCH_2CH_2)_i$ group, a $NA_8$-$(C_1-C_6)$alkyl-C(=O)$NA_7$-$(C_1-C_6)$alkyl group, a $NA_8$-$(C_1-C_6)$alkyl-C(=O)$NA_7$-$(C_1-C_6)$alkyl-$(OCH_2CH_2)_i$ group, a $NA_8$-$(C_1-C_6)$alkyl-$NA_7$-$(C_1-C_6)$alkyl group, a $NA_8$-$(C_1-C_6)$alkyl-$NA_7$-$(C_1-C_6)$alkyl-$(OCH_2CH_2)_i$ group, a $NA_8$-$(C_1-C_6)$alkyl-$(OCH_2CH_2)_i$—$NA_7$-$(C_1-C_6)$alky group, a C(=O)—$NA_8$-$(C_1-C_6)$alkyl-$NA_7$ group, a C(=O)—$NA_8$-$(C_1-C_6)$alkyl-$NA_7C(=O)$—$(C_1-C_6)$alkyl group, a C(=O)—$NA_8$-$(C_1-C_6)$alkyl-$NA_7C(=O)$—$(C_1-C_6)$alky-$(OCH_2CH_2)_i$ group, a C(=O)—$NA_8$-$(C_1-C_6)$alkyl-C(=O)$NA_7$-$(C_1-C_6)$alkyl group, a C(=O)—$NA_8$-$(C_1-C_6)$alkyl-C(=O)$NA_7$-$(C_1-C_6)$alkyl-$(OCH_2CH_2)_i$ group, a C(=O)—$NA_8$-$(C_1-C_6)$alkyl-$NA_7$-$(C_1-C_6)$alkyl group, a C(=O)—$NA_8$-$(C_1-C_6)$alkyl-$NA_7$-$(C_1-C_6)$alkyl-$(OCH_2CH_2)_i$ group or a C(=O)—$NA_8$-$(C_1-C_6)$alkyl-$(OCH_2CH_2)_i$—$NA_7$-$(C_1-C_6)$alkyl group;

if (AA)w represents a sequence of w non-substituted amino acids $AA_{ns}$, then L2 represents a $NA_7$-$(C_1-C_6)$alkyl group, a $(C_1-C_6)$alkyl-$NA_7$ group, a $NA_7$-$(CH_2CH_2O)_i(C_1-C_6)$alkyl group, a $NA_7$-aryl group, a $NA_7$-heteroaryl group, a $(C_1-C_6)$alkyl-$NA_7C(=O)$—$(C_1-C_6)$alkyl group, a $(C_1-C_6)$alkyl-$NA_7C(=O)$—$(C_1-C_6)$alkyl-$(OCH_2CH_2)_i$ group, a $(C_1-C_6)$alkyl-C(=O)$NA_7$-$(C_1-C_6)$alkyl group, a $(C_1-C_6)$alkyl-C(=O)$NA_7$-$(C_1-C_6)$alkyl-$(OCH_2CH_2)_i$ group, a $(C_1-C_6)$alkyl-$NA_7$-$(C_1-C_6)$alkyl group, a $(C_1-C_6)$alkyl-$NA_7$-$(C_1-C_6)$alkyl-$(OCH_2CH_2)_i$ group, a $(C_1-C_6)$alkyl-$(OCH_2CH_2)_i$—$NA_7$-$(C_1-C_6)$alkyl group, a C(=O)—$NA_7$-$(C_1-C_6)$alkyl group, a C(=O)—$(C_1-C_6)$alkyl-$NA_7$ group, a C(=O)—$NA_7$-$(CH_2CH_2O)_i(C_1-C_6)$alkyl group, a C(=O)—$NA_7$-aryl group, a C(=O)—$NA_7$-heteroaryl group, a C(=O)—$(C_1-C_6)$alkyl-$NA_7C(=O)$—$(C_1-C_6)$alkyl group, a C(=O)—$(C_1-C_6)$alkyl-$NA_7C(=O)$—$(C_1-C_6)$alkyl-$(OCH_2CH_2)_i$ group, a C(=O)—$(C_1-C_6)$alkyl-C(=O)$NA_7$-$(C_1-C_6)$alkyl group, a C(=O)—$(C_1-C_6)$alkyl-C(=O)$NA_7$-$(C_1-C_6)$alkyl-$(OCH_2CH_2)_i$ group, a C(=O)—$(C_1-C_6)$alkyl-$NA_7$-$(C_1-C_6)$alkyl group, a C(=O)—$(C_1-C_6)$alkyl-$NA_7$-$(C_1-C_6)$alkyl-$(OCH_2CH_2)_i$ group, a C(=O)—$(C_1-C_6)$alkyl-$(OCH_2CH_2)_i$—$NA_7$-$(C_1-C_6)$alkyl group, a $NA_8$-$(C_1-C_6)$alkyl-$NA_7$ group, a $NA_8$-$(C_1-C_6)$alkyl-$NA_7C(=O)$—$(C_1-C_6)$alkyl group, a $NA_8$-$(C_1-C_6)$alkyl-$NA_7C(=O)$—$(C_1-C_6)$alkyl-$(OCH_2CH_2)_i$ group, a $NA_8$-$(C_1-C_6)$alkyl-C(=O)$NA_7$-$(C_1-C_6)$alkyl group, a $NA_8$-$(C_1-C_6)$alkyl-C(=O)$NA_7$-$(C_1-C_6)$alkyl-$(OCH_2CH_2)_i$ group, a $NA_8$-$(C_1-C_6)$alkyl-$NA_7$-$(C_1-C_6)$alkyl group, a $NA_8$-$(C_1-C_6)$alkyl-$NA_7$-$(C_1-C_6)$alkyl-$(OCH_2CH_2)_i$ group, a $NA_8$-$(C_1-C_6)$alkyl-$(OCH_2CH_2)_i$—$NA_7$-$(C_1-C_6)$alkyl group, a C(=O)—$NA_8$-$(C_1-C_6)$alkyl-$NA_7$ group, a C(=O)—$NA_8$-$(C_1-C_6)$alkyl-$NA_7C(=O)$—$(C_1-C_6)$alkyl group, a C(=O)—$NA_8$-$(C_1-C_6)$alkyl-$NA_7C(=O)$—$(C_1-C_6)$alkyl-$(OCH_2CH_2)_i$ group, a C(=O)—$NA_8$-$(C_1-C_6)$alkyl-C(=O)$NA_7$-$(C_1-C_6)$alkyl group, a C(=O)—

$NA_8$-($C_1$-$C_6$)alkyl-C(=O)$NA_7$-($C_1$-$C_6$)alkyl-(OCH$_2$CH$_2$)$_i$ group, a C(=O)—$NA_8$-($C_1$-$C_6$)alkyl-$NA_7$-($C_1$-$C_6$)alkyl group, a C(=O)—$NA_8$-($C_1$-$C_6$)alkyl-$NA_7$-($C_1$-$C_6$)alkyl-(OCH$_2$CH$_2$)$_i$ group or a C(=O)—$NA_6$-($C_1$-$C_6$)alkyl-(OCH$_2$CH$_2$)$_i$—$NA_7$-($C_1$-$C_6$)alkyl group;

$A_7$ representing a straight or branched, saturated or unsaturated, optionally substituted $C_1$-$C_{160}$ hydrocarbon chain wherein optionally at least one methylene unit is independently replaced by —NHC(=O)—, —N(alkyl)C(=O)—, —C(=O)NH—, —C(=O)N(alkyl)-, —OC(=O)—, —C(=O)O—, —OC(=O)O—, —CH(OH)—, —CH(SO$_3$H)—, —O—, —C(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —NH$_2$, —NHalkyl, and —N(alkyl)$_2$, being understood that each $A_7$ comprising a SO$_3$H function can be under salt forms such as alkali metal salts, for instance sodium salts (SO$_3^-$ $^+$Na);

$A_8$ representing a hydrogen atom or a ($C_1$-$C_6$)alkyl group, for instance a hydrogen atom or a methyl group;

i representing an integer ranging from 1 to 50, for instance ranging from 1 to 35, wherein said substituted amino acids AA$_s$ have the formula (VI):

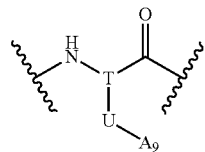

(VI)

wherein:
T represents a saturated or unsaturated, linear or branched, ($C_1$-$C_8$) trivalent alkyl group, preferably T is U group represents a single bond, —NHC(=O)—, —N(alkyl)C(=O)—, —C(=O)NH—, —C(=O)N(alkyl)-, —NHC(=O)NH—, —NHC(=NH)NH—, —OC(=O)—, —C(=O)O—, —OC(=O)O—, —S—, —Se—, —O—, —NH—, —N(alkyl)-, —C(=O)—, —OP(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, or —O—P(=O)(OH)—O, such as U group represents —NH—C(=O)—, or —C(=O)NH—;

$A_9$ represents a straight or branched, saturated or unsaturated, optionally substituted $C_1$-$C_{160}$ hydrocarbon chain wherein optionally at least one methylene unit is independently replaced by —NH—C(=O)—, —N(alkyl)C(=O)—, —C(=O)NH—, —C(=O)N(alkyl)-, —NHC(=O)NH—, —NHC(=NH)NH—, —OC(=O)—, —C(=O)O—, —OC(=O)O—, —CH(OH)—, —CH(SO$_3$H)—, —CH(Oalkyl)-, —CHF—, —CF$_2$—, —S—, —Se—, —O—, —NH—, —N(alkyl)-, —N$^+$H(alkyl)-, —N$^+$(alkyl)$_2$-, —C(=O)—, —OP(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —NH$_2$, —NHalkyl, and —N(alkyl)$_2$, for instance $A_9$ is —[(CH$_2$)$_2$—O]$_4$—CH$_3$, —[(CH$_2$)$_2$—O]$_{24}$—CH$_3$, or —[(CH$_2$)$_2$—O]$_4$—(CH$_2$)$_2$—C(=O)—NH—(CH$_2$)$_2$—SO$_3$H;

being understood that each $A_9$ comprising a SO$_3$H function can be under salt forms such as alkali metal salts, for instance sodium salts (SO$_3^-$ $^+$Na).

According to another particular embodiment, the disclosure relates to compounds of formula (I):

RCG1-L-P  (I)

wherein
RCG1 represents a reactive chemical group that is reactive towards a chemical group present on a polypeptide such as an antibody;

P represents a hydrogen atom, —OH or an activated O;

L represents a linker of formula (II):

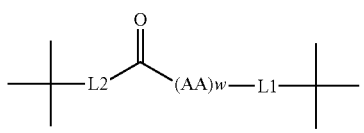

wherein:
L1 is of formula (III):

wherein:
when P represents a hydrogen atom, then x=0 or 1 and y=1 and z=0;
when P represents —OH, then x=y=z=0;
when P represents an activated O, then x=1 and y=z=0, or x=y=z=1;
$J_1$, $J_2$, $J_3$ and $J_4$ are chosen, independently of each other, from $CA_1$ and N;
ALK represents a ($C_1$-$C_{12}$)alkylene group, for instance ($C_1$-$C_6$)alkylene, such as of the form —$(CH_2)_n$—, n being an integer ranging from 1 to 12 and for example ranging from 1 to 6;
$A_1$, $A_2$, $A_3$, $A_4$, $A_5$, and $A_6$ represent, independently of each other, a hydrogen atom or a ($C_1$-$C_6$)alkyl group, such as a hydrogen atom or a methyl group.
(AA)w represents a sequence of w substituted $AA_s$ or non-substituted amino acids $AA_{ns}$ connected together via peptide bonds;
w represents an integer ranging from 1 to 12, for instance from 1 to 6, such as 2 or 3;
if (AA)w contains at least one substituted amino acid $AA_s$, then L2 represents a single bond, a ($C_1$-$C_6$)alkyl group, a ($C_1$-$C_6$)alkyl-($OCH_2CH_2)_i$ group, a ($C_1$-$C_6$)alkyl-($OCH_2CH_2)_i$—O($C_1$-$C_6$)alkyl group, a ($CH_2CH_2O)_i$($C_1$-$C_6$)alkyl group, a $CH(SO_3H)$—($C_1$-$C_6$)alkyl group, a ($C_1$-$C_6$)alkyl-$CH(SO_3H)$ group, a ($C_1$-$C_6$)alkyl-cyclohexyl group, a C(=O)—($C_1$-$C_6$)alkyl group, a C(=O)—($C_1$-$C_6$)alkyl-($OCH_2CH_2)_i$ group, a C(=O)—($C_1$-$C_6$)alkyl-($OCH_2CH_2)_i$—O($C_1$-$C_6$)alkyl group, a C(=O)—($CH_2CH_2O)_i$($C_1$-$C_6$)alkyl group, a C(=O)—$CH(SO_3H)$—($C_1$-$C_6$)alkyl group, a C(=O)—($C_1$-$C_6$)alkyl-$CH(SO_3H)$ group, a C(=O)—($C_1$-$C_6$)alkyl-cyclohexyl group, a $NA_8$-($C_1$-$C_6$)alkyl group, a $NA_8$-($C_1$-$C_6$)alkyl-($OCH_2CH_2)_i$ group, a $NA_8$-($C_1$-$C_6$)alkyl-($OCH_2CH_2)_i$—O($C_1$-$C_6$)alkyl group, a $NA_8$-($CH_2CH_2O)_i$($C_1$-$C_6$)alkyl group, a $NA_8$-($C_1$-$C_6$)alkyl-CH($SO_3H$) group, a C(=O)—$NA_8$-($C_1$-$C_6$)alkyl group, a C(=O)—$NA_8$-($C_1$-$C_6$)alkyl-($OCH_2CH_2)_i$ group, a C(=O)—$NA_8$-($C_1$-$C_6$)alkyl-($OCH_2CH_2)_i$—O($C_1$-$C_6$)alkyl group, a C(=O)—$NA_8$-($CH_2CH_2O)_i$($C_1$-$C_6$)alkyl group, a C(=O)—$NA_8$-($C_1$-$C_6$)alkyl-$CH(SO_3H)$ group, a $NA_7$-($C_1$-$C_6$)alkyl group, a ($C_1$-$C_6$)alkyl-$NA_7$ group, a $NA_7$-($CH_2CH_2O)_i$($C_1$-$C_6$)alkyl group, a $NA_7$-aryl group, a $NA_7$-heteroaryl group, a ($C_1$-$C_6$)alkyl-$NA_7$C(=O)—($C_1$-$C_6$)alkyl group, a ($C_1$-$C_6$)alkyl-$NA_7$C(=O)—($C_1$-$C_6$)alkyl-($OCH_2CH_2)_i$ group, a ($C_1$-$C_6$)alkyl-C(=O)$NA_7$-($C_1$-$C_6$)alkyl group, a ($C_1$-$C_6$)alkyl-C(=O)$NA_7$-($C_1$-$C_6$)alkyl-($OCH_2CH_2)_i$ group, a ($C_1$-$C_6$)alkyl-$NA_7$-($C_1$-$C_6$)alkyl group, a ($C_1$-$C_6$)alkyl-$NA_7$-($C_1$-$C_6$)alkyl-($OCH_2CH_2)_i$ group, a ($C_1$-$C_6$)alkyl-($OCH_2CH_2)_i$—$NA_7$-($C_1$-$C_6$)alkyl group, a C(=O)—$NA_7$-($C_1$-$C_6$)alkyl group, a C(=O)—($C_1$-$C_6$)alkyl-$NA_7$ group, a C(=O)—$NA_7$-($CH_2CH_2O)_i$($C_1$-$C_6$)alkyl group, a C(=O)—$NA_7$-aryl group, a C(=O)—$NA_7$-heteroaryl group, a C(=O)—($C_1$-$C_6$)alkyl-$NA_7$C(=O)—($C_1$-$C_6$)alkyl group, a C(=O)—($C_1$-$C_6$)alkyl-$NA_7$C(=O)—($C_1$-$C_6$)alkyl-($OCH_2CH_2)_i$ group, a C(=O)—($C_1$-$C_6$)alkyl-C(=O)$NA_7$-($C_1$-$C_6$)alkyl group, a C(=O)—($C_1$-$C_6$)alkyl-C(=O)$NA_7$-($C_1$-$C_6$)alkyl-($OCH_2CH_2)_i$ group, a C(=O)—($C_1$-$C_6$)alkyl-$NA_7$-($C_1$-$C_6$)alkyl group, a C(=O)—($C_1$-$C_6$)alkyl-$NA_7$-($C_1$-$C_6$)alkyl-($OCH_2CH_2)_i$ group, a C(=O)—($C_1$-$C_6$)alkyl-($OCH_2CH_2)_i$—$NA_7$-($C_1$-$C_6$)alkyl group, a $NA_8$-($C_1$-$C_6$)alkyl-$NA_7$ group, a $NA_8$-($C_1$-$C_6$)alkyl-$NA_7$C(=O)—($C_1$-$C_6$)alkyl group, a $NA_8$-($C_1$-$C_6$)alkyl-$NA_7$C(=O)—($C_1$-$C_6$)alkyl-($OCH_2CH_2)_i$ group, a $NA_8$-($C_1$-$C_6$)alkyl-C(=O)$NA_7$-($C_1$-$C_6$)alkyl group, a $NA_8$-($C_1$-$C_6$)alkyl-C(=O)$NA_7$-($C_1$-$C_6$)alkyl-($OCH_2CH_2)_i$ group, a $NA_8$-($C_1$-$C_6$)alkyl-$NA_7$-($C_1$-$C_6$)alkyl group, a $NA_8$-($C_1$-$C_6$)alkyl-$NA_7$-($C_1$-$C_6$)alkyl-($OCH_2CH_2)_i$ group, a $NA_8$-($C_1$-$C_6$)alkyl-($OCH_2CH_2)_i$—$NA_7$-($C_1$-$C_6$)alkyl group, a C(=O)—$NA_8$-($C_1$-$C_6$)alkyl-$NA_7$ group, a C(=O)—$NA_8$-($C_1$-$C_6$)alkyl-$NA_7$C(=O)—($C_1$-$C_6$)alkyl group, a C(=O)—$NA_8$-($C_1$-$C_6$)alkyl-$NA_7$C(=O)—($C_1$-$C_6$)alky-($OCH_2CH_2)_i$ group, a C(=O)—$NA_8$-($C_1$-$C_6$)alkyl-C(=O)$NA_7$-($C_1$-$C_6$)alkyl group, a C(=O)—$NA_8$-($C_1$-$C_6$)alkyl-C(=O)$NA_7$-($C_1$-$C_6$)alkyl-($OCH_2CH_2)_i$ group, a C(=O)—$NA_8$-($C_1$-$C_6$)alkyl-$NA_7$-($C_1$-$C_6$)alkyl group, a C(=O)—$NA_8$-($C_1$-$C_6$)alkyl-$NA_7$-($C_1$-$C_6$)alkyl-($OCH_2CH_2)_i$ group or a C(=O)—$NA_8$-($C_1$-$C_6$)alkyl-($OCH_2CH_2)_i$—$NA_7$-($C_1$-$C_6$)alkyl group;

if (AA)w represents a sequence of w non-substituted amino acids $AA_{ns}$, then L2 represents a $NA_7$-($C_1$-$C_6$)alkyl group, a ($C_1$-$C_6$)alkyl-$NA_7$ group, a $NA_7$-($CH_2CH_2O)_i$($C_1$-$C_6$)alkyl group, a $NA_7$-aryl group, a $NA_7$-heteroaryl group, a ($C_1$-$C_6$)alkyl-$NA_7$C(=O)—($C_1$-$C_6$)alkyl group, a ($C_1$-$C_6$)alkyl-$NA_7$C(=O)—($C_1$-$C_6$)alkyl-($OCH_2CH_2)_i$ group, a ($C_1$-$C_6$)alkyl-C(=O)$NA_7$-($C_1$-$C_6$)alkyl group, a ($C_1$-$C_6$)alkyl-C(=O)$NA_7$-($C_1$-$C_6$)alkyl-($OCH_2CH_2)_i$ group, a ($C_1$-$C_6$)alkyl-$NA_7$-($C_1$-$C_6$)alkyl group, a ($C_1$-$C_6$)alkyl-$NA_7$-($C_1$-$C_6$)alkyl-($OCH_2CH_2)_i$ group, a ($C_1$-$C_6$)alkyl-($OCH_2CH_2)_i$—$NA_7$-($C_1$-$C_6$)alkyl group, a C(=O)—$NA_7$-($C_1$-$C_6$)alkyl group, a C(=O)—($C_1$-$C_6$)alkyl-$NA_7$ group, a C(=O)—$NA_7$-($CH_2CH_2O)_i$($C_1$-$C_6$)alkyl group, a C(=O)—$NA_7$-aryl group, a C(=O)—$NA_7$-heteroaryl group, a C(=O)—($C_1$-$C_6$)alkyl-$NA_7$C(=O)—($C_1$-$C_6$)alkyl group, a C(=O)—($C_1$-$C_6$)alkyl-$NA_7$C(=O)—($C_1$-$C_6$)alkyl-($OCH_2CH_2)_i$ group, a C(=O)—($C_1$-$C_6$)alkyl-C(=O)$NA_7$-($C_1$-$C_6$)alkyl group, a C(=O)—($C_1$-$C_6$)alkyl-C(=O)$NA_7$-($C_1$-$C_6$)alkyl-($OCH_2CH_2)_i$ group, a C(=O)—($C_1$-$C_6$)alkyl-$NA_7$-($C_1$-$C_6$)alkyl group, a C(=O)—($C_1$-$C_6$)alkyl-$NA_7$-($C_1$-$C_6$)alkyl-($OCH_2CH_2)_i$ group, a $NA_8$-($C_1$-$C_6$)alkyl-$NA_7$ group, a $NA_8$-($C_1$-$C_6$)alkyl-$NA_7$C(=O)—($C_1$-$C_6$)alkyl group, a $NA_8$-($C_1$-$C_6$)alkyl-$NA_7$C(=O)—($C_1$-$C_6$)alkyl-($OCH_2CH_2)_i$ group, a $NA_8$-($C_1$-$C_6$)alkyl-C(=O)$NA_7$-($C_1$-$C_6$)alkyl group, a $NA_8$-($C_1$-$C_6$)alkyl-C(=O)$NA_7$-($C_1$-$C_6$)alkyl-($OCH_2CH_2)_i$ group, a $NA_8$-($C_1$-$C_6$)alkyl-$NA_7$-($C_1$-$C_6$)alkyl group, a $NA_8$-($C_1$-$C_6$)alkyl-$NA_7$-($C_1$-$C_6$)alkyl-($OCH_2CH_2)_i$ group, a $NA_8$-($C_1$-$C_6$)alkyl-($OCH_2CH_2)_i$—$NA_7$-($C_1$-$C_6$)alkyl group, a C(=O)—$NA_8$-($C_1$-$C_6$)alkyl-$NA_7$ group, a C(=O)—$NA_8$-($C_1$-$C_6$)alkyl-$NA_7$C(=O)—($C_1$-$C_6$)alkyl group, a C(=O)—$NA_8$-($C_1$-$C_6$)alkyl-$NA_7$C(=O)—($C_1$-$C_6$)alkyl-($OCH_2CH_2)_i$ group, a C(=O)—$NA_8$-($C_1$-$C_6$)alkyl-C(=O)$NA_7$-($C_1$-$C_6$)alkyl group, a C(=O)—

$NA_8$-$(C_1$-$C_6)$alkyl-C(=O)$NA_7$-$(C_1$-$C_6)$alkyl-$(OCH_2CH_2)_i$ group, a C(=O)—$NA_8$-$(C_1$-$C_6)$alkyl-$NA_7$-$(C_1$-$C_6)$alkyl group, a C(=O)—$NA_8$-$(C_1$-$C_6)$alkyl-$NA_7$-$(C_1$-$C_6)$alkyl-$(OCH_2CH_2)_i$ group or a C(=O)—$NA_8$-$(C_1$-$C_6)$alkyl-$(OCH_2CH_2)_i$—$NA_7$-$(C_1$-$C_6)$alkyl group;

$A_7$ representing a straight or branched, saturated or unsaturated, optionally substituted $C_1$-$C_{160}$ hydrocarbon chain wherein optionally at least one methylene unit is independently replaced by —NHC(=O)—, —N(alkyl)C(=O)—, —C(=O)NH—, —C(=O)N(alkyl)-, —OC(=O)—, —C(=O)O—, —OC(=O)O—, —CH(OH)—, —CH($SO_3$H)—, —O—, —C(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —$NH_2$, —NHalkyl, and —N(alkyl)$_2$, being understood that each $A_7$ comprising a $SO_3$H function can be under salt forms such as alkali metal salts, for instance sodium salts ($SO_3^-$ $^+$Na);

$A_8$ representing a hydrogen atom or a ($C_1$-$C_6$)alkyl group, for instance a hydrogen atom or a methyl group;

i representing an integer ranging from 1 to 50, for instance ranging from 1 to 35, wherein said substituted amino acids $AA_s$ have the formula (VI):

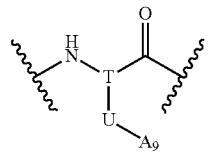

(VI)

wherein:
T represents a saturated or unsaturated, linear or branched, ($C_1$-$C_8$) trivalent alkyl group, preferably T is

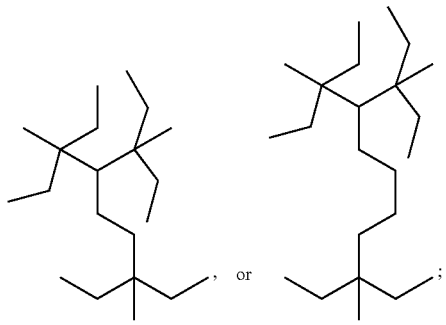

, or ;

U group represents a single bond, —NHC(=O)—, —N(alkyl)C(=O)—, —C(=O)NH—, —C(=O)N(alkyl)-, —NHC(=O)NH—, —NHC(=NH)NH—, —OC(=O)—, —C(=O)O—, —OC(=O)O—, —S—, —Se—, —O—, —NH—, —N(alkyl)-, —C(=O)—, —OP(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, or —O—P(=O)(OH)—O, such as U group represents —NH—C(=O)—, or —C(=O)NH—; $A_9$ represents a straight or branched, saturated or unsaturated, optionally substituted $C_1$-$C_{160}$ hydrocarbon chain wherein optionally at least one methylene unit is independently replaced by —NH—C(=O)—, —N(alkyl)C(=O)—, —C(=O)NH—, —C(=O)N(alkyl)-, —NHC(=NH)NH—, —OC(=O)—, —C(=O)O—, —OC(=O)O—, —CH(OH)—, —CH($SO_3$H)—, —CH(Oalkyl)-, —CHF—, —$CF_2$—, —S—, —Se—, —O—, —NH—, —N(alkyl)-, —$N^+$H(alkyl)-, —$N^+$(alkyl)$_2$-, —C(=O)—, —OP(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —$NH_2$, —NHalkyl, and —N(alkyl)$_2$, for instance $A_9$ is —[($CH_2)_2$—O]$_4$—$CH_3$, —[($CH_2)_2$—O]$_{24}$—$CH_3$,

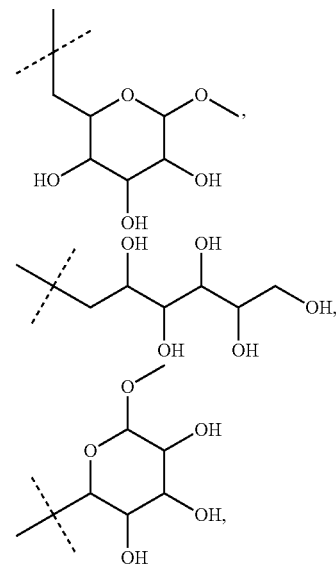

or —[($CH_2)_2$—O]$_4$—($CH_2)_2$—C(=O)—NH—($CH_2)_2$—$SO_3$H;

being understood that each $A_9$ comprising a $SO_3$H function can be under salt forms such as alkali metal salts, for instance sodium salts ($SO_3^-$ $^+$Na).

According to another particular embodiment, the disclosure relates to compounds of formula (I):

RCG1-L-P  (I)

wherein
RCG1 represents a reactive chemical group that is reactive towards a chemical group present on a polypeptide such as an antibody;
P represents a hydrogen atom, —OH or an activated O;
L represents a linker of formula (II):

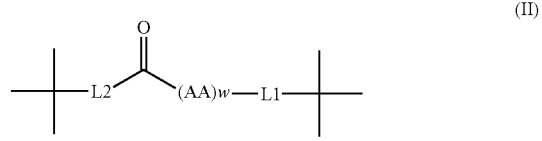

(II)

wherein:

L1 is of formula (III):

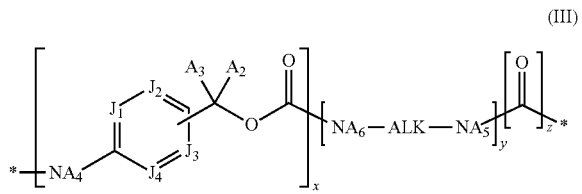

(III)

wherein:
- when P represents a hydrogen atom, then x=0 or 1 and y=1 and z=0;
- when P represents —OH, then x=y=z=0;
- when P represents an activated O, then x=1 and y=z=0, or x=y=z=1;
- $J_1$, $J_2$, $J_3$ and $J_4$ are chosen, independently of each other, from $CA_1$ and N;
- ALK represents a $(C_1-C_{12})$alkylene group, for instance $(C_1-C_6)$alkylene, such as of the form —$(CH_2)_n$—, n being an integer ranging from 1 to 12 and for example ranging from 1 to 6;
- $A_1$, $A_2$, $A_3$, $A_4$, $A_5$, and $A_6$ represent, independently of each other, a hydrogen atom or a $(C_1-C_6)$alkyl group, such as a hydrogen atom or a methyl group.
- (AA)w represents a sequence of w substituted $AA_s$ or non-substituted amino acids $AA_{ns}$ connected together via peptide bonds;
- w represents an integer ranging from 1 to 12, for instance from 1 to 6, such as 2 or 3;
- if (AA)w contains at least one substituted amino acid $AA_s$, then L2 represents a single bond, a $(C_1-C_6)$alkyl group, a $(C_1-C_6)$alkyl-$(OCH_2CH_2)_i$ group, a $(C_1-C_6)$alkyl-$(OCH_2CH_2)_i$—$O(C_1-C_6)$alkyl group, a $(CH_2CH_2O)_i(C_1-C_6)$alkyl group, a $CH(SO_3H)$—$(C_1-C_6)$alkyl group, a $(C_1-C_6)$alkyl-$CH(SO_3H)$ group, a $(C_1-C_6)$alkyl-cyclohexyl group, a $C(=O)$—$(C_1-C_6)$alkyl group, a $C(=O)$—$(C_1-C_6)$alkyl-$(OCH_2CH_2)_i$ group, a $C(=O)$—$(C_1-C_6)$alkyl-$(OCH_2CH_2)_i$—$O(C_1-C_6)$alkyl group, a $C(=O)$—$(CH_2CH_2O)_i(C_1-C_6)$alkyl group, a $C(=O)$—$CH(SO_3H)$—$(C_1-C_6)$alkyl group, a $C(=O)$—$(C_1-C_6)$alkyl-$CH(SO_3H)$ group, a $C(=O)$—$(C_1-C_6)$alkyl-cyclohexyl group, a $NA_8$-$(C_1-C_6)$alkyl group, a $NA_8$-$(C_1-C_6)$alkyl-$(OCH_2CH_2)_i$ group, a $NA_8$-$(C_1-C_6)$alkyl-$(OCH_2CH_2)_i$—$O(C_1-C_6)$alkyl group, a $NA_8$-$(CH_2CH_2O)_i(C_1-C_6)$alkyl group, a $NA_8$-$(C_1-C_6)$alkyl-$CH(SO_3H)$ group, a $C(=O)$—$NA_8$-$(C_1-C_6)$alkyl group, a $C(=O)$—$NA_8$-$(C_1-C_6)$alkyl-$(OCH_2CH_2)_i$ group, a $C(=O)$—$NA_8$-$(C_1-C_6)$alkyl-$(OCH_2CH_2)_i$—$O(C_1-C_6)$alkyl group, a $C(=O)$—$NA_8$-$(CH_2CH_2O)_i(C_1-C_6)$alkyl group, a $C(=O)$—$NA_8$-$(C_1-C_6)$alkyl-$CH(SO_3H)$ group, a $NA_7$-$(C_1-C_6)$alkyl group, a $(C_1-C_6)$alkyl-$NA_7$ group, a $NA_7$-$(CH_2CH_2O)_i(C_1-C_6)$alkyl group, a $NA_7$-aryl group, a $NA_7$-heteroaryl group, a $(C_1-C_6)$alkyl-$NA_7C(=O)$—$(C_1-C_6)$alkyl group, a $(C_1-C_6)$alkyl-$NA_7C(=O)$—$(C_1-C_6)$alkyl-$(OCH_2CH_2)_i$ group, a $(C_1-C_6)$alkyl-$C(=O)NA_7$-$(C_1-C_6)$alkyl group, a $(C_1-C_6)$alkyl-$C(=O)NA_7$-$(C_1-C_6)$alkyl-$(OCH_2CH_2)_i$ group, a $(C_1-C_6)$alkyl-$NA_7$-$(C_1-C_6)$alkyl group, a $(C_1-C_6)$alkyl-$NA_7$-$(C_1-C_6)$alkyl-$(OCH_2CH_2)_i$ group, a $(C_1-C_6)$alkyl-$(OCH_2CH_2)_i$—$NA_7$-$(C_1-C_6)$alkyl group, a $C(=O)$—$NA_7$-$(C_1-C_6)$alkyl group, a $C(=O)$—$(C_1-C_6)$alkyl-$NA_7$ group, a $C(=O)$—$NA_7$-$(CH_2CH_2O)_i(C_1-C_6)$alkyl group, a $C(=O)$—$NA_7$-aryl group, a $C(=O)$—$NA_7$-heteroaryl group, a $C(=O)$—$(C_1-C_6)$alkyl-$NA_7C(=O)$—$(C_1-C_6)$alkyl group, a $C(=O)$—$(C_1-C_6)$alkyl-$NA_7C(=O)$—$(C_1-C_6)$alkyl-$(OCH_2CH_2)_i$ group, a $C(=O)$—$(C_1-C_6)$alkyl-$C(=O)NA_7$-$(C_1-C_6)$alkyl group, a $C(=O)$—$(C_1-C_6)$alkyl-$C(=O)NA_7$-$(C_1-C_6)$alkyl-$(OCH_2CH_2)_i$ group, a $C(=O)$—$(C_1-C_6)$alkyl-$NA_7$-$(C_1-C_6)$alkyl group, a $C(=O)$—$(C_1-C_6)$alkyl-$NA_7$-$(C_1-C_6)$alkyl-$(OCH_2CH_2)_i$ group, a $C(=O)$—$(C_1-C_6)$alkyl-$(OCH_2CH_2)_i$—$NA_7$-$(C_1-C_6)$alkyl group, a $NA_8$-$(C_1-C_6)$alkyl-$NA_7$ group, a $NA_8$-$(C_1-C_6)$alkyl-$NA_7C(=O)$—$(C_1-C_6)$alkyl group, a $NA_8$-$(C_1-C_6)$alkyl-$NA_7C(=O)$—$(C_1-C_6)$alkyl-$(OCH_2CH_2)_i$ group, a $NA_8$-$(C_1-C_6)$alkyl-$C(=O)NA_7$-$(C_1-C_6)$alkyl group, a $NA_8$-$(C_1-C_6)$alkyl-$C(=O)NA_7$-$(C_1-C_6)$alkyl-$(OCH_2CH_2)_i$ group, a $NA_8$-$(C_1-C_6)$alkyl-$NA_7$-$(C_1-C_6)$alkyl group, a $NA_8$-$(C_1-C_6)$alkyl-$NA_7$-$(C_1-C_6)$alkyl-$(OCH_2CH_2)_i$ group, a $NA_8$-$(C_1-C_6)$alkyl-$(OCH_2CH_2)_i$—$NA_7$-$(C_1-C_6)$alky group, a $C(=O)$—$NA_8$-$(C_1-C_6)$alkyl-$NA_7$ group, a $C(=O)$—$NA_8$-$(C_1-C_6)$alkyl-$NA_7C(=O)$—$(C_1-C_6)$alkyl group, a $C(=O)$—$NA_8$-$(C_1-C_6)$alkyl-$NA_7C(=O)$—$(C_1-C_6)$alky-$(OCH_2CH_2)_i$ group, a $C(=O)$—$NA_8$-$(C_1-C_6)$alkyl-$C(=O)NA_7$-$(C_1-C_6)$alkyl group, a $C(=O)$—$NA_6$-$(C_1-C_6)$alkyl-$C(=O)NA_7$-$(C_1-C_6)$alkyl-$(OCH_2CH_2)_i$ group, a $C(=O)$—$NA_8$-$(C_1-C_6)$alkyl-$NA_7$-$(C_1-C_6)$alkyl group, a $C(=O)$—$NA_8$-$(C_1-C_6)$alkyl-$NA_7$-$(C_1-C_6)$alkyl-$(OCH_2CH_2)_i$ group or a $C(=O)$—$NA_8$-$(C_1-C_6)$alkyl-$(OCH_2CH_2)_i$—$NA_7$-$(C_1-C_6)$alkyl group;
- if (AA)w represents a sequence of w non-substituted amino acids $AA_{ns}$, then L2 represents a $NA_7$-$(C_1-C_6)$alkyl group, a $(C_1-C_6)$alkyl-$NA_7$ group, a $NA_7$-$(CH_2CH_2O)_i(C_1-C_6)$alkyl group, a $NA_7$-aryl group, a $NA_7$-heteroaryl group, a $(C_1-C_6)$alkyl-$NA_7C(=O)$—$(C_1-C_6)$alkyl group, a $(C_1-C_6)$alkyl-$NA_7C(=O)$—$(C_1-C_6)$alkyl-$(OCH_2CH_2)_i$ group, a $(C_1-C_6)$alkyl-$C(=O)NA_7$-$(C_1-C_6)$alkyl group, a $(C_1-C_6)$alkyl-$C(=O)NA_7$-$(C_1-C_6)$alkyl-$(OCH_2CH_2)_i$ group, a $(C_1-C_6)$alkyl-$NA_7$-$(C_1-C_6)$alkyl group, a $(C_1-C_6)$alkyl-$NA_7$-$(C_1-C_6)$alkyl-$(OCH_2CH_2)_i$ group, a $(C_1-C_6)$alkyl-$(OCH_2CH_2)_i$—$NA_7$-$(C_1-C_6)$alkyl group, a $C(=O)$—$NA_7$-$(C_1-C_6)$alkyl group, a $C(=O)$—$(C_1-C_6)$alkyl-$NA_7$ group, a $C(=O)$—$NA_7$-$(CH_2CH_2O)_i(C_1-C_6)$alkyl group, a $C(=O)$—$NA_7$-aryl group, a $C(=O)$—$NA_7$-heteroaryl group, a $C(=O)$—$(C_1-C_6)$alkyl-$NA_7C(=O)$—$(C_1-C_6)$alkyl group, a $C(=O)$—$(C_1-C_6)$alkyl-$NA_7C(=O)$—$(C_1-C_6)$alkyl-$(OCH_2CH_2)_i$ group, a $C(=O)$—$(C_1-C_6)$alkyl-$C(=O)NA_7$-$(C_1-C_6)$alkyl group, a $C(=O)$—$(C_1-C_6)$alkyl-$C(=O)NA_7$-$(C_1-C_6)$alkyl-$(OCH_2CH_2)_i$ group, a $C(=O)$—$(C_1-C_6)$alkyl-$NA_7$-$(C_1-C_6)$alkyl group, a $C(=O)$—$(C_1-C_6)$alkyl-$NA_7$-$(C_1-C_6)$alkyl-$(OCH_2CH_2)_i$ group, a $C(=O)$—$(C_1-C_6)$alkyl-$(OCH_2CH_2)_i$—$NA_7$-$(C_1-C_6)$alkyl group, a $NA_8$-$(C_1-C_6)$alkyl-$NA_7$ group, a $NA_8$-$(C_1-C_6)$alkyl-$NA_7C(=O)$—$(C_1-C_6)$alkyl group, a $NA_8$-$(C_1-C_6)$alkyl-$NA_7C(=O)$—$(C_1-C_6)$alkyl-$(OCH_2CH_2)_i$ group, a $NA_8$-$(C_1-C_6)$alkyl-$C(=O)NA_7$-$(C_1-C_6)$alkyl group, a $NA_8$-$(C_1-C_6)$alkyl-$C(=O)NA_7$-$(C_1-C_6)$alkyl-$(OCH_2CH_2)_i$ group, a $NA_8$-$(C_1-C_6)$alkyl-$NA_7$-$(C_1-C_6)$alkyl group, a $NA_8$-$(C_1-C_6)$alkyl-$NA_7$-$(C_1-C_6)$alkyl-$(OCH_2CH_2)_i$ group, a $NA_8$-$(C_1-C_6)$alkyl-$(OCH_2CH_2)_i$—$NA_7$-$(C_1-C_6)$alky group, a $C(=O)$—$NA_8$-$(C_1-C_6)$alkyl-$NA_7$ group, a $C(=O)$—$NA_8$-$(C_1-C_6)$alkyl-$NA_7C(=O)$—$(C_1-C_6)$alkyl group, a $C(=O)$—$NA_8$-$(C_1-C_6)$alkyl-$NA_7C(=O)$—$(C_1-C_6)$alkyl-$(OCH_2CH_2)_i$ group, a $C(=O)$—$NA_6$-$(C_1-C_6)$alkyl-$C(=O)NA_7$-$(C_1-C_6)$alkyl group, a $C(=O)$—$NA_8$-$(C_1-C_6)$alkyl-$C(=O)NA_7$-$(C_1-C_6)$alkyl-$(OCH_2CH_2)_i$ group, a $C(=O)$—$NA_8$-$(C_1-C_6)$alkyl-$NA_7$-$(C_1-C_6)$alkyl group, a $C(=O)$—$NA_8$-$(C_1-C_6)$alkyl-$NA_7$-$(C_1-C_6)$alkyl-$(OCH_2CH_2)_i$ group or a $C(=O)$—$NA_8$-$(C_1-C_6)$alkyl-$(OCH_2CH_2)_i$—$NA_7$-$(C_1-C_6)$alkyl group;
- $A_7$ representing a straight or branched, saturated or unsaturated, optionally substituted $C_1$-$C_{160}$ hydrocarbon chain wherein optionally at least one methylene unit is independently replaced by —$NHC(=O)$—, —$N(alkyl)C(=O)$—, —$C(=O)NH$—, —$C(=O)N$ (alkyl)-, —OC(=O)—, —C(=O)O—, —OC(=O)O—, —CH(OH)—, —CH(SO₃H)—, —O—, —C(=O)—, —S(=O)—, —S(=O)₂—, —NHS(=O)₂—, —N(alkyl)S(=O)₂—, —S(=O)₂NH—, —S(=O)₂N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —NH₂, —NHalkyl, and —N(alkyl)₂, being understood that each A₇ comprising a SO₃H function can be under salt forms such as alkali metal salts, for instance sodium salts (SO₃⁻ ⁺Na);

A₈ representing a hydrogen atom or a (C₁-C₆)alkyl group, for instance a hydrogen atom or a methyl group;

i representing an integer ranging from 1 to 50, for instance ranging from 1 to 35, wherein said substituted amino acids AA$_s$ have the formula (VI):

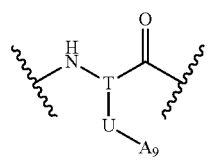

(VI)

wherein:

T represents a saturated or unsaturated, linear or branched, (C₁-C₈) trivalent alkyl group, preferably T is

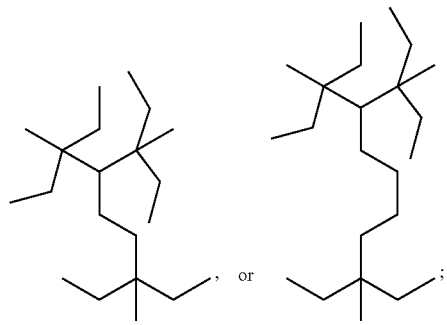

U group represents a single bond, —NHC(=O)—, —N(alkyl)C(=O)—, —C(=O)NH—, —C(=O)N(alkyl)-, —NHC(=O)NH—, —NHC(=NH)NH—, —OC(=O)—, —C(=O)O—, —OC(=O)O—, —S—, —Se—, —O—, —NH—, —N(alkyl)-, —C(=O)—, —OP(=O)—, —S(=O)—, —S(=O)₂—, —NHS(=O)₂—, —N(alkyl)S(=O)₂—, —S(=O)₂NH—, —S(=O)₂N(alkyl)-, —P(=O)(OH)—, —P(=O)(OH)O—, —O—P(=O)(OH)—, or —O—P(=O)(OH)—O, such as U group represents —NH—C(=O)—, or —C(=O)NH—;

A₉ represents a straight or branched, saturated or unsaturated, optionally substituted C₁-C₁₆₀ hydrocarbon chain wherein optionally at least one methylene unit is independently replaced by —NH—C(=O)—, —N(alkyl)C(=O)—, —C(=O)NH—, —C(=O)N(alkyl)-, —NHC(=NH)NH—, —OC(=O)—, —C(=O)O—, —OC(=O)O—, —CH(OH)—, —CH(SO₃H)—, —CH(Oalkyl)-, —CHF—, —CF₂—, —S—, —Se—, —O—, —N(alkyl)-, —N⁺H(alkyl)-, —N⁺(alkyl)₂-, —OP(=O)—, —S(=O)—, —S(=O)₂—, —NHS(=O)₂—, —N(alkyl)S(=O)₂—, —S(=O)₂NH—, —S(=O)₂N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —NH₂, —NHalkyl, and —N(alkyl)₂, for instance A₉ is —[(CH₂)₂—O]₄—CH₃, —[(CH₂)₂—O]₂₄—CH₃,

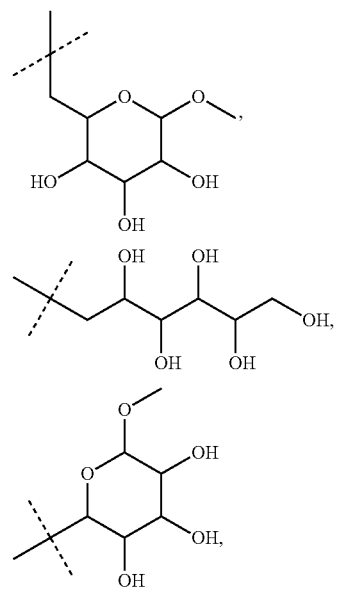

or —[(CH₂)₂—O]₄—(CH₂)₂—C(=O)—NH—(CH₂)₂—SO₃H;

being understood that each A₉ comprising a SO₃H function can be under salt forms such as alkali metal salts, for instance sodium salts (SO₃⁻ ⁺Na).

According to another particular embodiment, the disclosure relates to compounds of formula (I):

RCG1-L-P  (I)

wherein

RCG1 represents a reactive chemical group that is reactive towards a chemical group present on a polypeptide such as an antibody;

P represents a hydrogen atom, —OH or an activated O;

L represents a linker of formula (II):

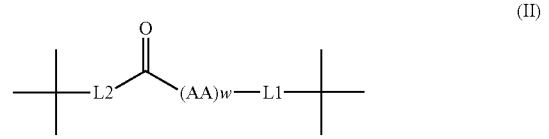

(II)

wherein:

L1 is of formula (III):

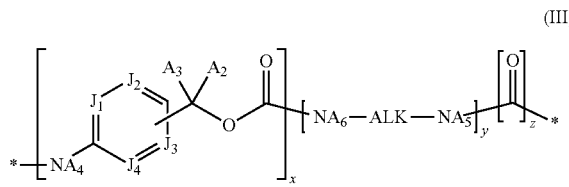

(III)

wherein:
when P represents a hydrogen atom, then x=0 or 1 and y=1 and z=0;
when P represents —OH, then x=y=z=0;
when P represents an activated O, then x=1 and y=z=0, or x=y=z=1;
$J_1$, $J_2$, $J_3$ and $J_4$ are chosen, independently of each other, from $CA_1$ and N;
ALK represents a ($C_1$-$C_{12}$)alkylene group, for instance ($C_1$-$C_6$)alkylene, such as of the form —($CH_2$)$_n$—, n being an integer ranging from 1 to 12 and for example ranging from 1 to 6;
$A_1$, $A_2$, $A_3$, $A_4$, $A_5$, and $A_6$ represent, independently of each other, a hydrogen atom or a ($C_1$-$C_6$)alkyl group, such as a hydrogen atom or a methyl group.

(AA)w represents a sequence of w substituted $AA_s$ or non-substituted amino acids $AA_{ns}$ connected together via peptide bonds;
w represents an integer ranging from 1 to 12, for instance from 1 to 6, such as 2 or 3;
if (AA)w contains at least one substituted amino acid $AA_s$, then L2 represents a single bond, a ($C_1$-$C_6$)alkyl group, a ($C_1$-$C_6$)alkyl-(OCH$_2$CH$_2$)$_i$ group, a ($C_1$-$C_6$)alkyl-(OCH$_2$CH$_2$)$_i$—O($C_1$-$C_6$)alkyl group, a (CH$_2$CH$_2$O)$_i$($C_1$-$C_6$)alkyl group, a CH(SO$_3$H)—($C_1$-$C_6$)alkyl group, a ($C_1$-$C_6$)alkyl-CH(SO$_3$H) group, a ($C_1$-$C_6$)alkyl-cyclohexyl group, a C(=O)—($C_1$-$C_6$)alkyl group, a C(=O)—($C_1$-$C_6$)alkyl-(OCH$_2$CH$_2$)$_i$ group, a C(=O)—($C_1$-$C_6$)alkyl-(OCH$_2$CH$_2$)$_i$—O($C_1$-$C_6$)alkyl group, a C(=O)—(CH$_2$CH$_2$O)$_i$($C_1$-$C_6$)alkyl group, a C(=O)—CH(SO$_3$H)—($C_1$-$C_6$)alkyl group, a C(=O)—($C_1$-$C_6$)alkyl-CH(SO$_3$H) group, a C(=O)—($C_1$-$C_6$)alkyl-cyclohexyl group, a NA$_8$-($C_1$-$C_6$)alkyl group, a NA$_8$-($C_1$-$C_6$)alkyl-(OCH$_2$CH$_2$)$_i$ group, a NA$_8$-($C_1$-$C_6$)alkyl-(OCH$_2$CH$_2$)$_i$—O($C_1$-$C_6$)alkyl group, a NA$_8$-(CH$_2$CH$_2$O)$_i$($C_1$-$C_6$)alkyl group, a NA$_8$-($C_1$-$C_6$)alkyl-CH(SO$_3$H) group, a C(=O)—NA$_8$-($C_1$-$C_6$)alkyl group, a C(=O)—NA$_8$-($C_1$-$C_6$)alkyl-(OCH$_2$CH$_2$)$_i$ group, a C(=O)—NA$_8$-($C_1$-$C_6$)alkyl-(OCH$_2$CH$_2$)$_i$—O($C_1$-$C_6$)alkyl group, a C(=O)—NA$_8$-(CH$_2$CH$_2$O)$_i$($C_1$-$C_6$)alkyl group, a C(=O)—NA$_8$-($C_1$-$C_6$)alkyl-CH(SO$_3$H) group, a NA$_7$-($C_1$-$C_6$)alkyl group, a ($C_1$-$C_6$)alkyl-NA$_7$ group, a NA$_7$-(CH$_2$CH$_2$O)$_i$($C_1$-$C_6$)alkyl group, a NA$_7$-aryl group, a NA$_7$-heteroaryl group, a ($C_1$-$C_6$)alkyl-NA$_7$C(=O)—($C_1$-$C_6$)alkyl group, a ($C_1$-$C_6$)alkyl-NA$_7$C(=O)—($C_1$-$C_6$)alkyl-(OCH$_2$CH$_2$)$_i$ group, a ($C_1$-$C_6$)alkyl-C(=O)NA$_7$-($C_1$-$C_6$)alkyl group, a ($C_1$-$C_6$)alkyl-C(=O)NA$_7$-($C_1$-$C_6$)alkyl-(OCH$_2$CH$_2$)$_i$ group, a ($C_1$-$C_6$)alkyl-NA$_7$-($C_1$-$C_6$)alkyl group, a ($C_1$-$C_6$)alkyl-NA$_7$-($C_1$-$C_6$)alkyl-(OCH$_2$CH$_2$)$_i$ group, a ($C_1$-$C_6$)alkyl-(OCH$_2$CH$_2$)$_i$—NA$_7$-($C_1$-$C_6$)alkyl group, a C(=O)—NA$_7$-($C_1$-$C_6$)alkyl group, a C(=O)—($C_1$-$C_6$)alkyl-NA$_7$ group, a C(=O)—NA$_7$-(CH$_2$CH$_2$O)$_i$($C_1$-$C_6$)alkyl group, a C(=O)—NA$_7$-aryl group, a C(=O)—NA$_7$-heteroaryl group, a C(=O)—($C_1$-$C_6$)alkyl-NA$_7$C(=O)—($C_1$-$C_6$)alkyl group, a C(=O)—($C_1$-$C_6$)alkyl-NA$_7$C(=O)—($C_1$-$C_6$)alkyl-(OCH$_2$CH$_2$)$_i$ group, a C(=O)—($C_1$-$C_6$)alkyl-C(=O)NA$_7$-($C_1$-$C_6$)alkyl group, a C(=O)—($C_1$-$C_6$)alkyl-C(=O)NA$_7$-($C_1$-$C_6$)alkyl-(OCH$_2$CH$_2$)$_i$ group, a C(=O)—($C_1$-$C_6$)alkyl-NA$_7$-($C_1$-$C_6$)alkyl group, a C(=O)—($C_1$-$C_6$)alkyl-NA$_7$-($C_1$-$C_6$)alkyl-(OCH$_2$CH$_2$)$_i$ group, a C(=O)—($C_1$-$C_6$)alkyl-(OCH$_2$CH$_2$)$_i$—NA$_7$-($C_1$-$C_6$)alky group, a C(=O)—NA$_8$-($C_1$-$C_6$)alkyl-NA$_7$ group, a C(=O)—NA$_8$-($C_1$-$C_6$)alkyl-NA$_7$C(=O)—($C_1$-$C_6$)alkyl group, a C(=O)—NA$_8$-($C_1$-$C_6$)alkyl-NA$_7$C(=O)—($C_1$-$C_6$)alky-(OCH$_2$CH$_2$)$_i$ group, a C(=O)—NA$_8$-($C_1$-$C_6$)alkyl-C(=O)NA$_7$-($C_1$-$C_6$)alkyl group, a C(=O)—NA$_8$-($C_1$-$C_6$)alkyl-C(=O)NA$_7$-($C_1$-$C_6$)alkyl-(OCH$_2$CH$_2$)$_i$ group, a C(=O)—NA$_8$-($C_1$-$C_6$)alkyl-NA$_7$-($C_1$-$C_6$)alkyl group, a C(=O)—NA$_8$-($C_1$-$C_6$)alkyl-NA$_7$-($C_1$-$C_6$)alkyl-(OCH$_2$CH$_2$)$_i$ group or a C(=O)—NA$_8$-($C_1$-$C_6$)alkyl-(OCH$_2$CH$_2$)$_i$—NA$_7$-($C_1$-$C_6$)alkyl group;

if (AA)w represents a sequence of w non-substituted amino acids $AA_{ns}$, then L2 represents a NA$_7$-($C_1$-$C_6$)alkyl group, a ($C_1$-$C_6$)alkyl-NA$_7$ group, a NA$_7$-(CH$_2$CH$_2$O)$_i$($C_1$-$C_6$)alkyl group, a NA$_7$-aryl group, a NA$_7$-heteroaryl group, a ($C_1$-$C_6$)alkyl-NA$_7$C(=O)—($C_1$-$C_6$)alkyl group, a ($C_1$-$C_6$)alkyl-NA$_7$C(=O)—($C_1$-$C_6$)alkyl-(OCH$_2$CH$_2$)$_i$ group, a ($C_1$-$C_6$)alkyl-C(=O)NA$_7$-($C_1$-$C_6$)alkyl group, a ($C_1$-$C_6$)alkyl-C(=O)NA$_7$-($C_1$-$C_6$)alkyl-(OCH$_2$CH$_2$)$_i$ group, a ($C_1$-$C_6$)alkyl-NA$_7$-($C_1$-$C_6$)alkyl group, a ($C_1$-$C_6$)alkyl-NA$_7$-($C_1$-$C_6$)alkyl-(OCH$_2$CH$_2$)$_i$ group, a ($C_1$-$C_6$)alkyl-(OCH$_2$CH$_2$)$_i$—NA$_7$-($C_1$-$C_6$)alkyl group, a C(=O)—NA$_7$-($C_1$-$C_6$)alkyl group, a C(=O)—($C_1$-$C_6$)alkyl-NA$_7$ group, a C(=O)—NA$_7$-(CH$_2$CH$_2$O)$_i$($C_1$-$C_6$)alkyl group, a C(=O)—NA$_7$-aryl group, a C(=O)—NA$_7$-heteroaryl group, a C(=O)—($C_1$-$C_6$)alkyl-NA$_7$C(=O)—($C_1$-$C_6$)alkyl group, a C(=O)—($C_1$-$C_6$)alkyl-NA$_7$C(=O)—($C_1$-$C_6$)alkyl-(OCH$_2$CH$_2$)$_i$ group, a C(=O)—($C_1$-$C_6$)alkyl-C(=O)NA$_7$-($C_1$-$C_6$)alkyl group, a C(=O)—($C_1$-$C_6$)alkyl-C(=O)NA$_7$-($C_1$-$C_6$)alkyl-(OCH$_2$CH$_2$)$_i$ group, a C(=O)—($C_1$-$C_6$)alkyl-NA$_7$-($C_1$-$C_6$)alkyl group, a C(=O)—($C_1$-$C_6$)alkyl-NA$_7$-($C_1$-$C_6$)alkyl-(OCH$_2$CH$_2$)$_i$ group, a C(=O)—($C_1$-$C_6$)alkyl-(OCH$_2$CH$_2$)$_i$—NA$_7$-($C_1$-$C_6$)alkyl group, a NA$_8$-($C_1$-$C_6$)alkyl-NA$_7$ group, a NA$_8$-($C_1$-$C_6$)alkyl-NA$_7$C(=O)—($C_1$-$C_6$)alkyl group, a NA$_8$-($C_1$-$C_6$)alkyl-NA$_7$C(=O)—($C_1$-$C_6$)alkyl-(OCH$_2$CH$_2$)$_i$ group, a NA$_8$-($C_1$-$C_6$)alkyl-C(=O)NA$_7$-($C_1$-$C_6$)alkyl group, a NA$_8$-($C_1$-$C_6$)alkyl-C(=O)NA$_7$-($C_1$-$C_6$)alkyl-(OCH$_2$CH$_2$)$_i$ group, a NA$_8$-($C_1$-$C_6$)alkyl-NA$_7$-($C_1$-$C_6$)alkyl group, a NA$_8$-($C_1$-$C_6$)alkyl-NA$_7$-($C_1$-$C_6$)alkyl-(OCH$_2$CH$_2$)$_i$ group, a NA$_8$-($C_1$-$C_6$)alkyl-(OCH$_2$CH$_2$)$_i$—NA$_7$-($C_1$-$C_6$)alkyl group, a C(=O)—NA$_8$-($C_1$-$C_6$)alkyl-NA$_7$ group, a C(=O)—NA$_8$-($C_1$-$C_6$)alkyl-NA$_7$C(=O)—($C_1$-$C_6$)alkyl group, a C(=O)—NA$_8$-($C_1$-$C_6$)alkyl-NA$_7$C(=O)—($C_1$-$C_6$)alkyl-(OCH$_2$CH$_2$)$_i$ group, a C(=O)—NA$_8$-($C_1$-$C_6$)alkyl-C(=O)NA$_7$-($C_1$-$C_6$)alkyl group, a C(=O)—NA$_8$-($C_1$-$C_6$)alkyl-C(=O)NA$_7$-($C_1$-$C_6$)alkyl-(OCH$_2$CH$_2$)$_i$ group, a C(=O)—NA$_8$-($C_1$-$C_6$)alkyl-NA$_7$-($C_1$-$C_6$)alkyl group, a C(=O)—NA$_8$-($C_1$-$C_6$)alkyl-NA$_7$-($C_1$-$C_6$)alkyl-(OCH$_2$CH$_2$)$_i$ group or a C(=O)—NA$_8$-($C_1$-$C_6$)alkyl-(OCH$_2$CH$_2$)$_i$—NA$_7$-($C_1$-$C_6$)alkyl group;

$A_7$ representing a straight or branched, saturated or unsaturated, optionally substituted $C_1$-$C_{160}$ hydrocarbon chain wherein optionally at least one methylene unit is independently replaced by —NHC(=O)—, —N(alkyl)C(=O)—, —C(=O)NH—, —C(=O)N (alkyl)-, —OC(=O)—, —C(=O)O—, —OC(=O)O—, —CH(OH)—, —CH(SO$_3$H)—, —O—, —C(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —NH$_2$, —NHalkyl, and —N(alkyl)$_2$, being understood that each A$_7$ comprising a SO$_3$H function can be under salt forms such as alkali metal salts, for instance sodium salts (SO$_3^-$ $^+$Na);

A$_8$ representing a hydrogen atom or a (C$_1$-C$_6$)alkyl group, for instance a hydrogen atom or a methyl group;

i representing an integer ranging from 1 to 50, for instance ranging from 1 to 35, wherein said substituted amino acids AA$_s$ have the formula (VI):

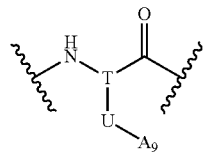

(VI)

wherein:

T represents a saturated or unsaturated, linear or branched, (C$_1$-C$_8$) trivalent alkyl group, preferably T is

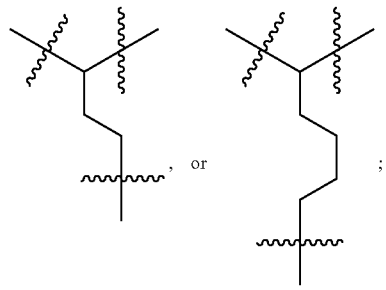 [SMILES: *CCC(*)* ; *CCCCC(*)*]

, or ;

U group represents a single bond, —NHC(=O)—, —N(alkyl)C(=O)—, —C(=O)NH—, —C(=O)N(alkyl)-, —NHC(=O)NH—, —NHC(=NH)NH—, —OC(=O)—, —C(=O)O—, —OC(=O)O—, —S—, —Se—, —O—, —NH—, —N(alkyl)-, —C(=O)—, —OP(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, or —O—P(=O)(OH)—O, such as U group represents —NH—C(=O)—, or —C(=O)NH—;

A$_9$ represents a straight or branched, saturated or unsaturated, optionally substituted C$_1$-C$_{160}$ hydrocarbon chain wherein optionally at least one methylene unit is independently replaced by —NH—C(=O)—, —N(alkyl)C(=O)—, —C(=O)NH—, —C(=O)N(alkyl)-, —C(=O)O—, —OC(=O)O—, —CH(OH)—, —CH(SO$_3$H)—, —CHF—, —CF$_2$—, —Se—, —O—, —N(alkyl)-, —N$^+$H(alkyl)-, —N$^+$(alkyl)$_2$-, —OP(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —NH$_2$, —NHalkyl, and —N(alkyl)$_2$, for instance A$_9$ is —[(CH$_2$)$_2$—O]$_4$—CH$_3$, —[(CH$_2$)$_2$—O]$_{24}$—CH$_3$,

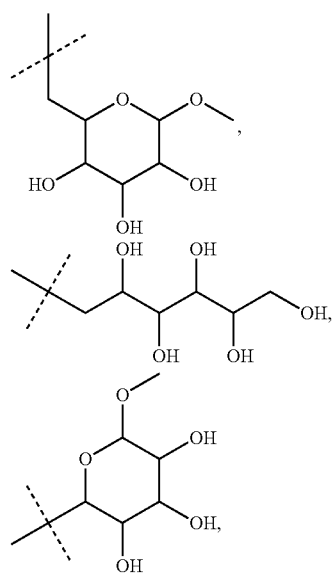

or —[(CH$_2$)$_2$—O]$_4$—(CH$_2$)$_2$—C(=O)—NH—(CH$_2$)$_2$—SO$_3$H;

being understood that each A$_9$ comprising a SO$_3$H function can be under salt forms such as alkali metal salts, for instance sodium salts (SO$_3^-$ $^+$Na).

According to another particular embodiment, the disclosure relates to compounds of formula (I):

RCG1-L-P  (I)

wherein

RCG1 represents a reactive chemical group that is reactive towards a chemical group present on a polypeptide such as an antibody;

P represents a hydrogen atom, —OH or an activated O;

L represents a linker of formula (II):

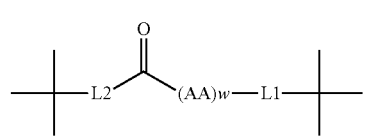

(II)

wherein:

L1 is of formula (III):

$$\left[\text{-}\left[NA_4\right]\underset{J_4}{\overset{J_1}{\underset{\|}{\bigcirc}}}\overset{J_2}{\underset{J_3}{\bigcirc}}\underset{A_1}{\overset{A_3}{\underset{|}{\text{C}}}}\underset{A_1}{\overset{A_2}{\underset{|}{\text{C}}}}\overset{O}{\underset{\|}{\text{C}}}\text{—O—}\right]_x\left[NA_6\text{—ALK—}NA_5\right]_y\left[\overset{O}{\underset{\|}{\text{C}}}\right]_z\text{*}\right]$$ (III)

wherein:
- when P represents a hydrogen atom, then x=0 or 1 and y=1 and z=0;
- when P represents —OH, then x=y=z=0;
- when P represents an activated O, then x=1 and y=z=0, or x=y=z=1;
- $J_1$, $J_2$, $J_3$ and $J_4$ are chosen, independently of each other, from $CA_1$ and N;
- ALK represents a $(C_1\text{-}C_{12})$alkylene group, for instance $(C_1\text{-}C_6)$alkylene, such as of the form —$(CH_2)_n$—, n being an integer ranging from 1 to 12 and for example ranging from 1 to 6;
- $A_1$, $A_2$, $A_3$, $A_4$, $A_5$, and $A_6$ represent, independently of each other, a hydrogen atom or a $(C_1\text{-}C_6)$alkyl group, such as a hydrogen atom or a methyl group.
- (AA)w represents a sequence of w substituted $AA_s$ or non-substituted amino acids $AA_{ns}$ connected together via peptide bonds;
- w represents an integer ranging from 1 to 12, for instance from 1 to 6, such as 2 or 3;
- (AA)w contains at least one substituted amino acid $AA_s$ and/or w non-substituted amino acid $AA_{ns}$ and L2 represents a $(C_1\text{-}C_6)$alkyl-$NA_7$-$(C_1\text{-}C_6)$alkyl group;
- $A_7$ is as defined above.

According to at least one embodiment, (AA)w contains at least one substituted amino acid $AA_s$ and L2 represents:
- a $(C_1\text{-}C_6)$alkyl group, such as a $(CH_2)_3$ group;
- a C(=O)—$(C_1\text{-}C_6)$alkyl group, such as a C(=O)—$(CH_2)_3$ group; or
- a $(C_1\text{-}C_6)$alkyl-$NA_7$-$(C_1\text{-}C_6)$alkyl group, such as a $(CH_2)_2$—$NA_7$-$(CH_2)_2$ group in which $A_7$ is as defined above.

According to at least one embodiment, (AA)w contains at least one substituted amino acid $AA_s$ and L2 represents:
- a $(C_1\text{-}C_6)$alkyl group, such as a $(CH_2)_3$ group;
- a C(=O)—$(C_1\text{-}C_6)$alkyl group, such as a C(=O)—$(CH_2)_3$ group; or
- a $(C_1\text{-}C_6)$alkyl-$NA_7$-$(C_1\text{-}C_6)$alkyl group, such as a $(CH_2)_2$—$NA_7$-$(CH_2)_2$ group in which $A_7$ is a —C(=O)—$(CH_2)_2$—C(=O)—NH—$(CH_2)_2$—$SO_3H$ group; being understood that each $A_7$ comprising a $SO_3H$ function can be under salt forms such as alkali metal salts, for instance sodium salts ($SO_3^-$ $^+Na$).

According to another embodiment, (AA)w contains w non-substituted amino acid $AA_{ns}$ and L2 represents:
a $(C_1\text{-}C_6)$alkyl-$NA_7$-$(C_1\text{-}C_6)$alkyl group, such as a $(CH_2)_2$—$NA_7$-$(CH_2)_2$ group in which $A_7$ is as defined above.

According to another embodiment, (AA)w contains w non-substituted amino acid $AA_{ns}$ and L2 represents:
a $(C_1\text{-}C_6)$alkyl-$NA_7$-$(C_1\text{-}C_6)$alkyl group, such as a $(CH_2)_2$—$NA_7$-$(CH_2)_2$ group in which $A_7$ represents:
- a C(=O)—$[(CH_2)_2$—O$]_a$—$CH_3$ group wherein "a" represents an integer ranging from 1 to 50, for instance ranging from 1 to 24, such as 4, 7 and 24, for example $A_7$ is a C(=O)—$[(CH_2)_2$—O$]_4$—$CH_3$ group, a C(=O)—$[(CH_2)_2$—O$]_7$—$CH_3$ group, or a C(=O)—$[(CH_2)_2$—O$]_{24}$—$CH_3$ group;
- a —C(=O)—$(CH_2)_2$—C(=O)—NH—$(CH_2)_2$—$SO_3H$ group; or
- a C(=O)—$(CH_2)_2$—C(=O)—NH—$[(CH_2)_2$—O$]_a$—$(CH_2)_2$—C(=O)—NH—$(CH_2)_2$—$SO_3H$ group wherein "a" represents an integer ranging from 1 to 50, such as ranging from 1 to 24, for example 4, such as $A_7$ is —C(=O)—$(CH_2)_2$—C(=O)—NH—$[(CH_2)_2$—O$]_4$—$(CH_2)_2$—C(=O)—NH—$(CH_2)_2$—$SO_3H$ group; being understood that each $A_7$ comprising a $SO_3H$ function can be under salt forms such as alkali metal salts, for instance sodium salts ($SO_3^-$ $^+Na$);

According to at least one embodiment, (AA)w contains at least one substituted amino acid $AA_s$ and/or w non-substituted amino acid $AA_{ns}$ and L2 represents:
a $NA_7$-$(C_1\text{-}C_6)$alkyl group, a $(C_1\text{-}C_6)$alkyl-$NA_7$ group, a $NA_7$-$(CH_2CH_2O)_i(C_1\text{-}C_6)$alkyl group, a $NA_7$-aryl group, a $NA_7$-heteroaryl group, a $(C_1\text{-}C_6)$alkyl-$NA_7C$(=O)—$(C_1$-$C_6)$alkyl group, a $(C_1\text{-}C_6)$alkyl-$NA_7C$(=O)—$(C_1\text{-}C_6)$alkyl-$(OCH_2CH_2)_i$ group, a $(C_1\text{-}C_6)$alkyl-C(=O)$NA_7$-$(C_1\text{-}C_6)$alkyl group, a $(C_1\text{-}C_6)$alkyl-C(=O)$NA_7$-$(C_1\text{-}C_6)$alkyl-$(OCH_2CH_2)_i$ group, a $(C_1\text{-}C_6)$alkyl-$NA_7$-$(C_1\text{-}C_6)$alkyl group, a $(C_1\text{-}C_6)$alkyl-$NA_7$-$(C_1\text{-}C_6)$alkyl-$(OCH_2CH_2)_i$ group, a $(C_1\text{-}C_6)$alkyl-$(OCH_2CH_2)_i$—$NA_7$-$(C_1\text{-}C_6)$alkyl group, a C(=O)—$NA_7$-$(C_1\text{-}C_6)$alkyl group, a C(=O)—$(C_1\text{-}C_6)$alkyl-$NA_7$ group, a C(=O)—$NA_7$-$(CH_2CH_2O)_i(C_1\text{-}C_6)$alkyl group, a C(=O)—$NA_7$-aryl group, a C(=O)—$NA_7$-heteroaryl group, a C(=O)—$(C_1\text{-}C_6)$alkyl-$NA_7C$(=O)—$(C_1\text{-}C_6)$alkyl group, a C(=O)—$(C_1\text{-}C_6)$alkyl-$NA_7C$(=O)—$(C_1\text{-}C_6)$alkyl-$(OCH_2CH_2)_i$ group, a C(=O)—$(C_1\text{-}C_6)$alkyl-C(=O)$NA_7$-$(C_1\text{-}C_6)$alkyl group, a C(=O)—$(C_1\text{-}C_6)$alkyl-C(=O)$NA_7$-$(C_1\text{-}C_6)$alkyl-$(OCH_2CH_2)_i$ group, a C(=O)—$(C_1\text{-}C_6)$alkyl-$NA_7$-$(C_1\text{-}C_6)$alkyl group, a C(=O)—$(C_1\text{-}C_6)$alkyl-$NA_7$-$(C_1\text{-}C_6)$alkyl-$(OCH_2CH_2)_i$ group, a C(=O)—$(C_1\text{-}C_6)$alkyl-$(OCH_2CH_2)_i$—$NA_7$-$(C_1\text{-}C_6)$alkyl group, a $NA_8$-$(C_1\text{-}C_6)$alkyl-$NA_7$ group, a $NA_8$-$(C_1\text{-}C_6)$alkyl-$NA_7C$(=O)—$(C_1\text{-}C_6)$alkyl group, a $NA_8$-$(C_1\text{-}C_6)$alkyl-$NA_7C$(=O)—$(C_1\text{-}C_6)$alkyl-$(OCH_2CH_2)_i$ group, a $NA_8$-$(C_1\text{-}C_6)$alkyl-C(=O)$NA_7$-$(C_1$-$C_6)$alkyl group, a $NA_8$-$(C_1\text{-}C_6)$alkyl-C(=O)$NA_7$-$(C_1\text{-}C_6)$alkyl-$(OCH_2CH_2)_i$ group, a $NA_8$-$(C_1\text{-}C_6)$alkyl-$NA_7$-$(C_1\text{-}C_6)$alkyl group, a $NA_8$-$(C_1\text{-}C_6)$alkyl-$NA_7$-$(C_1\text{-}C_6)$alkyl-$(OCH_2CH_2)_i$ group, a $NA_8$-$(C_1\text{-}C_6)$alkyl-$(OCH_2CH_2)_i$—$NA_7$-$(C_1\text{-}C_6)$alkyl group, a C(=O)—$NA_8$-$(C_1\text{-}C_6)$alkyl-$NA_7$ group, a C(=O)—$NA_8$-$(C_1\text{-}C_6)$alkyl-$NA_7C$(=O)—$(C_1\text{-}C_6)$alkyl group, a C(=O)—$NA_8$-$(C_1\text{-}C_6)$alkyl-$NA_7C$(=O)—$(C_1\text{-}C_6)$alkyl-$(OCH_2CH_2)_i$ group, a C(=O)—$NA_8$-$(C_1\text{-}C_6)$alkyl-C(=O)$NA_7$-$(C_1\text{-}C_6)$alkyl group, a C(=O)—$NA_8$-$(C_1\text{-}C_6)$alkyl-C(=O)$NA_7$-$(C_1\text{-}C_6)$alkyl-$(OCH_2CH_2)_i$ group, a C(=O)—$NA_8$-$(C_1\text{-}C_6)$alkyl-$NA_7$-$(C_1\text{-}C_6)$alkyl group, a C(=O)—$NA_8$-$(C_1\text{-}C_6)$alkyl-$NA_7$-$(C_1\text{-}C_6)$alkyl-$(OCH_2CH_2)_i$ group or a C(=O)—$NA_6$-$(C_1\text{-}C_6)$alkyl-$(OCH_2CH_2)_i$—$NA_7$-$(C_1\text{-}C_6)$alkyl group; wherein i, $A_7$ and $A_8$ are as defined above.

According to another embodiment, (AA)w contains at least one substituted amino acid $AA_s$ and/or w non-substituted amino acid $AA_{ns}$ and L2 represents:
a $NA_7$-$(C_1\text{-}C_6)$alkyl group, a $(C_1\text{-}C_6)$alkyl-$NA_7$ group, a $NA_7$-$(CH_2CH_2O)_i(C_1\text{-}C_6)$alkyl group, a $NA_7$-aryl group, a $NA_7$-heteroaryl group, a $(C_1\text{-}C_6)$alkyl-$NA_7C$(=O)—$(C_1$-$C_6)$alkyl group, a $(C_1\text{-}C_6)$alkyl-$NA_7C$(=O)—$(C_1\text{-}C_6)$alkyl-$(OCH_2CH_2)_i$ group, a $(C_1\text{-}C_6)$alkyl-C(=O)$NA_7$-$(C_1\text{-}C_6)$alkyl group, a $(C_1\text{-}C_6)$alkyl-C(=O)$NA_7$-$(C_1\text{-}C_6)$alkyl-$(OCH_2CH_2)_i$ group, a $(C_1\text{-}C_6)$alkyl-$NA_7$-$(C_1\text{-}C_6)$alkyl group, a $(C_1\text{-}C_6)$alkyl-$NA_7$-$(C_1\text{-}C_6)$alkyl-$(OCH_2CH_2)_i$ group, a $(C_1\text{-}C_6)$alkyl-$(OCH_2CH_2)_i$—$NA_7$-$(C_1\text{-}C_6)$alkyl group, a C(=O)—NA$_7$-(C$_1$-C$_6$)alkyl group, a C(=O)—(C$_1$-C$_6$)alkyl-NA$_7$ group, a C(=O)—NA$_7$-(CH$_2$CH$_2$O)$_i$(C$_1$-C$_6$)alkyl group, a C(=O)—NA$_7$-aryl group, a C(=O)—NA$_7$-heteroaryl group, a C(=O)—(C$_1$-C$_6$)alkyl-NA$_7$C(=O)—(C$_1$-C$_6$)alkyl group, a C(=O)—(C$_1$-C$_6$)alkyl-NA$_7$C(=O)—(C$_1$-C$_6$)alkyl-(OCH$_2$CH$_2$)$_i$ group, a C(=O)—(C$_1$-C$_6$)alkyl-C(=O)NA$_7$-(C$_1$-C$_6$)alkyl group, a C(=O)—(C$_1$-C$_6$)alkyl-C(=O)NA$_7$-(C$_1$-C$_6$)alkyl-(OCH$_2$CH$_2$)$_i$ group, a C(=O)—(C$_1$-C$_6$)alkyl-NA$_7$-(C$_1$-C$_6$)alkyl group, a C(=O)—(C$_1$-C$_6$)alkyl-NA$_7$-(C$_1$-C$_6$)alkyl-(OCH$_2$CH$_2$)$_i$ group, a NA$_8$-(C$_1$-C$_6$)alkyl-NA$_7$ group, a NA$_8$-(C$_1$-C$_6$)alkyl-NA$_7$C(=O)—(C$_1$-C$_6$)alkyl group, a NA$_8$-(C$_1$-C$_6$)alkyl-C(=O)NA$_7$-(C$_1$-C$_6$)alkyl group, a NA$_8$-(C$_1$-C$_6$)alkyl-NA$_7$-(C$_1$-C$_6$)alkyl group, a C(=O)—NA$_8$-(C$_1$-C$_6$)alkyl-NA$_7$ group, a C(=O)—NA-(C$_1$-C$_6$)alkyl-NA$_7$C(=O)—(C$_1$-C$_6$)alkyl group, a C(=O)—NA$_8$-(C$_1$-C$_6$)alkyl-C(=O)NA$_7$-(C$_1$-C$_6$)alkyl group, or a C(=O)—NA$_8$-(C$_1$-C$_6$)alkyl-NA$_7$-(C$_1$-C$_6$)alkyl group; wherein i, A$_7$ and A$_8$ are as defined above.

According to another embodiment, (AA)w contains at least one substituted amino acid AA$_s$ and/or w non-substituted amino acid AA$_{ns}$ and L2 represents:

a NA$_7$-(C$_1$-C$_6$)alkyl group, a (C$_1$-C$_6$)alkyl-NA$_7$ group, a NA$_7$-(CH$_2$CH$_2$O)$_i$(C$_1$-C$_6$)alkyl group, a (C$_1$-C$_6$)alkyl-NA$_7$C(=O)—(C$_1$-C$_6$)alkyl group, a (C$_1$-C$_6$)alkyl-NA$_7$C(=O)—(C$_1$-C$_6$)alkyl-(OCH$_2$CH$_2$)$_i$ group, a (C$_1$-C$_6$)alkyl-C(=O)NA$_7$-(C$_1$-C$_6$)alkyl group, a (C$_1$-C$_6$)alkyl-C(=O)NA$_7$-(C$_1$-C$_6$)alkyl-(OCH$_2$CH$_2$)$_i$ group, a (C$_1$-C$_6$)alkyl-NA$_7$-(C$_1$-C$_6$)alkyl group, a (C$_1$-C$_6$)alkyl-NA$_7$-(C$_1$-C$_6$)alkyl-(OCH$_2$CH$_2$)$_i$ group, a (C$_1$-C$_6$)alkyl-(OCH$_2$CH$_2$)$_i$-NA$_7$-(C$_1$-C$_6$)alkyl group, a C(=O)—NA$_7$-(C$_1$-C$_6$)alkyl group, a C(=O)—(C$_1$-C$_6$)alkyl-NA$_7$ group, a C(=O)—NA$_7$-(CH$_2$CH$_2$O)$_i$(C$_1$-C$_6$)alkyl group, a C(=O)—(C$_1$-C$_6$)alkyl-NA$_7$C(=O)—(C$_1$-C$_6$)alkyl group, a C(=O)—(C$_1$-C$_6$)alkyl-NA$_7$C(=O)—(C$_1$-C$_6$)alkyl-(OCH$_2$CH$_2$)$_i$ group, a C(=O)—(C$_1$-C$_6$)alkyl-C(=O)NA$_7$-(C$_1$-C$_6$)alkyl group, a C(=O)—(C$_1$-C$_6$)alkyl-C(=O)NA$_7$-(C$_1$-C$_6$)alkyl-(OCH$_2$CH$_2$)$_i$ group, a C(=O)—(C$_1$-C$_6$)alkyl-NA$_7$-(C$_1$-C$_6$)alkyl group, a C(=O)—(C$_1$-C$_6$)alkyl-NA$_7$-(C$_1$-C$_6$)alkyl-(OCH$_2$CH$_2$)$_i$ group, a NA$_8$-(C$_1$-C$_6$)alkyl-NA$_7$ group, a NA$_8$-(C$_1$-C$_6$)alkyl-NA$_7$C(=O)—(C$_1$-C$_6$)alkyl group, a NA$_8$-(C$_1$-C$_6$)alkyl-C(=O)NA$_7$-(C$_1$-C$_6$)alkyl group, a NA$_8$-(C$_1$-C$_6$)alkyl-NA$_7$-(C$_1$-C$_6$)alkyl group, a C(=O)—NA$_8$-(C$_1$-C$_6$)alkyl-NA$_7$ group, a C(=O)—NA$_8$-(C$_1$-C$_6$)alkyl-NA$_7$C(=O)—(C$_1$-C$_6$)alkyl group, a C(=O)—NA$_8$-(C$_1$-C$_6$)alkyl-C(=O)NA$_7$-(C$_1$-C$_6$)alkyl group, or a C(=O)—NA$_8$-(C$_1$-C$_6$)alkyl-NA$_7$-(C$_1$-C$_6$)alkyl group; wherein i, A$_7$ and A$_8$ are as defined above.

According to another embodiment, (AA)w contains at least one substituted amino acid AA$_s$ and/or w non-substituted amino acid AA$_{ns}$ and L2 represents:

a NA$_7$-(C$_1$-C$_6$)alkyl group, a (C$_1$-C$_6$)alkyl-NA$_7$ group, a (C$_1$-C$_6$)alkyl-NA$_7$C(=O)—(C$_1$-C$_6$)alkyl group, a (C$_1$-C$_6$)alkyl-C(=O)NA$_7$-(C$_1$-C$_6$)alkyl group, a (C$_1$-C$_6$)alkyl-NA$_7$-(C$_1$-C$_6$)alkyl group, a C(=O)—NA$_7$-(C$_1$-C$_6$)alkyl group, a C(=O)—(C$_1$-C$_6$)alkyl-NA$_7$ group, a C(=O)—(C$_1$-C$_6$)alkyl-NA$_7$C(=O)—(C$_1$-C$_6$)alkyl group, a C(=O)—(C$_1$-C$_6$)alkyl-C(=O)NA$_7$-(C$_1$-C$_6$)alkyl group, a C(=O)—(C$_1$-C$_6$)alkyl-NA$_7$-(C$_1$-C$_6$)alkyl group, a NA$_8$-(C$_1$-C$_6$)alkyl-NA$_7$ group, a NA$_8$-(C$_1$-C$_6$)alkyl-NA$_7$C(=O)—(C$_1$-C$_6$)alkyl group, a NA$_8$-(C$_1$-C$_6$)alkyl-C(=O)NA$_7$-(C$_1$-C$_6$)alkyl group, a NA$_8$-(C$_1$-C$_6$)alkyl-NA$_7$-(C$_1$-C$_6$)alkyl group, a C(=O)—NA$_8$-(C$_1$-C$_6$)alkyl-NA$_7$ group, a C(=O)—NA$_8$-(C$_1$-C$_6$)alkyl-NA$_7$C(=O)—(C$_1$-C$_6$)alkyl group, a C(=O)—NA$_8$-(C$_1$-C$_6$)alkyl-C(=O)NA$_7$-(C$_1$-C$_6$)alkyl group, or a C(=O)—NA$_8$-(C$_1$-C$_6$)alkyl-NA$_7$-(C$_1$-C$_6$)alkyl group; wherein A$_7$ and A$_8$ are as defined above.

According to at least another embodiment, (AA)w contains at least one substituted amino acid AA$_s$ and/or w non-substituted amino acid AA$_{ns}$ and L2 comprises a A$_7$ representing:

a C(=O)—[(CH$_2$)$_2$—O]$_4$—CH$_3$ group; a C(=O)—[(CH$_2$)$_2$—O]$_7$—CH$_3$ group; a C(=O)—[(CH$_2$)$_2$—O]$_{24}$—CH$_3$ group; a C(=O)—(CH$_2$)$_2$—C(=O)—NH—(CH$_2$)$_2$—SO$_3$H group; a C(=O)—(CH$_2$)$_2$—C(=O)—NH—[(CH$_2$)$_2$—O]$_4$—(CH$_2$)$_2$—C(=O)—NH—(CH$_2$)$_2$—SO$_3$H group; being understood that each A$_7$ comprising a SO$_3$H function can be under salt forms such as alkali metal salts, for instance sodium salts (SO$_3^-$ $^+$Na).

According to at least another embodiment, (AA)w contains at least one substituted amino acid AA$_s$ and/or w non-substituted amino acid AA$_{ns}$ and L2 represents:

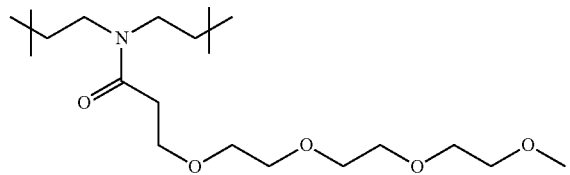

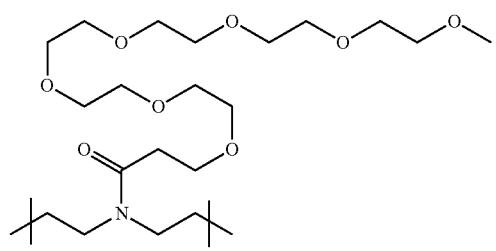

-continued

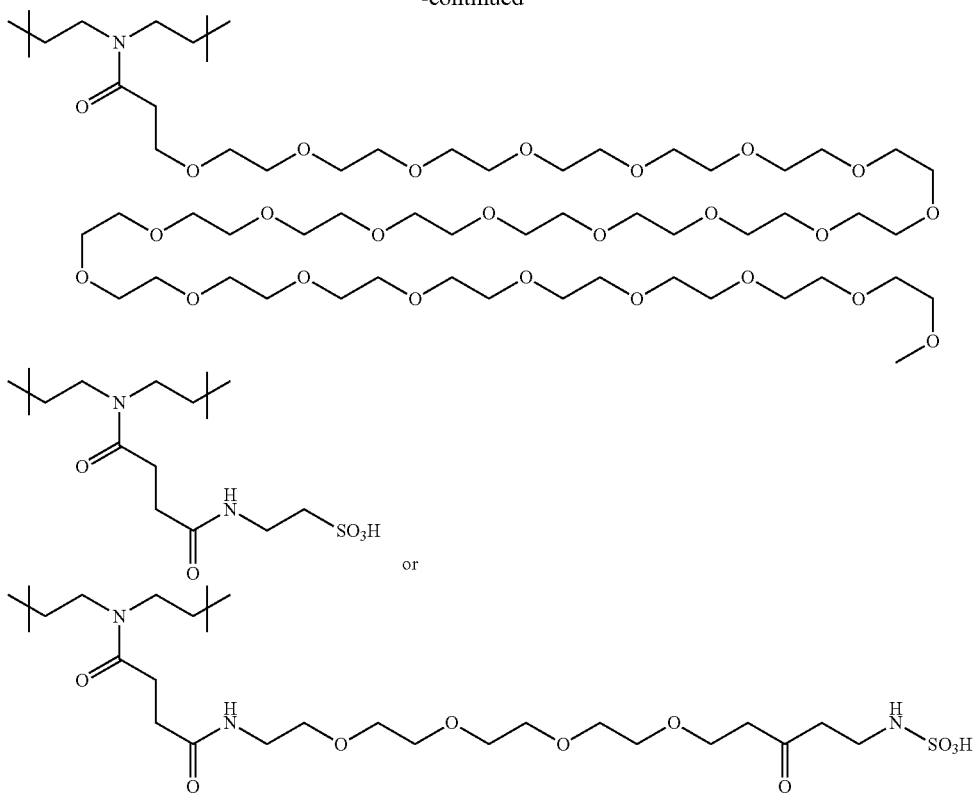

L1 may be one of the following (III1-5):

| P | Examples of L1 | |
|---|---|---|
| H | -NA$_6$-ALK-NA$_7$- | (III1) |
| | ![structure] -NA$_4$ with J$_1$,J$_2$,J$_3$,J$_4$ ring, A$_2$,A$_3$, -O-C(=O)-NA$_6$-ALK-NA$_5$- | (III2) |
| OH | — | (III3) |
| activated O | ![structure] -NA$_4$ with J ring, A$_2$,A$_3$, -O-C(=O)-CH$_3$ | (III4) |
| | ![structure] -NA$_4$ with J ring, A$_2$,A$_3$, -O-C(=O)-NA$_6$-ALK-NA$_5$-C(=O)- | (III5) | wherein:
- J$_1$, J$_2$, J$_3$ and J$_4$ are chosen, independently of each other, from CA$_1$ and N;
- ALK represents a (C$_1$-C$_{12}$)alkylene group, for instance (C$_1$-C$_6$)alkylene, such as of the form —(CH$_2$)$_n$—, n being an integer ranging from 1 to 12 and for example ranging from 1 to 6;
- A$_1$, A$_2$, A$_3$, A$_4$, A$_5$, and A$_6$ represent, independently of each other, a hydrogen atom or a (C$_1$-C$_6$)alkyl group, such as a hydrogen atom or a methyl group.

AA denotes an amino acid. An amino acid is a compound of formula NH$_2$—CHA$_{10}$-COOH wherein A$_{10}$ represents the side chain of the AA. AA can be a substituted AA$_s$ or non-substituted AA$_{ns}$ amino acid.

A non-substituted amino acid AA$_{ns}$ denotes natural or non-natural amino acid, of configuration D or L, identical to or derived from: alanine (Ala), β-alanine, γ-aminobutyric acid, 2-amino-2-cyclohexylacetic acid, 2-amino-2-phenylacetic acid, arginine (Arg), asparagine (Asn), aspartic acid (Asp), citrulline (Cit), cysteine (Cys), α,α-dimethyl-γ-aminobutyric acid, β,β-dimethyl-γ-aminobutyric acid, glutamine (Gln), glutamic acid (Glu), glycine (Gly), homocysteine, selenocysteine, homo-selenocysteine, histidine (His), isoleucine (Ile), leucine (Leu), lysine (Lys), ε-acetyl-lysine (AcLys), methionine (Met), ornithine (Orn), phenylalanine (Phe), proline (Pro), serine (Ser), threonine (Thr), tryptophan (Trp), tyrosine (Tyr), and valine (Val).

For example, AA$_{ns}$ represents alanine (Ala), citrulline (Cit), glycine (Gly), isoleucine (Ile), leucine (Leu), lysine (Lys), ε-acetyl-lysine (AcLys), phenylalanine (Phe), tryptophan (Trp) and valine (Val).

The substituted amino acids AA$_s$ have the formula (VI):

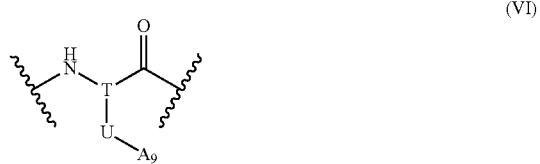

(VI)

wherein:
T represents a saturated or unsaturated, linear or branched, $(C_1\text{-}C_8)$ trivalent alkyl group, for instance T is

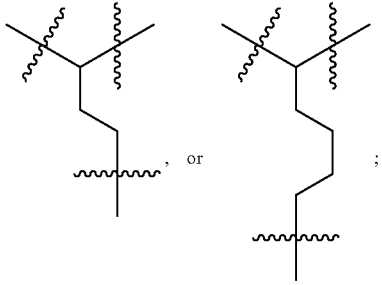 [SMILES: *CCC(*)* ; *CCCCC(*)*]

, or

U group represents a single bond, —NHC(=O)—, —N(alkyl)C(=O)—, —C(=O)NH—, —C(=O)N(alkyl)-, —NHC(=O)NH—, —NHC(=NH)NH—, —OC(=O)—, —C(=O)O—, —OC(=O)O—, —S—, —Se—, —O—, —NH—, —N(alkyl)-, —C(=O)—, —OP(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, or —O—P(=O)(OH)—O, such as U group represents —NH—C(=O)—, or —C(=O)NH—;

$A_9$ represents a straight or branched, saturated or unsaturated, optionally substituted $C_1\text{-}C_{160}$ hydrocarbon chain wherein optionally at least one methylene unit is independently replaced by —NH—C(=O)—, —N(alkyl)C(=O)—, —C(=O)NH—, —C(=O)N(alkyl)-, —NHC(=O)NH—, —NHC(=NH)NH—, —OC(=O)—, —C(=O)O—, —OC(=O)O—, —CH(OH)—, —CH(SO$_3$H)—, —CH(Oalkyl)-, —CHF—, —CF$_2$—, —S—, —Se—, —O—, —NH—, —N(alkyl)-, —N$^+$H(alkyl)-, —N$^+$(alkyl)$_2$-, —C(=O)—, —OP(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —NH$_2$, —NHalkyl, and —N(alkyl)$_2$, for instance $A_9$ is [(CH$_2$)$_2$—O]$_4$—CH$_3$, [(CH$_2$)$_2$—O]$_{24}$—CH$_3$,

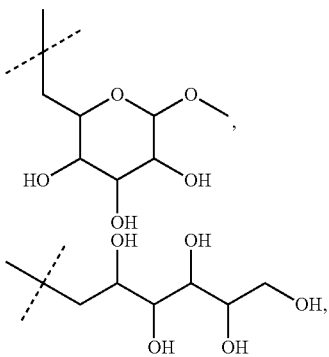

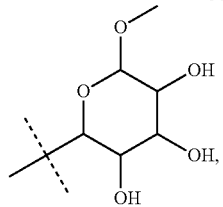

or [(CH$_2$)$_2$—O]$_4$—(CH$_2$)$_2$—C(=O)—NH—(CH$_2$)$_2$—SO$_3$H;

being understood that each $A_9$ comprising a SO$_3$H function can be under salt forms such as alkali metal salts, for instance sodium salts (SO$_3^-$ $^+$Na).

According to a particular embodiment, the substituted amino acids $AA_s$ have the formula (VI):

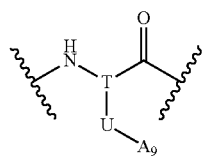

(VI)

wherein:
T represents a saturated or unsaturated, linear or branched, $(C_1\text{-}C_8)$ trivalent alkyl group, for instance T is

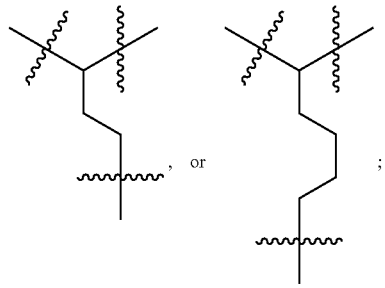 [SMILES: *CCC(*)* ; *CCCCC(*)*]

, or

U group represents a single bond, —NHC(=O)—, —N(alkyl)C(=O)—, —C(=O)NH—, —C(=O)N(alkyl)-, —NHC(=O)NH—, —NHC(=NH)NH—, —OC(=O)—, —C(=O)O—, —OC(=O)O—, —S—, —Se—, —O—, —NH—, —N(alkyl)-, —C(=O)—, —OP(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, or —O—P(=O)(OH)—O, such as U group represents —NH—C(=O)—, or —C(=O)NH—;

$A_9$ represents a straight or branched, saturated or unsaturated, optionally substituted $C_1\text{-}C_{160}$ hydrocarbon chain wherein optionally at least one methylene unit is independently replaced by —NH—C(=O)—, —N(alkyl)C(=O)—, —C(=O)NH—, —C(=O)N(alkyl)-, —NHC(=NH)NH—, —OC(=O)—, —C(=O)O—, —OC(=O)O—, —CH(OH)—, —CH(SO$_3$H)—, —CH(Oalkyl)-, —CHF—, —CF$_2$—, —S—, —Se—, —O—, —NH—, —N(alkyl)-, —N$^+$H(alkyl)-, —N$^+$(alkyl)$_2$-, —C(=O)—, —OP(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —NH$_2$, —NHalkyl, and —N(alkyl)$_2$, for instance A$_9$ is [(CH$_2$)$_2$—O]$_4$—CH$_3$, [(CH$_2$)$_2$—O]$_{24}$—CH$_3$,

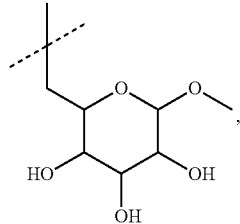

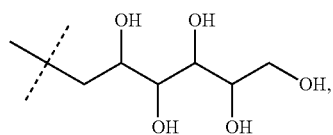

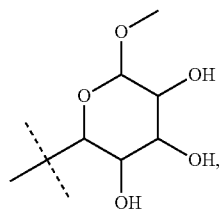

or [(CH$_2$)$_2$—O)]$_4$—(CH$_2$)$_2$—C(=O)—NH—(CH$_2$)$_2$—SO$_3$H;

being understood that each A$_9$ comprising a SO$_3$H function can be under salt forms such as alkali metal salts, for instance sodium salts (SO$_3^-$ $^+$Na).

According to another particular embodiment, the substituted amino acids AA$_s$ have the formula (VI):

(VI)

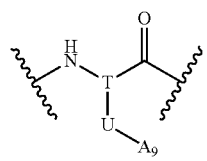

wherein:

T represents a saturated or unsaturated, linear or branched, (C$_1$-C$_8$) trivalent alkyl group, for instance T is

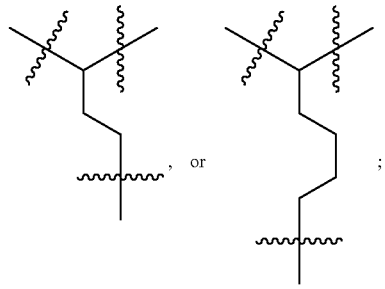 [SMILES: *CCC(*)* ; *CCCCC(*)*]

U group represents a single bond, —NHC(=O)—, —N(alkyl)C(=O)—, —C(=O)NH—, —C(=O)N(alkyl)-, —NHC(=O)NH—, —NHC(=NH)NH—, —OC(=O)—, —C(=O)O—, —OC(=O)O—, —S—, —Se—, —O—, —NH—, —N(alkyl)-, —C(=O)—, —OP(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, or —O—P(=O)(OH)—O, such as U group represents —NH—C(=O)—, or —C(=O)NH—;

A$_9$ represents a straight or branched, saturated or unsaturated, optionally substituted C$_1$-C$_{160}$ hydrocarbon chain wherein optionally at least one methylene unit is independently replaced by —NH—C(=O)—, —N(alkyl)C(=O)—, —C(=O)NH—, —C(=O)N(alkyl)-, —NHC(=NH)NH—, —OC(=O)—, —C(=O)O—, —OC(=O)O—, —CH(OH)—, —CH(SO$_3$H)—, —CH(Oalkyl)-, —CHF—, —CF$_2$—, —S—, —Se—, —O—, —N(alkyl)-, —N$^+$H(alkyl)-, —N$^+$(alkyl)$_2$-, —OP(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —NH$_2$, —NHalkyl, and —N(alkyl)$_2$, for instance A$_9$ is [(CH$_2$)$_2$—O]$_4$—CH$_3$, [(CH$_2$)$_2$—O]$_{24}$—CH$_3$,

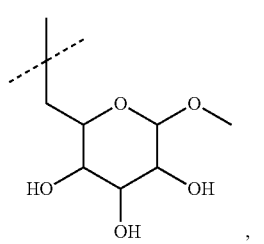

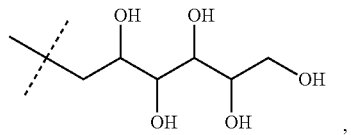

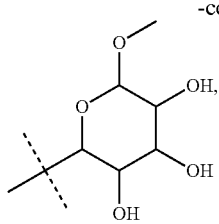

or [(CH$_2$)$_2$—O)]$_4$—(CH$_2$)$_2$—C(=O)—NH—(CH$_2$)$_2$—SO$_3$H;

being understood that each A$_9$ comprising a SO$_3$H function can be under salt forms such as alkali metal salts, for instance sodium salts (SO$_3^-$ $^+$Na).

According to another particular embodiment, the substituted amino acids AA$_s$ have the formula (VI):

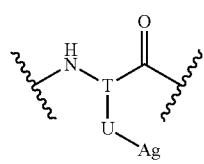

(VI)

wherein:

T represents a saturated or unsaturated, linear or branched, (C$_1$-C$_8$) trivalent alkyl group, for instance T is

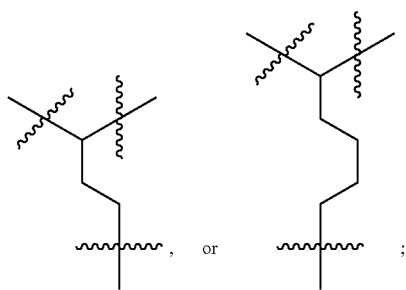 [SMILES: *CCC(*)* ; *CCCCC(*)*]

U group represents a single bond, —NHC(=O)—, —N(alkyl)C(=O)—, —C(=O)NH—, —C(=O)N(alkyl)-, —NHC(=O)NH—, —NHC(=NH)NH—, —OC(=O)—, —C(=O)O—, —OC(=O)O—, —S—, —Se—, —O—, —NH—, —N(alkyl)-, —C(=O)—, —OP(=O)—, —S(=O)—, —S(=O)$_2$—, —NHS(=O)$_2$—, —N(alkyl)S(=O)$_2$—, —S(=O)$_2$NH—, —S(=O)$_2$N(alkyl)-, —P(=O)(OH)—, —P(=O)(OH)O—, —O—P(=O)(OH)—, or —O—P(=O)(OH)—O, such as U group represents —NH—C(=O)—, or —C(=O)NH—;

A$_9$ represents a straight or branched, saturated or unsaturated, optionally substituted C$_1$-C$_{160}$ hydrocarbon chain wherein optionally at least one methylene unit is independently replaced by —NH—C(=O)—, —N(alkyl)C(=O)—, —C(=O)NH—, —C(=O)N(alkyl)-, —C(=O)O—, —OC(=O)O—, —CH(OH)—, —CH(SO$_3$H)—, —CH(Oalkyl)-, —CHF—, —CF$_2$—, —Se—, —O—, —N(alkyl)-, —N$^+$H(alkyl)-, —N$^+$(alkyl)$_2$-, —OP(=O)—, —S(=O)—, —S(=O)$_2$—, —NHS(=O)$_2$—, —N(alkyl)S(=O)$_2$—,
—S(=O)$_2$NH—, —S(=O)$_2$N(alkyl)-, —P(=O)(OH)—, —P(=O)(OH)O—, —O—P(=O)(OH)—, —O—P(=O)(OH)—O— or a heterocycloalkyl group optionally substituted with at least one substituent, identical or different, chosen from —OH, —Oalkyl, -alkyl, a halogen atom, —NH$_2$, —NHalkyl, and —N(alkyl)$_2$, for instance A$_9$ is [(CH$_2$)$_2$—O]$_4$—CH$_3$, [(CH$_2$)$_2$—O]$_{24}$—CH$_3$,

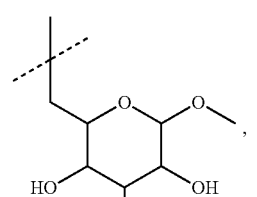

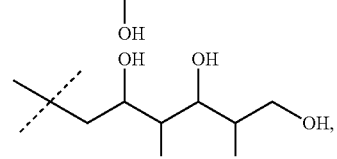

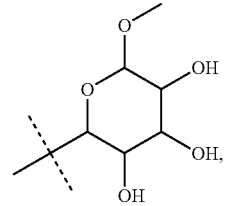

or [(CH$_2$)$_2$—O)]$_4$—(CH$_2$)$_2$—C(=O)—NH—(CH$_2$)$_2$—SO$_3$H;

being understood that each A$_9$ comprising a SO$_3$H function can be under salt forms such as alkali metal salts, for instance sodium salts (SO$_3^-$ $^+$Na).

Examples of T that may be mentioned include:

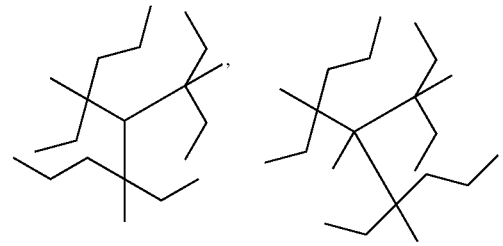

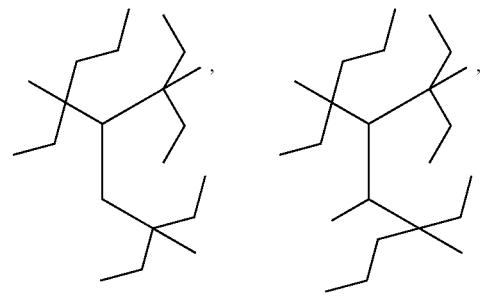

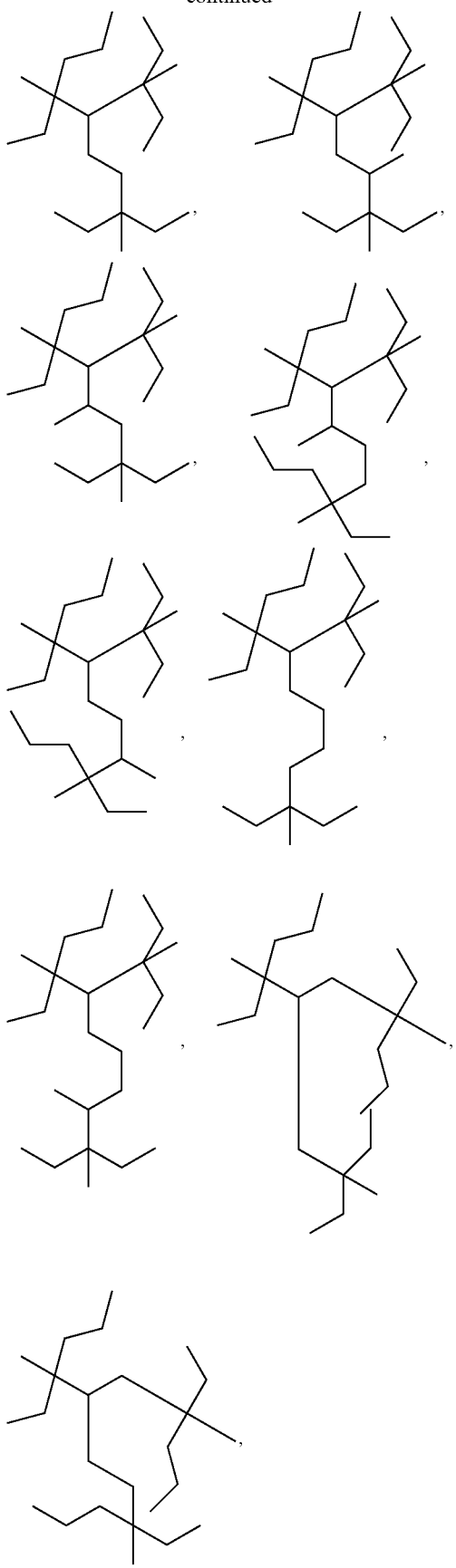

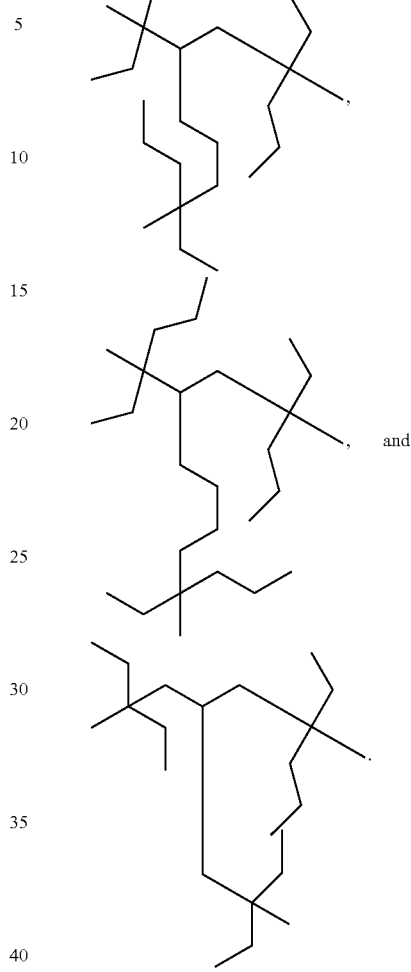

According at least one embodiment, the substituted amino acids $AA_s$ have the formula (VI) wherein:

T represents a saturated or unsaturated, linear or branched, $(C_1-C_8)$ trivalent alkyl group, such as

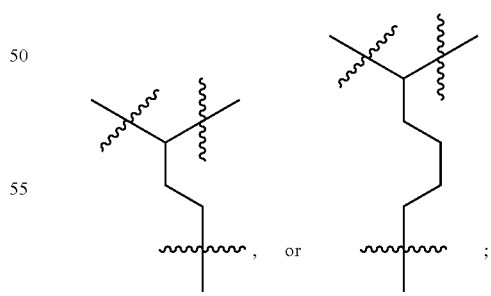

U group represents —NH—C(=O)—, or —C(=O)NH—;

$A_9$ represents a straight or branched, saturated or unsaturated, optionally substituted $C_1-C_{160}$ hydrocarbon chain wherein optionally at least one methylene unit is independently replaced by —C(=O)NH—, —CH(OH)—, —CH(SO$_3$H)—, —O—, —NH—, or —C(=O)—, or a heterocycloalkyl group optionally substituted with at least one substituent, identical or different, chosen from —OH, —Oalkyl, -alkyl, such as $A_9$ is $[(CH_2)_2—O]_4—CH_3$, $[(CH_2)_2—O)]_{24}—CH_3$,

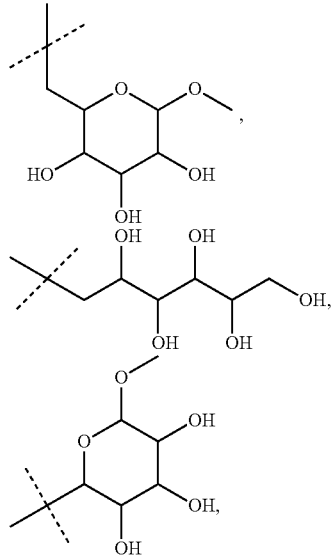

or $[(CH_2)_2—O]_4—(CH_2)_2—C(=O)—NH—(CH_2)_2—SO_3H$;

being understood that each $A_9$ comprising a $SO_3H$ function can be under salt forms such as alkali metal salts, for instance sodium salts ($SO_3^-$ $^+Na$).

According to another embodiment, the substituted amino acids $AA_s$ have the formula (VI) wherein:

T represents

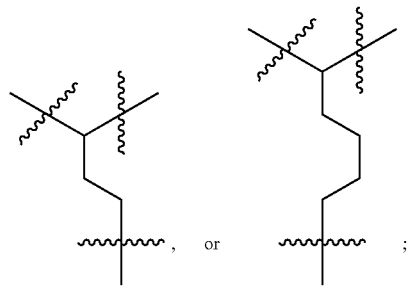 [SMILES: *CCC(*)* ; *CCCCC(*)*]

U group represents —NH—C(=O)—, or —C(=O)NH—;

$A_9$ represents $[(CH_2)_2—O]_4—CH_3$, $[(CH_2)_2—O]_{24}—CH_3$,

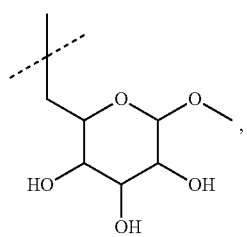

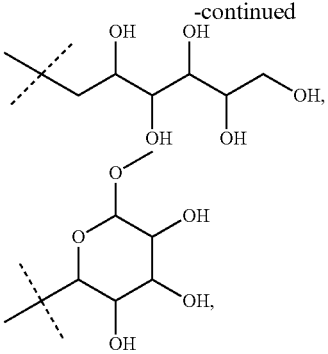

or $[(CH_2)_2—O]_4—(CH_2)_2—C(=O)—NH—(CH_2)_2—SO_3H$;

being understood that each $A_9$ comprising a $SO_3H$ function can be under salt forms such as alkali metal salts, for instance sodium salts ($SO_3^-$ $^+Na$).

According to a yet another embodiment, the substituted amino acids $AA_s$ have the formula (VI) wherein:

T represents

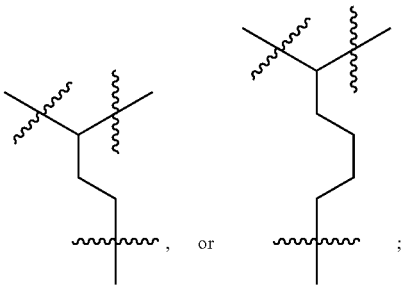 [SMILES: *CCC(*)* ; *CCCCC(*)*]

U group represents —NH—C(=O)—, or —C(=O)NH—;

$A_9$ represents —$[(CH_2)_2—O]_b—CH_3$ wherein "b" represents an integer ranging from 1 to 50, for instance ranging from 1 to 24, such as 4, 7 and 24, for example 4 or 24.

The sequence $(AA)_w$ has the formula:

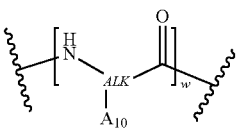

in which $A_{10}$ represents the side chain of one of the substituted $AA_s$ or non-substituted $AA_{ns}$ amino acids described above.

Examples of sequences of non-substituted amino acids $(AA_{ns})w$ are as follows: Gly-Gly, Phe-Lys, Val-Lys, Val-AcLys, Val-Cit, Phe-Phe-Lys, D-Phe-Phe-Lys, Gly-Phe-Lys, Ala-Lys, Val-Ala, Phe-Cit, Phe-Gly, Leu-Cit, Ile-Cit, Trp-Cit, Phe-Ala, Ala-Phe, Gly-Gly-Gly, Gly-Ala-Phe, Gly-Phe-Gly, Gly-Val-Cit, Gly-Phe-Leu-Cit (SEQ ID No. 3), Gly-Phe-Leu-Gly (SEQ ID No. 4), Ala-Leu-Ala-Leu (SEQ ID No. 5).

According to at least one embodiment, the sequence $(AA_{ns})_w$ of non-substituted amino acids $AA_{ns}$ is selected from the following list: Gly-Gly, Phe-Lys, Val-Lys, Val-AcLys, Val-Cit, Phe-Phe-Lys, D-Phe-Phe-Lys, Gly-Phe-Lys, Ala-Lys, Val-Ala, Phe-Cit, Phe-Gly, Leu-Cit, Ile-Cit, Trp-Cit, Phe-Ala, Ala-Phe, Gly-Gly-Gly, Gly-Ala-Phe, Gly-Phe-Gly, Gly-Val-Cit, Gly-Phe-Leu-Cit (SEQ ID No. 3), Gly-Phe-Leu-Gly (SEQ ID No. 4), and Ala-Leu-Ala-Leu (SEQ ID No. 5), such as Val-Ala and Val-Cit, for instance Val-Ala.

According to at least another embodiment, the sequence $(AA_s)_w$ containing at least one substituted amino acid $AA_s$ is selected from the list:

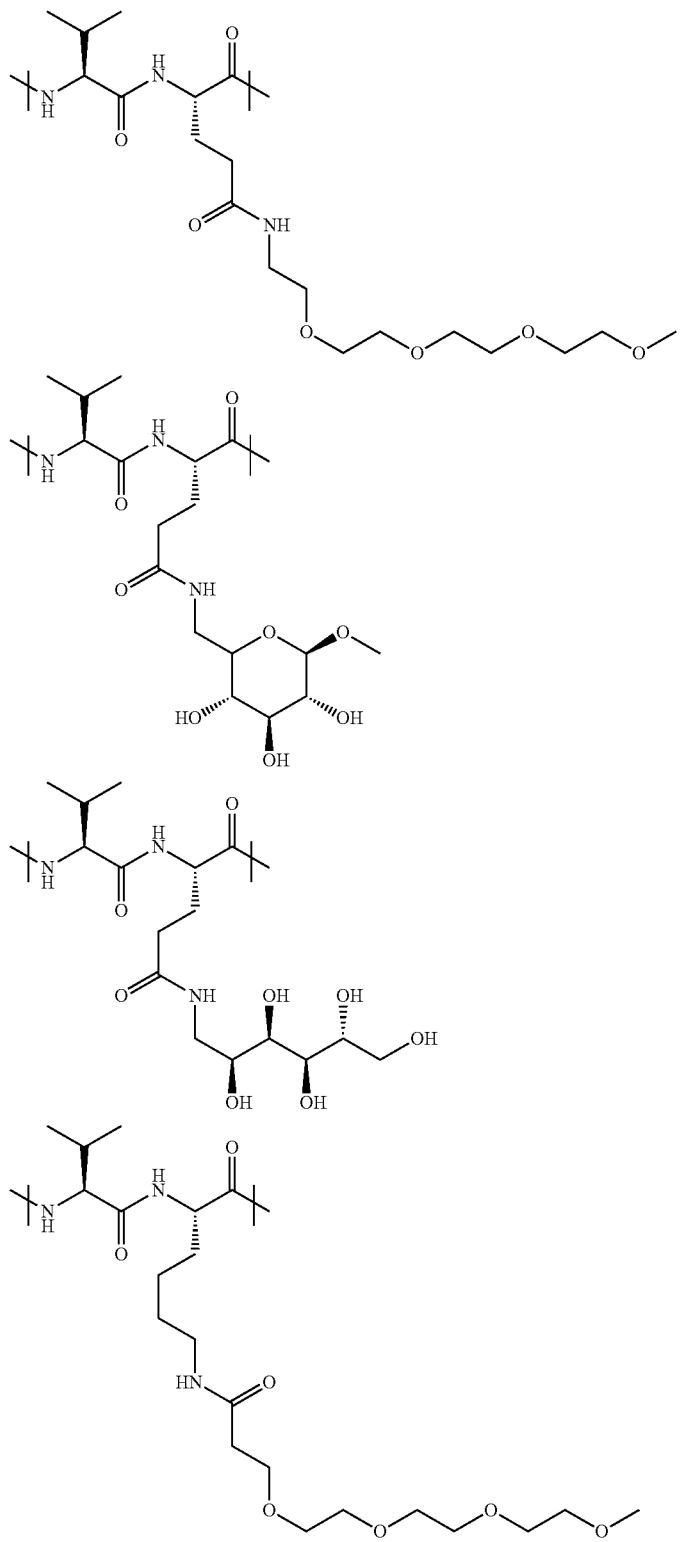

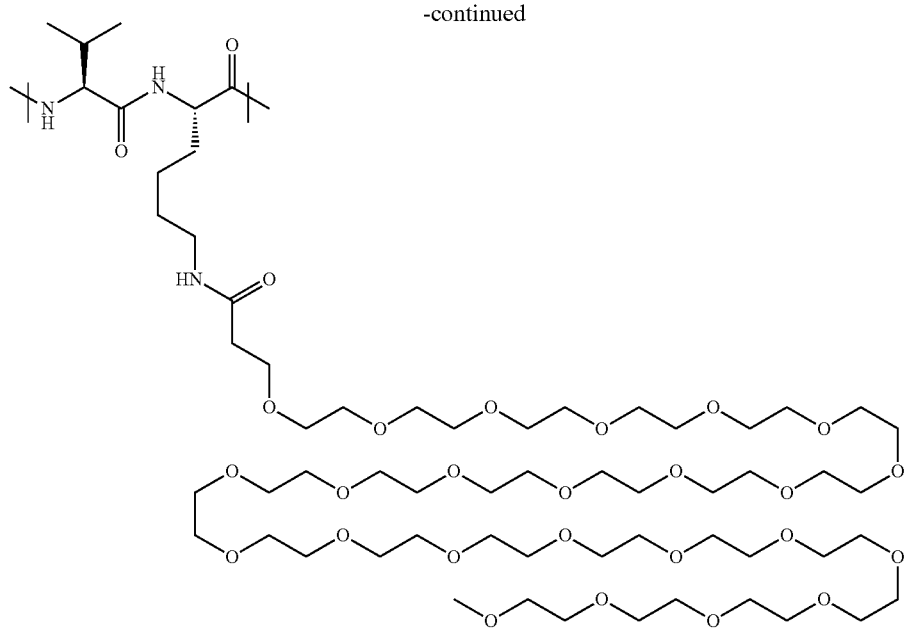
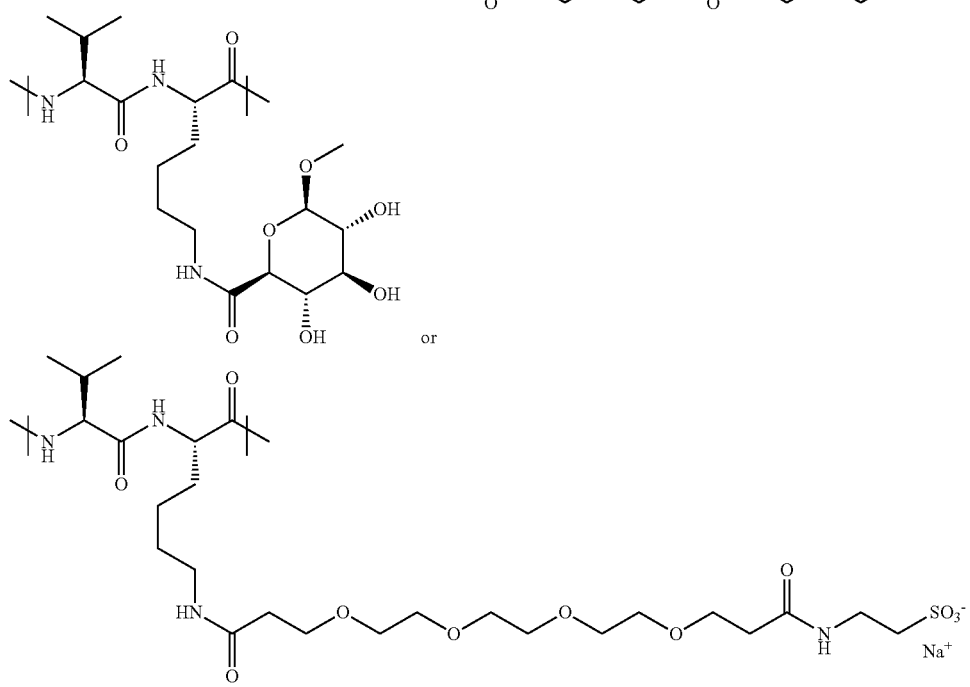
Among the linkers L of formula (II) that are the subject matter of the disclosure, mention may be made for example of the following compounds:
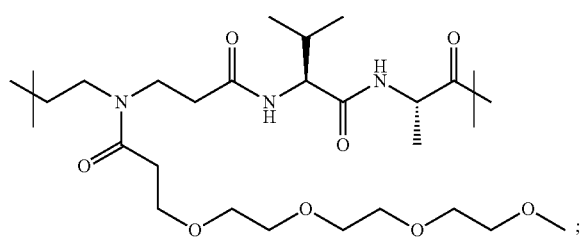

-continued
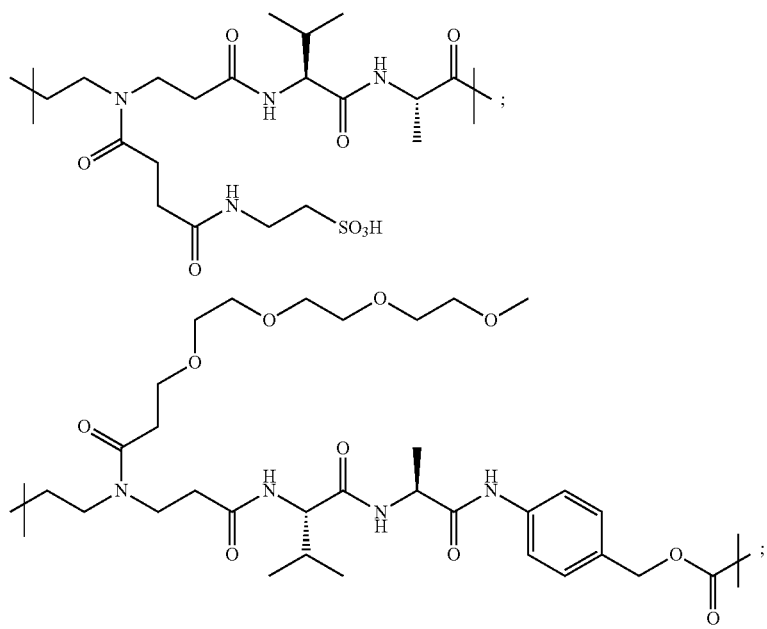
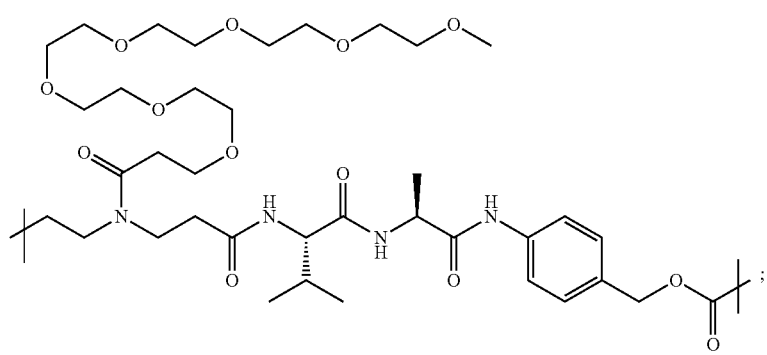
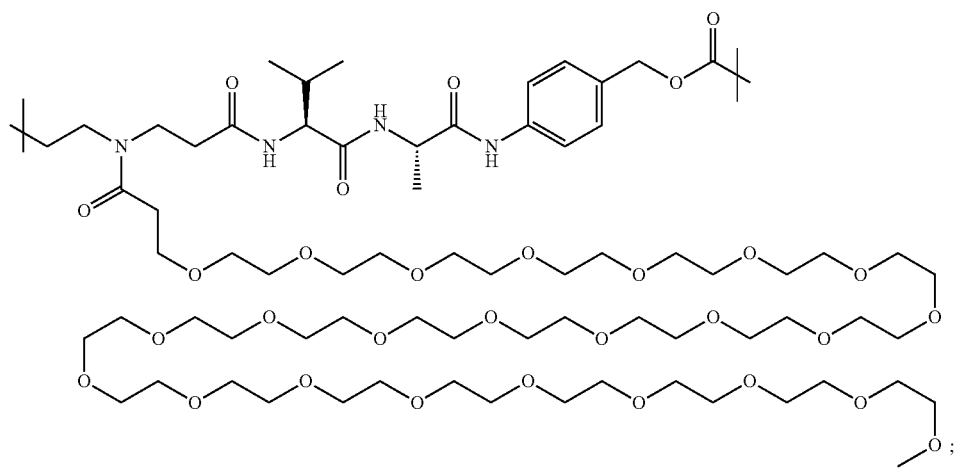

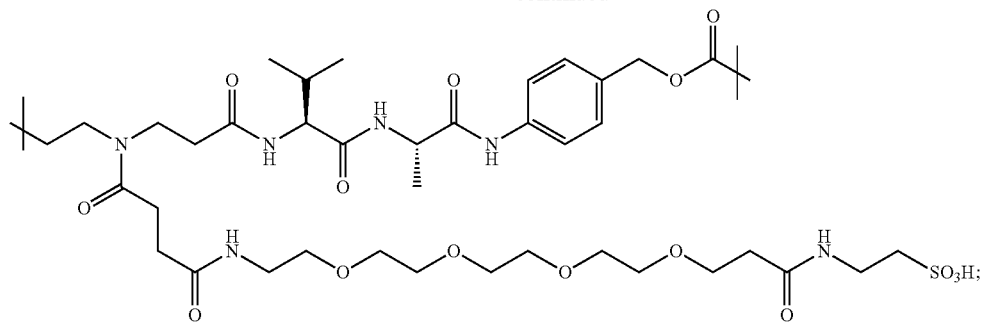
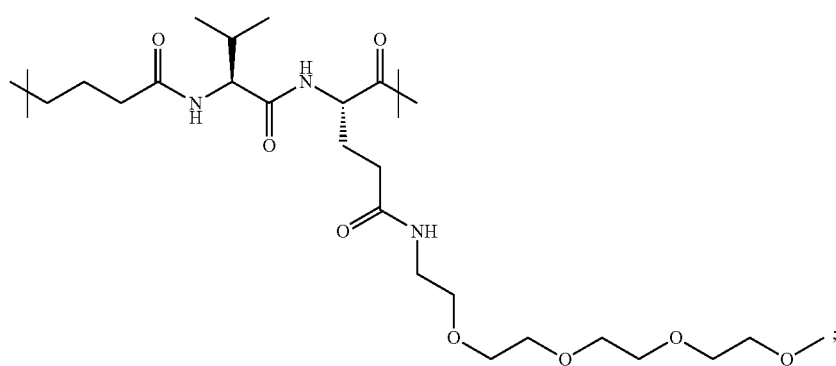
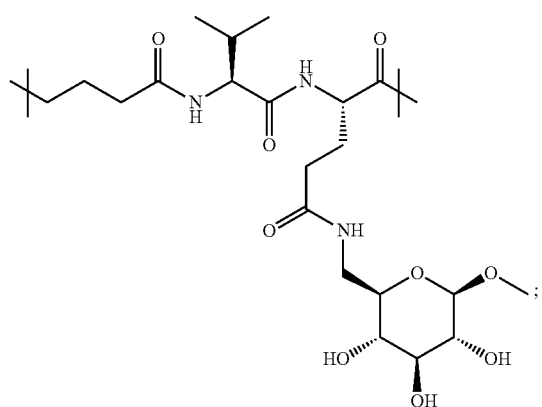
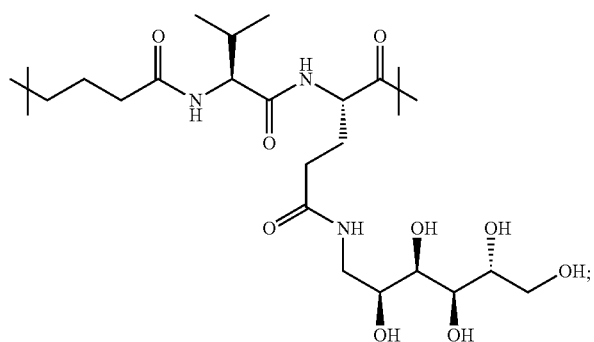

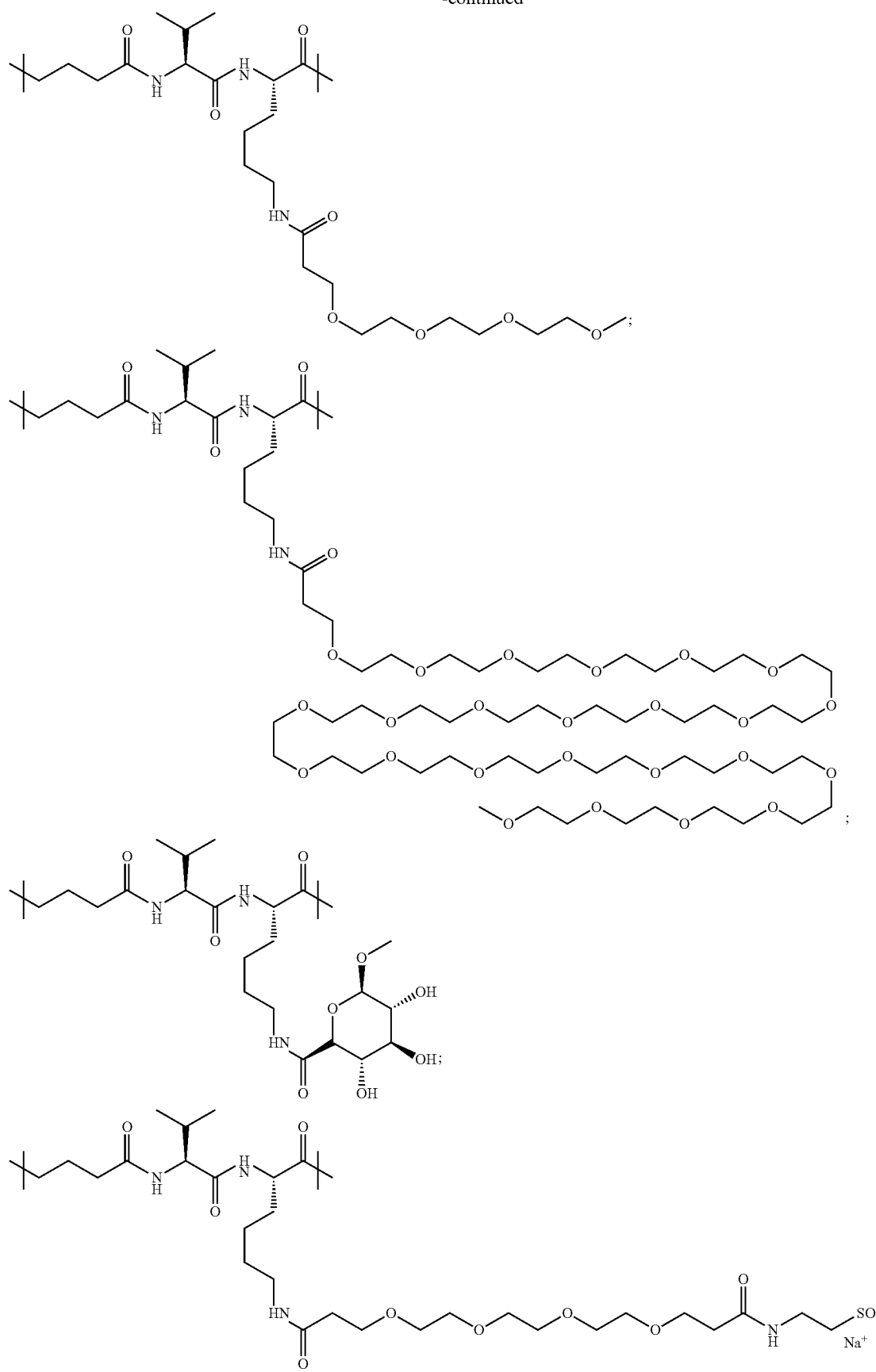

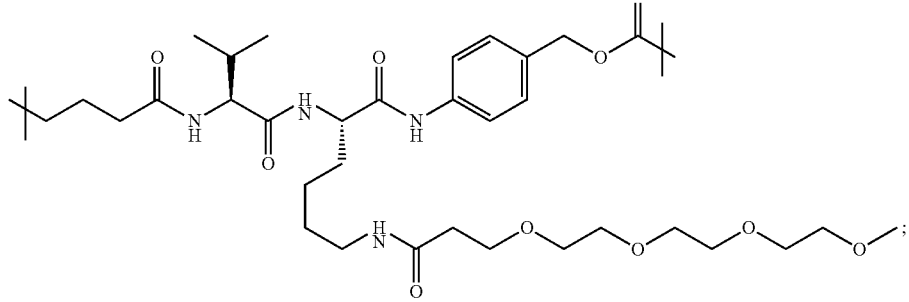
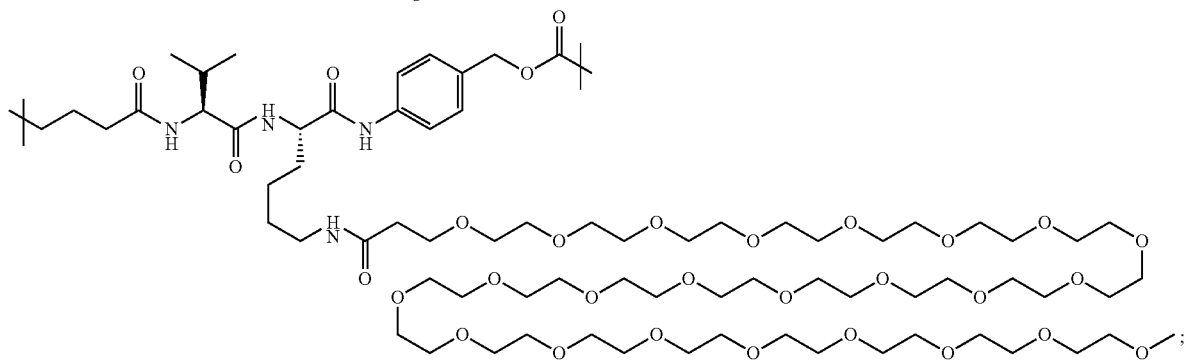
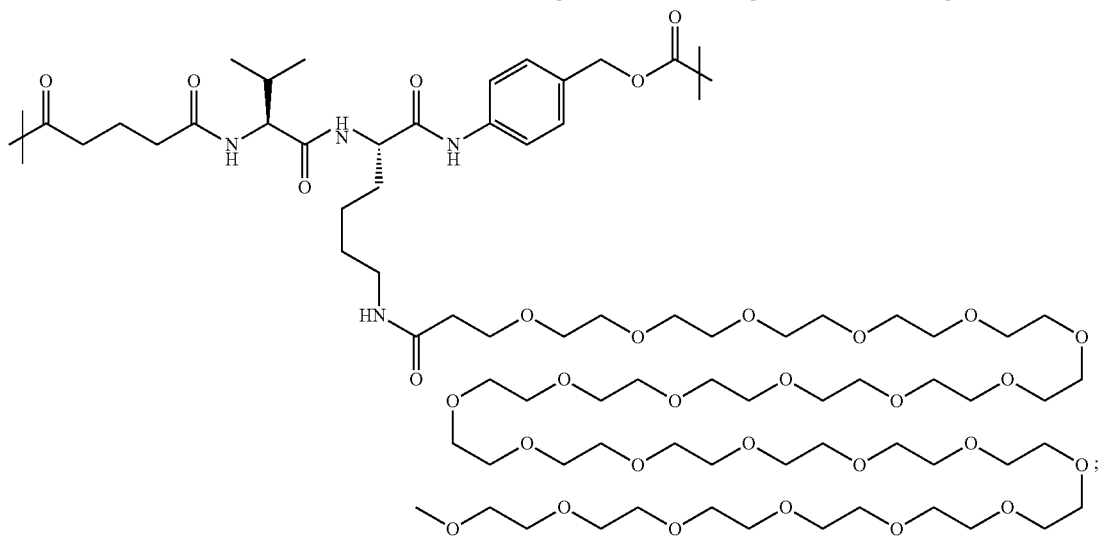
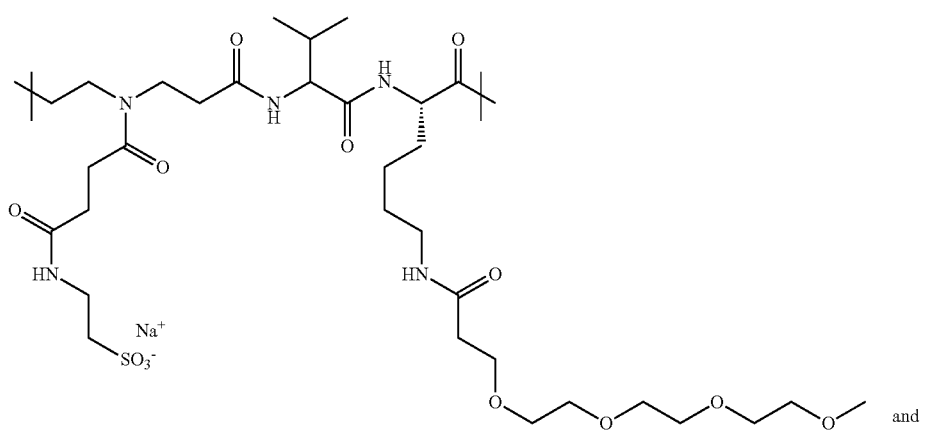

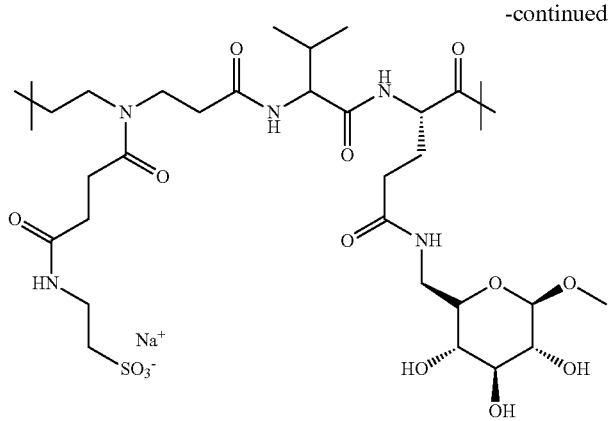

Examples of RCG1 that may be mentioned include:

(i) a $R_aZ_a$—C(=O)— reactive group for which:

$Z_a$ represents a single bond, —O— or —NH, such as —O—, and $R_a$ represents a hydrogen atom, a ($C_1$-$C_6$)alkyl, a ($C_3$-$C_7$) cycloalkyl, an alkenyl, an aryl, a heteroaryl or a ($C_3$-$C_7$)heterocycloalkyl group. The aryl group, the heteroaryl group and/or the ($C_3$-$C_7$)heterocycloalkyl group may be substituted by 1 to 5 atoms/groups chosen from a halogen atom, such as a fluorine atom, an alkyl group, an alkoxy group, a hydroxyl group, an oxo group, a nitro group and a cyano group;

(ii) one of the following reactive groups: a maleimido

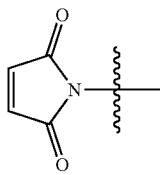

group; a haloacetamido Cl, Br or

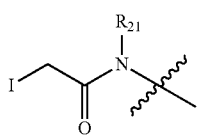

group with $R_{21}$ representing a hydrogen atom or a ($C_1$-$C_6$) alkyl group, such as Me; Cl—; $N_3$—; HO—; HS—; an activated disulfide such as H or

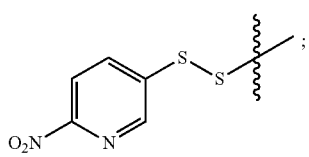 [SMILES: *SSc1ccc([N+](=O)[O-])nc1]

$H_2N$—; HC≡C— or an activated C≡C such as a cyclooctyne moiety for instance a DBCO-amine

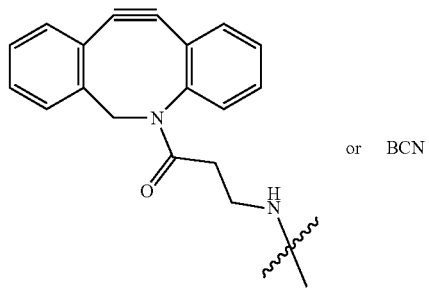

or BCN

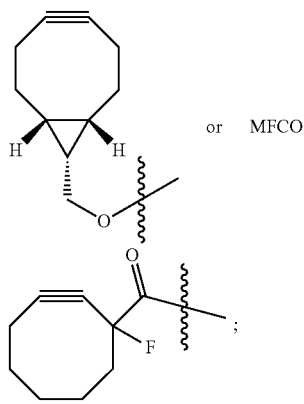

or MFCO an O-alkyl hydroxylamine or a Pictet-Spengler reaction substrate such as

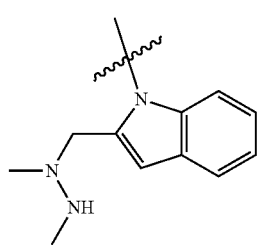 [SMILES: *n1c(CN(C)NC)cc2ccccc21]

described in Agarwal P., et al., *Bioconjugate Chem* 2013, 24, 846-851.

According to a particular embodiment, RCG1 may be:

(i) a $R_aZ_a$—C(=O)— reactive group for which:

$Z_a$ represents a single bond, —O— or —NH, such as —O—, and $R_a$ represents a hydrogen atom, a $(C_1-C_6)$alkyl, a $(C_3-C_7)$cycloalkyl, an alkenyl, an aryl, a heteroaryl or a $(C_3-C_7)$heterocycloalkyl group. The aryl group, the heteroaryl group and/or the $(C_3-C_7)$heterocycloalkyl group may be substituted by 1 to 5 atoms/groups chosen from a halogen atom, such as a fluorine atom, an alkyl group, an alkoxy group, a hydroxyl group, an oxo group, a nitro group and a cyano group;

(ii) one of the following reactive groups: a haloacetamido

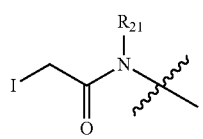

Cl, Br or

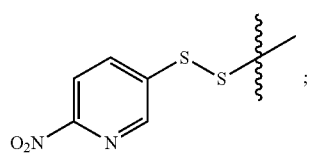

group with $R_{21}$ representing a hydrogen atom or a $(C_1-C_6)$ alkyl group, such as Me; Cl—; $N_3$—; HO—; HS—; an activated disulfide such as H or

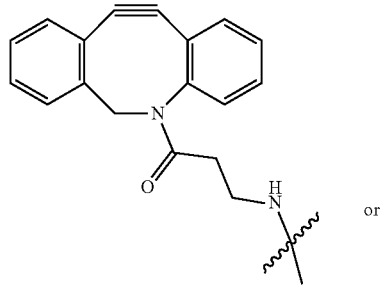

$H_2N$—; HC≡C— or an activated C≡C such as a cyclooctyne moiety for instance a DBCO-amine

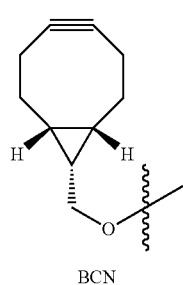 or 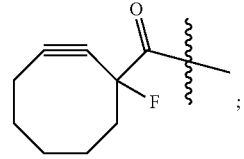

BCN                                    MFCO an O-alkyl hydroxylamine or a Pictet-Spengler reaction substrate such as

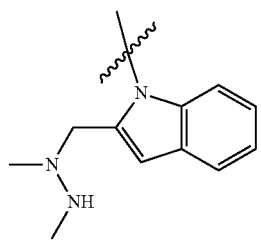 [SMILES: *n1c(CN(C)NC)cc2ccccc21]

described in Agarwal P., et al., *Bioconjugate Chem* 2013, 24, 846-851.

For instance, $R_aZ_a$— may represent HO—, $CH_3O$—, $CH_2=CH-CH_2O$—,

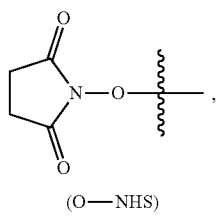

(O—NHS)

M = H or cation where cation represents for example sodium, potassium or cesium or,

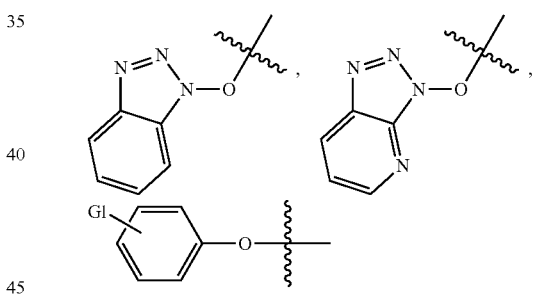

group in which GI represents at least one electroinductive group such as —$NO_2$ or a halogen atom, such as a fluorine atom (F). They may be, for example, the following groups:

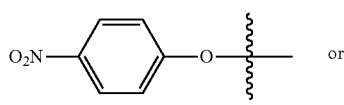 or

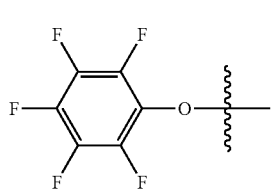

Another type of $R_aZ_a$—C(=O)— group is the following:

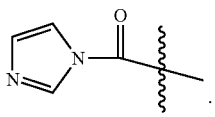 [SMILES: *C(=O)n1ccnc1]

For instance, RCG1 may be chosen from one of those described in the examples that is to say chosen from the following groups:

COOH,

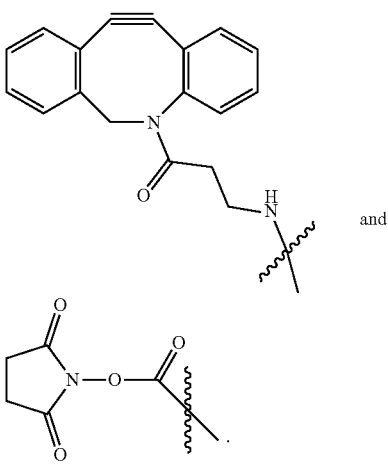

and

The present disclosure further relates to cryptophycin payloads of formula (IV):

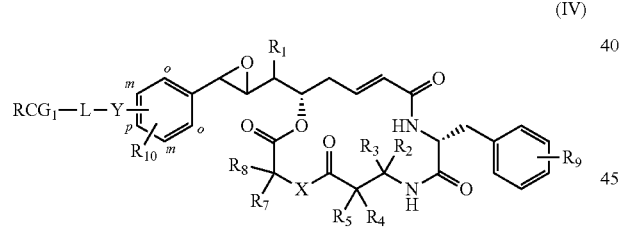

wherein:

$R_1$ represents a $(C_1-C_6)$alkyl group, $R_2$ and $R_3$ represent, independently of each other, a hydrogen atom or a $(C_1-C_6)$alkyl group;

or alternatively $R_2$ and $R_3$ form together with the carbon atom to which they are attached a $(C_3-C_6)$cycloalkyl or a $(C_3-C_6)$heterocycloalkyl group;

$R_4$ and $R_5$ represent, independently of each other, a hydrogen atom or a $(C_1-C_6)$alkyl group or a $(C_1-C_6)$alkyl-NH($R_{12}$) group or a $(C_1-C_6)$alkyl-OH group or a $(C_1-C_6)$alkyl-SH group or a $(C_1-C_6)$alkyl-C(=O)$_2$H group;

or alternatively $R_4$ and $R_5$ form together with the carbon atom to which they are attached a $(C_3-C_6)$cycloalkyl or a $(C_3-C_6)$heterocycloalkyl group;

X represents O or N($R_6$);

$R_6$ represents a hydrogen atom or a $(C_1-C_6)$alkyl group;

$R_7$ and $R_8$ represent, independently of each other, a hydrogen atom or a $(C_1-C_6)$alkyl group or a $(C_1-C_6)$alkyl-C(=O)$_2$H group or a $(C_1-C_6)$alkyl-N$(C_1-C_6)$alkyl$_2$ group;

or alternatively $R_7$ and $R_8$ form together with the carbon atom to which they are attached a $(C_3-C_6)$cycloalkyl group or a $(C_3-C_6)$heterocycloalkyl group;

$R_9$ represents at least one substituent of the phenyl nucleus chosen, independently of each other, from: a hydrogen atom, —OH, $(C_1-C_4)$alkoxy, a halogen atom, —NH$_2$, —NH$(C_1-C_6)$alkyl or —N$(C_1-C_6)$alkyl$_2$ or —NH$(C_1-C_6)$cycloalkyl or $(C_3-C_6)$heterocycloalkyl group;

$R_{10}$ represents at least one substituent of the phenyl nucleus chosen from a hydrogen atom and a $(C_1-C_4)$alkyl group;

Y represents

—NR$_{11}$—$(C_1-C_6)$alkyl-, such as —NR$_{11}$—(CH$_2$)$_n$— like

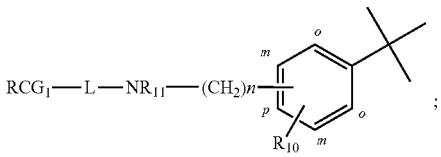

—O—$(C_1-C_6)$alkyl-, such as —O—(CH$_2$)$_n$— like

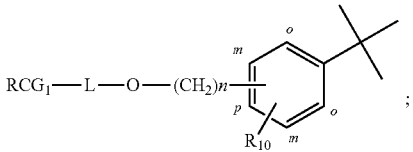

—S—$(C_1-C_6)$alkyl-, such as —S—(CH$_2$)$_n$— like

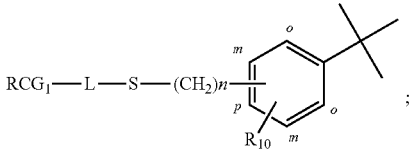

Y being positioned in an ortho (o), meta (m) or para (p) position of the phenyl nucleus;

$R_{11}$ and $R_{12}$ represent, independently of each other, a hydrogen atom or $(C_1-C_6)$alkyl, for instance a hydrogen atom or a methyl group;

n represents an integer ranging from 1 to 6;

L is defined as in formula (I) and represents a linker of formula (II) as defined in the present disclosure;

RCG1 represents a reactive chemical group present at the end of the linker L, RCG1 being reactive towards a chemical group present on a polypeptide such as an antibody. RCG1 is defined above.

Each substituent $R_1$ to $R_{12}$ may also adopt one of the spatial configurations (e.g. R or S or alternatively Z or E) as described in the examples. The compounds of formula (IV) may contain at least one asymmetric carbon atom. They may therefore exist in the form of enantiomers or diastereoisomers. These enantiomers and diastereoisomers, and also mixtures thereof, including racemic mixtures, form part of the disclosure.

As an example, the cryptophycin compound of formula (IV) may be one of the cryptophycin compounds of formula (I) described in WO2011/001052 (such as one of $D_1$-$D_8$) or in PCT/EP2016/076603, (such as one of $D_1$-D19), as mentioned above.

Or the cryptophycin compound may be an equivalent unit described in one of the examples.

Among the compounds of formula (IV) that are subject matter of the disclosure, a group of compounds is composed of the compounds for which $R_1$ represents a ($C_1$-$C_6$)alkyl, such as a methyl group.

Among the compounds of formula (IV) that are subject matter of the disclosure, a group of compounds is composed of the compounds for which each of $R_2$ and $R_3$ represents a hydrogen atom.

Among the compounds of formula (IV) that are subject matter of the disclosure, a group of compounds is composed of the compounds for which one of $R_2$ and $R_3$ represents a ($C_1$-$C_6$)alkyl, such as a methyl group, and the other one represents a hydrogen atom.

Among the compounds of formula (IV) that are subject matter of the disclosure, a group of compounds is composed of the compounds for which $R_2$ and $R_3$ form together with the carbon atom to which they are attached a ($C_3$-$C_6$) cycloalkyl group, such as a cyclopropyl group.

Among the compounds of formula (IV) that are subject matter of the disclosure, a group of compounds is composed of the compounds for which each of $R_4$ and $R_5$ represents a ($C_1$-$C_6$)alkyl, such as a methyl group.

Among the compounds of formula (IV) that are subject matter of the disclosure, a group of compounds is composed of the compounds for which X represents an oxygen atom, that is to say O.

Among the compounds of formula (IV) that are subject matter of the disclosure, a group of compounds is composed of the compounds for which X represents NH.

Among the compounds of formula (IV) that are subject matter of the disclosure, a group of compounds is composed of the compounds for which $R_7$ and $R_8$ represent independently of each other an hydrogen atom or a ($C_1$-$C_6$)alkyl group, such as an isobutyl group or a neopentyl group.

Among the compounds of formula (IV) that are subject matter of the disclosure, a group of compounds is composed of the compounds for which $R_9$ represents two substituents selected from a methoxy group and a chlorine atom, such as the two $R_9$ substituents are 3-Cl and 4-methoxy. For instance, the phenyl nucleus comprises two substituents in positions 3 and 4 on the phenyl nucleus.

Among the compounds of formula (IV) that are subject matter of the disclosure, a group of compounds is composed of the compounds for which $R_{10}$ represents a hydrogen atom.

Among the compounds of formula (IV) that are subject matter of the disclosure, a group of compounds is composed of the compounds for which Y is positioned in the para position of the phenyl nucleus.

Among the compounds of formula (IV) that are subject matter of the disclosure, a group of compounds is composed of the compounds for which Y represents $NR_{11}$—($C_1$-$C_6$) alkyl, such as $NR_{11}$—($C_1$-$C_3$)alkyl, for instance NH—$CH_2$.

Among the compounds of formula (IV) that are subject matter of the disclosure, a group of compounds is composed of the compounds for which L of formula (II) comprises at least one substituted amino acid $AA_s$ in the sequence of w amino acids (AA)w, L1 and L2 are as defined in formula (II).

Among the compounds of formula (IV) that are subject matter of the disclosure, a group of compounds is composed of the compounds for which L of formula (II) comprises a sequence of w non-substituted amino-acid $AA_{ns}$, L1 and L2 are as defined in formula (II).

Among the compounds of formula (IV) that are subject matter of the disclosure, a group of compounds is composed of the compounds for which (AA)w in L of formula (II) contains at least one substituted amino acid $AA_s$ and L2 represents:
  a ($C_1$-$C_6$)alkyl group, such as a $(CH_2)_3$ group;
  a C(=O)—($C_1$-$C_6$)alkyl group, such as a C(=O)—$(CH_2)_3$ group; or
  a ($C_1$-$C_6$)alkyl-$NA_7$-($C_1$-$C_6$)alkyl group, such as a $(CH_2)_2$—$NA_7$-$(CH_2)_2$ group in which $A_7$ is as defined above.

Among the compounds of formula (IV) that are subject matter of the disclosure, a group of compounds is composed of the compounds for which (AA)w in L of formula (II) contains at least one substituted amino acid $AA_s$ and L2 represents:
  a ($C_1$-$C_6$)alkyl group, such as a $(CH_2)_3$ group;
  a C(=O)—($C_1$-$C_6$)alkyl group, such as a C(=O)—$(CH_2)_3$ group; or
  a ($C_1$-$C_6$)alkyl-$NA_7$-($C_1$-$C_6$)alkyl group, such as a $(CH_2)_2$—$NA_7$-$(CH_2)_2$ group in which $A_7$ is a —C(=O)—$(CH_2)_2$—C(=O)—NH—$(CH_2)_2$—$SO_3H$ group;

being understood that each $A_7$ comprising a $SO_3H$ function can be under salt forms such as alkali metal salts, for instance sodium salts ($SO_3^-$ $^+Na$).

Among the compounds of formula (IV) that are subject matter of the disclosure, a group of compounds is composed of the compounds for which (AA)w in L of formula (II) contains w non-substituted amino acid $AA_{ns}$ and L2 represents:
a ($C_1$-$C_6$)alkyl-$NA_7$-($C_1$-$C_6$)alkyl group, such as a $(CH_2)_2$—$NA_7$-$(CH_2)_2$ group in which $A_7$ is as defined above.

Among the compounds of formula (IV) that are subject matter of the disclosure, a group of compounds is composed of the compounds for which (AA)w in L of formula (II) contains w non-substituted amino acid $AA_{ns}$ and L2 represents:
a ($C_1$-$C_6$)alkyl-$NA_7$-($C_1$-$C_6$)alkyl group, such as a $(CH_2)_2$—$NA_7$-$(CH_2)_2$ group in which $A_7$ represents:
  a C(=O)—$[(CH_2)_2$—O$]_a$—$CH_3$ group wherein "a" represents an integer ranging from 1 to 50, for instance ranging from 1 to 24, such as 4, 7 and 24, for example $A_7$ is a C(=O)—$[(CH_2)_2$—O$]_4$—$CH_3$ group, a C(=O)—$[(CH_2)_2$—O$]_7$—$CH_3$ group, or a C(=O)—$[(CH_2)_2$—O$]_{24}$—$CH_3$ group;
  a —C(=O)—$(CH_2)_2$—C(=O)—NH—$(CH_2)_2$—$SO_3H$ group; or
  a C(=O)—$(CH_2)_2$—C(=O)—NH—$[(CH_2)_2$—O$]_a$—$(CH_2)_2$—C(=O)—NH—$(CH_2)_2$—$SO_3H$ group wherein "a" represents an integer ranging from 1 to 50, such as ranging from 1 to 24, for example 4, such as $A_7$ is —C(=O)—$(CH_2)_2$—C(=O)—NH—$[(CH_2)_2$—O$]_4$—$(CH_2)_2$—C(=O)—NH—$(CH_2)_2$—$SO_3H$ group;

being understood that each $A_7$ comprising a $SO_3H$ function can be under salt forms such as alkali metal salts, for instance sodium salts ($SO_3^-$ $^+Na$);

Among the compounds of formula (IV) that are subject matter of the disclosure, a group of compounds is composed of the compounds for which (AA)w in L of formula (II) contains at least one substituted amino acid $AA_s$ and/or w non-substituted amino acid $AA_{ns}$ and L2 represents:
a $NA_7$-($C_1$-$C_6$)alkyl group, a ($C_1$-$C_6$)alkyl-$NA_7$ group, a $NA_7$-$(CH_2CH_2O)_t$($C_1$-$C_6$)alkyl group, a $NA_7$-aryl group, a $NA_7$-heteroaryl group, a $(C_1-C_6)$alkyl-$NA_7C(=O)-(C_1-C_6)$alkyl group, a $(C_1-C_6)$alkyl-$NA_7C(=O)-(C_1-C_6)$alkyl-$(OCH_2CH_2)_i$ group, a $(C_1-C_6)$alkyl-$C(=O)NA_7-(C_1-C_6)$alkyl group, a $(C_1-C_6)$alkyl-$C(=O)NA_7-(C_1-C_6)$alkyl-$(OCH_2CH_2)_i$ group, a $(C_1-C_6)$alkyl-$NA_7-(C_1-C_6)$alkyl group, a $(C_1-C_6)$alkyl-$NA_7-(C_1-C_6)$alkyl-$(OCH_2CH_2)_i$ group, a $(C_1-C_6)$alkyl-$(OCH_2CH_2)_i$-$NA_7-(C_1-C_6)$alkyl group, a $C(=O)-NA_7-(C_1-C_6)$alkyl group, a $C(=O)-(C_1-C_6)$alkyl-$NA_7$ group, a $C(=O)-NA_7-(CH_2CH_2O)_i(C_1-C_6)$alkyl group, a $C(=O)-NA_7$-aryl group, a $C(=O)-NA_7$-heteroaryl group, a $C(=O)-(C_1-C_6)$alkyl-$NA_7C(=O)-(C_1-C_6)$alkyl group, a $C(=O)-(C_1-C_6)$alkyl-$NA_7C(=O)-(C_1-C_6)$alkyl-$(OCH_2CH_2)_i$ group, a $C(=O)-(C_1-C_6)$alkyl-$C(=O)NA_7-(C_1-C_6)$alkyl group, a $C(=O)-(C_1-C_6)$alkyl-$C(=O)NA_7-(C_1-C_6)$alkyl-$(OCH_2CH_2)_i$ group, a $C(=O)-(C_1-C_6)$alkyl-$NA_7-(C_1-C_6)$alkyl group, a $C(=O)-(C_1-C_6)$alkyl-$NA_7-(C_1-C_6)$alkyl-$(OCH_2CH_2)_i$ group, a $C(=O)-(C_1-C_6)$alkyl-$(OCH_2CH_2)_i$-$NA_7-(C_1-C_6)$alkyl group, a $NA_8-(C_1-C_6)$alkyl-$NA_7$ group, a $NA_8-(C_1-C_6)$alkyl-$NA_7C(=O)-(C_1-C_6)$alkyl group, a $NA_8-(C_1-C_6)$alkyl-$NA_7C(=O)-(C_1-C_6)$alkyl-$(OCH_2CH_2)_i$ group, a $NA_8-(C_1-C_6)$alkyl-$C(=O)NA_7-(C_1-C_6)$alkyl group, a $NA_8-(C_1-C_6)$alkyl-$C(=O)NA_7-(C_1-C_6)$alkyl-$(OCH_2CH_2)_i$ group, a $NA_8-(C_1-C_6)$alkyl-$NA_7-(C_1-C_6)$alkyl group, a $NA_8-(C_1-C_6)$alkyl-$NA_7-(C_1-C_6)$alkyl-$(OCH_2CH_2)_i$ group, a $NA_8-(C_1-C_6)$alkyl-$(OCH_2CH_2)_i$-$NA_7-(C_1-C_6)$alkyl group, a $C(=O)-NA_8-(C_1-C_6)$alkyl-$NA_7$ group, a $C(=O)-NA_8-(C_1-C_6)$alkyl-$NA_7C(=O)-(C_1-C_6)$alkyl group, a $C(=O)-NA_8-(C_1-C_6)$alkyl-$NA_7C(=O)-(C_1-C_6)$alkyl-$(OCH_2CH_2)_i$ group, a $C(=O)-NA_8-(C_1-C_6)$alkyl-$C(=O)NA_7-(C_1-C_6)$alkyl group, a $C(=O)-NA_8-(C_1-C_6)$alkyl-$C(=O)NA_7-(C_1-C_6)$alkyl-$(OCH_2CH_2)_i$ group, a $C(=O)-NA_8-(C_1-C_6)$alkyl-$NA_7-(C_1-C_6)$alkyl group, a $C(=O)-NA_8-(C_1-C_6)$alkyl-$NA_7-(C_1-C_6)$alkyl-$(OCH_2CH_2)_i$ group or a $C(=O)-NA_8-(C_1-C_6)$alkyl-$(OCH_2CH_2)_i$-$NA_7-(C_1-C_6)$alkyl group; wherein i, $A_7$ and $A_8$ are as defined above.

Among the compounds of formula (IV) that are subject matter of the disclosure, a preferred group of compounds is composed of the compounds for which $(AA)w$ in L of formula (II) contains at least one substituted amino acid $AA_s$ and/or w non-substituted amino acid $AA_{ns}$ and L2 represents:

a $NA_7-(C_1-C_6)$alkyl group, a $(C_1-C_6)$alkyl-$NA_7$ group, a $NA_7-(CH_2CH_2O)_i(C_1-C_6)$alkyl group, a $NA_7$-aryl group, a $NA_7$-heteroaryl group, a $(C_1-C_6)$alkyl-$NA_7C(=O)-(C_1-C_6)$alkyl group, a $(C_1-C_6)$alkyl-$NA_7C(=O)-(C_1-C_6)$alkyl-$(OCH_2CH_2)_i$ group, a $(C_1-C_6)$alkyl-$C(=O)NA_7-(C_1-C_6)$alkyl group, a $(C_1-C_6)$alkyl-$C(=O)NA_7-(C_1-C_6)$alkyl-$(OCH_2CH_2)_i$ group, a $(C_1-C_6)$alkyl-$NA_7-(C_1-C_6)$alkyl group, a $(C_1-C_6)$alkyl-$NA_7-(C_1-C_6)$alkyl-$(OCH_2CH_2)_i$ group, a $(C_1-C_6)$alkyl-$(OCH_2CH_2)_i$-$NA_7-(C_1-C_6)$alkyl group, a $C(=O)-NA_7-(C_1-C_6)$alkyl group, a $C(=O)-(C_1-C_6)$alkyl-$NA_7$ group, a $C(=O)-NA_7-(CH_2CH_2O)(C_1-C_6)$alkyl group, a $C(=O)-NA_7$-aryl group, a $C(=O)-NA_7$-heteroaryl group, a $C(=O)-(C_1-C_6)$alkyl-$NA_7C(=O)-(C_1-C_6)$alkyl group, a $C(=O)-(C_1-C_6)$alkyl-$NA_7C(=O)-(C_1-C_6)$alkyl-$(OCH_2CH_2)_i$ group, a $C(=O)-(C_1-C_6)$alkyl-$C(=O)NA_7-(C_1-C_6)$alkyl group, a $C(=O)-(C_1-C_6)$alkyl-$C(=O)NA_7-(C_1-C_6)$alkyl-$(OCH_2CH_2)_i$ group, a $C(=O)-(C_1-C_6)$alkyl-$NA_7-(C_1-C_6)$alkyl group, a $C(=O)-(C_1-C_6)$alkyl-$NA_7-(C_1-C_6)$alkyl-$(OCH_2CH_2)_i$ group, a $NA_8-(C_1-C_6)$alkyl-$NA_7$ group, a $NA_8-(C_1-C_6)$alkyl-$NA_7C(=O)-(C_1-C_6)$alkyl group, a $NA_8-(C_1-C_6)$alkyl-$C(=O)NA_7-(C_1-C_6)$alkyl group, a $NA_8-(C_1-C_6)$alkyl-$NA_7-(C_1-C_6)$alkyl group, a $C(=O)-NA_8-(C_1-C_6)$alkyl-$NA_7$ group, a $C(=O)-NA_8-(C_1-C_6)$alkyl-$NA_7C(=O)-(C_1-C_6)$alkyl group, a $C(=O)-NA_8-(C_1-C_6)$alkyl-$C(=O)NA_7-(C_1-C_6)$alkyl group, or a $C(=O)-NA_8-(C_1-C_6)$alkyl-$NA_7-(C_1-C_6)$alkyl group; wherein i, $A_7$ and $A_8$ are as defined above.

Among the compounds of formula (IV) that are subject matter of the disclosure, a more preferred group of compounds is composed of the compounds for which $(AA)w$ in L of formula (II) contains at least one substituted amino acid $AA_s$ and/or w non-substituted amino acid $AA_{ns}$ and L2 represents:

a $NA_7-(C_1-C_6)$alkyl group, a $(C_1-C_6)$alkyl-$NA_7$ group, a $NA_7-(CH_2CH_2O)_i(C_1-C_6)$alkyl group, a $(C_1-C_6)$alkyl-$NA_7C(=O)-(C_1-C_6)$alkyl group, a $(C_1-C_6)$alkyl-$NA_7C(=O)-(C_1-C_6)$alkyl-$(OCH_2CH_2)_i$ group, a $(C_1-C_6)$alkyl-$C(=O)NA_7-(C_1-C_6)$alkyl group, a $(C_1-C_6)$alkyl-$C(=O)NA_7-(C_1-C_6)$alkyl-$(OCH_2CH_2)_i$ group, a $(C_1-C_6)$alkyl-$NA_7-(C_1-C_6)$alkyl group, a $(C_1-C_6)$alkyl-$NA_7-(C_1-C_6)$alkyl-$(OCH_2CH_2)_i$ group, a $(C_1-C_6)$alkyl-$(OCH_2CH_2)_i$-$NA_7-(C_1-C_6)$alkyl group, a $C(=O)-NA_7-(C_1-C_6)$alkyl group, a $C(=O)-(C_1-C_6)$alkyl-$NA_7$ group, a $C(=O)-NA_7-(CH_2CH_2O)_i(C_1-C_6)$alkyl group, a $C(=O)-(C_1-C_6)$alkyl-$NA_7C(=O)-(C_1-C_6)$alkyl group, a $C(=O)-(C_1-C_6)$alkyl-$NA_7C(=O)-(C_1-C_6)$alkyl-$(OCH_2CH_2)_i$ group, a $C(=O)-(C_1-C_6)$alkyl-$C(=O)NA_7-(C_1-C_6)$alkyl group, a $C(=O)-(C_1-C_6)$alkyl-$C(=O)NA_7-(C_1-C_6)$alkyl-$(OCH_2CH_2)_i$ group, a $C(=O)-(C_1-C_6)$alkyl-$NA_7-(C_1-C_6)$alkyl group, a $C(=O)-(C_1-C_6)$alkyl-$NA_7-(C_1-C_6)$alkyl-$(OCH_2CH_2)_i$ group, a $NA_8-(C_1-C_6)$alkyl-$NA_7$ group, a $NA_8-(C_1-C_6)$alkyl-$NA_7C(=O)-(C_1-C_6)$alkyl group, a $NA_8-(C_1-C_6)$alkyl-$C(=O)NA_7-(C_1-C_6)$alkyl group, a $NA_8-(C_1-C_6)$alkyl-$NA_7-(C_1-C_6)$alkyl group, a $C(=O)-NA_8-(C_1-C_6)$alkyl-$NA_7$ group, a $C(=O)-NA_8-(C_1-C_6)$alkyl-$NA_7C(=O)-(C_1-C_6)$alkyl group, a $C(=O)-NA_8-(C_1-C_6)$alkyl-$C(=O)NA_7-(C_1-C_6)$alkyl group, or a $C(=O)-NA_8-(C_1-C_6)$alkyl-$NA_7-(C_1-C_6)$alkyl group; wherein i, $A_7$ and $A_8$ are as defined above.

Among the compounds of formula (IV) that are subject matter of the disclosure, a still more preferred group of compounds is composed of the compounds for which $(AA)w$ in L of formula (II) contains at least one substituted amino acid $AA_s$ and/or w non-substituted amino acid $AA_{ns}$ and L2 represents:

a $NA_7-(C_1-C_6)$alkyl group, a $(C_1-C_6)$alkyl-$NA_7$ group, a $(C_1-C_6)$alkyl-$NA_7C(=O)-(C_1-C_6)$alkyl group, a $(C_1-C_6)$alkyl-$C(=O)NA_7-(C_1-C_6)$alkyl group, a $(C_1-C_6)$alkyl-$NA_7-(C_1-C_6)$alkyl group, a $C(=O)-NA_7-(C_1-C_6)$alkyl group, a $C(=O)-(C_1-C_6)$alkyl-$NA_7$ group, a $C(=O)-(C_1-C_6)$alkyl-$NA_7C(=O)-(C_1-C_6)$alkyl group, a $C(=O)-(C_1-C_6)$alkyl-$C(=O)NA_7-(C_1-C_6)$alkyl group, a $C(=O)-(C_1-C_6)$alkyl-$NA_7-(C_1-C_6)$alkyl group, a $NA_8-(C_1-C_6)$alkyl-$NA_7$ group, a $NA_8-(C_1-C_6)$alkyl-$NA_7C(=O)-(C_1-C_6)$alkyl group, a $NA_8-(C_1-C_6)$alkyl-$C(=O)NA_7-(C_1-C_6)$alkyl group, a $NA_8-(C_1-C_6)$alkyl-$NA_7-(C_1-C_6)$alkyl group, a $C(=O)-NA_8-(C_1-C_6)$alkyl-$NA_7$ group, a $C(=O)-NA_8-(C_1-C_6)$alkyl-$NA_7C(=O)-(C_1-C_6)$alkyl group, a $C(=O)-NA_8-(C_1-C_6)$alkyl-$C(=O)NA_7-(C_1-C_6)$alkyl group, or a $C(=O)-NA_8-(C_1-C_6)$alkyl-$NA_7-(C_1-C_6)$alkyl group; wherein $A_7$ and $A_8$ are as defined above.

Among the compounds of formula (IV) that are subject matter of the disclosure, a most preferred group of compounds is composed of the compounds for which $(AA)w$ in L of formula (II) contains at least one substituted amino acid $AA_s$ and/or w non-substituted amino acid $AA_{ns}$ and L2 represents:

a $(C_1-C_6)$alkyl-$NA_7-(C_1-C_6)$alkyl group; wherein $A_7$ is as defined above.

Among the compounds of formula (IV) that are subject matter of the disclosure, a group of compounds is composed of the compounds for which (AA)w in L of formula (II) contains at least one substituted amino acid $AA_s$ and/or w non-substituted amino acid $AA_{ns}$ and L2 comprises a $A_7$ representing:

a C(=O)—[(CH$_2$)$_2$—O]$_4$—CH$_3$ group; a C(=O)—[(CH$_2$)$_2$—O]$_7$—CH$_3$ group; a C(=O)—[(CH$_2$)$_2$—O]$_{24}$—CH$_3$ group; a C(=O)—(CH$_2$)$_2$—C(=O)—NH—(CH$_2$)$_2$—SO$_3$H group; a C(=O)—(CH$_2$)$_2$—C(=O)—NH—[(CH$_2$)$_2$—O]$_4$—(CH$_2$)$_2$—C(=O)—NH—(CH$_2$)$_2$—SO$_3$H group; being understood that each $A_7$ comprising a SO$_3$H function can be under salt forms such as alkali metal salts, for instance sodium salts (SO$_3^-$ $^+$Na).

Among the compounds of formula (IV) that are subject matter of the disclosure, a group of compounds is composed of the compounds for which (AA)w in L of formula (II) contains at least one substituted amino acid $AA_s$ and/or w non-substituted amino acid $AA_{ns}$ and L2 represents:

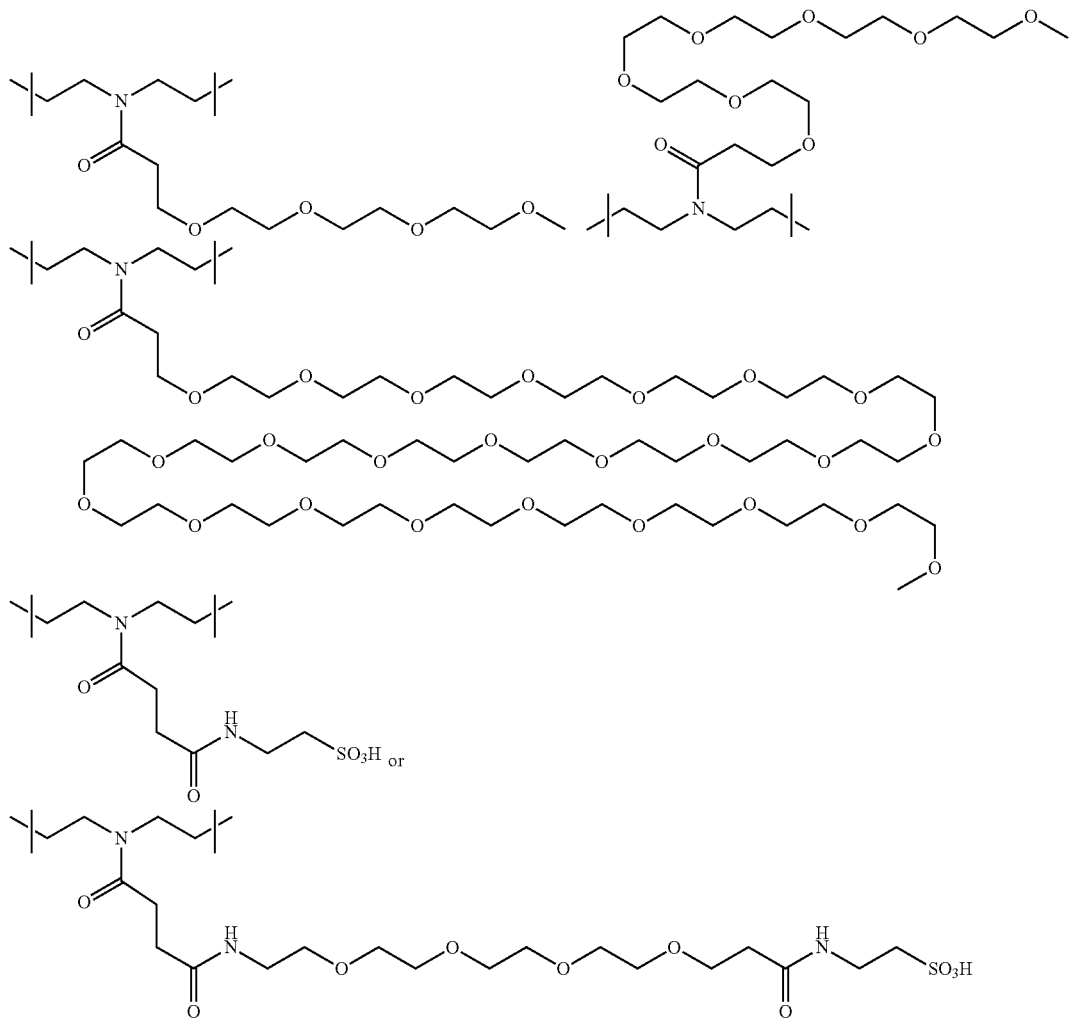

Among the compounds of formula (IV) that are subject matter of the disclosure, a group of compounds is composed of the compounds comprising in L a sequence $(AA_s)w$ containing at least one substituted amino acid $AA_s$, $(AA_s)w$ being selected from the list:

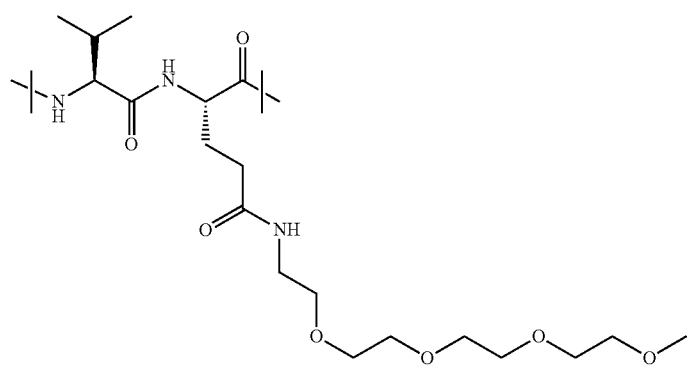
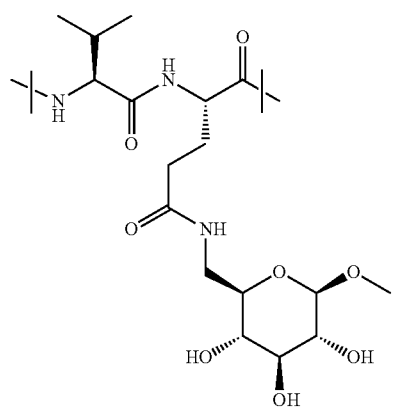
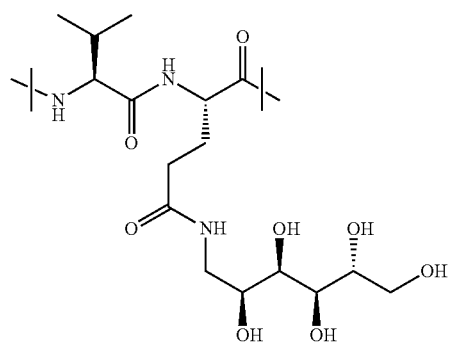
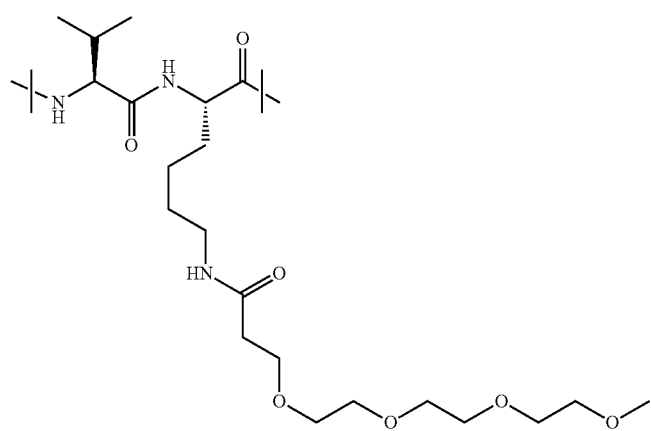

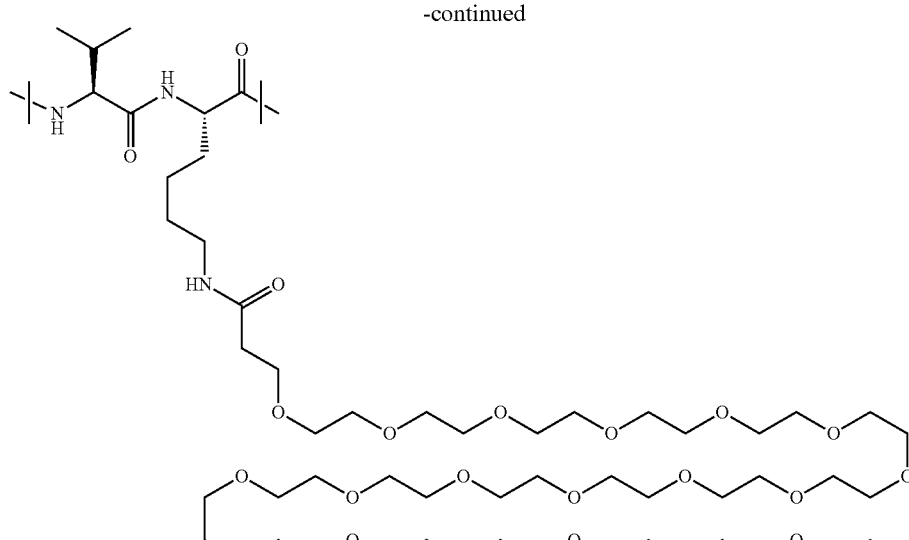
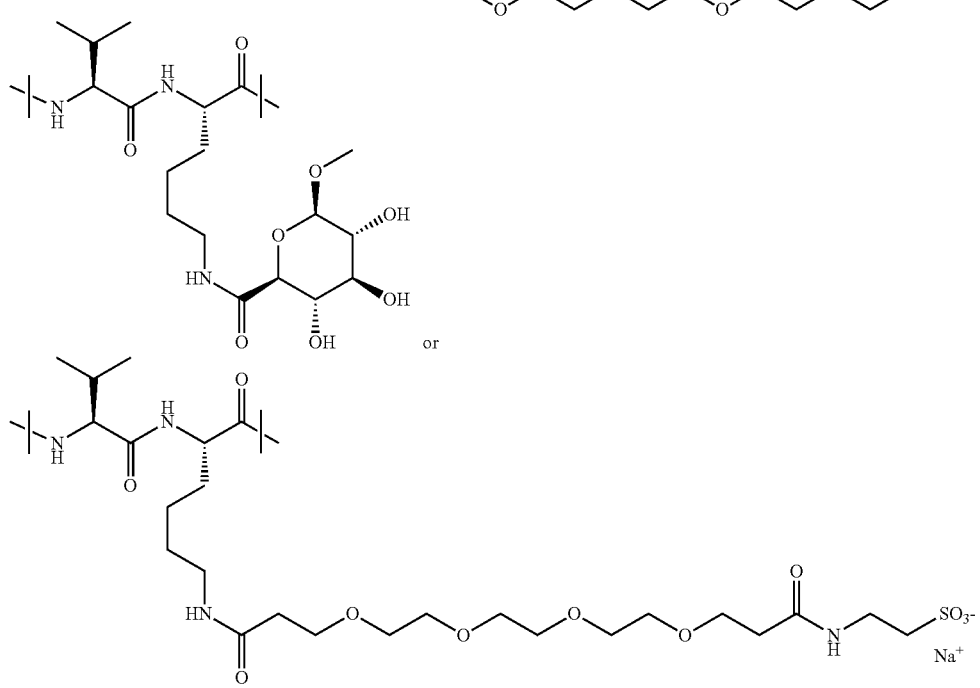
Among the compounds of formula (IV) that are subject matter of the disclosure, a group of compounds is composed of the compounds of the following structure (beta epoxide configuration):
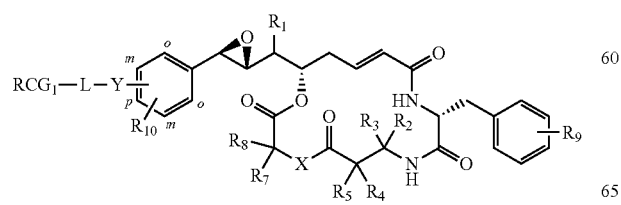

wherein:
R₁, R₂, R₃, R₄, R₅, R₆, R₇, R₈, R₉, R₁₀, R₁₁, R₁₂, n, RCG₁, X, Y and L are as defined in formula (IV).
All these sub-groups taken alone or in combination are part of the present disclosure.
According to at least one embodiment, the present disclosure relates to compounds of formula (IV) wherein:
RCG1 is COOH,
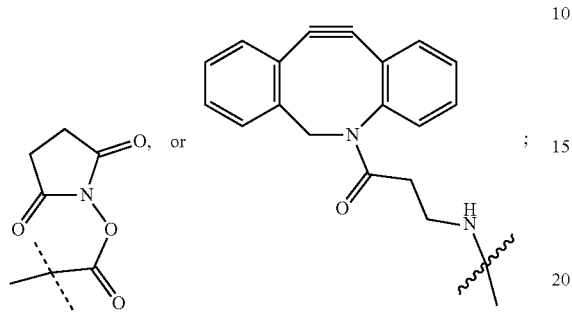
L represents one of the below compounds of formula (II):
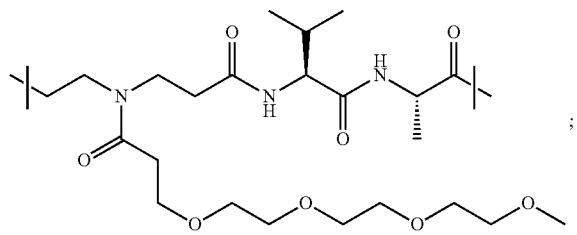
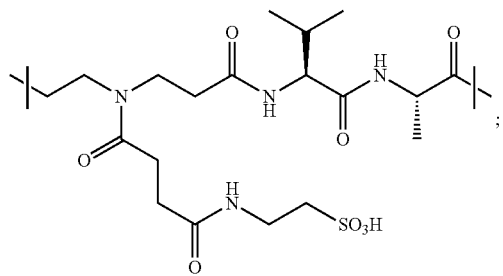
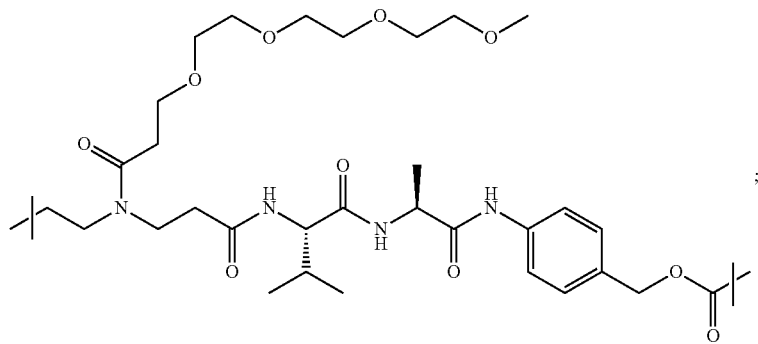

-continued
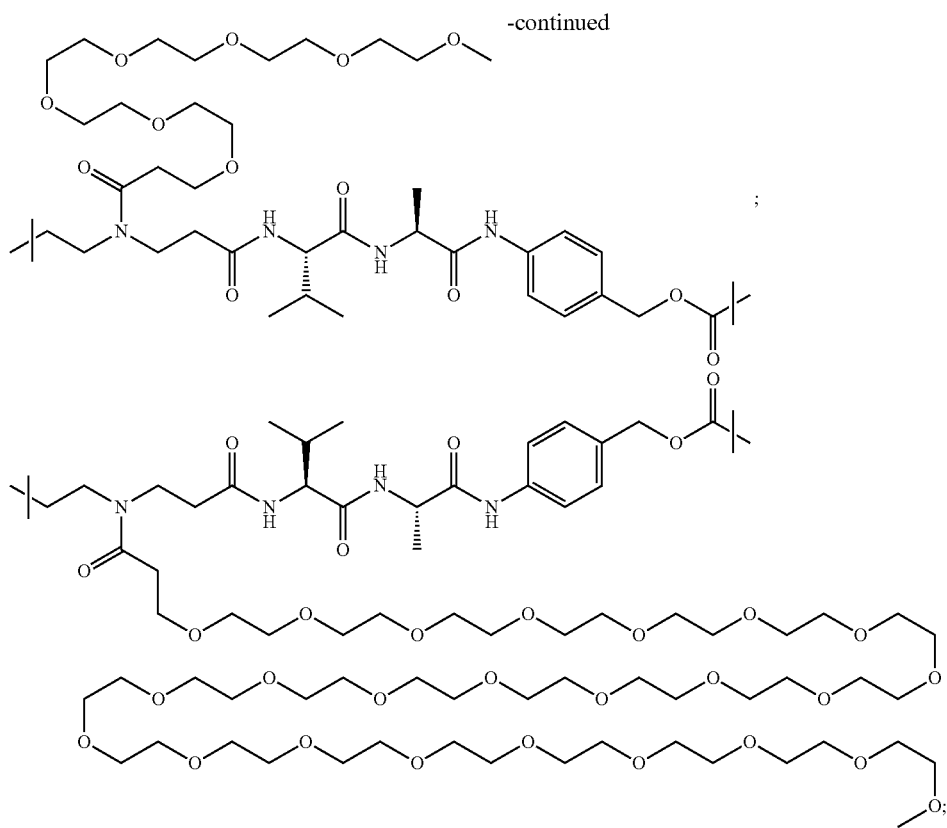
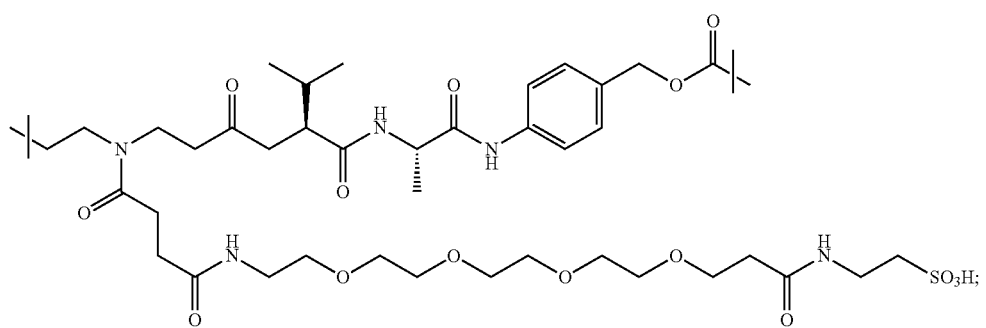
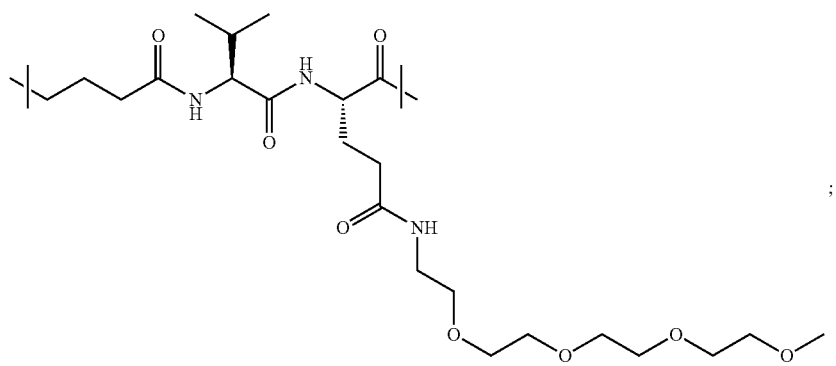

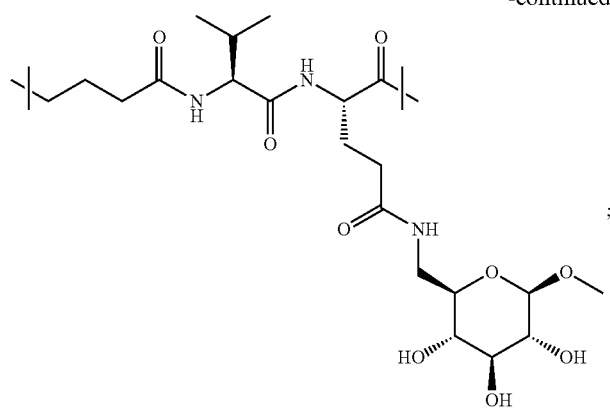
;
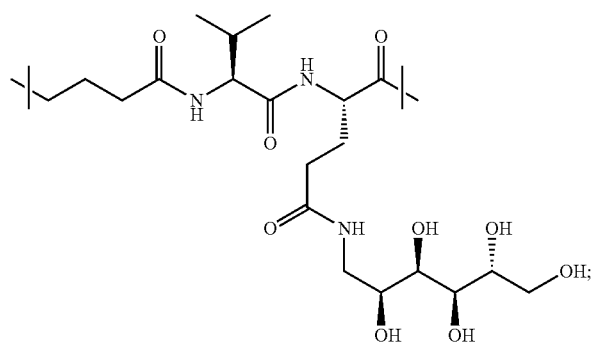
;
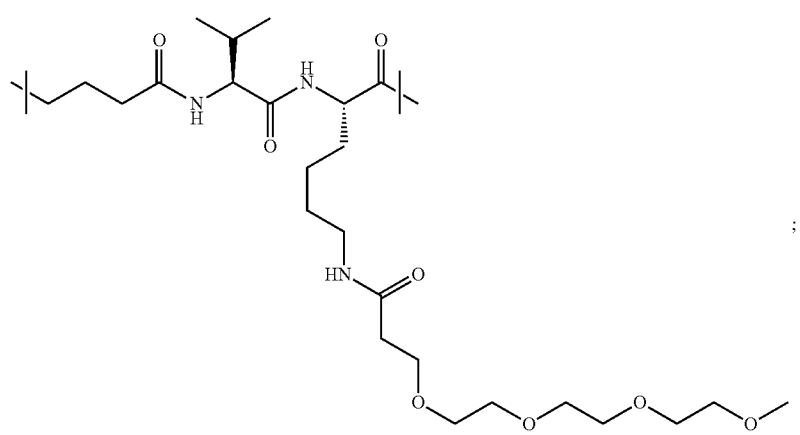
;

-continued
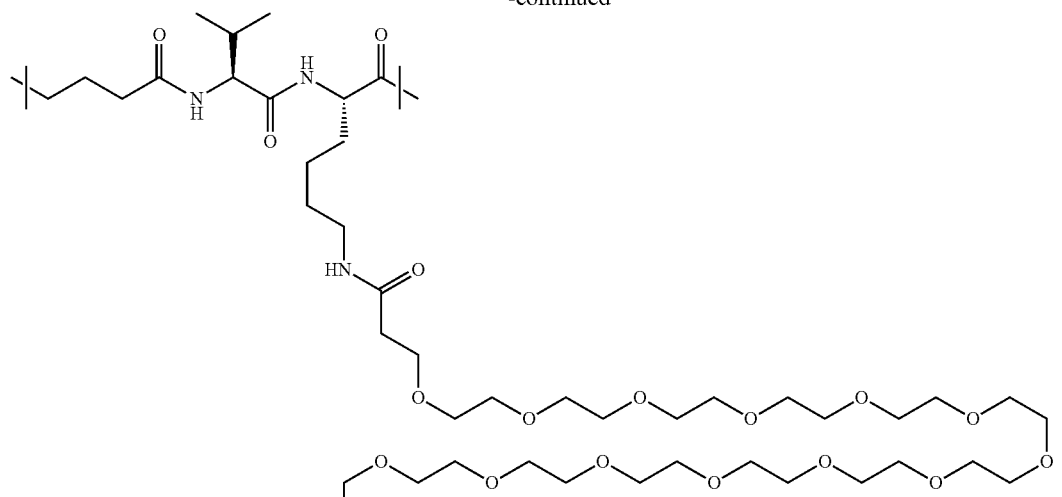
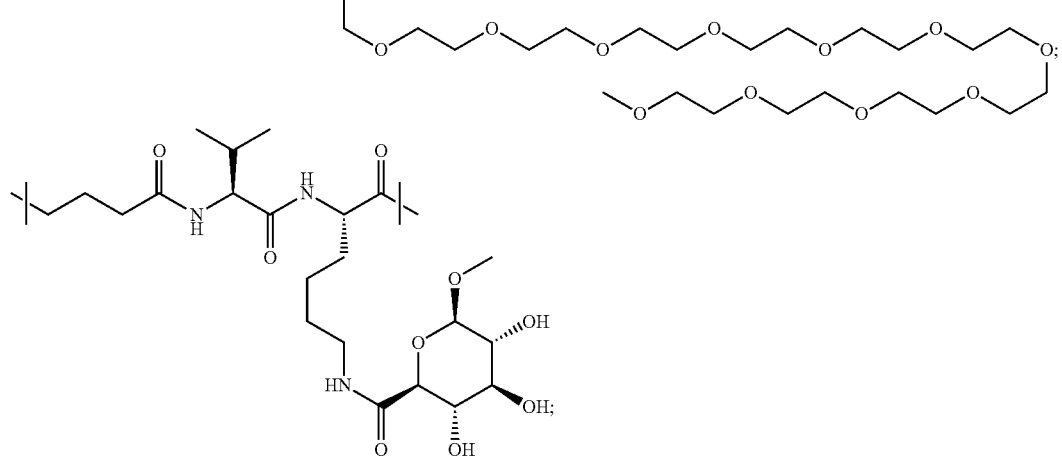
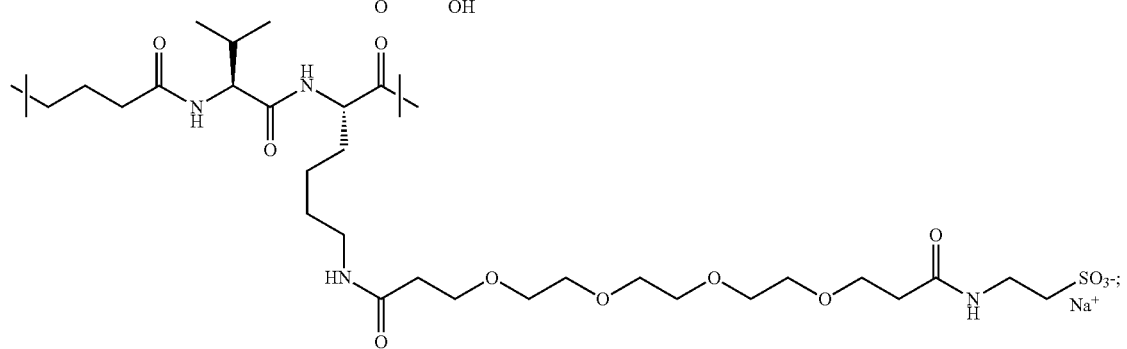
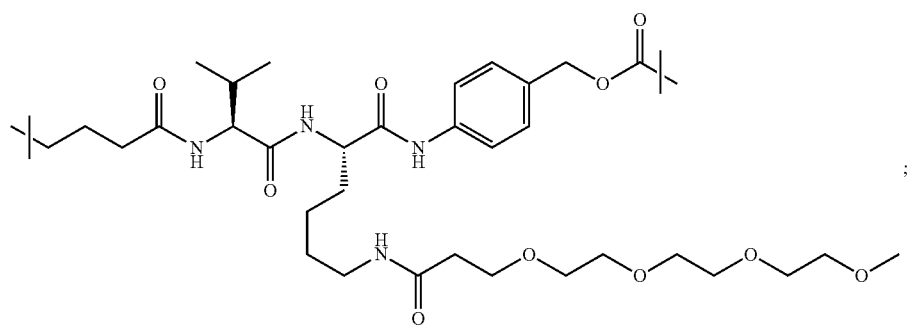

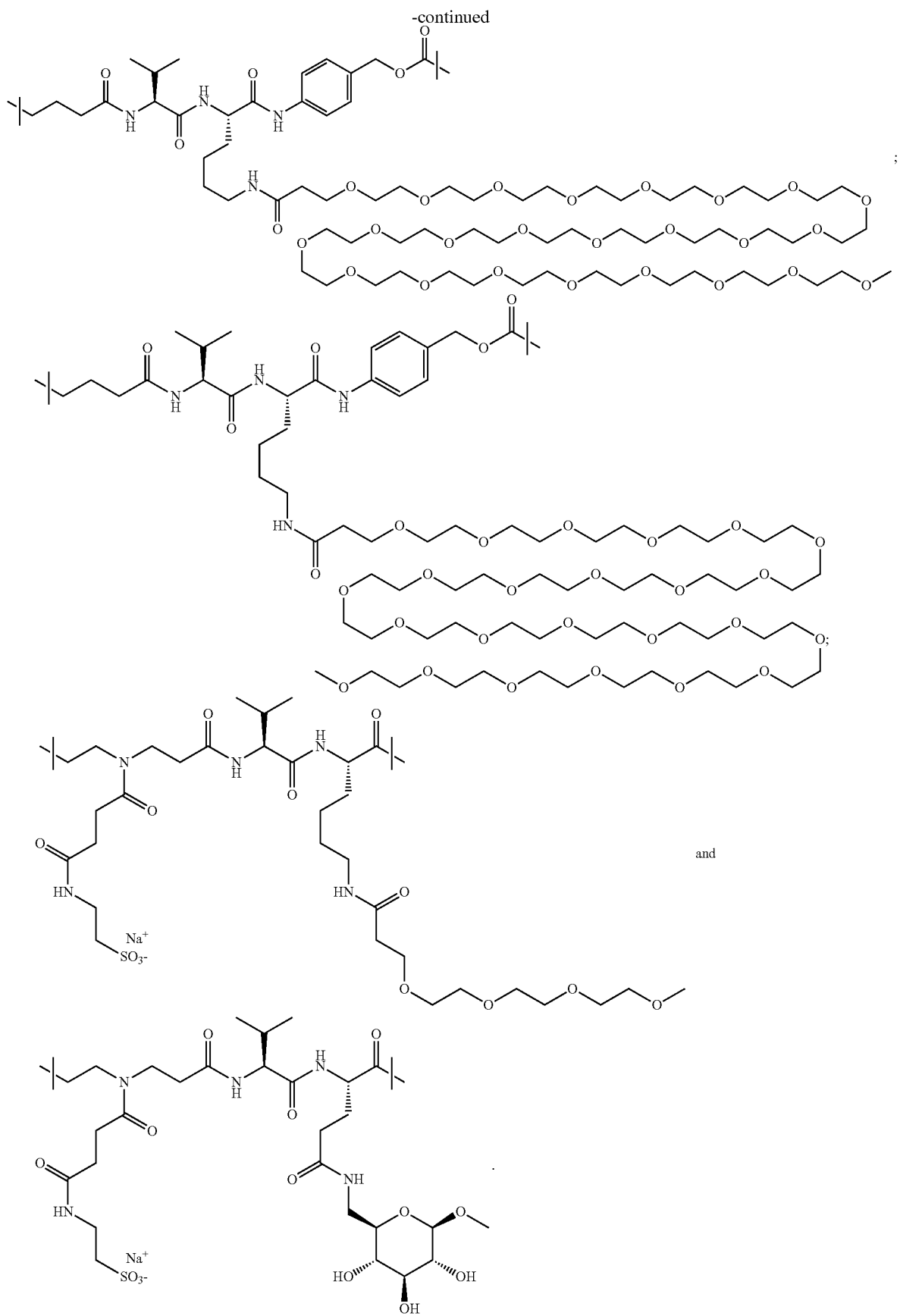

Y is a $NR_{11}$—$(C_{1-6})$alkyl in which $R_{11}$ is a hydrogen atom, such as Y is NH—$CH_2$;

$R_1$ represents a $(C_1$-$C_6)$alkyl group, such as a methyl group;

$R_2$ and $R_3$ represent independently of each other a hydrogen atom or a $(C_1$-$C_6)$alkyl group such as a methyl group;

$R_4$ and $R_5$ represent independently of each other a $(C_1$-$C_6)$alkyl group, such as a methyl group;

$R_7$ and $R_8$ represent independently of each other a hydrogen atom or a $(C_1$-$C_6)$alkyl group, such as an isobutyl group or a neopentyl group, for instance one of $R_7$ and $R_8$ represents a $(C_1$-$C_6)$alkyl group, for example an isobutyl group or a neopentyl group and the other of $R_7$ and $R_8$ represents a hydrogen atom;

X represents an oxygen atom or NH;

$R_9$ represents two substituents selected from a $(C_1$-$C_4)$ alkoxy group, such as a methoxy group, and a halogen atom, for instance a chlorine atom, such as $R_9$ represents 3-Cl and 4-methoxy; and $R_{10}$ represents a hydrogen atom.

Among the compounds of formula (IV) that are the subject matter of the present disclosure, mention may be made in particular of the following compounds:

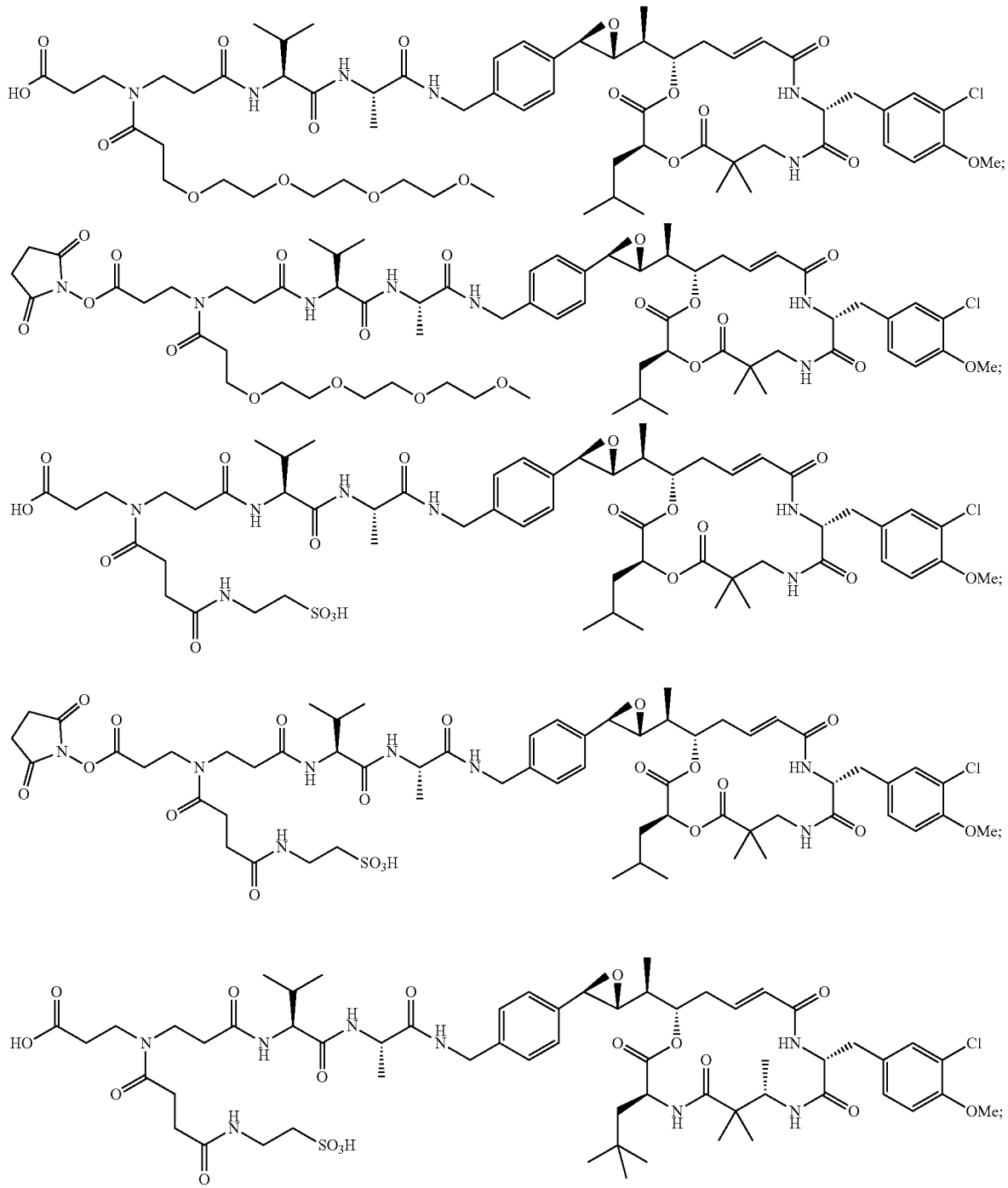

-continued
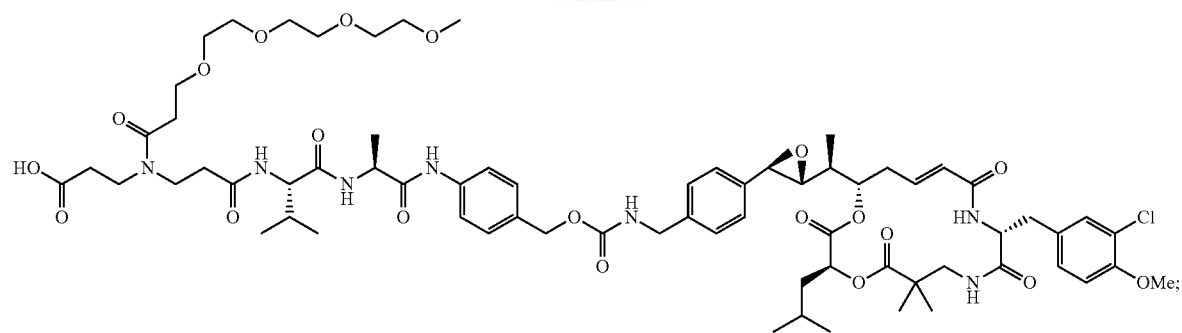
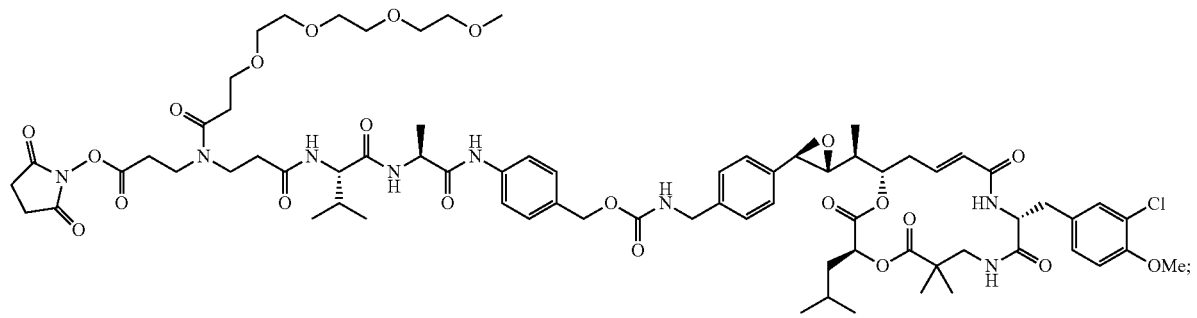
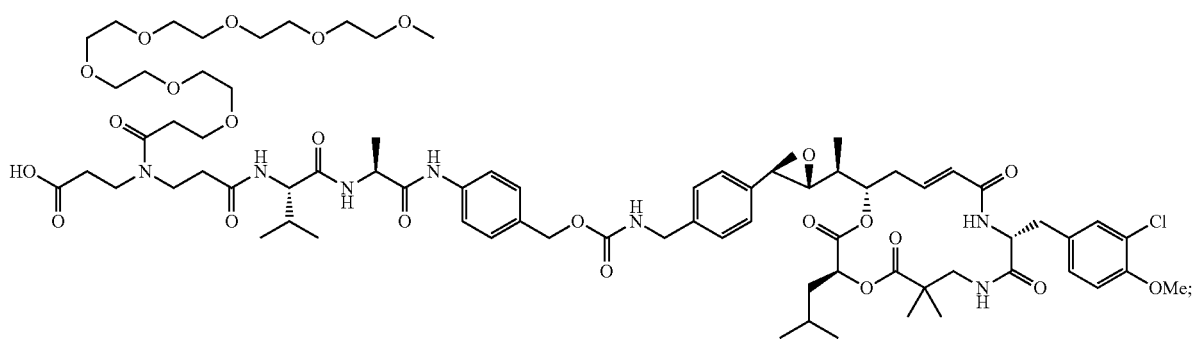
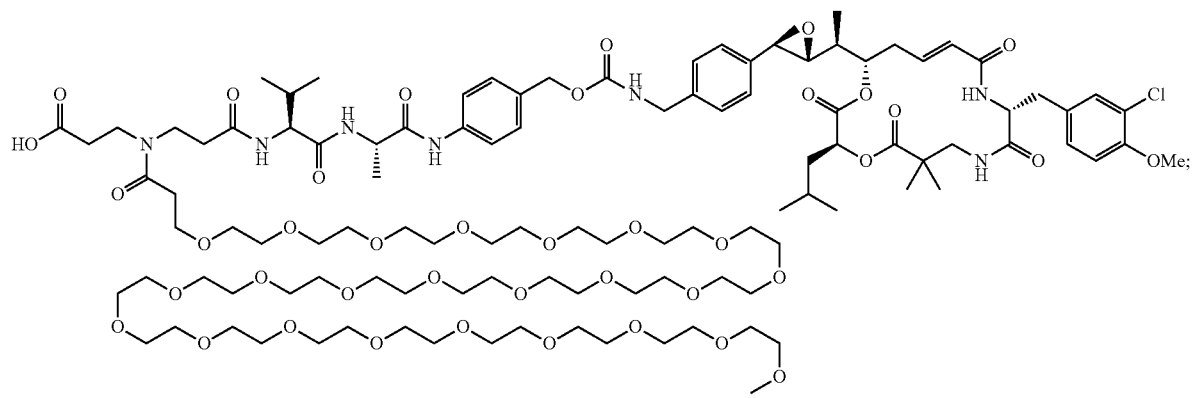

95
96
-continued
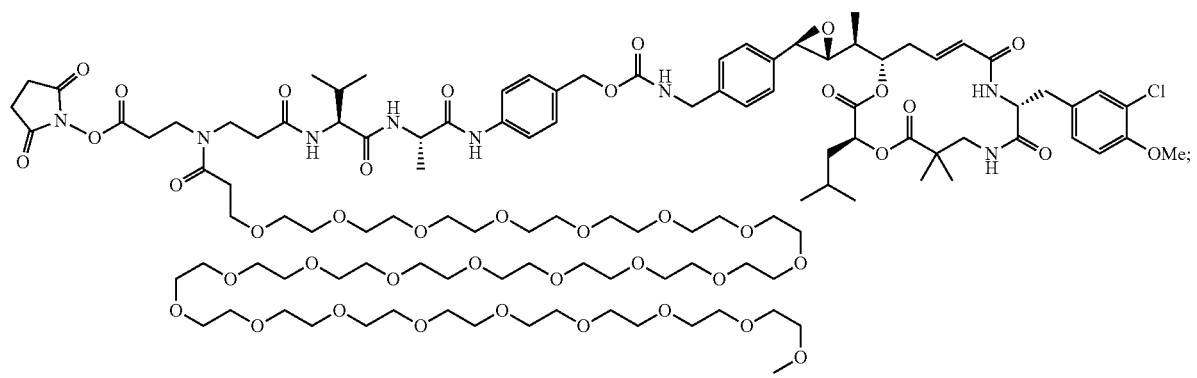
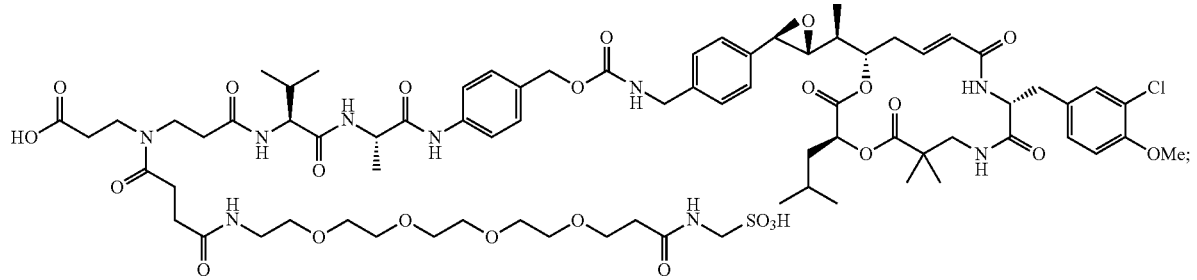
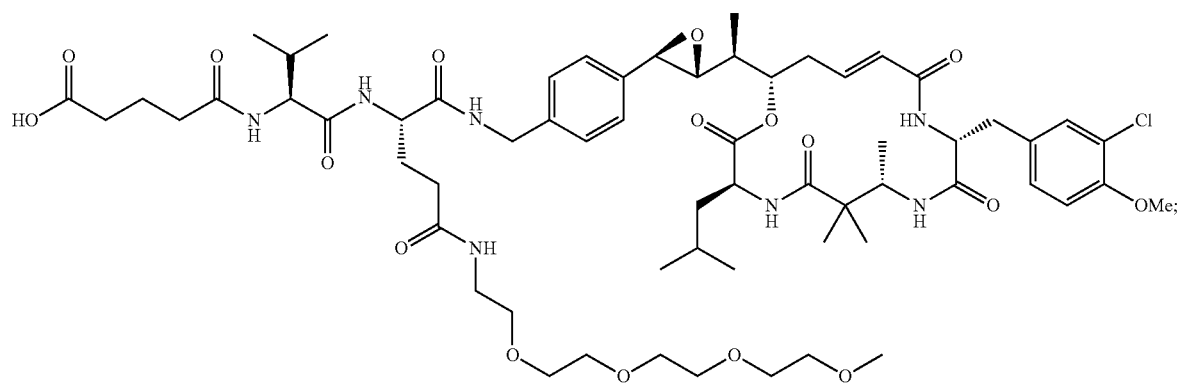
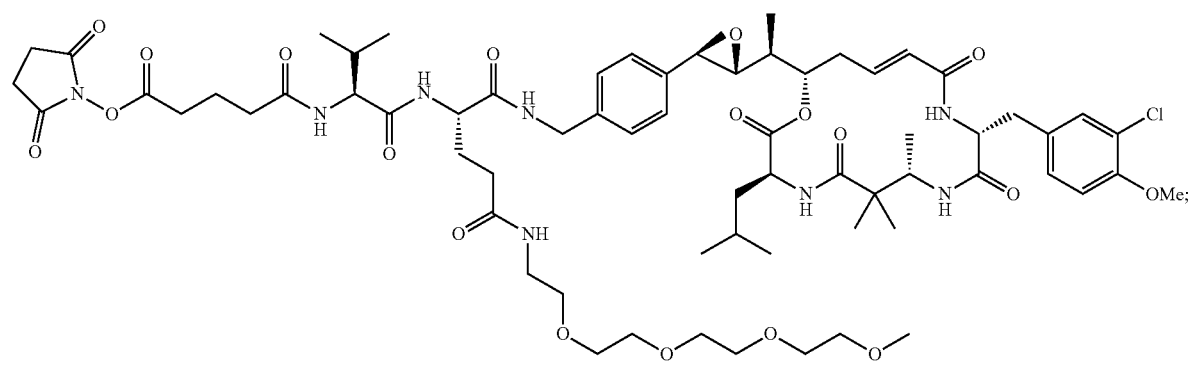

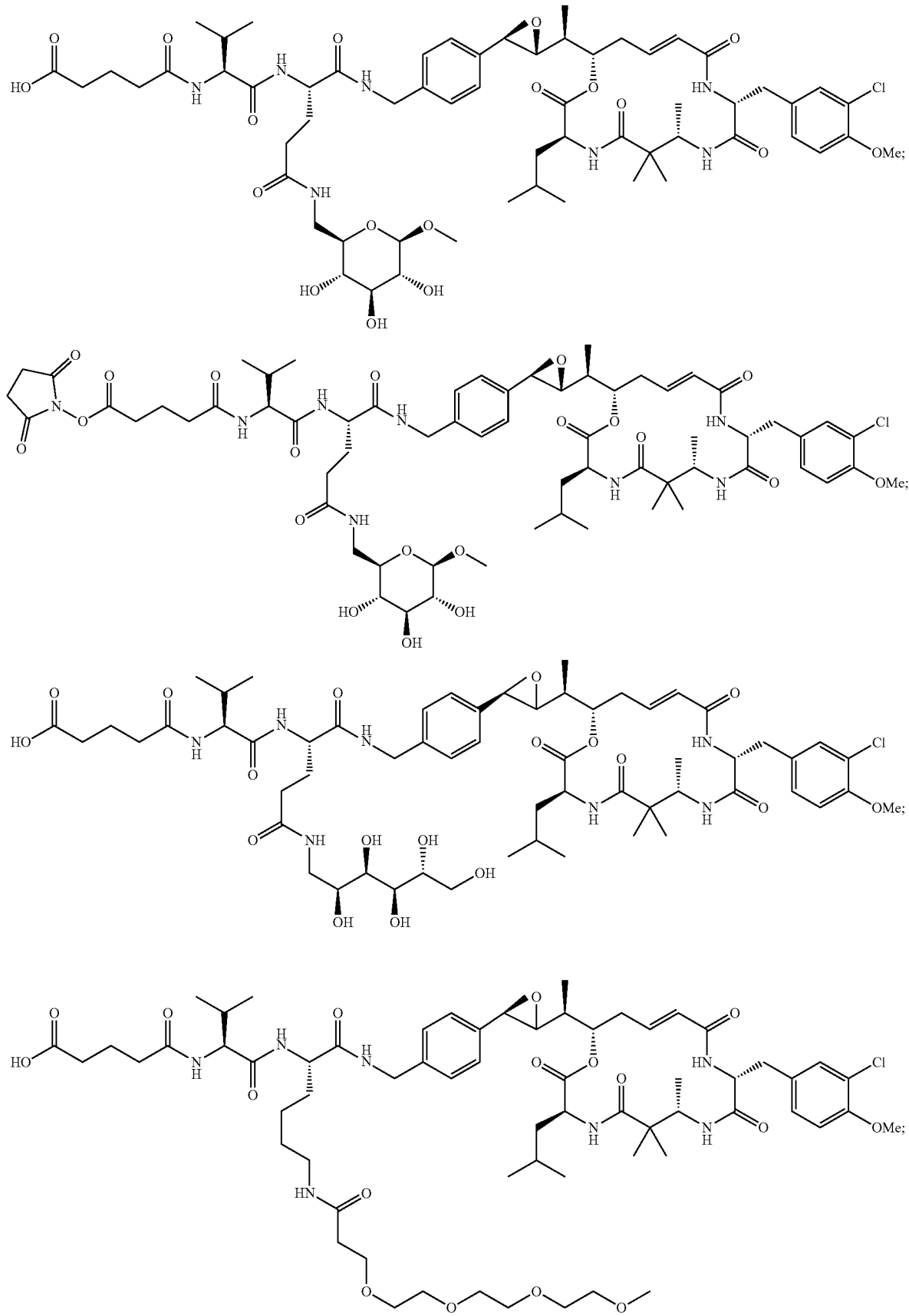

-continued
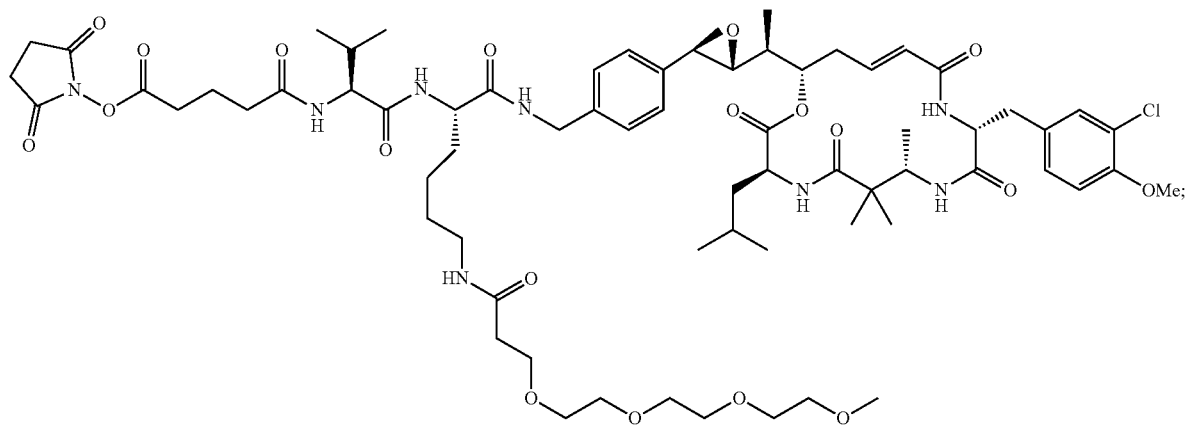
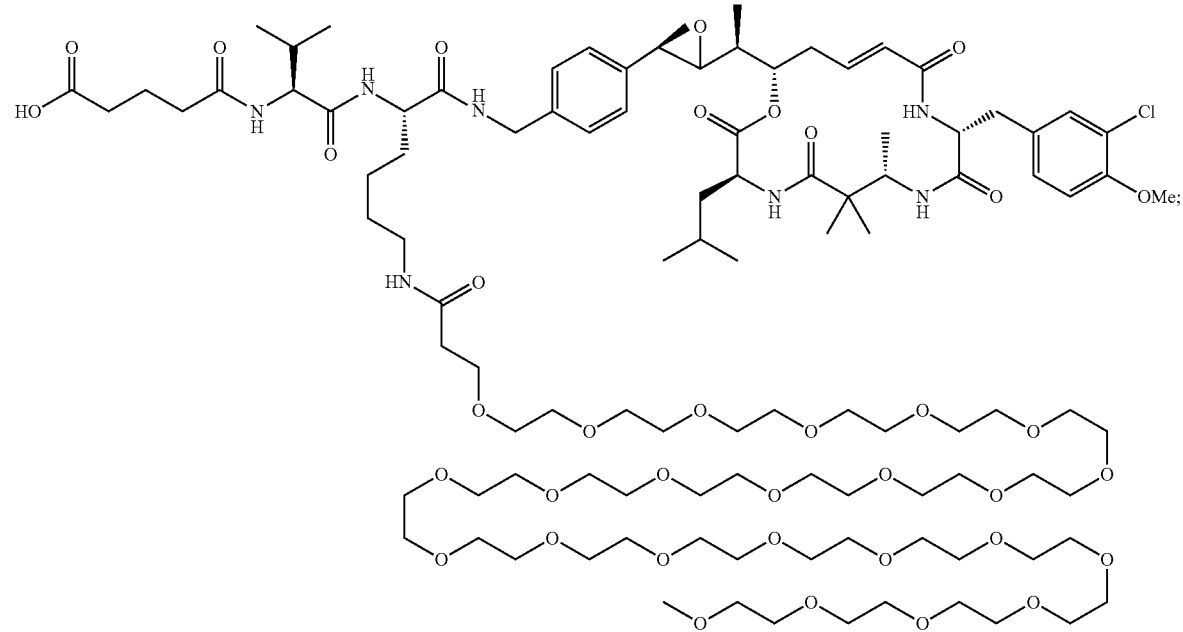
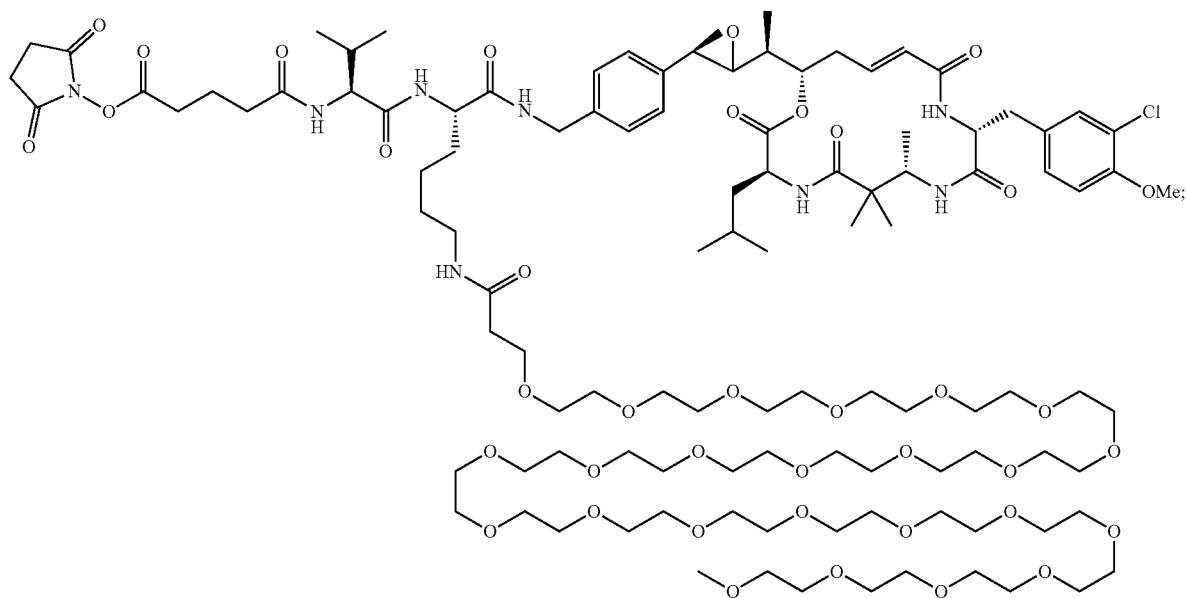

101
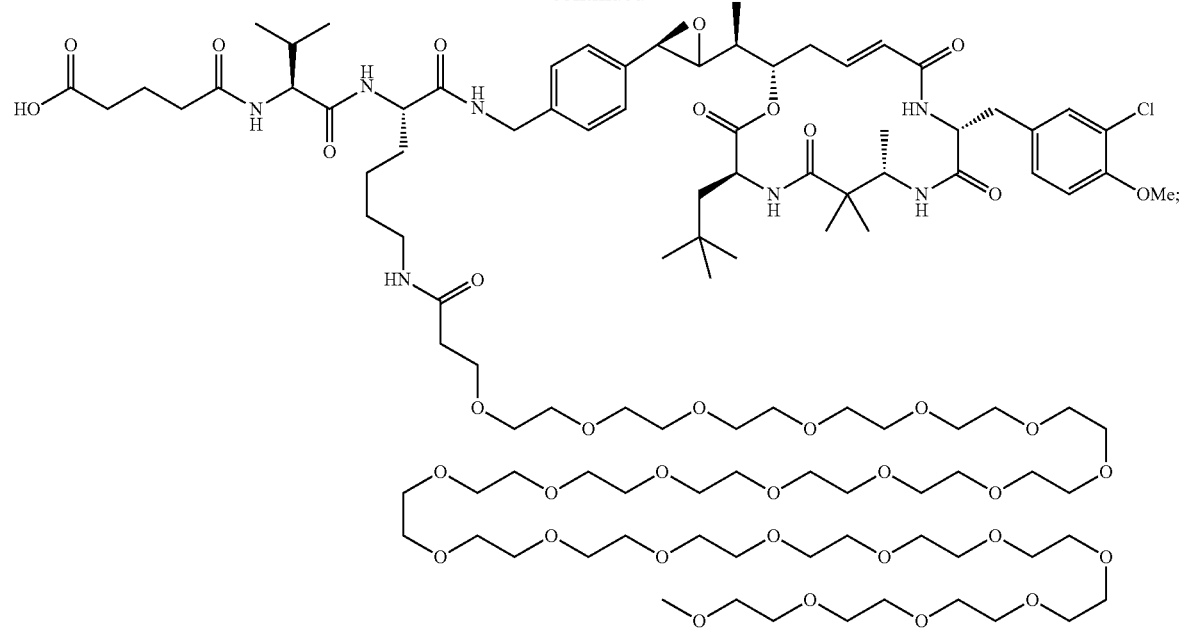
102
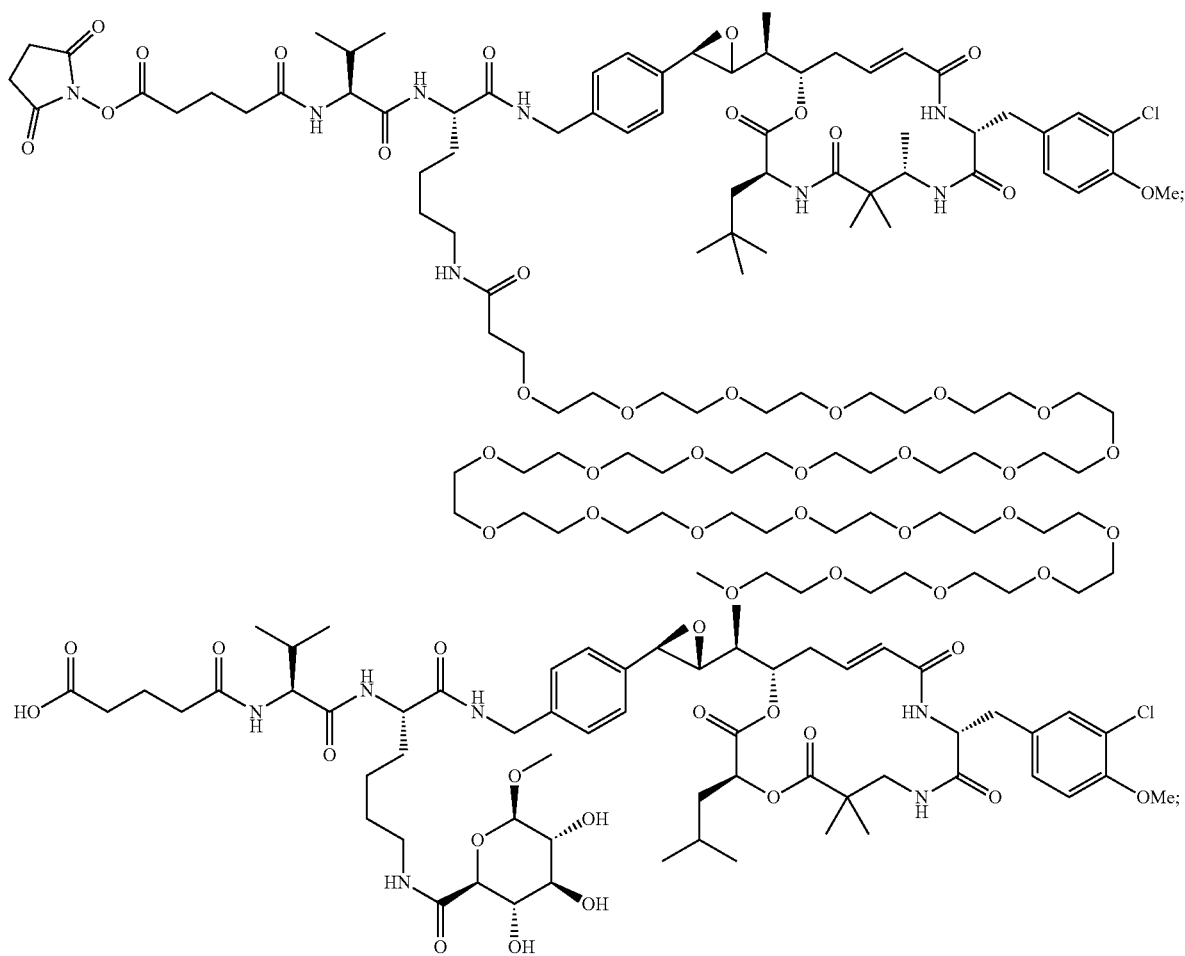

103 104
-continued
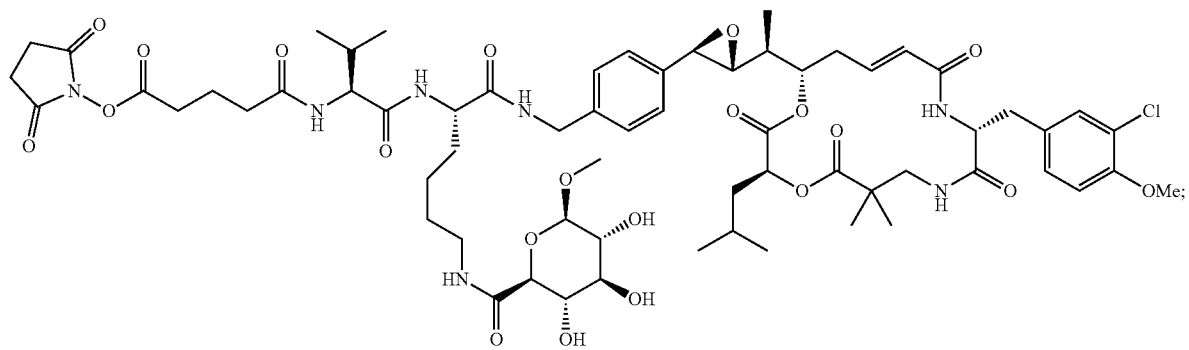
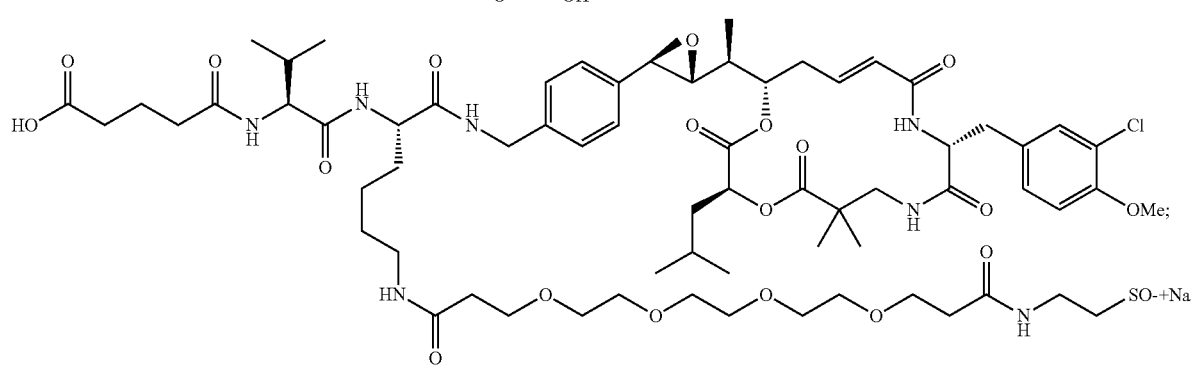
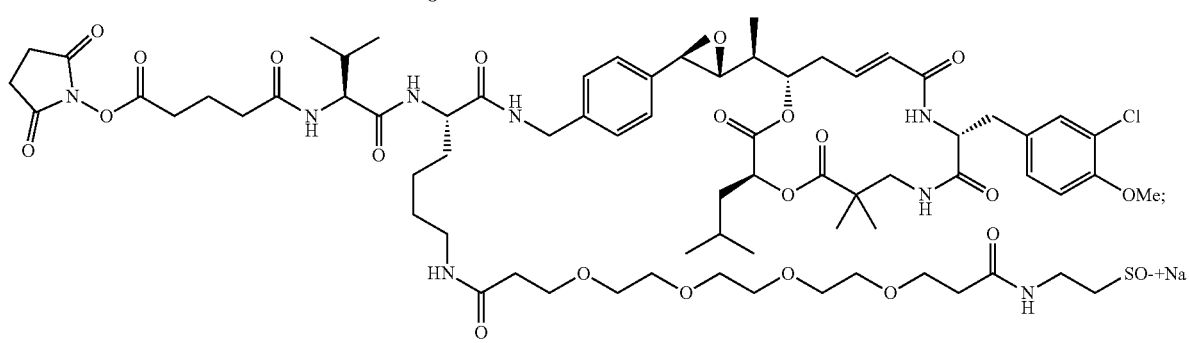
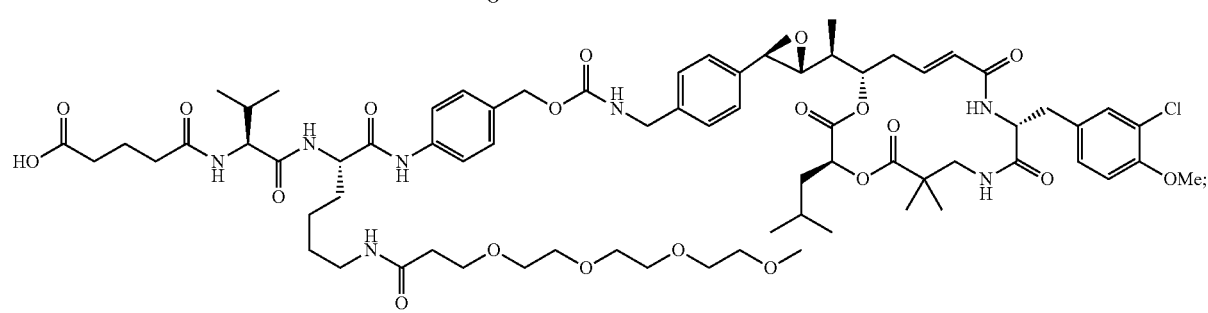
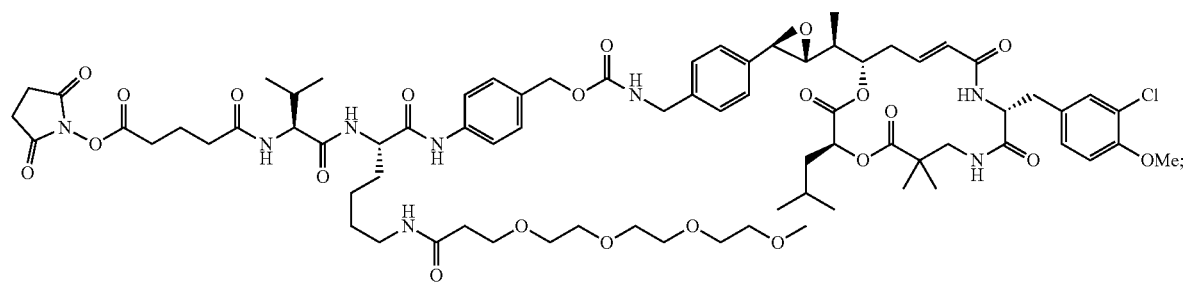

105
106
-continued
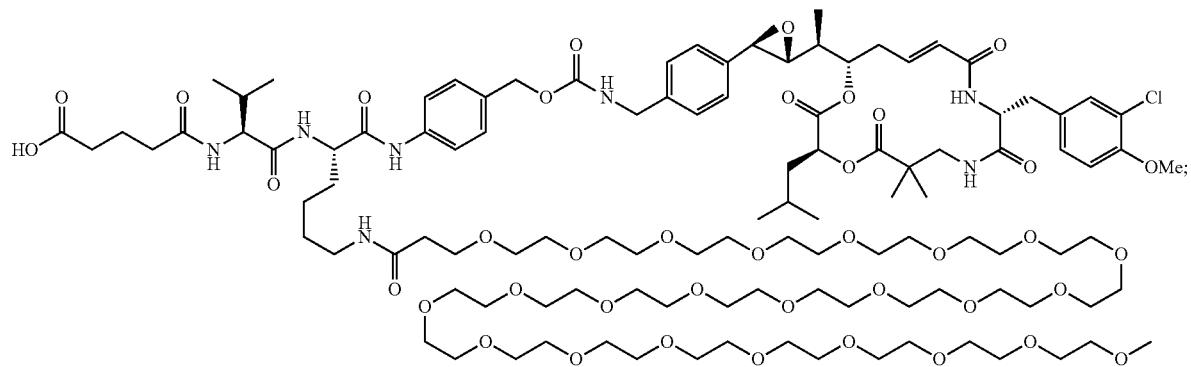
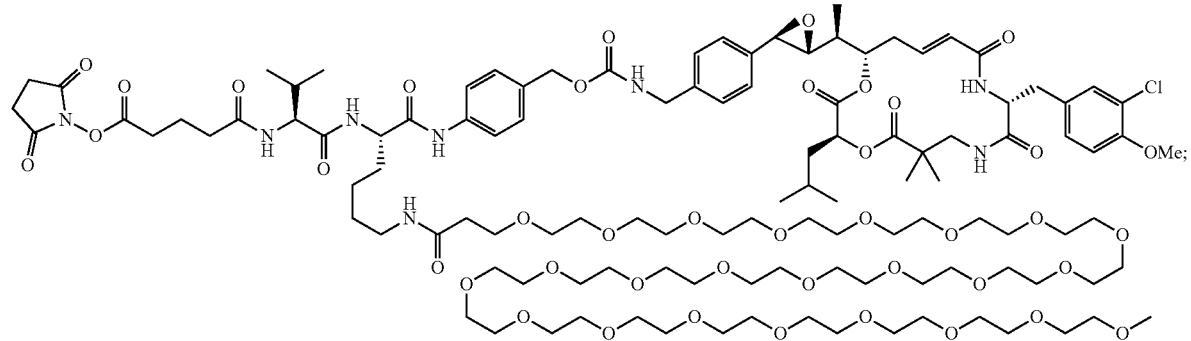
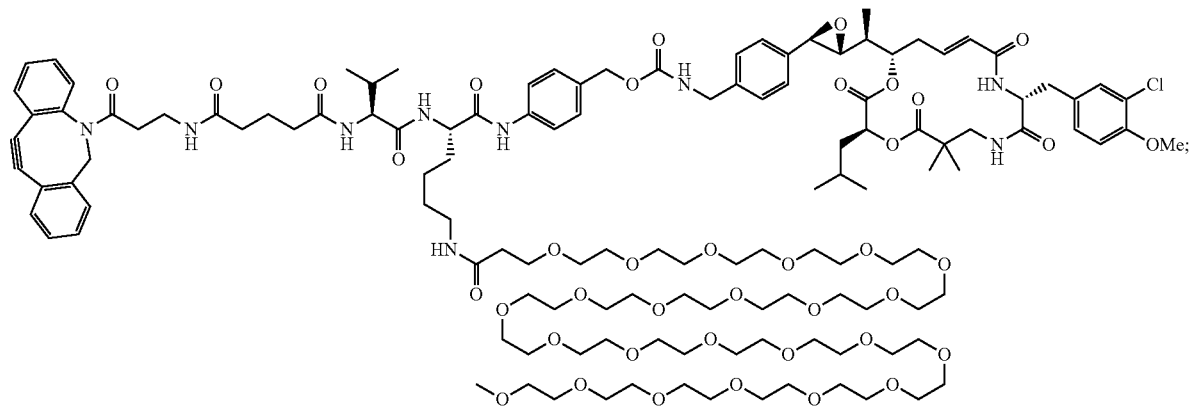 [SMILES: COCCOCCOCCOCCOCCOCCOCCOCCOCCOCCOCCOCCOCCOCCOCCOCCOCCOCCOCCOCCOCCOCCOCCOCCC(=O)NCCCC[C@H](NC(=O)[C@@H](NC(=O)CCCC(=O)NCCC(=O)N1Cc2ccccc2C#Cc2ccccc21)C(C)C)C(=O)Nc1ccc(COC(=O)NCc2ccc([C@@H](C)[C@H](O)[C@@H](C)[C@@H]3C/C=C/C(=O)N[C@H](Cc4ccc(OC)c(Cl)c4)C(=O)NCC(C)(C)C(=O)O[C@@H](CC(C)C)C(=O)O3)cc2)cc1]
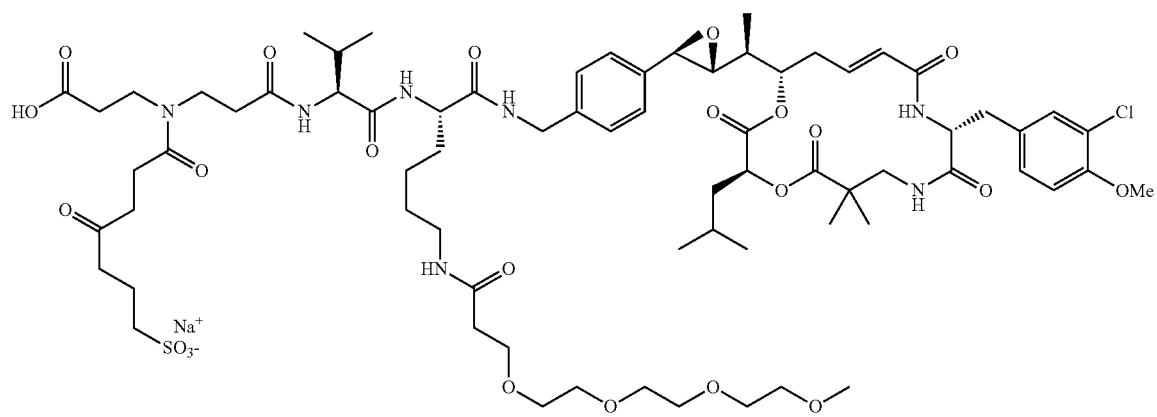
and

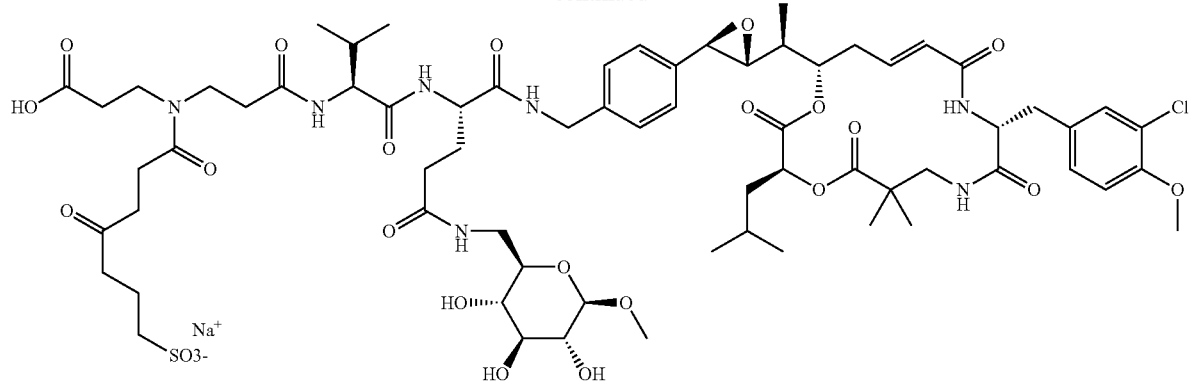

The disclosure further relates to conjugates of formula (V):

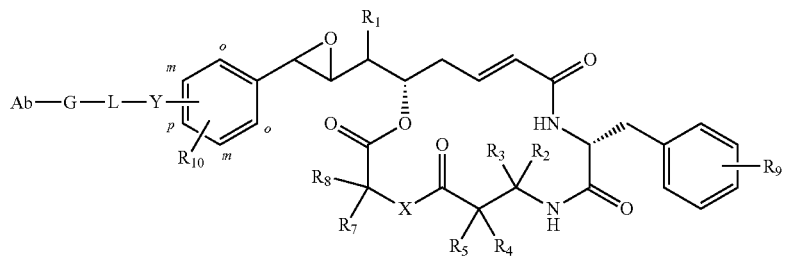

wherein:
$R_1$, $R_2$, $R_3$, $R_4$, $R_5$, $R_6$, $R_7$, $R_8$, $R_9$, $R_{10}$, $R_{11}$ and $R_{12}$ are as defined in formula (IV);
X, Y and L are as defined in formula (IV);
G represents the product of reaction between RCG1, a reactive chemical group present at the end of the linker L of formula (II), and RCG2, an orthogonal reactive chemical group present on a polypeptide such as the antibody (Ab);
Ab represents an antibody.

The attachment between the cryptophycin payload of formula (IV) and the antibody, in order to obtain the conjugate of formula (V), is produced by the reaction between the reactive chemical group RCG1 present on the payload as defined above that is reactive towards a reactive group RCG2 present on the polypeptide such as the antibody. The reaction between RCG1 and RCG2 ensures the attachment of the compound of formula (IV) to the antibody by formation of a covalent bond. In the conjugate of formula (V), parts of RCG1 and RCG2 can remain forming the attachment between the linker and the antibody.

Examples of RCG2 that may be mentioned include (Garnett M. C., et al., *Advanced Drug Delivery Reviews* 2001, 53, 171-216):

(i) ε-amino groups of lysines borne by the side chains of the lysine residues that are present at the surface of an antibody;
(ii) α-amino groups of N-terminal amino acids of antibody heavy and light chains;
(iii) the saccharide groups of the hinge region;
(iv) the thiols of cysteines generated by reducing intra-chain disulfide bonds or the thiols of engineered cysteines;
(v) amide groups borne by the side chains of some glutamine residues that are present at the surface of an antibody;
(vi) aldehyde groups introduced using formylglycine generating enzyme.

More recently, other conjugation approaches have been considered, for instance the introduction of cysteines by mutation (Junutula J. R., et al., *Nature Biotechnology* 2008, 26, 925-932), the introduction of unnatural amino acids allowing other types of chemistry (Axup J. Y., et al., *PNAS* 2012, 109, 40, 16101-16106) or the conjugation on antibody glycans (Zhou Q., et al., *Bioconjugate Chem.* 2014, 25, 510-520). Use of cysteine bridging dibromomaleimides (Behrens C. R., et al., *Mol. Pharmaceutics* 2015 3986-3998) and bis-sulfone reagents (Bryant P., et al., *Mol. Pharmaceutics* 2015 1872-1879) in order to cross-link antibodies have also been described and could be applied to the present disclosure.

Another approach for site-specific modifications of antibodies is based on enzymatic conjugation using for example bacterial transglutaminase (Jeger S., et al., *Angew. Chem. Int. Ed.* 2010, 49, 9995-9997; Strop P., et al., *Chem. Biol.* 2013, 20, 161-167) or formylglycine generating enzyme (Hudak J. E., et al., *Angew. Chem. Int. Ed.* 2012, 51, 4161-4165). For a review of site-specific conjugation strategies, see Agarwal P. and Bertozzi C. R., *Bioconjugate Chem* 2015, 26, 176-192. These conjugation technologies may also be applied to cryptophycin payloads described in the present disclosure.

It is also possible to chemically modify the polypeptide such as the antibody so as to introduce novel reactive chemical groups RCG2. Thus, it is well known to those skilled in the art how to modify an antibody with the aid of a modifying agent introducing for example activated disulfide, thiol, maleimido, haloacetamido, azido, alkyne or cycloalkyne groups (see especially WO2005/077090 page 14 and WO2011/001052). The modification makes it possible to improve the conjugation reaction and to use a wider variety of RCG1 groups.

For instance, in the case where RCG1 is of the type (ii) above, it is possible to chemically modify the antibody using an adequate modifying agent or to introduce one or more unnatural amino acids so as to introduce the adequate functions RCG2.

For example:

- when RCG1 represents a N-hydroxysuccinimidyl ester, RCG2 represents a —NH$_2$ group;
- when RCG1 represents a maleimido function, a haloacetamido function, a chorine atom or an activated disulfide, RCG2 may be a SH group;
- when RCG1 represents a N$_3$ group, RCG2 may be a C≡CH function or an activated C≡C function such as a cyclooctyne moiety;
- when RCG1 represents a OH group or NH$_2$ group, RCG2 may be a carboxylic acid or amide function;
- when RCG1 represents a SH group, RCG2 may be a maleimido function, a haloacetamido function or an activated disulfide function;
- when RCG1 represents a C≡CH function or an activated C≡C function, RCG2 may be a N$_3$ group;
- when RCG1 represents a O-alkyl hydroxylamine function or a Pictet-Spengler reaction substrate, RCG2 may be an aldehyde or ketone function.

Examples of G that may be mentioned include

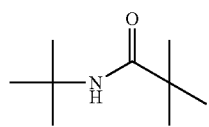
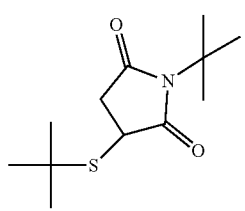
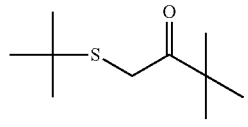
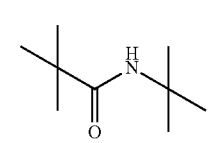
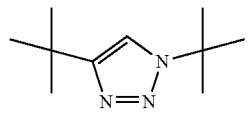
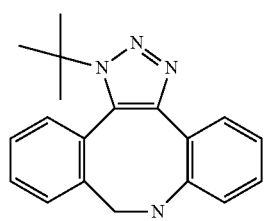
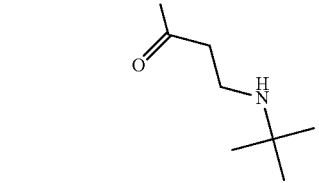

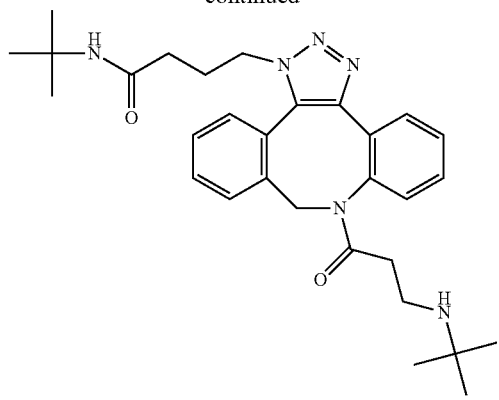

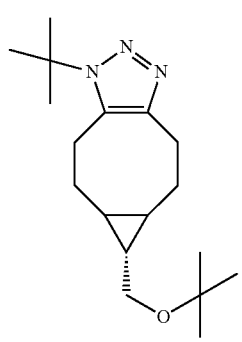

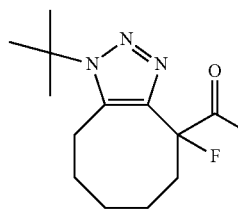

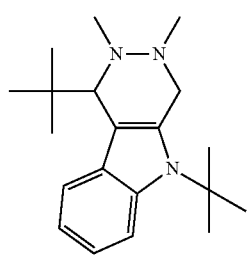

For instance, G represents the following groups:

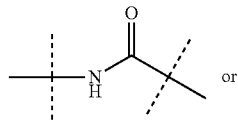 or

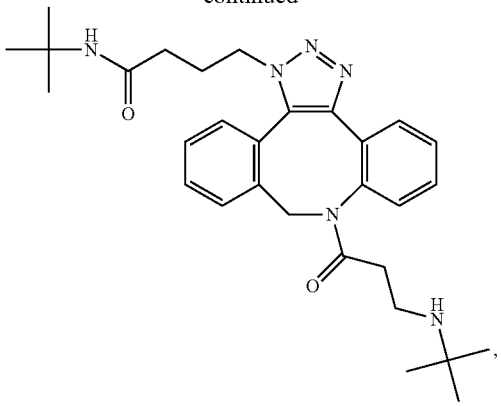

such as

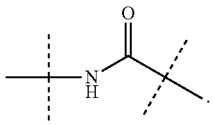

Among the compounds of formula (V) that are subject matter of the present disclosure, a group of compounds is composed of the compounds for which $R_1$ represents a $(C_1-C_6)$alkyl, such as a methyl group.

Among the compounds of formula (V) that are subject matter of the disclosure, a group of compounds is composed of the compounds for which each of $R_2$ and $R_3$ represents a hydrogen atom.

Among the compounds of formula (V) that are subject matter of the disclosure, a group of compounds is composed of the compounds for which one of $R_2$ and $R_3$ represents a $(C_1-C_6)$alkyl group, such as a methyl group and the other one represents a hydrogen atom.

Among the compounds of formula (V) that are subject matter of the disclosure, a group of compounds is composed of the compounds for which $R_2$ and $R_3$ form together with the carbon atom to which they are attached a $(C_3-C_6)$ cycloalkyl group, such as a cyclopropyl group.

Among the compounds of formula (V) that are subject matter of the disclosure, a group of compounds is composed of the compounds for which each of $R_4$ and $R_5$ represents a $(C_1-C_6)$alkyl group, in particular a methyl group.

Among the compounds of formula (V) that are subject matter of the disclosure, a group of compounds is composed of the compounds for which X represents an oxygen atom, that is to say O.

Among the compounds of formula (V) that are subject matter of the disclosure, a group of compounds is composed of the compounds for which X represents NH.

Among the compounds of formula (V) that are subject matter of the disclosure, a group of compounds is composed of the compounds for which $R_7$ and $R_8$ represent independently of each other a hydrogen atom or a $(C_1-C_6)$alkyl group, such as an isobutyl group or a neopentyl group.

Among the compounds of formula (V) that are subject matter of the disclosure, a group of compounds is composed of the compounds for which $R_9$ represents two substituents selected from a methoxy group and a chlorine atom. For instance, the phenyl nucleus comprises two substituents in positions 3 and 4 on the phenyl nucleus. For example 3-Cl and 4-methoxy.

Among the compounds of formula (V) that are subject matter of the disclosure, a group of compounds is composed of the compounds for which $R_{10}$ represents a hydrogen atom.

Among the compounds of formula (v) that are subject matter of the disclosure, a group of compounds is composed of the compounds for which Y is positioned in the para position of the phenyl nucleus.

Among the compounds of formula (V) that are subject matter of the disclosure, a group of compounds is composed of the compounds for which Y $NR_{11}$—$(C_1-C_6)$alkyl, such as $NR_{11}$—$(C_1-C_3)$alkyl, for instance NH—$CH_2$.

Among the compounds of formula (V) that are subject matter of the disclosure, a group of compounds is composed of the compounds for which L of formula (II) comprises at least one substituted amino acid $AA_s$ in the sequence of w amino acids $(AA)_w$, L1 and L2 are as defined in formula (II).

Among the compounds of formula (V) that are subject matter of the disclosure, a group of compounds is composed of the compounds for which L of formula (II) comprises a sequence of w non-substituted amino-acid $AA_{ns}$, L1 and L2 are as defined in formula (II).

Among the compounds of formula (V) that are subject matter of the disclosure, a group of compounds is composed of the compounds for which $(AA)_w$ in L of formula (II) contains at least one substituted amino acid $AA_s$ and L2 represents:
 a $(C_1-C_6)$alkyl group, such as a $(CH_2)_3$ group;
 a C(=O)—$(C_1-C_6)$alkyl group, such as a C(=O)—$(CH_2)_3$ group; or
 a $(C_1-C_6)$alkyl-$NA_7$-$(C_1-C_6)$alkyl group, such as a $(CH_2)_2$—$NA_7$-$(CH_2)_2$ group in which $A_7$ is as defined above.

Among the compounds of formula (V) that are subject matter of the disclosure, a group of compounds is composed of the compounds for which $(AA)_w$ in L of formula (II) contains at least one substituted amino acid $AA_s$ and L2 represents:
 a $(C_1-C_6)$alkyl group, such as a $(CH_2)_3$ group;
 a C(=O)—$(C_1-C_6)$alkyl group, such as a C(=O)—$(CH_2)_3$ group; or
 a $(C_1-C_6)$alkyl-$NA_7$-$(C_1-C_6)$alkyl group, such as a $(CH_2)_2$—$NA_7$-$(CH_2)_2$ group in which $A_7$ is a —C(=O)—$(CH_2)_2$—C(=O)—NH—$(CH_2)_2$—$SO_3H$ group;
being understood that each $A_7$ comprising a $SO_3H$ function can be under salt forms such as alkali metal salts, for instance sodium salts ($SO_3^-$ $^+Na$).

Among the compounds of formula (V) that are subject matter of the disclosure, a group of compounds is composed of the compounds for which $(AA)_w$ in L of formula (II) contains w non-substituted amino acid $AA_{ns}$ and L2 represents:
a $(C_1-C_6)$alkyl-$NA_7$-$(C_1-C_6)$alkyl group, such as a $(CH_2)_2$—$NA_7$-$(CH_2)_2$ group in which $A_7$ is as defined above.

Among the compounds of formula (V) that are subject matter of the disclosure, a group of compounds is composed of the compounds for which $(AA)_w$ in L of formula (II) contains w non-substituted amino acid $AA_{ns}$ and L2 represents:
a $(C_1-C_6)$alkyl-$NA_7$-$(C_1-C_6)$alkyl group, such as a $(CH_2)_2$—$NA_7$-$(CH_2)_2$ group in which $A_7$ represents:
 a C(=O)—$[(CH_2)_2—O]_a$—$CH_3$ group wherein "a" represents an integer ranging from 1 to 50, for instance ranging from 1 to 24, such as 4, 7 and 24, for example $A_7$ is a C(=O)—$[(CH_2)_2—O]_4$—$CH_3$ group, a C(=O)—$[(CH_2)_2—O]_7$—$CH_3$ group, or a C(=O)—$[(CH_2)_2—O]_{24}$—$CH_3$ group;
 a —C(=O)—$(CH_2)_2$—C(=O)—NH—$(CH_2)_2$—$SO_3H$ group; or a C(=O)—(CH$_2$)$_2$—C(=O)—NH—[(CH$_2$)$_2$—O]$_a$—(CH$_2$)$_2$—C(=O)—NH—(CH$_2$)$_2$—SO$_3$H group wherein "a" represents an integer ranging from 1 to 50, such as ranging from 1 to 24, for example 4, such as A$_7$ is —C(=O)—(CH$_2$)$_2$—C(=O)—NH—[(CH$_2$)$_2$—O]$_4$—(CH$_2$)$_2$—C(=O)—NH—(CH$_2$)$_2$—SO$_3$H group;

being understood that each A$_7$ comprising a SO$_3$H function can be under salt forms such as alkali metal salts, for instance sodium salts (SO$_3^-$ $^+$Na); Among the compounds of formula (V) that are subject matter of the disclosure, a group of compounds is composed of the compounds for which (AA)w in L of formula (II) contains at least one substituted amino acid AA$_s$ and/or w non-substituted amino acid AA$_{ns}$ and L2 represents:

a NA$_7$-(C$_1$-C$_6$)alkyl group, a (C$_1$-C$_6$)alkyl-NA$_7$ group, a NA$_7$-(CH$_2$CH$_2$O)$_i$(C$_1$-C$_6$)alkyl group, a NA$_7$-aryl group, a NA$_7$-heteroaryl group, a (C$_1$-C$_6$)alkyl-NA$_7$C(=O)—(C$_1$-C$_6$)alkyl group, a (C$_1$-C$_6$)alkyl-NA$_7$C(=O)—(C$_1$-C$_6$)alkyl-(OCH$_2$CH$_2$)$_i$ group, a (C$_1$-C$_6$)alkyl-C(=O)NA$_7$-(C$_1$-C$_6$)alkyl group, a (C$_1$-C$_6$)alkyl-C(=O)NA$_7$-(C$_1$-C$_6$)alkyl-(OCH$_2$CH$_2$)$_i$ group, a (C$_1$-C$_6$)alkyl-NA$_7$-(C$_1$-C$_6$)alkyl group, a (C$_1$-C$_6$)alkyl-NA$_7$-(C$_1$-C$_6$)alkyl-(OCH$_2$CH$_2$)$_i$ group, a (C$_1$-C$_6$)alkyl-(OCH$_2$CH$_2$)$_i$—NA$_7$-(C$_1$-C$_6$)alkyl group, a C(=O)—NA$_7$-(C$_1$-C$_6$)alkyl group, a C(=O)—(C$_1$-C$_6$)alkyl-NA$_7$ group, a C(=O)—NA$_7$-(CH$_2$CH$_2$O)$_i$(C$_1$-C$_6$)alkyl group, a C(=O)—NA$_7$-aryl group, a C(=O)—NA$_7$-heteroaryl group, a C(=O)—(C$_1$-C$_6$)alkyl-NA$_7$C(=O)—(C$_1$-C$_6$)alkyl group, a C(=O)—(C$_1$-C$_6$)alkyl-NA$_7$C(=O)—(C$_1$-C$_6$)alkyl-(OCH$_2$CH$_2$)$_i$ group, a C(=O)—(C$_1$-C$_6$)alkyl-C(=O)NA$_7$-(C$_1$-C$_6$)alkyl group, a C(=O)—(C$_1$-C$_6$)alkyl-C(=O)NA$_7$-(C$_1$-C$_6$)alkyl-(OCH$_2$CH$_2$)$_i$ group, a C(=O)—(C$_1$-C$_6$)alkyl-NA$_7$-(C$_1$-C$_6$)alkyl group, a C(=O)—(C$_1$-C$_6$)alkyl-NA$_7$-(C$_1$-C$_6$)alkyl-(OCH$_2$CH$_2$)$_i$ group, a C(=O)—(C$_1$-C$_6$)alkyl-(OCH$_2$CH$_2$)$_i$—NA$_7$-(C$_1$-C$_6$)alkyl group, a NA$_8$-(C$_1$-C$_6$)alkyl-NA$_7$ group, a NA$_8$-(C$_1$-C$_6$)alkyl-NA$_7$C(=O)—(C$_1$-C$_6$)alkyl group, a NA$_8$-(C$_1$-C$_6$)alkyl-NA$_7$C(=O)—(C$_1$-C$_6$)alkyl-(OCH$_2$CH$_2$)$_i$ group, a NA$_8$-(C$_1$-C$_6$)alkyl-C(=O)NA$_7$-(C$_1$-C$_6$)alkyl group, a NA$_8$-(C$_1$-C$_6$)alkyl-C(=O)NA$_7$-(C$_1$-C$_6$)alkyl-(OCH$_2$CH$_2$)$_i$ group, a NA$_8$-(C$_1$-C$_6$)alkyl-NA$_7$-(C$_1$-C$_6$)alkyl group, a NA$_8$-(C$_1$-C$_6$)alkyl-NA$_7$-(C$_1$-C$_6$)alkyl-(OCH$_2$CH$_2$)$_i$ group, a NA$_8$-(C$_1$-C$_6$)alkyl-(OCH$_2$CH$_2$)$_i$—NA$_7$-(C$_1$-C$_6$)alky group, a C(=O)—NA$_8$-(C$_1$-C$_6$)alkyl-NA$_7$ group, a C(=O)—NA$_8$-(C$_1$-C$_6$)alkyl-NA$_7$C(=O)—(C$_1$-C$_6$)alkyl group, a C(=O)—NA$_8$-(C$_1$-C$_6$)alkyl-NA$_7$C(=O)—(C$_1$-C$_6$)alkyl-(OCH$_2$CH$_2$)$_i$ group, a C(=O)—NA$_8$-(C$_1$-C$_6$)alkyl-C(=O)NA$_7$-(C$_1$-C$_6$)alkyl group, a C(=O)—NA$_8$-(C$_1$-C$_6$)alkyl-C(=O)NA$_7$-(C$_1$-C$_6$)alkyl-(OCH$_2$CH$_2$)$_i$ group, a C(=O)—NA$_8$-(C$_1$-C$_6$)alkyl-NA$_7$-(C$_1$-C$_6$)alkyl group, a C(=O)—NA-(C$_1$-C$_6$)alkyl-NA$_7$-(C$_1$-C$_6$)alkyl-(OCH$_2$CH$_2$)$_i$ group or a C(=O)—NA$_8$-(C$_1$-C$_6$)alkyl-(OCH$_2$CH$_2$)$_i$—NA$_7$-(C$_1$-C$_6$)alkyl group; wherein i, A$_7$ and A$_8$ are as defined above.

Among the compounds of formula (V) that are subject matter of the disclosure, a preferred group of compounds is composed of the compounds for which (AA)w in L of formula (II) contains at least one substituted amino acid AA$_s$ and/or w non-substituted amino acid AA$_{ns}$ and L2 represents:

a NA$_7$-(C$_1$-C$_6$)alkyl group, a (C$_1$-C$_6$)alkyl-NA$_7$ group, a NA$_7$-(CH$_2$CH$_2$O)$_i$(C$_1$-C$_6$)alkyl group, a NA$_7$-aryl group, a NA$_7$-heteroaryl group, a (C$_1$-C$_6$)alkyl-NA$_7$C(=O)—(C$_1$-C$_6$)alkyl group, a (C$_1$-C$_6$)alkyl-NA$_7$C(=O)—(C$_1$-C$_6$)alkyl-(OCH$_2$CH$_2$)$_i$ group, a (C$_1$-C$_6$)alkyl-C(=O)NA$_7$-(C$_1$-C$_6$)alkyl group, a (C$_1$-C$_6$)alkyl-C(=O)NA$_7$-(C$_1$-C$_6$)alkyl-(OCH$_2$CH$_2$)$_i$ group, a (C$_1$-C$_6$)alkyl-NA$_7$-(C$_1$-C$_6$)alkyl group, a (C$_1$-C$_6$)alkyl-NA$_7$-(C$_1$-C$_6$)alkyl-(OCH$_2$CH$_2$)$_i$ group, a (C$_1$-C$_6$)alkyl-(OCH$_2$CH$_2$)$_i$—NA$_7$-(C$_1$-C$_6$)alkyl group, a C(=O)—NA$_7$-(C$_1$-C$_6$)alkyl group, a C(=O)—(C$_1$-C$_6$)alkyl-NA$_7$ group, a C(=O)—NA$_7$-(CH$_2$CH$_2$O)$_i$(C$_1$-C$_6$)alkyl group, a C(=O)—(C$_1$-C$_6$)alkyl-NA$_7$C(=O)—(C$_1$-C$_6$)alkyl group, a C(=O)—(C$_1$-C$_6$)alkyl-NA$_7$C(=O)—(C$_1$-C$_6$)alkyl-(OCH$_2$CH$_2$)$_i$ group, a C(=O)—(C$_1$-C$_6$)alkyl-C(=O)NA$_7$-(C$_1$-C$_6$)alkyl group, a C(=O)—(C$_1$-C$_6$)alkyl-C(=O)NA$_7$-(C$_1$-C$_6$)alkyl-(OCH$_2$CH$_2$)$_i$ group, a C(=O)—(C$_1$-C$_6$)alkyl-NA$_7$-(C$_1$-C$_6$)alkyl group, a C(=O)—(C$_1$-C$_6$)alkyl-NA$_7$-(C$_1$-C$_6$)alkyl-(OCH$_2$CH$_2$)$_i$ group, a NA$_8$-(C$_1$-C$_6$)alkyl-NA$_7$ group, a NA$_8$-(C$_1$-C$_6$)alkyl-NA$_7$C(=O)—(C$_1$-C$_6$)alkyl group, a NA$_8$-(C$_1$-C$_6$)alkyl-C(=O)NA$_7$-(C$_1$-C$_6$)alkyl group, a NA$_8$-(C$_1$-C$_6$)alkyl-NA$_7$-(C$_1$-C$_6$)alkyl group, a C(=O)—NA$_8$-(C$_1$-C$_6$)alkyl-NA$_7$ group, a C(=O)—NA$_8$-(C$_1$-C$_6$)alkyl-NA$_7$C(=O)—(C$_1$-C$_6$)alkyl group, a C(=O)—NA$_8$-(C$_1$-C$_6$)alkyl-C(=O)NA$_7$-(C$_1$-C$_6$)alkyl group, or a C(=O)—NA$_8$-(C$_1$-C$_6$)alkyl-NA$_7$-(C$_1$-C$_6$)alkyl group; wherein i, A$_7$ and A$_8$ are as defined above.

Among the compounds of formula (V) that are subject matter of the disclosure, a more preferred group of compounds is composed of the compounds for which (AA)w in L of formula (II) contains at least one substituted amino acid AA$_s$ and/or w non-substituted amino acid AA$_{ns}$ and L2 represents:

a NA$_7$-(C$_1$-C$_6$)alkyl group, a (C$_1$-C$_6$)alkyl-NA$_7$ group, a NA$_7$-(CH$_2$CH$_2$O)$_i$(C$_1$-C$_6$)alkyl group, a (C$_1$-C$_6$)alkyl-NA$_7$C(=O)—(C$_1$-C$_6$)alkyl group, a (C$_1$-C$_6$)alkyl-NA$_7$C(=O)—(C$_1$-C$_6$)alkyl-(OCH$_2$CH$_2$)$_i$ group, a (C$_1$-C$_6$)alkyl-C(=O)NA$_7$-(C$_1$-C$_6$)alkyl group, a (C$_1$-C$_6$)alkyl-C(=O)NA$_7$-(C$_1$-C$_6$)alkyl-(OCH$_2$CH$_2$)$_i$ group, a (C$_1$-C$_6$)alkyl-NA$_7$-(C$_1$-C$_6$)alkyl group, a (C$_1$-C$_6$)alkyl-NA$_7$-(C$_1$-C$_6$)alkyl-(OCH$_2$CH$_2$)$_i$ group, a (C$_1$-C$_6$)alkyl-(OCH$_2$CH$_2$)$_i$-NA$_7$-(C$_1$-C$_6$)alkyl group, a C(=O)—NA$_7$-(C$_1$-C$_6$)alkyl group, a C(=O)—(C$_1$-C$_6$)alkyl-NA$_7$ group, a C(=O)—NA$_7$-(CH$_2$CH$_2$O)$_i$(C$_1$-C$_6$)alkyl group, a C(=O)—(C$_1$-C$_6$)alkyl-NA$_7$C(=O)—(C$_1$-C$_6$)alkyl group, a C(=O)—(C$_1$-C$_6$)alkyl-NA$_7$C(=O)—(C$_1$-C$_6$)alkyl-(OCH$_2$CH$_2$)$_i$ group, a C(=O)—(C$_1$-C$_6$)alkyl-C(=O)NA$_7$-(C$_1$-C$_6$)alkyl group, a C(=O)—(C$_1$-C$_6$)alkyl-C(=O)NA$_7$-(C$_1$-C$_6$)alkyl-(OCH$_2$CH$_2$)$_i$ group, a C(=O)—(C$_1$-C$_6$)alkyl-NA$_7$-(C$_1$-C$_6$)alkyl group, a C(=O)—(C$_1$-C$_6$)alkyl-NA$_7$-(C$_1$-C$_6$)alkyl-(OCH$_2$CH$_2$)$_i$ group, a NA$_8$-(C$_1$-C$_6$)alkyl-NA$_7$ group, a NA$_8$-(C$_1$-C$_6$)alkyl-NA$_7$C(=O)—(C$_1$-C$_6$)alkyl group, a NA$_8$-(C$_1$-C$_6$)alkyl-C(=O)NA$_7$-(C$_1$-C$_6$)alkyl group, a NA$_8$-(C$_1$-C$_6$)alkyl-NA$_7$-(C$_1$-C$_6$)alkyl group, a C(=O)—NA$_8$-(C$_1$-C$_6$)alkyl-NA$_7$ group, a C(=O)—NA$_8$-(C$_1$-C$_6$)alkyl-NA$_7$C(=O)—(C$_1$-C$_6$)alkyl group, a C(=O)—NA$_8$-(C$_1$-C$_6$)alkyl-C(=O)NA$_7$-(C$_1$-C$_6$)alkyl group, or a C(=O)—NA$_8$-(C$_1$-C$_6$)alkyl-NA$_7$-(C$_1$-C$_6$)alkyl group; wherein i, A$_7$ and A$_8$ are as defined above.

Among the compounds of formula (V) that are subject matter of the disclosure, a still more preferred group of compounds is composed of the compounds for which (AA)w in L of formula (II) contains at least one substituted amino acid AA$_s$ and/or w non-substituted amino acid AA$_{ns}$ and L2 represents:

a NA$_7$-(C$_1$-C$_6$)alkyl group, a (C$_1$-C$_6$)alkyl-NA$_7$ group, a (C$_1$-C$_6$)alkyl-NA$_7$C(=O)—(C$_1$-C$_6$)alkyl group, a (C$_1$-C$_6$)alkyl-C(=O)NA$_7$-(C$_1$-C$_6$)alkyl group, a (C$_1$-C$_6$)alkyl-NA$_7$-(C$_1$-C$_6$)alkyl group, a C(=O)—NA$_7$-(C$_1$-C$_6$)alkyl group, a C(=O)—(C$_1$-C$_6$)alkyl-NA$_7$ group, a C(=O)—(C$_1$-C$_6$)alkyl-NA$_7$C(=O)—(C$_1$-C$_6$)alkyl group, a C(=O)—(C$_1$-C$_6$)alkyl-C(=O)NA$_7$-(C$_1$-C$_6$)alkyl group, a C(=O)—(C$_1$-C$_6$)alkyl-NA$_7$-(C$_1$-C$_6$)alkyl group, a NA$_8$-(C$_1$-C$_6$)alkyl-NA$_7$ group, a NA$_8$-(C$_1$-C$_6$)alkyl-NA$_7$C(=O)—(C$_1$-C$_6$)alkyl group, a NA$_8$-(C$_1$-C$_6$)alkyl-C(=O)NA$_7$-(C$_1$-C$_6$)alkyl group, a NA$_8$-(C$_1$-C$_6$)alkyl-NA$_7$-(C$_1$-C$_6$)alkyl group, a C(=O)—NA$_8$-(C$_1$-C$_6$)alkyl-NA$_7$ group, a C(=O)—NA$_8$-(C$_1$-C$_6$)alkyl-NA$_7$C(=O)—(C$_1$-C$_6$)alkyl group, a C(=O)—NA$_8$-(C$_1$-C$_6$)alkyl-C(=O)NA$_7$-(C$_1$-C$_6$)alkyl group, or a C(=O)—NA$_8$-(C$_1$-C$_6$)alkyl-NA$_7$-(C$_1$-C$_6$)alkyl group; wherein A$_7$ and A$_8$ are as defined above.

Among the compounds of formula (V) that are subject matter of the disclosure, a most preferred group of compounds is composed of the compounds for which (AA)w in L of formula (II) contains at least one substituted amino acid AA$_s$ and/or w non-substituted amino acid AA$_{ns}$ and L2 represents:
a (C$_1$-C$_6$)alkyl-NA$_7$-(C$_1$-C$_6$)alkyl group; wherein A$_7$ is as defined above.

Among the compounds of formula (V) that are subject matter of the disclosure, a group of compounds is composed of the compounds for which (AA)w in L of formula (II) contains at least one substituted amino acid AA$_s$ and/or w non-substituted amino acid AA$_{ns}$ and L2 comprises a A$_7$ representing:
a C(=O)—[(CH$_2$)$_2$—O]$_4$—CH$_3$ group; a C(=O)—[(CH$_2$)$_2$—O]$_7$—CH$_3$ group; a C(=O)—[(CH$_2$)$_2$—O]$_{24}$—CH$_3$ group; a C(=O)—(CH$_2$)$_2$—C(=O)—NH—(CH$_2$)$_2$—SO$_3$H group; a C(=O)—(CH$_2$)$_2$—C(=O)—NH—[(CH$_2$)$_2$—O]$_4$—(CH$_2$)$_2$—C(=O)—NH—(CH$_2$)$_2$—SO$_3$H group;
being understood that each A$_7$ comprising a SO$_3$H function can be under salt forms such as alkali metal salts, for instance sodium salts (SO$_3^-$ $^+$Na).

Among the compounds of formula (V) that are subject matter of the disclosure, a group of compounds is composed of the compounds for which (AA)w in L of formula (II) contains at least one substituted amino acid AA$_s$ and/or w non-substituted amino acid AA$_{ns}$ and L2 represents:

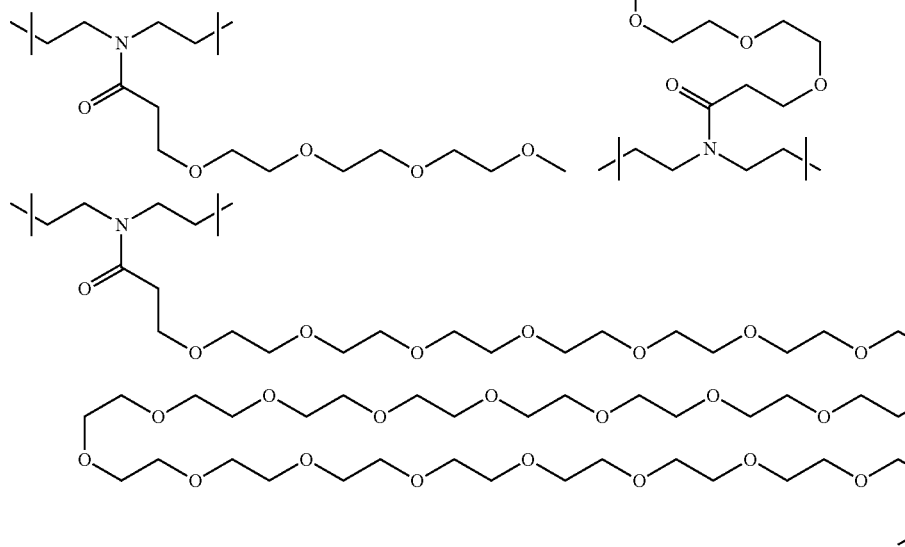

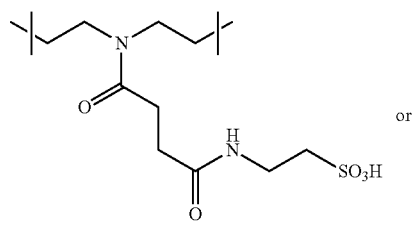

or

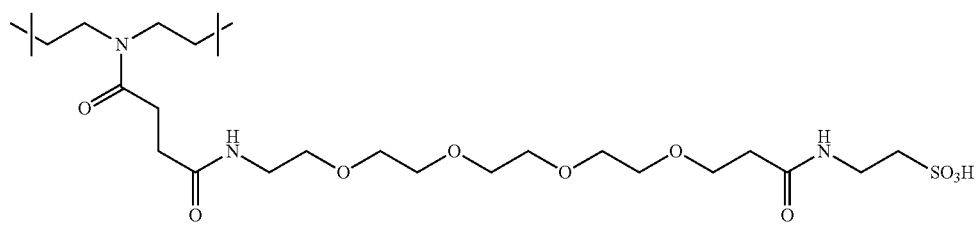

Among the compounds of formula (V) that are subject matter of the disclosure, a group of compounds is composed of the compounds comprising in L a sequence $(AA_s)w$ containing at least one substituted amino acid $AA_s$, $(AA_s)w$ being selected from the list:
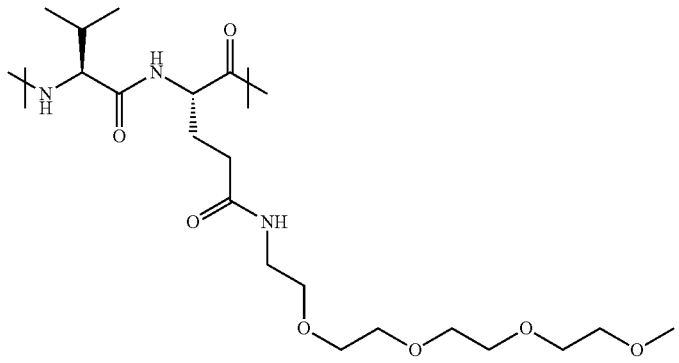
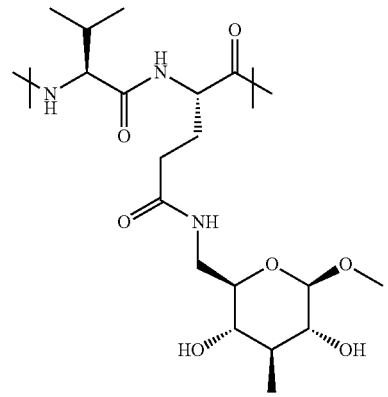
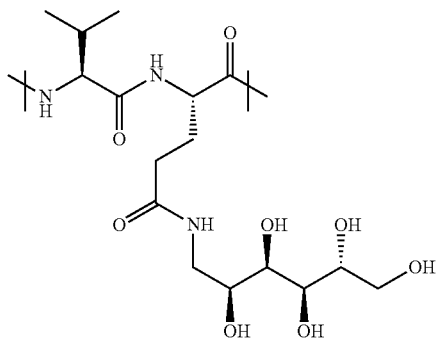
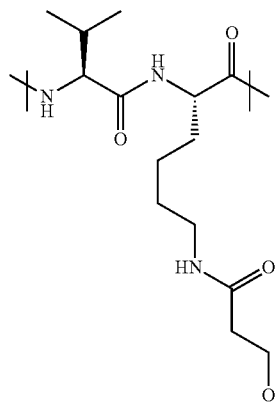
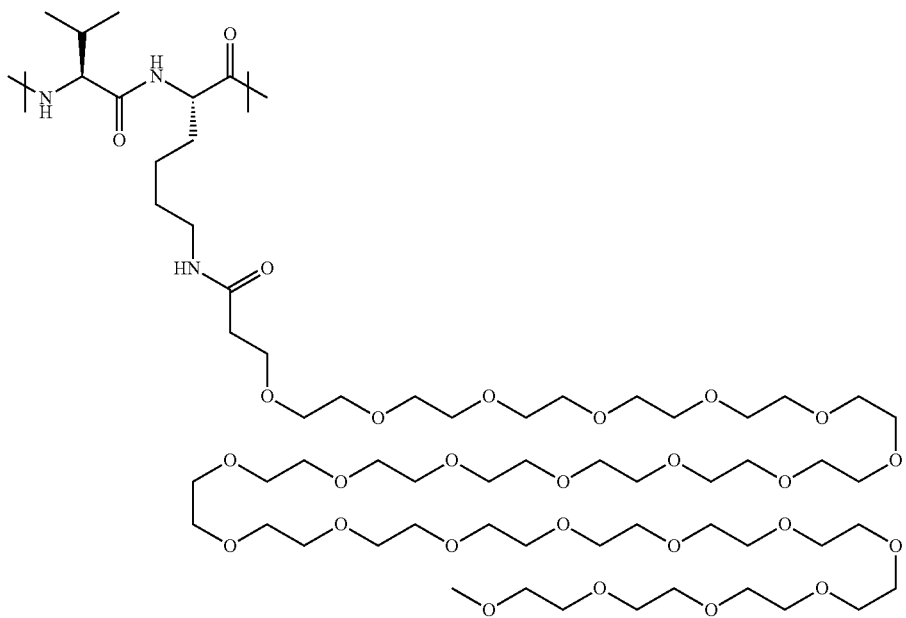

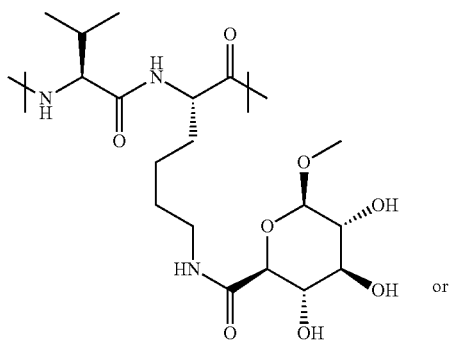

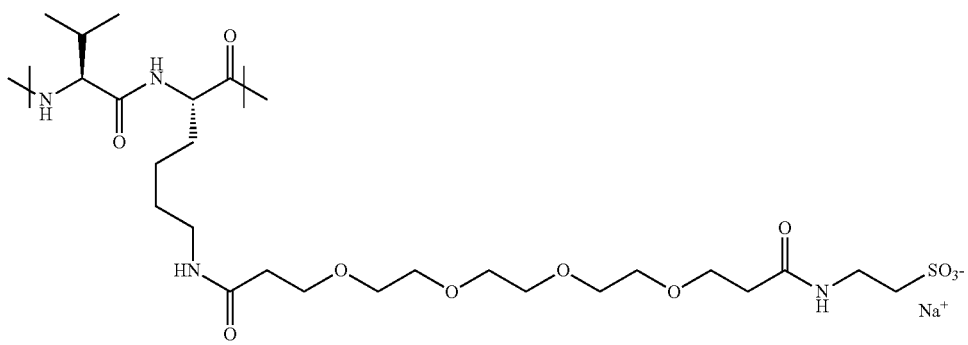

Among the compounds of formula (V) that are subject matter of the disclosure, a group of compounds is composed of the compounds for which Ab is an anti-Epha2 antibody, for instance hu2H11_R35R74 antibody as represented by SEQ ID NO: 1 (light chain of antibody hu2H11_R35R74) and by SEQ ID NO: 2 (heavy chain of antibody hu2H11_R35R74) corresponding to respectively SEQ ID NO: 16 and SEQ ID NO:18 represented in WO2011039724 A1.

According to at least one embodiment, the present disclosure relates to compounds of formula (V) wherein:

Ab represents an antibody;

G represents:

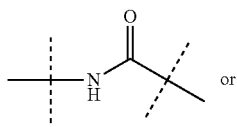

-continued

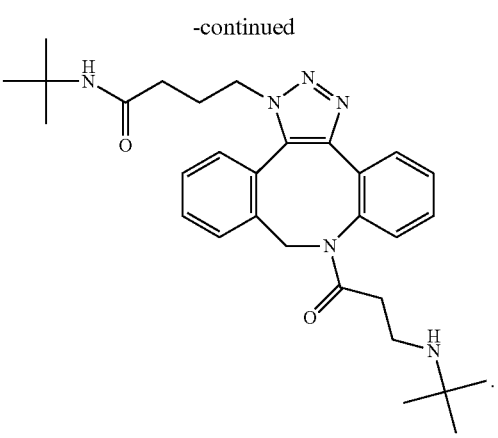

Y is a $NR_{11}$—$(C_1\text{-}6)$alkyl group in which $R_{11}$ is a hydrogen atom, for instance Y is a NH—$CH_2$ group;

L represents:

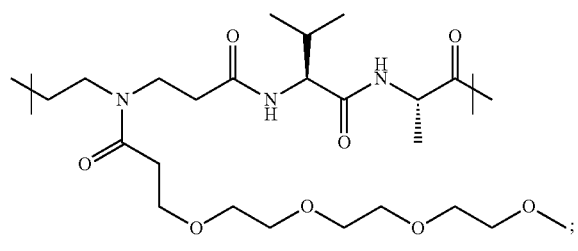

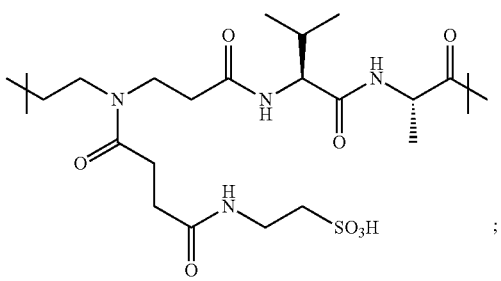

-continued
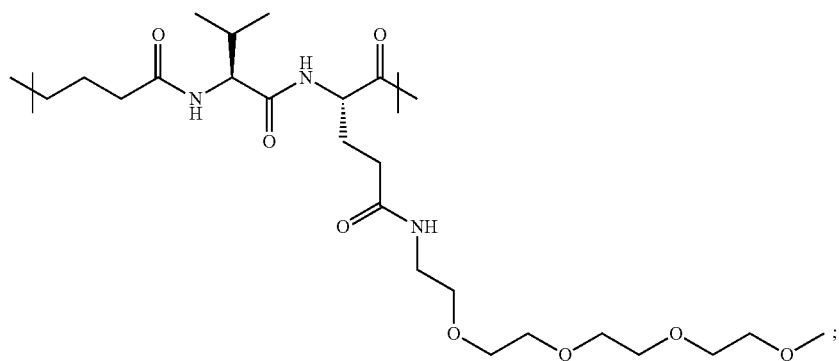
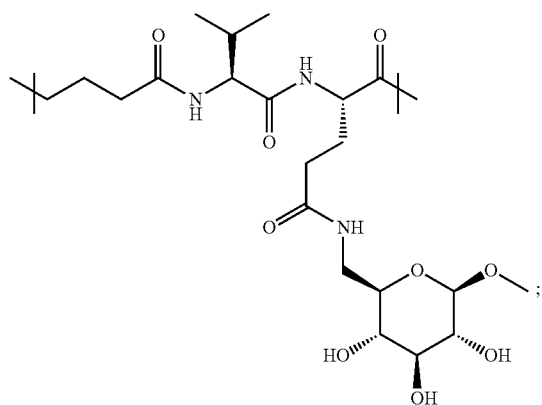
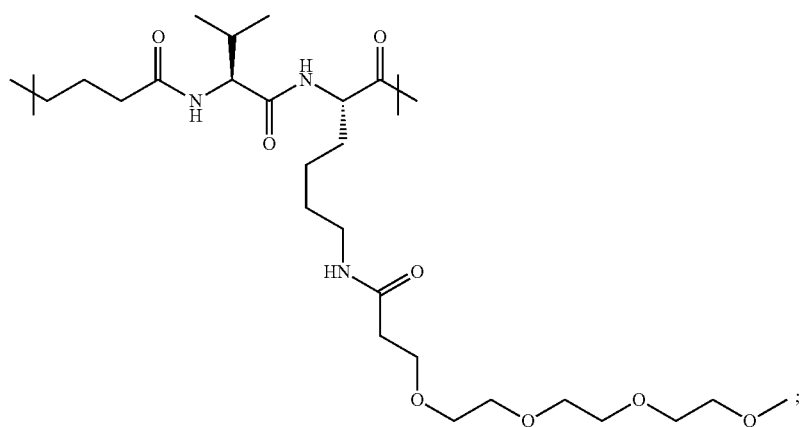

123
124
-continued
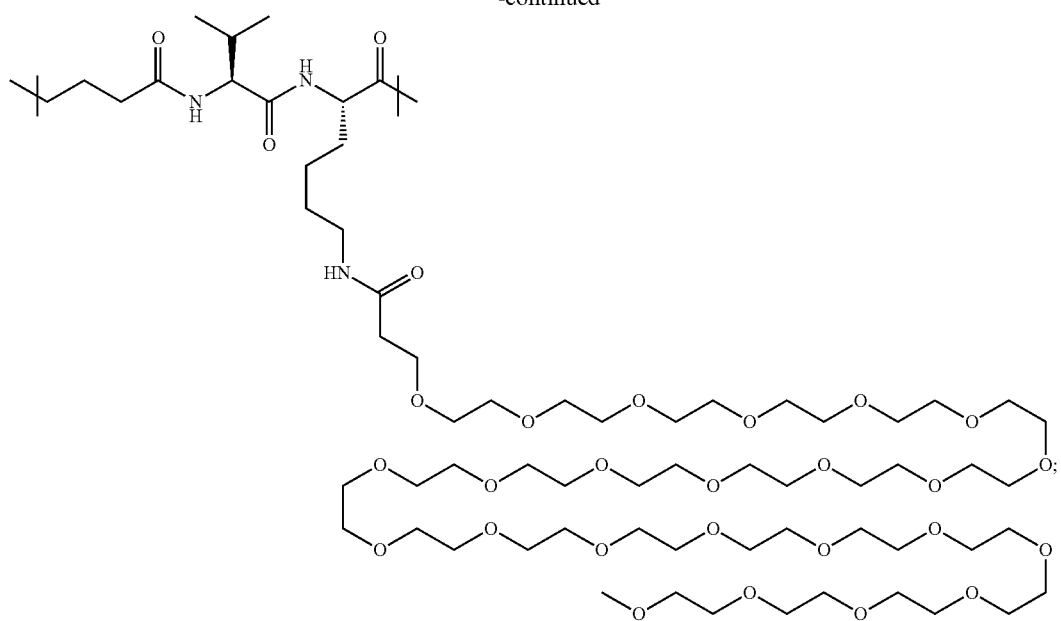
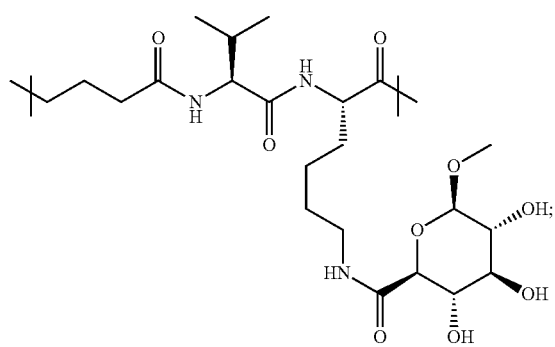
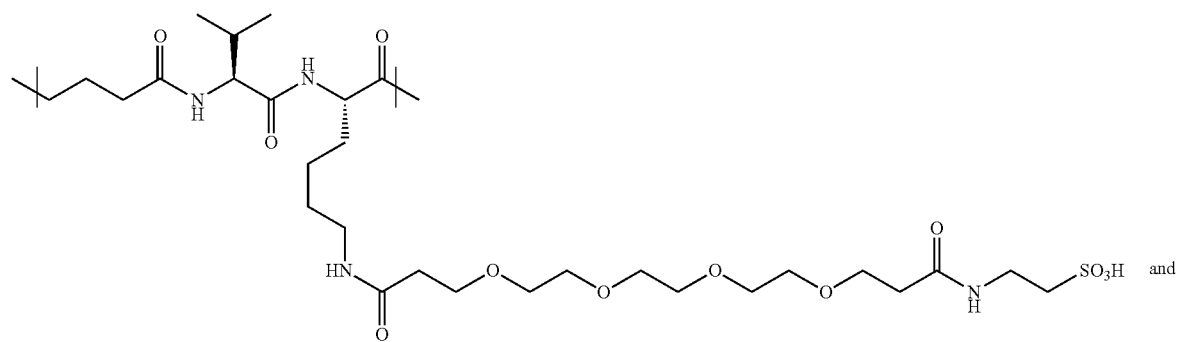
and

-continued

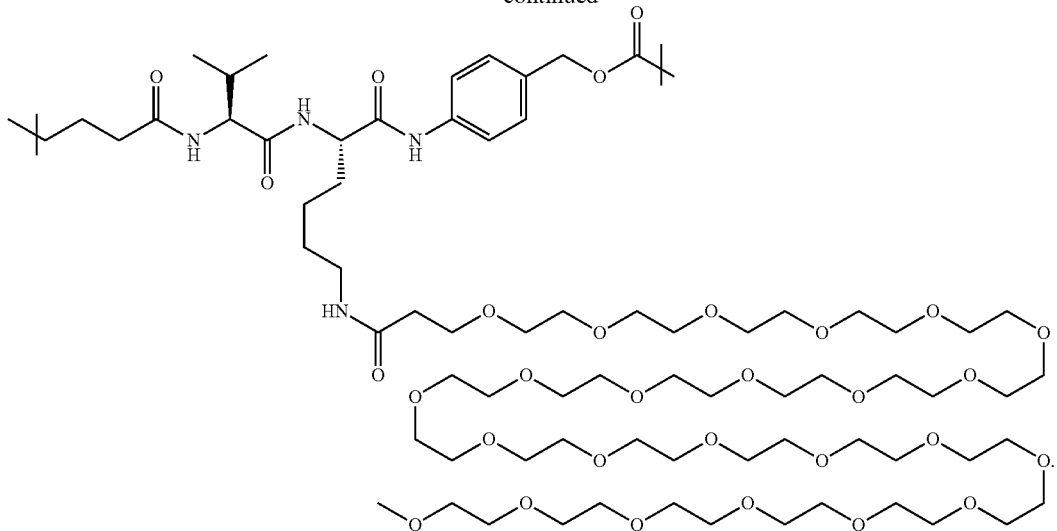 [SMILES: CCCCC(=O)N[C@H](C(=O)N[C@@H](CCCCNC(=O)CCOCCOCCOCCOCCOCCOCCOCCOCCOCCOCCOCCOCCOCCOCCOCCOCCOCCOCCOCCOCCOCCOCCOCCOC)C(=O)Nc1ccc(COC(C)=O)cc1)C(C)C]

$R_1$ represents a $(C_1-C_6)$alkyl group, such as a methyl group;

$R_2$ and $R_3$ represent independently of each other a hydrogen atom or a $(C_1-C_6)$alkyl group such as a methyl group;

$R_4$ and $R_5$ represent independently of each other a $(C_1-C_6)$alkyl group, such as a methyl group;

$R_7$ and $R_8$ represent independently of each other a hydrogen atom or a $(C_1-C_6)$alkyl group, such as an isobutyl group or a neopentyl group, for instance one of $R_7$ and $R_8$ represents a $(C_1-C_6)$alkyl group, such as an isobutyl group or a neopentyl group and the other of $R_7$ and $R_8$ represents a hydrogen atom;

X represents an oxygen atom or NH;

$R_9$ represents two substituents selected from a $(C_1-C_4)$ alkoxy group, such as a methoxy group, and a halogen atom, such as a chlorine atom, for instance $R_9$ represents 3-Cl and 4-methoxy; and $R_{10}$ represents a hydrogen atom.

Among the compounds of formula (V) that are subject matter of the disclosure, a group of compounds is composed of the compounds of the following structure (beta epoxide configuration):

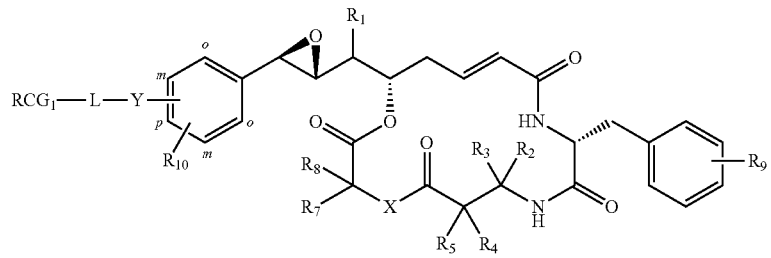

wherein:

$R_1, R_2, R_3, R_4, R_5, R_6, R_7, R_8, R_9, R_{10}, R_{11}, R_{12}, n, RCG_1$, X, Y and L are as defined in formula (IV).

All these sub-groups taken alone or in combination are part of the present disclosure.

Among the compounds of formula (V) that are the subject matter of the disclosure, mention may be made of the following compounds:
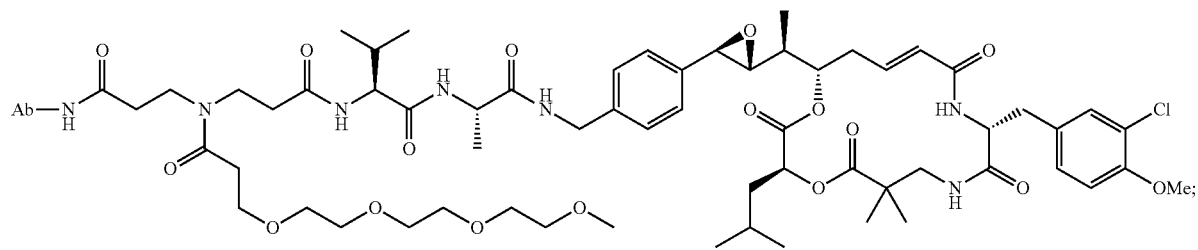
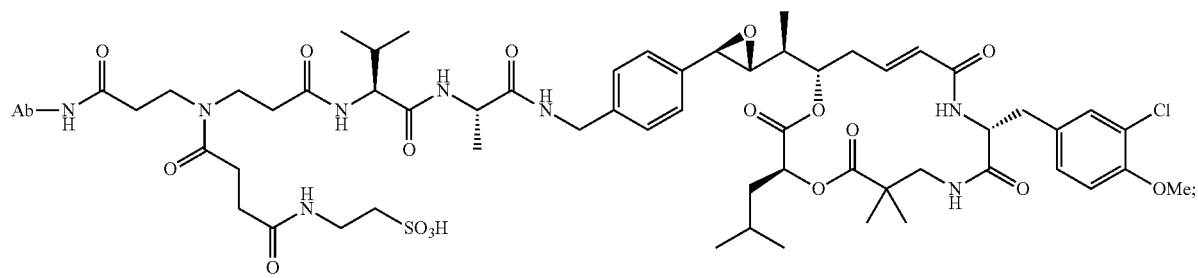
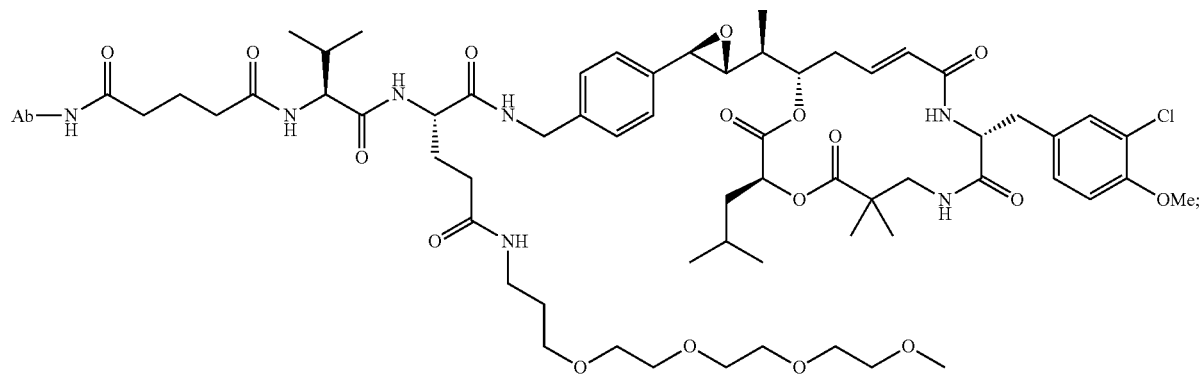
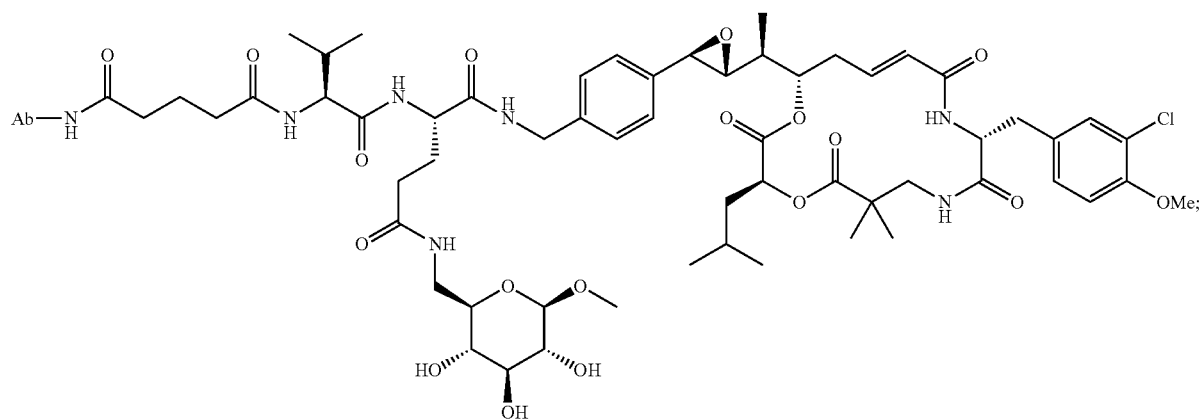

129
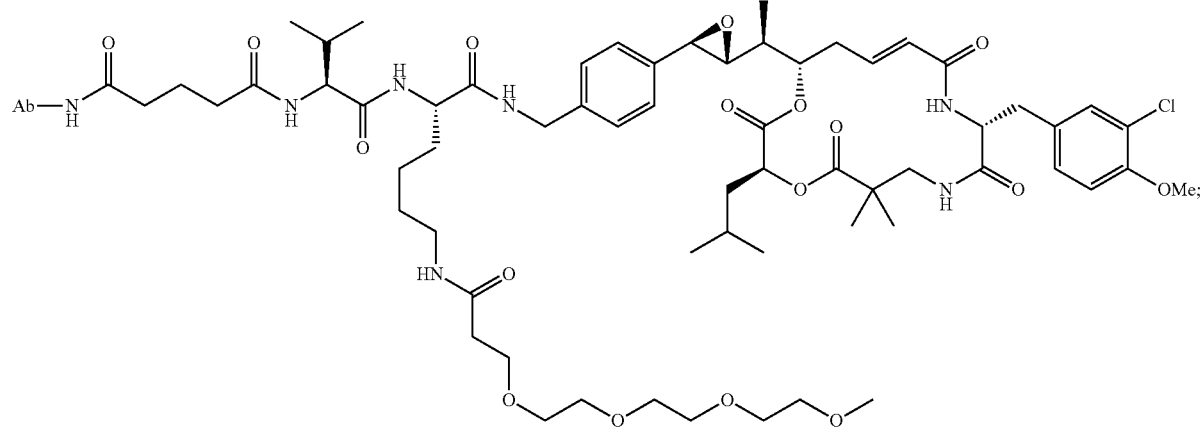
-continued
130
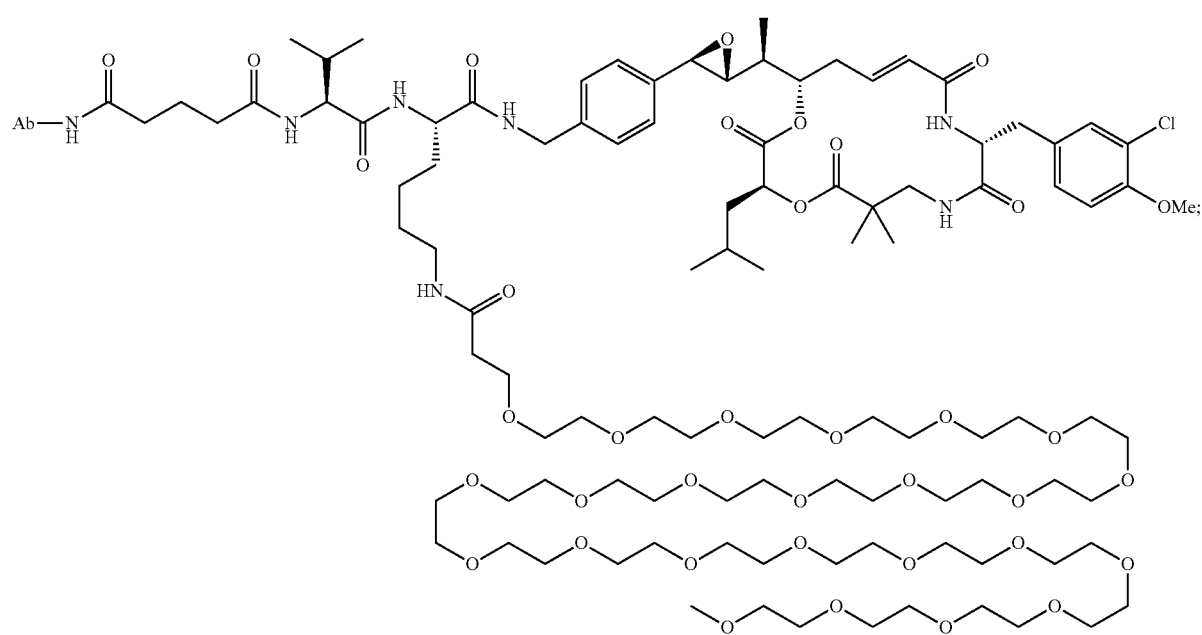

-continued
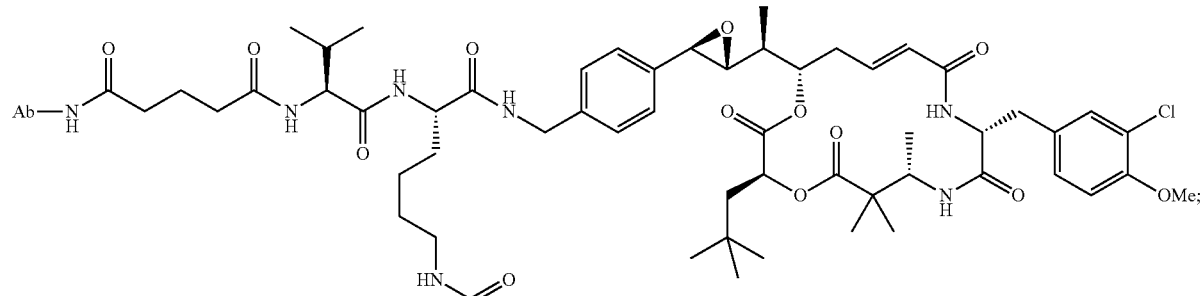
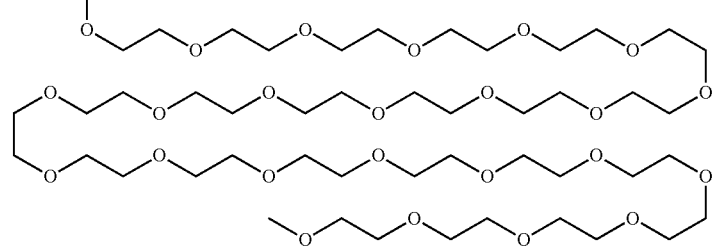
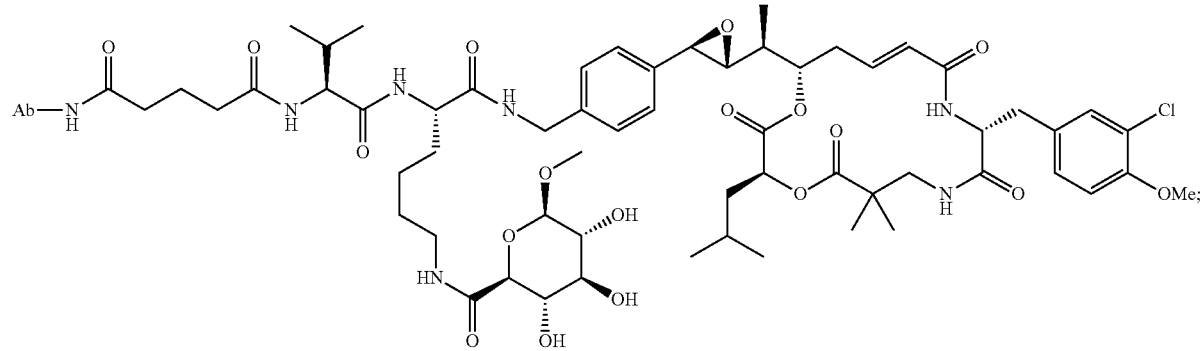
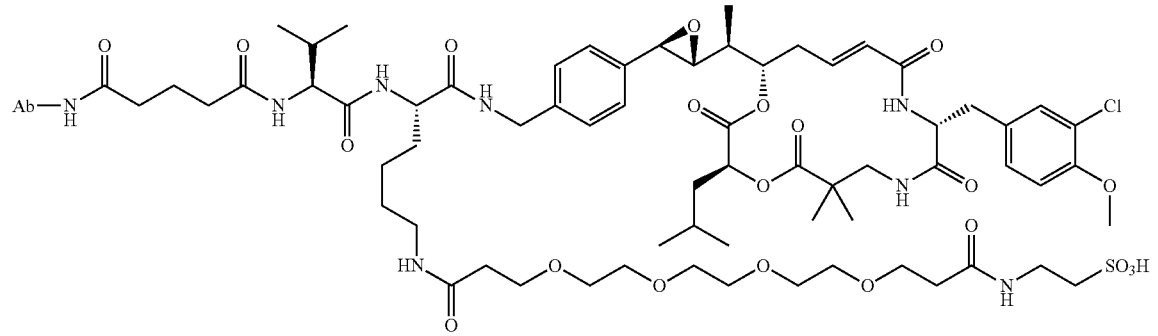
and
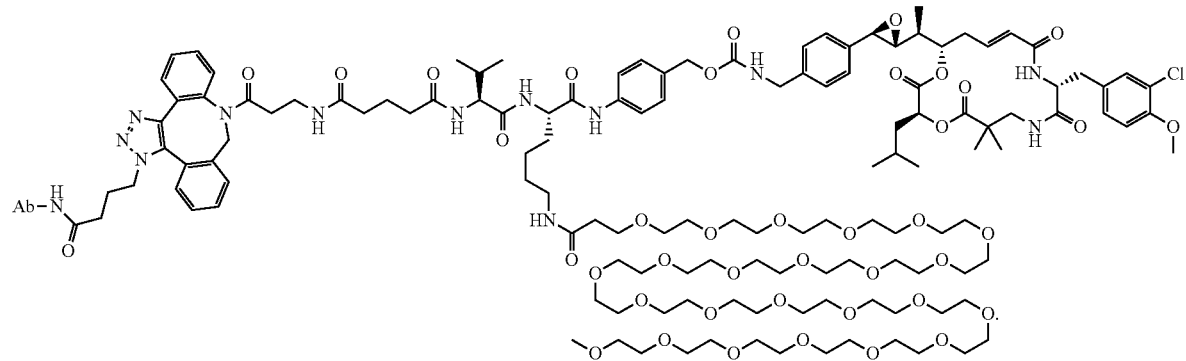

wherein Ab is as defined in formula (V) of the present disclosure.
In accordance with the disclosure, the compounds of general formula (I), (11), (Ill), (IV) and (V) can be prepared by the following processes.
Preparation of the Linkers of Formula (II)
Preparation of the Spacers with Improved Hydrophilicity
Scheme 1
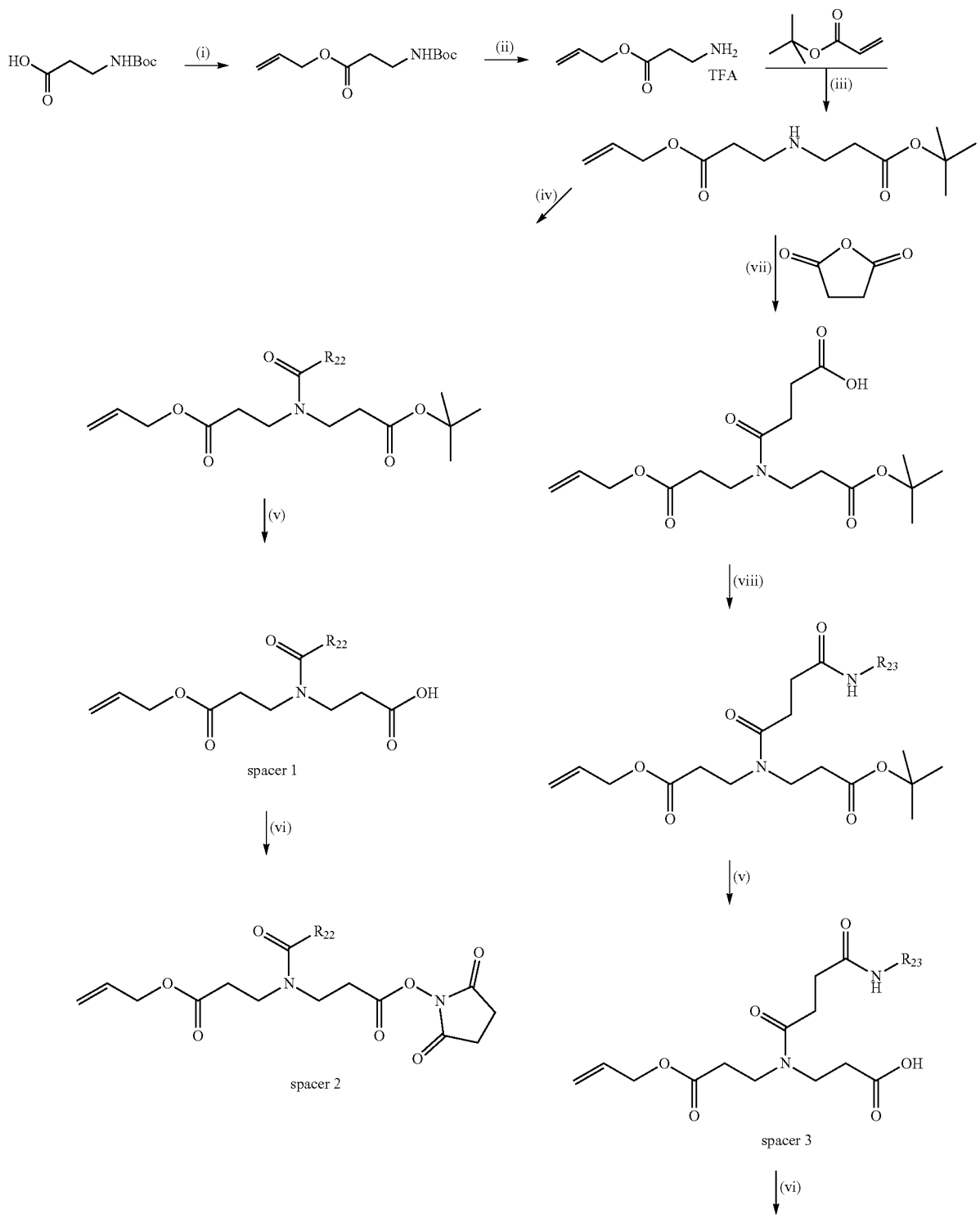

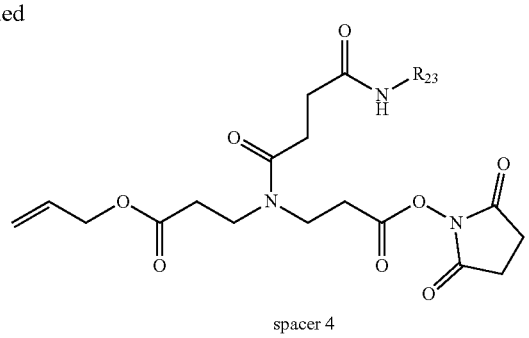

spacer 4

Step (i): protection of the carboxylic acid as an allyl ester using allyl bromide and a base such as, for example, cesium carbonate;

Step (ii): deprotection of the Boc amine using a solution of HCl (for example solution in dioxane) or of TFA;

Step (iii): addition of the amine on tert-butyl acrylate in the presence of a base such as, for example, DIEA;

Step (iv): coupling between the amine and an activated carboxylic acid such as a NHS ester or an acyl chloride in the presence of a base such as, for example, DIEA;

Step (v): deprotection of the tert-butyl ester using a solution of HCl (for example solution in dioxane) or of TFA;

Scheme 1 depicted the synthesis starting with Boc-$R_3$-Ala-OH (CAS number [3303-84-2]) but may also apply to other Boc protected amino-alkyl acids which are commercially available for n ranging from 3 to 10. It depicted the synthesis using succinic anhydride but may also apply to glutaric anhydre or alkyl diacids which are commercially available for n ranging from 3 to 10.

Combination of the Spacers with Improved Hydrophilicity and the Classical Dipeptides

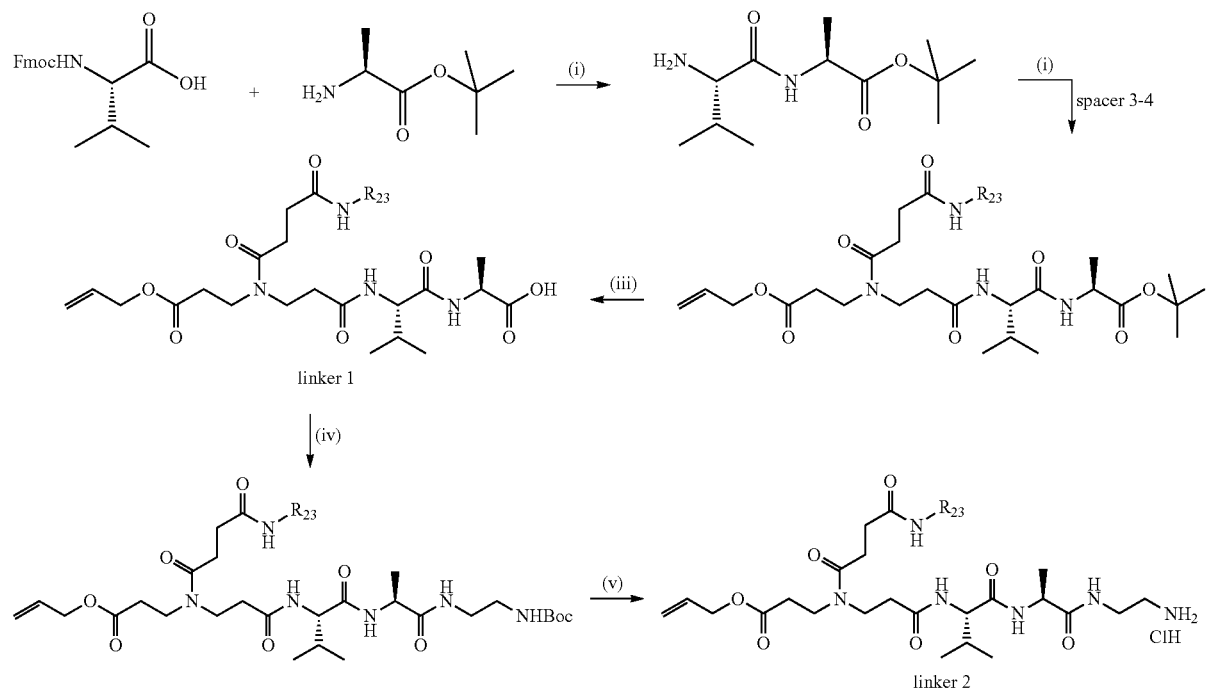

Step (vi): activation of the carboxylic acid as a NHS ester by treatment with DSC in the presence of a base such as, for example, DIEA;

Step (vii): coupling to succinic anhydride;

Step (viii): activation of the carboxylic acid as a NHS ester by treatment with DSC in the presence of a base such as, for example, DIEA and coupling with an amine.

Step (i): peptidic coupling using coupling reagents such as, for example, EDC and HOBt and deprotection of the Fmoc amine in the presence of a base such as, for example, piperidine;

Step (ii): for spacer 3, activation of the carboxylic acid as a NHS ester by treatment with DSC in the presence of a base such as, for example, DIEA and coupling of spacers 3 and 4 with the dipeptide;

Step (iii): deprotection of the tert-butyl ester using a solution of HCl (for example solution in dioxane) or of TFA;

Step (iv): activation of the carboxylic acid as a NHS ester by treatment with DSC in the presence of a base such as, for example, DIEA and coupling with the amine;

Step (v): deprotection of the Boc amine using a solution of HCl (for example solution in dioxane) or of TFA.

Scheme 2 depicted the synthesis of linkers using a Val-Ala dipeptide but may also apply to other dipeptides; it depicted the synthesis using spacers 3 or 4 but may also apply to spacers 1 or 2; it depicted the synthesis using Boc-monoprotected ethylenediamine but may also apply to other Boc-monoprotected diamines which are commercially available for n ranging from 3 to 10.

Preparation of the Dipeptides with Improved Hydrophilicity

Preparation of the Dipeptides with Improved Hydrophilicity Based on Amino Acids Bearing a Carboxylic Acid Group on their Side Chain

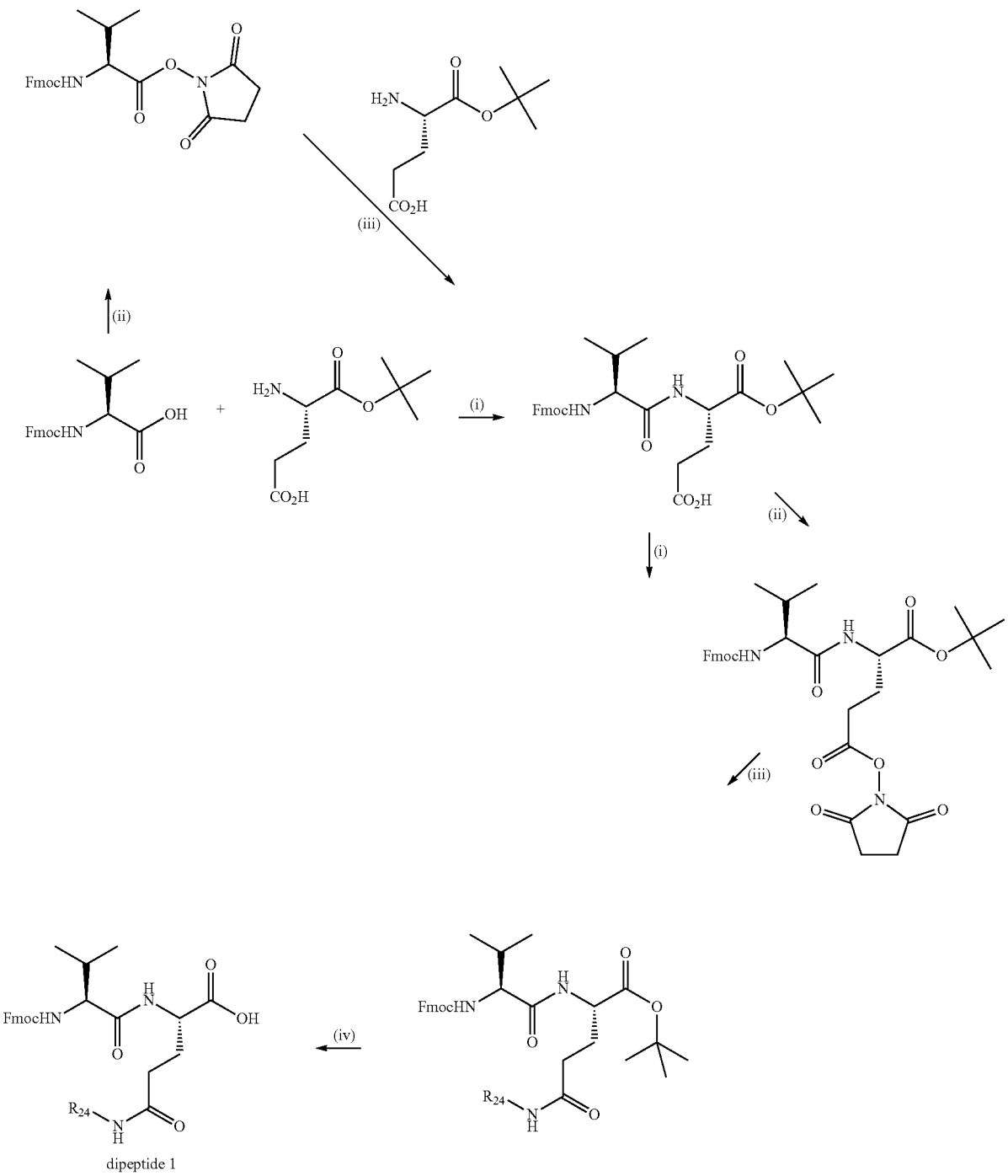

Scheme 3

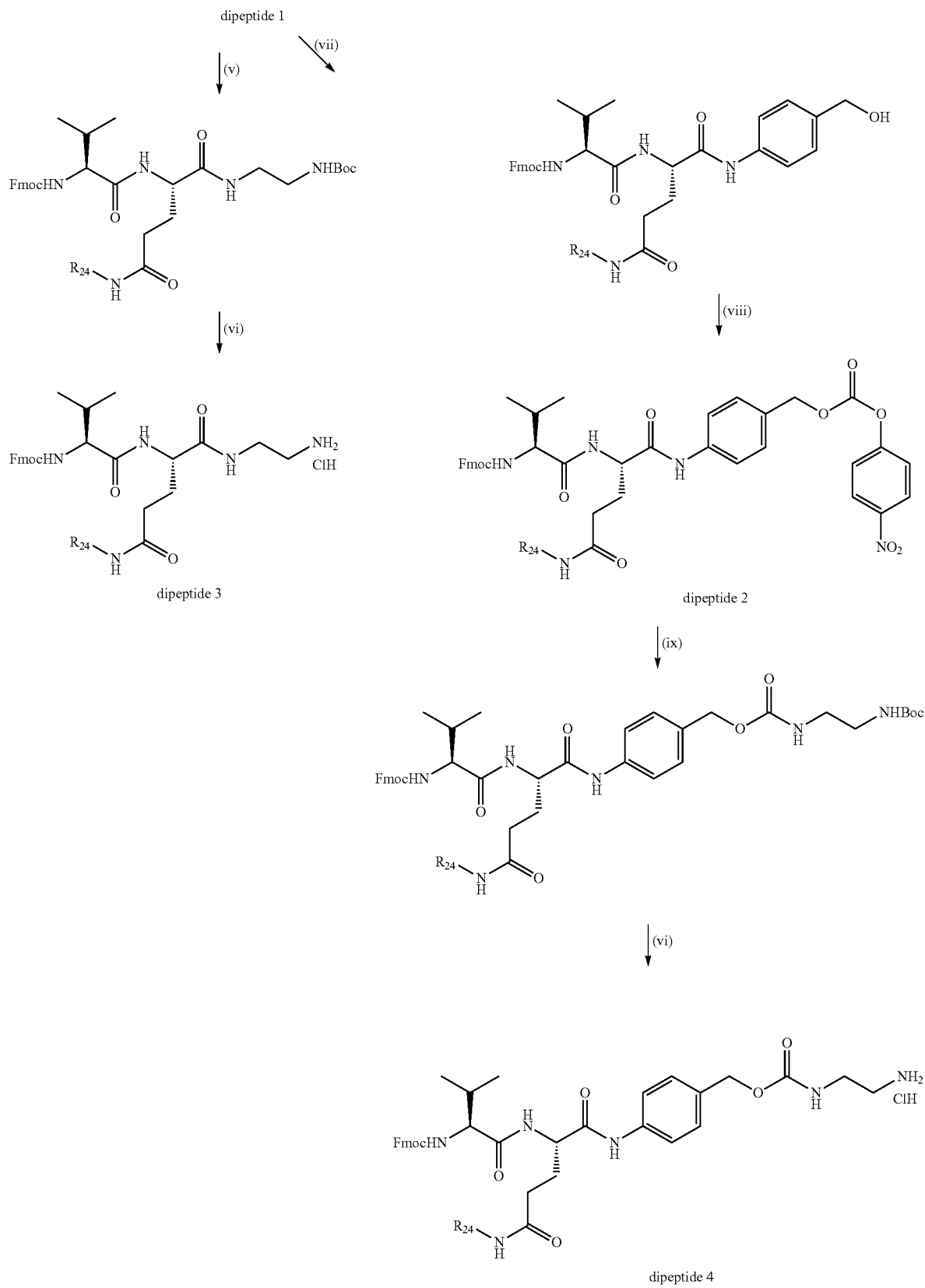
Scheme 4

Step (i): peptidic coupling between the carboxylic acid and an amine using coupling reagents such as, for example, EDC and HOBt;

Step (ii): activation of the carboxylic acid as a NHS ester by treatment with DSC in the presence of a base such as, for example, DIEA;

Step (iii): peptidic coupling between the NHS ester and an amine in the presence of a base such as, for example, sodium bicarbonate or DIEA;

Step (iv): deprotection of the tert-butyl ester using a solution of HCl (for example solution in dioxane) or of TFA;

Step (v): peptidic coupling of the dipeptide with Boc-monoprotected ethylene diamine using a coupling reagent such as for example, T3P;

Step (vi): deprotection of the Boc amine using a solution of HCl (for example solution in dioxane) or of TFA;

Step (vii): peptidic coupling of the dipeptide with p-aminobenzyl alcohol using coupling reagents such as, for example, EEDQ;

Step (viii): activation of the benzylic alcohol as a p-nitrophenyl carbonate by treatment with p-nitrophenyl-chloroformate in the presence of a base such as, for example, DIEA;

Step (ix): formation of a carbamate between the activated alcohol and the amine in the presence of a base such as, for example, DIEA.

Scheme 3 depicted the synthesis of dipeptides starting with Val but may apply to other amino acids listed above; it depicted the synthesis using L-Glu tert-butyl ester (CAS number [45120-30-7]) but may also apply to other amino acids bearing a carboxylic acid on their side chain such as, for example, L-Asp tert-butyl ester (CAS number [4125-93-3]), D-Asp tert-butyl ester (CAS number [148823-36-3]), D-Glu tert-butyl ester (CAS number [25456-76-2]), 2-amino-hexanedioic acid 1-tert-butyl ester (CAS number [1245806-58-9]) or 2-amino-heptanedioic acid 1-tert-butyl ester (CAS number [1888498-03-0]). Scheme 4 depicted the synthesis of dipeptides using p-aminobenzyl alcohol (CAS number [623-04-1]) but may also apply to other aminobenzyl alcohol compounds which are commercially available such as, for example, 4-(1-hydroxyethyl)-aniline (racemic (CAS number [14572-89-5]) or enantiopure (R) (CAS number [210754-25-9]) or (S) (CAS number [500229-84-5])), 4-amino-α,α-dimethyl-benzene-methanol (CAS number [23243-04-1]), 4-amino-α-methoxy-α-methyl-benzenemethanol (CAS number [1379318-81-6]), 4-amino-α-methyl-α-trifluoromethyl-benzenemethanol (CAS number [851652-56-7]), 2-amino-benzenemethanol (CAS number [5344-90-1]), 2-amino-α-methyl-benzenemethanol (racemic (CAS number [10517-50-7]) or enantiopure (R) (CAS number [3205-21-8]) or (S) (CAS number [3205-21-8])), 6-amino-3-pyridinemethanol (CAS number [113293-71-3]), 6-amino-α-methyl-3-pyridinemethanol (CAS number [1335054-83-5]), 6-amino-α-ethyl-3-pyridinemethanol (CAS number [1355225-85-2]), 6-amino-α,α-dimethyl-3-pyridinemethanol (CAS number [843646-03-8]), 5-amino-3-pyridinemethanol (CAS number [873651-92-4]), 2-amino-3-pyridinemethanol (CAS number [23612-57-9]), 2-amino-α-methyl-3-pyridinemethanol (racemic (CAS number [869567-91-9]) or enantiopure (R) (CAS number [936718-01-3]) or (S) (CAS number [936718-00-2])), 2-amino-α-ethyl-3-pyridinemethanol (CAS number [914223-90-8]), 2-amino-α,α-dimethyl-3-pyridinemethanol (CAS number [213666-96-7]), 3-amino-4-pyridinemethanol (CAS number [152398-05-5]), 3-amino-α-methyl-4-pyridinemethanol (CAS number [1242470-88-7]), 3-amino-α,α-methyl-4-pyridinemethanol (CAS number [13357-81-8]), 4-amino-3-pyridinemethanol (CAS number [138116-34-4]), 4-amino-α-methyl-3-pyridinemethanol (CAS number [741223-49-4]), 4-amino-α,α-methyl-3-pyridinemethanol (CAS number [1339013-26-1]), 3-amino-2-pyridinemethanol (CAS number [52378-63-9]), 3-amino-α-methyl-2-pyridinemethanol (CAS number [954240-54-1]), 3-amino-α,α-methyl-2-pyridinemethanol (CAS number [899438-57-4]); it depicted the synthesis using Boc-monoprotected ethylenediamine but may also apply to other Boc-monoprotected diamines which are commercially available for n ranging from 3 to 10.

Preparation of the Dipeptides with Improved Hydrophilicity Based on Amino Acids Bearing an Amino Group on their Side Chain Scheme 5

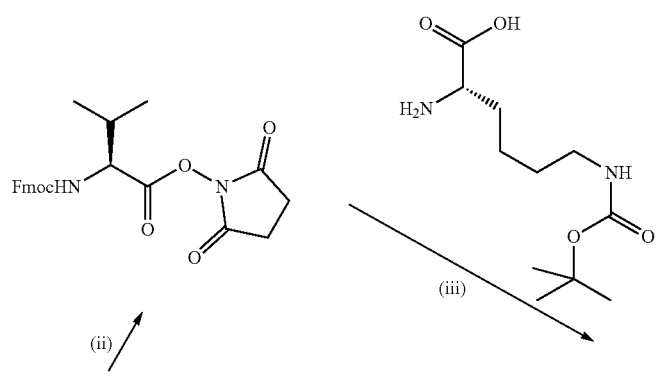

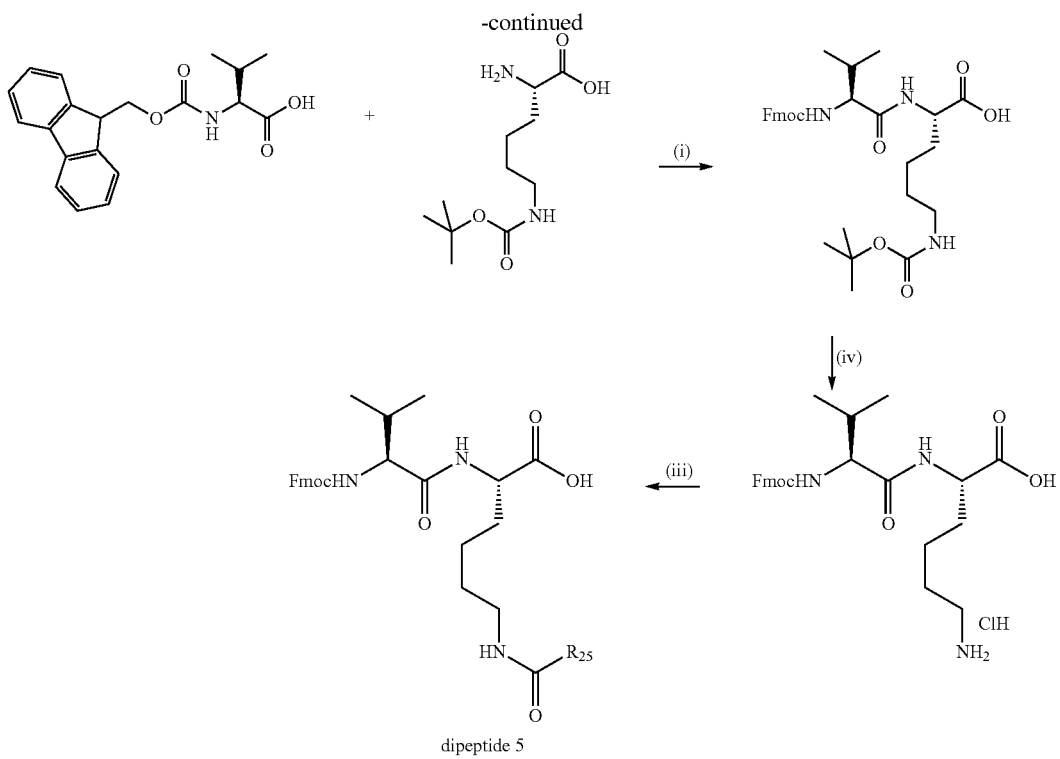
Or alternatively dipeptide 5 can be prepared following the synthesis described in Scheme 6.
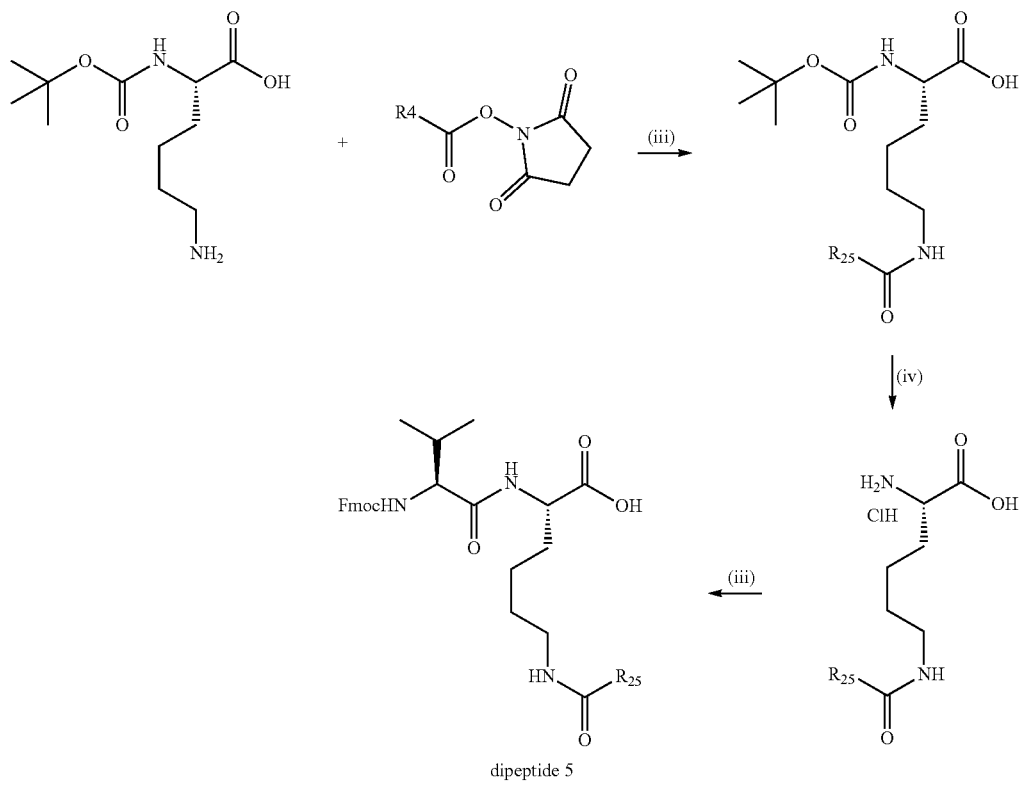

Scheme 7
dipeptide 5
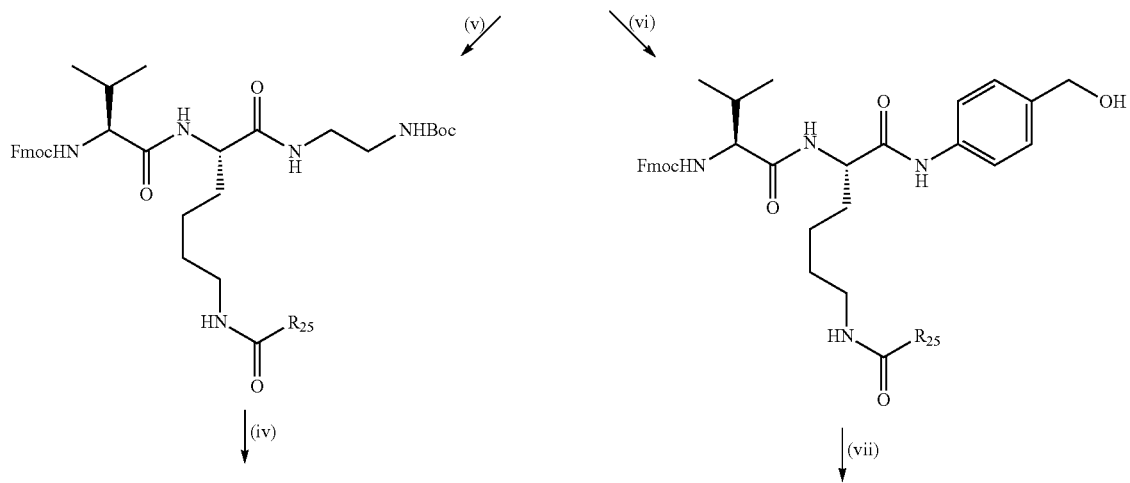
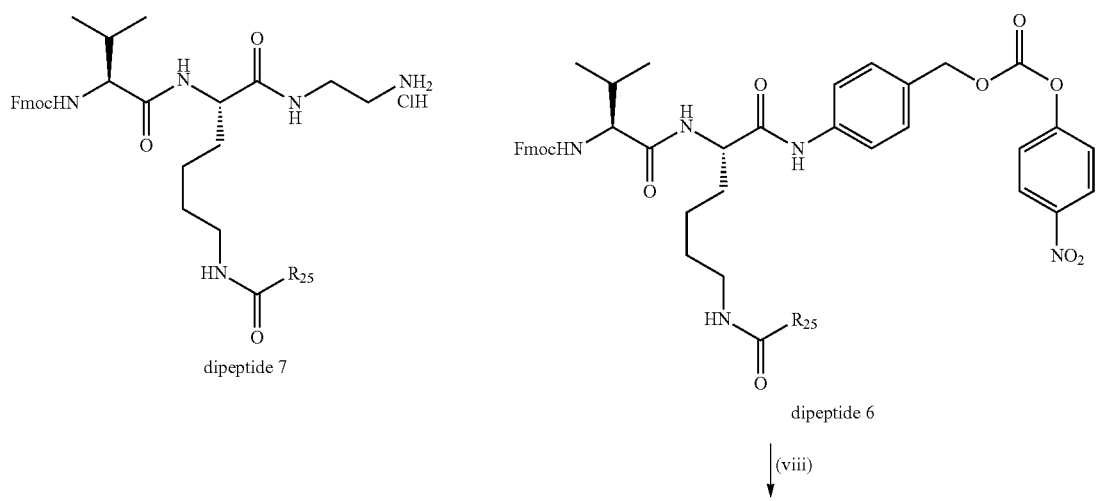
dipeptide 7
dipeptide 6
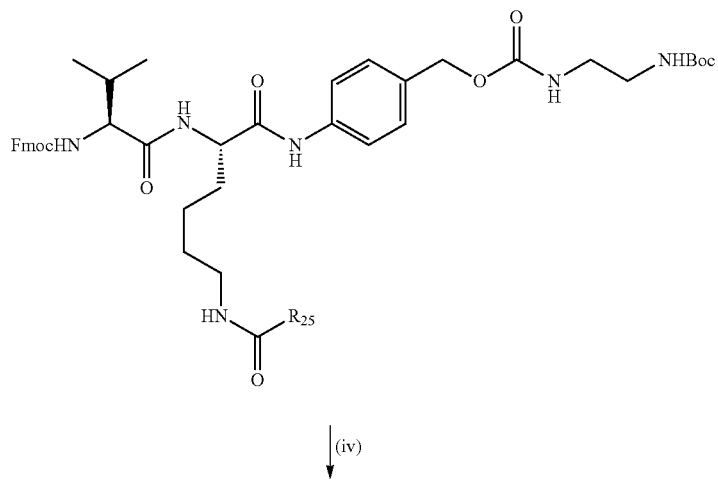

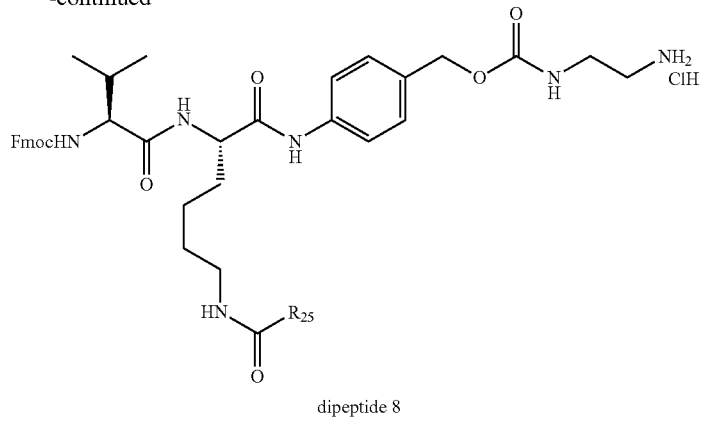

dipeptide 8

Step (i): peptidic coupling between the carboxylic acid and an amine using coupling reagents such as, for example, EDC and HOBt;

Step (ii): activation of the carboxylic acid as a NHS ester by treatment with DSC in the presence of a base such as, for example, DIEA;

Step (iii): peptidic coupling between the NHS ester and an amine in the presence of a base such as, for example, sodium bicarbonate or DIEA;

Step (iv): deprotection of the Boc amine using a solution of HCl (for example solution in dioxane) or of TFA;

Step (v): peptidic coupling of the dipeptide with Boc-monoprotected ethylene diamine using a coupling reagent such as for example, T3P;

Step (vi): peptidic coupling of the dipeptide with p-aminobenzyl alcohol using coupling reagents such as, for example, EEDQ;

Step (vii): activation of the benzylic alcohol as a p-nitrophenyl carbonate by treatment with p-nitrophenyl-chloroformate in the presence of a base such as, for example, DIEA;

Step (viii): formation of a carbamate between the activated alcohol and the amine in the presence of a base such as, for example, DIEA.

Schemes 5 and 6 depicted the synthesis of dipeptides starting with Val but may apply to other amino acids listed above. Scheme 5 depicted the synthesis using L-Lys Boc-protected on the side chain (CAS number [2418-95-3]) but may also apply to other amino acids bearing an amino group on their side chain such as, for example, (S)-3-amino-2-(tert-butoxycarbonylamino)propanoic acid (CAS number [73259-81-1]), (S)-3-amino-2-(tert-butoxycarbonylamino) propanoic acid (CAS number [76387-70-7]), (S)-4-amino-2-(tert-butoxycarbonylamino)butanoic acid (CAS number [25691-37-6]), (R)-4-amino-2-(tert-butoxycarbonylamino) butanoic acid (CAS number [80445-78-9]), L-ornithine Boc-protected on the side chain (CAS number [21887-64-9]), D-ornithine Boc-protected on the side chain (CAS number [159877-12-0]), D-Lys Boc-protected on the side chain (CAS number [106719-44-2]), (2S)-2-amino-7-[[(1,1-dimethylethoxy)carbonyl]amino]heptanoic acid (CAS number [1142814-17-2]) or (2R)-2-amino-7-[[(1,1-dimethylethoxy)carbonyl]amino]heptanoic acid (CAS number [117833-90-6]). Scheme 7 depicted the synthesis of dipeptides using p-aminobenzyl alcohol (CAS number [623-04-1]) but may also apply to other aminobenzyl alcohol compounds which are commercially available such as, for example, 4-(1-hydroxyethyl)-aniline (racemic (CAS number [14572-89-5]) or enantiopure (R) (CAS number [210754-25-9]) or (S) (CAS number [500229-84-5])), 4-amino-α,α-dimethyl-benzene-methanol (CAS number [23243-04-1]), 4-amino-α-methoxy-α-methyl-benzenemethanol (CAS number [1379318-81-6]), 4-amino-α-methyl-α-trifluoromethyl-benzenemethanol (CAS number [851652-56-7]), 2-amino-benzenemethanol (CAS number [5344-90-1]), 2-amino-α-methyl-benzenemethanol (racemic (CAS number [10517-50-7]) or enantiopure (R) (CAS number [3205-21-8]) or (S) (CAS number [3205-21-8])), 6-amino-3-pyridinemethanol (CAS number [113293-71-3]), 6-amino-α-methyl-3-pyridinemethanol (CAS number [1335054-83-5]), 6-amino-α-ethyl-3-pyridinemethanol (CAS number [1355225-85-2]), 6-amino-α,α-dimethyl-3-pyridinemethanol (CAS number [843646-03-8]), 5-amino-3-pyridinemethanol (CAS number [873651-92-4]), 2-amino-3-pyridinemethanol (CAS number [23612-57-9]), 2-amino-α-methyl-3-pyridinemethanol (racemic (CAS number [869567-91-9]) or enantiopure (R) (CAS number [936718-01-3]) or (S) (CAS number [936718-00-2])), 2-amino-α-ethyl-3-pyridinemethanol (CAS number [914223-90-8]), 2-amino-α,α-dimethyl-3-pyridinemethanol (CAS number [213666-96-7]), 3-amino-4-pyridinemethanol (CAS number [152398-05-5]), 3-amino-α-methyl-4-pyridinemethanol (CAS number [1242470-88-7]), 3-amino-α,α-methyl-4-pyridinemethanol (CAS number [13357-81-8]), 4-amino-3-pyridinemethanol (CAS number [138116-34-4]), 4-amino-α-methyl-3-pyridinemethanol (CAS number [741223-49-4]), 4-amino-α,α-methyl-3-pyridinemethanol (CAS number [1339013-26-1]), 3-amino-2-pyridinemethanol (CAS number [52378-63-9]), 3-amino-α-methyl-2-pyridinemethanol (CAS number [954240-54-1]), 3-amino-α,α-methyl-2-pyridinemethanol (CAS number [899438-57-4]); it depicted the synthesis using Boc-monoprotected ethylenediamine but may also apply to other Boc-monoprotected diamines which are commercially available for n ranging from 3 to 10.

Preparation of the Cryptophycin Compounds
Cryptophycin compounds may be prepared as described in WO2011/001052 for X=O and in PCT/EP2016/076603 for X=NH.
Preparation of the New Cryptophycin Payloads of Formula (IV) for Y=NH—CH$_2$
Preparation of the New Cryptophycin Payloads Bearing a Spacer with Improved Hydrophilicity
Without PABA Moiety
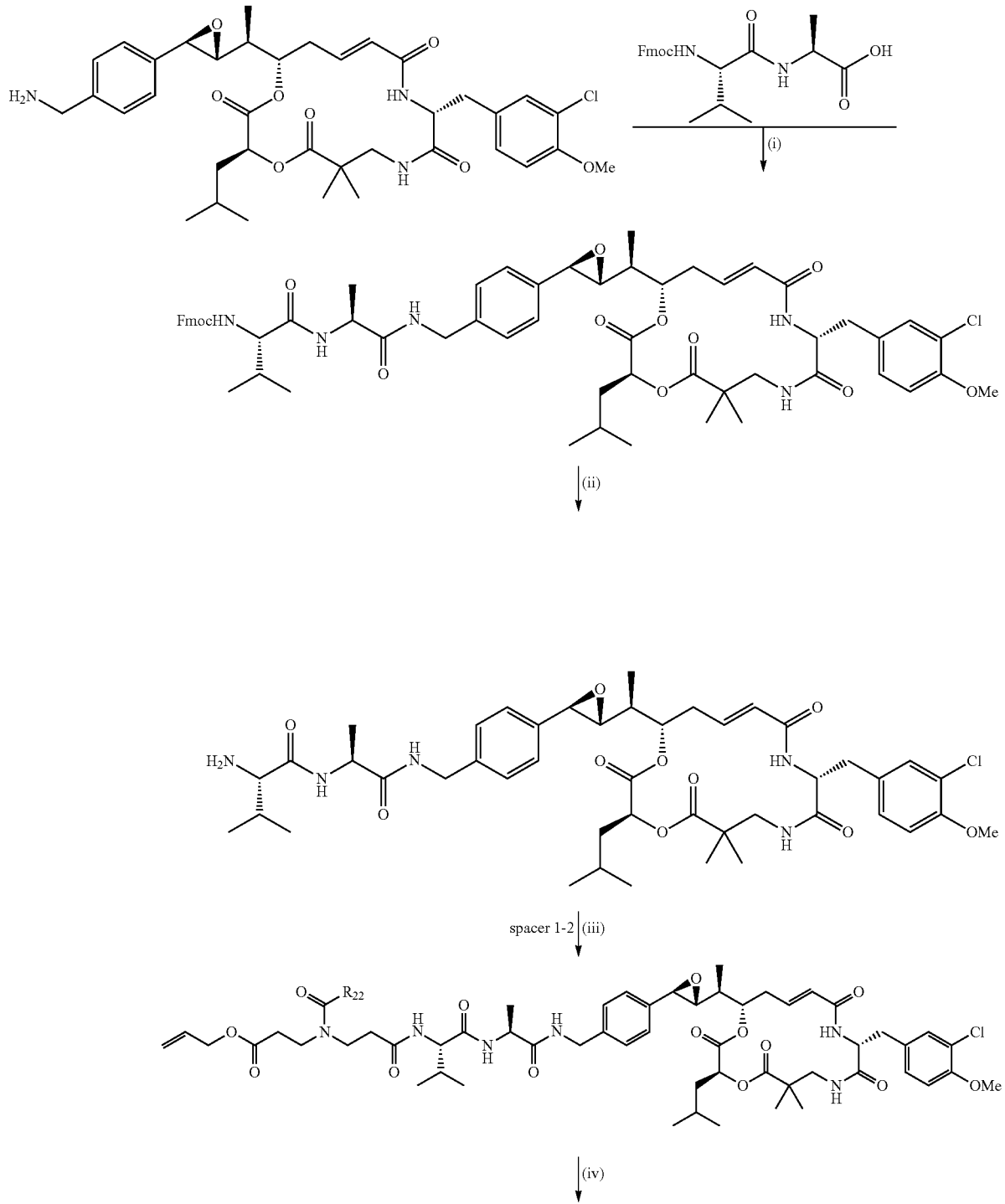
Scheme 8

-continued

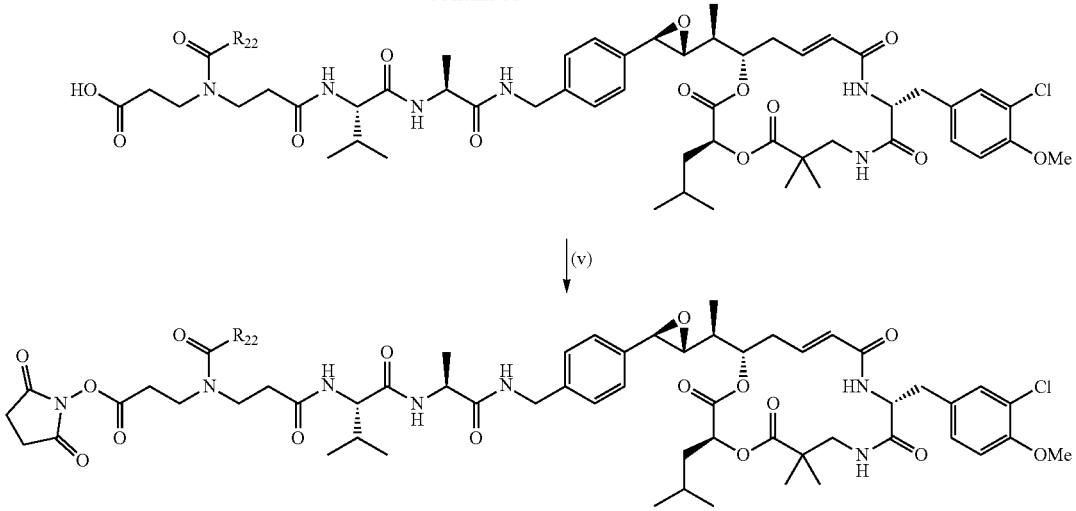

Step (i): peptidic coupling between the cryptophycin derivative and the dipeptide using coupling reagents such as, for example, EDC and HOBt;

Step (ii): deprotection of the Fmoc amine in the presence of a base such as, for example, piperidine;

Step (iii): peptidic coupling with spacer 1 using coupling reagents such as, for example, EDC and HOBt, or coupling with spacer 2 in the presence of a base such as, for example, DIEA;

Step (iv): deprotection of the allyl ester in the presence of a catalyst such as, for example, tetrakis-(triphenylphosphine)palladium;

Step (v): activation of the carboxylic acid as a NHS ester by treatment with DSC in the presence of a base such as, for example, DIEA.

Alternatively, new cryptophycin payloads bearing a spacer with improved hydrophilicity may also be prepared as depicted in Scheme 9.

Scheme 9

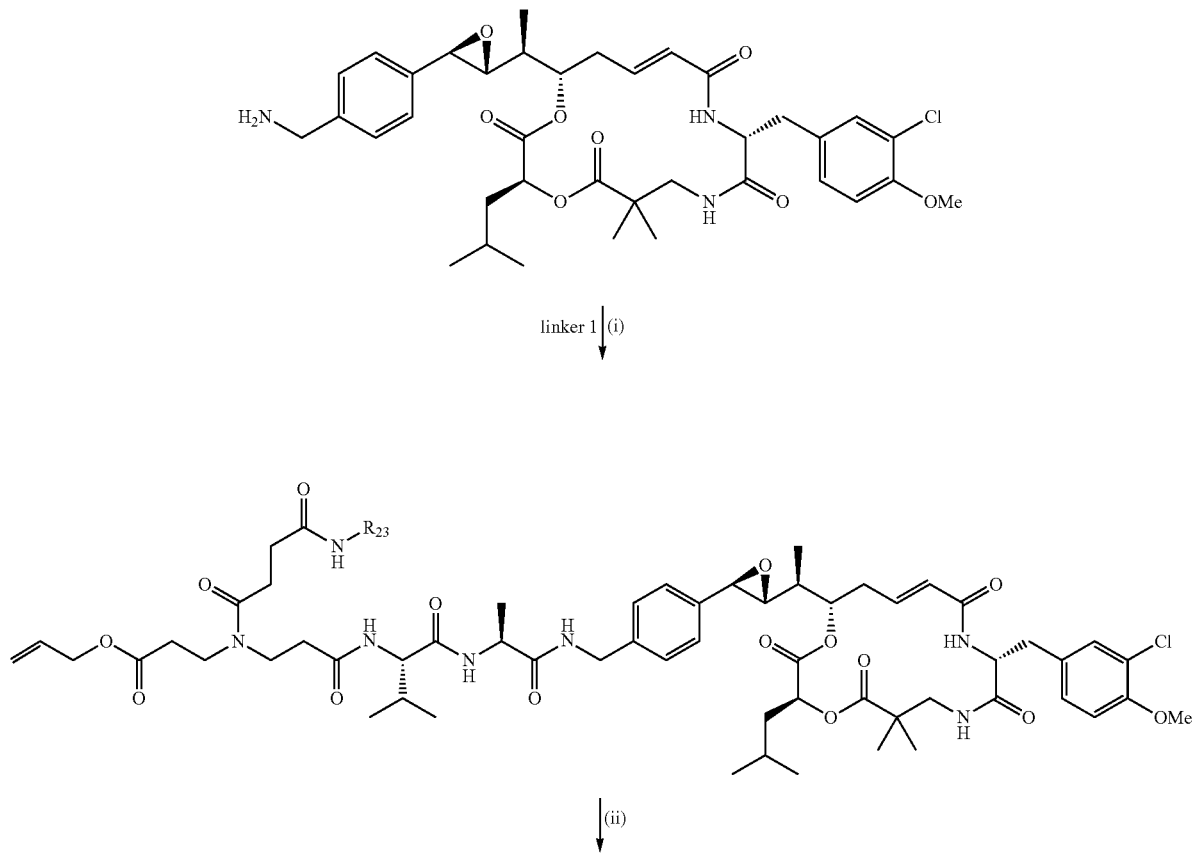

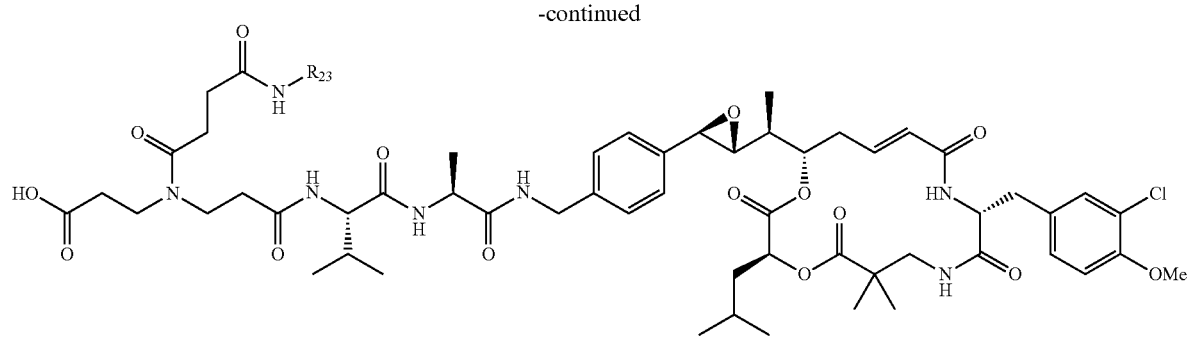

|(iii)

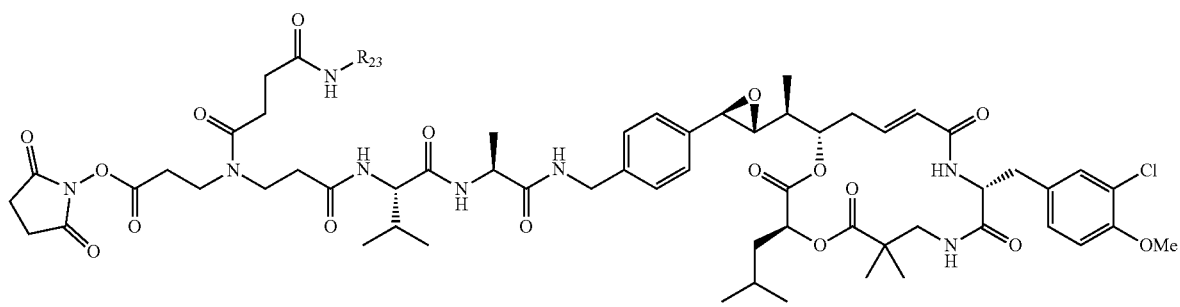

Step (i): activation of the carboxylic acid of linker 1 as a NHS ester by treatment with DSC in the presence of a base such as, for example, DIEA and coupling with the cryptophycin amine.

Step (ii): deprotection of the allyl ester in the presence of a catalyst such as, for example, tetrakis-(triphenylphosphine)palladium;

Step (iii): activation of the carboxylic acid as a NHS ester by treatment with DSC in the presence of a base such as, for example, DIEA.

Schemes 8 and 9 depicted the synthesis of payloads using the p-benzylic amine of C52 but may also apply to other cryptophycin compounds; it depicted the synthesis using Val-Ala dipeptides but may also apply to other dipeptides; it depicted the synthesis using spacers 1 or 2 but may also apply to spacers 3 or 4.

With PABA Moeity

Scheme 10

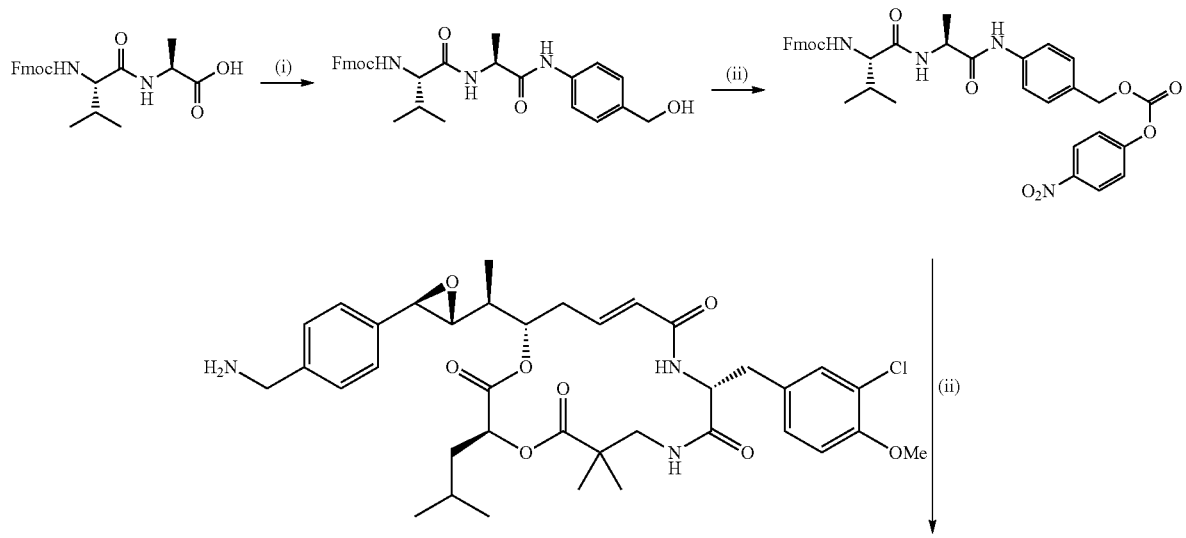

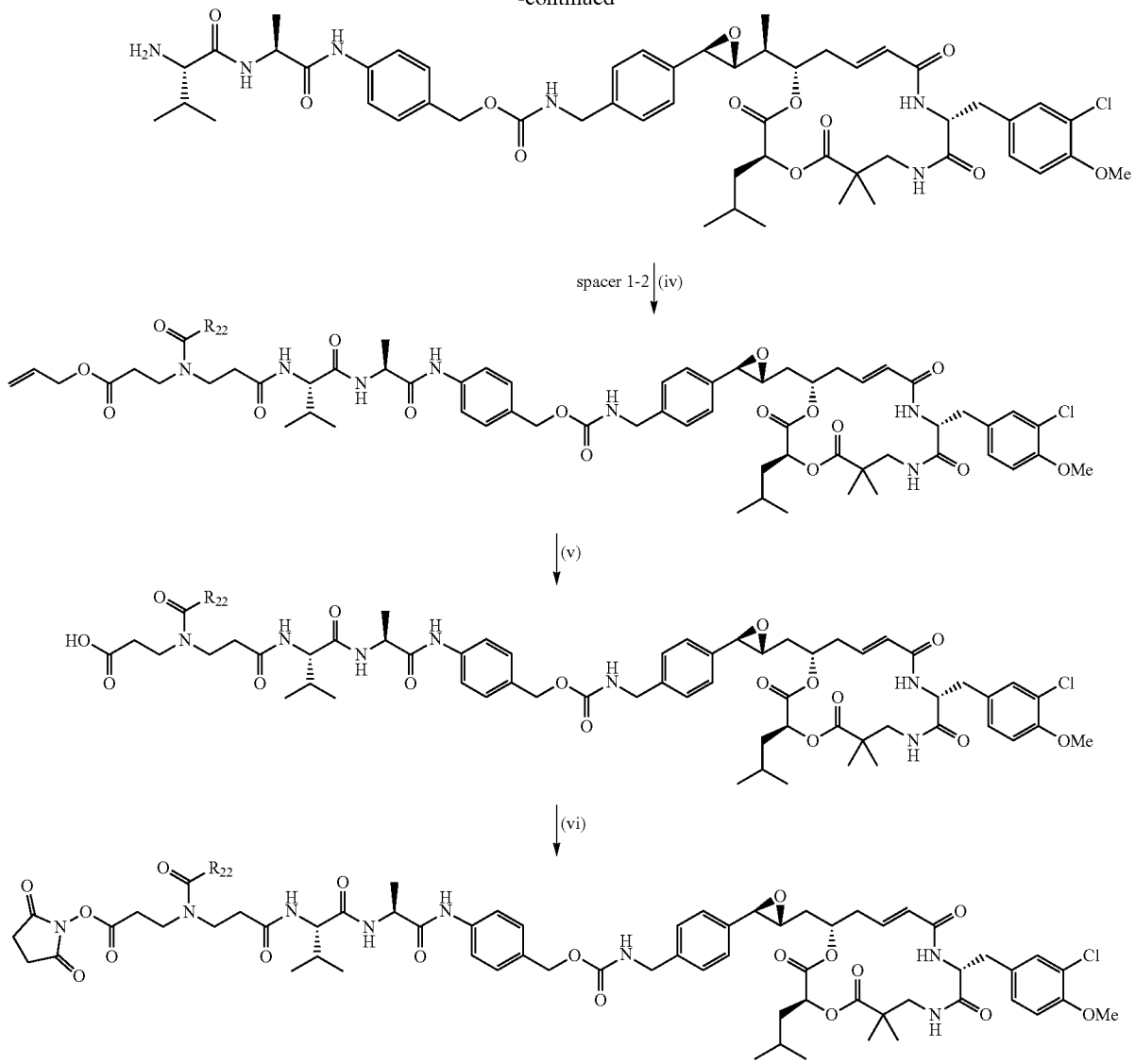

Step (i): peptidic coupling between Fmoc-Val-Ala-OH and 4-aminobenzyl alcohol in the presence of a coupling reagent such as, for example, EEDQ;

Step (ii): activation of the benzylic alcohol as a p-nitrophenyl carbonate by treatment with p-nitrophenyl-chloroformate in the presence of a base such as, for example, DIEA;

Step (iii): formation of a carbamate between the activated alcohol and the cryptophycin amine in the presence of a base such as, for example, DIEA and deprotection of the Fmoc amine in the presence of a base such as, for example, piperidine;

Step (iv): peptidic coupling with spacer 1 using coupling reagents such as, for example, EDC and HOBt, or coupling with spacer 2 in the presence of a base such as, for example, DIEA;

Step (v): deprotection of the allyl ester in the presence of a catalyst such as, for example, tetrakis-(triphenylphosphine)palladium;

Step (vi): activation of the carboxylic acid as a NHS ester by treatment with DSC in the presence of a base such as, for example, DIEA.

Scheme 10 depicted the synthesis of payloads using Val-Ala dipeptides but may also apply to other dipeptides; it depicted the synthesis using p-aminobenzyl alcohol (CAS number [623-04-1]) but may also apply to other aminobenzyl alcohol compounds which are commercially available such as, for example, 4-(1-hydroxyethyl)-aniline (racemic (CAS number [14572-89-5]) or enantiopure (R) (CAS number [210754-25-9]) or (S) (CAS number [500229-84-5])), 4-amino-α,α-dimethyl-benzene-methanol (CAS number [23243-04-1]), 4-amino-α-methoxy-α-methyl-benzenemethanol (CAS number [1379318-81-6]), 4-amino-α-methyl-α-trifluoromethyl-benzenemethanol (CAS number [851652-56-7]), 2-amino-benzenemethanol (CAS number [5344-90-1]), 2-amino-α-methyl-benzenemethanol (racemic (CAS number [10517-50-7]) or enantiopure (R) (CAS number [3205-21-8]) or (S) (CAS number [3205-21-8])), 6-amino-3-pyridinemethanol (CAS number [113293-71-3]), 6-amino-α-methyl-3-pyridinemethanol (CAS number [1335054-83-5]), 6-amino-α-ethyl-3-pyridinemethanol (CAS number [1355225-85-2]), 6-amino-α,α-dimethyl-3-pyridinemethanol (CAS number [843646-03-8]), 5-amino- 3-pyridinemethanol (CAS number [873651-92-4]), 2-amino-3-pyridinemethanol (CAS number [23612-57-9]), 2-amino-α-methyl-3-pyridinemethanol (racemic (CAS number [869567-91-9]) or enantiopure (R) (CAS number [936718-01-3]) or (S) (CAS number [936718-00-2])), 2-amino-α-ethyl-3-pyridinemethanol (CAS number [914223-90-8]), 2-amino-α,α-dimethyl-3-pyridinemethanol (CAS number [213666-96-7]), 3-amino-4-pyridinemethanol (CAS number [152398-05-5]), 3-amino-α-methyl-4-pyridinemethanol (CAS number [1242470-88-7]), 3-amino-α,α-methyl-4-pyridinemethanol (CAS number [13357-81-8]), 4-amino-3-pyridinemethanol (CAS number [138116-34-4]), 4-amino-α-methyl-3-pyridinemethanol (CAS number [741223-49-4]), 4-amino-α,α-methyl-3-pyridinemethanol (CAS number [1339013-26-1]), 3-amino-2-pyridinemethanol (CAS number [52378-63-9]), 3-amino-α-methyl-2-pyridinemethanol (CAS number [954240-54-1]), 3-amino-α,α-methyl-2-pyridinemethanol (CAS number [899438-57-4]); it depicted the synthesis using the p-benzylic amine of C52 but may also apply to other cryptophycin compounds; it depicted the synthesis using spacers 1 or 2 but may also apply to spacers 3 or 4.

Preparation of the New Cryptophycin Payloads of Formula (IV) Bearing a Dipeptide with Improved Hydrophilicity Without PABA Moiety Scheme 11

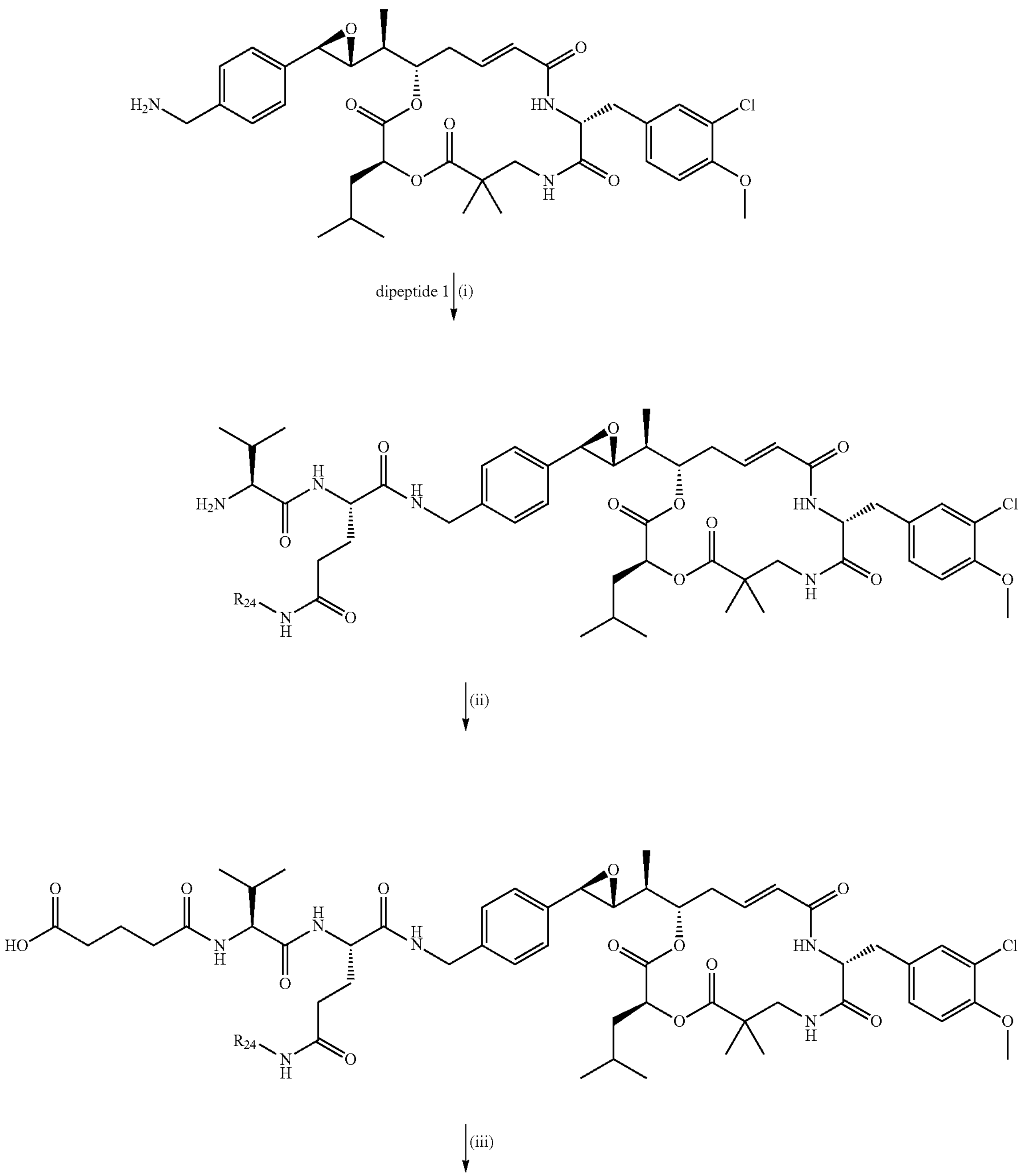

-continued

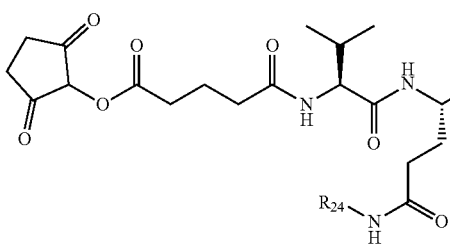 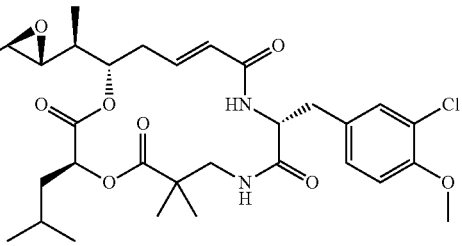

Step (i): peptidic coupling between the cryptophycin derivative and the dipeptide using coupling reagents such as, for example, EDC and HOBt and deprotection of the Fmoc amine in the presence of a base such as, for example, piperidine;

Step (ii): coupling to glutaric anhydride; one additional deprotection step of the side chain of substituted amino acid may be required prior to step (iii);

Step (iii): activation of the carboxylic acid as a NHS ester by treatment with DSC in the presence of a base such as, for example, DIEA.

Scheme 11 depicted the synthesis of payloads using the p-benzylic amine of C52 but may also apply to other cryptophycin compounds; it depicted the synthesis using dipeptide 1 but may also apply to dipeptide 5; it depicted the synthesis using glutaric anhydride but may also apply to succinic anhydride or alkyl diacids which are commercially available for n ranging from 3 to 10.

With PABA Moiety

Scheme 12

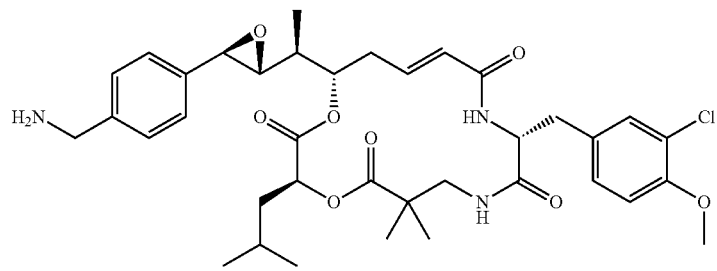

dipeptide 6 | (i)

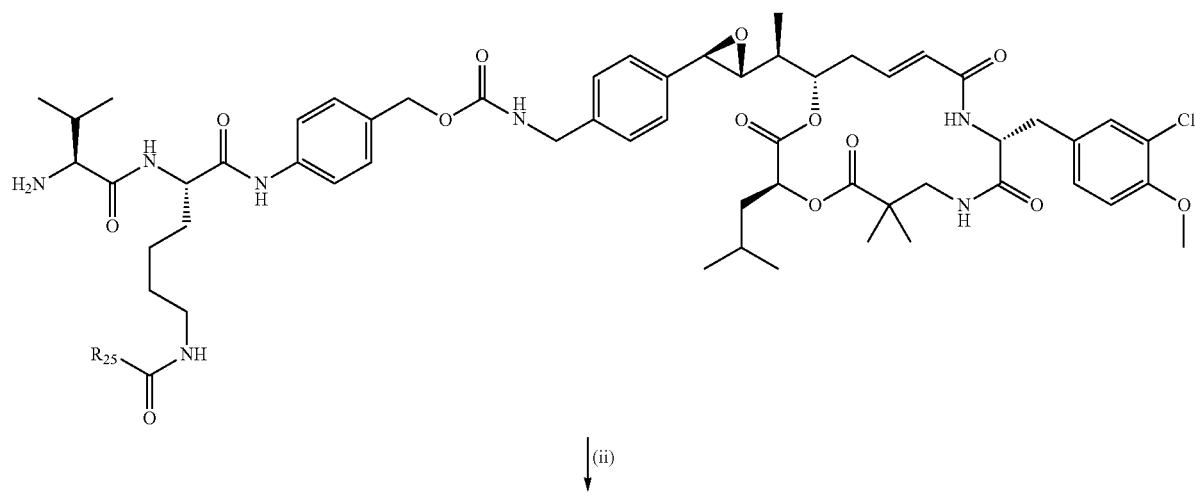

| (ii)

161

162

-continued

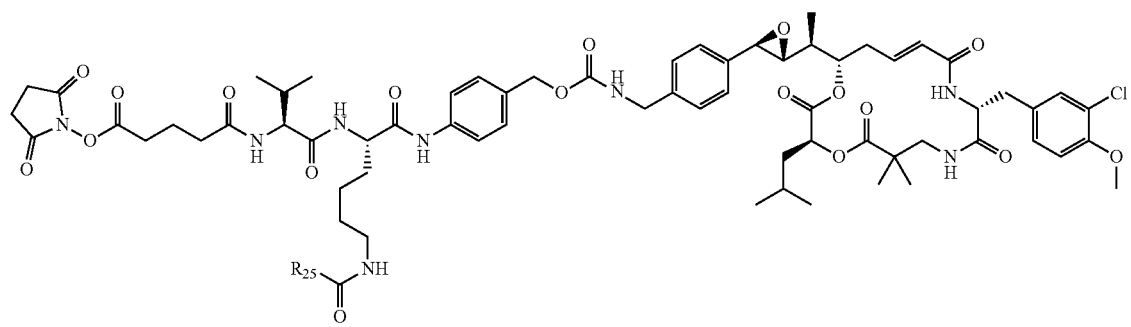

↓(iii)

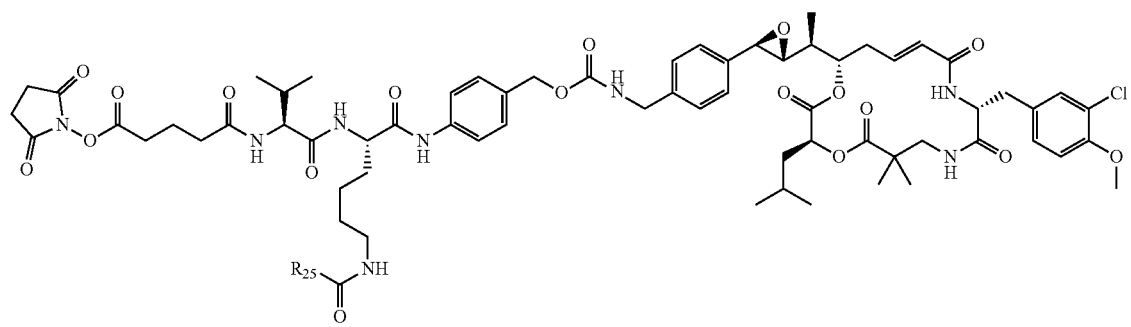

Step (i): formation of a carbamate between the activated alcohol and the cryptophycin amine in the presence of a base such as, for example, DIEA and deprotection of the Fmoc amine in the presence of a base such as, for example, piperidine;

Step (ii): coupling to glutaric anhydride; one additional deprotection step of the side chain of substituted amino acid may be required prior to step (iii);

Step (iii): activation of the carboxylic acid as a NHS ester by treatment with DSC in the presence of a base such as, for example, DIEA.

Scheme 12 depicted the synthesis of payloads using the p-benzylic amine of C52 but may also apply to other cryptophycin compounds; it depicted the synthesis using dipeptide 6 but may also apply to dipeptide 2.

Preparation of the New Cryptophycin Payloads of Formula (IV) Bearing Both a Spacer and a Dipeptide with Improved Hydrophilicity Without PABA Moeity Scheme 13

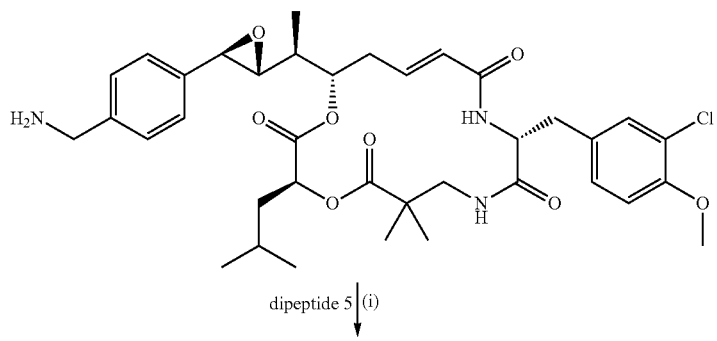

dipeptide 5 ↓(i)

163 164
-continued
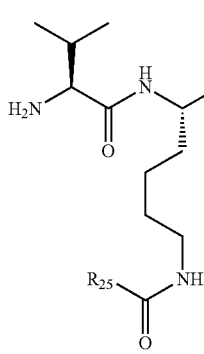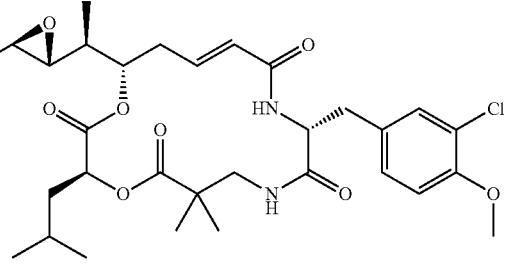
spacer 3-4 ↓(ii)
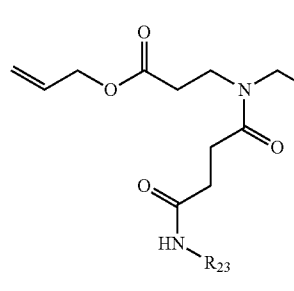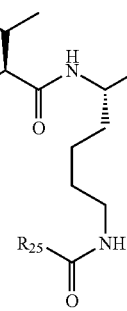
↓(iii)
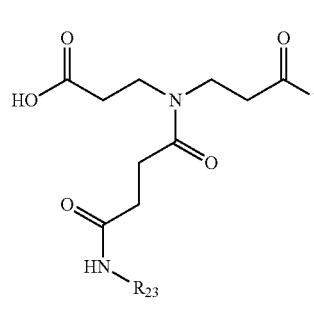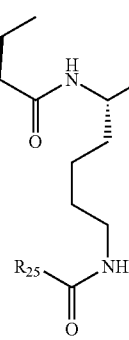
↓(iv)
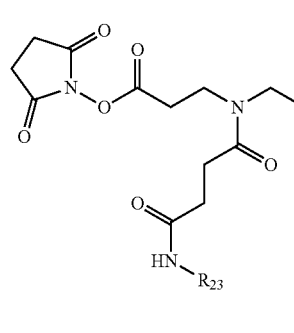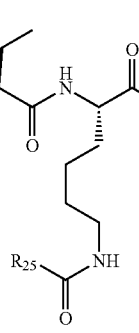

Step (i): peptidic coupling between the cryptophycin derivative and the dipeptide using coupling reagents such as, for example, EDC and HOBt and deprotection of the Fmoc amine in the presence of a base such as, for example, piperidine;

Step (ii): peptidic coupling with spacer 3 using coupling reagents such as, for example, EDC and HOBt, or coupling with spacer 4 in the presence of a base such as, for example, DIEA;

Step (iii): deprotection of the allyl ester in the presence of a catalyst such as, for example, tetrakis-(triphenylphosphine)palladium; one additional deprotection step of the side chain of substituted amino acid may be required prior to step (iv);

Step (iv): activation of the carboxylic acid as a NHS ester by treatment with DSC in the presence of a base such as, for example, DIEA.

Scheme 13 depicted the synthesis of payloads using the p-benzylic amine of C52 but may also apply to other cryptophycin compounds; it depicted the synthesis using dipeptide 5 but may also apply to dipeptide 1; it depicted the synthesis using spacers 3 or 4 but may also apply to spacers 1 or 2.

With PABA Moiety

Scheme 14

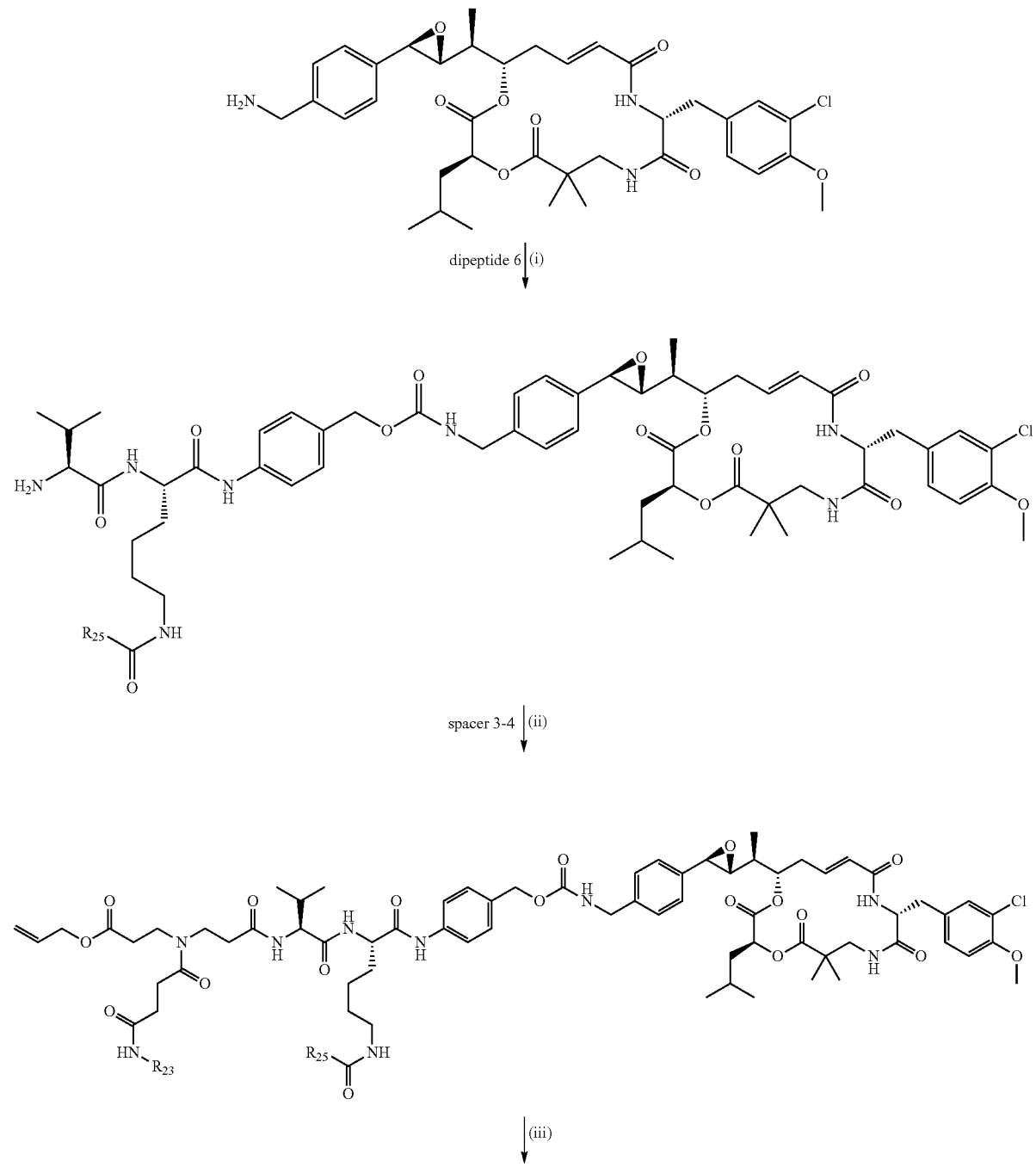

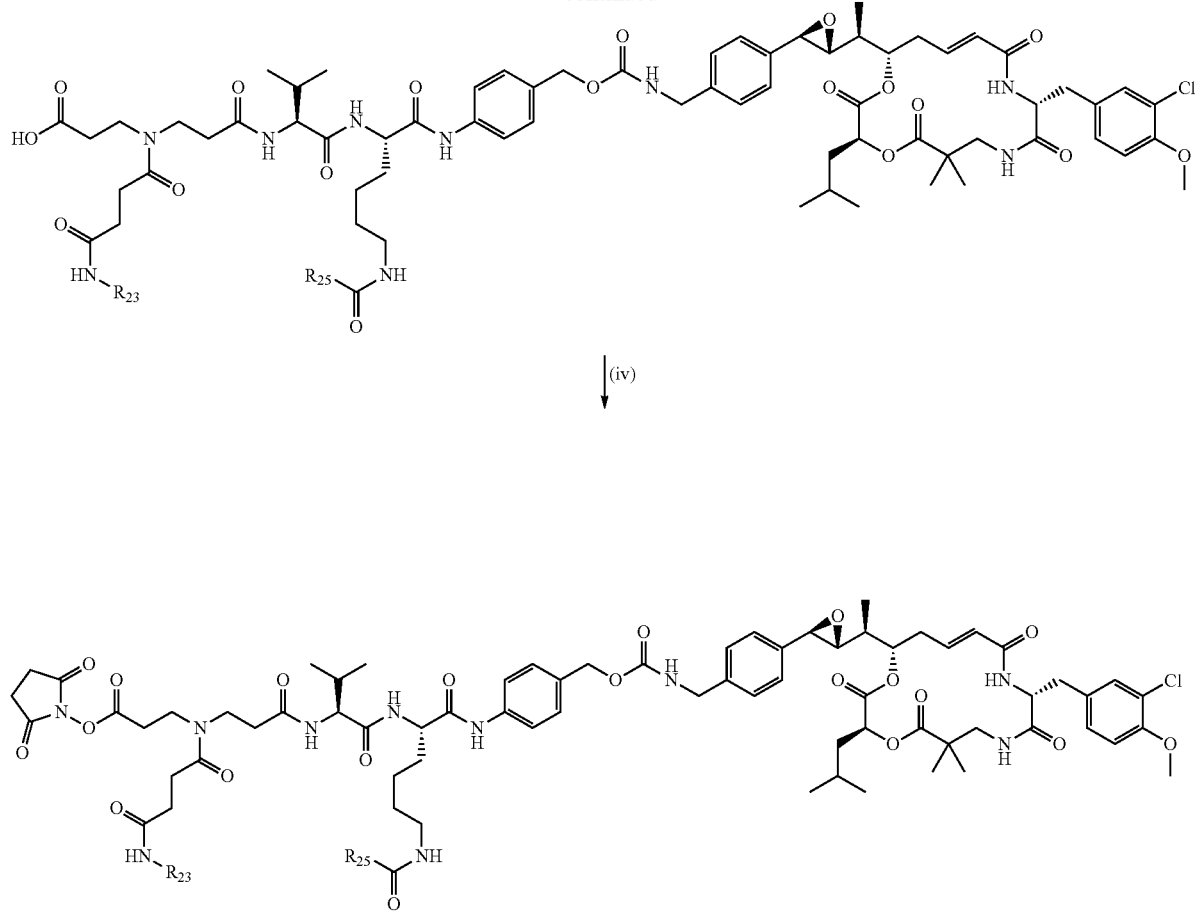

Step (i): formation of a carbamate between the activated alcohol and the cryptophycin amine in the presence of a base such as, for example, DIEA and deprotection of the Fmoc amine in the presence of a base such as, for example, piperidine;

Step (ii): peptidic coupling with spacer 3 using coupling reagents such as, for example, EDC and HOBt, or coupling with spacer 4 in the presence of a base such as, for example, DIEA;

Step (iii): deprotection of the allyl ester in the presence of a catalyst such as, for example, tetrakis-(triphenylphosphine)palladium; one additional deprotection step of the side chain of substituted amino acid may be required prior to step (iv);

Step (iv): activation of the carboxylic acid as a NHS ester by treatment with DSC in the presence of a base such as, for example, DIEA.

Scheme 14 depicted the synthesis of payloads using the p-benzylic amine of C52 but may also apply to other cryptophycin compounds; it depicted the synthesis using dipeptide 6 but may also apply to dipeptide 2; it depicted the synthesis using spacers 3 or 4 but may also apply to spacers 1 or 2.

Preparation of the New Cryptophycin Payloads of Formula (IV) for Y=O—CH2 or S—CH2

Preparation of the New Cryptophycin Payloads Bearing a Spacer with Improved Hydrophilicity Without PABA Moiety Scheme 15

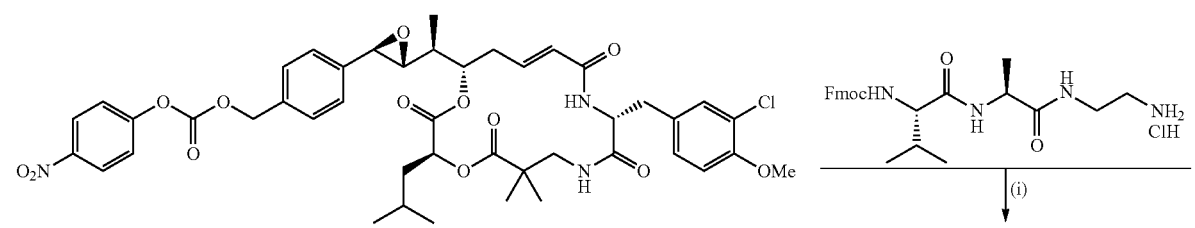

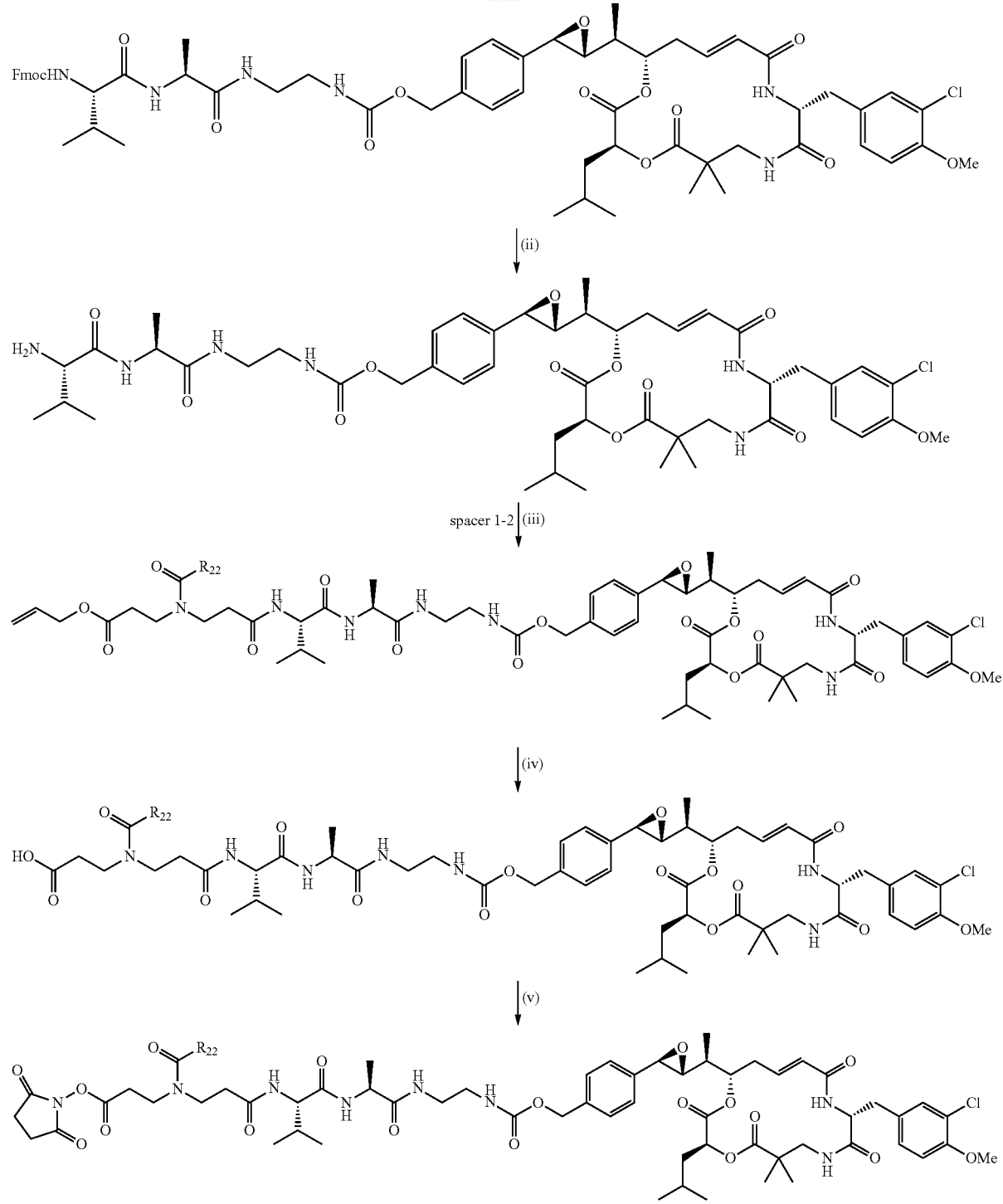

Step (i): formation of a carbamate between the cryptophycin activated alcohol and the amine in the presence of a base such as, for example, DIEA;

Step (ii): deprotection of the Fmoc amine in the presence of a base such as, for example, piperidine;

Step (iii): peptidic coupling with spacer 1 using coupling reagents such as, for example, EDC and HOBt, or coupling with spacer 2 in the presence of a base such as, for example, DIEA;

Step (iv): deprotection of the allyl ester in the presence of a catalyst such as, for example, tetrakis-(triphenylphosphine)palladium;

Step (v): activation of the carboxylic acid as a NHS ester by treatment with DSC in the presence of a base such as, for example, DIEA.

Scheme 15 depicted the synthesis of payloads using the activated p-benzylic alcohol of C52 but may also apply to other cryptophycin compounds; it depicted the synthesis using Val-Ala dipeptides but may also apply to other dipeptides; it depicted the synthesis using Boc-monoprotected ethylenediamine but may also apply to other Boc-monoprotected diamines which are commercially available for n ranging from 3 to 10; it depicted the synthesis using spacers 1 or 2 but may also apply to spacers 3 or 4.

Alternatively, new cryptophycin payloads of formula (IV) bearing a spacer with improved hydrophilicity may also be prepared as depicted in Scheme 16.

Step (i): formation of a carbamate between the cryptophycin activated alcohol and linker 2 in the presence of a base such as, for example, DIEA;

Step (ii): deprotection of the allyl ester in the presence of a catalyst such as, for example, tetrakis-(triphenylphosphine)palladium;

Step (iii): activation of the carboxylic acid as a NHS ester by treatment with DSC in the presence of a base such as, for example, DIEA.

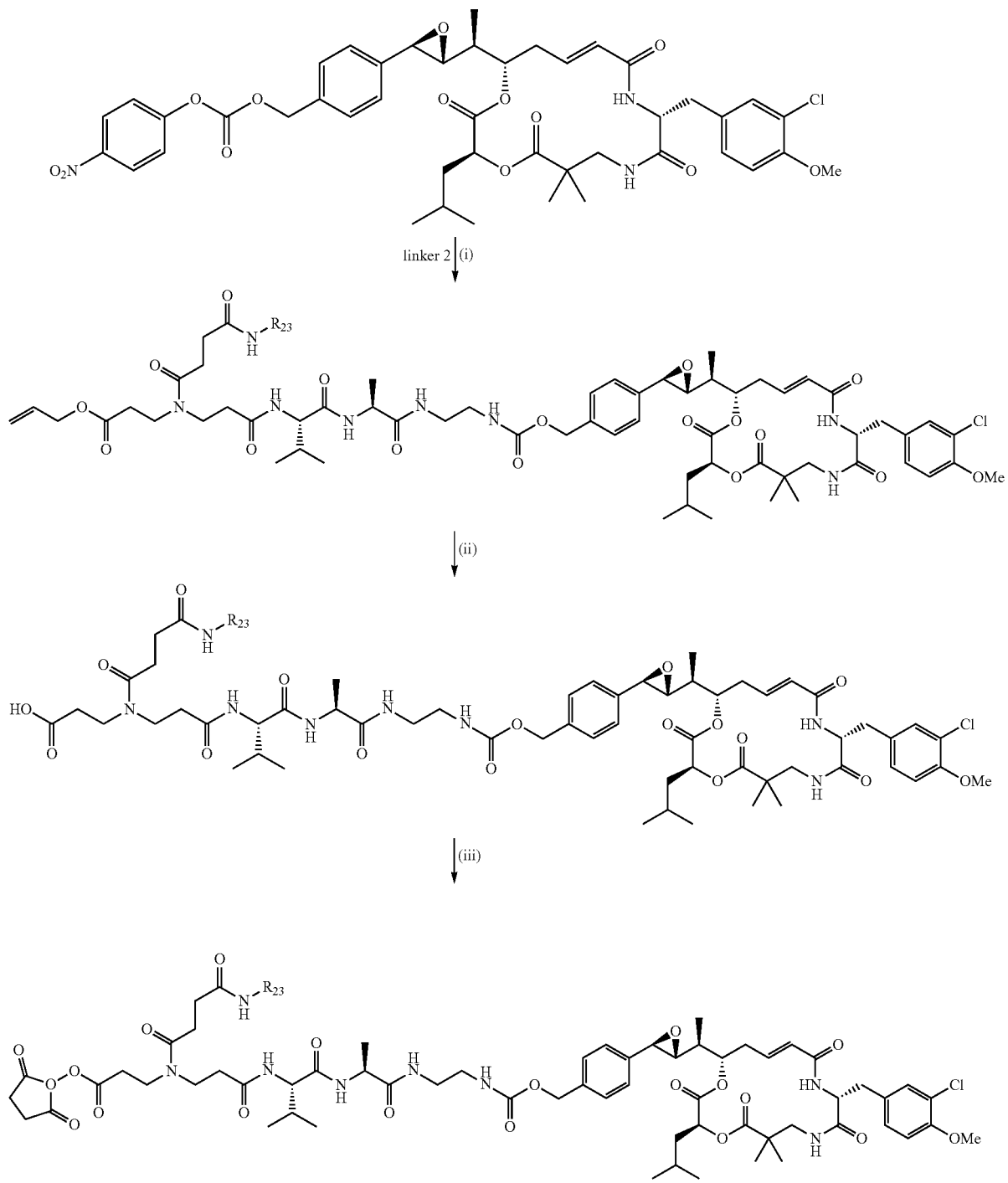

Scheme 16

Scheme 16 depicted the synthesis of payloads using the activated p-benzylic alcohol of C52 but may also apply to other cryptophycin compounds.
With PABA Moeity
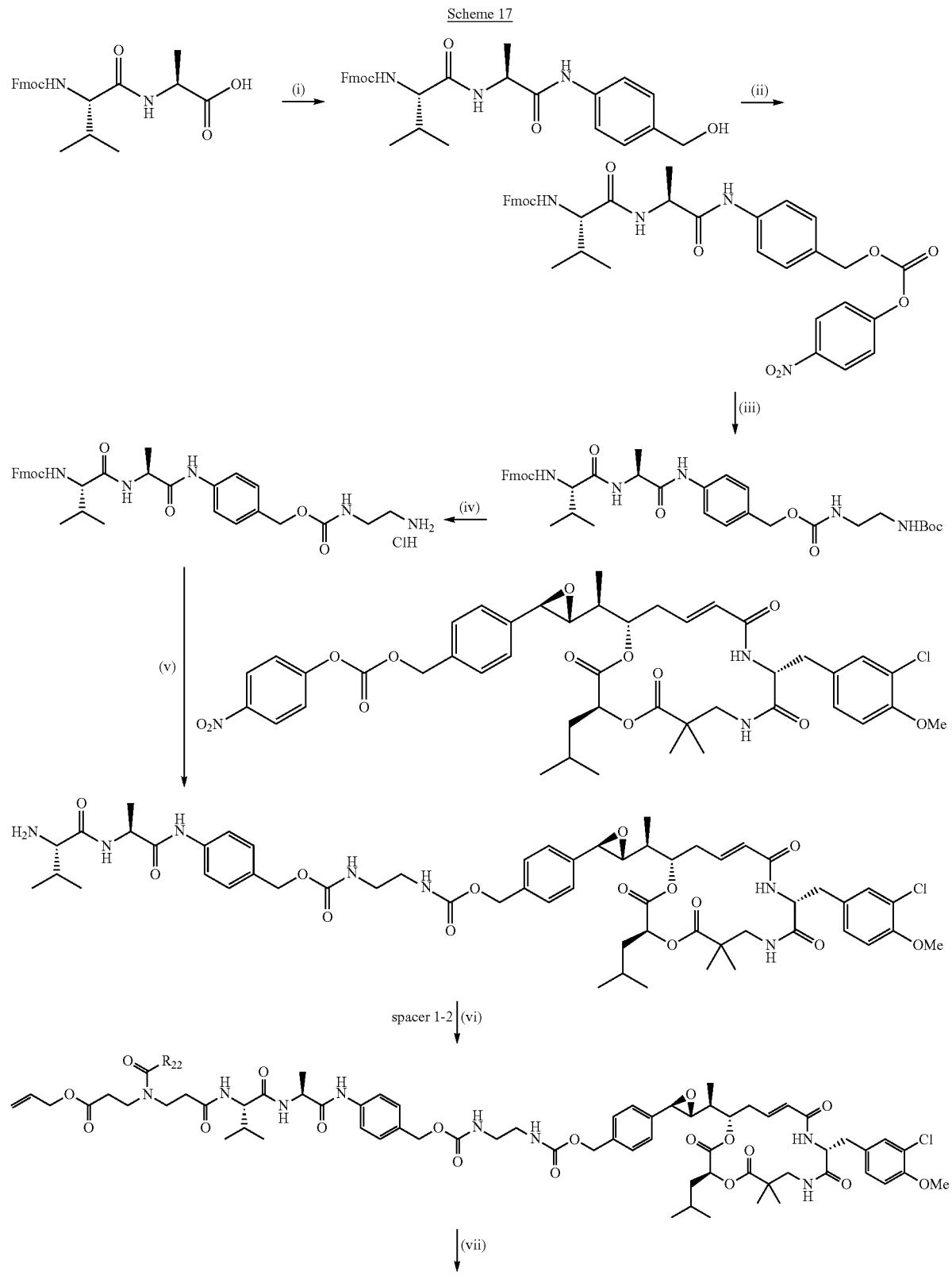
Scheme 17

-continued

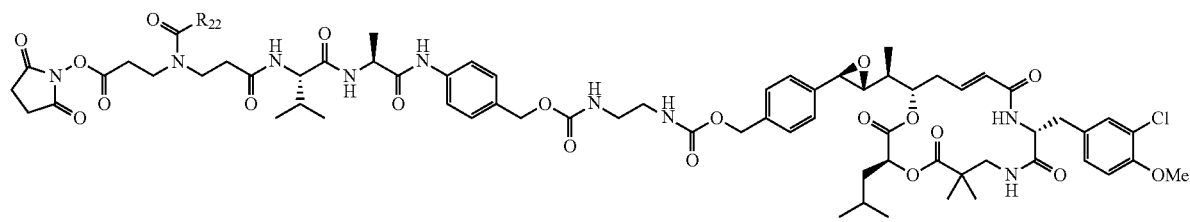

(viii)↓

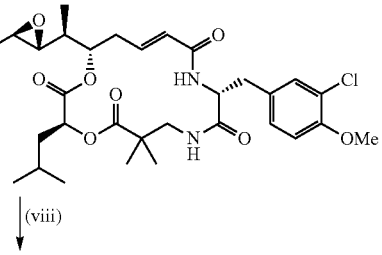

Step (i): peptidic coupling between Fmoc-Val-Ala-OH and 4-aminobenzyl alcohol in the presence of a coupling reagent such as, for example, EEDQ;

Step (ii): activation of the benzylic alcohol as a p-nitrophenyl carbonate by treatment with p-nitrophenyl-chloroformate in the presence of a base such as, for example, DIEA;

Step (iii): formation of a carbamate between the activated alcohol and Boc-monoprotected ethylene diamine in the presence of a base such as, for example, DIEA;

Step (iv): deprotection of the Boc amine using a solution of HCl (for example solution in dioxane) or of TFA;

Step (v): formation of a carbamate between the cryptophycin activated alcohol and the amine in the presence of a base such as, for example, DIEA and deprotection of the Fmoc amine in the presence of a base such as, for example, piperidine;

Step (vi): peptidic coupling with spacer 1 using coupling reagents such as, for example, EDC and HOBt, or coupling with spacer 2 in the presence of a base such as, for example, DIEA;

Step (vii): deprotection of the allyl ester in the presence of a catalyst such as, for example, tetrakis-(triphenylphosphine)palladium;

Step (viii): activation of the carboxylic acid as a NHS ester by treatment with DSC in the presence of a base such as, for example, DIEA.

Scheme 17 depicted the synthesis of payloads using Val-Ala dipeptides but may also apply to other dipeptides; it depicted the synthesis using p-aminobenzyl alcohol (CAS number [623-04-1]) but may also apply to other aminobenzyl alcohol compounds which are commercially available such as, for example, 4-(1-hydroxyethyl)-aniline (racemic (CAS number [14572-89-5]) or enantiopure (R) (CAS number [210754-25-9]) or (S) (CAS number [500229-84-5])), 4-amino-α,α-dimethyl-benzene-methanol (CAS number [23243-04-1]), 4-amino-α-methoxy-α-methyl-benzenemethanol (CAS number [1379318-81-6]), 4-amino-α-methyl-α-trifluoromethyl-benzenemethanol (CAS number [851652-56-7]), 2-amino-benzenemethanol (CAS number [5344-90-1]), 2-amino-α-methyl-benzenemethanol (racemic (CAS number [10517-50-7]) or enantiopure (R) (CAS number [3205-21-8]) or (S) (CAS number [3205-21-8])), 6-amino-3-pyridinemethanol (CAS number [113293-71-3]), 6-amino-α-methyl-3-pyridinemethanol (CAS number [1335054-83-5]), 6-amino-α-ethyl-3-pyridinemethanol (CAS number [1355225-85-2]), 6-amino-α,α-dimethyl-3-pyridinemethanol (CAS number [843646-03-8]), 5-amino-3-pyridinemethanol (CAS number [873651-92-4]), 2-amino-3-pyridinemethanol (CAS number [23612-57-9]), 2-amino-α-methyl-3-pyridinemethanol (racemic (CAS number [869567-91-9]) or enantiopure (R) (CAS number [936718-01-3]) or (S) (CAS number [936718-00-2])), 2-amino-α-ethyl-3-pyridinemethanol (CAS number [914223-90-8]), 2-amino-α,α-dimethyl-3-pyridinemethanol (CAS number [213666-96-7]), 3-amino-4-pyridinemethanol (CAS number [152398-05-5]), 3-amino-α-methyl-4-pyridinemethanol (CAS number [1242470-88-7]), 3-amino-α, α-methyl-4-pyridinemethanol (CAS number [13357-81-8]), 4-amino-3-pyridinemethanol (CAS number [138116-34-4]), 4-amino-α-methyl-3-pyridinemethanol (CAS number [741223-49-4]), 4-amino-α,α-methyl-3-pyridinemethanol (CAS number [1339013-26-1]), 3-amino-2-pyridinemethanol (CAS number [52378-63-9]), 3-amino-α-methyl-2-pyridinemethanol (CAS number [954240-54-1]), 3-amino-α,α-methyl-2-pyridinemethanol (CAS number [899438-57-4]); it depicted the synthesis using Boc-monoprotected ethylenediamine but may also apply to other Boc-monoprotected diamines which are commercially available for n ranging from 3 to 10; it depicted the synthesis using the activated p-benzylic alcohol of C52 but may also apply to other cryptophycin compounds; it depicted the synthesis using spacers 1 or 2 but may also apply to spacers 3 or 4.

Preparation of the New Cryptophycin Payloads of Formula (IV) Bearing a Dipeptide with Improved Hydrophilicity
Without PABA Moiety
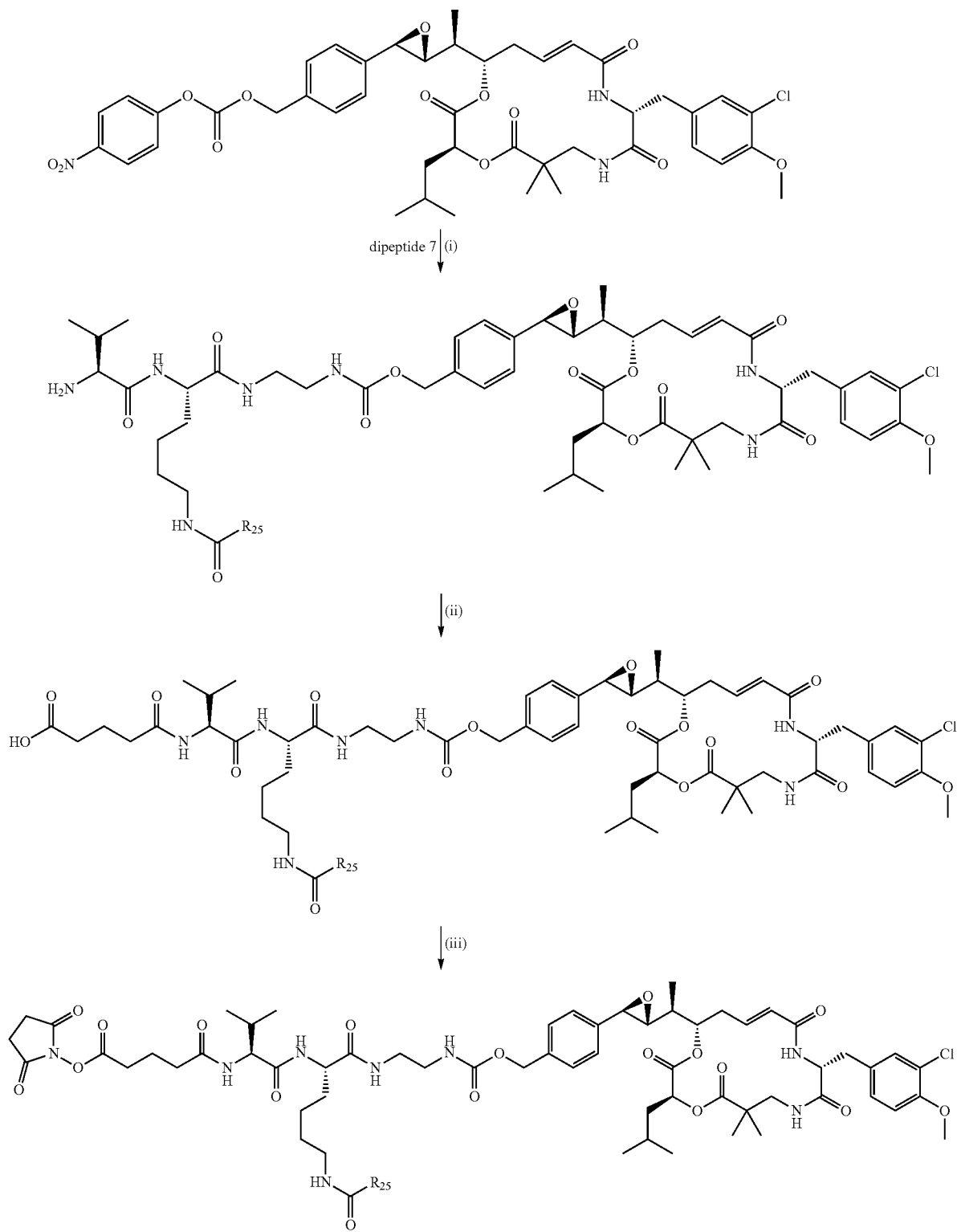
Scheme 18

Step (i): formation of a carbamate between the cryptophycin activated alcohol and the dipeptide in the presence of a base such as, for example, DIEA and deprotection of the Fmoc amine in the presence of a base such as, for example, piperidine;

Step (ii): coupling with glutaric anhydride; one additional deprotection step of the side chain of substituted amino acid may be required prior to step (iii)

Step (iii): activation of the carboxylic acid as a NHS ester by treatment with DSC in the presence of a base such as, for example, DIEA.

Scheme 18 depicted the synthesis of payloads using the activated p-benzylic alcohol of C52 but may also apply to other cryptophycin compounds; it depicted the synthesis using dipeptide 7 but may also apply to dipeptide 3; it depicted the synthesis using glutaric anhydride but may also apply to succinic anhydride or alkyl diacids which are commercially available for n ranging from 3 to 10.

With PABA Moiety

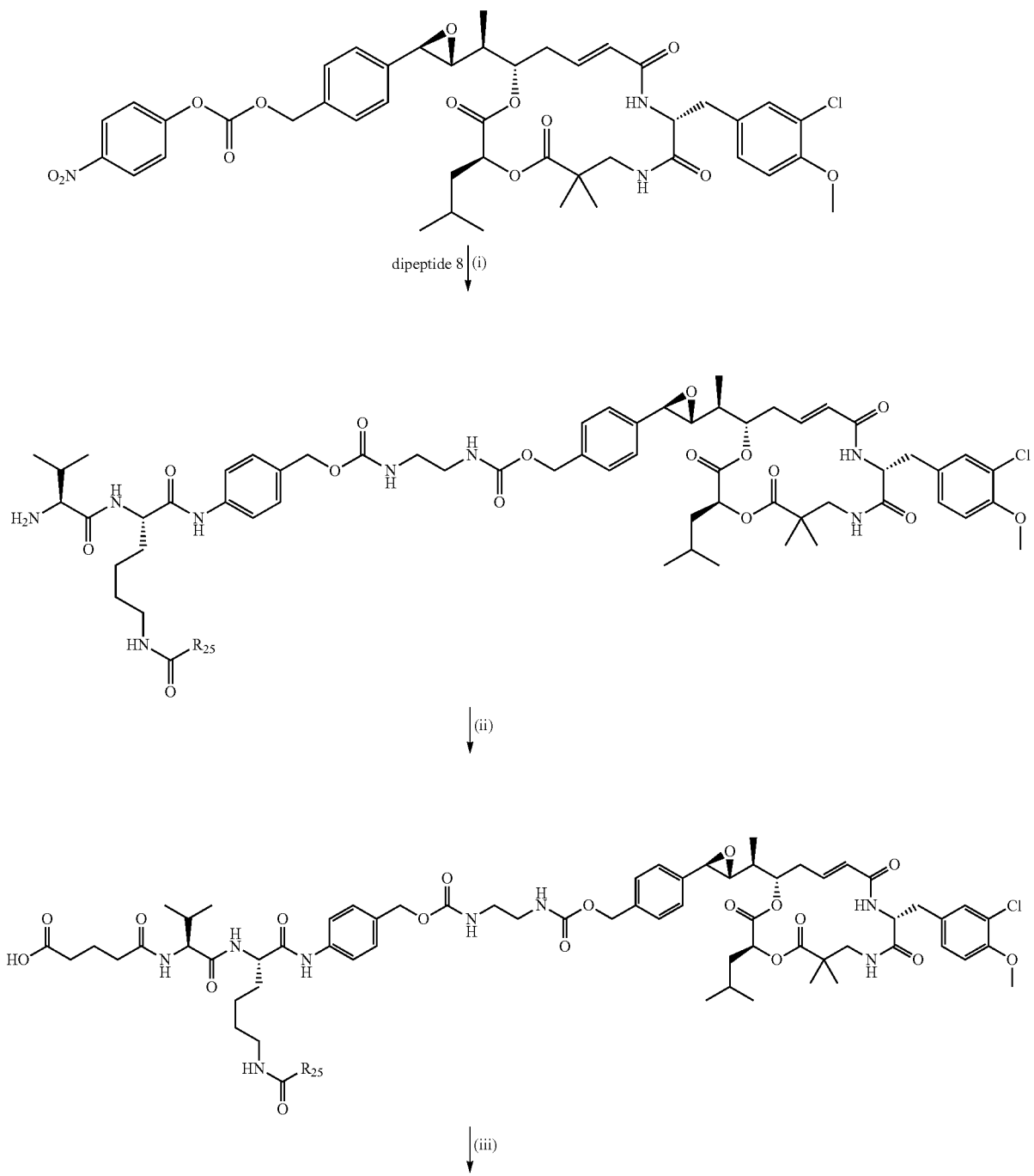

Scheme 19

181

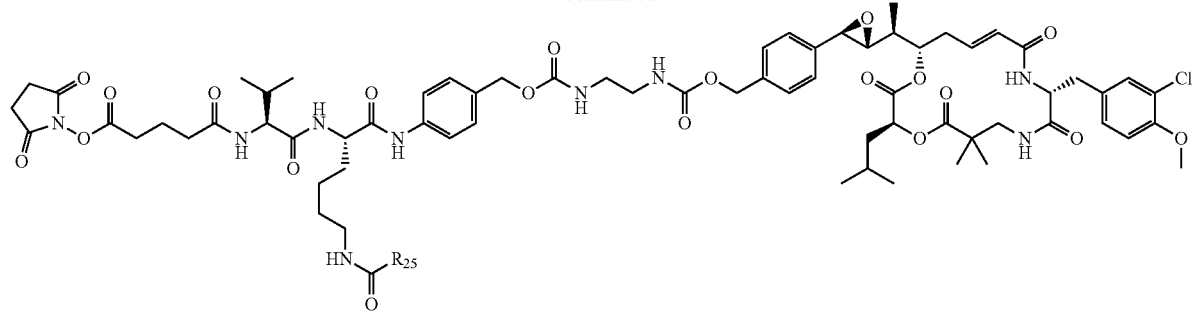

-continued

Step (i): formation of a carbamate between the cryptophycin activated alcohol and the dipeptide in the presence of a base such as, for example, DIEA and deprotection of the Fmoc amine in the presence of a base such as, for example, piperidine;

Step (ii): coupling with glutaric anhydride; one additional deprotection step of the side chain of substituted amino acid may be required prior to step (iii)

Step (iii): activation of the carboxylic acid as a NHS ester by treatment with DSC in the presence of a base such as, for example, DIEA.

Scheme 19 depicted the synthesis of payloads using the activated p-benzylic alcohol of C52 but may also apply to other cryptophycin compounds; it depicted the synthesis using dipeptide 8 but may also apply to dipeptide 4; it depicted the synthesis using glutaric anhydride but may also apply to succinic anhydride or alkyl diacids which are commercially available for n ranging from 3 to 10.

Preparation of the New Cryptophycin Payloads of Formula (IV) Bearing Both a Spacer and a Dipeptide with Improved Hydrophilicity Without PABA Moeity Scheme 20

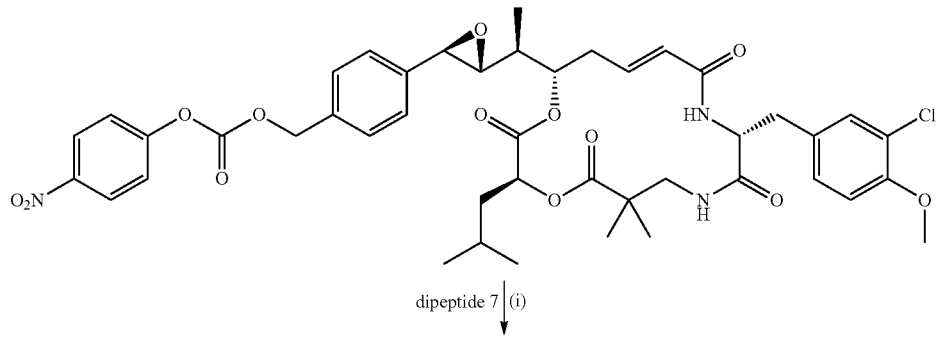

dipeptide 7 ↓ (i)

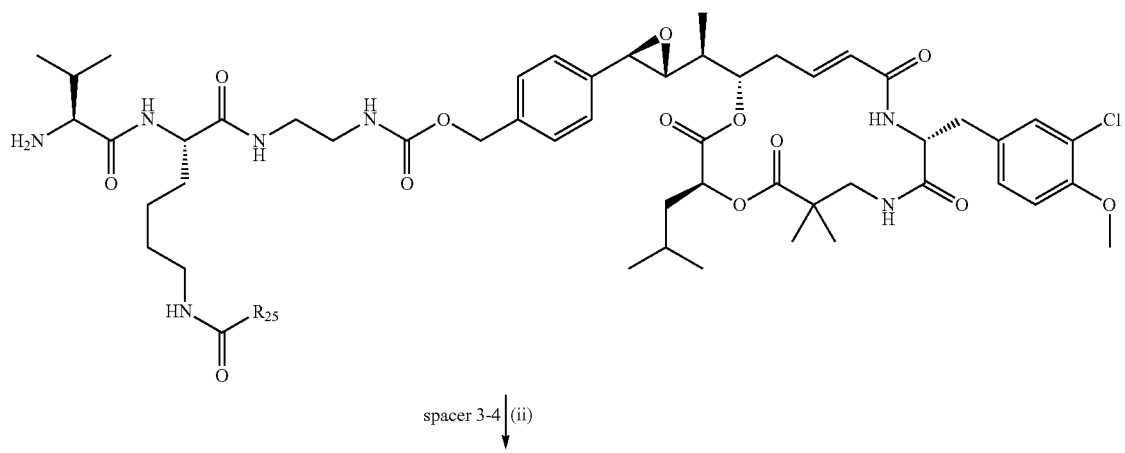

spacer 3-4 ↓ (ii)

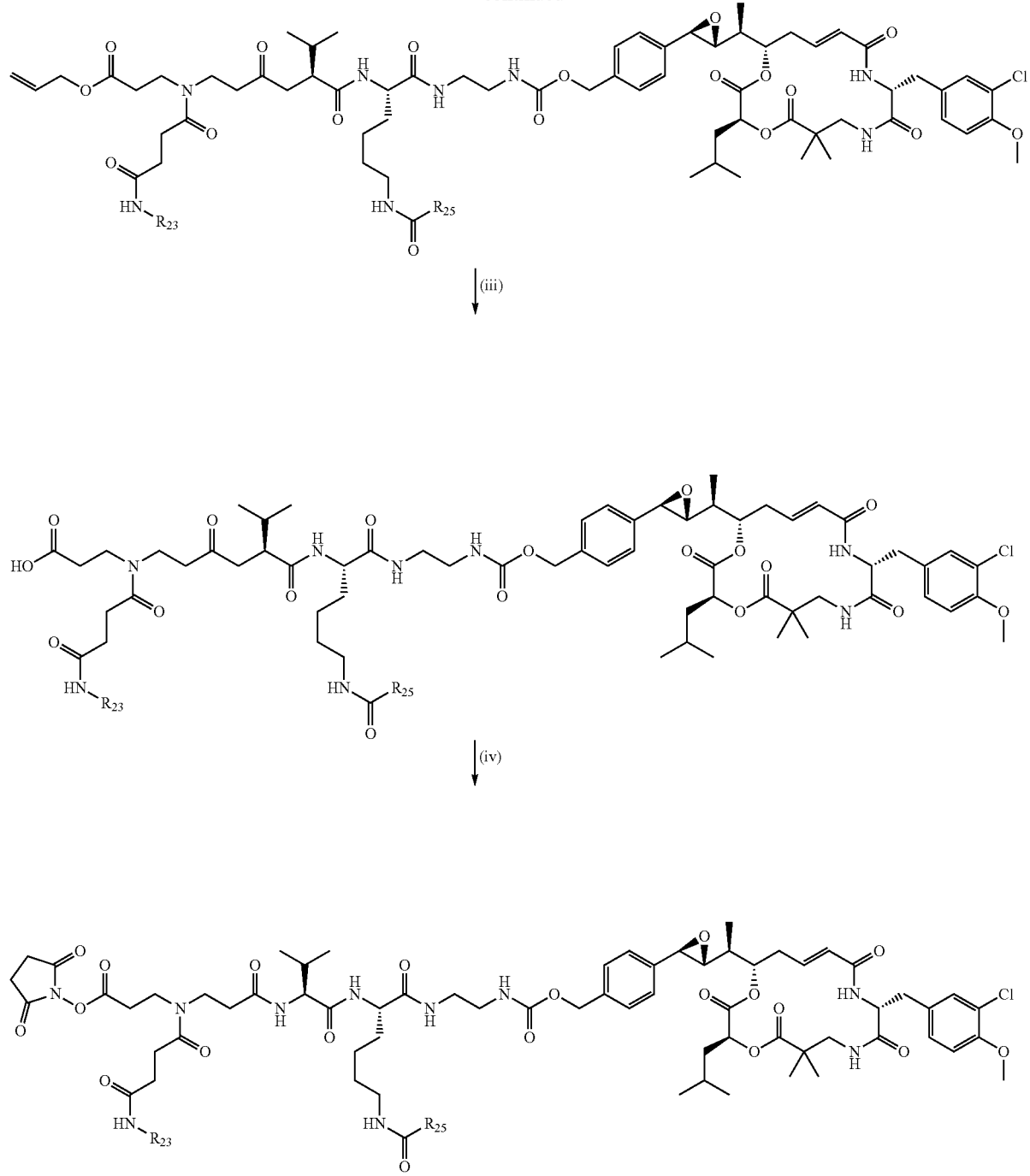

Step (i): formation of a carbamate between the cryptophycin activated alcohol and the dipeptide in the presence of a base such as, for example, DIEA and deprotection of the Fmoc amine in the presence of a base such as, for example, piperidine;

Step (ii): peptidic coupling with spacer 3 using coupling reagents such as, for example, EDC and HOBt, or coupling with spacer 4 in the presence of a base such as, for example, DIEA;

Step (iii): deprotection of the allyl ester in the presence of a catalyst such as, for example, tetrakis-(triphenylphosphine)palladium; one additional deprotection step of the side chain of substituted amino acid may be required prior to step (iv)

Step (iv): activation of the carboxylic acid as a NHS ester by treatment with DSC in the presence of a base such as, for example, DIEA.

Scheme 20 depicted the synthesis of payloads using the p-benzylic amine of C52 but may also apply to other cryptophycin compounds; it depicted the synthesis using dipeptide 7 but may also apply to dipeptide 3; it depicted the synthesis using spacers 3 or 4 but may also apply to spacers 1 or 2.

With PABA Moiety
Scheme 21
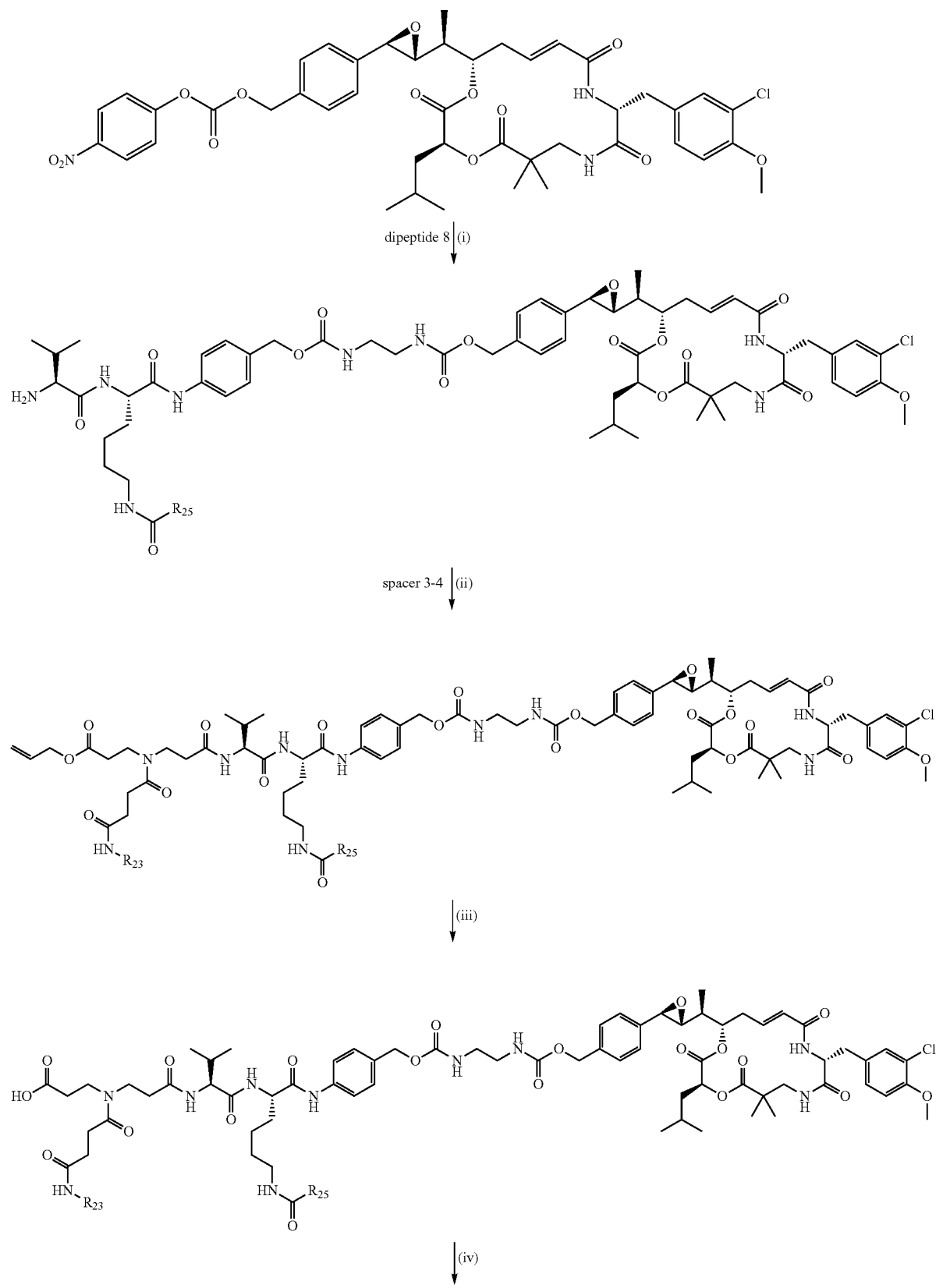

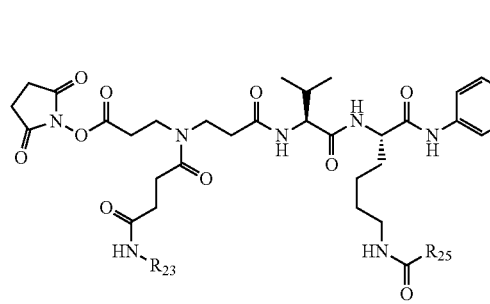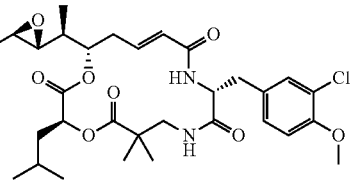

Step (i): formation of a carbamate between the cryptophycin activated alcohol and the dipeptide in the presence of a base such as, for example, DIEA and deprotection of the Fmoc amine in the presence of a base such as, for example, piperidine;

Step (ii): peptidic coupling with spacer 3 using coupling reagents such as, for example, EDC and HOBt, or coupling with spacer 4 in the presence of a base such as, for example, DIEA;

Step (iii): deprotection of the allyl ester in the presence of a catalyst such as, for example, tetrakis-(triphenylphosphine)palladium; one additional deprotection step of the side chain of substituted amino acid may be required prior to step (iv);

Step (iv): activation of the carboxylic acid as a NHS ester by treatment with DSC in the presence of a base such as, for example, DIEA.

Scheme 21 depicted the synthesis of payloads using the p-benzylic amine of C52 but may also apply to other cryptophycin compounds; it depicted the synthesis using dipeptide 8 but may also apply to dipeptide 4; it depicted the synthesis using spacers 3 or 4 but may also apply to spacers 1 or 2.

Preparation of the Conjugates of Formula (V)

The conjugates of formula (V) of the present invention can obtained via the process comprising at least the steps of:
(i) placing in contact and leaving to react:
an optionally buffered aqueous solution of an antibody, optionally modified by means of a modifying agent, and
a solution of a cryptophycin payload of formula (IV) as defined in the present invention,
the chemical group RCG1 of the cryptophycin payload of formula (IV) being reactive towards the chemical groups RCG2 present on the polypeptide such as the antibody especially towards the amino groups present on antibodies, the said chemical groups RCG2 having been introduced, where appropriate, by the modifying agent, so as to attach the cryptophycin payload of formula (IV) to the antibody by formation of a covalent bond;
(ii) and then optionally to separate the conjugate of formula (V) formed in step (i) from the cryptophycin payload of formula (IV) and/or from the unreacted antibody and/or from any aggregates that may have formed.

According to one variant for example, in step (ii) the conjugate of formula (V) from step (i) is separated only from the unreacted cryptophycin payload of formula (IV) and from any aggregates formed, and any unreacted antibody is left in the solution.

The function of the placing in contact is to react the chemical groups RCG1 and RCG2 in order to ensure attachment of the cryptophycin payload of formula (IV) to the polypeptide such as the antibody by formation of a covalent bond; such as, when RCG1 represents $R_aZ_a$—C(=O), the reaction preferably takes place on the amino functions of the antibody, such as the ε-amino groups borne by the side chains of the lysine (Lys) residues of the antibody and the α-amino groups of N-terminal amino acids of antibody heavy and light chains. A conjugate of the following formula is obtained in this case: mAb-[NH—C(=O)-L*-Y-Crypto]$_d$ with L* representing a fragment of a linker L comprising as RCG1 a $R_aZ_a$—C(=O) group and d representing the drug-to-antibody ratio or DAR;

when RCG1 represents a chlorine atom or a maleimido or haloacetamido group, the antibody may comprise thiol chemical groups;

when RCG1 represents an azido group, the antibody may comprise a C≡CH moiety or an activated triple bond such as a cyclooctyne group;

when RCG1 represents $NH_2$ group, the reaction may take place on amide function of the antibody using an enzymatic catalysis, such as the amide groups borne by the side chains of glutamine (Gln) residues of an antibody. A conjugate of the following formula is obtained in this case: mAb-[C(=O)—NH-L*-Crypto]$_d$ with L* representing a fragment of a linker L comprising as RCG1 a $NH_2$ group and such that L representing a L*$NH_2$ group and d representing the drug-to-antibody ratio or DAR;

when RCG1 represents a C≡CH group or an activated C≡C group such as a cyclooctyne moiety, the antibody may comprises azido groups.

The term "aggregates" means associations that may form between two or more antibodies, the antibodies possibly having been modified by conjugation. Aggregates are liable to form under the influence of a wide variety of parameters such as a high concentration of antibody in the solution, the pH of the solution, high shear forces, the number of grafted drugs and their hydrophobic nature, the temperature (see the references cited in the introduction of *J. Membrane Sci.* 2008, 318, 311-316), the influence of some of them, however, having not been clearly elucidated. In the case of proteins or antibodies, reference may be made to *AAPS Journal*, "Protein Aggregation and Bioprocessing" 2006, 8(3), E572-E579. The aggregate content may be determined via known techniques such as SEC (see in this respect Analytical Biochemistry 1993, 212 (2), 469-480).

The aqueous solution of the antibody may be buffered with buffers for example, potassium phosphate or HEPES or a mixture of buffers such as buffer A described later. The buffer depends on the nature of the antibody. The cryptophycin payload of formula (IV) is dissolved in a polar organic solvent such as DMSO or DMA.

The reaction takes place at a temperature generally ranging from 20° C. to 40° C. The reaction time may be ranging from 1 to 24 hours. The reaction between the antibody and the cryptophycin payload of formula (IV) may be monitored by SEC with a refractometric and/or ultraviolet detector and/or HRMS in order to determine its degree of progress. If the degree of substitution is insufficient, the reaction can be left for longer and/or cryptophycin compound can be added. Reference may be made to the example section for further details regarding particular conditions. Particular embodiments are described in Examples 3, 6, 16, 19, 23, 26, 29, 32, 35 and 41.

A person skilled in the art has at his disposal various chromatographic techniques for the separation of step (ii): the conjugate may be purified, for example, by steric exclusion chromatography (SEC), by adsorption chromatography (for instance ion exchange, IEC), by hydrophobic interaction chromatography (HIC), by affinity chromatography, by chromatography on mixed supports such as ceramic hydroxyapatite, or by HPLC. Purification by dialysis or diafiltration may also be used.

After step (i) or (ii), the solution of the conjugate may undergo an ultrafiltration and/or diafiltration step (iii). After these steps, the conjugate in aqueous solution is thus obtained.

Antibody

The antibody can be a monoclonal antibody selected from the group consisting of a murine, chimeric, a humanized and a human antibody.

In one embodiment, the antibody is a monospecific antibody, i.e. an antibody specifically binding to one single target. Alternatively, it might be a multispecific antibody.

In one embodiment, the antibody is a IgG antibody, for instance an $IgG_1$, an $IgG_2$, an $IgG_3$ or an $IgG_4$ antibody.

The antibody according to the invention specifically binds to a target, thereby directing the biologically active compound as a cytotoxic compound towards said target. As used herein, "specifically binds" or "binds specifically to" or "binds to" or the like, means that an antibody or antigen-binding fragment thereof forms a complex with an antigen that is relatively stable under physiological conditions. Specific binding can be characterized by an equilibrium dissociation constant ($K_D$) of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like.

As described herein, antibodies have been characterized, for example, by their specific binding to target and/or target antigen using surface plasmon resonance, e.g., BIA-CORE™.

The target typically corresponds to a protein expressed at the cell surface, e.g. a protein expressed at the surface of tumour cells.

In one embodiment, the target is the EphA2 receptor. The EphA2 receptor is an Ephrin receptor, and is also referred to as "Eph receptor $A_2$" or "Epithelial Cell Receptor Protein-Tyrosine kinase". The antibody specifically binding to the EphA2 receptor might for instance correspond to one of the antibodies described in WO2008/010101 or WO2011/039724.

The antibody may optionally be modified with a modifying agent so as to promote the attachment of the cryptophycin payload as previously described. The antibody may especially be monoclonal, polyclonal or multispecific. It may also be an antibody fragment. It may also be a murine, human, humanized or chimeric antibody. The antibody used in the examples of the present invention is hu2H11_R3574, an antagonist antibody against EphA2 receptor. The sequence of hu2H11_R3574 is represented by SEQ ID NO: 1 (light chain of antibody hu2H11_R35R74) and by SEQ ID NO:2 (heavy chain of antibody hu2H11_R35R74) which correspond to respectively SEQ ID NO: 16 and SEQ ID NO:18 represented in WO2011039724 A1.

Conjugate

A conjugate generally comprises from about 1 to 10 cryptophycin compounds covalently attached to the antibody (this is the degree of grafting or "drug-to-antibody ratio" or "DAR"). This number varies as a function of the nature of the antibody and of the cryptophycin compound, and also of the operating conditions used in the conjugation process (for example the number of equivalents of cryptophycin compound relative to the antibody, the reaction time, the nature of the solvent and of any cosolvent). Placing of the antibody and the cryptophycin compound in contact leads to a mixture comprising several conjugates that are individually distinguished from each other by different DARs; optionally the unreacted antibody; optionally aggregates. The DAR that is determined on the final solution thus corresponds to an average DAR. The DAR may be calculated from the deconvolution of the SEC-HRMS spectrum of the conjugate. The DAR (HRMS) is for example greater than 0.5, for instance ranging from 1 to 10, such as ranging from 2 to 7.

The conjugate may be used as an anticancer agent. Owing to the presence of the antibody, the conjugate is made highly selective towards tumor cells rather than healthy cells. This makes it possible to direct the cryptophycin compound in an environment similar thereto or directly therein. It is possible to treat solid or liquid cancers. The conjugate may be used alone or in combination with at least one other anticancer agent.

The conjugate is formulated in the form of a buffered aqueous solution at a concentration generally ranging from 1 to 10 mg/mL. This solution may be injected in perfusion form per se or may be rediluted to form a perfusion solution.

EXAMPLES

The examples which follow describe the preparation of certain compounds in accordance with the invention. These examples are not limitative, and merely illustrate the present invention.

Analytical Methods Used

High Pressure Liquid Chromatoqraphy-Mass Spectrometry (LCMS)

Method A

Spectra have been obtained on a Waters UPLC-SQD system in positive and/or negative electrospray mode (ES+/−). Chromatographic conditions were the following: Column: ACQUITY BEH C18—1.7 µm—2.1×50 mm; solvents: A: $H_2O$ (0.1% formic acid), B: $CH_3CN$ (0.1% formic acid); column temperature: 50° C.; flow rate: 0.8 mL/min; gradient (2.5 min): from 5 to 100% of B in 1.8 min; 2.4 min: 100% of B; 2.45 min: from 100 to 5% of B in 0.05 min.

Method B

Spectra have been obtained on a Waters UPLC-SQD system in positive and/or negative electrospray mode (ES+/−). Chromatographic conditions were the following: Column: ACQUITY BEH C18—1.7 µm—2.1×50 mm; solvents: A: $H_2O$ (0.1% formic acid), B: $CH_3CN$ (0.1% formic acid); column temperature: 50° C.; flow rate: 0.6 mL/min;

gradient (2 min): from 5 to 50% of B in 1 min; from 50 to 100% of B in 0.3 min; 100% of B during 0.15 min; from 100 to 5% de B in 0.3 min and 5% of B during 0.25 min.

Method C

Spectra have been obtained on a Waters UPLC-SQD system in positive and/or negative electrospray mode (ES+/−). Chromatographic conditions were the following: Column: ACQUITY BEH C18—1.7 μm—2.1×50 mm; solvents: A: $H_2O$ (0.1% formic acid), B: $CH_3CN$ (0.1% formic acid); column temperature: 50° C.; flow rate: 0.8 mL/min; gradient (5 min): from 5 to 100% of B in 4.2 min; 4.6 min: 100% of B; 4.8 min: 5% of B.

Method D

Spectra have been obtained on a Waters XeVo-Qtof system in positive electrospray mode (ES+). Chromatographic conditions were the following: Column: ACQUITY BEH C18—1.7 μm—2.1×100 mm; solvents: A: $H_2O$ (0.1% formic acid), B: $CH_3CN$ (0.1% formic acid); column temperature: 45° C.; flow rate: 0.6 mL/min; gradient (5.3 min): 5% of B from 0 to 0.3 min, 4 min: 100% of B; 4.6 min: 100% of B; 5.3 min: 5% of B.

Method E

Spectra have been obtained on a Waters UPLC-SQD system in positive and/or negative electrospray mode (ES+/−). Chromatographic conditions were the following: Column: ACQUITY BEH C18—1.7 μm—2.1×50 mm; solvents: A: $H_2O$ (0.1% formic acid), B: $CH_3CN$ (0.1% formic acid); column temperature: 45° C.; flow rate: 0.8 mL/min; gradient (10 min): from 5 to 100% of B in 8.6 min; 9.6 min: 100% of B; 9.8 min: 5% of B.

$^1H$ Nuclear Magnetic Resonance (NMR)

The $^1H$ NMR spectra were acquired on a Bruker Avance spectrometer, either of model DRX-300, DRX-400 or DRX-500. The chemical shifts (δ) are given in ppm.

Size Exclusion Chromatography-High Resolution Mass Spectrometry (SEC-HRMS)

The chromatographic analysis was performed on an Agilent HP1100 machine and a Waters BEH SEC 200 1.7 μm (2.1×150 mm) column at 30° C. with a flow rate of 0.5 mL/min and an isocratic elution of (A) 25 mM ammonium formate+1% formic acid/(B) CH3CN+0.1% formic acid 70/30 for 15 minutes. The mass spectrometry was performed on a Waters QTOF-II machine with electrospray ionization in positive mode (ES+). The mass spectra were deconvoluted with the Waters MaxEnt1 software.

Analytical Size Exclusion Chromatography (SEC)

The analysis was performed on a Waters Alliance HPLC system or a Hitachi Lachrom HPLC system equipped with a photodiode array detector and a Tosoh Bioscience TSKgel G3000 SWXL 5 μm column (7.8×300 mm) with a flow rate of 0.5 mL/min and an isocratic elution of 30 minutes with a pH 7 buffer containing 0.2 M of KCl, 0.052 M of $KH_2PO_4$, 0.107 M of $K_2HPO_4$ and 20% by volume of isopropanol.

Buffers

Buffer A (pH 6.5): NaCl (50 mM), potassium phosphate buffer (50 mM), EDTA (2 mM)

Buffer B (pH 6.5): NaCl (140 mM), potassium and sodium phosphate (9.6 mM)

DPBS (pH 7.2): KCl (2.7 mM), NaCl (137 mM), $KH_2PO_4$ (1.47 mM), $Na_2HPO_4$ (8.10 mM)

PBS (pH 7.4): $KH_2PO_4$ (1.06 mM), NaCl (155.17 mM), $Na_2HPO_4$-$7H_2O$ (2.97 mM)

General Method Used for the Preparation of Antibody-Drug Conjugate (ADC)

A solution of antibody in an aqueous buffer composed of a 96:4 mixture of buffer A and 1 N HEPES was treated with an excess (5 to 10 equivalents) of a solution at approximatively 10 mM of cryptophycin payload in DMA such that the final antibody concentration is 3 mg/mL and the percentage of DMA in the aqueous buffer is 20%. After stirring for 1 to 4 hours, the mixture was analysed by SEC-HRMS to determine the DAR on the population of monomeric antibodies. If the DAR was found insufficient (<3.5-4), the mixture was treated with a further excess (1 to 5 equivalents) of cryptophycin solution in DMA for 2 to 4 additional hours at RT under stirring. The mixture was purified by gel filtration using a Superdex 200 pg matrix (HiLoad 16/60 or 26/60 desalting column, GEHealthcare) pre-equilibrated in aqueous buffer pH 6.5 (buffer B or DPBS) containing 10 to 20% of NMP or a Sephadex™ G25 matrix (Hiprep 26/10 desalting column, GEHealthcare) pre-equilibrated in aqueous buffer pH 6.5 (buffer B or DPBS) containing 5 to 10% of NMP. The fractions containing the monomeric conjugated antibody were pooled and concentrated on Amicon Ultra-15 (10k or 50k Ultracel membrane, Millipore) to a concentration of between 2 and 5 mg/mL. A buffer exchange or a dilution in the appropriate buffer was then performed to formulate the conjugate in the final buffer. In the case of a buffer exchange, it was realized by gel filtration using a Sephadex™ G25 matrix (NAP-5, NAP-10, NAP-25/PD-10 or Hiprep 26/10 desalting columns, GEHealthcare) pre-equilibrated with the final aqueous buffer whose composition and pH are suited to each conjugate. The conjugate was finally filtered through a Steriflip® filter unit (0.22 μm Durapore® PVDF membrane, Millipore). The final conjugate was assayed by UV spectrometry or SEC-HPLC so as to measure the conjugate concentration, by SEC-HPLC so as to determine the monomeric purity and by SEC-HRMS so as to determine the DAR from the deconvolution of the mass spectrum of the conjugate.

Synthesis of Examples 1 to 3: PEG4-Val-Ala-C52 Benzylic Amine, NHS Ester of PEG4-Val-Ala-C52 Benzylic Amine and Corresponding ADC

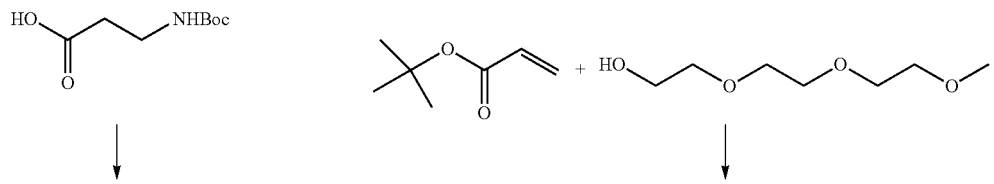

193
194
-continued
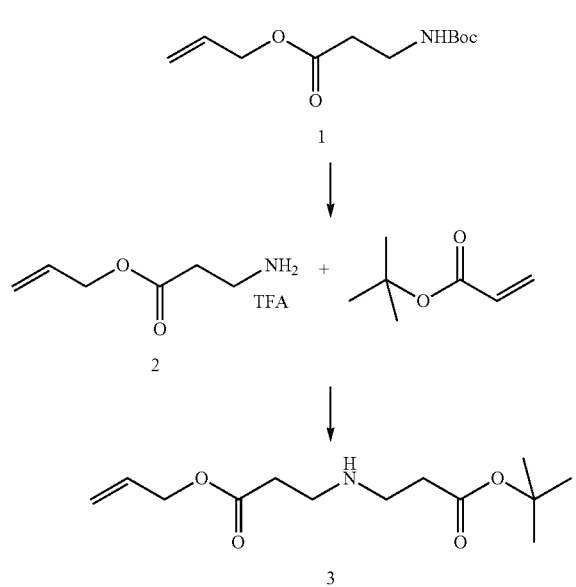
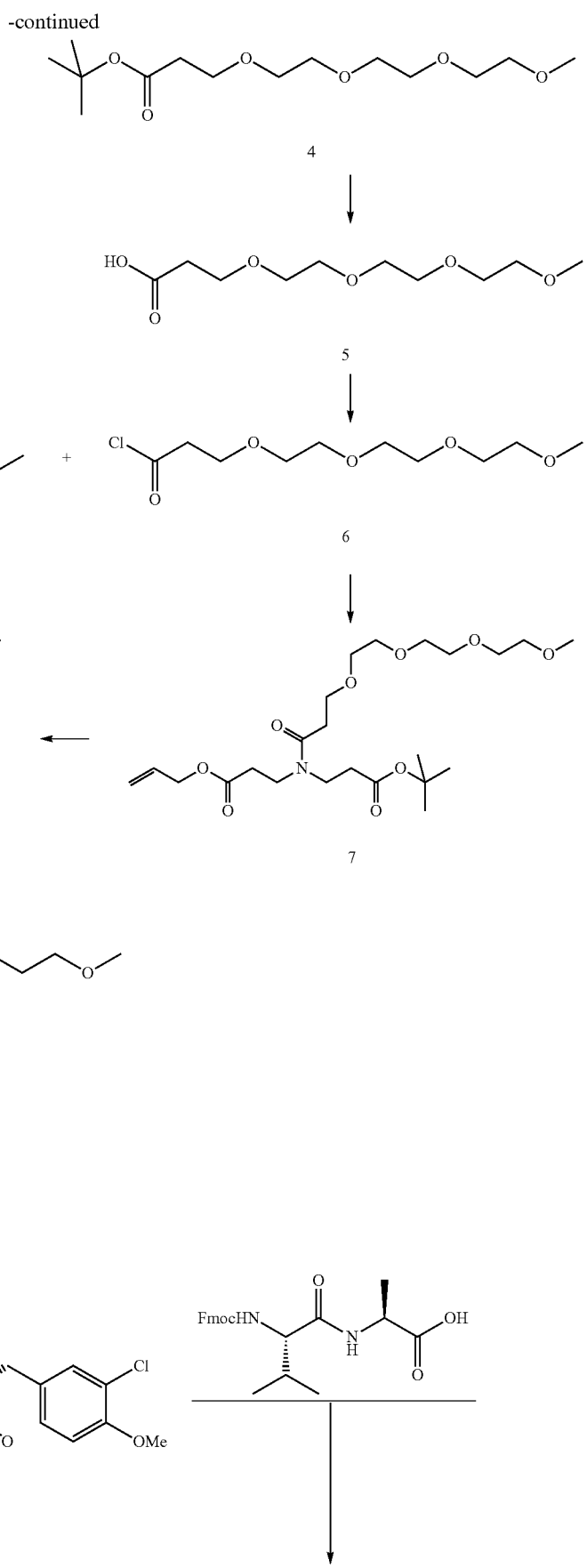

-continued
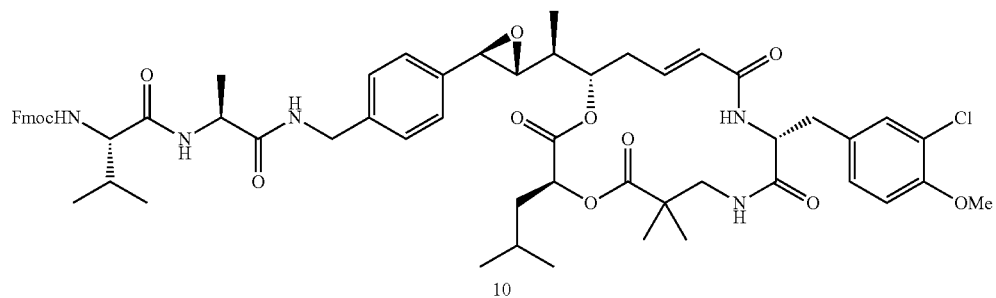
10
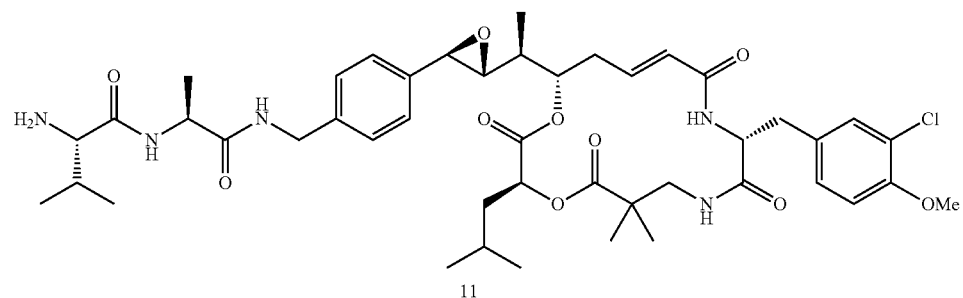
11
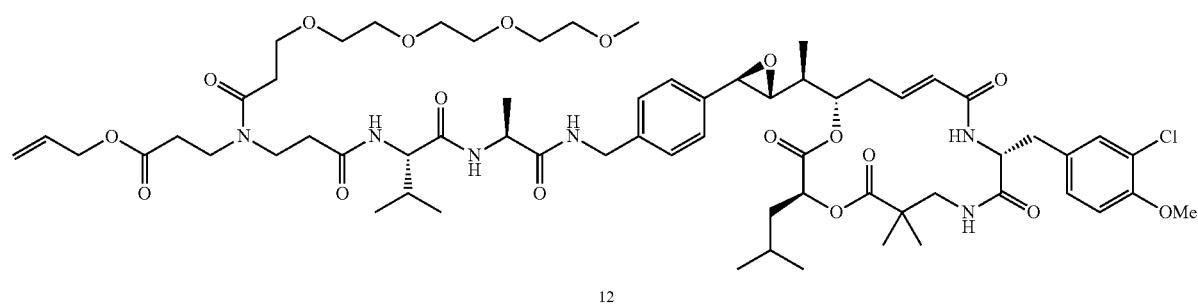
12
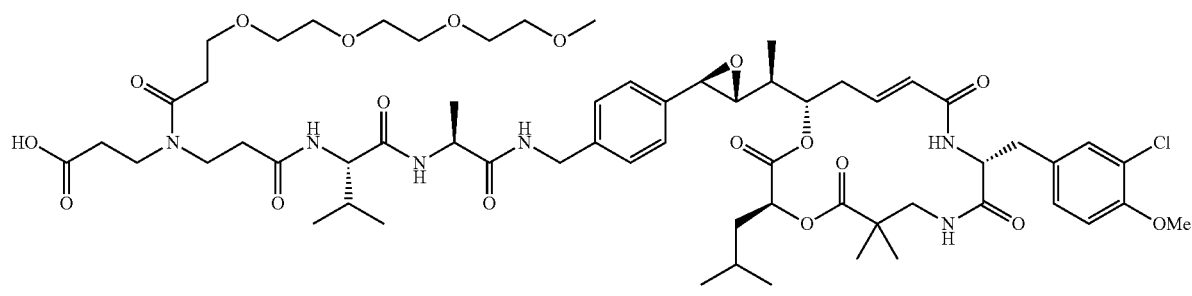
Example 1

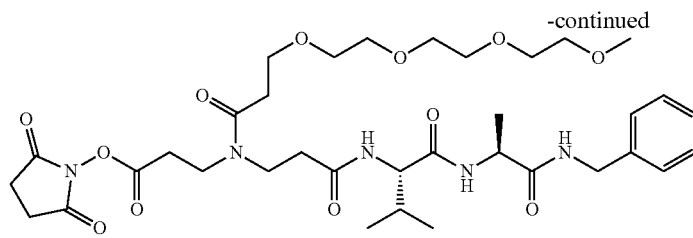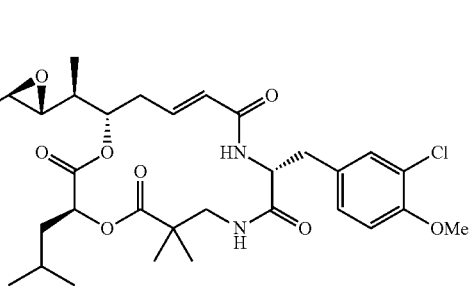

Example 2

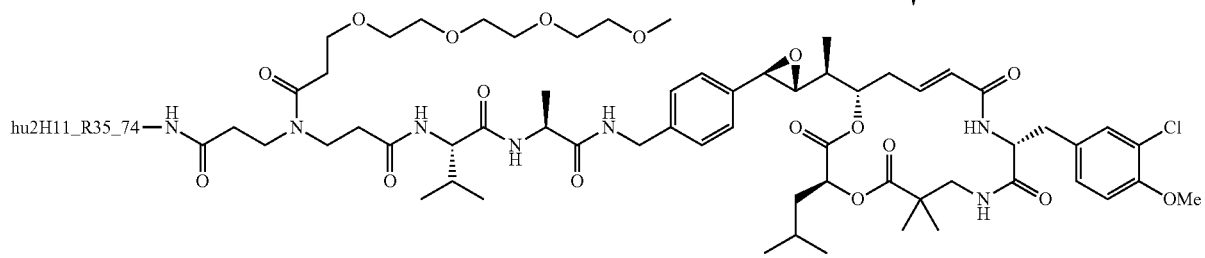

Example 3

Compound 1: allyl 3-((tert-butoxycarbonyl)amino)propanoate

To a solution of Boc-β-Ala-OH (CAS number [3303-84-2], 2 g, 10.04 mmol) in DMF (50 mL) were added cesium carbonate (6.88 g, 21.09 mmol) and allyl bromide (965.52 µL, 11.05 mmol). The reaction medium was stirred at RT overnight. At this time, the reaction medium was concentrated in vacuo, then diluted with toluene and concentrated in vacuo several times. The crude product was diluted with water (100 mL) and extracted with EtOAc (3×300 mL). The combined organic phases were washed with brine, dried over MgSO₄, filtered, concentrated in vacuo and purified by flash chromatography on 90 g of silica gel (gradient elution DCM/MeOH) to give 1.5 g of compound 1 (65%).

RMN $^1$H (400 MHz, δ in ppm, DMSO-d6): 1.37 (s, 9H); 2.45 (t, J=6.9 Hz, 2H); 3.17 (q, J=6.9 Hz, 2H); 4.54 (m, 2H); 5.20 (qd, J=1.5 and 10.6 Hz, 1H); 5.29 (qd, J=1.9 and 17.3 Hz, 1H); 5.91 (m, 1H); 6.85 (broad t, J=6.9 Hz, 1H).

Compound 2: allyl 3-aminopropanoate 2,2,2-trifluoroacetate

To a solution of compound 1 (1.5 g, 6.54 mmol) in DCM (30 mL) was added TFA (5.09 mL, 65.42 mmol). The reaction medium was stirred at RT overnight. At this time, the reaction medium was concentrated in vacuo, then diluted with toluene and concentrated in vacuo twice to afford 1.6 g of compound 2 (quant.).

Compound 3: allyl 3-((3-(tert-butoxy)-3-oxopropyl)amino)propanoate

To a solution of compound 2 (1.6 g, 6.58 mmol) in DMSO (15 mL) were added DIEA (2.30 mL, 13.16 mmol) and tert-butyl acrylate (973.49 µL, 6.58 mmol). The reaction medium was heated 1 h at 60° C. using microwaves. At this time, the reaction medium was diluted with H₂O (10 mL) and extracted with EtOAc. The combined organic phases were washed with brine, dried over MgSO₄, filtered, concentrated in vacuo and purified by flash chromatography on 80 g of silica gel (gradient elution DCM/MeOH) to give 678 mg of compound 3 (40%).

RMN $^1$H (400 MHz, δ in ppm, DMSO-d6): 1.39 (s, 9H); 1.73 (broad m, 1H); 2.29 (t, J=6.9 Hz, 2H); 2.44 (t, J=6.9 Hz, 2H); 2.68 (t, J=6.9 Hz, 2H); 2.73 (t, J=6.9 Hz, 2H); 4.53 (m, 2H); 5.20 (qd, J=1.5 and 10.6 Hz, 1H); 5.30 (qd, J=1.9 and 17.3 Hz, 1H); 5.91 (m, 1H).

Compound 4: tert-butyl 2,5,8,11-tetraoxatetradecan-14-oate

Under argon, a mixture of triethylene glycol monomethyl ether (CAS number [112-35-6], 3 g, 17.36 mmol) and sodium (3.99 mg, 173.57 µmol) in THF (9 mL) was stirred for 2 h at 50° C. then overnight at RT. At this time, tert-butyl acrylate (3.08 ml, 20.83 mmol) was added, stirred for 2 h at 40° C. then overnight at RT. After that, the reaction medium was concentrated in vacuo, then diluted H₂O and extrated with EtOAc. The combined organic phases were washed with brine, dried over MgSO₄, filtered, concentrated in vacuo and purified by flash chromatography on 90 g of silica gel (gradient elution heptane/EtOAc) to give 3.3 g of compound 4 (65%).

Compound 5: 2,5,8,11-tetraoxatetradecan-14-oic Acid

To a solution of compound 4 (2.5 g, 8.55 mmol) in DCM (30 mL) was added TFA (6.65 mL, 85.51 mmol). The reaction medium was stirred overnight at RT. At this time, the reaction medium was concentrated in vacuo, then diluted with toluene and concentrated in vacuo three times to give 3 g of compound 5 (quant.).

Compound 6: 2,5,8,11-tetraoxatetradecan-14-oyl chloride

To compound 5 (800 mg, 3.39 mmol) was added thionyl chloride (3.68 mL, 50.79 mmol). The reaction medium was heated 3 h at 60° C. After cooling, the reaction medium was concentrated in vacuo, diluted with DCM and concentrated in vacuo twice to give 870 mg of compound 6 (quant.).

Compound 7: allyl 15-(3-(tert-butoxy)-3-oxopropyl)-14-oxo-2,5,8,11-tetraoxa-15-azaoctadecan-18-oate At 0° C., under argon, to a solution of compound 3 (678 mg, 2.63 mmol) and DIEA (533.21 µL, 3.16 mmol) in DCM (10 mL) was added a solution of compound 6 (738.21 mg, 2.90 mmol) in DCM (3 mL). After 2 h, the reaction medium was washed with $H_2O$ (10 mL) then brine, dried over $MgSO_4$, filtered, concentrated in vacuo and purified by flash chromatography on 40 g of silica gel (gradient elution DCM/MeOH) to give 410 mg of compound 7 (33%).

RMN $^1$H (400 MHz, δ in ppm, DMSO-d6): 50/50 conformer mixture; 1.39 (s, 4.5H); 1.40 (s, 4.5H); 2.39 (t, J=7.2 Hz, 1H); 2.47 to 2.60 (partially masked m, 4H); 2.66 (t, J=7.2 Hz, 1H); 3.23 (s, 1.5H); 3.24 (s, 1.5H); 3.38 to 3.65 (m, 18H); 4.54 (m, 2H); 5.19 to 5.34 (m, 2H); 5.85 to 5.97 (m, 1H).

Compound 8: 15-(3-(allyloxy)-3-oxopropyl)-14-oxo-2,5,8,11-tetraoxa-15-azaoctadecan-18-oic Acid A solution of compound 7 (150 mg, 315.41 µmol) in DCM (3 mL) and TFA (236.66 µL, 3.15 mmol) was stirred at RT overnight. At this time, the reaction medium was concentrated in vacuo, diluted with toluene and concentrated in vacuo three times to give 130 mg of compound 8 (98%).

Compound 9: allyl 15-(3-((2,5-dioxopyrrolidin-1-yl)oxy)-3-oxopropyl)-14-oxo-2,5,8,11-tetraoxa-15-azaoctadecan-18-oate To a solution of compound 8 (130 mg, 309.92 µmol) in THF (5 mL) were added DIEA (104.53 µL, 619.83 µmol) and DSC (97.21 mg, 371.90 µmol). The reaction medium was stirred at RT overnight. At this time, the reaction medium was concentrated in vacuo and purified by flash chromatography on 4 g of silica gel (gradient elution DCM/iPrOH) to give 107 mg of compound 9 (67%).

Compound 10: (9H-fluoren-9-yl)methyl ((2S)-1-(((2S)-1-((4-((2R,3S)-3-(1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)amino)-1-oxopropan-2-yl)amino)-3-methyl-1-oxobutan-2-yl)carbamate To a solution of (3S,10R,16S,E)-16-((S)-1-((2R,3R)-3-(4-(aminomethyl)phenyl)-oxiran-2-yl)ethyl)-10-(3-chloro-4-methoxybenzyl)-3-isobutyl-6,6-dimethyl-1,4-dioxa-8,11-diazacyclohexadec-13-ene-2,5,9,12-tetraone (the synthesis of which was described in WO2011001052, compound 77, 150 mg, 214.82 µmol) in DCM was added HOBt (31.93 mg, 236.31 µmol), EDC (41.83 µL, 236.31 µmol) and Fmoc-Val-Ala-OH (CAS number [150114-97-9], 79.36 mg, 193.34 µmol). The reaction medium was stirred for 3 h at RT. Then $H_2O$ (20 mL) was added and the mixture was extracted with DCM (2×15 mL). The combined organic phases were washed with brine, dried over $MgSO_4$, filtered, concentrated in vacuo and purified by flash chromatography on 5 g of silica gel (gradient elution DCM/MeOH) to give 200 mg of compound 10 (85%).

Compound 11: (2S)-2-amino-N-((2S)-1-((4-((2R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)amino)-1-oxopropan-2-yl)-3-methylbutanamide A mixture of compound 10 (200 mg, 183.37 µmol) in DCM (10 mL) and piperidine (183.39 µL, 1.83 mmol) was stirred for 2 h at RT. The reaction medium was concentrated in vacuo, solubilized in DCM before addition of $Et_2O$. The precipitate was filtered, washed with $Et_2O$ and dried to give 180 mg of crude that was purified by flash chromatography on 10 g of amino-propyl modified silica gel (gradient elution DCM/MeOH) to give 136 mg of compound 11 (85%).

Compound 12: allyl 15-(3-(((2S)-1-(((2S)-1-((4-((2R,3S)-3-(1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)amino)-1-oxopropan-2-yl)amino)-3-methyl-1-oxobutan-2-yl)amino)-3-oxopropyl)-14-oxo-2,5,8,11-tetraoxa-15-azaoctadecan-18-oate To a solution of compound 11 (60 mg, 69.09 µmol) in THF (5 mL) were added compound 9 (42.82 mg, 82.91 µmol) and DIEA (17.48 µL, 103.63 µmol). The reaction medium was stirred for 3 h at RT. At this time, it was concentrated in vacuo and purified by flash chromatography on 10 g of silica gel (gradient elution DCM/MeOH) to give 60 mg of compound 12 (68%).

RMN $^1$H (MHz, δ in ppm, DMSO-d6): 60/40 conformer mixture; 0.78 (d, J=7.0 Hz, 6H); 0.80 to 0.87 (m, 6H); 1.00 (s, 3H); 1.04 (d, J=7.0 Hz, 3H); 1.12 (s, 3H); 1.24 (split d, J=7.0 Hz, 3H); 1.30 (m, 1H); 1.51 to 1.63 (m, 2H); 1.75 to 1.83 (m, 1H); 1.95 (m, 1H); 2.26 (m, 1H); 2.30 to 2.73 (m, 8H); 2.95 to 3.05 (m, 3H); 3.23 (s, 3H); 3.31 (masked m, 1H); 3.40 to 3.64 (m, 18H); 3.81 (s, 3H); 3.87 (d, J=2.1 Hz, 1H); 4.12 to 4.33 (m, 5H); 4.53 (m, 1.2H); 4.55 (m, 0.8H); 4.91 (m, 1H); 5.11 (m, 1H); 5.21 (m, 1H); 5.28 (qd, J=1.9 and 17.3 Hz, 0.6H); 5.31 (qd, J=1.9 and 17.3 Hz, 0.4H); 5.78 (split d, J=15.7 Hz, 1H); 5.85 to 5.95 (m, 1H); 6.47 (ddd, J=4.2, 11.5 and 15.7 Hz, 1H); 7.05 (d, J=8.7 Hz, 1H); 7.17 (dd, J=2.3 and 8.7 Hz, 1H); 7.19 to 7.26 (m, 5H); 7.28 (d, J=2.3 Hz, 1H); 7.94 (d, J=9.2 Hz, 0.4H); 8.04 (m, 1H); 8.10 (d, J=7.6 Hz, 0.6H); 8.32 (m, 1H); 8.35 (d, J=8.2 Hz, 1H).

Example 1: 15-(3-(((S)-1-(((S)-1-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)amino)-1-oxopropan-2-yl)amino)-3-methyl-1-oxobutan-2-yl)amino)-3-oxopropyl)-14-oxo-2,5,8,11-tetraoxa-15-azaoctadecan-18-oic Acid Under argon, to a solution of compound 12 (60 mg, 47.25 µmol) in DCM (5 mL) were added tetrakis(triphenylphosphine)palladium(0) (2.76 mg, 2.36 µmol) and 1,3-dimethylbarbituric acid (22.58 mg, 141.74 µmol). The reaction medium was stirred for 1 h at RT and concentrated in vacuo.

The crude product was purified by flash chromatography on 4 g of silica gel (gradient elution DCM/MeOH) to give 31 mg of example 1 (53%).

RMN ¹H (500 MHz, δ in ppm, DMSO-d6): 0.79 (d, J=7.0 Hz, 6H); 0.80 to 0.88 (m, 6H); 1.00 (s, 3H); 1.04 (d, J=7.0 Hz, 3H); 1.12 (s, 3H); 1.23 (m, 3H); 1.31 (m, 1H); 1.51 to 1.62 (m, 2H); 1.80 (m, 1H); 1.95 (m, 1H); 2.27 (m, 1H); 2.35 to 2.60 (partially masked m, 6H); 2.62 to 2.73 (m, 2H); 2.93 to 3.06 (m, 3H); 3.23 (s, 3H); 3.28 to 3.35 (masked m, 1H); 3.36 to 3.65 (m, 18H); 3.81 (s, 3H); 3.87 (d, J=2.0 Hz, 1H); 4.11 to 4.34 (m, 5H); 4.91 (m, 1H); 5.10 (m, 1H); 5.79 (d, J=15.5 Hz, 1H); 6.48 (ddd, J=3.8, 11.3 and 15.5 Hz, 1H); 7.05 (d, J=8.7 Hz, 1H); 7.17 (dd, J=2.0 and 8.7 Hz, 1H); 7.24 (m, 5H); 7.29 (d, J=2.0 Hz, 1H); 7.95 to 8.18 (m, 2H); 8.30 to 8.46 (m, 2H); 12.27 (broad m, 1H). LCMS (A): ES m/z=615 [M+2H]²⁺; m/z=1227 [M−H]⁻; m/z=1229 [M+H]⁺; t$_R$=1.26 min.

Example 2: 2,5-dioxopyrrolidin-1-yl 15-(3-(((S)-1-(((S)-1-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)amino)-1-oxopropan-2-yl)amino)-3-methyl-1-oxobutan-2-yl)amino)-3-oxopropyl)-14-oxo-2,5,8,11-tetraoxa-15-azaoctadecan-18-oate To a solution of example 1 (30 mg, 24.39 µmol) in THF (5 mL) were added DSC (7.65 mg, 29.27 µmol) and DIEA (9.88 µL, 58.54 µmol). The reaction medium was stirred at RT overnight then concentrated in vacuo and purified by flash chromatography on 5 g of diol modified silica gel (gradient elution DCM/iPrOH) to give 17 mg of example 2 (53%).

RMN ¹H (500 MHz, δ in ppm, DMSO-d6): 70/30 conformer mixture; 0.79 (d, J=7.0 Hz, 6H); 0.80 to 0.87 (m, 6H); 1.00 (s, 3H); 1.04 (d, J=7.0 Hz, 3H); 1.12 (s, 3H); 1.21 to 1.34 (m, 4H); 1.51 to 1.62 (m, 2H); 1.80 (m, 1H); 1.93 (m, 1H); 2.27 (m, 1H); 2.35 to 2.72 (partially masked m, 6H); 2.81 (s large, 4H); 2.88 to 3.06 (m, 5H); 3.23 (s, 3H); 3.28 to 3.37 (masked m, 1H); 3.40 to 3.79 (m, 18H); 3.81 (s, 3H); 3.88 (s, 1H); 4.13 to 4.33 (m, 5H); 4.90 (m, 1H); 5.10 (m, 1H); 5.79 (d, J=15.5 Hz, 1H); 6.46 (ddd, J=3.8, 11.5 and 15.5 Hz, 1H); 7.05 (d, J=8.7 Hz, 1H); 7.17 (broad s, 1H); 7.24 (m, 5H); 7.29 (broad s, 1H); 7.94 (d, J=8.8 Hz, 0.3H); 8.06 (m, 1H); 8.12 (d, J=8.1 Hz, 0.7H); 8.32 (m, 1H); 8.36 (d, J=8.1 Hz, 1H). LCMS (A): ES m/z=663.5 [M+2H]²⁺; m/z=1324 [M−H]⁻; m/z=1326 [M+H]⁺; m/z=1374 [M−H+HCO₂H]⁻; t$_R$=1.3 min.

Example 3: hu2H11_R35-74-Ex2

The general method described previously was used for the preparation of example 3. 15 mg of hu2H11_R35-74 were reacted with 55.2 µL of a 9.1 mM solution of example 2 in DMA (10 eq.) for 3 h 30. After purification on Superdex 200 pg in buffer B pH 6.5+10% NMP, concentration on Amicon Ultra-15, buffer exchange on Nap-10 in buffer B pH 6.5+5% NMP and filtration on 0.22 µm PVDF filter, 3.36 mg of example 3 were obtained as a colorless limpid solution at a concentration of 2.24 mg/mL with a DAR of 3.4 (HRMS), a monomeric purity of 99.8% and a global yield of 22%.

SEC-HRMS: m/z=149354 (naked mAb); m/z=150563 (D1); m/z=151774 (D2); m/z=152966 (D3); m/z=154169 (D4); m/z=155410 (D5); m/z=156623 (D6); m/z=157835 (D7); m/z=159051 (D8).

Synthesis of Examples 4 to 6: sulfo-Val-Ala-C52 Benzylic Amine, NHS Ester of sulfo-Val-Ala-C52 Benzylic Amine and Corresponding ADC

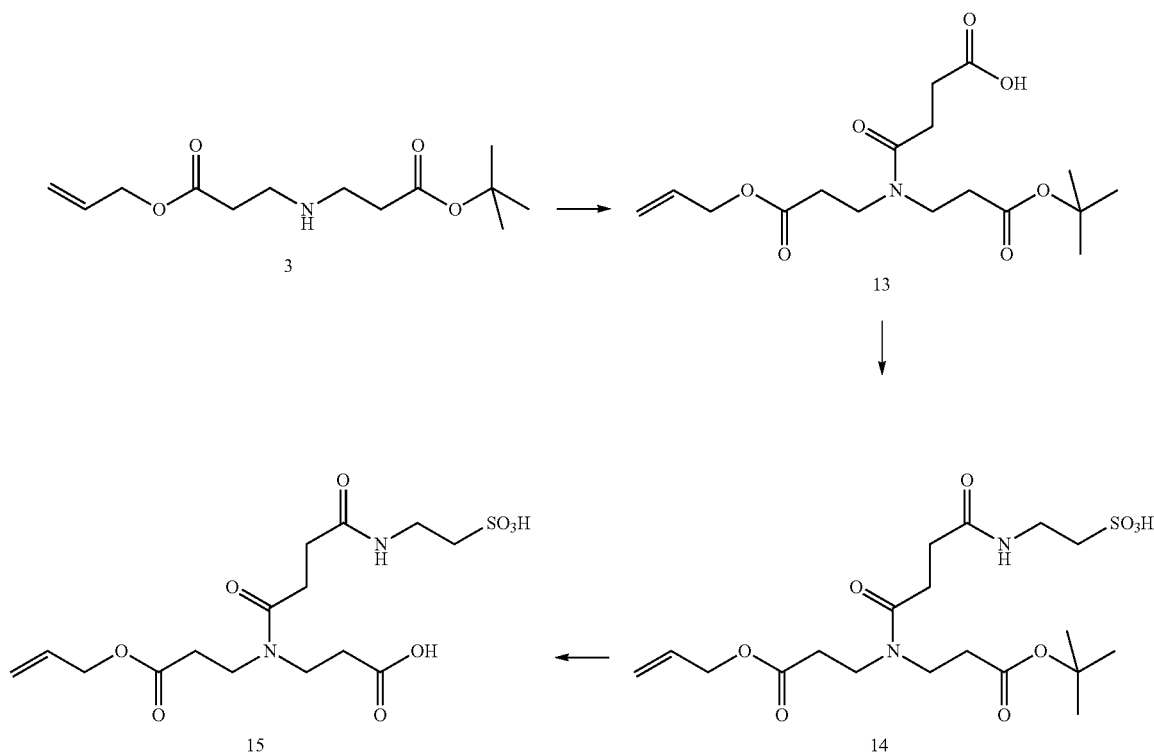

-continued
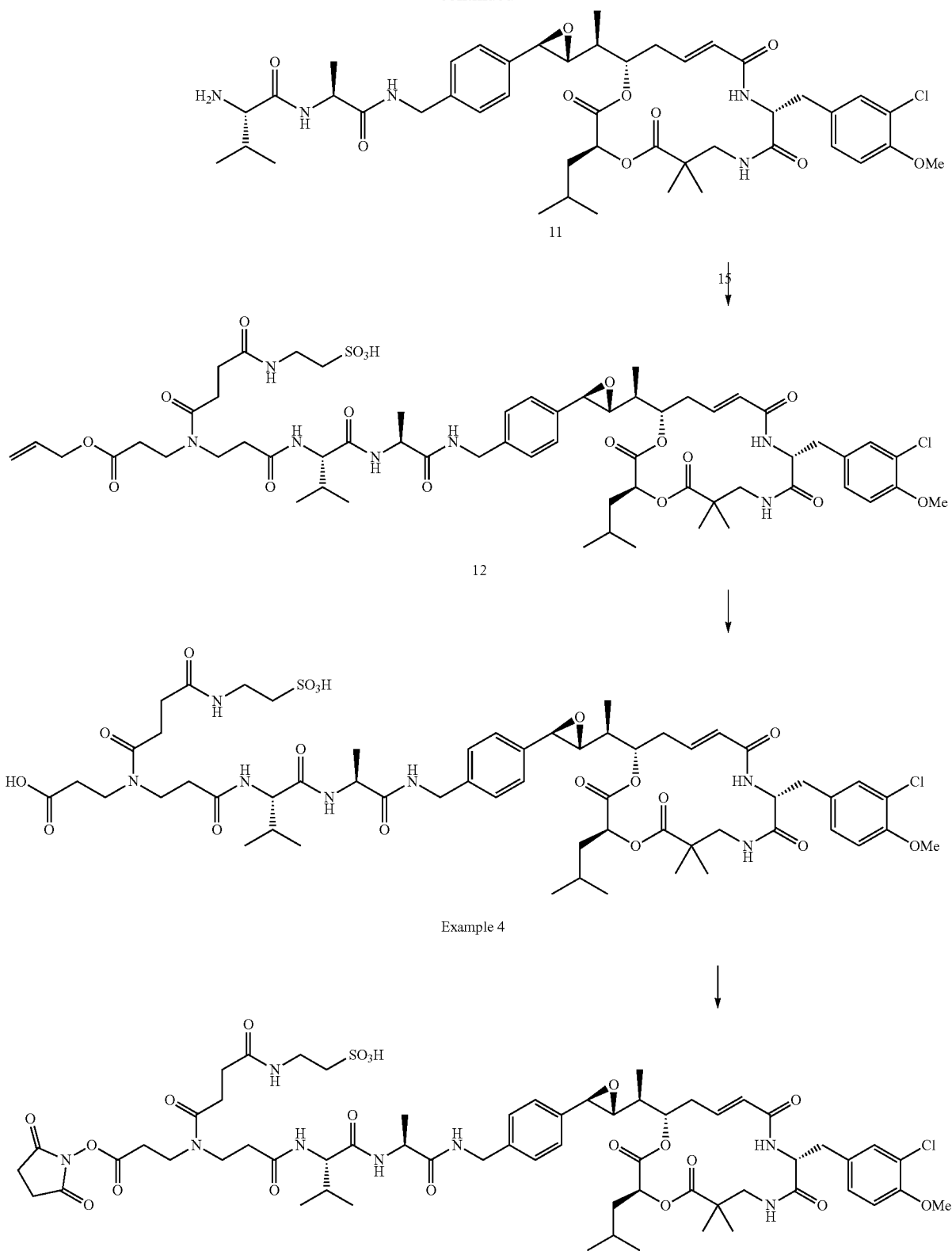
11
12
Example 4
Example 5

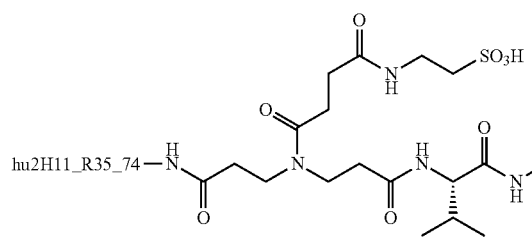
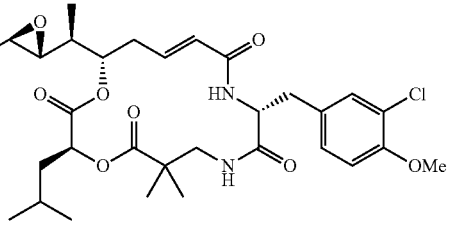

Example 6

Compound 13: 4-((3-(allyloxy)-3-oxopropyl)(3-(tert-butoxy)-3-oxopropyl)amino)-4-oxobutanoic Acid A solution of compound 3 (958 mg, 3.72 mmol) in DCM (5 mL) and succinic anhydride (752.65 mg, 7.45 mmol) was stirred for 3 h at RT. The reaction medium was concentrated in vacuo and purified by flash chromatography on 24 g of silica gel (gradient elution DCM/MeOH) to give 1.3 g of compound 13 (98%).

RMN $^1$H (400 MHz, δ in ppm, DMSO-d6): 50/50 conformer mixture; 1.39 (s, 4.5H); 1.40 (s, 4.5H); 2.33 to 2.43 (m, 3H); 2.45 to 2.55 (partially masked m, 4H); 2.69 (t, J=7.5 Hz, 1H); 3.40 (t, J=7.5 Hz, 1H); 3.45 (t, J=7.5 Hz, 1H); 3.53 (t, J=7.5 Hz, 1H); 3.59 (t, J=7.5 Hz, 1H); 4.53 (m, 1H); 4.59 (m, 1H); 5.19 to 5.35 (m, 2H); 5.91 (m, 1H); 12.06 (broad m, 1H).

Compound 14: 2-(4-((3-(allyloxy)-3-oxopropyl)(3-(tert-butoxy)-3-oxopropyl)amino)-4-oxobutanamido)ethanesulfonic Acid A mixture of compound 13 (1.3 g, 3.64 mmol) in THF (12 mL) and DSC (1.14 g, 4.36 mmol) and DIEA (1.84 mL, 10.91 mmol) was stirred for 5 h at RT. After this time, a solution of taurine (718.75 mg, 5.46 mmol) in water (9 mL) was added and the medium was stirred at RT overnight. At that time, DSC (1.14 g, 4.36 mmol) and DIEA (1.84 mL, 10.91 mmol) were added and the medium was stirred at RT overnight. At this time, taurine (2.4 g, 18.2 mmol) in water (5 mL) were added and the reaction medium was stirred for 1 h at RT then concentrated and purified by flash chromatography on 70 g of C18-grafted silica gel (gradient elution CH$_3$CN/H$_2$O) to give 1.28 g of compound 14 (76%).

RMN $^1$H (400 MHz, δ in ppm, DMSO-d6): 50/50 conformer mixture; 1.39 (s, 4.5H); 1.40 (s, 4.5H); 2.26 (t, J=7.2 Hz, 2H); 2.38 (t, J=7.5 Hz, 1H); 2.47 to 2.55 (partially masked m, 6H); 2.69 (t, J=7.5 Hz, 1H); 3.28 (m, 2H); 3.40 (t, J=7.5 Hz, 1H); 3.44 (t, J=7.5 Hz, 1H); 3.52 (t, J=7.5 Hz, 1H); 3.58 (t, J=7.5 Hz, 1H); 4.53 (m, 1H); 4.58 (m, 1H); 5.19 to 5.35 (m, 2H); 5.91 (m, 1H); 7.70 (t large, J=6.5 Hz, 1H).

Compound 15: 3-(N-(3-(allyloxy)-3-oxopropyl)-4-oxo-4-((2-sulfoethyl)-amino)butanamido)propanoic Acid A solution of compound 14 (300 mg, 645.81 μmol) in DCM (5 mL) and TFA (484.57 μL, 6.46 mmol) was stirred at RT overnight. At this time, TFA (250 μL) was added. The reaction medium was stirred several hours and concentrated in vacuo, then diluted with toluene and concentrated in vacuo twice to give 260 mg of compound 15 (99%).

RMN $^1$H (400 MHz, δ in ppm, DMSO-d6): 50/50 conformer mixture; 2.27 (t, J=7.2 Hz, 2H); 2.40 (t, J=7.6 Hz, 1H); 2.48 to 2.56 (partially masked m, 6H); 2.68 (t, J=7.6 Hz, 1H); 3.28 (m, 2H); 3.40 (t, J=7.6 Hz, 1H); 3.46 (t, J=7.6 Hz, 1H); 3.50 (t, J=7.6 Hz, 1H); 3.59 (t, J=7.6 Hz, 1H); 4.54 (m, 1H); 4.57 (m, 1H); 5.18 to 5.35 (m, 2H); 5.91 (m, 1H); 7.65 (broad t, J=6.5 Hz, 1H). LCMS (D): ES m/z=409 [M+H]$^+$; $t_R$=1.49 min.

Compound 16: (4S,7S)-12-(3-(allyloxy)-3-oxopropyl)-1-(4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)phenyl)-7-isopropyl-4-methyl-3,6,9,13,16-pentaoxo-2,5,8,12,17-pentaazanonadecane-19-sulfonic Acid Under argon, to a solution of compound 15 (28.22 mg, 69.09 μmol) in DMF (3 mL) were added DIEA (23.30 μL, 138.18 μmol), HOBt (9.72 mg, 69.09 μmol), EDC (12.49 μL, 69.09 μmol) and a solution of compound 11 (60 mg, 69.09 μmol) in DMF (2 mL). The reaction medium was stirred at RT overnight. To complete the reaction, compound 15 (28.22 mg, 69.09 μmol), DIEA (23.30 μL, 138.18 μmol), HOBt (9.72 mg, 69.09 μmol), EDC (12.49 μL, 69.09 μmol) were added and the reaction medium was stirred at RT for 1 d. At this time, the reaction medium was concentrated in vacuo and purified by flash chromatography on 70 g of C18-grafted silica gel (gradient elution CH$_3$CN/H$_2$O) to give 24 mg of compound 16 (24%).

RMN $^1$H (500 MHz, δ in ppm, DMSO-d6): 60/40 conformer mixture; 0.79 (d, J=7.0 Hz, 6H); 0.80 to 0.87 (m, 6H); 1.00 (s, 3H); 1.04 (d, J=7.0 Hz, 3H); 1.11 (s, 3H); 1.23 (d, J=7.0 Hz, 3H); 1.30 (m, 1H); 1.52 to 1.63 (m, 2H); 1.80 (m, 1H); 1.95 (m, 1H); 2.27 (m, 3H); 2.34 to 2.58 (partially masked m, 6H); 2.63 to 2.73 (m, 2H); 2.93 to 3.03 (m, 3H); 3.25 to 3.59 (partially masked m, 9H); 3.81 (s, 3H); 3.88 (d, J=1.4 Hz, 1H); 4.10 to 4.33 (m, 5H); 4.53 (m, 1.2H); 4.56 (m, 0.8H); 4.91 (m, 1H); 5.10 (m, 1H); 5.20 (m, 1H); 5.29 (qd, J=1.8 and 17.3 Hz, 0.6H); 5.31 (qd, J=1.8 and 17.3 Hz, 0.4H); 5.79 (dd, J=1.8 and 15.4 Hz, 1H); 5.90 (m, 1H); 6.47 (ddd, J=3.8, 11.8 and 15.4 Hz, 1H); 7.05 (d, J=8.7 Hz, 1H); 7.18 (dd, J=2.4 and 8.7 Hz, 1H); 7.24 (m, 5H); 7.29 (d, J=2.4 Hz, 1H); 7.69 (t, J=5.8 Hz, 1H); 7.97 (d, J=8.8 Hz, 0.4H); 8.04 (d, J=7.7 Hz, 0.4H); 8.07 (d, J=8.8 Hz, 0.6H); 8.11 (d, J=7.7 Hz, 0.6H); 8.31 (t, J=6.3 Hz, 1H); 8.38 (d, J=8.3 Hz, 1H); 11.83 (broad m, 1H). LCMS (D): ES m/z=1256 [M−H]$^-$; $t_R$=2.58 min.

Example 4: (4S,7S)-1-(4-((2R,3R)-3-((S)-1-((3S,10R,16S,E)-10-(3-chloro-4-methoxybenzyl)-3-isobutyl-6,6-dimethyl-2,5,9,12-tetraoxo-8,11-diazacyclohexadec-13-en-16-yl)ethyl)oxiran-2-yl)phenyl)-7-isopropyl-4-methyl-3,6,9-trioxo-12-(4-oxo-4-((2-sulfoethyl)amino)butanoyl)-2,5,8,12-tetraazapentadecan-15-oic Acid Under argon, to a solution of compound 16 (24 mg, 19.06 µmol) in CH$_3$CN (2 mL) were added DMF (0.5 mL), 1,3-dimethylbarbituric acid (9.11 mg, 57.19 µmol) and tetrakis(triphenylphosphine)palladium(0) (1.11 mg, 0.953 µmol). The reaction medium was stirred for 1 h at RT, then concentrated in vacuo and purified by flash chromatography on 10 g of C18-grafted silica gel (gradient elution CH$_3$CN/H$_2$O) to give 16 mg of example 4 (70%).

RMN $^1$H (500 MHz, δ in ppm, DMSO-d6): 60/40 conformer mixture; 0.79 (d, J=7.0 Hz, 6H); 0.80 to 0.86 (m, 6H); 0.99 (s, 3H); 1.04 (d, J=7.0 Hz, 3H); 1.12 (s, 3H); 1.24 (d, J=7.0 Hz, 3H); 1.31 (m, 1H); 1.52 to 1.62 (m, 2H); 1.80 (m, 1H); 1.95 (m, 1H); 2.21 to 2.31 (m, 3H); 2.34 to 2.59 (partially masked m, 8H); 2.62 to 2.75 (m, 2H); 2.94 to 3.05 (m, 3H); 3.25 to 3.58 (partially masked m, 7H); 3.81 (s, 3H); 3.88 (d, J=1.9 Hz, 1H); 4.09 to 4.33 (m, 5H); 4.90 (m, 1H); 5.10 (m, 1H); 5.79 (d, J=15.5 Hz, 1H); 6.47 (ddd, J=4.0, 11.4 and 15.5 Hz, 1H); 7.05 (d, J=8.7 Hz, 1H); 7.17 (dd, J=2.2 and 8.7 Hz, 1H); 7.21 to 7.26 (m, 5H); 7.29 (d, J=2.2 Hz, 1H); 7.69 (m, 1H); 7.97 (d, J=9.0 Hz, 0.4H); 8.04 (d, J=7.7 Hz, 0.4H); 8.08 (d, J=9.0 Hz, 0.6H); 8.12 (d, J=7.7 Hz, 0.6H); 8.31 (t, J=6.5 Hz, 1H); 8.38 (d, J=8.2 Hz, 1H); 12.2 (broad m, 1H). LCMS (A): ES m/z=609.5 [M+2H]$^{2+}$; m/z=1216 [M−H]$^-$; m/z=1218 [M+H]$^+$; t$_R$=1.72 min.

Example 5: (4S,7S)-1-(4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)phenyl)-12-(3-((2,5-dioxopyrrolidin-1-yl)oxy)-3-oxopropyl)-7-isopropyl-4-methyl-3,6,9,13,16-pentaoxo-2,5,8,12,17-pentaazanonadecane-19-sulfonic Acid Under argon, a mixture of example 4 (16 mg, 13.13 µmol) in DMF (1 mL), DSC (4.12 mg, 15.75 µmol) and DIEA (2.66 µL, 15.75 µmol) was stirred at RT overnight.

At this time, the reaction medium was concentrated in vacuo and purified by flash chromatography on 5 g of C18-grafted silica gel (gradient elution CH$_3$CN/H$_2$O) to give 12.5 mg of example 5 (73%).

RMN $^1$H (500 MHz, δ in ppm, DMSO-d6): 60/40 conformer mixture; 0.79 (d, J=7.0 Hz, 6H); 0.80 to 0.86 (m, 6H); 0.99 (s, 3H); 1.04 (d, J=7.0 Hz, 3H); 1.11 (s, 3H); 1.23 (d, J=7.0 Hz, 3H); 1.31 (m, 1H); 1.51 to 1.62 (m, 2H); 1.80 (m, 1H); 1.93 (m, 1H); 2.21 to 2.31 (m, 3H); 2.35 to 2.59 (partially masked m, 6H); 2.62 to 2.74 (m, 2H); 2.81 (broad s, 4H); 2.85 to 3.05 (m, 4H); 3.20 to 3.68 (partially masked m, 8H); 3.81 (s, 3H); 3.88 (d, J=1.9 Hz, 1H); 4.10 to 4.33 (m, 5H); 4.90 (m, 1H); 5.10 (m, 1H); 5.79 (d, J=15.5 Hz, 1H); 6.46 (ddd, J=4.0, 11.4 and 15.5 Hz, 1H); 7.05 (d, J=8.7 Hz, 1H); 7.18 (dd, J=2.2 and 8.7 Hz, 1H); 7.21 to 7.26 (m, 5H); 7.29 (d, J=2.2 Hz, 1H); 7.69 (m, 1H); 7.97 (d, J=9.0 Hz, 0.4H); 8.05 (d, J=7.7 Hz, 0.4H); 8.08 (d, J=9.0 Hz, 0.6H); 8.12 (d, J=7.7 Hz, 0.6H); 8.31 (t, J=6.5 Hz, 1H); 8.38 (d, J=8.2 Hz, 1H). LCMS (A): ES m/z=658 [M+2H]$^{2+}$; m/z=1313 [M−H]$^-$; m/z=1315 [M+H]$^+$; t$_R$=1.82 min.

Example 6: hu2H11_R35-74-Ex5

The general method described previously was used for the preparation of example 6. 15 mg of hu2H11_R35-74 were reacted with 42 µL of a 10 mM solution of example 5 in DMA (4 eq.) for 1 h 20 then were successively added 42 µL of a 10 mM solution of example 5 in DMA (4 eq.) for 1 h 20, 53 µL of a 10 mM solution of example 5 in DMA (5 eq.) for 1 h 30 and finally 42 µL of a 10 mM solution of example 5 in DMA (4 eq.) for 1 h. After purification on Superdex 200 pg in buffer B pH 6.5+20% NMP, concentration on Amicon Ultra-15, buffer exchange on PD-10 in buffer B pH 6.5+5% NMP and filtration on 0.22 µm PVDF filter, 3.33 mg of example 6 were obtained as a colorless limpid solution at a concentration of 1.33 mg/mL with a DAR of 4.05 (HRMS), a monomeric purity of 99% and a global yield of 22%.

SEC-HRMS: m/z=150568 (D1); m/z=151768 (D2); m/z=152971 (D3); m/z=154172 (D4); m/z=155375 (D5); m/z=156574 (D6); m/z=157944 (D7); m/z=158984 (D8).

Synthesis of Example 7: sulfo-Val-Ala-aza-crypto Benzylic Amine

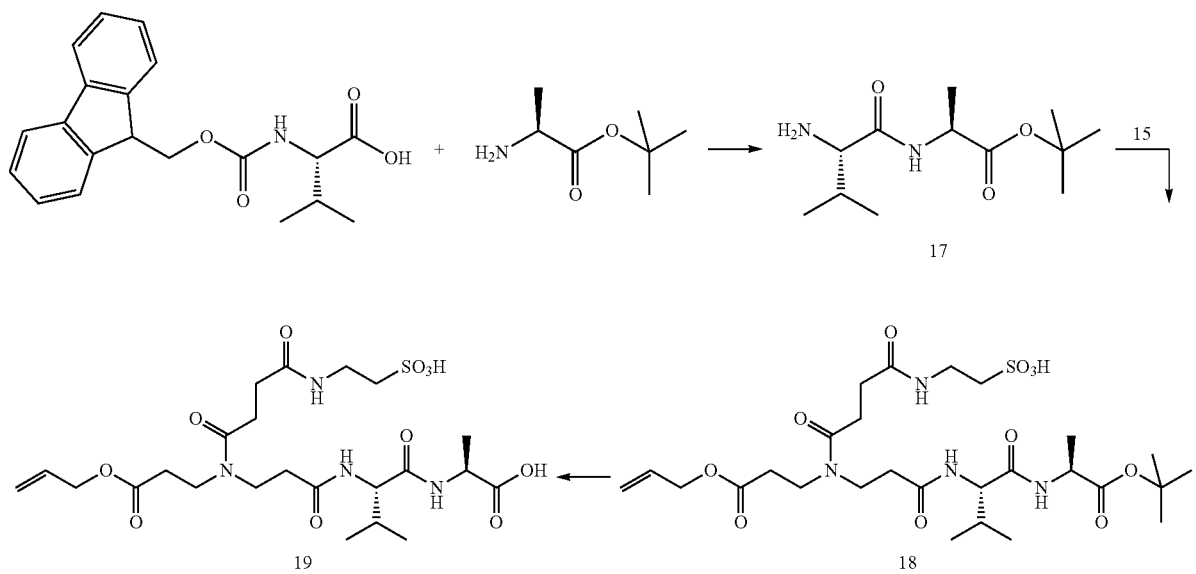

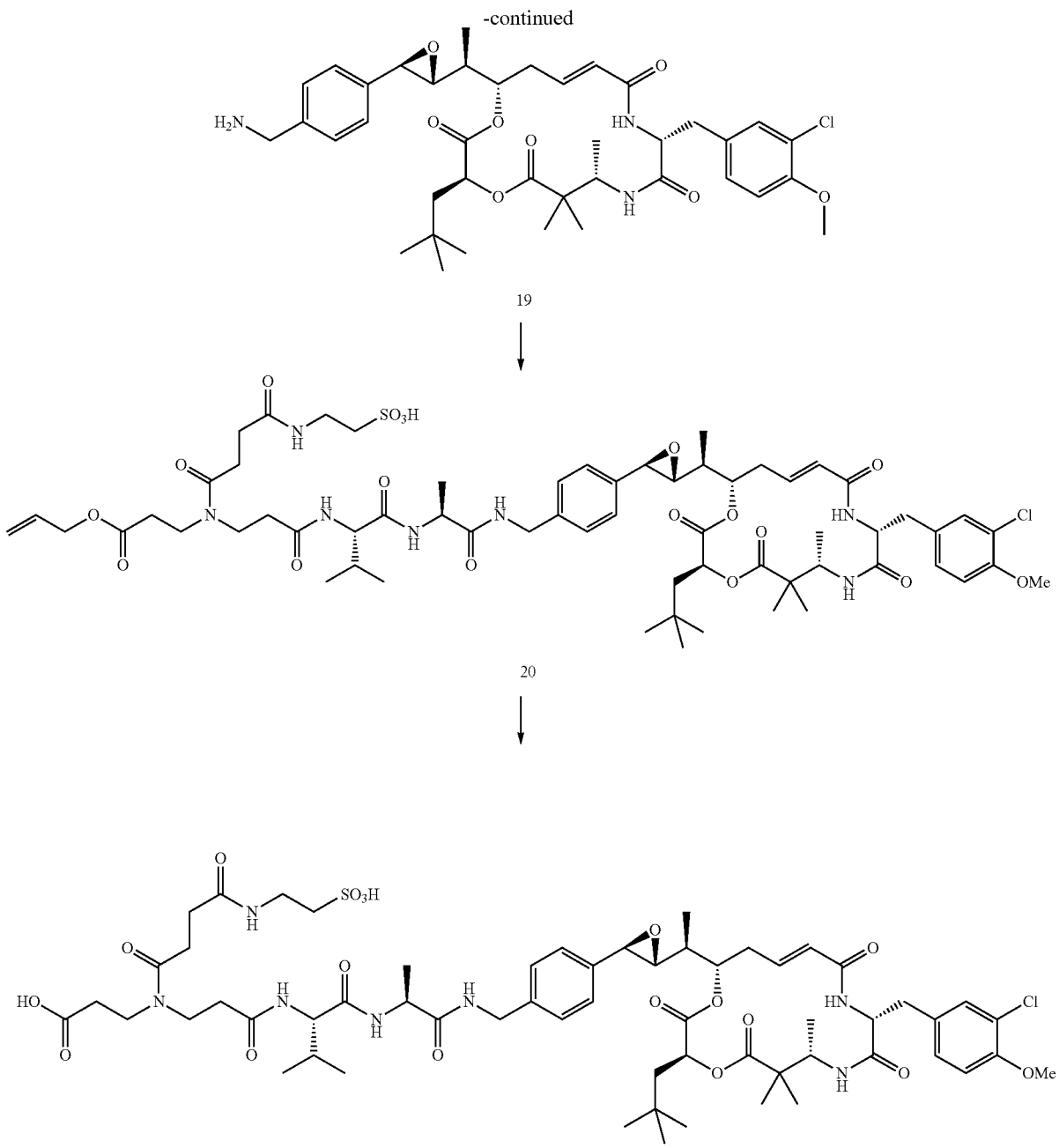

Example 7

Compound 17: tert-Butyl L-valyl-L-alaninate

To a solution of Fmoc-Val-OH (CAS number [68858-20-8], 3 g, 8.66 mmol) in DCM (60 mL) were added, under Ar, EDC (2.02 g, 12.99 mmol), HOBt (1.46 g, 10.40 mmol) and L-alanine tert-butyl ester hydrochloride (CAS number [13404-22-3], 1.61 g, 8.66 mmol). The reaction medium was stirred for 1 d at RT, quenched with H₂O (30 mL) and extracted with DCM (3×30 mL). The combined organic phases were washed with brine, dried over MgSO₄, filtered, concentrated in vacuo to give 5 g of Fmoc-protected dipeptide as a white solid (quant.). To a solution of this intermediate (5 g, 8.66 mmol) in DCM (50 mL) was added piperidine (8.64 mL, 86.63 mmol). The reaction medium was stirred for 1 h at RT and concentrated in vacuo. The crude product was diluted with Et₂O and filtered to give 1.77 g of a solid that was further purified by two consecutive flash chromatographies on 120 g and 50 g of silica gel (gradient elution DCM/MeOH) to give 500 mg of compound 17 as a white solid (24%).

RMN ¹H (400 MHz, δ in ppm, DMSO-d6): 0.79 (d, J=6.9 Hz, 3H); 0.89 (d, J=6.9 Hz, 3H); 1.24 (d, J=7.3 Hz, 3H); 1.40 (s, 9H); 1.62 (broad s, 2H); 1.86 (m, 1H); 2.95 (d, J=5.2 Hz, 1H); 4.15 (m, 1H); 8.09 (broad d, J=7.3 Hz, 1H).

Compound 18: (5S,8S)-13-(3-(allyloxy)-3-oxopropyl)-8-isopropyl-2,2,5-trimethyl-4,7,10,14,17-pentaoxo-3-oxa-6,9,13,18-tetraazaicosane-20-sulfonic Acid To a solution of compound 15 (250 mg, 612.1 μmol) in DMF (6 mL) were added, under Ar, DIEA (309.7 μL, 1.84 mmol) and DSC (163.34 mg, 612.1 μmol). The reaction medium was stirred for 1 h at RT then was added a solution of compound 17 (149.56 mg, 612.1 μL) in DMF (1 mL). The reaction medium was stirred for 2 h at RT and purified by reverse phase chromatography on a 5 μm C18 column 30×100 mm (gradient elution MeCN+0.07% TFA/H$_2$O+0.07% TFA) to give 215 mg of compound 18 as a white foam (55%).

RMN $^1$H (400 MHz, δ in ppm, DMSO-d6): 60/40 conformer mixture; 0.84 (d, J=6.9 Hz 3H); 0.87 (d, J=6.9 Hz, 3H); 1.12 (d, J=7.3 Hz, 3H); 1.39 (s, 9H); 1.92 (m, 1H); 2.20 to 2.70 (partially masked m, 10H); 3.28 (m, 2H); 3.34 to 3.60 (m, 4H); 4.10 (m, 1H); 4.20 (m, 1H); 4.53 (td, J=1.6 and 5.5 Hz, 1.2H); 4.57 (td, J=1.6 and 5.5 Hz, 0.8H); 5.20 (m, 1H); 5.30 (m, 1H); 5.90 (m, 1H); 7.69 (broad t, J=6.4 Hz, 1H); 7.91 (d, J=9.6 Hz, 0.4H); 8.04 (d, J=9.6 Hz, 0.6H); 8.23 (d, J=7.2 Hz, 0.4H); 8.30 (d, J=7.2 Hz, 0.6H).

Compound 19: (3-(N-(3-(allyloxy)-3-oxopropyl)-4-oxo-4-((2-sulfoethyl)amino)-butanamido)-propanoyl)-L-valyl-L-alanine To a solution of compound 18 (215 mg, 338.72 μmol) in DCM (5 mL) was added TFA (508.3 μL, 6.77 mmol). The reaction medium was stirred for 1 d at RT, concentrated in vacuo and co-evaporated with toluene (3×) to give 200 mg of compound 19 as a white foam (quant.).

Compound 20: (4S,7S)-12-(3-(allyloxy)-3-oxopropyl)-1-(4-((2R,3R)-3-((S)-1-((3S,7S,10R,16S,E)-10-(3-chloro-4-methoxybenzyl)-6,6,7-trimethyl-3-neopentyl-2,5,9,12-tetraoxo-1-oxa-4,8,11-triazacyclohexadec-13-en-16-yl)ethyl)oxiran-2-yl)phenyl)-7-isopropyl-4-methyl-3,6,9,13,16-pentaoxo-2,5,8,12,17-pentaazanona-decane-19-sulfonic Acid To a solution of compound 19 (200 mg, 345.6 μmol) in DMF (9 mL), were added DSC (108 mg, 413.2 μmol) and DIEA (200 μL, 1.185 mmol). The reaction medium was stirred for 6 h at RT then were added added DSC (108 mg, 413.2 μmol) and DIEA (200 μL, 1.185 mmol). The reaction medium was stirred at RT overnight then were added DSC (50 mg, 191.3 μmol) and DIEA (100 μL, 592.5 μmol) and stirring carried on for 1 h at RT. To 3 mL of the solution of activated ester were added (3S,7S,10R,16S,E)-16-((S)-1-((2R,3R)-3-(4-(aminomethyl)phenyl)oxiran-2-yl)ethyl)-10-(3-chloro-4-methoxybenzyl)-6,6,7-trimethyl-3-neopentyl-1-oxa-4,8,11-triazacyclo-hexadec-13-ene-2,5,9,12-tetraone (that can be synthesized as described in PCT/EP2016/076603 starting from methyl (3S)-3-amino-2,2-dimethylbutanoate, [MFCD09256689], 70 mg, 96.51 μmol), EDC (17 μL, 77.8 μmol) and HOBt (19 mg, 124 μmol). The reaction medium was stirred for 1 h at RT, concentrated in vacuo and purified by flash chromatography on 10 g of C18-modified silica gel (gradient elution MeCN/H$_2$O) to give 30 mg of compound 20 as a white lacquer (24%).

RMN $^1$H (600 MHz, δ in ppm, DMSO-d6): 0.79 to 0.90 (m, 15H); 0.98 (m, 3H); 1.00 (s, 3H); 1.03 (d, J=7.3 Hz, 3H); 1.19 (s, 3H); 1.24 (split d, J=7.0 Hz, 3H); 1.34 (d, J=14.1 Hz, 1H); 1.81 (m, 1H); 1.91 (m, 1H); 1.98 (dd, J=9.3 and 14.1 Hz, 1H); 2.25 (m, 3H); 2.38 (m, 1H); 2.50 (partially masked m, 5H); 2.60 (m, 1H); 2.68 (m, 1H); 2.91 (m, 1H); 2.96 (m, 2H); 3.25 to 3.58 (partially masked m, 9H); 3.80 (s, 3H); 3.91 (m, 1H); 4.00 to 4.35 (m, 6H); 4.53 (m, 2H); 5.03 (m, 1H); 5.20 (m, 1H); 5.30 (m, 1H); 5.89 (d, J=16.1 Hz, 1H); 5.91 (m, 1H); 6.44 (ddd, J=5.0, 10.5 and 16.1 Hz, 1H); 7.03 (d, J=8.7 Hz, 1H); 7.19 to 7.28 (m, 5H); 7.31 (s, 1H); 7.69 (m, 1H); 7.86 (d, J=8.2 Hz, 1H); 7.91 (m, 1H); 7.95 to 8.17 (m, 2H); 8.32 (m, 1H); 8.39 (m, 1H). LCMS (A): ES m/z=1283 [M−H]$^−$; m/z=1285 [M+H]$^+$; m/z=1307 [M+Na]$^+$; $t_R$=1.93 min.

Example 7: (4S,7S)-1-(4-((2R,3R)-3-((S)-1-((3S,7S,10R,16S,E)-10-(3-chloro-4-methoxybenzyl)-6,6,7-trimethyl-3-neopentyl-2,5,9,12-tetraoxo-1-oxa-4,8,11-triazacyclohexadec-13-en-16-yl)ethyl)-oxiran-2-yl)phenyl)-7-isopropyl-4-methyl-3,6,9-trioxo-12-(4-oxo-4-((2-sulfoethyl)amino)butanoyl)-2,5,8,12-tetraazapentadecan-15-oic Acid To a solution of compound 20 (30 mg, 23.33 μmol) in DCM (2 mL) and DMF (0.3 mL) were added, under Ar, tetrakis(triphenylphosphine)palladium(0) (1.38 mg, 1.17 μmol) and 1,3-dimethyl-barbituric acid (11.15 mg, 69.99 μmol). The reaction medium was stirred for 1 h at RT and purified by reverse phase chromatography on 1 g of C18-modified silica gel (gradient elution MeCN/H$_2$O) to give 15 mg of a white powder that was further purified on silica gel (gradient elution DCM/MeOH/H$_2$O) to give 7 mg of example 7 as a white lacquer (24%).

Synthesis of Examples 8 & 9: PEG4-Val-Ala-PABA-C52 Benzylic Amine and NHS Ester of PEG4-Val-Ala-PABA-C52 Benzylic Amine

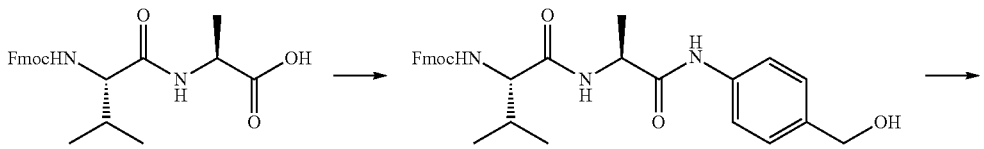

213 214
-continued
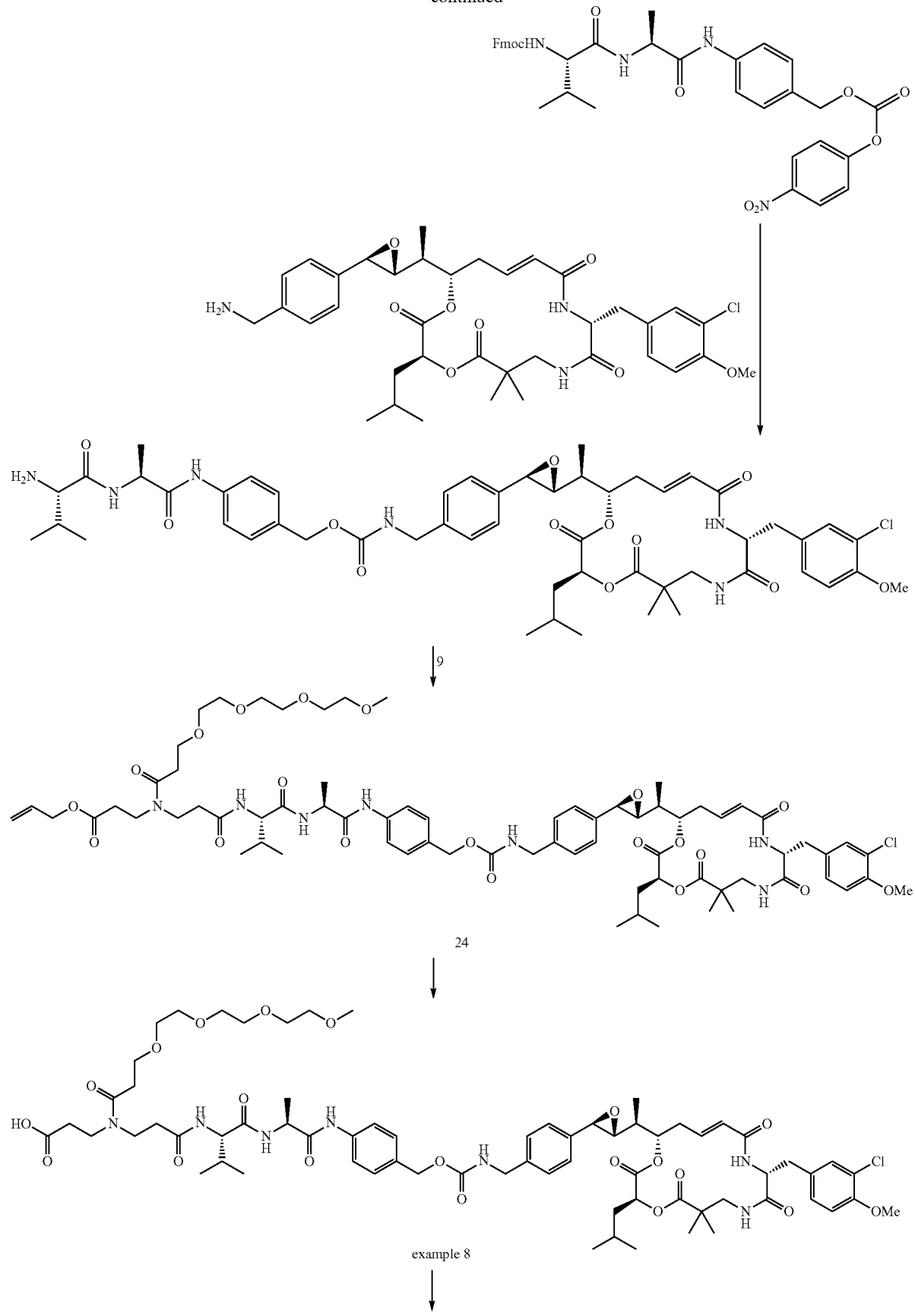

-continued

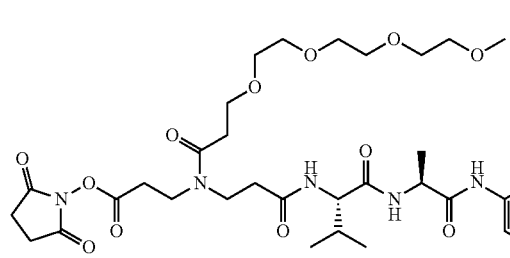 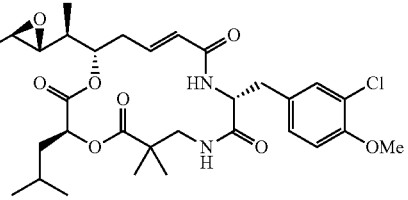

example 9

Compound 21: (9H-fluoren-9-yl)methyl ((S)-1-(((S)-1-((4-(hydroxymethyl)phenyl)-amino)-1-oxopropan-2-yl)amino)-3-methyl-1-oxobutan-2-yl)carbamate To a solution of Fmoc-Val-Ala-OH (CAS number [150114-97-9], 1 g, 2.44 mmol) in DCM (30 mL) and MeOH (15 mL) were added 4-aminobenzyl alcohol (612 mg, 4.87 mmol) and EEDQ (1.22 g, 4.87 mmol). The reaction medium was stirred at RT for 24 h then additional 4-aminobenzyl alcohol (612 mg, 4.87 mmol) and EEDQ (1.22 g, 4.87 mmol) were added and the stirring carried on 2 h. The reaction medium was then concentrated in vacuo; Et$_2$O was added to the crude product, the mixture was stirred and filtered to give a brown solid that was diluted in Et$_2$O and the mixture was stirred at RT overnight. It was then filtered and the precipitate was dried to give 1.3 g of compound 21 as a brown solid (quant.).

RMN $^1$H (400 MHz, δ in ppm, DMSO-d6): 0.86 (d, J=7.0 Hz, 3H); 0.89 (d, J=7.0 Hz, 3H); 1.30 (d, J=7.0 Hz, 3H); 2.00 (m, 1H); 3.91 (m, 1H); 4.19 to 4.34 (m, 4H); 4.43 (d, J=5.7 Hz, 2H); 5.08 (t, J=5.7 Hz, 1H); 7.23 (d, J=7.9 Hz, 2H); 7.31 (t, J=7.9 Hz, 2H); 7.40 (m, 3H); 7.53 (d, J=9.1 Hz, 2H); 7.73 (t, J=8.6 Hz, 2H); 7.89 (d, J=7.9 Hz, 2H); 8.16 (d, J=7.3 Hz, 1H); 9.91 (s, 1H). LCMS (A): ES m/z=292; m/z=393; m/z=516 [M+H]$^+$; t$_R$=1.21 min.

Compound 22: (9H-fluoren-9-yl)methyl ((S)-3-methyl-1-(((S)-1-((4-(((4-nitrophenoxy)carbonyl)oxy)methyl)phenyl)amino)-1-oxopropan-2-yl)amino)-1-oxobutan-2-yl)carbamate To a solution of compound 21 (1.3 g, 2.52 mmol) in DMF (10 mL), was added, under Ar, DIEA (2.55 mL, 15.13 mmol), the solution was cooled down at 0° C. before the addition of 4-nitrophenyl chloroformate (1.57 g, 7.56 mmol). The reaction medium was stirred for 2 h at RT. 20 mL of H$_2$O were added and the medium was extracted twice with EtOAc (10 mL). The combined organic phases were washed with brine, dried over MgSO$_4$, filtered, concentrated in vacuo and purified by flash chromatography on 120 g of silica gel (gradient elution DCM/MeOH) to give 600 mg of compound 22 as a solid (35%).

RMN $^1$H (400 MHz, δ in ppm, DMSO-d6): 0.86 (d, J=7.0 Hz, 3H); 0.89 (d, J=7.0 Hz, 3H); 1.31 (d, J=7.0 Hz, 3H); 1.99 (m, 1H); 3.91 (m, 1H); 4.18 to 4.35 (m, 3H); 4.43 (m, 1H); 5.24 (s, 2H); 7.31 (t, J=7.9 Hz, 2H); 7.35 to 7.44 (m, 5H); 7.56 (d, J=9.1 Hz, 2H); 7.63 (d, J=8.6 Hz, 2H); 7.74 (m, 2H); 7.88 (d, J=7.9 Hz, 2H); 8.19 (d, J=7.3 Hz, 1H); 8.31 (d, J=9.1 Hz, 2H); 10.07 (s, 1H).

Compound 23: 4-(((S)-2-((S)-2-amino-3-methylbutanamido)propanamido)benzyl 4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzylcarbamate To a solution of (3S,10R,16S,E)-16-((S)-1-((2R,3R)-3-(4-(aminomethyl)phenyl)oxiran-2-yl)ethyl)-10-(3-chloro-4-methoxybenzyl)-3-isobutyl-6,6-dimethyl-1,4-dioxa-8,11-diazacyclohexadec-13-ene-2,5,9,12-tetraone (the synthesis of which was described in WO2011001052, compound 77, 100 mg, 143.2 µmol) in THF (5 mL), were added, under argon compound 22 (117 mg, 171.9 µmol) and DIEA (60.4 µL, 358 µmol). The reaction medium was stirred at RT under Ar overnight. Then piperidine (142.9 µL, 1.43 mmol) was added and the reaction medium stirred for 1 h at RT. After concentrating in vacuo, the crude medium was purified by flash chromatography on 5 g of silica gel (gradient elution DCM/MeOH) to give 100 mg of compound 23 as a white solid (73%).

Compound 24: allyl 15-(3-(((S)-1-(((S)-1-((4-((((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclo-hexadec-13-en-16-yl)ethyl)oxiran-2-yl)benzyl)carbamoyl)oxy)methyl)phenyl)amino)-1-oxopropan-2-yl)amino)-3-methyl-1-oxobutan-2-yl)amino)-3-oxopropyl)-14-oxo-2,5,8,11-tetraoxa-15-azaoctadecan-18-oate To a solution of compound 23 (100 mg, 98.3 µmol) in THF (5 mL), were added, under Ar, compound 9 (50.8 mg, 98.3 µmol) and DIEA (24.9 µL, 147.4 µmol). The reaction medium was stirred for 1 h at RT, concentrated in vacuo and purified by flash chromatography on 5 g of silica gel (gradient elution DCM/MeOH) to give 128 mg of compound 24 as a white solid (91%).

RMN $^1$H (500 MHz, δ in ppm, DMSO-d6): 60:40 conformer mixture; 0.78 (d, J=6.8 Hz, 6H); 0.82 (d, J=7.0 Hz, 1.8H); 0.84 (d, J=7.0 Hz, 1.2H); 0.86 (d, J=7.0 Hz, 1.8H); 0.88 (d, J=7.0 Hz, 1.2H); 1.00 (s, 3H); 1.04 (d, J=7.0 Hz, 3H); 1.11 (s, 3H); 1.30 (m, 4H); 1.57 (m, 2H); 1.80 (m, 1H); 1.95 (m, 1H); 2.26 (m, 1H); 2.40 (m, 2H); 2.52 to 2.72 (m, 6H); 2.95 to 3.04 (m, 3H); 3.22 (s, 3H); 3.30 (m, 1H); 3.38 to 3.63 (m, 18H); 3.80 (s, 3H); 3.87 (d, J=2.3 Hz, 1H); 4.15 to 4.28 (m, 4H); 4.40 (m, 1H); 4.51 to 4.57 (m, 2H); 4.90 (dd, J=3.8 and 9.8 Hz, 1H); 4.98 (s, 2H); 5.10 (m, 1H); 5.20 (m, 1H); 5.30 (m, 1H); 5.80 (d, J=16.0 Hz, 1H); 5.91 (m, 1H); 6.47 (ddd, J=4.7, 10.5 and 16.0 Hz, 1H); 7.05 (d, J=8.6

Hz, 1H); 7.16 (dd, J=2.5 and 8.6 Hz, 1H); 7.29 to 7.32 (m, 8H); 7.58 (m, 2H); 7.76 (t, J=6.5 Hz, 1H); 7.92 (d, J=9.0 Hz, 0.4H); 8.04 (d, J=9.0 Hz, 0.6H); 8.15 (d, J=7.0 Hz, 0.4H); 8.21 (d, J=7.0 Hz, 0.6H); 8.32 (d, J=8.0 Hz, 1H); 9.88 (s, 0.4H); 9.93 (s, 0.6H). LCMS (A): ES m/z=677; m/z=1418 [M+H]$^+$; m/z=1462 [M−H+HCO$_2$H]$^−$; $t_R$=1.21 min.

Example 8: 15-(3-(((S)-1-(((S)-1-((4-((((4-((2R,3R)-3-((S)-1-((3S,10R,16S,E)-10-(3-chloro-4-methoxy-benzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)oxy)methyl)-phenyl)amino)-1-oxopropan-2-yl)amino)-3-methyl-1-oxobutan-2-yl)amino)-3-oxopropyl)-14-oxo-2,5,8,11-tetraoxa-15-azaoctadecan-18-oic Acid To a solution of compound 24 (58 mg, 40.9 µmol) in DCM (20 mL), were added, under Ar, 1,3-dimethylpyrimidine-2,4,6(1H, 3H, 5H)-trione (19.5 mg, 122.6 µmol) and tetrakis (triphenylphosphine)palladium (0) (2.4 mg, 2.0 µmol). The reaction medium was stirred for 3 h at RT, concentrated in vacuo and purified by flash chromatography on 5 g of silica gel (gradient elution DCM/MeOH) to give 53 mg of example 8 as a white solid (94%).

RMN $^1$H (500 MHz, δ in ppm, DMSO-d6): conformer mixture; 0.78 (d, J=6.8 Hz, 6H); 0.86 (m, 6H); 0.99 (s, 3H); 1.04 (d, J=7.0 Hz, 3H); 1.11 (s, 3H); 1.30 (m, 1H); 1.38 (m, 3H); 1.57 (m, 2H); 1.79 (m, 1H); 2.04 (m, 1H); 2.10 to 2.59 (partially masked m, 7H); 2.69 (m, 2H); 2.93 to 3.03 (m, 3H); 3.22 (s, 3H); 3.30 (masked m, 1H); 3.40 to 3.64 (m, 18H); 3.80 (s, 3H); 3.87 (d, J=2.3 Hz, 1H); 4.05 to 4.27 (m, 4H); 4.36 (m, 1H); 4.90 (dd, J=3.8 and 9.8 Hz, 1H); 4.97 (s, 2H); 5.10 (m, 1H); 5.80 (d, J=16.0 Hz, 1H); 5.90 (ddd, J=4.7, 10.5 and 16.0 Hz, 1H); 6.46 (ddd, J=4.7, 10.5 and 16.0 Hz, 1H); 7.05 (d, J=8.6 Hz, 1H); 7.16 (dd, J=2.5 and 8.6 Hz, 1H); 7.20 to 7.32 (m, 8H); 7.68 (m, 2H); 7.82 (m, 1H); 8.40 to 8.65 (m, 2H); 9.21 (m, 1H); 10.20 (s, 1H). LCMS (A): ES m/z=637; m/z=1376 [M−H]$^−$; m/z=1378 [M+H]$^+$; $t_R$=1.3 min.

Example 9: 2,5-dioxopyrrolidin-1-yl 15-(3-(((S)-1-(((S)-1-((4-((((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)oxy)methyl)-phenyl)amino)-1-oxopropan-2-yl)amino)-3-methyl-1-oxobutan-2-yl)amino)-3-oxopropyl)-14-oxo-2,5,8,11-tetraoxa-15-azaoctadecan-18-oate To a solution of example 8 (49 mg, 35.5 µmol) in DMF (2 mL), were added, under Ar, DSC (13.9 mg, 53.3 µmol) and DIEA (9.0 µL, 53.3 µmol). The reaction medium was stirred at RT overnight. Additional DSC (13.9 mg, 53.3 µmol) and DIEA (9.0 µL, 53.3 µmol) were added and the stirring carried over 8 h. The reaction medium was concentrated in vacuo and purified by flash chromatography on 10 g of diol-modified silica gel (gradient elution DCM/iPrOH) to give 20 mg of example 9 as a white solid (38%).

RMN $^1$H (500 MHz, δ in ppm, DMSO-d6): 70:30 conformer mixture; 0.78 (d, J=6.8 Hz, 6H); 0.82 (d, J=7.0 Hz, 2.1H); 0.84 (d, J=7.0 Hz, 0.9H); 0.86 (d, J=7.0 Hz, 2.1H); 0.88 (d, J=7.0 Hz, 0.9H); 1.00 (s, 3H); 1.05 (d, J=7.0 Hz, 3H); 1.11 (s, 3H); 1.27 (m, 1H); 1.30 (m, 3H); 1.57 (m, 2H); 1.80 (m, 1H); 1.95 (m, 1H); 2.25 (m, 1H); 2.40 (m, 1H); 2.52 to 2.75 (m, 7H); 2.80 (s, 4H); 2.87 to 3.08 (m, 3H); 3.22 (s, 3H); 3.32 (masked m, 1H); 3.40 to 3.68 (m, 18H); 3.80 (s, 3H); 3.88 (d, J=2.3 Hz, 1H); 4.16 to 4.28 (m, 4H); 4.38 (m, 1H); 4.90 (dd, J=3.8 and 9.8 Hz, 1H); 4.97 (s, 2H); 5.10 (m, 1H); 5.79 (d, J=16.0 Hz, 1H); 6.46 (ddd, J=4.7, 10.5 and 16.0 Hz, 1H); 7.05 (d, J=8.6 Hz, 1H); 7.16 (dd, J=2.5 and 8.6 Hz, 1H); 7.20 to 7.31 (m, 8H); 7.58 (m, 2H); 7.78 (t, J=6.0 Hz, 1H); 7.94 (d, J=9.0 Hz, 0.3H); 8.08 (d, J=9.0 Hz, 0.7H); 8.19 (d, J=7.0 Hz, 0.3H); 8.25 (d, J=7.0 Hz, 0.7H); 8.35 (d, J=8.0 Hz, 1H); 9.90 (s, 0.3H); 9.95 (s, 0.7H). LCMS (A): ES m/z=698; m/z=1475 [M+H]$^+$; $t_R$=1.35 min.

Synthesis of Example 10:
PEG7-Val-Ala-PABA-C52 Benzylic Amine

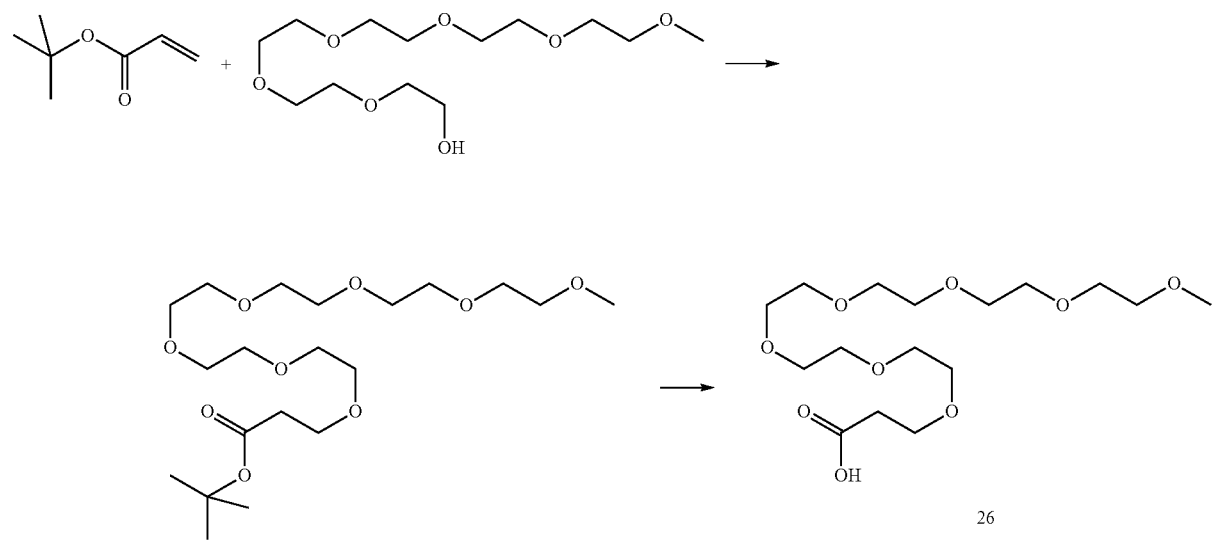

219 -continued 220
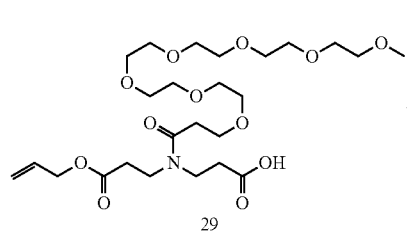
29
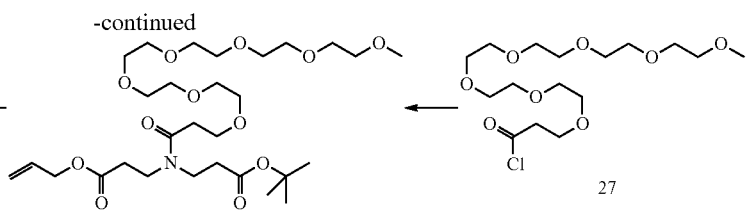
28 27
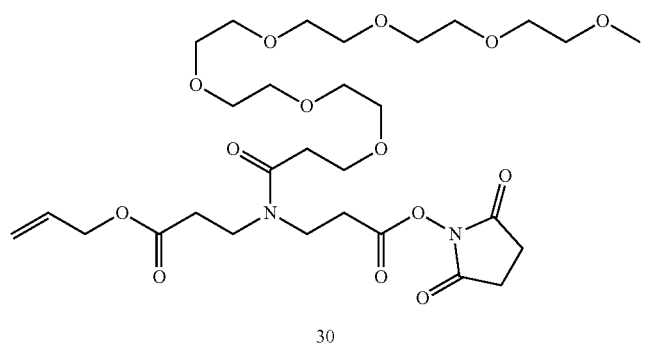
30
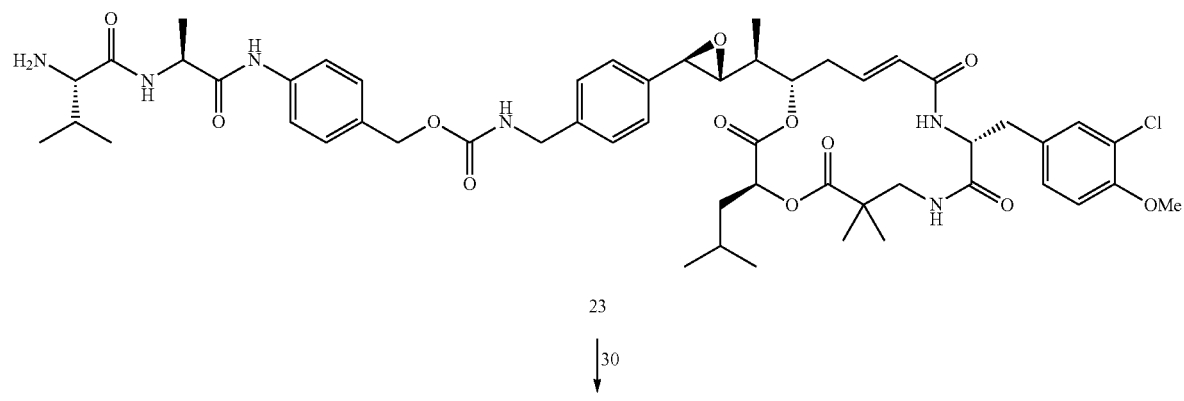
23
↓ 30
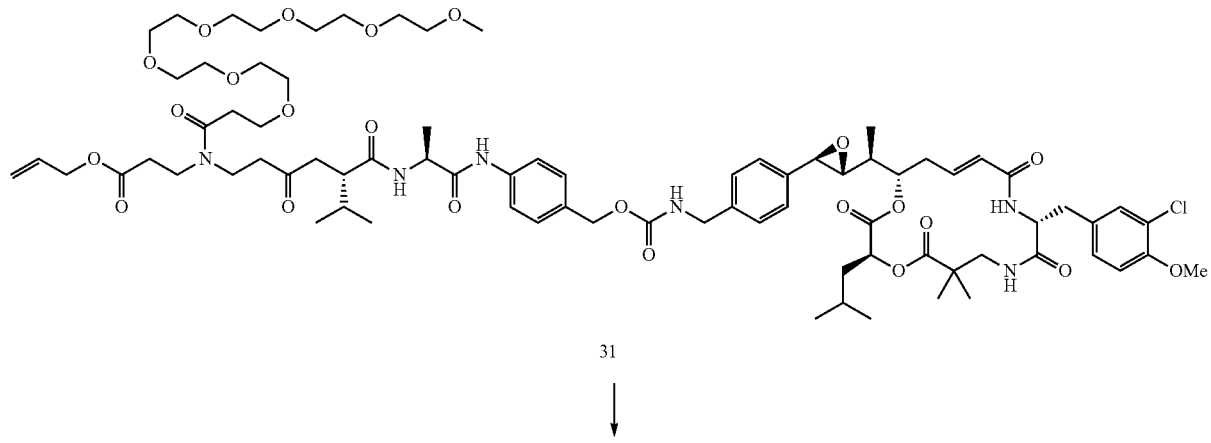
31
↓

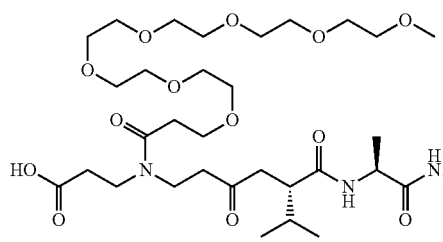
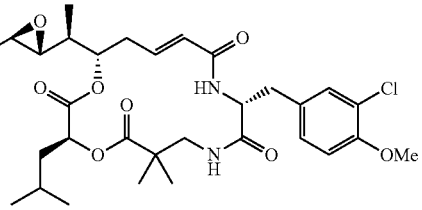

example 10

Compound 25: tert-butyl 2,5,8,11,14,17,20-heptaoxatricosan-23-oate

To a solution of hexaethylene glycol monomethyl ether (926.0 µL, 3.24 mmol) in THF (3 mL), was added, under Ar, Na (0.7 mg, 32.4 µmol). The reaction medium was stirred for 1 h at RT until complete dissolution of Na then tert-butyl acrylate (570 µL, 3.89 mmol) was added and the stirring carried on at RT overnight. The reaction medium was then concentrated in vacuo, diluted with $H_2O$ and extracted with EtOAc (3×). The combined organic phases were washed with brine, dried over $MgSO_4$, filtered and concentrated in vacuo to give 1.04 g of compound 25 as a colorless oil (76%).

RMN $^1$H (400 MHz, δ in ppm, DMSO-d6): 1.40 (s, 9H); 2.40 (t, J=6.4 Hz, 2H); 3.23 (s, 3H); 3.43 (m, 2H); 3.47 to 3.54 (m, 22H); 3.59 (t, J=6.4 Hz, 2H).

Compound 26: 2,5,8,11,14,17,20-heptaoxatricosan-23-oic Acid

To a solution of compound 25 (1.04 g, 2.45 mmol) in DCM (15 mL) was added TFA (1.84 mL, 24.5 mmol). The reaction medium was stirred at RT overnight, concentrated in vacuo, diluted with DCM and co-evaporated with toluene (3×) to give 1 g of compound 26 as a colorless oil (quant.).

Compound 27: 2,5,8,11,14,17,20-heptaoxatricosan-23-oyl Chloride

To compound 26 (400 mg, 1.09 mmol) was added MsCl (1.27 mL, 16.3 mmol); the reaction medium was heated 3 h at 60° C., concentrated in vacuo, diluted with DCM and concentrated in vacuo (3×) to give 420 mg of compound 27 as a colorless oil (quant.).

Compound 28: allyl 24-(3-(tert-butoxy)-3-oxopropyl)-23-oxo-2,5,8,11,14,17,20-heptaoxa-24-azaheptacosan-27-oate To a solution of compound 3 (200 mg, 777.2 µmol) in DCM (5 mL) was added DIEA (262 µL, 1.55 mmol). The reaction medium was cooled down at 0° C. and a solution of compound 27 (360.8 mg, 932.7 µmol) in DCM (2 mL) was added dropwise at 0° C. The reaction medium was stirred for 1 h at RT and concentrated in vacuo. The crude product was purified by two consecutive flash chromatographies on 12 g and 10 g of silica gel (gradient elution DCM/MeOH) to give 72 mg of compound 28 (15%).

RMN $^1$H (400 MHz, δ in ppm, DMSO-d6): 50:50 conformer mixture; 1.39 (s, 4.5H); 1.40 (s, 4.5H); 2.22 to 2.75 (partially masked m, 6H); 3.23 (s, 3H); 3.38 to 3.63 (m, 30H); 4.55 (m, 2H); 5.19 to 5.36 (m, 2H); 5.90 (m, 1H).

Compound 29: 24-(3-(allyloxy)-3-oxopropyl)-23-oxo-2,5,8,11,14,17,20-heptaoxa-24-azahepta-cosan-27-oic Acid To a solution of compound 28 (72 mg, 118.5 µmol) in DCM (3 mL) was added TFA (100 µL, 1.33 mmol); the reaction medium was stirred at RT overnight then additional TFA (100 µL, 1.33 mmol) was added and the stirring carried on for 1 d. The reaction medium was concentrated in vacuo, diluted with DCM and co-evaporated with toluene (3×) to give 66 mg of compound 29 (quant.).

Compound 30: allyl 24-(3-((2,5-dioxopyrrolidin-1-yl)oxy)-3-oxopropyl)-23-oxo-2,5,8,11,14,17,20-heptaoxa-24-azaheptacosan-27-oate To a solution of compound 29 (66 mg, 119.7 µmol) in THF (2 mL), were added, under Ar, DIEA (20.2 µL, 119.9 µmol) and DSC (34.4 mg, 131.6 µmol); the reaction medium was stirred for 4 d at RT, concentrated in vacuo and purified by flash chromatography on 900 mg of diol-modified silica gel (gradient elution DCM/iPrOH) to give 35 mg of compound 30 (45%).

Compound 31: allyl 24-(3-(((S)-1-(((S)-1-((4-((((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclo-hexadec-13-en-16-yl)ethyl)oxiran-2-yl)benzyl)carbamoyl)oxy)-methyl)phenyl)amino)-1-oxopropan-2-yl)amino)-3-methyl-1-oxobutan-2-yl)amino)-3-oxopropyl)-23-oxo-2,5,8,11,14,17,20-heptaoxa-24-azaheptacosan-27-oate To a solution of compound 23 (45 mg, 44.2 µmol) in THF (5 mL) were added compound 30 (28.7 mg, 44.2 µmol) and DIEA (11.2 µL, 66.3 µmol). The reaction medium was stirred at RT overnight, diluted with H$_2$O (10 mL) and extracted with EtOAc (3×10 mL). The combined organic phases were washed with brine, dried over MgSO$_4$, filtered, concentrated in vacuo and purified by flash chromatography on 5 g of silica gel (gradient elution DCM/MeOH) to give 35 mg of compound 31 as a white solid (51%).

RMN $^1$H (500 MHz, δ in ppm, DMSO-d6): 60:40 conformer mixture; 0.80 (split d, J=6.8 Hz, 6H); 0.82 (d, J=7.0 Hz, 1.8H); 0.84 (d, J=7.0 Hz, 1.2H); 0.86 (d, J=7.0 Hz, 1.8H); 0.88 (d, J=7.0 Hz, 1.2H); 1.00 (s, 3H); 1.04 (d, J=7.0 Hz, 3H); 1.11 (s, 3H); 1.28 (m, 1H); 1.30 (m, 3H); 1.56 (m, 2H); 1.79 (m, 1H); 1.95 (m, 1H); 2.27 (m, 1H); 2.35 to 2.60 (partially masked m, 6H); 2.62 to 2.73 (m, 2H); 2.93 to 3.05 (m, 3H); 3.23 (s, 3H); 3.33 (masked m, 1H); 3.38 to 3.64 (m, 30H); 3.80 (s, 3H); 3.87 (d, J=2.3 Hz, 1H); 4.15 to 4.27 (m, 4H); 4.38 (m, 1H); 4.52 to 4.58 (m, 2H); 4.90 (dd, J=3.8 and 9.8 Hz, 1H); 4.97 (s, 2H); 5.10 (m, 1H); 5.50 (m, 1H); 5.30 (m, 1H); 5.80 (d, J=16.0 Hz, 1H); 5.90 (m, 1H); 6.47 (ddd, J=4.7, 10.5 and 16.0 Hz, 1H); 7.05 (d, J=8.6 Hz, 1H); 7.15 (dd, J=2.5 and 8.6 Hz, 1H); 7.20 to 7.32 (m, 8H); 7.59 (m, 2H); 7.78 (t, J=6.5 Hz, 1H); 7.95 (d, J=9.0 Hz, 0.4H); 8.07 (d, J=9.0 Hz, 0.6H); 8.18 (d, J=7.0 Hz, 0.4H); 8.27 (d, J=7.0 Hz, 0.6H); 8.36 (d, J=8.0 Hz, 1H); 9.90 (s, 0.4H); 9.95 (s, 0.6H). LCMS (A): ES m/z=698; m/z=1552 [M+H]$^+$; m/z=1595 [M−H+HCO$_2$H]$^-$; $t_R$=1.39 min.

Example 10: 24-(3-(((S)-1-(((S)-1-((4-((((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)oxy) methyl)-phenyl)amino)-1-oxopropan-2-yl)amino)-3-methyl-1-oxobutan-2-yl)amino)-3-oxopropyl)-23-oxo-2,5,8,11,14,17,20-heptaoxa-24-azaheptacosan-27-oic Acid To a solution of compound 31 (30 mg, 19.3 µmol) in DCM (5 mL) were added, under Ar, dimethylbarbituric acid (9.24 mg, 58.0 µmol) and tetrakis(triphenylphosphine)palladium (0) (1.13 mg, 0.97 µmol). The reaction medium was stirred for 3 h at RT then concentrated in vacuo and purified by two consecutive flash chromatographies on 5 g and 0.9 g of silica gel (gradient elution DCM/MeOH) to give 14 mg of example 10 as a white solid (50%).

RMN $^1$H (500 MHz, δ in ppm, DMSO-d6): 50:50 conformer mixture; 0.78 (split d, J=6.8 Hz, 6H); 0.81 to 0.89 (m, 6H); 1.00 (s, 3H); 1.04 (d, J=7.0 Hz, 3H); 1.12 (s, 3H); 1.28 (m, 1H); 1.30 (d, J=7.0 Hz, 1.5H); 1.32 (d, J=7.0 Hz, 1.5H); 1.51 to 1.62 (m, 2H); 1.79 (m, 1H); 1.96 (m, 1H); 2.26 (m, 1H); 2.33 to 2.60 (partially masked m, 6H); 2.61 to 2.73 (m, 2H); 2.93 to 3.03 (m, 3H); 3.22 (s, 3H); 3.30 (masked m, 1H); 3.38 to 3.62 (m, 30H); 3.80 (s, 3H); 3.87 (d, J=2.3 Hz, 1H); 4.12 to 4.29 (m, 4H); 4.39 (m, 1H); 4.90 (dd, J=3.8 and 9.8 Hz, 1H); 4.96 (s, 2H); 5.10 (m, 1H); 5.78 (d, J=16.0 Hz, 1H); 6.46 (ddd, J=4.7, 10.5 and 16.0 Hz, 1H); 7.05 (d, J=8.6 Hz, 1H); 7.16 (dd, J=2.5 and 8.6 Hz, 1H); 7.20 to 7.32 (m, 8H); 7.59 (m, 2H); 7.79 (m, 1H); 8.04 (m, 0.5H); 8.10 (d, J=9.0 Hz, 0.5H); 8.25 to 8.41 (m, 2H); 9.95 (s, 0.5H); 9.98 (s, 0.5H); 12.20 (m, 1H). LCMS (D): ES m/z=769; m/z=1511 [M+H]$^+$; tR=3.16 min.

Synthesis of Examples 11 & 12:
PEG24-Val-Ala-PABA-C52 Benzylic Amine and NHS Ester of PEG24-Val-Ala-PABA-C52 Benzylic Amine

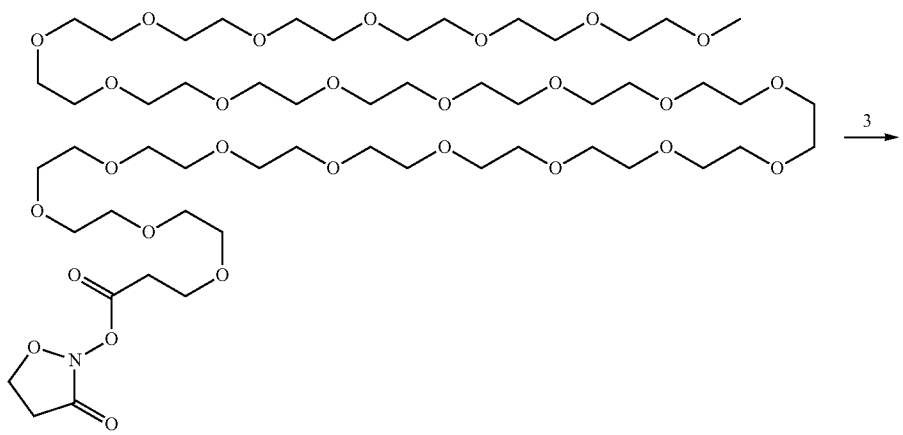

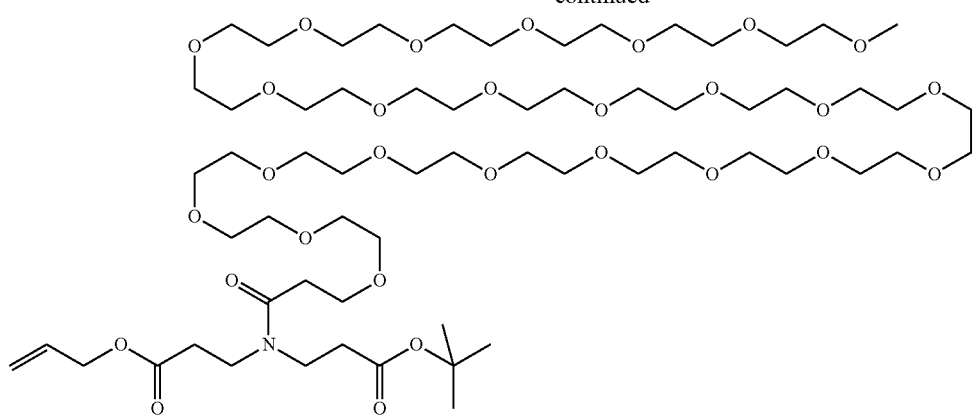
32
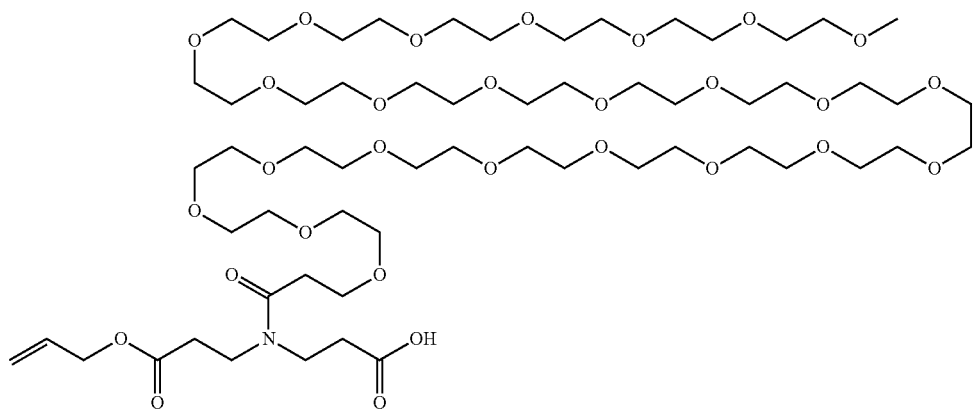
33
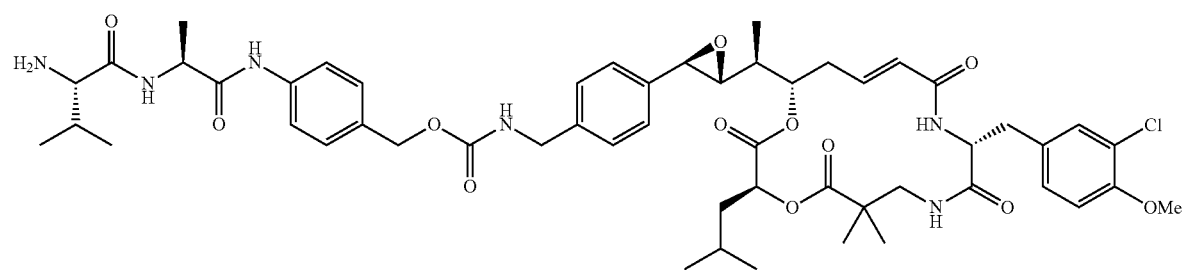
23

227 228
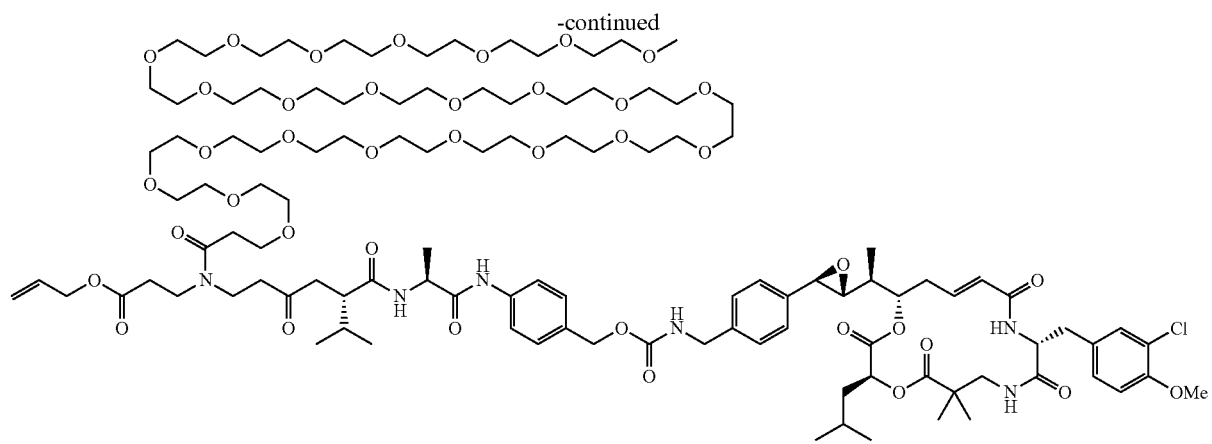
34
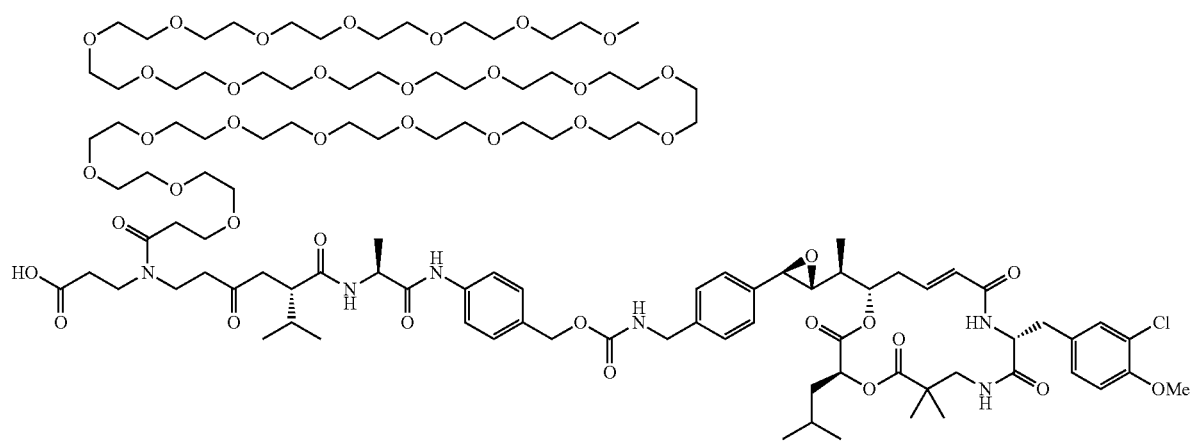
example 11
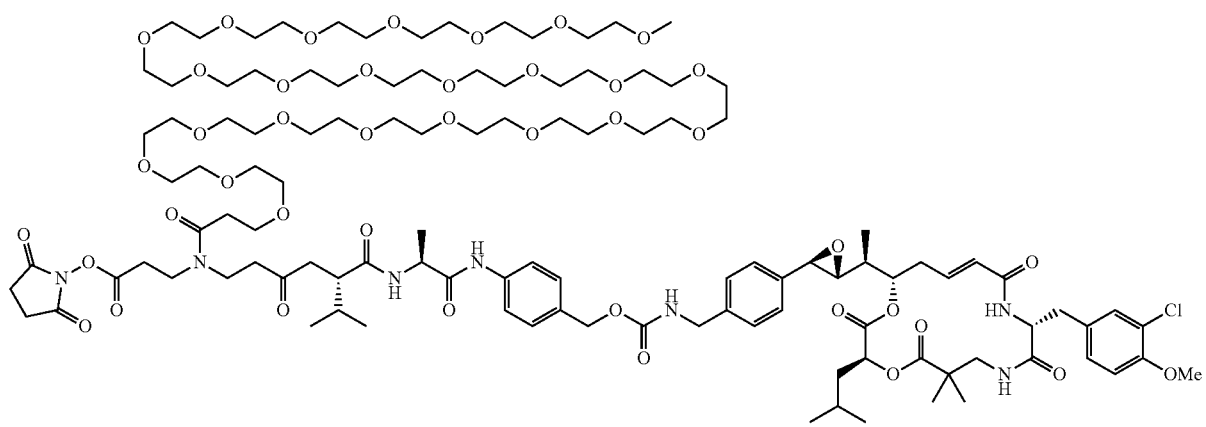
example 12

Compound 32: allyl 75-(3-(tert-butoxy)-3-oxopropyl)-74-oxo-2,5,8,11,14,17,20,23,26,29,32,35,38,41,47,50,53,56,59,62,65,68,71-tetracosaoxa-75-azaoctaheptacontan-78-oate To a solution of compound 3 (45 mg, 174.9 μmol) in THF (5 mL) were added, under Ar, MEO-DPEG(24)-NHS (212.4 mg, 174.9 μmol) and DIEA (44.2 μL, 262.3 μmol).
The reaction medium was stirred at RT overnight then concentrated in vacuo and purified by flash chromatography on 20 g of silica gel (gradient elution DMC/MeOH) to give 125 mg of a mixture of compound 32 (60%) and MEO-DPEG(24)-NHS (40%). This mixture was diluted in THF (3 mL), 15 mg of compound 3 and 20 μL of DIEA were added; the reaction medium was stirred at RT overnight then concentrated in vacuo and purified by flash chromatography on 12 g of silica gel to give 105 mg of compound 32 (44%).
RMN $^1$H (400 MHz, δ in ppm, DMSO-d6): 1.40 (s, 9H); 2.25 to 2.78 (m, 6H); 3.22 (s, 3H); 3.32 to 3.70 (m, 98H); 4.52 (m, 2H); 5.20 (m, 1H); 5.30 (m, 1H); 5.90 (m, 1H). LCMS (A): ES m/z=679 [M+2H]$^{2+}$; m/z=1356 [M+H]$^+$; m/z=1400 [M−H+HCO$_2$H]$^-$; $t_R$=1.15 min.

Compound 33: 75-(3-(allyloxy)-3-oxopropyl)-74-oxo-2,5,8,11,14,17,20,23,26,29,32,35,38,41,44,47,50,53,56,59,62,65,68,71-tetracosaoxa-75-azaoctaheptacontan-78-oic Acid To a solution of compound 32 (105 mg, 77.4 μmol) in DCM (2 mL) was added TFA (116.2 μL, 1.55 mmol); the reaction medium was stirred at RT overnight, 150 μL of TFA were then added and the reaction carried on one more day. The reaction medium was then concentrated in vacuo, diluted with DCM and co-evaporated with toluene (3×) to give 110 mg of crude product that were purified by RP-HPLC on a 5 μm C18 SunFire column (Waters, 30×100 mm, gradient elution MeCN+0.07% TFA/H$_2$O+0.07% TFA) to provide 60 mg of compound 33 (60%).
RMN $^1$H (400 MHz, δ in ppm, DMSO-d6): 50:50 conformer mixture; 2.37 to 2.60 (partially masked m, 6H); 3.23 (s, 3H); 3.32 to 3.44 (partially masked m, 38H); 3.47 to 3.52 (m, 58H); 3.60 (m, 2H); 4.54 (m, 2H); 5.22 (dm, J=10.5 Hz, 1H); 5.30 (dm, J=17.3 Hz, 1H); 5.84 to 5.98 (m, 1H); 12.32 (broad m, 1H).

Compound 34: allyl 75-(3-(((S)-1-(((S)-1-((4-((((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclo-hexadec-13-en-16-yl)ethyl)oxiran-2-yl)benzyl)carbamoyl)oxy)-methyl)phenyl)amino)-1-oxopropan-2-yl)amino)-3-methyl-1-oxobutan-2-yl)amino)-3-oxopropyl)-74-oxo-2,5,8,11,14,17,20,23,26,29,32,35,38,41,44,47,50,53,56,59,62,65,68,71-tetracosaoxa-75-azaoctaheptacontan-78-oate To a solution of compound 33 (30 mg, 23.1 μmol) in THF (5 mL) were added, under Ar, DIEA (11.7 μL, 69.2 μmol) and DSC (6.03 mg, 23.1 μmol). The reaction medium was stirred for 3 h at RT then was added compound 23 (23.5 mg, 23.1 μmol) and the stirring carried on 1 h. The reaction medium was concentrated in vacuo and purified by flash chromatography on 5 g of silica gel to give 23 mg of compound 34 (40%).
RMN $^1$H (500 MHz, δ in ppm, DMSO-d6): 60:40 conformer mixture: 0.80 (split d, J=6.8 Hz, 6H); 0.82 (d, J=7.0 Hz, 1.8H); 0.84 (d, J=7.0 Hz, 1.2H); 0.86 (d, J=7.0 Hz, 1.8H); 0.88 (d, J=7.0 Hz, 1.2H); 1.00 (s, 3H); 1.04 (d, J=7.0 Hz, 3H); 1.11 (s, 3H); 1.28 (m, 1H); 1.30 (d, J=7.0 Hz, 3H); 1.51 to 1.62 (m, 2H); 1.80 (m, 1H); 1.96 (m, 1H); 2.26 (m, 1H); 2.38 (m, 1H); 2.45 to 2.61 (partially masked m, 5H); 2.61 to 2.72 (m, 2H); 2.93 to 3.05 (m, 3H); 3.23 (s, 3H); 3.32 (masked m, 1H); 3.40 to 3.77 (m, 98H); 3.80 (s. 3H); 3.88 (d, J=2.3 Hz, 1H); 4.14 to 4.27 (m, 4H); 4.39 (m, 1H); 4.51 to 4.60 (m, 2H); 4.90 (dd, J=3.8 and 9.8 Hz, 1H); 4.97 (s, 2H); 5.10 (m, 1H); 5.18 to 5.33 (m, 2H); 5.78 (d, J=16.0 Hz, 1H); 5.90 (m, 1H); 6.45 (m, 1H); 7.05 (d, J=8.6 Hz, 1H); 7.16 (dd, J=2.5 and 8.6 Hz, 1H); 7.20 to 7.32 (m, 8H); 7.59 (m, 2H); 7.77 (t, J=6.5 Hz, 1H); 7.95 (d, J=9.0 Hz, 0.4H); 8.07 (d, J=9.0 Hz, 0.6H); 8.19 (d, J=7.0 Hz, 0.4H); 8.25 (d, J=7.0 Hz, 0.6H); 8.36 (d, J=8.0 Hz, 1H); 9.90 (s, 0.4H); 9.96 (s, 0.6H).

Example 11: 75-(3-(((S)-1-(((S)-1-((4-((((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)oxy) methyl)-phenyl)amino)-1-oxopropan-2-yl)amino)-3-methyl-1-oxobutan-2-yl)amino)-3-oxopropyl)-74-oxo-2,5,8,11,14,17,20,23,26,29,32,35,38,41,44,47,50,53,56,59,62,65,68,71-tetracosaoxa-75-azaoctaheptacontan-78-oic Acid To a solution of compound 34 (37 mg, 161 μmol) in DCM were added, under Ar, 1,3-dimethylbarbituric acid (5.13 mg, 32.2 μmol) and tetrakis(triphenylphosphine)palladium(0) (0.94 mg, 0.80 μmol); the reaction medium was stirred at RT for 2 h then concentrated in vacuo and purified by flash chromatography on 5 g of diol-modified silica gel (gradient elution DCM/MeOH) to give 16 mg of example 11 (44%).
RMN $^1$H (500 MHz, δ in ppm, DMSO-d6): 0.77 (d, J=7.0 Hz, 6H); 0.80 to 0.90 (m, 6H); 0.99 (s, 3H); 1.04 (d, J=7.0 Hz, 3H); 1.11 (s, 3H); 1.28 (m, 1H); 1.30 (d, J=7.0 Hz, 1.5H); 1.32 (d, J=7.0 Hz, 1.5 H); 1.52 to 1.61 (m, 2H); 1.79 (m, 1H); 1.98 (m, 1H); 2.22 to 2.58 (partially masked m, 7H); 2.68 (m, 2H); 2.92 to 3.04 (m, 3H); 3.21 (s, 3H); 3.30 (partially masked m, 1H); 3.37 to 3.67 (m, 98H); 3.81 (s, 3H); 3.88 (s, 1H); 4.08 to 4.28 (m, 4H); 4.39 (m, 1H); 4.90 (m, 1H); 4.98 (s, 2H); 5.10 (m, 1H); 5.80 (d, J=16.0 Hz, 1H); 6.48 (ddd, J=4.7, 10.5 and 16.0 Hz, 1H); 7.04 (d, J=8.6 Hz, 1H); 7.16 (broad d, J=8.6 Hz, 1H); 7.20 to 7.32 (m, 8H); 7.57 to 7.67 (m, 2H); 7.80 (m, 1H); 8.20 (m, 1H); 8.35 to 8.70 (m, 2H); 10.08 (m, 1H); 12.30 (broad m, 1H). LCMS (D): ES m/z=698; m/z=2259 [M+H]$^+$; $t_R$=3.14 min.

Example 12: 2,5-dioxopyrrolidin-1-yl 75-(3-(((S)-1-(((S)-1-((4-((((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)-carbamoyl)oxy)methyl)phenyl)amino)-1-oxopropan-2-yl)amino)-3-methyl-1-oxobutan-2-yl)amino)-3-oxopropyl)-74-oxo-2,5,8,11,14,17,20,23,26,29,32,35,38,41,44,47,50,53,56,59,62,65,68,71-tetracosaoxa-75-azaoctaheptacontan-78-oate To a solution of example 11 (16 mg, 7.1 μmol) in DCM were added DIEA (1.2 μL, 7.1 μmol) and DSC (1.8 mg, 7.1 μmol). The reaction medium was stirred for 3 h at RT then concentrated in vacuo and purified by flash chromatography on 1.3 g of diol-modified silica gel (gradient elution DCM/iPrOH) to give 5 mg of a mixture of example 12 (30%) and example 11 (70%).
LCMS (D): ES m/z=698; m/z=2356 [M+H]$^+$; $t_R$=3.2 min.

Synthesis of Example 13:
sulfo-PEG4-Val-Ala-PABA-C52 Benzylic Amine
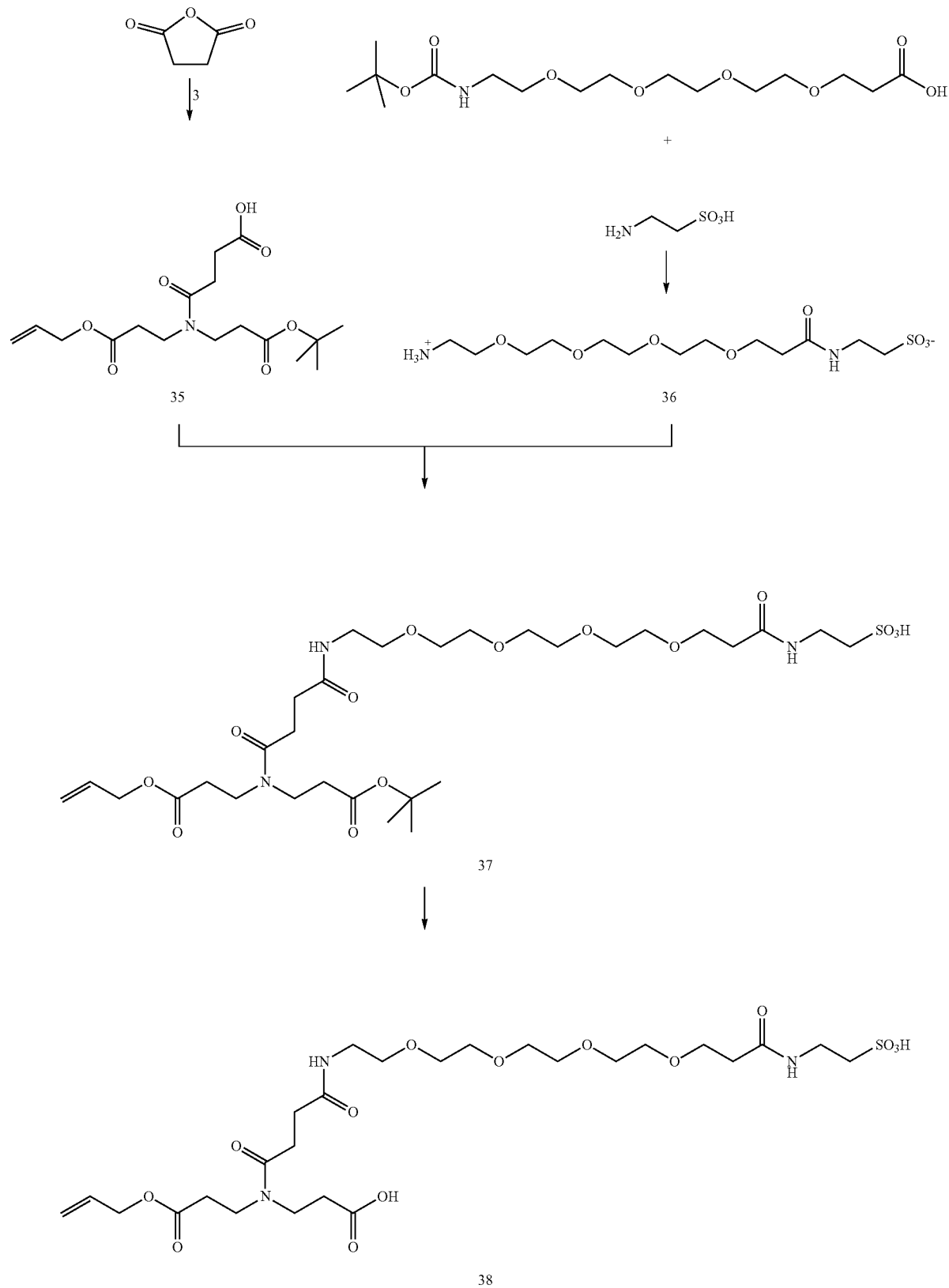

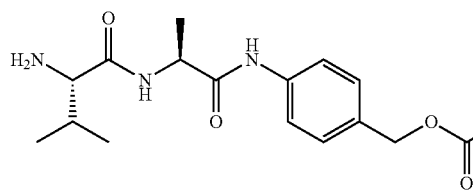
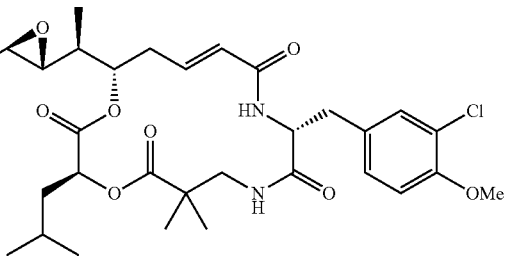
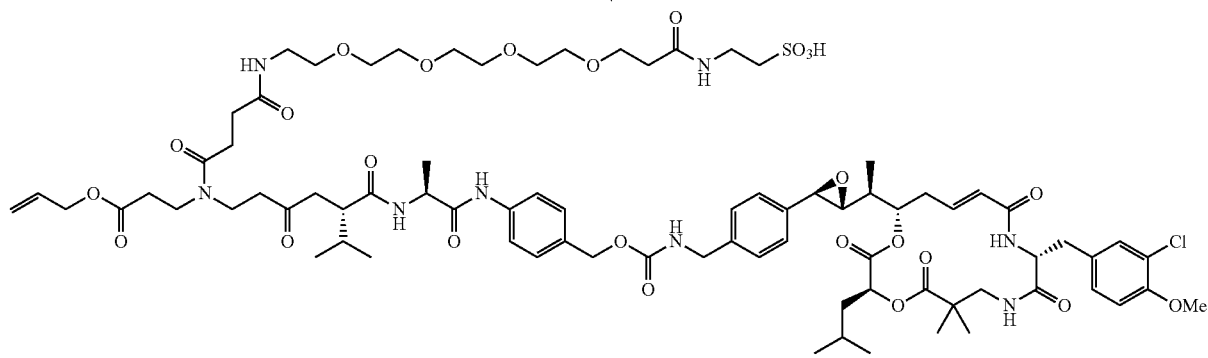
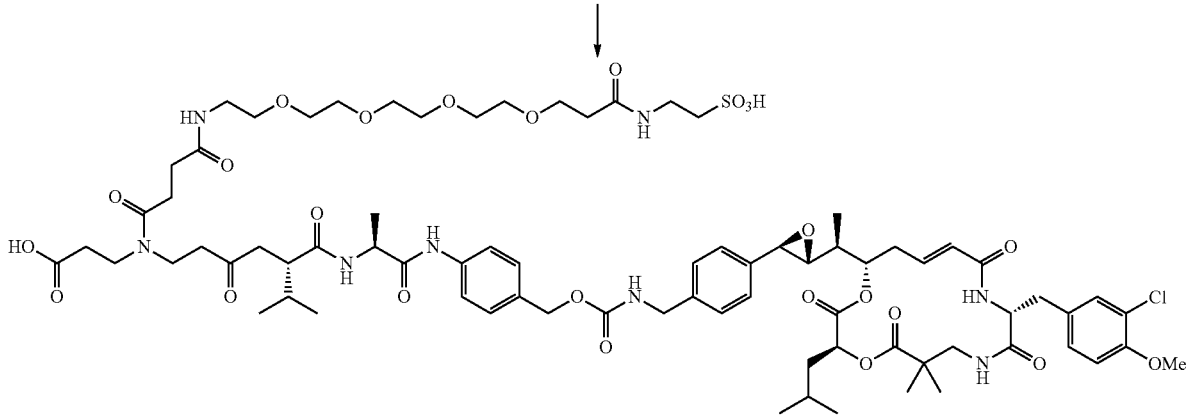

example 13

Compound 35: 4-((3-(allyloxy)-3-oxopropyl)(3-(tert-butoxy)-3-oxopropyl)amino)-4-oxobutanoic Acid To a solution of compound 3 (100 mg, 388.6 µmol) in DCM (5 mL) was added succinic anhydride (78.6 mg, 777.2 µmol). The reaction medium was stirred at RT overnight then concentrated in vacuo and purified by flash chromatography on 4 g of silica gel (gradient elution DCM/MeOH) to give 102 mg of compound 35 as a colorless oil (73%).

Compound 36: 1-ammonio-15-oxo-3,6,9,12-tetraoxa-16-azaoctadecane-18-sulfonate To a solution of 15-(Boc-amino)-4,7,10,13-tetraoxapentadecanoic acid (500 mg, 1.3 mmol) in THF (5 mL) were added, under Ar, DIEA (438.4 µL, 2.6 mmol) and DSC (381.6 mg, 1.43 mmol). The reaction medium was stirred for 6 h at RT then 50 mg of DSC were added and the stirring was carried on at RT overnight. At that time, taurine (821.6 mg, 6.5 mmol) and H$_2$O (1 mL) were added to the reaction medium. The reaction medium was stirred at RT overnight, concentrated in vacuo and purified by preparative LCMS on a 5 µm C18 SunFire column (Waters, 30×100 mm, gradient elution MeCN+0.07% TFA/H$_2$O+0.07% TFA) to give 341 mg of compound 36 (70%).

RMN $^1$H (400 MHz, δ in ppm, DMSO-d6): 2.28 (t, J=6.5 Hz, 2H); 2.60 (m, 2H); 2.99 (m, 2H); 3.32 (m, 2H); 3.45 to 3.65 (m, 16H); 7.77 (broad m, 4H). IR spectrum as a KBr pellet; main absorption bands in reciprocal centimeters: 3000; 1780; 1648; 1556; 1200-1170; 1200; 1100; 1040.

Compound 37: 24-(3-(tert-butoxy)-3-oxopropyl)-4, 20,23,27-tetraoxo-7,10,13,16,28-pentaoxa-3,19,24-triazahentriacont-30-ene-1-sulfonate To a solution of compound 35 (100 mg, 279.8 µmol) in THF were added DIEA (141.6 µL, 839.4 µmol) and DSC (73.1 mg, 279.8 µmol). The reaction mixture was stirred for 2 h at RT then a solution of compound 36 (104.2 mg, 279.8 µmol) in DMF and DIEA (141.6 µL, 839.4 µmol) were added. The reaction medium was stirred for 2 h at RT, concentrated in vacuo and purified by preparative LCMS on a 5 µm C18 SunFire column (Waters, 30×100 mm, gradient elution MeCN+0.07% TFA/H$_2$O+0.07% TFA) to give 118 mg of compound 37 (60%).

RMN $^1$H (400 MHz, δ in ppm, DMSO-d6): 50:50 conformer mixture; 1.39 (s, 4.5H); 1.40 (s, 4.5H); 2.27 (t, J=6.5 Hz, 2H); 2.31 (t, J=7.0 Hz, 2H); 2.38 (t, J=7.0 Hz, 1H); 2.45 to 2.56 (masked m, 6H); 2.68 (m, 1H); 3.18 (q, J=6.0 Hz, 2H); 3.29 (m, 2H); 3.36 to 3.60 (m, 20H); 4.51 to 4.59 (m, 2H); 5.17 to 5.25 (m, 2H); 5.85 to 5.95 (m, 1H); 7.75 (t, J=6.0 Hz, 1H); 7.88 (t, J=6.0 Hz, 1H).

Compound 38: 24-(2-carboxyethyl)-4,20,23,27-tetraoxo-7,10,13,16,28-pentaoxa-3,19,24-triazahentriacont-30-ene-1-sulfonate To a solution of compound 37 (118 mg, 166.0 µmol) in DCM (5 mL) was added TFA (249 µL, 3.32 mmol). The reaction medium was stirred at RT overnight, concentrated in vacuo, diluted with DCM and co-evaporated with toluene (3×) to give 100 mg of compound 38 as a colorless oil (92%).

Compound 39: (2S,5S)-10-(3-(allyloxy)-3-oxopropyl)-1-((4-(((((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)oxy)methyl)phenyl)amino)-5-isopropyl-2-methyl-1,4,7,11,14,30-hexaoxo-18,21,24,27-tetraoxa-3,6,10,15,31-pentaazatritria-contane-33-sulfonic Acid To a solution of compound 38 (100 mg, 152.7 µmol) in THF (3 mL) and DMF (1 mL) were added DIEA (77 µL, 458.2 µmol) and DSC (39.9 mg, 152.7 µmol). The reaction medium was stirred for 2 h at RT before the addition of a solution of compound 23 (124 mg, 121.9 µmol) in THF (1 mL) and DMF (0.5 mL) and DIEA (100 µL). The reaction medium was stirred for 2 h at RT, concentrated in vacuo and purified by reverse phase flash chromatography on 75 g of C18-modified silica gel (gradient elution H$_2$O/MeCN) to give 60 mg of compound 39 as a white solid (24%).

RMN $^1$H (500 MHz, δ in ppm, DMSO-d6): 60:40 conformer mixture; 0.78 (d, J=6.8 Hz, 6H); 0.82 (d, J=7.0 Hz, 1.8H); 0.84 (d, J=7.0 Hz, 1.2H); 0.86 (d, J=7.0 Hz, 1.8H); 0.88 (d, J=7.0 Hz, 1.2H); 0.99 (s, 3H); 1.04 (d, J=7.0 Hz, 3H); 1.11 (s, 3H); 1.28 (m, 1H); 1.30 (d, J=7.0 Hz, 3H); 1.50 to 1.62 (m, 2H); 1.80 (m, 1H); 1.96 (m, 1H); 2.20 to 2.55 (partially masked m, 11H); 2.61 to 2.75 (m, 2H); 2.94 to 3.05 (m, 3H); 3.10 to 3.65 (partially masked, 27H); 3.80 (s, 3H); 3.87 (d, J=2.3 Hz, 1H); 4.13 to 4.28 (m, 4H); 4.38 (m, 1H); 4.53 (m, 1.2H); 4.56 (m, 0.8H); 4.90 (dd, J=3.8 and 9.8 Hz, 1H); 4.97 (s, 2H); 5.10 (m, 1H); 5.18 to 5.33 (m, 2H); 5.80 (d, J=16.0 Hz, 1H); 5.90 (m, 1H); 6.47 (ddd, J=4.7, 10.5 and 16.0 Hz, 1H); 7.05 (d, J=8.6 Hz, 1H); 7.16 (dd, J=2.5 and 8.6 Hz, 1H); 7.20 to 7.32 (m, 8H); 7.59 (m, 2H); 7.72 (t, J=6.5 Hz, 1H); 7.79 (t, J=6.0 Hz, 1H); 7.89 (t, J=6.5 Hz, 1H); 7.95 (d, J=9.0 Hz, 0.4H); 8.08 (d, J=9.0 Hz, 0.6H); 8.19 (d, J=7.0 Hz, 0.4H); 8.25 (d, J=7.0 Hz, 0.6H); 8.36 (d, J=8.0 Hz, 1H); 9.90 (s, 0.4H); 9.95 (s, 0.6H). LCMS (D): ES m/z=913; m/z=1654 [M+H]$^+$; t$_R$=3.87 min.

Example 13: 24-(3-(((S)-1-(((S)-1-((4-((((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)oxy)methyl)-phenyl)amino)-1-oxopropan-2-yl)amino)-3-methyl-1-oxobutan-2-yl)amino)-3-oxopropyl)-4,20, 23-trioxo-1-sulfo-7,10,13,16-tetraoxa-3,19,24-triazaheptacosan-27-oic Acid To a solution of compound 39 (60 mg, 36.3 µmol) in DMF (5 mL) were added 1,3-dimethylbarbituric acid (17.3 mg, 108.8 µmol) and tetrakis (triphenylphosphine)palladium(0) (2.1 mg, 1.8 µmol). The reaction medium was stirred at RT overnight, concentrated in vacuo and purified by two flash chromatographies on 30 g and 20 g of C18-modified silica gel to give two batches of 6 mg of example 13 as a white solid (20% global yield).

RMN $^1$H (500 MHz, δ in ppm, DMSO-d6): 60:40 conformer mixture; 0.78 (d, J=6.8 Hz, 6H); 0.81 to 0.89 (m, 6H); 1.00 (s, 3H); 1.04 (d, J=7.0 Hz, 3H); 1.11 (s, 3H); 1.28 (m, 1H); 1.30 (d, J=7.0 Hz, 3H); 1.58 (m, 2H); 1.80 (m, 1H); 1.96 (m, 1H); 2.21 to 2.58 (partially masked m, 11H); 2.69 (m, 2H); 2.93 to 3.68 (partially masked m, 28H); 3.80 (s, 3H); 3.88 (d, J=2.3 Hz, 1H); 4.11 to 4.28 (m, 4H); 4.38 (m, 1H); 4.90 (dd, J=3.8 and 9.8 Hz, 1H); 4.98 (s, 2H); 5.10 (m, 1H); 5.79 (d, J=16.0 Hz, 1H); 6.47 (ddd, J=4.7, 10.5 and 16.0 Hz, 1H); 7.05 (d, J=8.6 Hz, 1H); 7.17 (dd, J=2.5 and 8.6 Hz, 1H); 7.20 to 7.32 (m, 8H); 7.59 (m, 2H); 7.72 (t, J=6.5 Hz, 1H); 7.79 (t, J=6.0 Hz, 1H); 7.89 (t, J=6.5 Hz, 1H); 7.97 (d, J=9.0 Hz, 0.4H); 8.08 (d, J=9.0 Hz, 0.6H); 8.19 (d, J=7.0 Hz, 0.4H); 8.25 (d, J=7.0 Hz, 0.6H); 8.36 (d, J=8.0 Hz, 1H); 9.90 (s, 0.4H); 9.94 (s, 0.6H); 12.15 (broad m, 1H). LCMS (A): ES m/z=807.5 [M+2H]$^{2+}$; m/z=1612 [M−H]$^-$; m/z=1614 [M+H]$^+$; t$_R$=1.72 min.

Synthesis of Examples 14 to 16: glutaryl-Val-PEG4Gln-C52 Benzylic Amine, NHS Ester of glutaryl-Val-PEG4Gln-C52 Benzylic Amine and Corresponding ADC

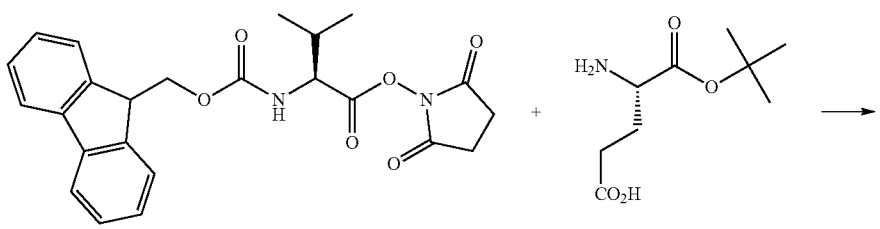

237 238
-continued
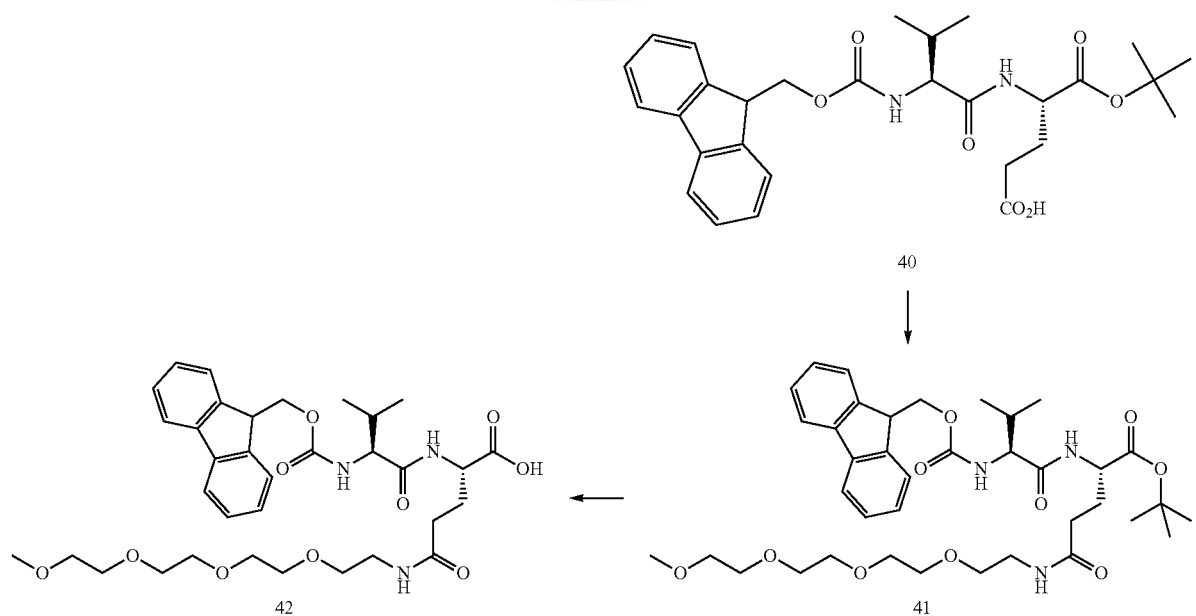
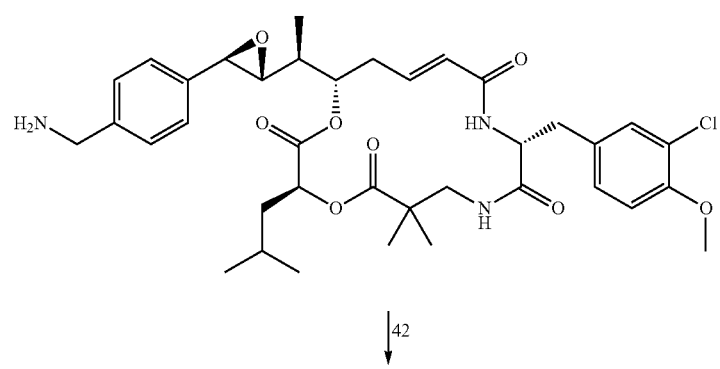
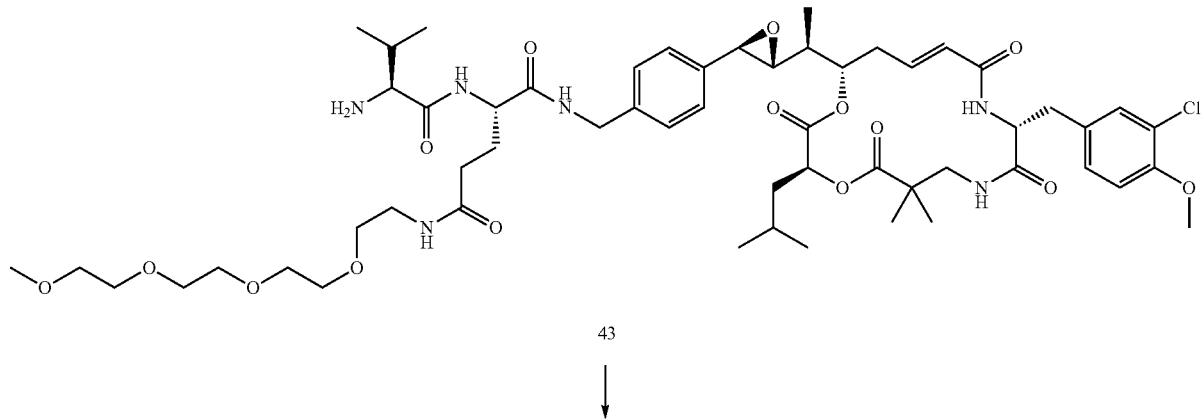

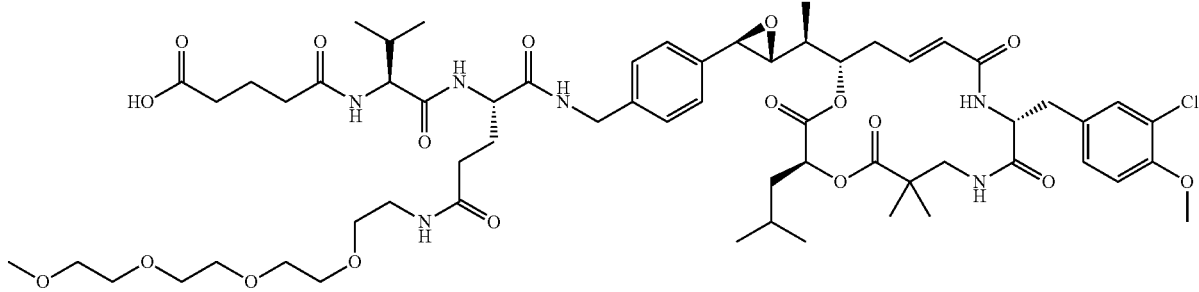

example 14

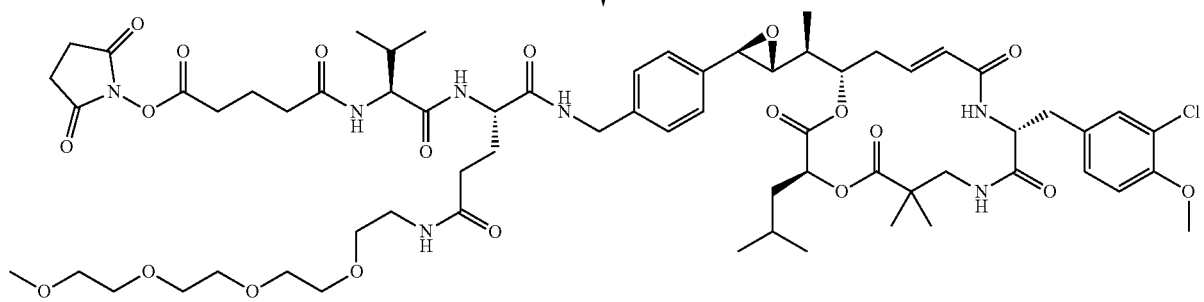

example 15

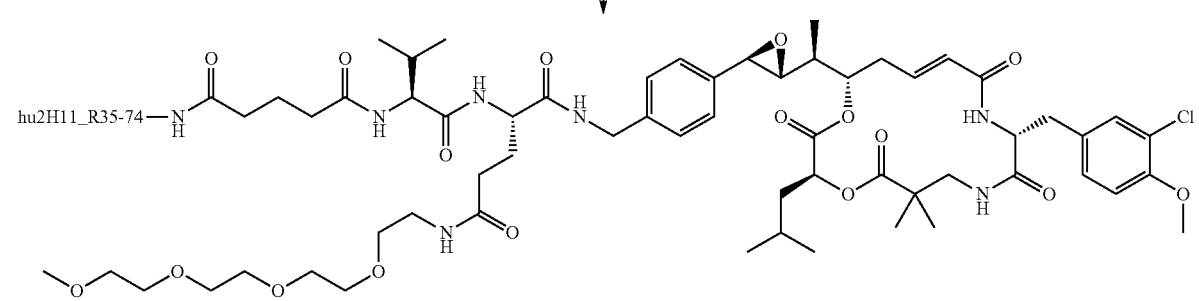

example 16

Compound 40: (S)-4-((S)-2-(((((9H-fluoren-9-yl)methoxy)carbonyl)amino)-3-methylbutanamido)-5-(tert-butoxy)-5-oxopentanoic Acid To a solution of H-Glu-OtBu (CAS number [45120-30-7], 959 mg, 4.7 mmol) and NaHCO$_3$ (400 mg, 4.77 mmol) in H$_2$O (80 mL), was added dropwise, under magnetic stirring, a solution of (S)-2,5-dioxopyrrolidin-1-yl 2-((((9H-fluoren-9-yl)methoxy)-carbonyl)amino)-3-methylbutanoate (2 g, 4.6 mmol) in THF (80 mL). The reaction medium was stirred at RT overnight. The medium was concentrated in vacuo, then saturated aqueous NaHCO$_3$ (1 L) was added, followed by extraction with Et$_2$O (2×250 mL), organic phases were excluded. The aqueous phase was acidified with QS of aqueous 1N HCl to reach pH 2, and extracted with DCM (3×250 mL), the combined organic phases were dried over MgSO$_4$, filtered and concentrated in vacuo to give 2.05 g compound 40 (85%).

RMN $^1$H (400 MHz, δ in ppm, DMSO-d6): 0.87 (d, J=6.9 Hz, 3H); 0.90 (d, J=6.9 Hz, 3H); 1.38 (s, 9H); 1.73 to 2.02 (m, 3H); 2.24 to 2.30 (m, 2H); 3.90 (dd, J=7.3 and 9.0 Hz, 1H); 4.14 (m, 1H); 4.19 to 4.32 (m, 3H); 7.27 to 7.45 (m, 5H); 7.75 (t, J=7.6 Hz, 2H); 7.89 (d, J=7.6 Hz, 2H); 8.22 (broad d, J=7.0 Hz, 1H); 12.05 (broad s, 1H).

Compound 41: (S)-tert-butyl 18-((S)-2-((((9H-fluoren-9-yl)methoxy)carbonyl)amino)-3-methylbutanamido)-15-oxo-2,5,8,11-tetraoxa-14-azanonadecan-19-oate To a solution of compound 40 (200 mg, 381 µmol) in DCM (6 mL) were added, under magnetic stirring, PEG4-NH$_2$ (CAS number [85030-56-4], 115 mg, 554.9 µmol), HOBt (82 mg, 606.8 µmol) and EDC (100 µL, 565 µmol). The reaction medium was stirred at RT overnight. The crude medium was purified twice by flash chromatography on silica gel (gradient elution DCM/MeOH) to give 190 mg of compound 41 (70%).

RMN $^1$H (400 MHz, δ in ppm, DMSO-d6): 0.87 (d, J=6.8 Hz, 3H); 0.90 (d, J=6.8 Hz, 3H); 1.38 (s, 9H); 1.72 to 1.93

(m, 2H); 1.99 (m, 1H); 2.14 (t, J=7.8 Hz, 2H); 3.18 (m, 2H); 3.23 (s, 3H); 3.37 (t, J=6.0 Hz, 2H); 3.41 (m, 2H); 3.46 to 3.53 (m, 10H); 3.92 (dd, J=7.1 and 8.8 Hz, 1H); 4.09 (m, 1H); 4.17 to 4.34 (m, 3H); 7.32 (m, 3H); 7.41 (t, J=7.6 Hz, 2H); 7.70 to 7.81 (m, 3H); 7.88 (d, J=7.6 Hz, 2H); 8.18 (d, J=7.3 Hz, 1H). LCMS (A): ES m/z=714 [M+H]$^+$; m/z=758 [M−H+HCO$_2$H]$^−$; t$_R$=1.41 min.

Compound 42: (S)-18-((S)-2-(((((9H-fluoren-9-yl) methoxy)carbonyl)amino)-3-methylbutanamido)-15-oxo-2,5,8,11-tetraoxa-14-azanonadecan-19-oic Acid To compound 41 (190 mg, 266 μmol) was added, under magnetic stirring, a 4M solution of HCl in 1,4-dioxane (5 mL). The reaction medium was stirred at RT for 4 h. At this time, the reaction medium was concentrated in vacuo and purified by flash chromatography on 15 g of silica gel (gradient elution DCM/MeOH/NH$_4$OH) to give 70 mg of compound 42 (40%).
RMN $^1$H (400 MHz, δ in ppm, DMSO-d6): 0.84 (d, J=6.6 Hz, 3H); 0.86 (d, J=6.6 Hz, 3H); 1.70 to 1.90 (m, 2H); 2.01 to 2.15 (m, 3H); 3.15 (m, 2H); 3.23 (s, 3H); 3.36 (t, J=6.4 Hz, 2H); 3.42 (m, 2H); 3.45 to 3.53 (m, 10H); 3.80 (broad m, 1H); 3.83 (dd, J=6.8 and 8.7 Hz, 1H); 4.19 to 4.34 (m, 3H); 7.33 (m, 2H); 7.41 (t, J=7.6 Hz, 2H); 7.59 (broad m, 2H); 7.73 (d, J=7.6 Hz, 1H); 7.76 (d, J=7.6 Hz, 1H); 7.89 (d, J=7.6 Hz, 2H); 8.00 (broad m, 1H). LCMS (A): ES m/z=656 [M−H]$^−$; m/z=658 [M+H]$^+$; RT=1.19 min.

Compound 43: (S)-2-((S)-2-amino-3-methylbutanamido)-N1-(4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)-N5-(2,5,8,11-tetraoxatridecan-13-yl) pentanediamide To a solution of (E)-(3S,10R,16S)-16-{(S)-1-[(2R,3R)-3-(4-aminomethyl-phenyl)-oxiranyl]-ethyl}-10-(3-chloro-4-methoxy-benzyl)-3-isobutyl-6,6-dim ethyl-1,4-dioxa-8,11-diaza-cyclohexadec-13-ene-2,5,9,12-tetraone (the synthesis of which was described in WO2011001052, compound 77, 58 mg, 83 μmol) in DMF (5 mL), under magnetic stirring, were added compound 42 (70 mg, 106 μmol), HOBt (20 mg, 148 μmol) and EDC (23 μL, 130 μmol). The reaction medium was stirred at RT for 24 h. At this time, piperidine (80 μL, 810 μmol) was added to the medium, and stirring was maintained for 1 h. Then, the reaction medium was concentrated in vacuo and purified by flash chromatography on 20 g silica gel (gradient elution DCM/MeOH) to give 60 mg of compound 43 (65%).
RMN $^1$H (500 MHz, δ in ppm, DMSO-d6): 0.77 (d, J=6.9 Hz, 3H); 0.79 (d, J=6.3 Hz, 6H); 0.87 (d, J=6.9 Hz, 3H); 1.00 (s, 3H); 1.04 (d, J=6.4 Hz, 3H); 1.12 (s, 3H); 1.31 (m, 1H); 1.52 to 1.63 (m, 2H); 1.72 to 1.98 (m, 4H); 2.05 to 2.15 (m, 2H); 2.26 (m, 1H); 2.62 to 2.73 (m, 2H); 2.94 to 3.04 (m, 4H); 3.18 (q, J=5.9 Hz, 2H); 3.23 (s, 3H); 3.33 (partially masked m, 1H); 3.39 (t, J=5.9 Hz, 2H); 3.42 (m, 2H); 3.47 to 3.52 (m, 10H); 3.81 (s, 3H); 3.87 (d, J=1.4 Hz, 1H); 4.21 to 4.36 (m, 4H); 4.91 (dd, J=3.6 and 9.6 Hz, 1H); 5.10 (dd, J=5.5 and 11.8 Hz, 1H); 5.79 (d, J=15.3 Hz, 1H); 6.46 (ddd, J=3.8, 11.6 and 15.3 Hz, 1H); 7.05 (d, J=8.5 Hz, 1H); 7.17 (dd, J=1.9 and 8.5 Hz, 1H); 7.21 to 7.25 (m, 5H); 7.28 (d, J=1.9 Hz, 1H); 7.89 (t, J=5.5 Hz, 1H); 8.07 (m large, 1H); 8.37 (d, J=8.0 Hz, 1H); 8.45 (t, J=5.9 Hz, 1H). LCMS (A): ES m/z=558 [M+2H]$^{2+}$; m/z=1115 [M+H]$^+$; m/z=1159 [M−H+HCO$_2$H]$^−$; t$_R$=0.96 min.

Example 14: (18S,21S)-18-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)-21-isopropyl-15,20,23-trioxo-2,5,8,1 I-tetraoxa-14,19,22-triazaheptacosan-27-oic Acid To a solution of compound 43 (55 mg, 49.3 μmol) in DMF (3 mL) was added glutaric anhydride (9 mg, 79 μmol), the reaction medium was stirred at RT for 2 h. At this time, the medium was concentrated in vacuo and purified by flash chromatography on 10 g of silica gel (gradient elution DCM/MeOH) to give 38 mg of example 14 (62%).
RMN $^1$H (500 MHz, δ in ppm, DMSO-d6): 0.81 (split d, J=6.6 Hz, 6H); 0.85 (d, J=6.3 Hz, 3H); 0.87 (d, J=6.3 Hz, 3H); 0.98 (s, 3H); 1.03 (d, J=6.6 Hz, 3H); 1.11 (s, 3H); 1.35 (m, 1H); 1.52 to 2.34 (m, 15H); 2.71 (m, 2H); 2.89 to 3.02 (m, 3H); 3.09 to 3.21 (m, 2H); 3.23 (s, 3H); 3.30 to 3.40 (partially masked m, 3H); 3.42 (m, 2H); 3.46 to 3.51 (m, 10H); 3.81 (s, 3H); 3.87 (s, 1H); 4.03 to 4.24 (m, 4H); 4.37 (m, 1H); 4.96 (m, 1H); 5.11 (m, 1H); 5.81 (d, J=15.3 Hz, 1H); 6.46 (ddd, J=3.3, 11.4 and 15.3 Hz, 1H); 7.04 (d, J=8.5 Hz, 1H); 7.19 (dd, J=1.9 and 8.5 Hz, 1H); 7.22 (d, J=8.3 Hz, 2H); 7.27 (d, J=8.3 Hz, 2H); 7.30 (d, J=1.9 Hz, 1H); 7.32 (m, 1H); 7.85 to 8.99 (broad m, 5H); 12.12 (broad m, 1H). LCMS (A): ES m/z=615 [M+2H]$^{2+}$; m/z=1227 [M−H]$^−$; m/z=1229 [M+H]$^+$; t$_R$=1.26 min.

Example 15: (18S,21 S)-2,5-dioxopyrrolidin-1-yl 18-((4-((2R,3R)-3-((S)-1-((3S,10R,16S,E)-10-(3-chloro-4-methoxybenzyl)-3-isobutyl-6,6-dimethyl-2, 5,9,12-tetraoxo-1,4-dioxa-8,11-diazacyclohexadec-13-en-16-yl)ethyl)oxiran-2-yl)benzyl)carbamoyl)-21-isopropyl-15,20,23-trioxo-2,5,8,1 I-tetraoxa-14, 19,22-triazaheptacosan-27-oate To a solution of example 14 (32 mg, 26 μmol) in DMF (3 mL), under magnetic stirring, were added DSC (8 mg, 31.2 μmol) and DIEA (8.6 μL, 52 μmol). The reaction medium was stirred at RT overnight. Then, 4 mg of DSC were added and stirring at RT was maintained for 1 h. At this time, the reaction medium was diluted with MeTHF (10 mL), washed with H$_2$O (5 mL). The aqueous phase was extracted with MeTHF (3×5 mL). The combined organic phases were dried over MgSO$_4$, filtered and concentrated in vacuo. The medium was purified by flash chromatography on 4 g of silica gel (gradient elution DCM/iPrOH) to give 28 mg of example 15 (81%).
RMN $^1$H (500 MHz, δ in ppm, DMSO-d6): 0.78 (d, J=6.6 Hz, 6H); 0.83 (d, J=6.9 Hz, 3H); 0.85 (d, J=6.9 Hz, 3H); 1.00 (s, 3H); 1.04 (d, J=6.4 Hz, 3H); 1.12 (s, 3H); 1.30 (m, 1H); 1.52 to 1.64 (m, 2H); 1.75 to 1.93 (m, 5H); 1.98 (m, 1H); 2.12 (m, 2H); 2.22 to 2.34 (m, 3H); 2.62 to 2.72 (m, 4H); 2.81 (s, 4H); 2.93 to 3.04 (m, 3H); 3.18 (q, J=6.0 Hz, 2H); 3.23 (s, 3H); 3.33 (partially masked m, 1H); 3.39 (t, J=6.0 Hz, 2H); 3.42 (m, 2H); 3.47 to 3.52 (m, 10H); 3.81 (s, 3H); 3.87 (d, J=1.6 Hz, 1H); 4.15 (dd, J=6.6 and 8.2 Hz, 1H); 4.19 to 4.32 (m, 4H); 4.91 (dd, J=3.6 and 9.6 Hz, 1H); 5.10 (m, 1H); 5.79 (d, J=15.3 Hz, 1H); 6.47 (ddd, J=3.7, 11.3 and 15.3 Hz, 1H); 7.05 (d, J=8.5 Hz, 1H); 7.17 (dd, J=2.2 and 8.5 Hz, 1H); 7.21 to 7.26 (m, 5H); 7.28 (d, J=2.2 Hz, 1H); 7.85 (t, J=6.0 Hz, 1H); 7.92 (d, J=8.2 Hz, 1H); 8.08 (d, J=7.7 Hz, 1H); 8.32 (t, J=6.0 Hz, 1H); 8.37 (d, J=8.0 Hz, 1H). LCMS (A): ES m/z=1326 [M+H]⁺; m/z=1348 [M+Na]⁺; m/z=1370 [M−H+HCO₂H]⁻; $t_R$=1.31 min.

Example 16: hu2H11_R35-74-Ex15

The general method described previously was used for the preparation of example 16. 28.8 mg of hu2H11_R35-74 were reacted with 115.2 μL of a 10.05 mM solution of example 15 in DMA (6 eq.) for 2 h 30. After purification on Superdex 200 pg in buffer B pH 6.5+10% NMP, concentration on Amicon Ultra-15, dilution in buffer B pH 6.5 to a final concentration of NMP at 5% and filtration on 0.22 μm PVDF filter, 16.12 mg of ADC were obtained that contained 2.2% of residual example 14. This batch was concentrated on Amicon Ultra-15 and purified on Sephadex G25 to provide 13.16 mg of example 16 as a colorless limpid solution at a concentration of 1.4 mg/mL with a DAR of 2.8 (HRMS), a monomeric purity of 99.7% and a global yield of 43%.

SEC-HRMS: m/z=149398 (naked mAb); m/z=150610 (D1); m/z=151822 (D2); m/z=153035 (D3); m/z=154248 (D4); m/z=155458 (D5); m/z=156672 (D6); m/z=1578881 (D7).

Synthesis of Examples 17 to 19:
glutaryl-Val-GlucoseGln-C52 Benzylic Amine,
NHS Ester of glutaryl-Val-GlucoseGln-C52
Benzylic Amine and Corresponding ADC

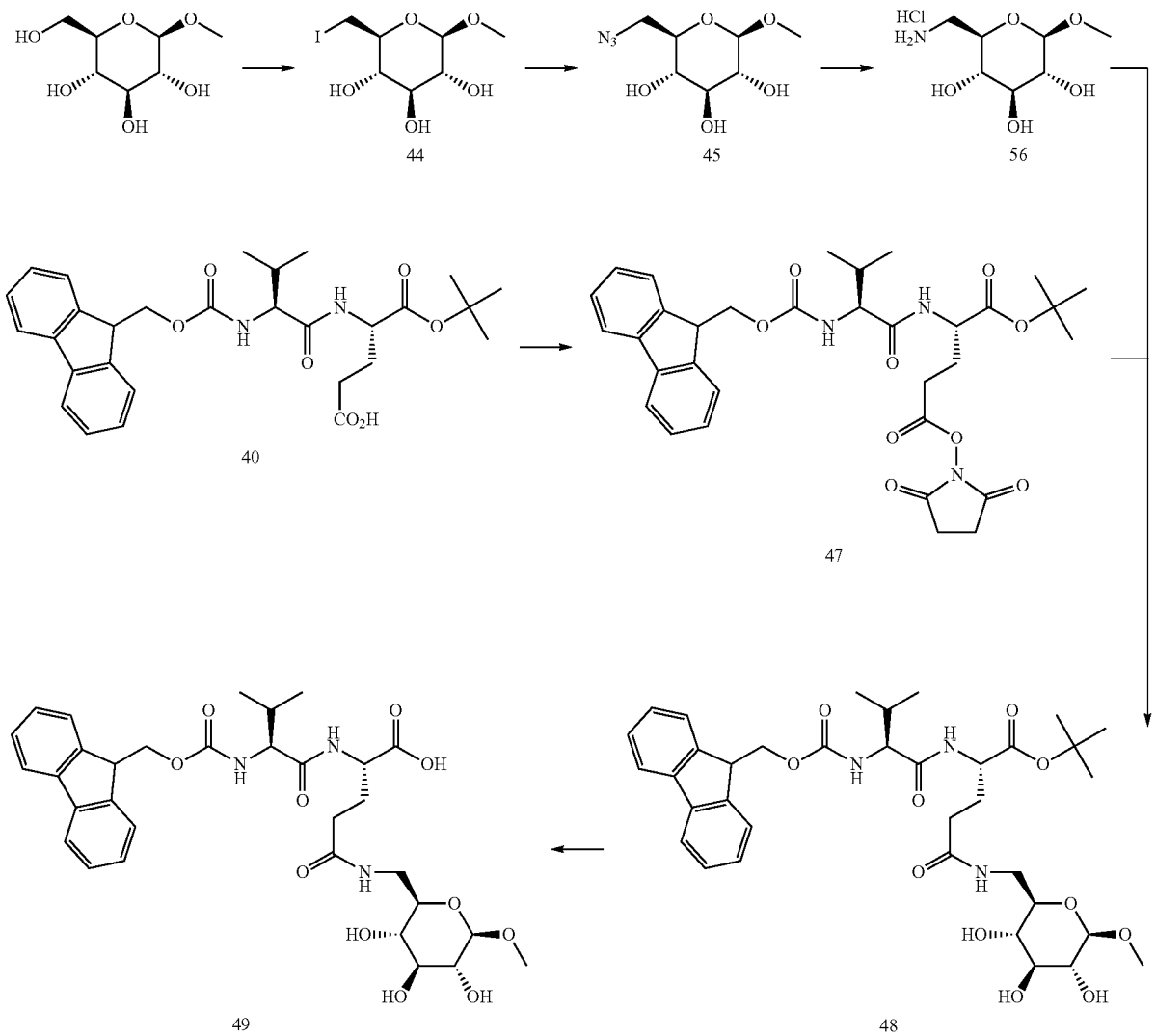

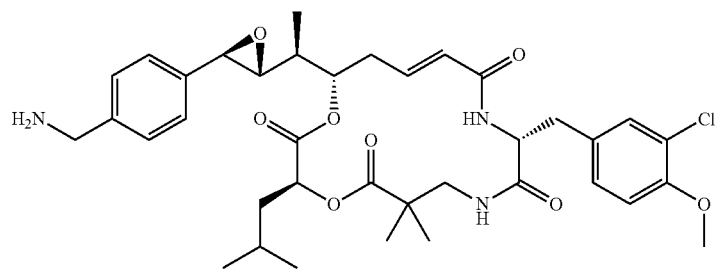
↓ 49
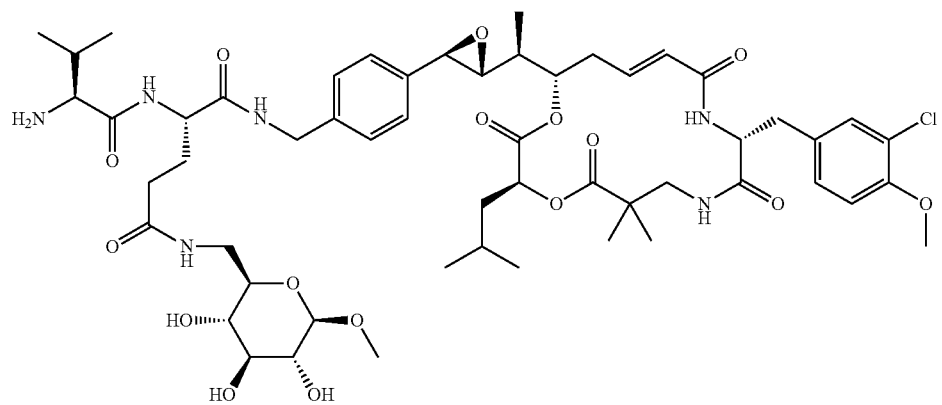
↓ 50
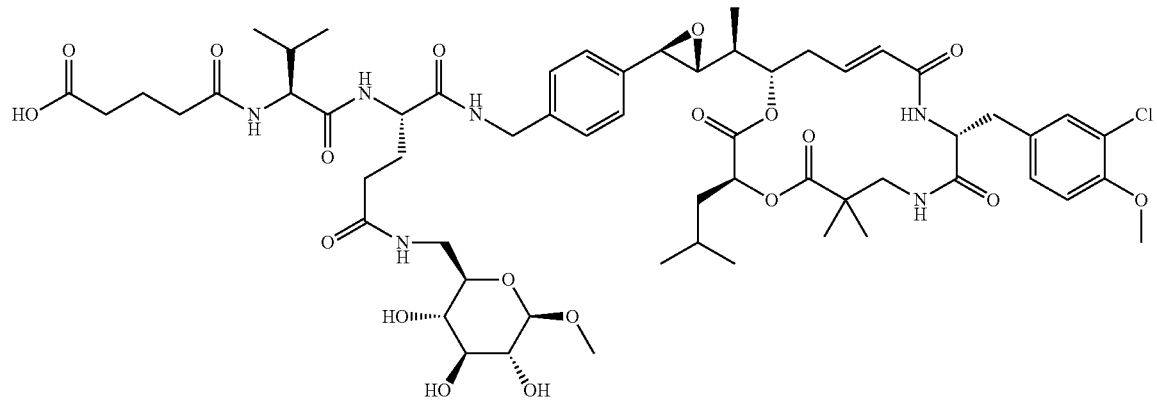
example 17
↓

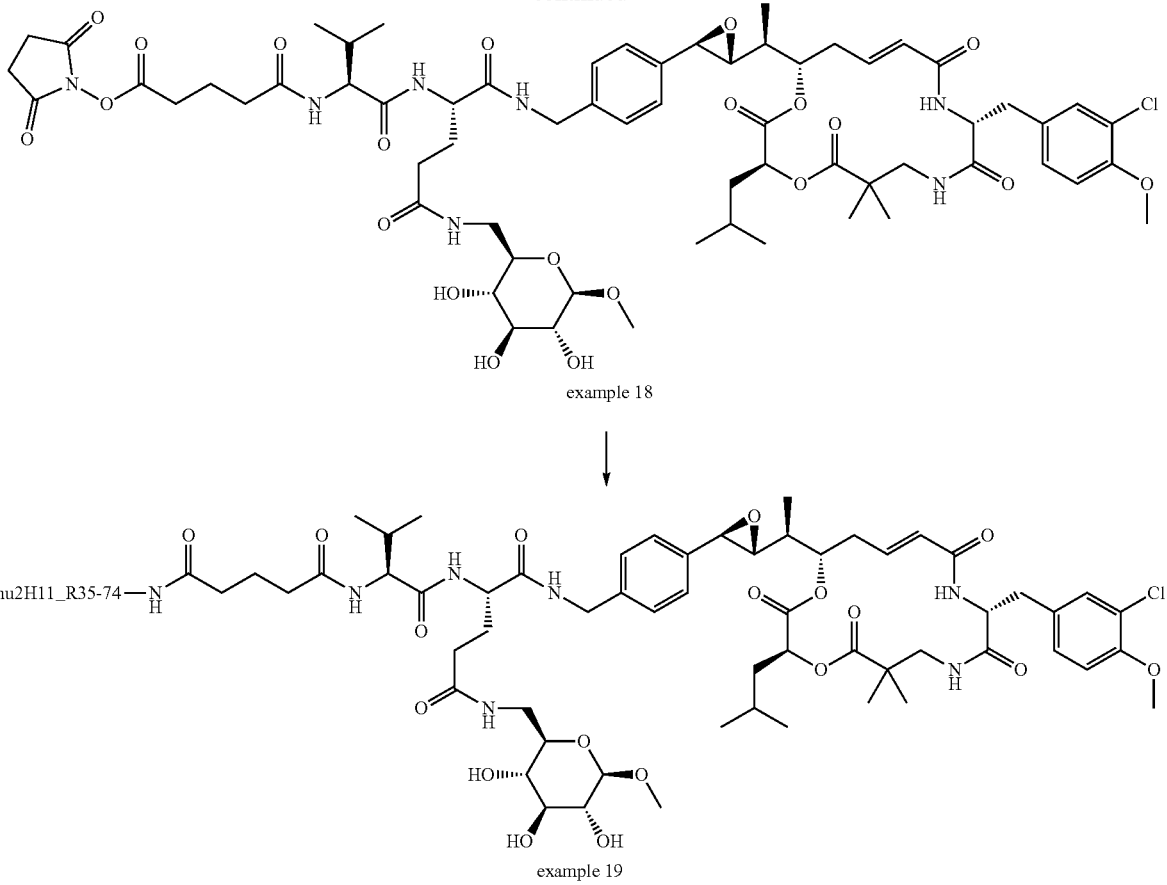

example 18 example 19

Compound 44: (2S,3S,4S,5R,6R)-2-(iodomethyl)-6-methoxytetrahydro-2H-pyran-3,4,5-triol To a solution of methyl R-D-glucopyranoside hemihydrate (CAS number [7000-27-3], 1 g, 4.67 mmol), imidazole (642 mg, 9.34 mmol) and triphenylphosphine (2.47 g, 9.33 mmol) in THF (50 mL) stirred at reflux, was added dropwise a solution of iodine (2.37 g, 9.33 mmol) in THF (10 mL). Reflux was maintained for 3 h. After cooling at 0° C., the reaction medium was filtered, the filtrate was concentrated in vacuo. The mixture was purified by flash chromatography on 150 g of silica gel (gradient DCM/MeOH) to give 1 g of compound 44 (63%).

Compound 45: (2R,3S,4S,5R,6R)-2-(azidomethyl)-6-methoxytetrahydro-2H-pyran-3,4,5-triol To a solution of compound 44 (1 g, 3.29 mmol) in DMF (10 mL), under magnetic stirring, was added NaN₃ (322 mg, 4.93 mmol). The reaction medium was heated at 50° C. for 16 h. At this time, after cooling at RT, the medium was concentrated in vacuo and purified by flash chromatography on 80 g of silica gel (gradient elution DCM/MeOH) to give 550 mg of compound 45 (76%).

Compound 46: (2R,3S,4S,5R,6R)-2-(aminomethyl)-6-methoxytetrahydro-2H-pyran-3,4,5-triol hydrochloride A solution of compound 45 (550 mg, 2.51 mmol) and triphenylphosphine (1.33 g, 5.02 mmol) in 1,4-dioxane (12 mL) and MeOH (3 mL) was stirred at RT for 30 min. At this time, water (1.5 mL) was added to the reaction medium and stirring at RT was maintained overnight. The crude medium was concentrated in vacuo, then diluted with DCM (10 mL) and aqueous 1N HCl (5 mL), the aqueous phase was extracted with DCM (2×10 mL). The aqueous phase was concentrated in vacuo, then diluted with MeOH and concentrated in vacuo to afford 560 mg of compound 46 (97%).

Compound 47: (S)-1-tert-butyl 5-(2,5-dioxopyrrolidin-1-yl) 2-((S)-2-((((9H-fluoren-9-yl)methoxy)carbonyl)amino)-3-methylbutanamido)pentanedioate To a solution of compound 40 (2 g, 3.81 mmol) in THF (100 mL) were added successively, under magnetic stirring, DIEA (1.29 mL, 7.62 mmol), DSC (1.95 g, 7.62 mmol) and DMF (20 mL). The reaction medium was stirred at RT under Ar overnight. After concentration in vacuo, the mixture was purified by flash chromatography on 150 g of silica gel (elution DCM/EtOAc) to give 1.67 g of compound 47 (71%).

RMN $^1$H (400 MHz, δ in ppm, DMSO-d6): 0.89 (d, J=6.8 Hz, 3H); 0.91 (d, J=6.8 Hz, 3H); 1.39 (s, 9H); 1.84 to 2.10 (m, 3H); 2.65 to 2.77 (m, 2H); 2.80 (s, 4H); 3.88 (dd, J=7.2 and 8.7 Hz, 1H); 4.18 to 4.31 (m, 4H); 7.32 (m, 2H); 7.41 (m, 3H); 7.73 (d, J=7.6 Hz, 1H); 7.75 (d, J=7.6 Hz, 1H); 7.88 (d, J=7.6 Hz, 2H); 8.31 (broad d, J=7.1 Hz, 1H). LCMS (A): ES m/z=566; m/z=622 [M+H]⁺; m/z=666 [M–H+HCO₂H]⁻; $t_R$=1.49 min.

Compound 48: (S)-tert-butyl 2-((S)-2-(((((9H-fluoren-9-yl)methoxy)carbonyl)amino)-3-methylbutanamido)-5-oxo-5-((((2R,3S,4S,5R,6R)-3,4,5-trihydroxy-6-methoxytetrahydro-2H-pyran-2-yl)methyl)amino)pentanoate To a solution of compound 47 (500 mg, 804 µmol) in DMF (10 mL) were added, under magnetic stirring, compound 46 (185 mg, 805 µmol) and DIEA (165 µL, 978 µmol). The reaction medium was stirred at RT for 4 h. At this time, 37 mg of compound 46 and 35 µL of DIEA were added to the reaction medium, stirring was maintained for 1 h. Then, the medium was concentrated in vacuo and purified by flash chromatography on 50 g of silica gel (gradient elution DCM/MeOH) to give 480 mg of compound 48 (85%).

RMN $^1$H (400 MHz, δ in ppm, DMSO-d6): 0.87 (d, J=6.7 Hz, 3H); 0.89 (d, J=6.7 Hz, 3H); 1.38 (s, 9H); 1.70 to 2.04 (m. 3H); 2.19 (t, J=7.9 Hz, 2H); 2.86 to 2.98 (m, 2H); 3.01 to 3.16 (m, 3H); 3.35 (s, 3H); 3.52 (m, 1H); 3.92 (dd, J=7.2 and 8.4 Hz, 1H); 3.99 (d, J=7.6 Hz, 1H); 4.09 (m, 1H); 4.16 to 4.36 (m, 3H); 4.95 (broad d, J=4.6 Hz, 1H); 4.99 (d, J=5.1 Hz, 1H); 5.03 (d, J=4.9 Hz, 1H); 7.27 to 7.37 (m, 3H); 7.41 (t, J=7.6 Hz, 2H); 7.75 (split d, J=7.0 Hz, 2H); 7.85 (broad m, 1H); 7.89 (d, J=7.6 Hz, 2H); 8.23 (broad d, J=7.1 Hz, 1H). LCMS (A): ES m/z=700 [M+H]$^+$; m/z=744 [M−H+HCO$_2$H]$^−$; $t_R$=1.22 min.

Compound 49: (S)-2-((S)-2-(((((9H-fluoren-9-yl)methoxy)carbonyl)amino)-3-methylbutanamido)-5-oxo-5-((((2R,3S,4S,5R,6R)-3,4,5-trihydroxy-6-methoxytetrahydro-2H-pyran-2-yl)methyl)amino)pentanoic Acid To compound 48 (480 mg, 686 µmol), under magnetic stirring, was added a 4M solution of HCl in 1,4-dioxane (30 mL). The reaction medium was stirred at RT for 4 h. At this time, the medium was concentrated in vacuo and purified by flash chromatography on 30 g of silica gel (elution DCM/MeOH/H$_2$O) to give 260 mg of compound 49 (59%).

RMN $^1$H (400 MHz, δ in ppm, DMSO-d6): 0.83 (d, J=6.6 Hz, 3H); 0.85 (d, J=6.6 Hz, 3H); 1.69 to 1.90 (m, 2H); 2.01 to 2.15 (m, 3H); 2.86 to 2.97 (m, 2H); 2.99 to 3.16 (m, 3H); 3.35 (s, 3H); 3.51 (m, 1H); 3.82 (m, 2H); 3.99 (d, J=7.8 Hz, 1H); 4.20 to 4.33 (m, 3H); 4.95 (broad d, J=3.7 Hz, 1H); 5.03 (d, J=4.9 Hz, 1H); 5.06 (broad d, J=4.6 Hz, 1H); 7.33 (m, 2H); 7.40 (t, J=7.6 Hz, 2H); 7.52 (broad d, J=6.4 Hz, 1H); 7.61 (broad d, J=9.3 Hz, 1H); 7.73 (d, J=7.6 Hz, 1H); 7.76 (d, J=7.6 Hz, 1H); 7.89 (d, J=7.6 Hz, 2H); 8.10 (broad m, 1H). LCMS (A): ES m/z=642 [M−H]$^−$; m/z=644 [M+H]$^+$; $t_R$=1.01 min.

Compound 50: (S)-2-((S)-2-amino-3-methylbutanamido)-N1-(4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)-N5-(((2R,3S,4S,5R,6R)-3,4,5-trihydroxy-6-methoxytetrahydro-2H-pyran-2-yl)methyl)pentanediamide To a solution of (E)-(3S,10R,16S)-16-{(S)-1-[(2R,3R)-3-(4-aminomethyl-phenyl)-oxiranyl]-ethyl}-10-(3-chloro-4-methoxy-benzyl)-3-isobutyl-6,6-dim ethyl-1,4-dioxa-8,11-diaza-cyclohexadec-13-ene-2,5,9,12-tetraone (the synthesis of which was described in WO2011001052, compound 77, 110 mg, 157 µmol) in DMF (6 mL) were added, under magnetic stirring, compound 49 (122 mg, 189 µmol), HOBt (34 mg, 252 µmol) and EDC (43 µL, 236 µmol). The reaction medium was stirred at RT overnight. Then, 25 mg of compound 49 and 25 µL of EDC were added to the medium, stirring was maintained for 1 h. At this time, piperidine (160 µL, 1.58 mmol) was added to the medium. After 2 h, the medium was concentrated in vacuo and purified by flash chromatography on 20 g of silica gel (gradient elution DCM/MeOH) to give 78 mg of compound 50 (45%).

RMN $^1$H (500 MHz, δ in ppm, DMSO-d6): 0.76 (d, J=6.9 Hz, 3H); 0.79 (d, J=6.3 Hz, 6H); 0.87 (d, J=6.9 Hz, 3H); 1.00 (s, 3H); 1.04 (d, J=6.6 Hz, 3H); 1.12 (s, 3H); 1.30 (m, 1H); 1.50 to 1.98 (m, 8H); 2.12 (m, 2H); 2.26 (m, 1H); 2.68 (m, 2H); 2.86 to 3.14 (m, 9H); 3.32 (partially masked m, 1H); 3.38 (s, 3H); 3.52 (m, 1H); 3.81 (s, 3H); 3.87 (s, 1H); 4.01 (d, J=7.4 Hz, 1H); 4.20 to 4.36 (m, 4H); 4.90 (m, 1H); 4.98 (broad d, J=3.6 Hz, 1H); 5.02 (d, J=4.9 Hz, 1H); 5.06 (d, J=4.7 Hz, 1H); 5.10 (m, 1H); 5.79 (d, J=15.6 Hz, 1H); 6.47 (m, 1H); 7.05 (d, J=8.5 Hz, 1H); 7.17 (broad d, J=8.5 Hz, 1H); 7.21 to 7.26 (m, 5H); 7.29 (broad s, 1H); 7.90 (m, 1H); 8.08 (m large, 1H); 8.37 (d, J=8.0 Hz, 1H); 8.48 (m, 1H). LCMS (A): ES m/z=551 [M+2H]$^{2+}$; m/z=1099 [M−H]$^−$; m/z=1101 [M+H]$^+$; m/z=1145 [M−H+HCO$_2$H]$^−$; $t_R$=0.9 min.

Example 17: 5-(((S)-1-(((S)-1-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)amino)-1,5-dioxo-5-((((2R,3S,4S,5R,6R)-3,4,5-trihydroxy-6-methoxytetrahydro-2H-pyran-2-yl)methyl)amino)pentan-2-yl)amino)-3-methyl-1-oxobutan-2-yl)amino)-5-oxopentanoic Acid To a solution of compound 50 (77 mg, 69.9 µmol) in DMF (4 mL) was added, under magnetic stirring, glutaric anhydride (14 mg, 125.8 µmol). The reaction medium was stirred at RT for 2 h. Then, the reaction medium was concentrated in vacuo and purified by flash chromatography on 10 g of silica gel (gradient elution DCM/MeOH) to give 54 mg of example 17 (64%).

RMN $^1$H (500 MHz, δ in ppm, DMSO-d6): 0.80 (d, J=6.0 Hz, 6H); 0.86 (d, J=6.6 Hz, 3H); 0.88 (d, J=6.6 Hz, 3H); 0.99 (s, 3H); 1.03 (d, J=6.6 Hz, 3H); 1.12 (s, 3H); 1.34 (m, 1H); 1.53 to 1.85 (m, 6H); 1.90 to 2.33 (m, 9H); 2.65 to 2.76 (m, 2H); 2.87 to 3.14 (m, 8H); 3.32 (partially masked m, 1H); 3.35 (s, 3H); 3.53 (m, 1H); 3.81 (s, 3H); 3.87 (d, J=1.9 Hz, 1H); 4.00 (d, J=7.9 Hz, 1H); 4.03 to 4.26 (m, 4H); 4.33 (m, 1H); 4.93 (m, 1H); 5.02 (broad m, 3H); 5.10 (m, 1H); 5.80 (d, J=15.3 Hz, 1H); 6.46 (ddd, J=3.5, 11.0 and 15.3 Hz, 1H); 7.05 (d, J=8.5 Hz, 1H); 7.18 (dd, J=2.2 and 8.5 Hz, 1H); 7.22 (d, J=8.2 Hz, 2H); 7.26 (d, J=8.2 Hz, 2H); 7.30 (m, 2H); 7.98 to 8.65 (broad m, 5H). LCMS (A): ES m/z=608 [M+2H]$^{2+}$; m/z=1213 [M−H]$^−$; m/z=1215 [M+H]$^+$; $t_R$=1.15 min.

Example 18: 2,5-dioxopyrrolidin-1-yl 5-(((S)-1-(((S)-1-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)amino)-1,5-dioxo-5-((((2R,3S,4S,5R,6R)-3,4,5-trihydroxy-6-methoxytetrahydro-2H-pyran-2-yl)methyl)amino)pentan-2-yl)amino)-3-methyl-1-oxobutan-2-yl)amino)-5-oxopentanoate Example 17 (45 mg, 37 µmol) was diluted in toluene and concentrated in vacuo. Then, to a solution of example 17 in THF (5 mL), DCM (2 mL) and DMF (1 mL) were added, under magnetic stirring, DSC (11.4 mg, 44.4 µmol) and DIEA (19 µL, 112.6 µmol). The reaction medium was stirred at RT under Ar for 3 h. Then, DMF and DSC were added to the medium until completion of the reaction. After 3 h, the medium was diluted with water (5 mL), and extracted with MeTHF (3×10 mL). The combined organic phases were dried over $MgSO_4$, filtered and concentrated in vacuo. The mixture was purified by flash chromatography on 4 g of silica gel (gradient elution DCM/iPrOH) to give 21 mg of example 18 (43%).

RMN $^1$H (500 MHz, δ in ppm, DMSO-d6): 0.78 (d, J=6.0 Hz, 6H); 0.83 (d, J=6.9 Hz, 3H); 0.85 (d, J=6.9 Hz, 3H); 1.00 (s, 3H); 1.04 (d, J=6.3 Hz, 3H); 1.12 (s, 3H); 1.30 (m, 1H); 1.52 to 1.63 (m, 2H); 1.75 to 2.02 (m, 6H); 2.09 to 2.34 (m, 5H); 2.68 (m, 4H); 2.81 (s, 4H); 2.88 to 3.18 (m, 7H); 3.32 (partially masked m, 1H); 3.38 (s, 3H); 3.51 (m, 1H); 3.81 (s, 3H); 3.88 (s, 1H); 4.01 (d, J=7.7 Hz, 1H); 4.16 (dd, J=7.1 and 7.7 Hz, 1H); 4.19 to 4.35 (m, 5H); 4.90 (m, 1H); 4.97 (d, J=4.1 Hz, 1H); 5.01 (d, J=4.9 Hz, 1H); 5.06 (d, J=4.9 Hz, 1H); 5.10 (m, 1H); 5.79 (d, J=15.3 Hz, 1H); 6.47 (m, 1H); 7.05 (d, J=8.5 Hz, 1H); 7.17 (d large, J=8.5 Hz, 1H); 7.20 to 7.26 (m, 5H); 7.28 (broad s, 1H); 7.86 (broad t, J=5.6 Hz, 1H); 7.91 (d, J=7.9 Hz, 1H); 8.08 (d, J=7.4 Hz, 1H); 8.33 (t, J=5.8 Hz, 1H); 8.38 (d, J=8.2 Hz, 1H). LCMS (A): ES m/z=1310 [M−H]$^-$; m/z=1356 [M−H+HCO$_2$H]$^-$; m/z=1312 [M+H]$^+$; m/z=656.5 [M+2H]$^{2+}$; $t_R$=1.2 min.

Example 19: hu2H11_R35-74-Ex18

The general method described previously was used for the preparation of example 19. 29.02 mg of hu2H11_R35-74 were reacted with 116.6 µL of a 10 mM solution of example 18 in DMA (6 eq.) for 2 h 30. After purification on Superdex 200 pg in buffer B pH 6.5+10% NMP, concentration on Amicon Ultra-15, dilution in buffer B pH 6.5 to a final concentration of NMP at 5% and filtration on 0.22 µm PVDF filter, 23.1 mg of example 19 were obtained as a colorless limpid solution at a concentration of 2.2 mg/mL with a DAR of 2.8 (HRMS), a monomeric purity of 99.9% and a global yield of 78%. Free-drug level was above the threshold of 1%: the ADC was concentrated on Amicon Ultra-15, purified on Sephadex G25 in buffer B pH 6.5+5% NMP and filtrated on 0.22 µm PVDF filter to provide 17.25 mg of example 19 as a colorless limpid solution at a concentration of 1.50 mg/mL with a DAR of 2.55 (HRMS), a monomeric purity of 99.7% and a global yield of 59%.

SEC-HRMS: m/z=149405 (naked mAb); m/z=150602 (D1); m/z=151800 (D2); m/z=152997 (D3); m/z=154196 (D4); m/z=155393 (D5); m/z=156589 (D6); m/z=157791 (D7).

Synthesis of Example 20:
glutaryl-Val-GlucamineGln-C52 Benzylic Amine

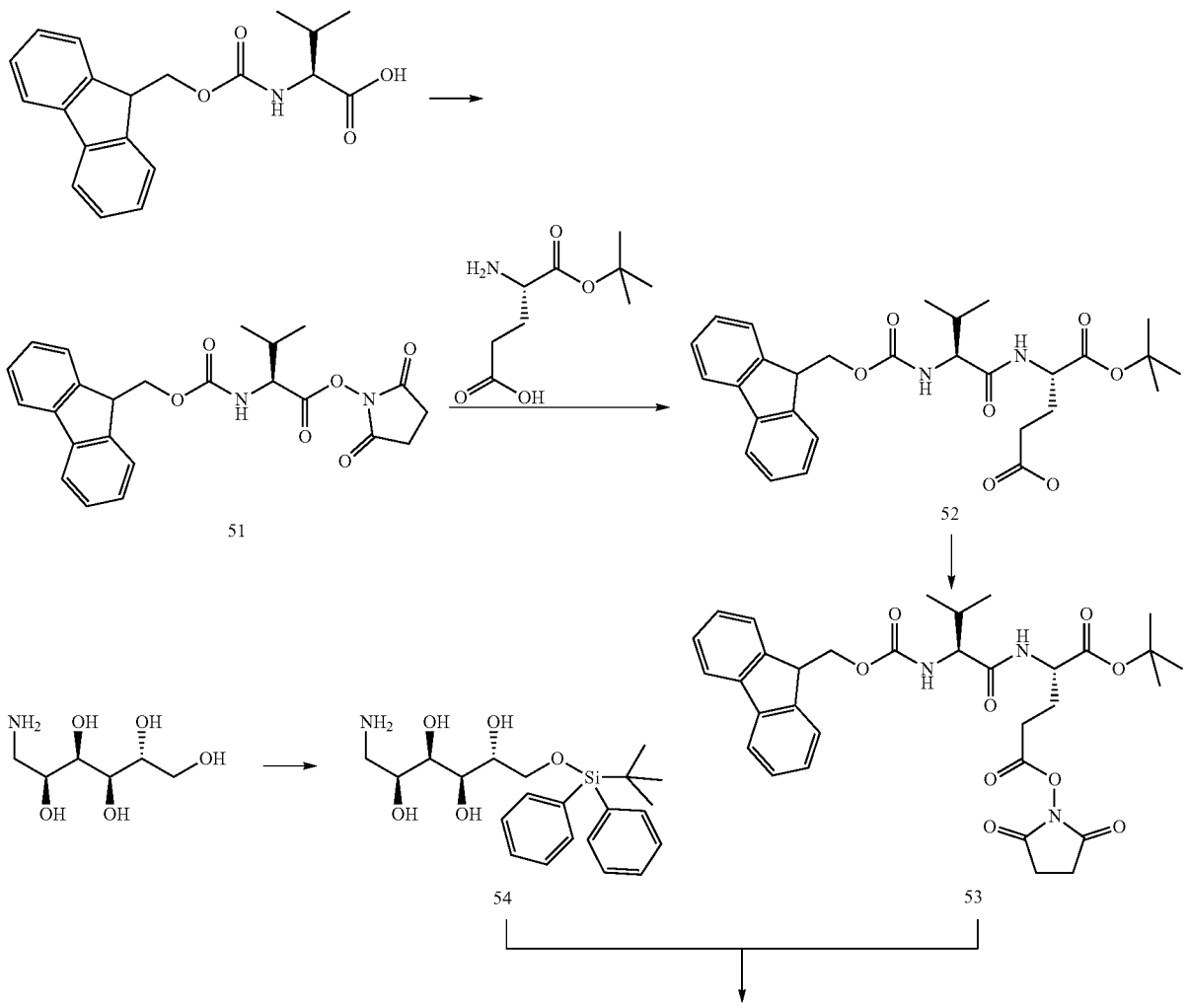

253  254
-continued
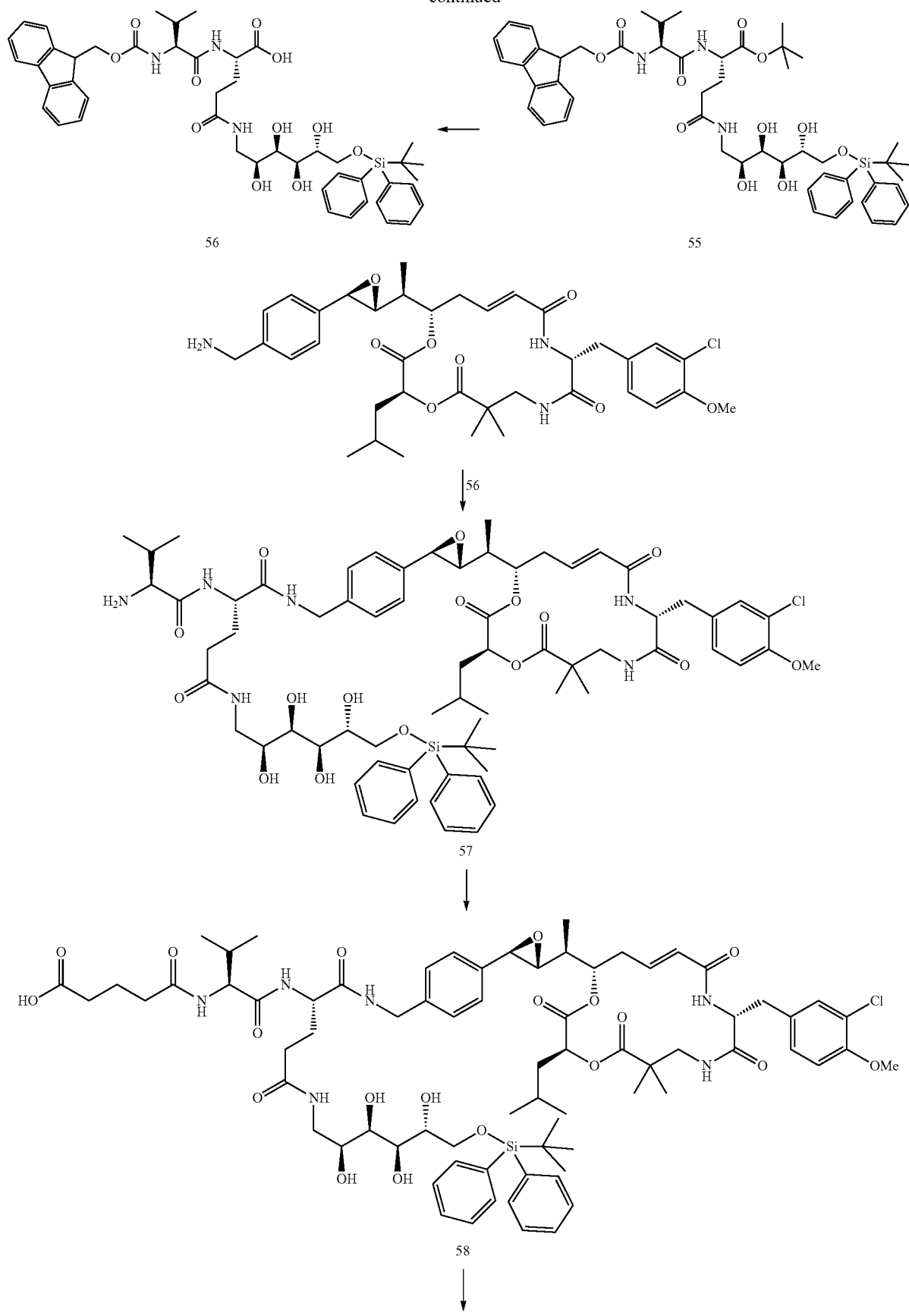

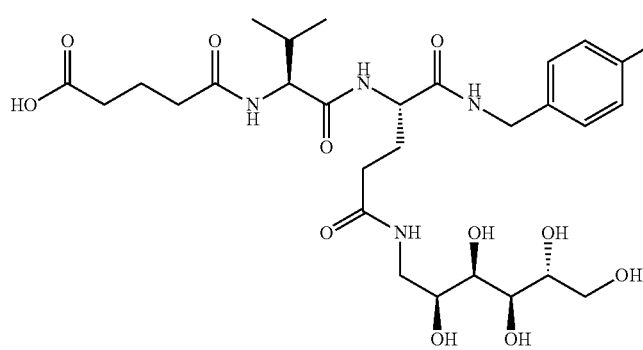
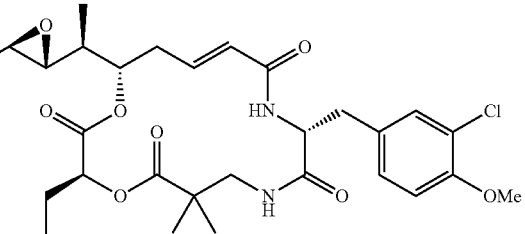

example 20

Compound 51: (S)-2,5-dioxopyrrolidin-1-yl 2-((((9H-fluoren-9-yl)methoxy)carbonyl)amino)-3-methylbutanoate To a solution of Fmoc-Val-OH (CAS number [68858-20-8], 5 g, 14.44 mmol) in THF (40 mL) were added NHS (1.71 g, 14.44 mmol) and DCC (2.98 g, 14.44 mmol). The reaction medium was stirred for 5 h at RT, then 0.2 equivalents of NHS and DCC were added and stirring was carried on for 4 h at RT. The medium was filtered, the solid washed twice with THF (2×25 mL) and the filtrate concentrated in vacuo to give 6.5 g of compound 51 as a white meringue (quant.).

RMN $^1$H (400 MHz, δ in ppm, DMSO-d6): 1.03 (d, J=6.9 Hz, 6H); 2.20 (m, 1H); 2.81 (s, 4H); 4.18 to 4.39 (m, 4H); 7.32 (m, 2H); 7.42 (m, 2H); 7.74 (m, 2H); 7.90 (d, J=7.6 Hz, 2H); 8.12 (d, J=8.5 Hz, 1H).

Compound 52: (S)-4-((S)-2-((((9H-fluoren-9-yl)methoxy)carbonyl)amino)-3-methylbutanamido)-5-(tert-butoxy)-5-oxopentanoic Acid To a solution of H-Glu-OtBu (CAS number [45120-30-7], 3.14 g, 15.16 mmol) and sodium bicarbonate (1.40 g, 16.46 mmol) in H$_2$O (60 mL) was added a solution of compound 51 (6.3 g, 14.43 mmol) in THF (240 mL). The reaction medium was stirred for 16 h at RT and concentrated in vacuo. The crude product was diluted in H$_2$O (700 mL) forming a gel that was stirred for 15 min then extracted twice with Et$_2$O (200 mL). The aqueous suspension was acidified to pH 3 with 5 N HCl and extracted with DCM (4×200 mL). The combined organic phases were dried over MgSO$_4$, filtered and concentrated in vacuo to give 7.98 g of compound 52 as a white meringue (quant.).

RMN $^1$H (400 MHz, δ in ppm, DMSO-d6): 0.87 (d, J=6.9 Hz, 3H); 0.90 (d, J=6.9 Hz, 3H); 1.38 (s, 9H); 1.77 (m, 1H); 1.91 (m, 1H); 1.98 (m, 1H); 2.28 (m, 2H); 3.90 (dd, J=7.1 and 9.1 Hz, 1H); 4.10 to 4.37 (m, 4H); 7.32 (m, 2H); 7.38 (d, J=9.1 Hz, 1H); 7.41 (m, 2H); 7.73 (m, 2H); 7.89 (d, J=7.6 Hz, 2H); 8.20 (d, J=7.5 Hz, 1H); 12.21 (broad m, 1H).

Compound 53: (S)-1-tert-butyl 5-(2,5-dioxopyrrolidin-1-yl) 2-((S)-2-((((9H-fluoren-9-yl)methoxy)carbonyl)amino)-3-methylbutanamido)pentanedioate To a solution of compound 52 (500 mg, 953.1 µmol) in THF (30 mL) were added DIEA (320 µL, 1.9 mmol), DSC (498.3 mg, 1.91 mmol) and DMF (6 mL). The reaction medium was stirred at RT overnight then 30 mg of DSC were added to the medium and stirring was carried on 24 h. The reaction medium was concentrated in vacuo, co-evaporated twice with toluene and purified by flash chromatography on 50 g of silica gel (gradient elution DCM/iPrOH) to give 506 mg of compound 53 as a white oil (85%).

RMN $^1$H (400 MHz, δ in ppm, DMSO-d6): 0.89 (d, J=6.9 Hz, 3H); 0.91 (d, J=6.9 Hz, 3H); 1.39 (s, 9H); 1.75 to 2.11 (m, 3H); 2.73 (m, 2H); 2.80 (s, 4H); 3.89 (dd, J=7.3 and 9.1 Hz, 1H); 4.20 to 4.38 (m, 4H); 7.32 (m, 2H); 7.42 (m, 3H); 7.75 (m, 2H); 7.80 (m, 2H); 8.31 (d, J=7.5 Hz, 1H).

Compound 54: (2S,3R,4R,5R)-1-amino-6-((tert-butyldiphenylsilyl)oxy)hexane-2,3,4,5-tetraol A suspension of D-glucamine (CAS number [488-43-7], 200 mg, 1.10 mmol) in DMF (2 mL) was cooled at 0° C. then were added imidazole (82.0 mg, 1.19 mmol) and tert-butylchlorodiphenylsilane (334.4 mg, 1.19 mmol). The reaction medium was stirred for 1 h at 0° C., quenched with H$_2$O (20 mL) and stirring carried on 10 min. The medium was extracted with EtOAc (3×50 mL), the combined organic phases were dried over MgSO$_4$, filtered, concentrated in vacuo, co-evaporated twice with toluene and purified by reverse phase flash chromatography on 31 g of C18-modified silica gel (gradient elution H$_2$O/MeCN) to give 218 mg of compound 54 as a white foam (47%).

RMN $^1$H (400 MHz, δ in ppm, DMSO-d6): 1.00 (s, 9H); 2.62 (dd, J=6.3 and 12.7 Hz, 1H); 2.74 (dd, J=4.5 and 12.7 Hz, 1H); 3.40 (partially masked m, 1H); 3.49 (m, 1H); 3.55 to 3.72 (m, 3H); 3.88 (m, 1H); 4.48 (broad m, 4H); 7.42 (m, 6H); 7.69 (m, 4H).

Compound 55: (S)-tert-butyl 2-((S)-2-((((9H-fluoren-9-yl)methoxy)carbonyl)amino)-3-methylbutanamido)-5-(((2S,3R,4R,5R)-6-((tert-butyldiphenylsilyl)oxy)-2,3,4,5-tetrahydroxyhexyl) amino)-5-oxopentanoate To a solution of compound 53 (300 mg, 482.6 µmol) in DMF (2 mL) was added a solution of compound 54 (214.6 mg, 511.5 µmol) in DMF (3 mL). The reaction medium was stirred for 1 h at RT, concentrated in vacuo, co-evaporated with toluene (3×) and purified by flash chromatography on 25 g of silica gel (gradient elution DCM/MeOH/H$_2$O) to give 270 mg of compound 55 as a white foam (60%).

RMN $^1$H (400 MHz, δ in ppm, DMSO-d6): 0.87 (d, J=6.9 Hz, 3H); 0.90 (d, J=6.9 Hz, 3H); 0.99 (s, 9H); 1.38 (s, 9H); 1.80 (m, 1H); 1.90 (m, 1H); 1.98 (m, 1H); 2.17 (t, J=7.7 Hz, 2H); 3.03 (m, 1H); 3.26 (m, 1H); 3.49 (m, 1H); 3.52 to 3.60 (m, 4H); 3.83 (m, 1H); 3.92 (dd, J=7.3 and 9.2 Hz, 1H); 4.08 (m, 1H); 4.18 to 4.31 (m, 4H); 4.33 (d, J=6.4 Hz, 1H); 4.63 (d, J=5.8 Hz, 1H); 4.78 (d, J=4.7 Hz, 1H); 7.31 (m, 2H); 7.36

(d, J=9.2 Hz, 1H); 7.41 (m, 8H); 7.67 (m, 4H); 7.69 to 7.76 (m, 3H); 7.89 (m, 2H); 8.23 (d, J=7.5 Hz, 1H).

Compound 56: (S)-2-((S)-2-((((9H-fluoren-9-yl)methoxy)carbonyl)amino)-3-methylbutanamido)-5-(((2S,3R,4R,5R)-6-((tert-butyldiphenylsilyl)oxy)-2,3,4,5-tetrahydroxyhexyl)amino)-5-oxopentanoic Acid Compound 55 was diluted in DCM forming a gel that was cooled at 0° C. before slowly adding, at 0° C., a 1:1 mixture of DCM/TFA. The reaction medium was stirred for 30 min at 0° C. then 5 h at RT, concentrated in vacuo and co-evaporated with toluene (3×) to give a white solid that was grinded up in iPr$_2$O, filtered, washed twice with Et$_2$O (5 mL), dried and finally purified by flash chromatography on 15 g of silica gel (gradient elution DCM/MeOH/H$_2$O) to give 149 mg of compound 56 as a white solid (59%).

RMN $^1$H (400 MHz, δ in ppm, DMSO-d6): 0.84 (d, J=6.8 Hz, 3H); 0.86 (d, J=6.8 Hz, 3H); 0.99 (s, 9H); 1.82 (m, 1H); 1.90 (m, 1H); 2.03 to 2.14 (m, 3H); 3.00 (m, 1H); 3.25 (m, 1H); 3.48 (m, 1H); 3.65 (m, 4H); 3.82 to 3.92 (m, 3H); 4.20 to 4.37 (m, 3H); 4.40 (d, J=6.0 Hz, 1H); 4.45 (d, J=6.0 Hz, 1H); 4.80 (m, 1H); 5.12 (m, 1H); 7.32 (m, 2H); 7.41 (m, 8H); 7.55 (m, 2H); 7.65 to 7.82 (m, 7H); 7.89 (d, J=8.0 Hz, 2H). LCMS (A): m/z=868 [M−H]$^−$; m/z=870 [M+H]$^+$; $t_R$=1.55 min.

Compound 57: (S)-2-((S)-2-amino-3-methylbutanamido)-N5-((2S,3R,4R,5R)-6-((tert-butyldiphenylsilyl)oxy)-2,3,4,5-tetrahydroxyhexyl)-N1-(4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclo-hexadec-13-en-16-yl)ethyl)oxiran-2-yl)benzyl)-pentanediamide To a solution of compound 56 (67.3 mg, 77.3 μmol) and (3S,10R,16S,E)-16-((S)-1-((2R,3R)-3-(4-(aminomethyl)phenyl)oxiran-2-yl)ethyl)-10-(3-chloro-4-methoxybenzyl)-3-isobutyl-6,6-dimethyl-1,4-dioxa-8,11-diazacyclohexadec-13-ene-2,5,9,12-tetraone (the synthesis of which was described in WO2011001052, compound 77, 45 mg, 64.5 μmol) in DMF and DCM (10 mL) were added HOBt (11.5 mg, 85.1 μmol) and EDC (11.4 mg, 70.9 μmol). The reaction medium was stirred for 3 h at RT then quenched with H$_2$O (15 mL) and stirring was carried on 10 min. The aqueous phase was extracted with DCM (3×20 mL), the combined organic phases were dried over MgSO$_4$, filtered, concentrated in vacuo and purified by flash chromatography on 5 g of silica gel (gradient elution DCM/MeOH) to give 64 mg of Fmoc-protected dipeptide-cryptophycin intermediate as a white solid (64%).

RMN $^1$H (500 MHz, δ in ppm, DMSO-d6): 0.76 (d, J=6.8 Hz, 6H); 0.82 (d, J=7.0 Hz, 3H); 0.86 (d, J=7.0 Hz, 3H); 0.99 (s, 12H); 1.04 (d, J=7.1 Hz, 3H); 1.10 (s, 3H); 1.30 (m, 1H); 1.55 (m, 2H); 1.80 (m, 2H); 1.90 (m, 1H); 2.00 (m, 1H); 2.14 (m, 2H); 2.26 (m, 1H); 2.68 (m, 2H); 2.92 to 3.08 (m, 4H); 3.22 to 3.38 (partially masked m, 2H); 3.49 (m, 1H); 3.58 to 3.69 (m, 4H); 3.81 (s, 3H); 3.82 (m, 1H); 3.87 (d, J=2.0 Hz, 1H); 3.91 (m, 1H); 4.18 to 4.38 (m, 9H); 4.68 (m, 1H); 4.82 (m, 1H); 4.90 (dd, J=3.8 and 9.8 Hz, 1H); 5.10 (m, 1H); 5.79 (broad d, J=16.0 Hz, 1H); 6.47 (ddd, J=4.7, 10.5 and 16.0 Hz, 1H); 7.05 (d, J=8.0 Hz, 1H); 7.17 (dd, J=2.5 and 8.0 Hz, 1H); 7.20 to 7.27 (m, 5H); 7.29 (d, J=2.3 Hz, 1H); 7.31 (t, J=7.8 Hz, 2H); 7.34 to 7.48 (m, 7H); 7.65 to 7.79 (m, 9H); 7.90 (d, J=7.8 Hz, 2H); 8.10 (d, J=8.3 Hz, 1H); 8.38 (d, J=8.0 Hz, 1H); 8.41 (t, J=6.5 Hz, 1H). LCMS (A): ES m/z=775 [M+2H]$^{2+}$; m/z=1549 [M+H]$^+$; m/z=1593 [M−H+HCO$_2$H]$^−$; $t_R$=1.78 min.

To a solution of this intermediate (62 mg, 40.0 μmol) in DCM (8 mL) was added piperidine (59.8 μL, 600.0 μmol). The reaction medium was stirred for 4 h at RT, concentrated in vacuo and purified by flash chromatography on 5 g of silica gel (gradient elution DCM/MeOH/H$_2$O) to give 49 mg of compound 57 as a white lacquer (92%).

Compound 58: (6R,7R,8R,9S,15S,18S)-15-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)-6,7,8,9-tetrahydroxy-18-isopropyl-2,2-dimethyl-12,17,20-trioxo-3,3-diphenyl-4-oxa-11,16,19-triaza-3-silatetracosan-24-oic Acid To a solution of compound 57 (23 mg, 17.3 μmol) in DCM (3 mL) was added a solution of glutaric anhydride (2.22 mg, 19.1 μmol) in DCM (2 mL). The reaction medium was stirred for 3 h at RT, partly concentrated in vacuo (down to 2 mL) and purified by flash chromatography on 5 g of silica gel (gradient elution DCM/MeOH/H$_2$O) to give 17 mg of compound 58 as a white lacquer (68%).

RMN $^1$H (500 MHz, δ in ppm, DMSO-d6): 0.80 (split d, J=6.8 Hz, 6H); 0.6 (split d, J=7.0 Hz, 6H); 0.99 (s, 12H); 1.04 (d, J=7.1 Hz, 3H); 1.11 (s, 3H); 1.32 (m, 1H); 1.52 to 1.60 (m, 2H); 1.72 to 2.00 (m, 7H); 2.08 (m, 1H); 2.13 (m, 1H); 2.20 to 2.37 (m, 3H); 2.69 (m, 2H); 2.92 to 3.07 (m, 4H); 3.20 (m, 1H); 3.30 (masked m, 1H); 3.45 (m, 1H); 3.55 to 3.70 (m, 4H); 3.80 (s, 3H); 3.83 (m, 1H); 3.87 (d, J=2.3 Hz, 1H); 4.07 to 5.00 (m, 11H); 5.10 (m, 1H); 5.80 (dd, J=2.0 and 15.8 Hz, 1H); 6.47 (m, 1H); 7.04 (d, J=8.6 Hz, 1H); 7.18 (dd, J=2.4 and 8.6 Hz, 1H); 7.20 to 7.28 (m, 5H); 7.29 (d, J=2.3 Hz, 1H); 7.41 (m, 6H); 7.68 (m, 4H); 8.05 (d, J=7.9 Hz, 1H; 8.23 (t, J=6.5 Hz, 1H); 8.30 to 8.60 (m, 3H). LCMS (A): ES m/z=721 [M+2H]$^{2+}$; m/z=1439 [M−H]$^−$; m/z=1441 [M+H]$^+$; $t_R$=1.52 min.

Example 20: 5-(((S)-1-(((S)-1-((4-((2R,3R)-3-((S)-1-((3S,10R,16S,E)-10-(3-chloro-4-methoxy-benzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)amino)-1,5-dioxo-5-(((2S,3R,4R,5R)-2,3,4,5,6-pentahydroxyhexyl)-amino)pentan-2-yl)amino)-3-methyl-1-oxobutan-2-yl)amino)-5-oxopentanoic Acid A solution of compound 57 (46 mg, 31.9 μmol) in THF (3 mL) was cooled at 0° C. then was added, dropwise at 0° C., a 1 M TBAF solution in THF (35.1 μL, 35.1 μmol). The reaction medium was stirred for 2 h at 0° C., quenched with H$_2$O (100 μL), stirred for 10 min and extracted with DCM (5 mL). The organic phase was dried over MgSO$_4$, filtered and concentrated in vacuo: LCMS analysis showed the presence of residual starting material. The crude product was dissolved in DCM (3 mL), the solution cooled at 0° C. before adding, dropwise at 0° C., a 1 M TBAF solution in THF (35.1 μL, 35.1 μmol). The reaction medium was stirred for 3 h at 0° C., quenched with H$_2$O (100 μL), stirred for 10 min and extracted with DCM (20 mL). The organic phase was dried over MgSO$_4$, filtered, concentrated in vacuo and purified by flash chromatography on 5 g of silica gel (gradient elution DCM/MeOH/H$_2$O to MeOH) then by reverse phase flash chromatography on 3 g of C18-modified silica gel (gradient elution H₂O/MeCN) to give 17 mg of example 20 as a white lacquer (44%).

RMN ¹H (500 MHz, δ in ppm, DMSO-d6): 0.80 (split d, J=6.8 Hz, 6H); 0.6 (split d, J=7.0 Hz, 6H); 0.99 (s, 12H); 1.04 (d, J=7.1 Hz, 3H); 1.11 (s, 3H); 1.32 (m, 1H); 1.52 to 1.60 (m, 2H); 1.72 to 2.00 (m, 7H); 2.08 (m, 1H); 2.13 (m, 1H); 2.20 to 2.37 (m, 3H); 2.69 (m, 2H); 2.92 to 3.07 (m, 4H); 3.20 (m, 1H); 3.30 (masked m, 1H); 3.45 (m, 1H); 3.55 to 3.70 (m, 4H); 3.80 (s, 3H); 3.83 (m, 1H); 3.87 (d, J=2.3 Hz, 1H); 4.07 to 5.00 (m, 11H); 5.10 (m, 1H); 5.80 (dd, J=2.0 and 15.8 Hz, 1H); 6.47 (m, 1H); 7.04 (d, J=8.6 Hz, 1H); 7.18 (dd, J=2.4 and 8.6 Hz, 1H); 7.20 to 7.28 (m, 5H); 7.29 (d, J=2.3 Hz, 1H); 7.41 (m, 6H); 7.68 (m, 4H); 8.05 (d, J=7.9 Hz, 1H); 8.23 (t, J=6.5 Hz, 1H); 8.30 to 8.60 (m, 3H). LCMS (A): ES m/z=602 [M+2H]²⁺; m/z=1201 [M−H]⁻; m/z=1203 [M+H]⁺; t_R=1.1 min.

Synthesis of Examples 21 to 23:
glutaryl-Val-PEG4Lys-C52 Benzylic Amine, NHS Ester of glutaryl-Val-PEG4Lys-C52 Benzylic Amine and Corresponding ADC

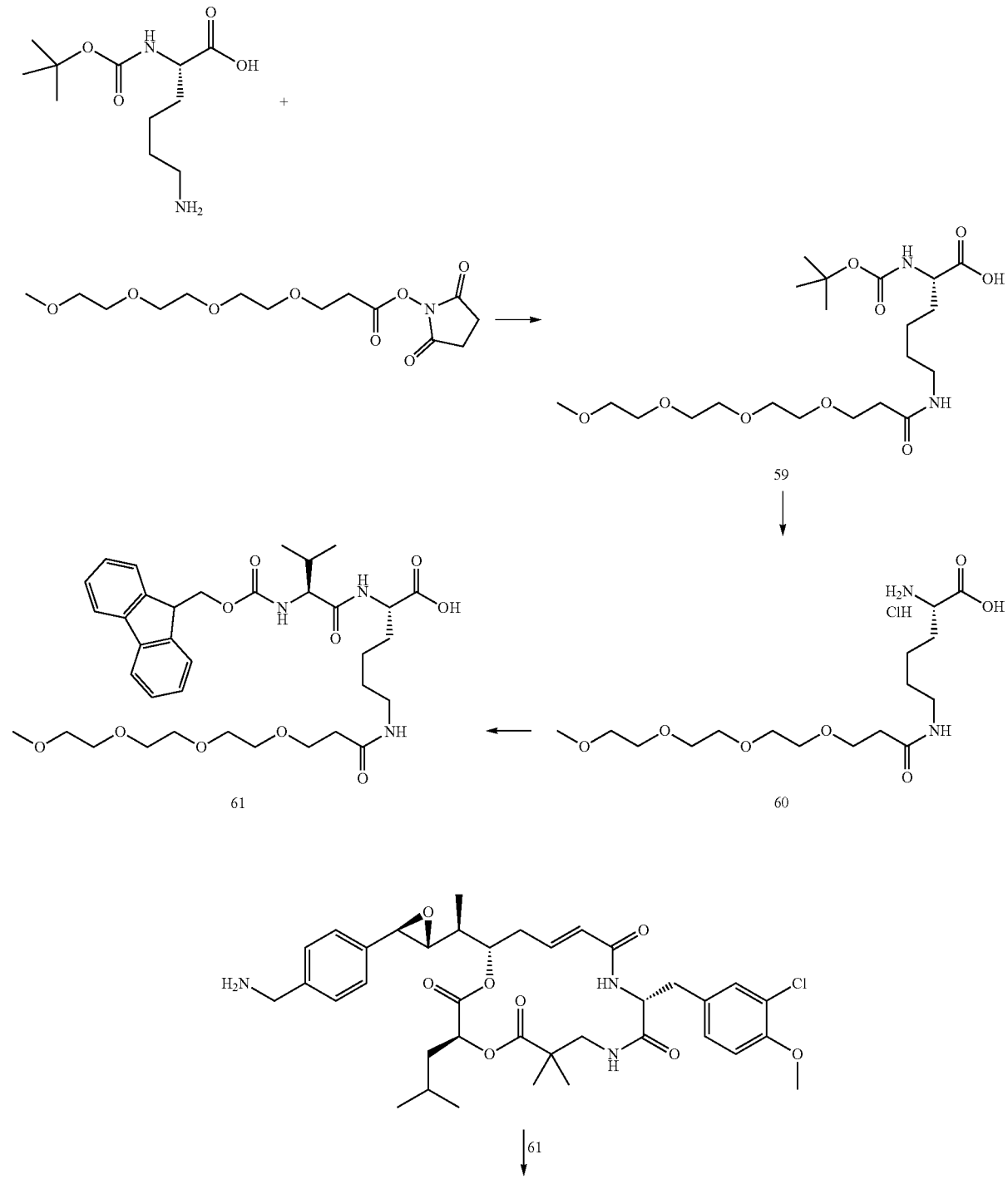

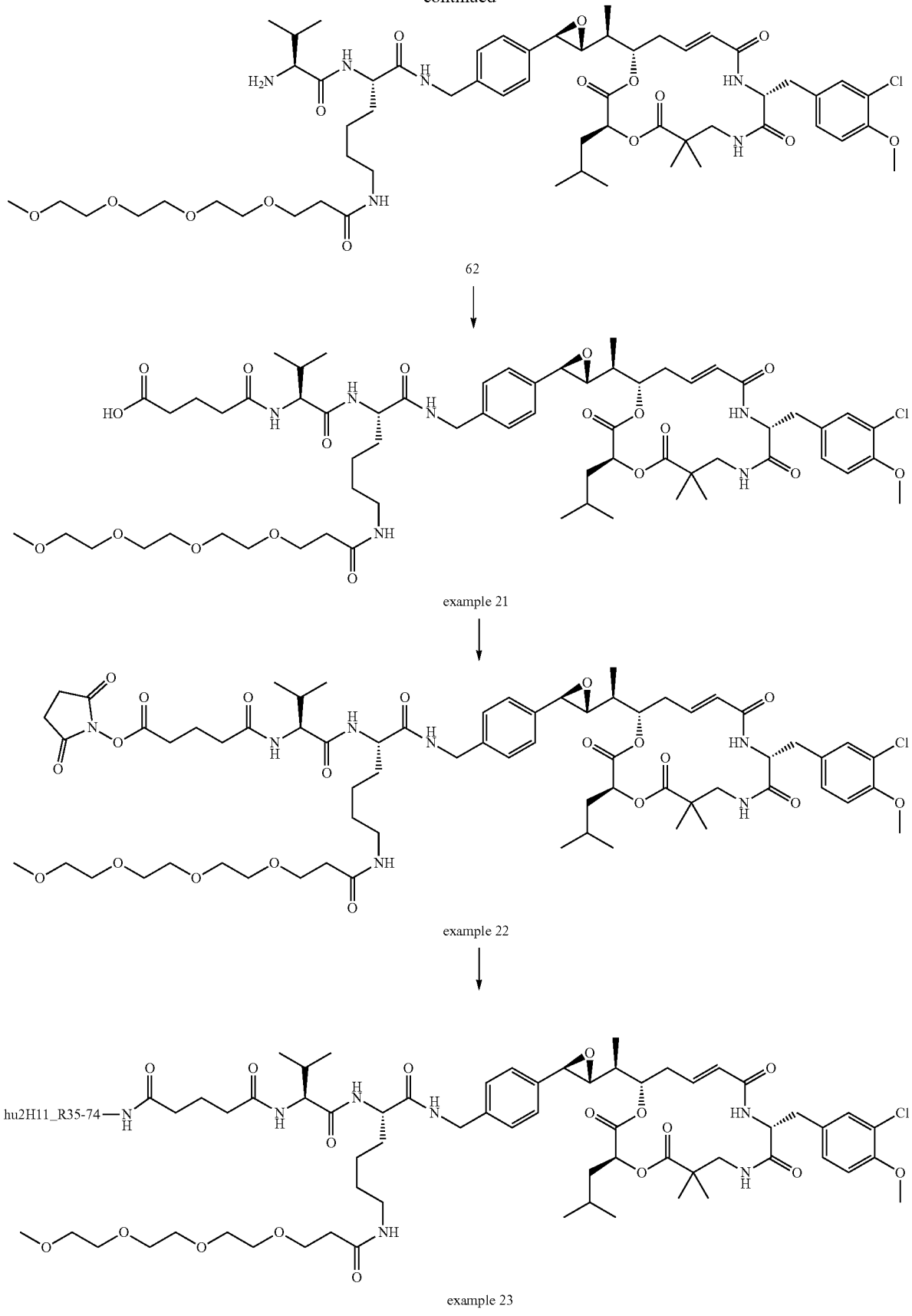

Compound 59: (S)-20-((tert-butoxycarbonyl)amino)-14-oxo-2,5,8,11-tetraoxa-15-azahenicosan-21-oic Acid To a solution of (S)-6-amino-2-((ter-butoxycarbonyl)amino)hexanoic acid (CAS number [13734-28-6], 73.9 mg, 300 µmol) in THF (300 µL) were added, under magnetic stirring, 2,5-dioxopyrrolidin-1-yl 2,5,8,11-tetraoxatetradecan-14-oate (CAS number [622405-78-1], 100 mg, 300 µmol), DIEA (53.3 µL, 300 µmol) and $H_2O$ (100 µL). The reaction medium was stirred at RT overnight then concentrated in vacuo. The crude medium was purified by flash chromatography on 5 g of C18-grafted silica gel (gradient elution $H_2O/CH_3CN$) to give 81 mg of compound 59 (58%). LCMS (B): ES m/z=463 [M−H]$^-$; m/z=465 [M+H]$^+$; $t_R$=0.86 min.

Compound 60: (S)-20-amino-14-oxo-2,5,8,11-tetraoxa-15-azahenicosan-21-oic acid hydrochloride To compound 59 (150.6 mg, 324.2 µmol), under magnetic stirring, was added a 4M solution of HCl in 1,4-dioxane (1 mL). The reaction medium was stirred at RT overnight then concentrated in vacuo. EtOAc was added and the mixture was concentrated in vacuo to give 156 mg of compound 60 (quant.).
LCMS (B): ES m/z=508 [M−H]$^-$; m/z=510 [M+H]$^+$; $t_R$=1.23 min.

Compound 61: (S)-20-((S)-2-((((9H-fluoren-9-yl)methoxy)carbonyl)amino)-3-methylbutanamido)-14-oxo-2,5,8,11-tetraoxa-15-azahenicosan-21-oic Acid To a solution of compound 60 (130 mg, 275 µmol) in water (0.5 mL) was added, under magnetic stirring, $NaHCO_3$ (55.6 mg, 661 µmol), followed by (S)-2,5-dioxopyrrolidin-1-yl 2-((((9H-fluoren-9-yl)methoxy)carbonyl)amino)-3-methylbutanoate (CAS number [130878-68-1], 144.4 mg, 330.8 µmol) in THF (1.5 mL). The reaction medium was stirred at RT overnight. Then, $NaHCO_3$ (30 mg), THF (500 µL), $H_2O$ (200 µL) and (S)-2,5-dioxopyrrolidin-1-yl 2-((((9H-fluoren-9-yl)methoxy)carbonyl)amino)-3-methylbutanoate (28 mg) were added to the reaction medium. After 3 h, the medium was concentrated in vacuo, then diluted with $H_2O$ (20 mL) and ~2-3 mL of aqueous saturated $Na_2CO_3$. The aqueous phase was extracted twice with EtOAc (20 mL). The combined organic phases were washed with brine (20 mL), dried over $MgSO_4$, filtered and concentrated in vacuo. The mixture was purified by flash chromatography on 15 g of silica gel (elution 85:1:0.5 v/v EtOAc/MeOH/$H_2O$). After concentration, the crude product was diluted with toluene and concentrated in vacuo to give 75.6 mg of compound 61 (40%).
RMN $^1$H (400 MHz, δ in ppm, DMSO-d6): 0.85 (d, J=7.1 Hz, 3H); 0.87 (d, J=7.1 Hz, 3H); 1.21 to 1.40 (m, 4H); 1.50 to 1.73 (m, 2H); 2.01 (m, 1H); 2.27 (t, J=6.6 Hz, 2H); 2.98 (m, 2H); 3.23 (s, 3H); 3.41 (m, 2H); 3.43 to 3.52 (m, 10H); 3.57 (t, J=6.6 Hz, 2H); 3.88 (m, 1H); 4.01 (m, 1H); 4.19 to 4.34 (m, 3H); 7.31 (m, 2H); 7.38 to 7.46 (m, 3H); 7.70 to 7.91 (m, 6H); 12.51 (m, 1H). LCMS (A): ES m/z=684 [M−H]$^-$; m/z=686 [M+H]$^+$; $t_R$=1.2 min.

Compound 62: N—((S)-5-((S)-2-amino-3-methylbutanamido)-6-((4-((2R,3R)-3-((S)-1-((3S,10R,16S,E)-10-(3-chloro-4-methoxy-benzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)amino)-6-oxohexyl)-2,5,8,11-tetraoxatetradecan-14-amide To compound 61 (70 mg, 102.1 µmol), under magnetic stirring and Ar, was added a solution of (E)-(3S,10R,16S)-16-{(S)-1-[(2R,3R)-3-(4-aminomethyl-phenyl)-oxiranyl]-ethyl}-10-(3-chloro-4-methoxy-benzyl)-3-isobutyl-6,6-dimethyl-1,4-dioxa-8,11-diaza-cyclohexadec-13-ene-2,5,9,12-tetraone (the synthesis of which was described in WO2011001052, compound 77, 76.2 mg, 109.1 µmol) in THF (3 mL), followed by HOBt (17.7 mg, 131 µmol) and EDC (23 µL, 131 µmol). The reaction medium was stirred at RT overnight. Then, piperidine (32.8 µL, 327.4 µmol) was added to the medium, and stirring was maintained for 4 h 30. At this time, the medium was concentrated in vacuo, diluted with DMA and purified by flash chromatography on 15 g of C18-grafted silica gel (gradient elution $H_2O/CH_3CN$) to give 66 mg of compound 62(53%).
LCMS (B): ES m/z=572; m/z=1187 [M−H+$HCO_2H$]$^-$; $t_R$=1.18 min.

Example 21: (20S,23S)-20-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)-23-isopropyl-14,22,25-trioxo-2,5,8,11-tetraoxa-15,21,24-triazanonacosan-29-oic Acid To a solution of compound 62 (66 mg, 57.7 µmol) in DMF (4 mL), under magnetic stirring, was added glutaric anhydride (11.85 mg, 103.8 µmol). The reaction medium was stirred at RT for 2 h. At this time, the medium was concentrated in vacuo and purified by flash chromatography on 10 g of silica gel (gradient elution DCM/MeOH) to give 48.6 mg of example 21 (80%).
RMN $^1$H (500 MHz, δ in ppm, DMSO-d6): 0.81 (m, 6H); 0.85 (d, J=7.5 Hz, 3H); 0.87 (d, J=7.5 Hz, 3H); 0.98 (s, 3H); 1.04 (d, J=7.1 Hz, 3H); 1.10 (s, 3H); 1.16 to 1.44 (m, 5H); 1.55 to 1.79 (m, 7H); 1.90 to 2.10 (m, 3H); 2.14 to 2.29 (m, 3H); 2.31 (t, J=6.7 Hz, 2H); 2.66 to 2.78 (m, 2H); 2.85 to 2.99 (m, 4H); 3.05 (m, 1H); 3.23 (s, 3H); 3.32 (partially masked m, 1H); 3.42 (m, 2H); 3.44 to 3.51 (m, 10H); 3.57 (m, 2H); 3.81 (s, 3H); 3.88 (d, J=1.6 Hz, 1H); 4.04 to 4.25 (m, 4H); 4.35 (m, 1H); 4.94 (m, 1H); 5.10 (m, 1H); 5.80 (d, J=15.0 Hz, 1H); 6.45 (ddd, J=4.0, 11.2 and 15.0 Hz, 1H); 7.04 (d, J=8.6 Hz, 1H); 7.19 (dd, J=1.7 and 8.6 Hz, 1H); 7.22 (d, J=8.4 Hz, 2H); 7.28 (d, J=8.4 Hz, 2H); 7.30 (d, J=1.7 Hz, 1H); 7.32 (broad m, 1H); 7.75 to 9.42 (broad m, 5H); 12.06 (broad m, 1H). LCMS (A): ES m/z=629 [M+2H]$^{2+}$; m/z=1255 [M−H]$^-$; m/z=1257 [M+H]$^+$; $t_R$=1.26 min.

Example 22: (20S,23S)-2,5-dioxopyrrolidin-1-yl 20-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)-23-isopropyl-14,22,25-trioxo-2,5,8,11-tetraoxa-15,21,24-triazanonacosan-29-oate Toluene (10 mL) was added to example 21 (46 mg, 36.6 µmol) and concentrated in vacuo, followed by dilution with THF (5 mL), DCM (2 mL) and DMF (200 µL). Then, DSC (11.5 mg, 43.9 µmol) was added, followed by DIEA (18.5 µL, 109.7 µmol). The reaction medium was stirred at RT for 4 h. At this time, MeTHF (7 mL) and $H_2O$ (3 mL) were added, the aqueous phase was extracted twice with MeTHF (5 mL). The combined organic phases were washed with $H_2O$ (3 mL), dried over $MgSO_4$, filtered and concentrated in vacuo. The crude medium was purified by flash chromatography on 4 g of silica gel (gradient elution DCM/iPrOH) to give 33.3 mg of example 22 (67%).

RMN ¹H (500 MHz, δ in ppm, DMSO-d6): 0.78 (d, J=6.6 Hz, 6H); 0.83 (d, J=7.1 Hz, 3H); 0.84 (d, J=7.1 Hz, 3H); 1.00 (s, 3H); 1.04 (d, J=6.9 Hz, 3H); 1.12 (s, 3H); 1.20 to 1.43 (m, 5H); 1.50 to 1.69 (m, 4H); 1.76 to 1.87 (m, 3H); 1.98 (m, 1H); 2.21 to 2.35 (m, 5H); 2.62 to 2.73 (m, 4H); 2.81 (s, 4H); 2.94 to 3.04 (m, 5H); 3.23 (s, 3H); 3.32 (partially masked m, 1H); 3.42 (m, 2H); 3.44 to 3.51 (m, 10H); 3.58 (t, J=6.4 Hz, 2H); 3.81 (s, 3H); 3.87 (d, J=1.1 Hz, 1H); 4.17 (dd, J=7.3 and 7.8 Hz, 1H); 4.21 to 4.31 (m, 4H); 4.90 (m, 1H); 5.10 (m, 1H); 5.79 (d, J=15.1 Hz, 1H); 6.47 (ddd, J=3.5, 11.5 and 15.1 Hz, 1H); 7.05 (d, J=8.5 Hz, 1H); 7.17 (dd, J=1.6 and 8.5 Hz, 1H); 7.20 to 7.25 (m, 5H); 7.28 (d, J=1.6 Hz, 1H); 7.79 (t, J=5.7 Hz, 1H); 7.91 (d, J=8.5 Hz, 1H); 7.95 (d, J=8.3 Hz, 1H); 8.37 (m, 2H). LCMS (C): ES m/z=677.5 [M+2H]$^{2+}$; m/z=1354 [M+H]$^+$; m/z=1399 [M−H+HCO$_2$H]$^-$; $t_R$=4.41 min.

Example 23: hu2H11_R35-74-Ex22

The general method described previously was used for the preparation of example 23. 44.64 mg of hu2H11_R35-74 were reacted with 209.2 μL of a 10 mM solution of example 22 in DMA (7 eq.) for 3 h 30. After purification on Sephadex G25 in buffer B pH 6.5+5% NMP and concentration on Amicon Ultra-15, 36.6 mg of example 23 were obtained as a colorless limpid solution at a concentration of 1.83 mg/mL with a DAR of 3.6 (HRMS), a monomeric purity of 98.8% and a global yield of 82%. Free-drug level was above the threshold of 1%: the ADC was concentrated on Amicon Ultra-15, purified on Sephadex G25 in buffer B pH 6.5+5% NMP and filtrated on 0.22 μm PVDF filter to provide 32.6 mg of example 23 as a colorless limpid solution at a concentration of 1.63 mg/mL with a DAR of 3.3 (HRMS), a monomeric purity of 98.3% and a global yield of 73%.

SEC-HRMS: m/z=149411 (naked mAb); m/z=150649 (D1); m/z=151889 (D2); m/z=153129 (D3); m/z=154369 (D4); m/z=155608 (D5); m/z=156850 (D6); m/z=158091 (D7); m/z=159331 (D8); m/z=160583 (D9).

Synthesis of Examples 24 to 26:
glutaryl-Val-PEG24Lys-C52 Benzylic Amine, NHS Ester of glutaryl-Val-PEG24Lys-C52 Benzylic Amine and Corresponding ADC

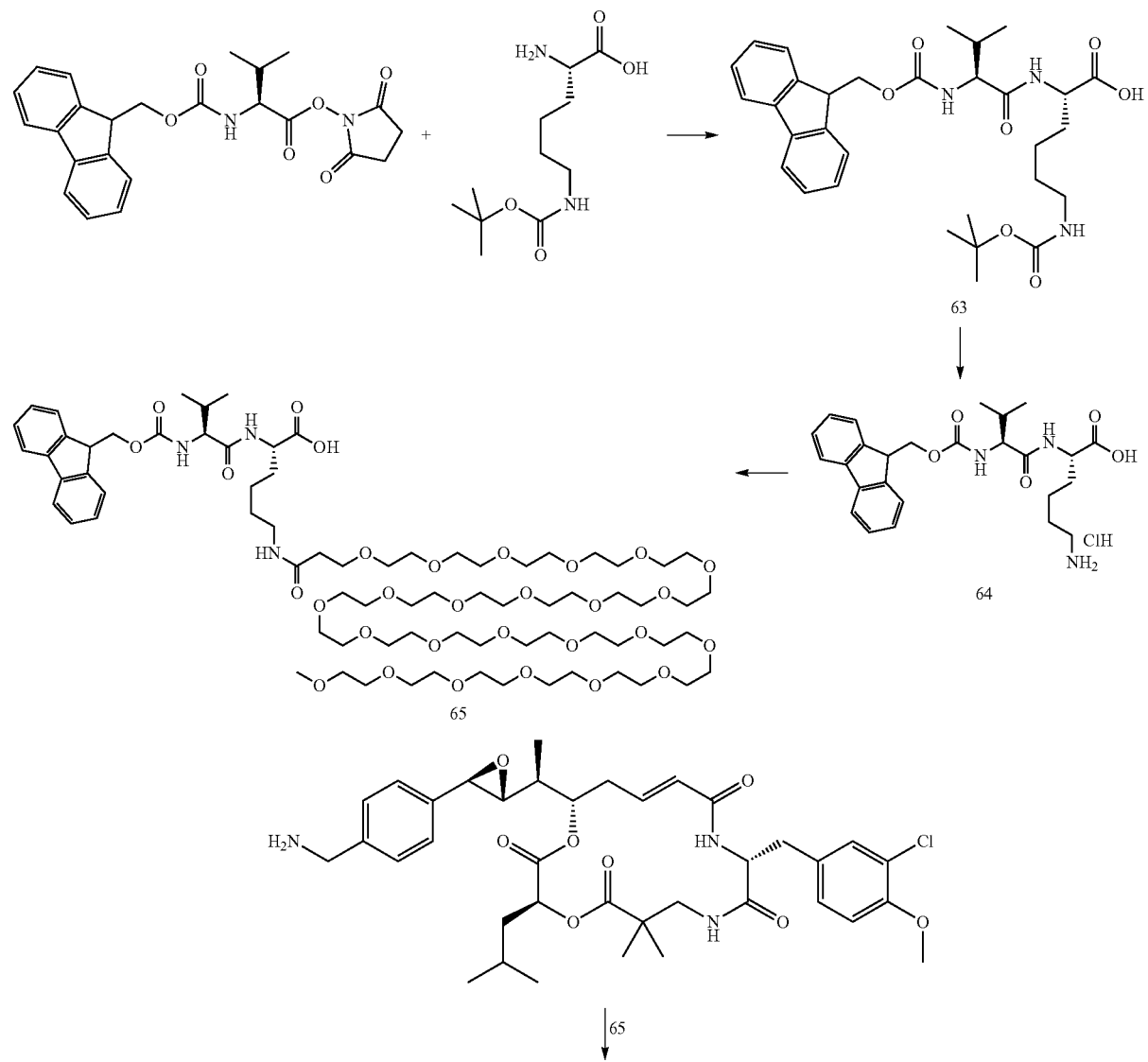

-continued
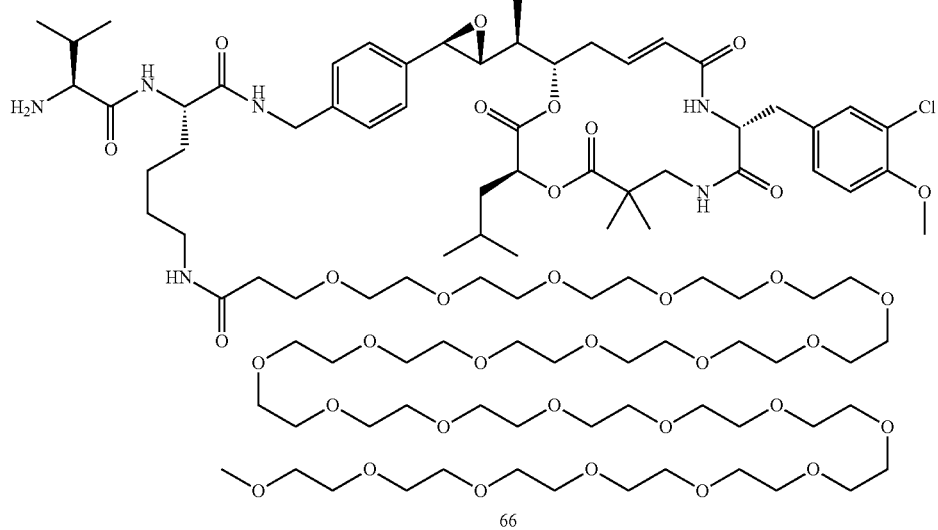
66
↓
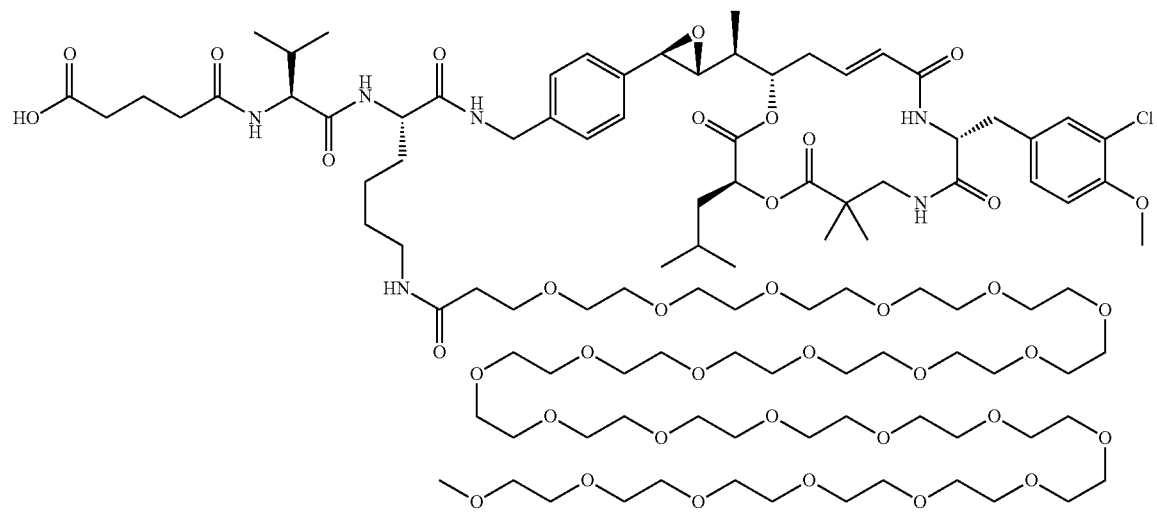
example 24
↓

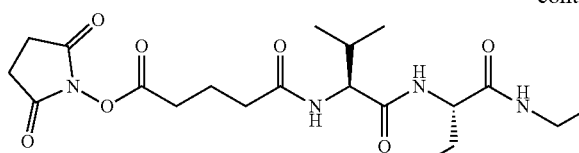
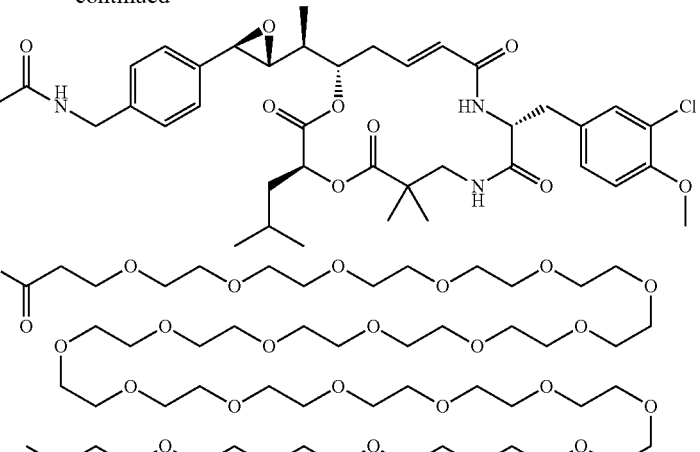

example 25

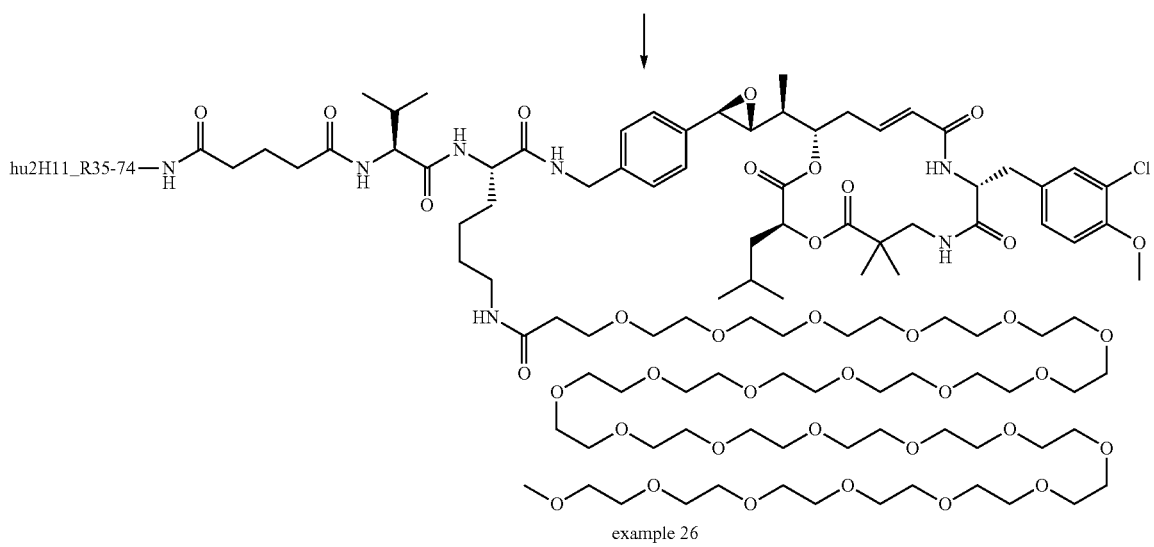

example 26

Compound 63: (S)-2-((S)-2-((((9H-fluoren-9-yl)methoxy)carbonyl)amino)-3-methylbutanamido)-6-((tert-butoxycarbonyl)amino)hexanoic Acid To a solution of H-Lys(Boc)-OH (CAS number [2418-95-3], 310 mg, 1.26 mmol) and NaHCO$_3$ (105 mg, 1.25 mmol) in water (5 mL) and THF (5 mL) was added dropwise, under magnetic stirring, a solution of (S)-2,5-dioxopyrrolidin-1-yl 2-((((9H-fluoren-9-yl)methoxy)carbonyl)amino)-3-methylbutanoate (CAS number [68858-20-8], 310 mg, 1.15 mmol) in THF (15 mL). The reaction medium was stirred at RT for 3 h. At this time, the reaction medium was concentrated in vacuo, then diluted with water (200 mL), acidified with QS of aqueous 5N HCl, and extracted with DCM (2×200 mL). The combined organic phases were dried over MgSO$_4$, filtered and concentrated in vacuo to afford 510 mg of compound 63 (53%).

RMN $^1$H (400 MHz, δ in ppm, DMSO-d6): 0.85 (d, J=6.8 Hz, 3H); 0.87 (d, J=6.8 Hz, 3H); 1.20 to 1.39 (m, 4H); 1.34 (s, 9H); 1.48 to 1.73 (m, 2H); 1.99 (m, 1H); 2.86 (m, 2H); 3.89 (dd, J=7.7 and 8.4 Hz, 1H); 4.08 (m, 1H); 4.17 to 4.32 (m, 3H); 6.72 (broad m, 1H); 7.32 (m, 2H); 7.38 to 7.46 (m, 3H); 7.74 (m, 2H); 7.89 (d, J=7.6 Hz, 2H); 8.00 (broad m, 1H); 12.54 (broad s, 1H). LCMS (A): ES m/z=344; m/z=468; m/z=566 [M−H]$^-$; m/z=568 [M+H]$^+$; t$_R$=1.41 min.

Compound 64: (S)-2-((S)-2-((((9H-fluoren-9-yl)methoxy)carbonyl)amino)-3-methylbutanamido)-6-aminohexanoic acid hydrochloride To compound 63 (340 mg, 599 μmol) was added a solution of 4M HCl in 1,4-dioxane, the reaction medium was stirred at RT for 1 h. At this time, the reaction medium was concentrated in vacuo, followed by addition of Et$_2$O and filtration. The white solid obtained was purified by flash chromatography on 15 g of silica gel (elution 12:3:0.5 v/v/v DCM/MeOH/NH$_4$OH) to give 190 mg of compound 64 (63%).

RMN $^1$H (400 MHz, δ in ppm, DMSO-d6): 0.83 (d, J=6.6 Hz, 3H); 0.85 (d, J=6.6 Hz, 3H); 1.21 to 1.70 (m, 6H); 2.04 (m, 1H); 2.71 (t, J=7.1 Hz, 2H); 3.84 (dd, J=6.7 and 8.7 Hz, 1H); 3.91 (m, 1H); 4.18 to 4.35 (m, 3H); 7.22 (broad m, 3H); 7.33 (m, 2H); 7.42 (t, J=7.6 Hz, 2H); 7.54 (d, J=9.0 Hz, 1H); 7.69 (broad m, 1H); 7.74 (m, 2H); 7.89 (d, J=7.6 Hz, 2H). LCMS (A): ES m/z=244; m/z=466 [M−H]$^-$; m/z=468 [M+H]$^+$; t$_R$=0.81 min.

Compound 65: (S)-80-((S)-2-((((9H-fluoren-9-yl)methoxy)carbonyl)amino)-3-methylbutanamido)-74-oxo-2,5,8,11,14,17,20,23,26,29,32,35,38,41,44,47,50,53,56,59,62,65,68,71-tetracosaoxa-75-azahenoctacontan-81-oic Acid To a solution of compound 64 (130 mg, 258.0 µmol) in THF (20 mL) were added a solution of sodium bicarbonate (50 mg, 589.2 µmol) in $H_2O$ (8 mL) and MEO-DPEG(24)-NHS (CAS number [756525-94-7], 400 mg, 329.4 µmol). The reaction medium was stirred for 20 h at RT, partly concentrated in vacuo then diluted with $H_2O$ (10 mL), acidified to pH 3 with IR-120 (H) Amberlite resin (CAS number [78922-04-0]), filtered, concentrated in vacuo and purified by three consecutive flash chromatographies on 40 g, 25 g and 12 g of silica gel (gradient elution DCM/MeOH/$H_2O$) to give 214 mg of compound 65 as a white lacquer (53%).

RMN $^1$H (400 MHz, δ in ppm, DMSO-d6): 0.86 (d, J=7.0 Hz, 3H); 0.89 (d, J=7.0 Hz, 3H); 1.22 to 1.40 (m, 4H); 1.58 (m, 1H); 1.67 (m, 1H); 1.99 (m, 1H); 2.28 (t, J=6.6 Hz, 2H); 2.99 (m, 2H); 3.23 (s, 3H); 3.40 to 3.70 (m, 92H); 3.56 (t, J=6.6 Hz, 2H); 3.90 (m, 1H); 4.08 (broad m, 1H); 4.19 to 4.31 (m, 3H); 7.31 (broad t, J=7.8 Hz, 2H); 7.41 (broad t, J=7.8 Hz, 3H); 7.73 (t, J=7.8 Hz, 2H); 7.76 (m, 1H); 7.89 (d, J=7.8 Hz, 2H); 8.00 (m, 1H); 12.53 (m, 1H). LCMS (D): ES m/z=794 [M+H+Na]$^{2+}$; m/z=1567 [M+H]+; $t_R$=2.9 min.

Compound 66: N—((S)-5-((S)-2-amino-3-methylbutanamido)-6-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4dioxa-8,11-diazacyclohexadec-13-en-16-yl)ethyl)oxiran-2-yl)benzyl)-amino)-6-oxohexyl)-2,5,8,11,14,17,20,23,26,29,32,35,38,41,44,47,50,53,56,59,62,65,68,71-tetracosaoxatetraheptacontan-74-amide To a solution of (E)-(3S,10R,16S)-16-{(S)-1-[(2R,3R)-3-(4-aminomethyl-phenyl)-oxiranyl]-ethyl}-10-(3-chloro-4-methoxy-benzyl)-3-isobutyl-6,6-dim ethyl-1,4-dioxa-8,11-diaza-cyclohexadec-13-ene-2,5,9,12-tetraone (the synthesis of which was described in WO2011001052, compound 77, 71 mg, 101.7 µmol) in DMF (5 mL) were added a solution of compound 65 (214 mg, 136.6 µmol) in DMF (5 mL), HOBt (22 mg, 156.3 µmol) and EDC (27 µL, 152.5 µmol). The reaction medium was stirred for 3 h at RT before adding piperidine (91 µL, 915.3 µmol). Stirring was carried on for 1 h 30 at RT then the reaction medium was concentrated in vacuo and purified by two consecutive flash chromatographies on 25 g and 12 g of silica gel (gradient elution DCM/MeOH) to give 58 mg of compound 66 as a colorless lacquer (28%).

RMN $^1$H (500 MHz, δ in ppm, DMSO-d6): 0.76 (d, J=7.0 Hz, 3H); 0.78 (d, J=6.8 Hz, 6H); 0.88 (d, J=7.0 Hz, 3H); 0.99 (s, 3H); 1.04 (d, J=7.1 Hz, 3H); 1.12 (s, 3H); 1.25 to 1.41 (m, 5H); 1.51 to 1.70 (m, 4H); 1.80 (m, 1H); 1.93 (m, 1H); 2.25 (m, 1H); 2.28 (t, J=6.7 Hz, 2H); 2.55 (broad m, 2H); 2.68 (m, 2H); 2.99 (m, 5H); 3.23 (s, 3H); 3.32 (masked m, 1H); 3.40 to 3.55 (m, 92H); 3.58 (t, J=6.7 Hz, 2H); 3.80 (s, 3H); 3.88 (d, J=2.3 Hz, 1H); 4.20 to 4.35 (m, 4H); 4.91 (dd, J=3.8 and 9.8 Hz, 1H); 5.10 (m, 1H); 5.80 (dd, J=2.0 and 15.8 Hz, 1H); 6.46 (ddd, J=4.7, 10.5 and 15.8 Hz, 1H); 7.05 (d, J=8.6 Hz, 1H); 7.17 (dd, J=2.4 et 8.6 Hz, 1H); 7.22 (m, 5H); 7.29 (d, J=2.4 Hz, 1H); 7.79 (t, J=6.7 Hz, 2H); 8.00 (d, J=8.8 Hz, 1H); 8.36 (d, J=8.0 Hz, 1H); 8.47 (t, J=6.2 Hz, 1H). LCMS (D): ES m/z=1013 [M+2H]$^{2+}$; m/z=2025 [M+H]+; $t_R$=2.64/2.62 min (85/15 isomer mixture).

Example 24: (80S,83S)-80-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)-83-isopropyl-74,82,85-trioxo-2,5,8,11,14,17,20,23,26,29,32,35,38,41,44,47,50,53,56,59,62,65,68,71-tetracosaoxa-75,81,84-triazanonaoctacontan-89-oic Acid To a solution of compound 66 (58 mg, 28.7 µmol) in DCM (7 mL) was added glutaric anhydride (5.85 mg, 48.7 µmol). The reaction medium was stirred for 2 h at RT, concentrated in vacuo and purified by flash chromatography on 4 g of silica gel (gradient elution DCM/MeOH/H2O) to give 35 mg of example 24 as a white lacquer (57%).

RMN $^1$H (500 MHz, δ in ppm, DMSO-d6): 0.78 (d, J=6.8 Hz, 6H); 0.82 (d, J=7.0 Hz, 3H); 0.84 (d, J=7.0 Hz, 3H); 1.00 (s, 3H); 1.04 (d, J=7.1 Hz, 3H); 1.11 (s, 3H); 1.18 to 1.41 (m, 5H); 1.50 to 1.75 (m, 6H); 1.80 (m, 1H); 1.98 (m, 1H); 2.15 to 2.27 (m, 5H); 2.30 (t, J=6.7 Hz, 2H); 2.69 (m, 2H); 2.98 (m, 5H); 3.23 (s, 3H); 3.32 (masked m, 1H); 3.40 to 3.65 (m, 94H); 3.80 (s, 3H); 3.87 (d, J=2.3 Hz, 1H); 4.14 (m, 1H); 4.20 to 4.33 (m, 4H); 4.90 (dd, J=3.8 and 9.8 Hz, 1H); 5.10 (m, 1H); 5.79 (d, J=15.8 Hz, 1H); 6.47 (ddd, J=4.7, 10.5 and 15.8 Hz, 1H); 7.05 (d, J=8.6 Hz, 1H); 7.16 (dd, J=2.4 and 8.6 Hz, 1H); 7.24 (m, 5H); 7.29 (d, J=2.4 Hz, 1H); 7.80 (t, J=6.0 Hz, 1H); 7.86 (d, J=8.8 Hz, 1H); 7.92 (d, J=8.0 Hz, 1H); 8.37 (m, 2H); 12.10 (broad m, 1H). LCMS (D): ES m/z=1069.5 [M+2H]$^{2+}$; m/z=2138 [M+H]+; $t_R$=2.96/2.93 min (85/15 isomer mixture).

Example 25: (80S,83S)-2,5-dioxopyrrolidin-1-yl 80-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclo-hexadec-13-en-16-yl)ethyl)oxiran-2-yl)benzyl)carbamoyl)-83-isopropyl-74,82,85-trioxo-2,5,8,11,14,17,20,23,26,29,32,35,38,41,44,47,50,53,56,59,62,65,68,71-tetracosaoxa-75,81,84-triazanona-octacontan-89-oate To a solution of example 24 (35 mg, 16.4 µmol) in THF (3 mL) were added DSC (4.28 mg, 16.4 µmol) and DIEA (2.7 µL, 16.4 µmol). The reaction medium was stirred for 20 h at RT, concentrated in vacuo and purified by flash chromatography on 4 g of silica gel (gradient elution DCM/iPrOH) to give 12.0 mg of example 25 as a white lacquer (33%).

RMN $^1$H (500 MHz, δ in ppm, DMSO-d6): 0.78 (d, J=6.8 Hz, 6H); 0.82 (d, J=7.0 Hz, 3H); 0.84 (d, J=7.0 Hz, 3H); 1.00 (s, 3H); 1.04 (d, J=7.1 Hz, 3H); 1.12 (s, 3H); 1.15 to 1.40 (m, 5H); 1.50 to 1.71 (m, 4H); 1.75 to 1.86 (m, 3H); 1.97 (m, 1H); 2.18 to 2.32 (m, 5H); 2.67 (m, 4H); 2.80 (s, 4H); 2.98 (m, 5H); 3.22 (s, 3H); 3.32 (masked m, 1H); 3.40 to 3.77 (m, 94H); 3.80 (s, 3H); 3.88 (d, J=2.3 Hz, 1H); 4.16 (m, 1H); 4.20 to 4.32 (m, 4H); 4.90 (dd, J=3.8 and 9.8 Hz, 1H); 5.10 (m, 1H); 5.78 (dd, J=2.0 and 15.8 Hz, 1H); 6.47 (ddd, J=4.7, 10.5 and 15.8 Hz, 1H); 7.05 (d, J=8.6 Hz, 1H); 7.16 (dd, J=2.4 and 8.6 Hz, 1H); 7.24 (m, 5H); 7.29 (d, J=2.4 Hz, 1H); 7.79 (t, J=6.0 Hz, 1H); 7.90 (d, J=8.8 Hz, 1H); 7.94 (d, J=8.0 Hz, 1H); 8.36 (m, 2H). LCMS (D): ES m/z=746; m/z=2235 [M+H]+; $t_R$=3.08/3.06 min (89/11 isomer mixture).

Example 26: hu2H11_R35-74-Ex25

The general method described previously was used for the preparation of example 26. 55.8 mg of hu2H11_R35-74 were reacted with 261.6 μL of a 10 mM solution of example 25 in DMA (7 eq.) for 3 h 15 then were added 131 μL of a 10 mM solution of example 25 in DMA (3.5 eq.) for 5 h 30. After storage overnight at 4° C., purification on Superdex 200 pg in buffer B pH 6.5+20% NMP, concentration on Amicon Ultra-15, buffer exchange on Sephadex G25 in buffer B pH 6.5+5% NMP, concentration on Amicon Ultra-15 and filtration on 0.22 μm PVDF filter, 33.35 mg of example 26 were obtained as a colorless limpid solution at a concentration of 2.9 mg/mL with a DAR of 3.9 (HRMS), a monomeric purity of 100% and a global yield of 60%.

SEC-HRMS: m/z=151487 (D1); m/z=153615 (D2); m/z=155740 (D3); m/z=157863 (D4); m/z=159981 (D5); m/z=162112 (D6); m/z=164240 (D7); m/z=166356 (D8).

Synthesis of Examples 27 to 29:
glutaryl-Val-PEG24Lys-aza-crypto Benzylic Amine, NHS Ester of glutaryl-Val-PEG24Lys-aza-crypto Benzylic Amine and Corresponding ADC

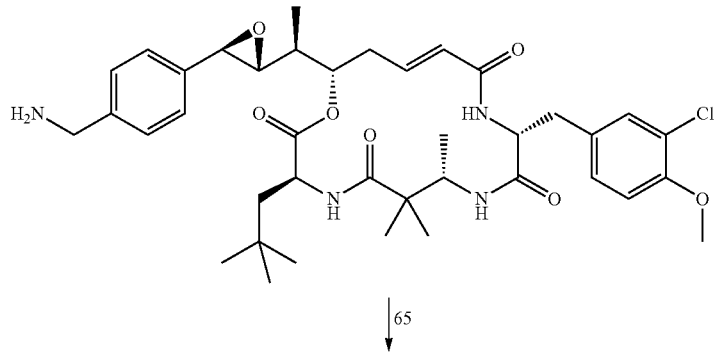

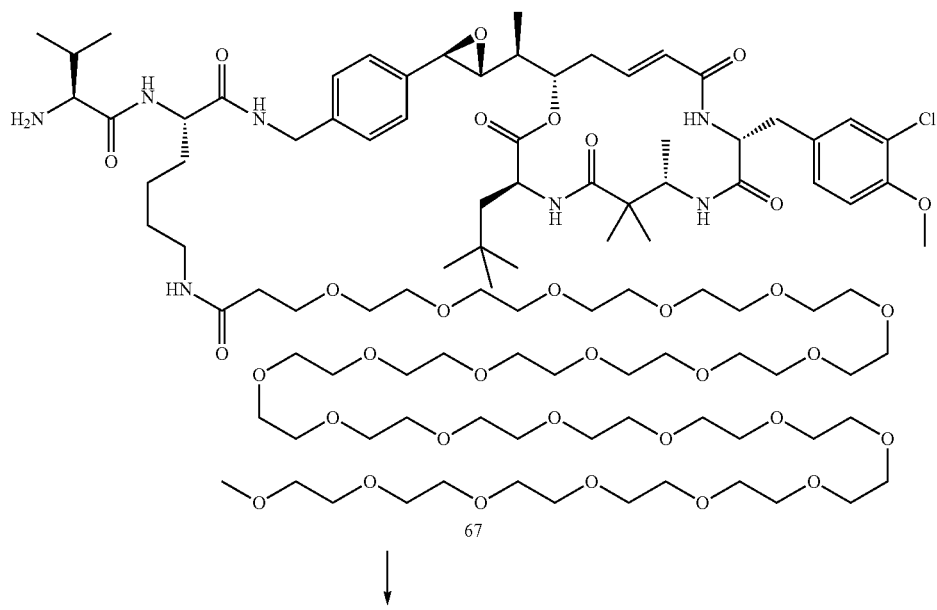

-continued
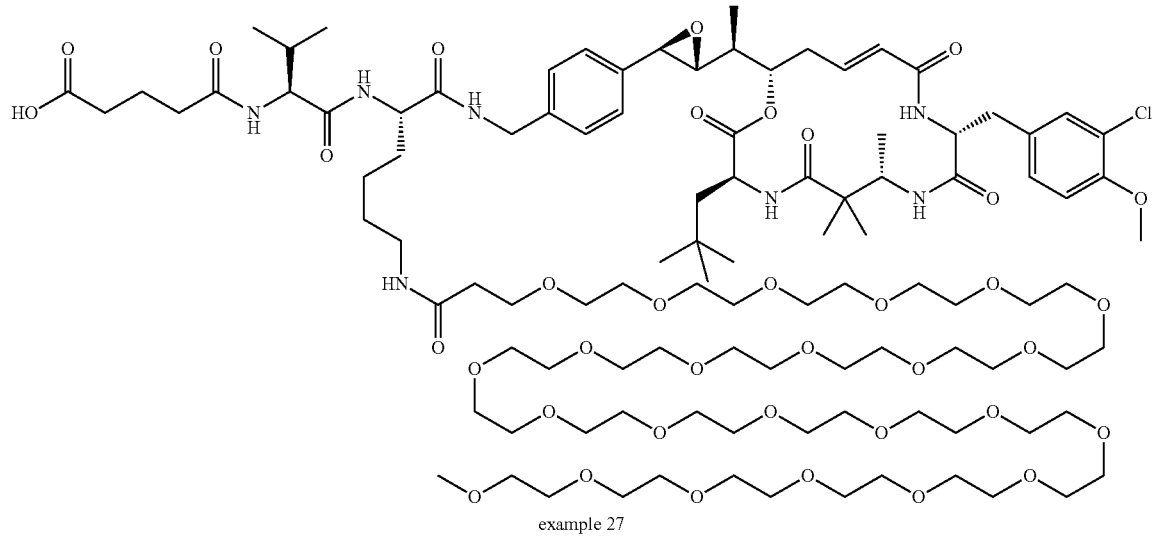
example 27
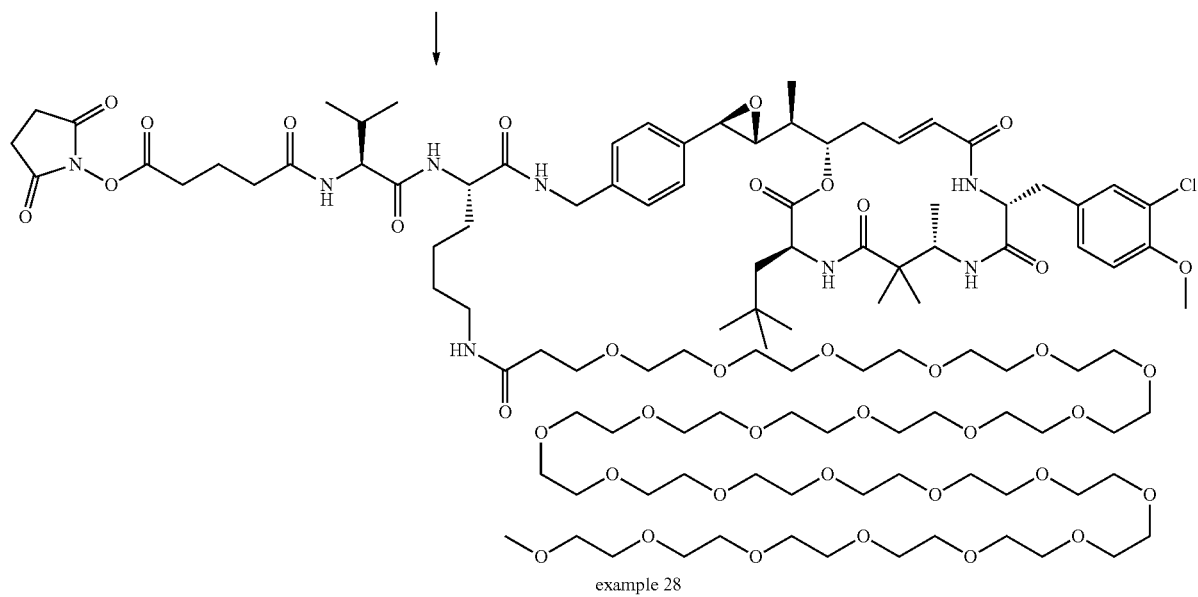
example 28
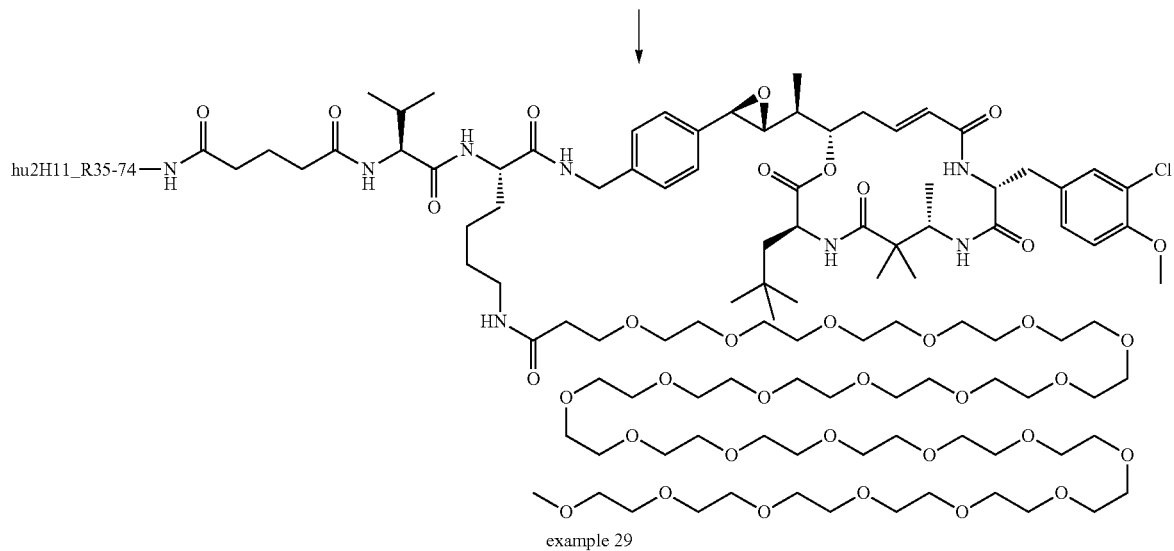
example 29

Compound 67:
N—((S)-5-((S)-2-amino-3-methylbutanamido)-6-((4-((2R,3R)-3-((S)-1-((3S,7S,10R,16S,E)-10-(3-chloro-4-methoxybenzyl)-6,6,7-trimethyl-3-neopentyl-2,5,9,12-tetraoxo-1-oxa-4,8,11-triazacyclohexadec-13-en-16-yl)ethyl)oxiran-2-yl)benzyl)amino)-6-oxohexyl)-2,5,8,11,14,17,20,23,26,29,32,35,38,41,44,47,50,53,56,59,62,65,68,71-tetracosaoxatetraheptacontan-74-amide To a solution of (3S,7S,10R,16S,E)-16-((S)-1-((2R,3R)-3-(4-(aminomethyl)phenyl)-oxiran-2-yl)ethyl)-10-(3-chloro-4-methoxybenzyl)-6,6,7-trimethyl-3-neopentyl-1-oxa-4,8,11-triazacyclo-hexadec-13-ene-2,5,9,12-tetraone (that can be synthesized as described in PCT/EP2016/076603 starting from methyl (3S)-3-amino-2,2-dimethylbutanoate, [MFCD09256689], 75 mg, 103.4 µmol) in DMF (5 mL) were added a solution of compound 65 (211 mg, 134.7 µmol) in DMF (5 mL), HOBt (21 mg, 155.4 µmol) and EDC (20 µL 123.0 µmol). The reaction medium was stirred for 4 h at RT before adding piperidine (95 µL, 961.9 µmol); stirring was carried on for 2 h at RT then the reaction medium was concentrated in vacuo and purified by flash chromatography on 25 g of silica gel (gradient elution DCM/MeOH) to give 132 mg of compound 67 as a colorless oil (62%).

RMN $^1$H (500 MHz, δ in ppm, DMSO-d6): 0.76 (d, J=7.0 Hz, 3H); 0.87 (m, 15H); 1.00 (s, 3H); 1.03 (d, J=7.1 Hz, 3H); 1.15 to 1.40 (m, 5H); 1.18 (s, 3H); 1.46 to 2.00 (m, 8H); 2.25 (m, 1H); 2.28 (t, J=6.7 Hz, 2H); 2.60 (m, 1H); 2.69 (dd, J=11.2 and 14.5 Hz, 1H); 2.91 (dd, J=2.3 and 7.5 Hz, 1H); 2.92 to 3.04 (m, 4H); 3.23 (s, 3H); 3.34 to 3.77 (m, 95H); 3.80 (s, 3H); 3.88 (d, J=2.3 Hz, 1H); 4.08 (m, 2H); 4.20 to 4.34 (m, 3H); 5.04 (m, 1H); 5.78 (dd, J=2.0 and 15.8 Hz, 1H); 6.44 (ddd, J=4.7, 10.5 and 15.8 Hz, 1H); 7.02 (d, J=8.6 Hz, 1H); 7.17 to 7.25 (m, 5H); 7.32 (d, J=2.4 Hz, 1H); 7.78 (t, J=6.0 Hz, 1H); 7.85 (d, J=8.0 Hz, 1H); 7.92 (d, J=7.0 Hz, 1H); 8.00 (d, J=8.8 Hz, 1H); 8.40 (t, J=7.5 Hz, 1H); 8.46 (t, J=6.0 Hz, 1H). LCMS (D): ES m/z=2051 [M+H]$^+$; $t_R$=2.57/2.55 min (isomer mixture 95/5).

Example 27: (80S,83S)-80-((4-((2R,3R)-3-((S)-1-((3S,7S,10R,16S,E)-10-(3-chloro-4-methoxybenzyl)-6,6,7-trimethyl-3-neopentyl-2,5,9,12-tetraoxo-1-oxa-4,8,11-triazacyclohexadec-13-en-16-yl)ethyl)oxiran-2-yl)benzyl)carbamoyl)-83-isopropyl-74,82,85-trioxo-2,5,8,11,14,17,20,23,26,29,32,35,38,41,44,47,50,53,56,59,62,65,68,71-tetracosaoxa-75,81,84-triazanonaoctacontan-89-oic Acid To a solution of compound 67 (132 mg, 64.3 µmol) in DCM (10 mL) was added glutaric anhydride (9 mg, 78.9 µmol). The reaction medium was stirred for 2 h at RT, concentrated in vacuo and purified by two consecutive flash chromatographies on 4 g and 12 g of silica gel (gradient elution DCM/MeOH/H$_2$O) to give 71 mg of example 27 as a white lacquer (51%).

RMN $^1$H (500 MHz, δ in ppm, DMSO-d6): 0.80 to 0.90 (m, 18H); 1.00 (s, 3H); 1.03 (d, J=7.1 Hz, 3H); 1.15 to 1.42 (m, 5H); 1.18 (s, 3H); 1.51 to 1.74 (m, 4H); 1.80 (m, 1H); 1.98 (m, 2H); 2.15 to 2.32 (m, 7H); 2.60 (m, 1H); 2.70 (dd, J=11.2 and 14.5 Hz, 1H); 2.91 (dd, J=2.3 and 7.5 Hz, 1H); 2.95 (dd, J=3.4 and 14.5 Hz, 1H); 3.00 (m, 2H); 3.24 (s, 3H); 3.40 to 3.67 (m, 95H); 3.80 (s, 3H); 3.90 (d, J=2.3 Hz, 1H); 4.00 to 4.34 (m, 6H); 5.04 (m, 1H); 5.80 (dd, J=2.0 and 15.8 Hz, 1H); 6.44 (ddd, J=4.7, 10.5 and 15.8 Hz, 1H); 7.02 (d, J=8.6 Hz, 1H); 7.17 to 7.25 (m, 5H); 7.32 (d, J=2.4 Hz, 1H); 7.80 (t, J=6.0 Hz, 1H); 7.86 (d, J=8.6 Hz, 2H); 7.92 (t, J=6.5 Hz, 2H); 8.37 (t, J=6.0 Hz, 1H); 8.41 (t, J=7.5 Hz, 1H); 12.00 (m, 1H). LCMS (D): ES m/z=722; m/z=2165 [M+H]$^+$; $t_R$=2.95/2.92 min (isomer mixture 95/5).

Example 28: 2,5-dioxopyrrolidin-1-yl (80S,83S)-80-((4-((2R,3R)-3-((S)-1-((3S,7S,10R,16S,E)-10-(3-chloro-4-methoxybenzyl)-6,6,7-trimethyl-3-neopentyl-2,5,9,12-tetraoxo-1-oxa-4,8,11-triazacyclohexadec-13-en-16-yl)ethyl)oxiran-2-yl)benzyl)carbamoyl)-83-isopropyl-74,82,85-trioxo-2,5,8,11,14,17,20,23,26,29,32,35,38,41,44,47,50,53,56,59,62,65,68,71-tetracosaoxa-75,81,84-triazanonaoctacontan-89-oate To a solution of example 27 (33 mg, 15.2 µmol) in THF (3 mL) were added DSC (4 mg, 15.6 µmol) and DIEA (2.55 µL, 15.4 µmol). The reaction medium was stirred for 20 h at RT then were added DSC (1 mg, 3.9 µmol) and DIEA (1 µL, 6.0 µmol).

The reaction medium was stirred for 2 h at RT, concentrated in vacuo and purified by flash chromatography on 4 g of silica gel (gradient elution DCM/iPrOH/MeCN) to give 11 mg of example 28 as a white lacquer (32%).

RMN $^1$H (500 MHz, δ in ppm, DMSO-d6): 0.80 to 0.90 (m, 18H); 1.00 (s, 3H); 1.03 (d, J=7.1 Hz, 3H); 1.12 to 1.42 (m, 5H); 1.19 (s, 3H); 1.55 (m, 1H); 1.65 (m, 1H); 1.82 (m, 3H); 1.96 (m, 2H); 2.28 (m, 3H); 2.67 (m, 4H); 2.80 (s, 4H); 2.91 (dd, J=2.3 and Hz, 1H); 2.95 (dd, J=3.4 and 14.5 Hz, 1H); 3.00 (m, 2H); 3.23 (s, 3H); 3.35 to 3.67 (m, 95H); 3.80 (s, 3H); 3.90 (d, J=2.3 Hz, 1H); 4.03 to 4.32 (m, 6H); 5.03 (m, 1H); 5.90 (dd, J=2.0 and 15.8 Hz, 1H); 6.44 (ddd, J=4.7, 10.5 and 15.8 Hz, 1H); 7.03 (d, J=8.6 Hz, 1H); 7.17 to 7.25 (m, 5H); 7.32 (d, J=2.4 Hz, 1H); 7.79 (t, J=6.0 Hz, 1H); 7.85 (d, J=8.7 Hz, 1H); 7.90 (d, J=8.7 Hz, 1H); 7.93 (m, 2H); 8.35 (t, J=6.5 Hz, 1H); 8.40 (d, J=7.1 Hz, 1H).

Example 29: hu2H11_R35-74-Ex28

The general method described previously was used for the preparation of example 29. 44.64 mg of hu2H11_R35-74 were reacted with 210 µL of a 10 mM solution of example 28 in DMA (7 eq.) for 2 h then were successively added 210 µL of a 10 mM solution of example 28 in DMA (7 eq.) for 2 h 30 and 90 µL of a 10 mM solution of example 28 in DMA (3 eq.) for 2 h. After storage overnight at 4° C., purification on Superdex 200 pg in buffer B pH 6.5+20% NMP, concentration on Amicon Ultra-15, buffer exchange on Sephadex G25 in buffer B pH 6.5+5% NMP and filtration on 0.22 µm PVDF filter, 30.1 mg of example 29 were obtained as a colorless limpid solution at a concentration of 2.51 mg/mL with a DAR of 4 (HRMS), a monomeric purity of 98.4% and a global yield of 67%.

SEC-HRMS: m/z=151502 (D1); m/z=153649 (D2); m/z=155798 (D3); m/z=157939 (D4); m/z=160100 (D5); m/z=162262 (D6).

Synthesis of Examples 30 to 32:
glutaryl-Val-GlucuronicLys-C52 Benzylic Amine,
NHS Ester of glutaryl-Val-GlucuronicLys-C52
Benzylic Amine and Corresponding ADC
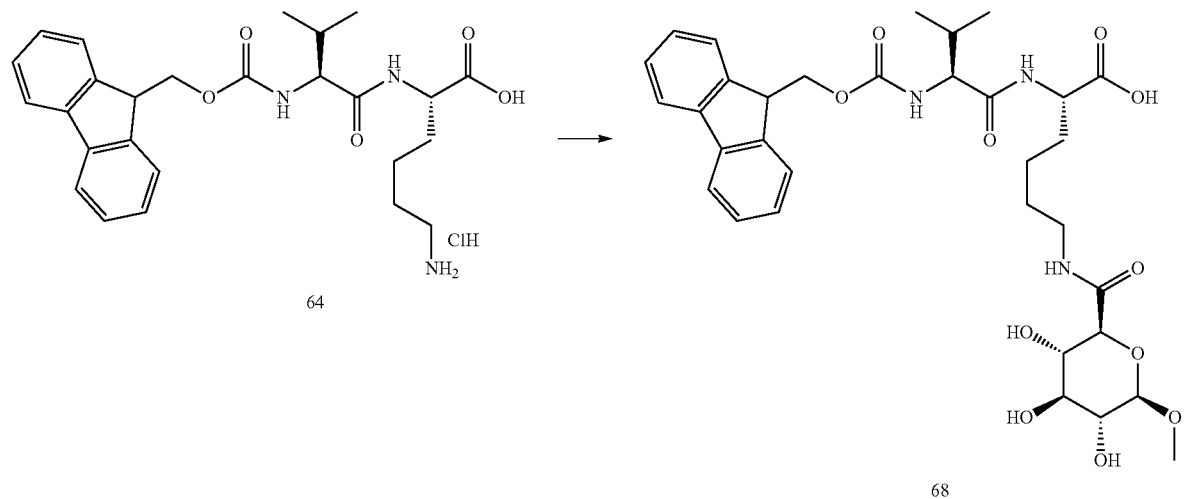
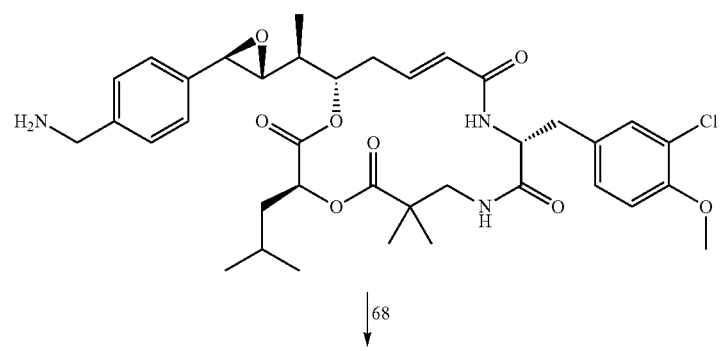
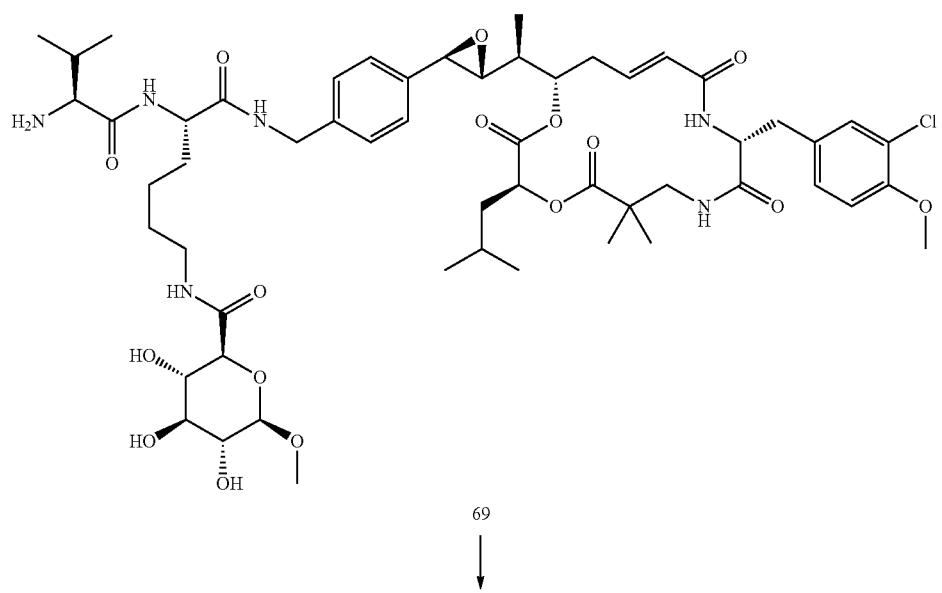

281
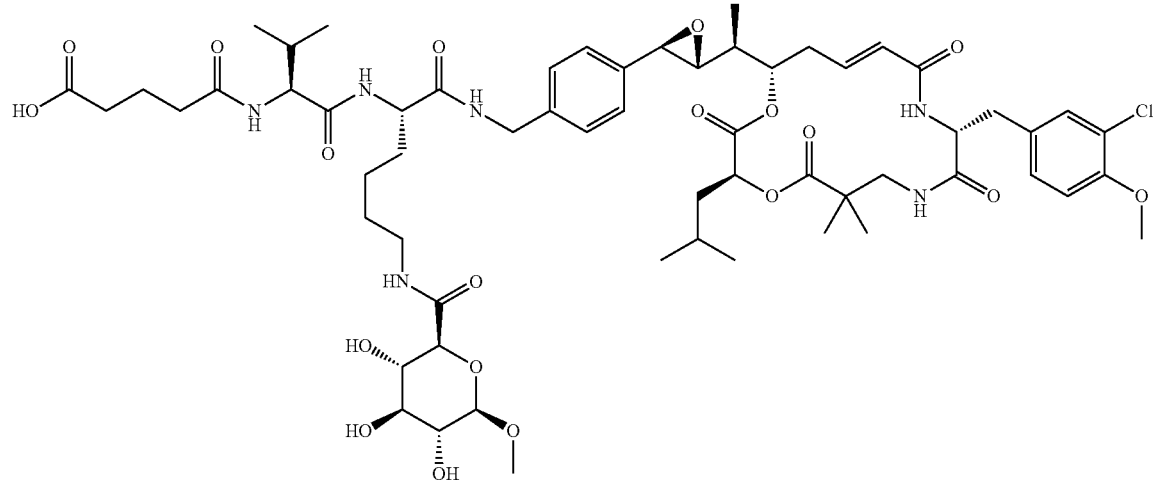
example 30
example 31
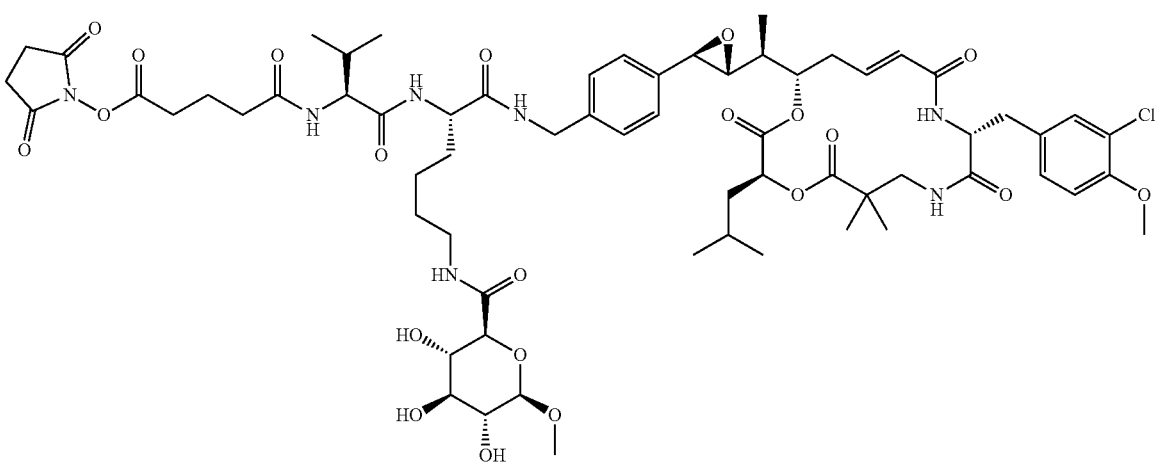
example 32
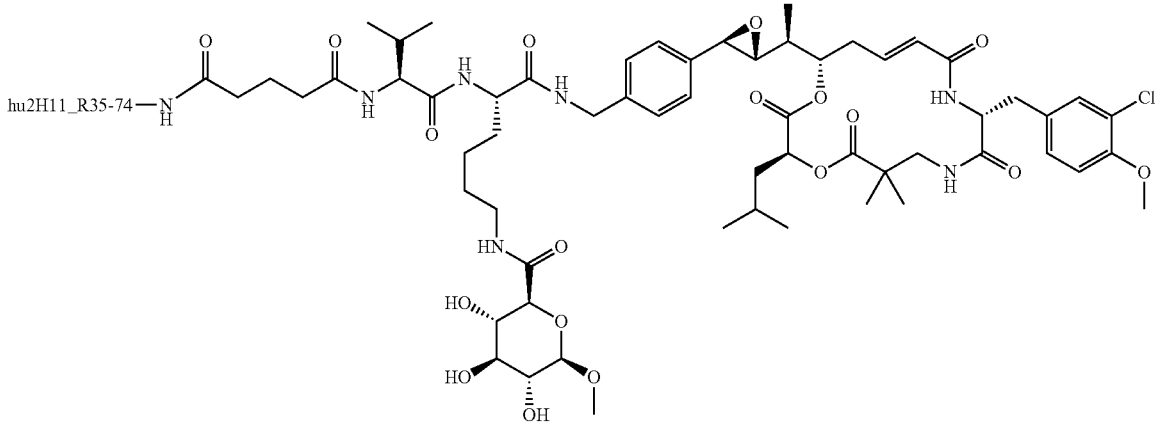
282
-continued

Compound 68: (S)-2-(((S)-2-((((9H-fluoren-9-yl)methoxy)carbonyl)amino)-3-methylbutanamido)-6-((2S,3S,4S,5R,6R)-3,4,5-trihydroxy-6-methoxytetrahydro-2H-pyran-2-carboxamido)hexanoic Acid In a round bottom flask, under magnetic stirring, 1-O-methyl-β-D-glucuronic acid, sodium salt (CAS number [58189-74-5], 100 mg, 434 µmol) was introduced, followed by water (5 mL) and QS of Amberlite (CAS number [9037-24-5]) to reach pH 2, the medium was filtered.

In a round bottom flask, under magnetic stirring, NaHCO$_3$ (43 mg, 511 µmol) in water (5 mL) was added to a solution compound 64 (50 mg, 99 µmol) in THF (4 mL); the reaction medium was stirred at RT for 5 min. Then, the glucuronic acid solution described above was added to the reaction medium, followed by 4-(4,6-dimethoxy-1,3,5-triazin-2-yl)-4-methylmorpholinium chloride N-hydrate (CAS number [3945-69-5], 67 mg, 242 µmol). The reaction medium was stirred at RT overnight, then concentrated in vacuo. The crude medium was purified by flash chromatography on 5 g of silica gel (gradient elution DCM/MeOH/H$_2$O) to give 23 mg of compound 68 (35%).

RMN $^1$H (400 MHz, δ in ppm, DMSO-d6): 0.84 (d, J=6.7 Hz, 3H); 0.86 (d, J=6.7 Hz, 3H); 1.13 to 1.42 (m, 4H); 1.52 to 1.72 (m, 2H); 2.05 (m, 1H); 2.96 to 3.08 (m, 2H); 3.14 (m, 1H); 3.30 (partially masked m, 1H); 3.38 (s, 3H); 3.53 (m, 1H); 3.78 to 3.97 (m, 2H); 4.09 (dd, J=2.3 and 7.8 Hz, 1H); 4.19 to 4.34 (m, 3H); 5.01 to 5.08 (broad m, 1H); 5.13 (broad m, 1H); 5.27 (m, 1H); 7.33 (m, 2H); 7.42 (t, J=7.6 Hz, 2H); 7.52 to 7.62 (broad m, 2H); 7.75 (m, 2H); 7.89 (d, J=7.6 Hz, 2H); 7.93 (broad m, 1H); 12.00 (m, 1H). LCMS (A): ES m/z=656 [M−H]$^-$; m/z=658 [M+H]$^+$; t$_R$=1.05 min.

Compound 69: (2S,3S,4S,5R,6R)—N—((S)-5-((S)-2-amino-3-methylbutanamido)-6-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)-oxiran-2-yl)benzyl)amino)-6-oxohexyl)-3,4,5-trihydroxy-6-methoxytetrahydro-2H-pyran-2-carboxamide To a solution of (E)-(3S,10R,16S)-16-{(S)-1-[(2R,3R)-3-(4-aminomethyl-phenyl)-oxiranyl]-ethyl}-10-(3-chloro-4-methoxy-benzyl)-3-isobutyl-6,6-dim ethyl-1,4-dioxa-8,11-diaza-cyclohexadec-13-ene-2,5,9,12-tetraone (the synthesis of which was described in WO2011001052, compound 77, 90 mg, 129 µmol) was added, under magnetic stirring, a solution of compound 68 (135 mg, 205 µmol) in DMF (5 mL), followed by HOBt (30 mg, 222 µmol) and EDC (36 µL, 203 µmol). The reaction medium was stirred at RT for 1 h. At this time, DMA (1 mL) was added, and stirring was maintained overnight. Then, EDC (20 µL) was added and the reaction medium was stirred for 2 more hours. Piperidine (12.9 µL, 129 µmol) was then added to the medium. After 1 h30 of stirring, the reaction medium was concentrated in vacuo and purified by 3 consecutive flash chromatographies on silica gel (isocratic elution 40:5:0.5 v/v/v DCM/MeOH/H$_2$O and 12:3:0.5 v/v/v DCM/MeOH/NH$_4$OH) to give 47 mg of compound 69 (33%).

RMN $^1$H (500 MHz, δ in ppm, DMSO-d6): 0.77 to 0.81 (m, 9H); 0.88 (d, J=6.6 Hz, 3H); 1.00 (s, 3H); 1.04 (d, J=6.6 Hz, 3H); 1.12 (s, 3H); 1.20 to 1.71 (m, 9H); 1.80 (m, 1H); 1.93 (m, 1H); 2.28 (m, 1H); 2.62 to 2.73 (m, 2H); 2.93 to 3.14 (m, 9H); 3.28 to 3.36 (partially masked m, 2H); 3.39 (s, 3H); 3.53 (d, J=9.5 Hz, 1H); 3.81 (s, 3H); 3.87 (d, J=1.7 Hz, 1H); 4.09 (m, 1H); 4.19 to 4.36 (m, 4H); 4.91 (m, 1H); 5.00 to 5.15 (m, 4H); 5.79 (d, J=15.9 Hz, 1H); 6.48 (m, 1H); 7.05 (d, J=8.6 Hz, 1H); 7.17 (dd, J=2.1 and 8.6 Hz, 1H); 7.20 to 7.25 (m, 5H); 7.28 (d, J=2.1 Hz, 1H); 7.92 (broad t, J=5.9 Hz, 1H); 8.02 (broad m, 1H); 8.35 (d, J=7.8 Hz, 1H); 8.46 (broad t, J=6.2 Hz, 1H). LCMS (A): ES m/z=558 [M+2H]$^{2+}$; m/z=1113 [M−H]$^-$; m/z=1115 [M+H]$^+$; m/z=1159 [M−H+HCO$_2$H]$^-$; t$_R$=0.9 min.

Example 30: 5-(((S)-1-(((S)-1-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)amino)-1-oxo-6-((2S,3S,4S,5R,6R)-3,4,5-trihydroxy-6-methoxytetrahydro-2H-pyran-2-carboxamido)hexan-2-yl)amino)-3-methyl-1-oxobutan-2-yl)amino)-5-oxopentanoic Acid To compound 69 (47 mg, 42.1 µmol) was added DMF (4 mL) and, under magnetic stirring, glutaric anhydride (8.5 mg, 74.5 µmol); the reaction medium was stirred at RT for 2 h. At this time, the crude medium was concentrated in vacuo, and purified by 2 consecutive flash chromatographies on silica gel (gradient elution DCM/MeOH/H$_2$O and DCM/MeOH/NH$_4$OH) to give 17 mg of example 30 (33%).

RMN $^1$H (500 MHz, δ in ppm, DMSO-d6): 0.81 (split d, J=6.4 Hz, 6H); 0.84 (d, J=6.6 Hz, 3H); 0.86 (d, J=6.6 Hz, 3H); 0.98 (s, 3H); 1.04 (d, J=6.6 Hz, 3H); 1.11 (s, 3H); 1.17 to 2.32 (broad m, 18H); 2.66 to 2.74 (m, 2H); 2.91 to 3.03 (m, 5H); 3.10 (m large, 1H); 3.18 (t, J=8.8 Hz, 1H); 3.28 to 3.36 (partially masked m, 2H); 3.37 (s, 3H); 3.60 (m, 1H); 3.81 (s, 3H); 3.87 (d, J=1.6 Hz, 1H); 4.07 (m, 2H); 4.14 to 4.26 (m, 3H); 4.31 (m, 1H); 4.92 (m, 1H); 5.06 to 5.13 (m, 2H); 5.35 (m, 2H); 5.80 (d, J=15.3 Hz, 1H); 6.45 (ddd, J=3.6, 11.1 and 15.3 Hz, 1H); 7.05 (d, J=8.5 Hz, 1H); 7.18 (dd, J=2.1 and 8.5 Hz, 1H); 7.22 (d, J=8.4 Hz, 2H); 7.25 (d, J=8.4 Hz, 2H); 7.29 (d, J=2.1 Hz, 1H); 7.31 (m, 1H); 7.77 to 8.81 (m, 5H). LCMS (A): ES m/z=1227 [M−H]$^-$; m/z=1229 [M+H]$^+$; m/z=615; t$_R$=1.16 min.

Example 31: 2,5-dioxopyrrolidin-1-yl 5-(((S)-1-(((S)-1-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)amino)-1-oxo-6-((2S,3S,4S,5R,6R)-3,4,5-trihydroxy-6-methoxytetrahydro-2H-pyran-2-carboxamido)hexan-2-yl)amino)-3-methyl-1-oxobutan-2-yl)amino)-5-oxopentanoate To example 30 (14 mg, 11.4 µmol), under magnetic stirring, were added DMF (3 mL), DSC (4.2 mg, 15.6 µmol) and DIEA (6 µL, 34.5 µmol). The reaction medium was stirred at RT for 4 h. At this time, the medium was diluted with MeTHF (10 mL) and washed with H$_2$O (5 mL). The aqueous phase was extracted with MeTHF (10 mL), the combined organic phases were dried over MgSO$_4$, filtered concentrated in vacuo and purified by flash chromatography on 4 g of silica gel (gradient elution DCM/iPrOH) to give 3.5 mg of example 31 (23%).

RMN $^1$H (500 MHz, δ in ppm, DMSO-d6): 0.78 (d, J=6.6 Hz, 6H); 0.82 (d, J=7.1 Hz, 3H); 0.84 (d, J=7.1 Hz, 3H); 0.99 (s, 3H); 1.04 (d, J=6.6 Hz, 3H); 1.12 (s, 3H); 1.17 to 1.70 (m, 9H); 1.77 to 1.87 (m, 3H); 1.98 (m, 1H); 2.23 to 2.32 (m, 3H); 2.65 to 2.70 (m, 4H); 2.81 (s, 4H); 2.93 to 3.07 (m, 6H); 3.15 (m, 1H); 3.28 to 3.38 (partially masked m, 2H); 3.40 (s, 3H); 3.53 (d, J=9.6 Hz, 1H); 3.81 (s, 3H); 3.87 (d, J=1.4 Hz, 1H); 4.09 (d, J=7.7 Hz, 1H); 4.17 (dd, J=6.9 and 8.2 Hz, 1H);

4.20 to 4.33 (m, 4H); 4.90 (dd, J=3.4 and 9.5 Hz, 1H); 5.04 (m, 2H); 5.10 (m, 1H); 5.14 (d, J=5.2 Hz, 1H); 5.79 (dd, J=0.8 and 15.3 Hz, 1H); 6.47 (m, 1H); 7.05 (d, J=8.8 Hz, 1H); 7.17 (dd, J=1.6 and 8.8 Hz, 1H); 7.20 to 7.25 (m, 5H); 7.28 (d, J=1.6 Hz, 1H); 7.86 to 7.99 (m, 3H); 8.37 (m, 2H). LCMS (A): ES m/z=1370 [M−H+HCO$_2$H]$^-$; ES m/z=1326 [M+H]$^+$; m/z=663.5; $t_R$=1.21 min.

Example 32: hu2H11_R35-74-Ex31

The general method described previously was used for the preparation of example 32. 27.9 mg of hu2H11_R35-74 were reacted with 107 μL of a 10.5 mM solution of example 31 in DMA (6 eq.) for 2 h 30 then were added 107 μL of a 10.5 mM solution of example 31 in DMA (6 eq.) for 4 h 30. After purification on Superdex 200 pg in buffer B pH 6.5+10% NMP, concentration on Amicon Ultra-15, dilution in buffer B pH 6.5 to a final concentration of NMP at 5% and filtration on 0.22 μm PVDF filter, 16.7 mg of example 32 were obtained as a colorless limpid solution at a concentration of 2.23 mg/mL with a DAR of 3 (HRMS), a monomeric purity of 100% and a global yield of 60%.

SEC-HRMS: m/z=149407 (naked mAb); m/z=150619 (D1); m/z=151831 (D2); m/z=153044 (D3); m/z=154256 (D4); m/z=155468 (D5); m/z=156685 (D6); m/z=157899 (D7); m/z=159014 (D8).

Synthesis of Examples 33 to 35:
glutaryl-Val-sulfoPEG4Lys-C52 Benzylic Amine, NHS Ester of glutaryl-Val-sulfoPEG4Lys-C52 Benzylic Amine and Corresponding ADC

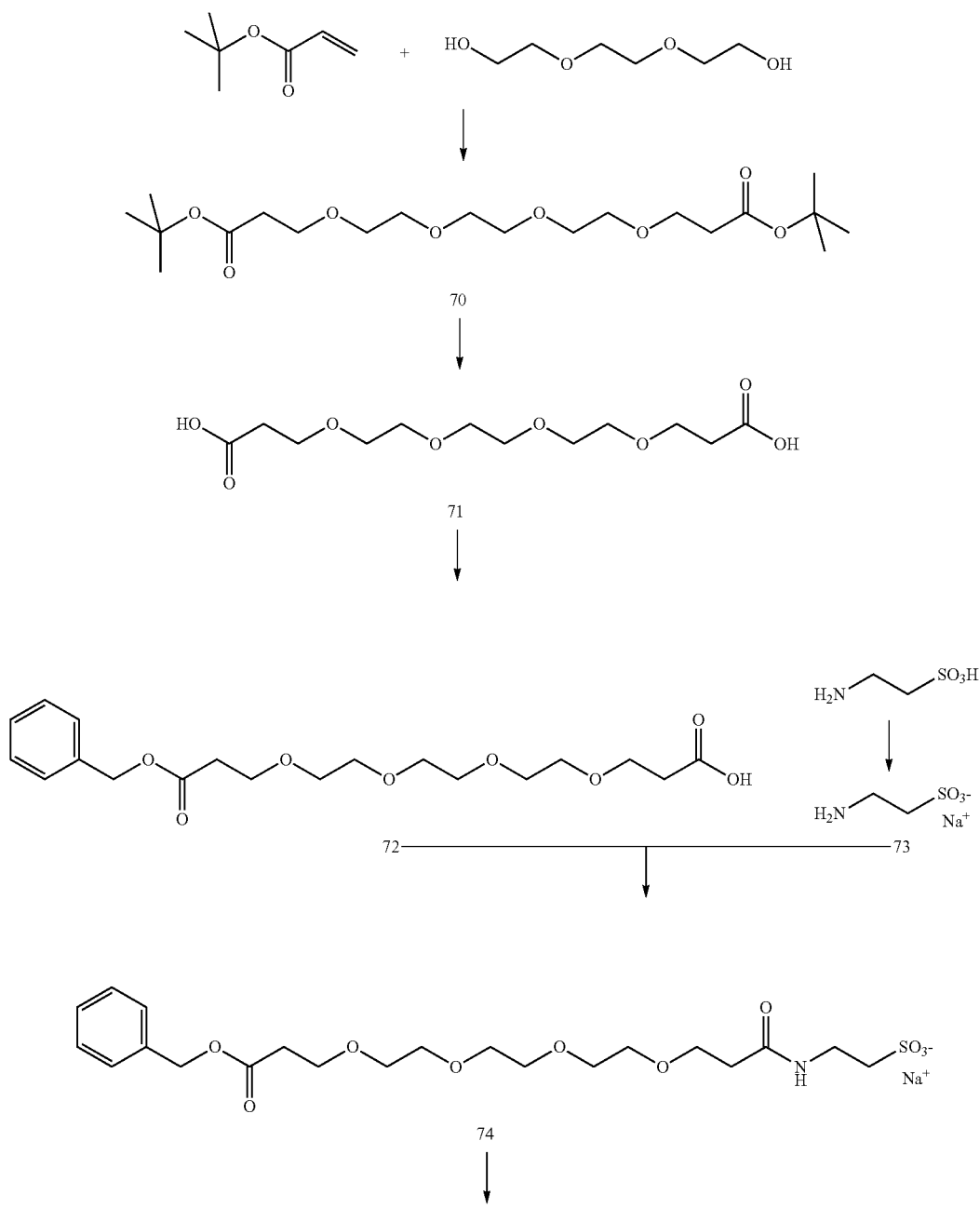

287 288
-continued
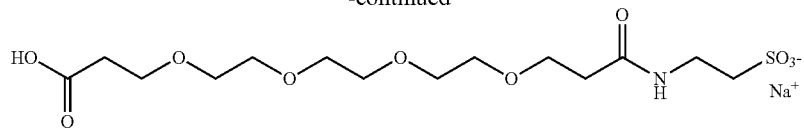
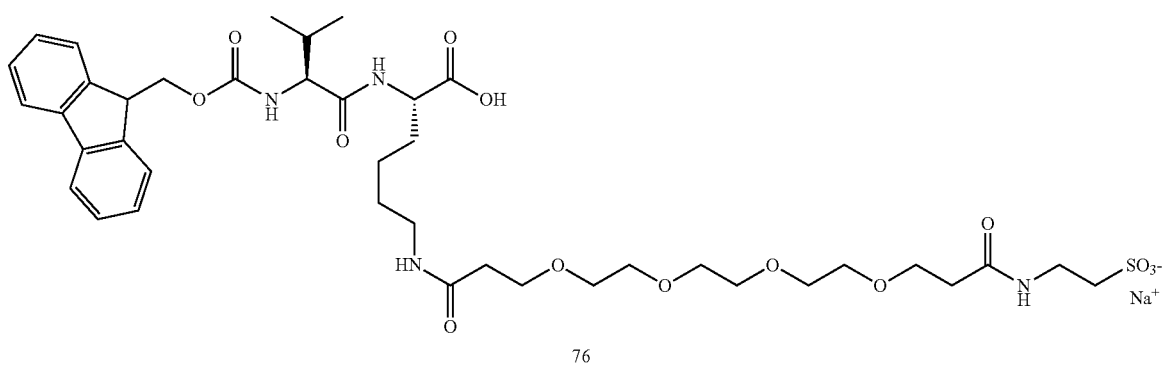
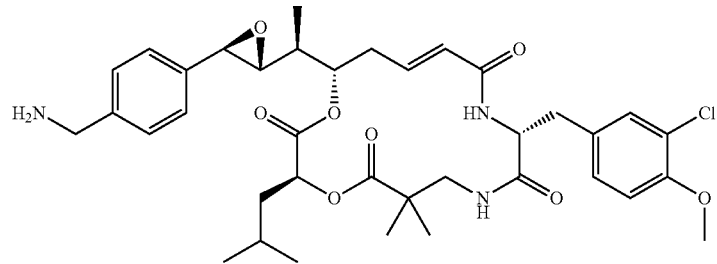
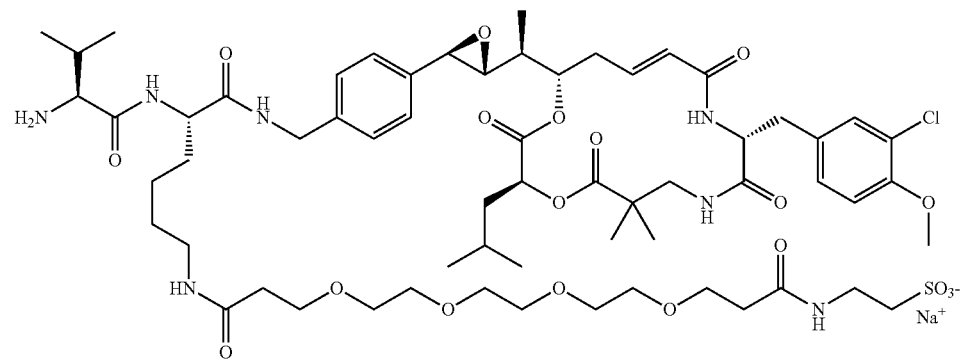

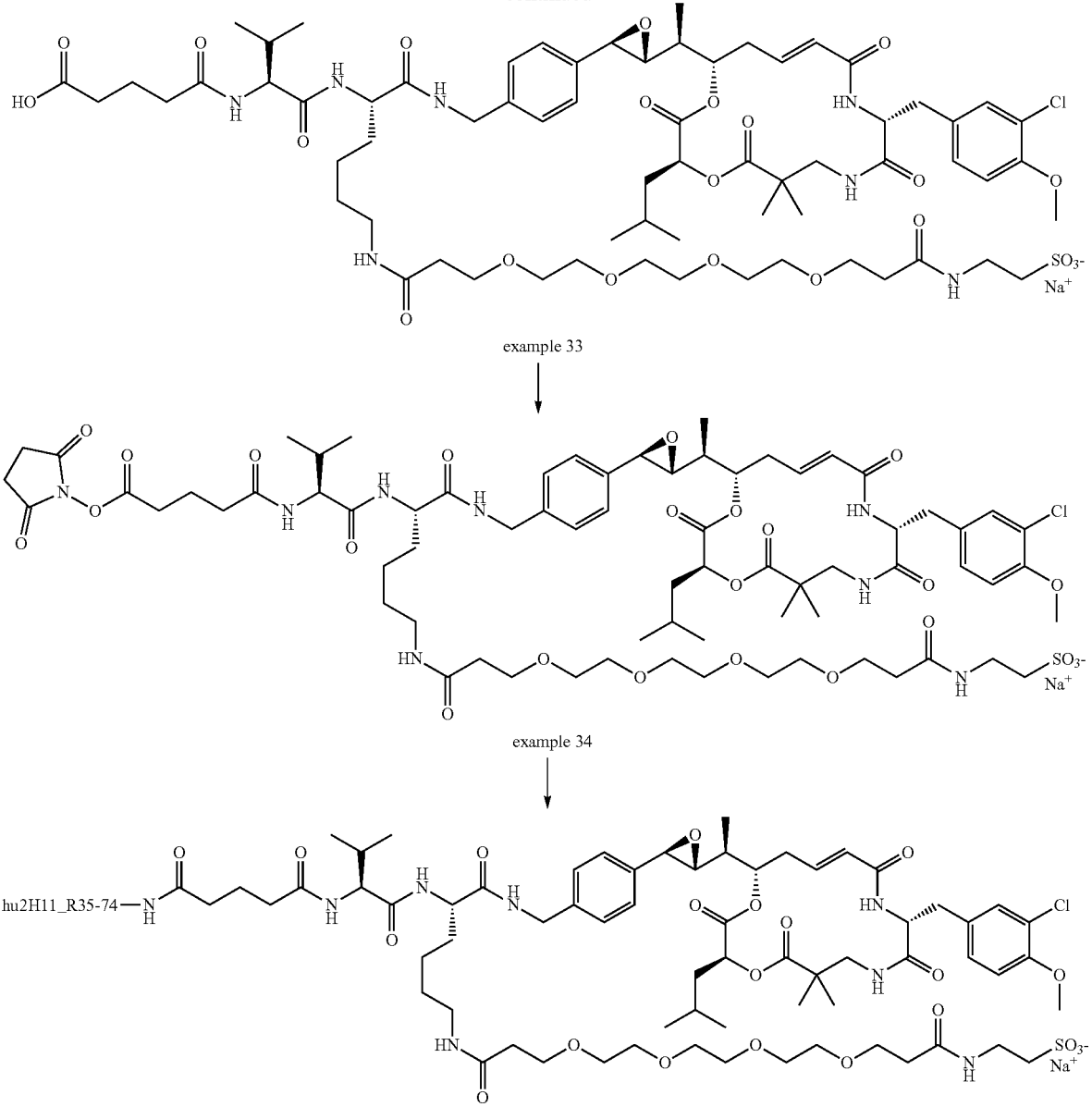

example 33 example 34 example 35

Compound 70: di-tert-butyl 4,7,10,13-tetraoxahexadecane-1,16-dioate

To a solution of triethylene glycol (5 mL, 37.5 mmol) in THF (15 mL) was added sodium (18 mg, 783.0 µmol). The reaction medium was stirred for 2 h at RT then was added dropwise over 5 min tert-butyl acrylate (14 mL, 95.58 mmol). The reaction medium was stirred for 20 h at RT then quenched with brine (300 mL) and extracted twice with EtOAc (300 mL). The combined organic phases were dried over MgSO$_4$, filtered, concentrated in vacuo and purified by flash chromaography on 200 g of silica gel (gradient elution heptane/EtOAc) to five 8.05 g of compound 70 as a colorless oil (53%).

RMN $^1$H (400 MHz, δ in ppm, DMSO-d6): 1.40 (s, 18H); 2.40 (t, J=6.5 Hz, 4H); 3.48 (m, 12H); 3.58 (t, J=6.5 Hz, 4H). LCMS (A): ES m/z=407 [M+H]$^+$; m/z=429 [M+Na]$^+$; t$_R$=1.32 min.

Compound 71: 4,7,10,13-tetraoxahexadecane-1,16-dioic Acid

To compound 70 (8.05 g, 19.8 mmmol) was added formic acid (40 mL, 1.04 mol). The reaction medium was stirred for 1 d at RT, concentrated in vacuo and co-evaporated with EtOAc (20 mL) to give 5.9 g of compound 71 as a colorless oil (quant.).

RMN $^1$H (300 MHz, δ in ppm, DMSO-d6): 2.44 (t, J=6.5 Hz, 4H); 3.48 (s, 8H); 3.50 (s, 4H); 3.59 (d, J=6.5 Hz, 4H); 12.25 (broad m, 2H).

Compound 72: 3-oxo-1-phenyl-2,6,9,12,15-pentaoxaoctadecan-18-oic Acid

To a solution of compound 71 (5.9 g, 20.05 mmol) in DMF (50 mL) were added DIEA (3.6 mL, 20.67 mmol) and dropwise over 10 min a solution of benzyl bromide (2.43 mL, 20.05 mmol) in DMF (50 mL). The reaction medium was stirred for 20 h at RT, quenched with 1N HCl (500 mL) and extracted twice with EtOAc (200 mL). The combined organic phases were dried over $MgSO_4$, filtered, concentrated in vacuo and purified by two consecutive flash chromatographies on 400 g and 100 g of silica gel (gradient elution DCM/MeOH) to give 2.7 g of compound 72 as a pale green oil (35%).

RMN $^1$H (300 MHz, δ in ppm, DMSO-d6): 2.42 (m, 2H); 2.60 (t, J=6.5 Hz, 2H); 3.47 (s, 6H); 3.49 (s, 6H); 3.59 (m, 2H); 3.66 (d, J=6.5 Hz, 2H); 5.10 (s, 2H); 7.29 to 7.41 (m, 5H).

Compound 73: sodium 2-aminoethanesulfonate

To a solution of taurine (2 g, 15.98 mmol) in $H_2O$ (30 mL) was added sodium hydrogenocarbonate (1.34 g, 15.98 mmol). The reaction medium was stirred for 2 h at RT then concentrated in vacuo. The crude product was dissolved in $H_2O$ (100 mL) and lyophilized to give 2.5 g of compound 73 as a white powder (quant.).

IR spectrum as a KBr pellet; main absorption bands in reciprocal centimeters: 1458; 1344; 1212; 1184; 1046; 1037; 742; 737; 598; 576; 533 & 523.

Compound 74: sodium 3,18-dioxo-1-phenyl-2,6,9,12,15-pentaoxa-19-azahenicosane-21-sulfonate To a solution of compound 72 (1 g, 2.69 mmol) in DMF (40 mL) were added NHS (367 mg, 3.13 mmol) and EDC (565 µL, 3.12 mmol). The reaction medium was stirred for 20 h at RT then were added a solution of compound 73 (1.9 g, 12.91 mmol) in $H_2O$ (20 mL) and sodium bicarbonate (219 mg, 2.61 mmol). The reaction medium was stirred for 2 h at RT then acidified to pH 3 with Amberlite IR-120 (H) (CAS number [78922-04-0], filtered, concentrated in vacuo and purified by flash chromatography on 150 g of silica gel (DCM/MeOH/$H_2O$) to give 824 mg of compound 74 as a colorless solid 61%).

LCMS (A): ES m/z=490 [M−H]$^-$; m/z=492 [M+H]$^+$; $t_R$=1.1 min.

Compound 75: sodium 1-carboxy-15-oxo-3,6,9,12-tetraoxa-16-azaoctadecane-18-sulfonate A solution of compound 74 (820 mg, 1.60 mmol) in 8:2 MeOH/$H_2O$ (30 mL) was filtered over 0.22 µm and subjected to hydrogenolysis on a 10% Pd/C cartridge using a H-cube system at 20° C. The reaction medium was concentrated in vacuo to give 530 mg of compound 75 as a yellow gum (78%).

RMN $^1$H (300 MHz, δ in ppm, DMSO-d6): 2.27 (t, J=6.6 Hz, 2H); 2.40 (t, J=6.6 Hz, 2H); 2.52 (partially masked m, 2H); 3.28 (partially masked m, 2H); 3.49 (m, 12H); 3.59 (m, 4H); 7.72 (broad t, J=6.4 Hz, 1H); 12.08 (broad m, 1H).

Compound 76: Sodium (5S,8S)-8-carboxy-1-(9H-fluoren-9-yl)-5-isopropyl-3,6,14,29-tetraoxo-2,17,20,23,26-pentaoxa-4,7,13,30-tetraazadotriacontane-32-sulfonate To a solution of compound 75 (300 mg, 708.5 µmol) in DMF (15 mL) were added NHS (98 mg, 851.5 µmol) and EDC (150 µL, 855.1 µmol). The reaction medium was stirred for 20 h at RT then were added a solution of compound 64 (416 mg, 825.4 µmol) in DMF (15 mL) and a solution of sodium biacarbonate (180 mg, 2.13 mmol) in $H_2O$ (10 mL). The reaction medium was stirred for 1 h at RT, acidified to pH 3 with Amberlit IR-120 (H) (CAS number [78922-04-0]), filtered, washed with DMF (5 mL), concentrated in vacuo and purified by flash chromatography on 100 g of silica gel (gradient elution DCM/MeOH/acetic acid) to give 447 mg of a colorless lacquer. This lacquer was dissolved in 2:1 THF/$H_2O$ (120 mL), acidified to pH 3.3 with 0.1N HCl (about 4 mL) and concentrated in vacuo to give 354 mg of compound 76 as a white translucent solid (57%).

RMN $^1$H (400 MHz, δ in ppm, DMSO-d6): 0.86 (d, J=7.0 Hz, 3H); 0.89 (d, J=7.0 Hz, 3H); 1.20 to 1.41 (m, 4H); 1.50 to 1.74 (m, 2H); 1.98 (m, 1H); 2.26 (t, J=6.8 Hz, 2H); 2.28 (t, J=6.8 Hz, 2H); 2.52 (masked m, 2H); 3.00 (m, 2H); 3.28 (partially masked m, 2H); 3.45 (m, 12H); 3.58 (t, J=6.8 Hz, 4H); 3.91 (dd, J=7.0 and 9.2 Hz, 1H); 4.14 (m, 1H); 4.19 to 4.31 (m, 3H); 7.32 (m, 2H); 7.37 (d, J=9.2 Hz, 1H); 7.41 (dt, J=1.0 and 7.8 Hz, 2H); 7.75 (m, 3H); 7.80 (t, J=6.0 Hz, 1H); 7.89 (d, J=7.8 Hz, 2H); 8.07 (d, J=8.0 Hz, 1H); 12.49 (m, 1H). LCMS (A): ES m/z=849 [M−H]$^-$; m/z=851 [M+H]$^+$; $t_R$=1.44 min.

Compound 77: sodium (25S,28S)-28-amino-25-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclo-hexadec-13-en-16-yl)ethyl)oxiran-2-yl)benzyl)carbamoyl)-29-methyl-4,19,27-trioxo-7,10,13,16-tetraoxa-3,20,26-triazatriacontane-1-sulfonate To a solution (E)-(3S,10R,16S)-16-{(S)-1-[(2R,3R)-3-(4-aminomethyl-phenyl)-oxiranyl]-ethyl}-10-(3-chloro-4-methoxy-benzyl)-3-isobutyl-6,6-dim ethyl-1,4-dioxa-8,11-diaza-cyclohexadec-13-ene-2,5,9,12-tetraone (the synthesis of which was described in WO2011001052, compound 77, 106 mg, 151.8 µmol) in DMF (5 mL) were added a solution of compound 76 (225 mg, 257.7 µmol) in DMF (5 mL), HOBt (30 mg, 213.1 µmol) and EDC (40 µL, 226.0 µmol). The reaction medium as stirred for 2 h at RT then was added piperidine (134 µL, 1.36 mmol) and the stirring was carried on for 2 h. The reaction medium was concentrated in vacuo and purified by two consecutive flash chromatographies on 50 g and 4 g of silica gel (gradient elution DCM/MeOH/$H_2O$) to give 73 mg of compound 77 as a white solid (36%).

RMN $^1$H (500 MHz, δ in ppm, DMSO-d6): 0.78 (d, J=6.8 Hz, 6H); 0.91 (d, J=7.0 Hz, 3H); 0.93 (d, J=7.0 Hz, 3H); 1.00 (s, 3H); 1.04 (d, J=7.1 Hz, 3H); 1.12 (s, 3H); 1.18 to 1.45 (m, 5H); 1.51 to 1.72 (m, 4H); 1.80 (m, 1H); 2.05 (m, 1H); 2.23 to 2.35 (m, 5H); 2.56 (m, 2H); 2.68 (m, 2H); 2.95 to 3.04 (m, 5H); 3.32 (m, 3H); 3.48 (m, 12H); 3.57 (t, J=6.7 Hz, 2H); 3.59 (t, J=6.7 Hz, 2H); 3.66 (d, J=6.0 Hz, 1H); 3.80 (s, 3H); 3.87 (d, J=2.3 Hz, 1H); 4.20 to 4.36 (m, 4H); 4.90 (dd, J=3.8 and 9.8 Hz, 1H); 5.12 (m, 1H); 5.80 (dd, J=2.0 and 15.2 Hz, 1H); 6.47 (ddd, J=3.8, 11.3 and 15.2 Hz, 1H); 7.05 (d, J=8.6 Hz, 1H); 7.16 (dd, J=2.4 and 8.6 Hz, 1H); 7.24 (m, 5H); 7.29 (d, J=2.4 Hz, 1H); 7.76 (t, J=6.0 Hz, 1H); 7.86 (t, J=8.0 Hz, 1H); 7.93 (broad m, 3H); 8.38 (d, J=8.0 Hz, 1H); 8.49 (d, J=8.0 Hz, 1H); 8.59 (t, J=6.0 Hz, 1H). LCMS (A): ES m/z=655 [M+2H]$^{2+}$; m/z=1306 [M−H]$^-$; m/z=1308 [M+H]$^+$; $t_R$=1.07 min.

Example 33: Sodium (25S,28S)-33-carboxy-25-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclo-hexadec-13-en-16-yl)ethyl)oxiran-2-yl)benzyl)carbamoyl)-28-isopropyl-4,19,27,30-tetraoxo-7,10,13,16-tetraoxa-3,20,26,29-tetraazatritriacontane-1-sulfonate To a solution of compound 77 (73 mg, 54.9 μmol) in DMF was added glutaric anhydride (11 mg, 96.4 μmol). The reaction medium was stirred for 20 h at RT, concentrated in vacuo and purified by flash chromatography on 4 g of silica gel (DCM/MeOH/H$_2$O) to give 40 mg of example 33 as a white lacquer (50%).
RMN $^1$H (400 MHz, δ in ppm, DMSO-d6): 0.81 (s, 9H); 1.04 (d, J=7.0 Hz, 3H); 1.38 (s, 9H); 1.50 (dd, J=3.0 and 14.5 Hz, 1H); 1.58 (dd, J=9.1 and 14.5 Hz, 1H); 2.38 to 2.48 (partially masked m, 3H); 4.04 (m, 1H); 4.19 (m, 2H); 4.30 (m, 1H); 4.49 (s, 2H); 4.91 (m, 1H); 5.80 (d, J=16.0 Hz, 1H); 6.17 (dd, J=8.4 and 16.0 Hz, 1H); 6.43 (d, J=16.0 Hz, 1H); 6.70 (m, 1H); 7.23 to 7.44 (m, 8H); 7.68 (m, 2H); 7.79 (d, J=8.3 Hz, 1H); 7.88 (d, J=7.8 Hz, 2H). LCMS (A): ES m/z=712 [M+2H]$^{2+}$; m/z=1420 [M−H]$^−$; m/z=1422 [M+H]$^+$; $t_R$=1.57 min.

Example 34: Sodium (25S,28S)-25-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)-34-((2,5-dioxopyrrolidin-1-yl)oxy)-28-isopropyl-4,19,27,30,34-pentaoxo-7,10,13,16-tetraoxa-3,20,26,29-tetraazatetratriacontane-1-sulfonate To a solution of example 33 (3.57 mg, 2.47 μmol) in DMA (93 μL) were added NHS (27.2 μL, 2.72 μmol) and EDC (111 μL, 2.22 μmol). The reaction medium was stirred for 48 h at RT: LCMS analysis showed that the presence of expected example 34 at 95% with 5% of residual example 33. This solution was used such as for conjugation and the preparation of example 35.

Example 35: hu2H11_R35-74-Ex34

The general method described previously was used for the preparation of example 35. 11.16 mg of hu2H11_R35-74 were reacted with 53 μL of a 10 mM solution of example 34 in DMA (7 eq.) for 2 h 30 then were added 15 μL of a 10 mM solution of example 34 in DMA (2 eq.) for 2 h 30. After purification on PD-10 and Nap-10 columns in buffer B pH 6.5+5% NMP, 9.5 mg of example 34 were obtained as a colorless limpid solution at a concentration of 1.9 mg/mL with a DAR of 3.8 (HRMS), a monomeric purity of 97.5% and a global yield of 82%.

SEC-HRMS: m/z=149330 (naked mAb); m/z=150744 (D1); m/z=152147 (D2); m/z=153554 (D3); m/z=154959 (D4); m/z=156366 (D5); m/z=157771 (D6); m/z=159172 (D7); m/z=160578 (D8).

Synthesis of Examples 36 & 37: glutaryl-Val-PEG4Lys-PABA-C52 Benzylic Amine and NHS Ester of glutaryl-Val-PEG4Lys-PABA-C52 Benzylic Amine

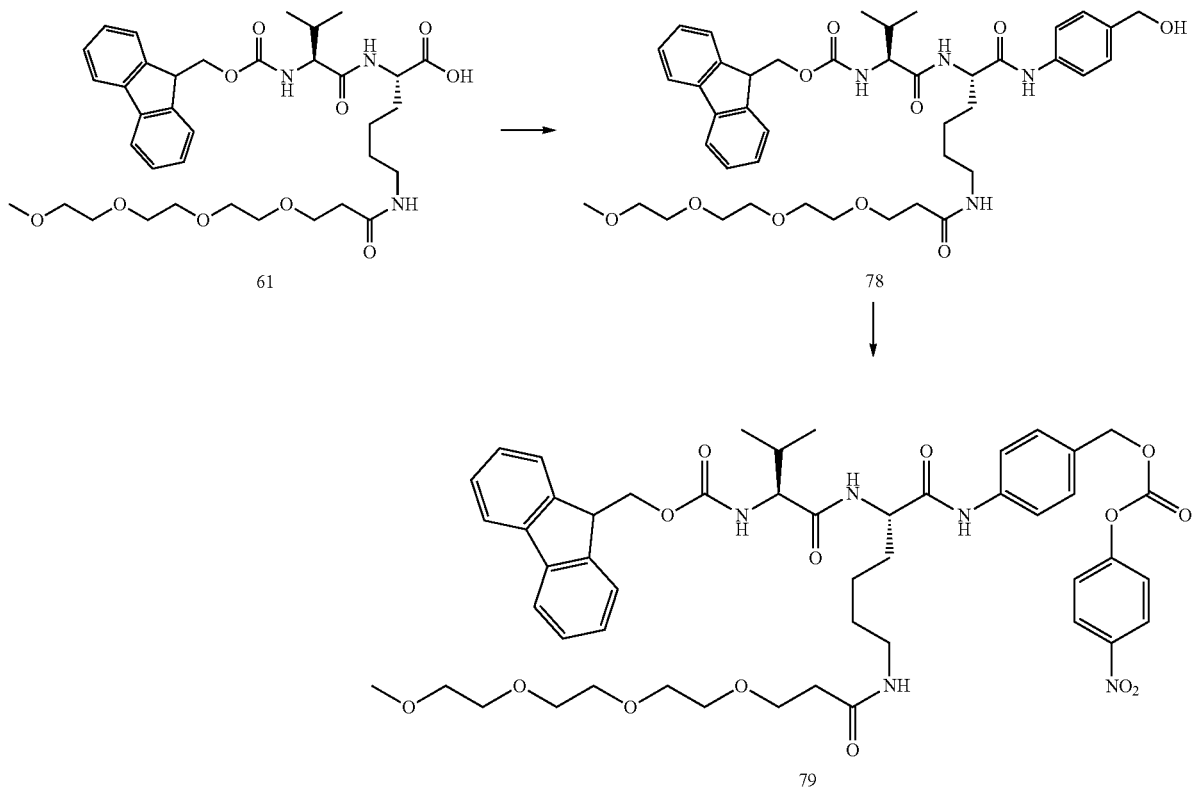

295 296
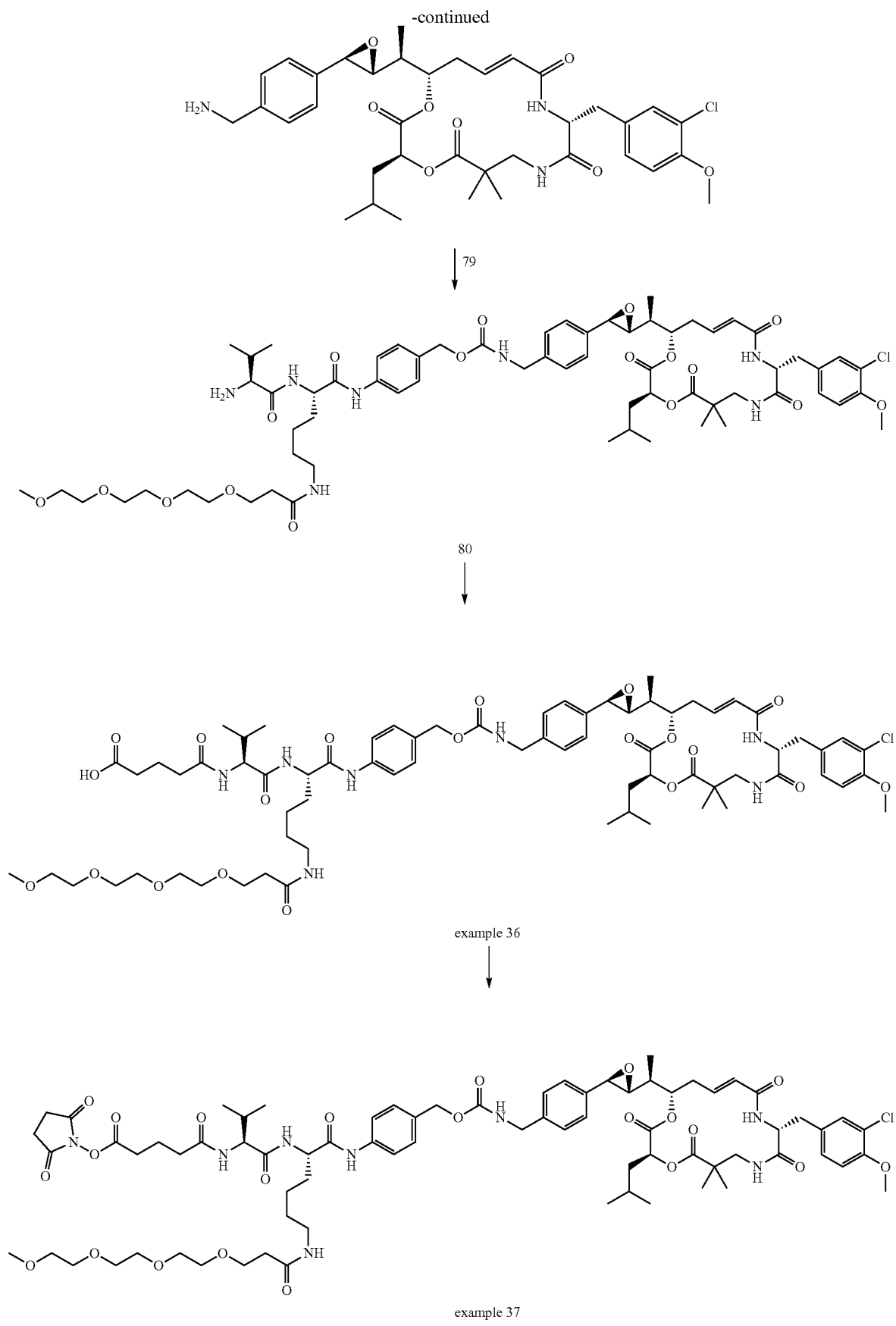
-continued
↓ 79
↓ 80
example 36
↓
example 37

Compound 78: (9H-fluoren-9-yl)methyl ((20S,23S)-20-((4-(hydroxymethyl)phenyl)carbamoyl)-24-methyl-14,22-dioxo-2,5,8,11-tetraoxa-15,21-diazapentacosan-23-yl)carbamate To a solution of compound 61 (180 mg, 257.2 µmol) in MeCN (35 mL) were added, under Ar, DIEA (130 µL, 771.7 µmol), 4-aminobenzyl alcohol (48 mg, 385.8 µmol), HOAt (41 mg, 295.8 µmol), HATU (147 mg, 385.8 µmol). The reaction medium was stirred for 17 h at RT then were added MeOH (30 mL) and silica, the mixture was concentrated in vacuo and purified by flash chromatography on 30 g of silica gel (gradient elution DCM/MeOH) to give 94 mg of compound 78 as a beige solid (46%).

RMN $^1$H (300 MHz, δ in ppm, DMSO-d6): 0.85 (d, J=7.0 Hz, 3H); 0.88 (d, J=7.0 Hz, 3H); 1.18 to 1.45 (m, 4H); 1.52 to 1.70 (m, 2H); 1.99 (m, 1H); 2.27 (m, 2H); 3.00 (m, 2H); 3.22 (s, 3H); 3.35 to 3.51 (m, 12H); 3.55 (t, J=6.8 Hz, 2H); 3.90 (dd, J=7.2 and 9.1 Hz, 1H); 4.18 to 4.56 (m, 4H); 4.42 (d, J=5.9 Hz, 2H); 5.07 (t, J=5.9 Hz, 1H); 7.22 (d, J=8.9 Hz, 2H); 7.31 (dt, J=1.8 and 7.8 Hz, 2H); 7.40 (m, 3H); 7.53 (d, J=8.9 Hz, 2H); 7.73 (m, 3H); 7.88 (d, J=7.8 Hz, 2H); 8.02 (d, J=8.2 Hz, 1H); 9.92 (s, 1H).

Compound 79: (9H-fluoren-9-yl)methyl ((20S,23S)-24-methyl-20-((4-((((4-nitrophenoxy)-carbonyl)oxy)methyl)phenyl)carbamoyl)-4,22-dioxo-2,5,8,11-tetraoxa-15,21-diazapentacosan-23-yl)carbamate To a solution of compound 78 (94 mg, 118.9 µmol) in DMF were added bis (4-nitrophenyl) carbonate (112 mg, 357.1 µmol) and DIEA (40 µL, 237.2 µmol). The reaction medium was stirred 20 h at RT, concentrated in vacuo, diluted with DCM (10 mL) and washed with H$_2$O (10 mL). The organic phase was dried over MgSO$_4$, filtered, concentrated in vacuo and purified by flash chromatography on 12 g of silica gel (gradient elution DCM/MeOH) to give 55 mg of compound 79 as a brown solid (48%).

RMN $^1$H (400 MHz, δ in ppm, DMSO-d6): 0.86 (d, J=7.0 Hz, 3H); 0.88 (d, J=7.0 Hz, 3H); 1.18 to 1.45 (m, 4H); 1.55 to 1.77 (m, 2H); 1.99 (m, 1H); 2.27 (t, J=6.8 Hz, 2H); 3.00 (m, 2H); 3.21 (s, 3H); 3.40 to 3.52 (m, 12H); 3.57 (t, J=6.8 Hz, 2H); 3.91 (m, 1H); 4.20 to 4.41 (m, 4H); 5.24 (s, 2H); 7.31 (t, J=7.8 Hz, 2H); 7.35 to 7.48 (m, 5H); 7.58 (d, J=9.2 Hz, 2H); 7.63 (d, J=8.8 Hz, 2H); 7.74 (m, 2H); 7.80 (t, J=6.0 Hz, 1H); 7.90 (d, J=7.8 Hz, 2H); 8.10 (d, J=8.0 Hz, 1H); 8.32 (d, J=9.2 Hz, 2H); 10.12 (s, 1H). LCMS (A): ES m/z=956 [M+H]$^+$; m/z=978 [M+Na]$^+$; m/z=1000 [M−H+HCO$_2$H]$^-$; t$_R$=1.45 min.

Compound 80: 4-((S)-20-((S)-2-amino-3-methylbutanamido)-14-oxo-2,5,8,11-tetraoxa-15-azahenicosanamido)benzyl 4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16yl)ethyl)-oxiran-2-yl)benzylcarbamate To a solution (E)-(3S,10R,16S)-16-{(S)-1-[(2R,3R)-3-(4-aminomethyl-phenyl)-oxiranyl]-ethyl}-10-(3-chloro-4-methoxy-benzyl)-3-isobutyl-6,6-dim ethyl-1,4-dioxa-8,11-diaza-cyclohexadec-13-ene-2,5,9,12-tetraone (the synthesis of which was described in WO2011001052, compound 77, 19 mg, 27.2 µmol) in DCM (2.5 mL) were added a solution of compound 79 (58 mg, 60.7 µmol) in DCM (2.5 mL) and DIEA (15 µL, 86.6 µmol). The reaction medium was stirred for 20 h at RT, concentrated in vacuo and purified by flash chromatography on 4 g of silica gel (gradient elution DCM/MeOH) to give 38 mg of Fmoc-protected intermediate as a colorless lacquer (92%).

RMN $^1$H (400 MHz, δ in ppm, DMSO-d6): 0.79 (d, J=6.7 Hz, 6H); 0.86 (d, J=7.0 Hz, 3H); 0.88 (d, J=7.0 Hz, 3H); 1.00 (s, 3H); 1.03 (d, J=7.0 Hz, 3H); 1.12 (s, 3H); 1.20 to 1.45 (m, 5H); 1.50 to 1.75 (m, 4H); 1.80 (m, 1H); 2.00 (m, 1H); 2.27 (m, 3H); 2.69 (m, 2H); 2.92 to 3.04 (m, 5H); 3.21 (s, 3H); 3.32 (masked m, 1H); 3.35 to 3.51 (m, 12H); 3.56 (t, J=6.6 Hz, 2H); 3.80 (s, 3H); 3.87 (d, J=2.2 Hz, 1H); 3.91 (dd, J=7.1 and 9.1 Hz, 1H); 4.15 to 4.42 (m, 7H); 4.90 (dd, J=3.7 and 9.8 Hz, 1H); 4.97 (s, 2H); 5.10 (m, 1H); 5.79 (dd, J=2.0 and 15.2 Hz, 1H); 6.48 (ddd, J=3.8, 11.1 and 15.2 Hz, 1H); 7.04 (d, J=8.6 Hz, 1H); 7.17 (dd, J=2.4 and 8.6 Hz, 1H); 7.20 to 7.34 (m, 10H); 7.41 (m, 3H); 7.58 (d, J=8.6 Hz, 2H); 7.70 to 7.80 (m, 4H); 7.89 (d, J=7.8 Hz, 2H); 8.06 (d, J=7.6 Hz, 1H); 8.35 (d, J=8.3 Hz, 1H); 10.03 (s, 1H). LCMS (A): ES m/z=698; m/z=1514 [M+H]$^+$; m/z=1558 [M−H+HCO$_2$H]$^-$; t$_R$=1.56 min.

To a solution of this intermediate (35 mg, 23.1 µmol) in DCM (5 mL) was added piperidine (20 µL, 201.5 µmol). The reaction medium was stirred for 1 h 30 at RT then DMF (1 mL) was added and stirring carried on for 1 h 30. Then was added piperidine (2 µL); the reaction medium was stirred for 1 h at RT, concentrated in vacuo and purified by flash chromatography on 4 g of silica gel (gradient elution DCM/MeOH) to give 25 mg of compound 80 as a colorless lacquer (83%).

RMN $^1$H (400 MHz, δ in ppm, DMSO-d6): 0.78 (d, J=6.7 Hz, 6H); 0.82 (d, J=7.0 Hz, 3H); 0.89 (d, J=7.0 Hz, 3H); 1.00 (s, 3H); 1.04 (d, J=7.1 Hz, 3H); 1.11 (s, 3H); 1.22 to 1.48 (m, 5H); 1.51 to 1.75 (m, 6H); 1.80 (m, 1H); 1.98 (m, 1H); 2.28 (m, 3H); 2.69 (m, 2H); 2.92 to 3.05 (m, 7H); 3.15 (m, 1H); 3.21 (s, 3H); 3.32 (masked m, 1H); 3.35 to 3.51 (m, 12H); 3.57 (t, J=6.7 Hz, 2H); 3.80 (s, 3H); 3.87 (d, J=2.2 Hz, 1H); 4.19 (d, J=6.4 Hz, 2H); 4.23 (ddd, J=3.9, 8.3 and 11.8 Hz, 1H); 4.43 (m, 2H); 4.90 (dd, J=3.7 and 9.8 Hz, 1H); 4.98 (s, 2H); 5.10 (m, 1H); 5.80 (dd, J=2.0 and 15.2 Hz, 1H); 6.48 (ddd, J=3.9, 11.3 and 15.2 Hz, 1H); 7.05 (d, J=8.6 Hz, 1H); 7.18 (dd, J=2.4 and 8.6 Hz, 1H); 7.20 to 7.32 (m, 8H); 7.59 (d, J=8.6 Hz, 2H); 7.79 (t, J=6.0 Hz, 1H); 7.82 (t, J=6.4 Hz, 1H); 8.21 (m, 1H); 8.39 (d, J=8.3 Hz, 1H); 10.13 (s, 1H). LCMS (A): ES m/z=646.5; m/z=1292 [M+H]$^+$; t$_R$=1.05 min.

Example 36: (20S,23S)-20-((4-(((((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)oxy)methyl)-phenyl)carbamoyl)-23-isopropyl-14,22,25-trioxo-2,5,8,11-tetraoxa-15,21,24-triazanonacosan-29-oic Acid To a solution of compound 80 (25 mg, 19.3 µmol) in DCM (5 mL) was added glutaric anhydride (4 mg, 19.3 µmol). The reaction medium was stirred for 2 h 30 at RT then were added glutaric anhydride (4 mg, 19.3 µmol) and DMF (0.5 mL) and stirring carried on for 26 h. The reaction medium was concentrated in vacuo and purified by flash chromatography on 4 g of silica gel (gradient elution DCM/MeOH) to give 10 mg of example 36 as a white lacquer (37%).

Example 37: (20S,23S)-2,5-dioxopyrrolidin-1-yl 20-((4-((((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)-carbamoyl)oxy)methyl)phenyl)-carbamoyl)-23-isopropyl-14,22,25-trioxo-2,5,8,11-tetraoxa-15,21,24-triazanonacosan-29-oate To a solution of example 36 (10 mg, 7.11 µmol) in THF (2 mL) were added DSC (2 mg, 7.65 µmol) and DIEA (1.2 µL, 7.26 µmol). The reaction medium was stirred for 20 h at RT, concentrated in vacuo and purified by two consecutive flash chromatographies on 0.6 g and 2 g of silica gel (gradient elution DCM/iPrOH) to give 3.3 mg of example 37 as a white lacquer (31%).

Synthesis of Examples 38 & 39:
glutaryl-Val-PEG24Lys-PABA-C52 Benzylic Amine and NHS Ester of glutaryl-Val-PEG24Lys-PABA-C52 Benzylic Amine

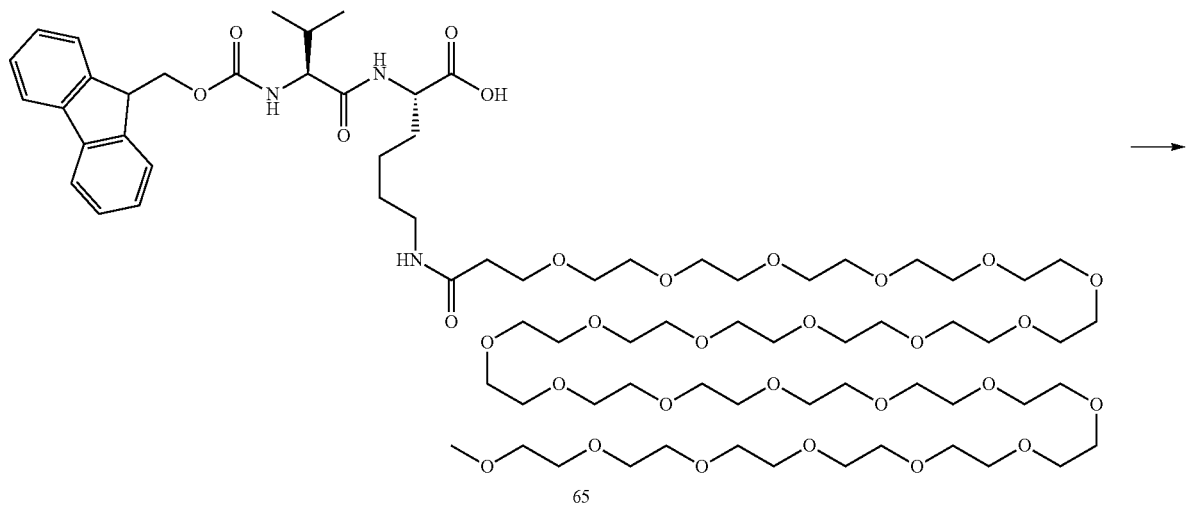
65

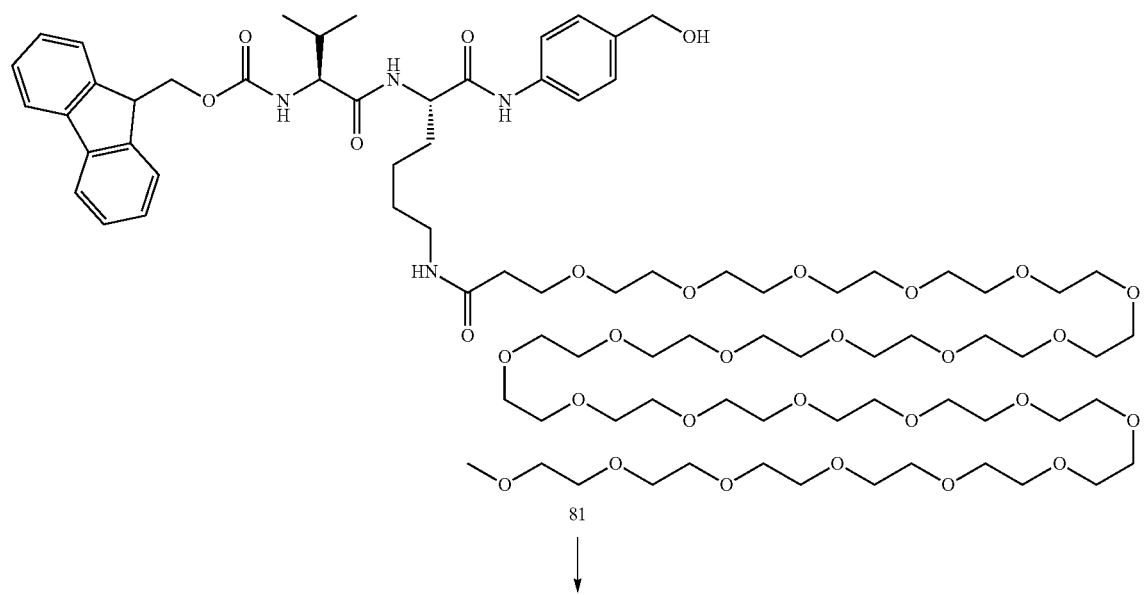
81

301 302
-continued
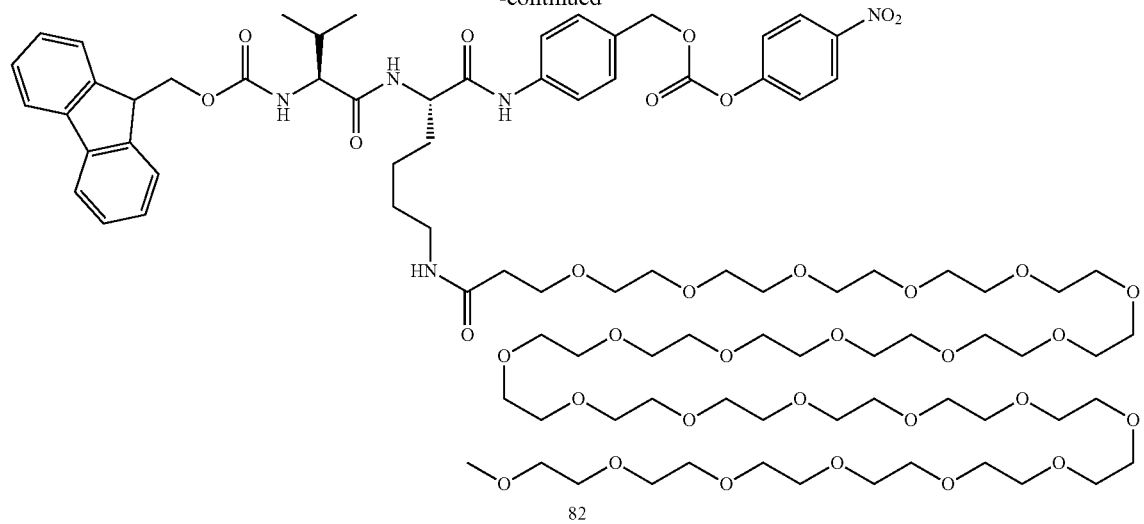
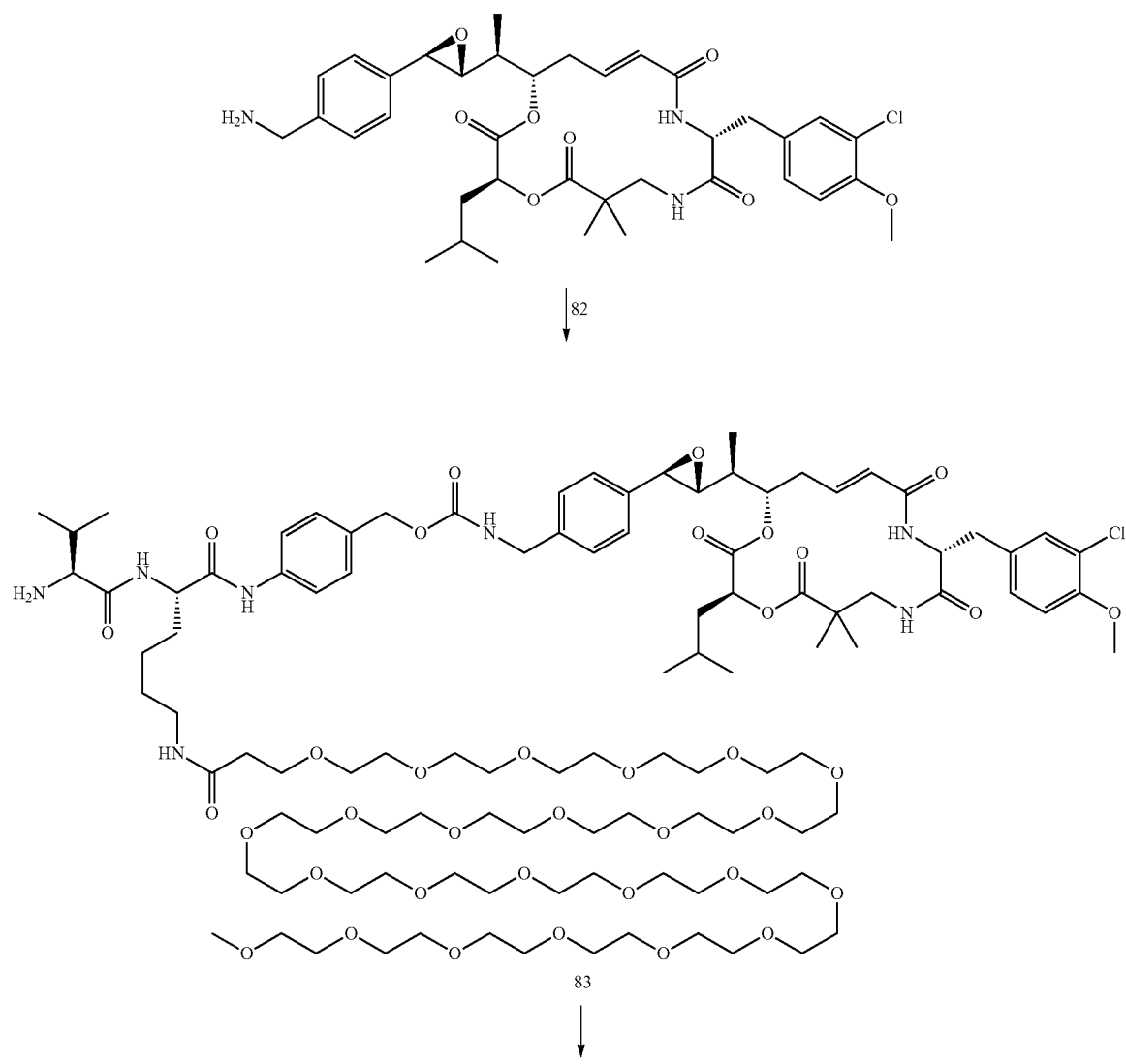

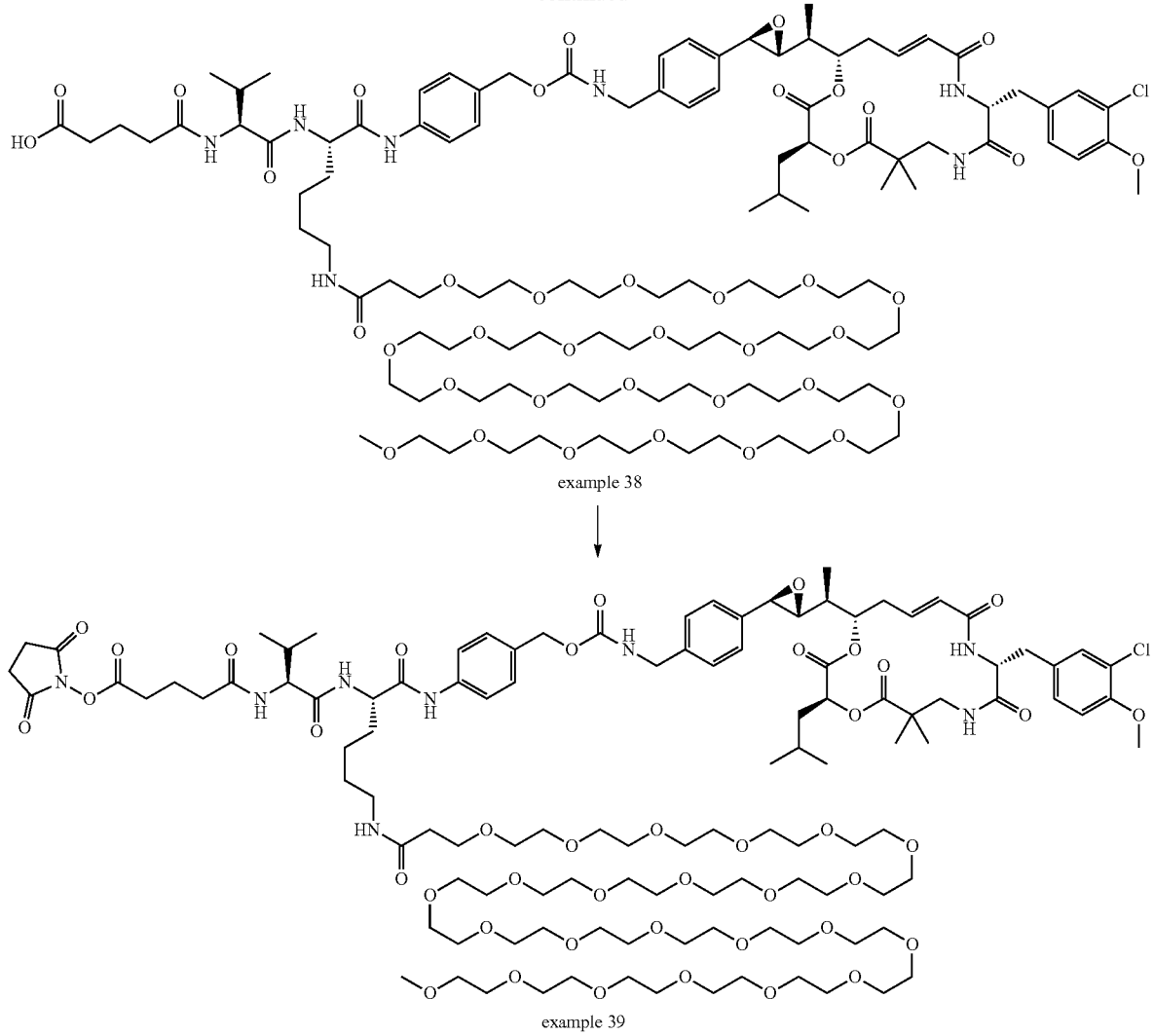

example 38 example 39

Compound 81: (9H-fluoren-9-yl)methyl ((80S,83S)-80-((4-(hydroxymethyl)phenyl)carbamoyl)-84-methyl-74,82-dioxo2,5,8,11,14,17,20,23,26,29,32,35,38,41,44,47,50,53,56,59,62,65,68,71-tetracosaoxa-75,81-diazapentaoctacontan-83-yl)carbamate To a solution of compound 65 (360 mg, 229.8 µmol) in MeCN (70 mL) were added DIEA (77 µL, 456.6 µmol), 4-aminobenzyl alcohol (43 mg, 342.2 µmol), HOAt (36 mg, 264.5 µmol) and HATU (109 mg, 278.1 µmol). The reaction medium was stirred for 2 h at RT, concentrated in vacuo and purified by flash chromatography on 25 g of silica gel (gradient elution DCM/MeOH/H$_2$O) to give 307 mg of compound 81 as a white solid (80%).

RMN $^1$H (400 MHz, δ in ppm, DMSO-d6): 0.85 (d, J=7.0 Hz, 3H); 0.88 (d, J=7.0 Hz, 3H); 1.21 to 1.42 (m, 4H); 1.54 to 1.78 (m, 2H); 1.99 (m, 1H); 2.27 (t, J=6.8 Hz, 2H); 3.00 (m, 2H); 3.22 (s, 3H); 3.40 to 3.52 (m, 92H); 3.54 (t, J=6.8 Hz, 2H); 3.91 (dd, J=6.9 and 9.0 Hz, 1H); 4.18 to 4.32 (m, 3H); 4.39 (m, 1H); 4.42 (d, J=5.9 Hz, 2H); 5.08 (t, J=5.9 Hz, 1H); 7.22 (d, J=8.9 Hz, 2H); 7.32 (dt, J=1.2 and 7.8 Hz, 2H); 7.41 (m, 3H); 7.53 (d, J=8.9 Hz, 2H); 7.75 (m, 3H); 7.89 (d, J=7.8 Hz, 2H); 8.02 (d, J=8.2 Hz, 1H); 9.92 (s, 1H). LCMS (d): ES m/z=827; m/z=1671 [M+H]$^+$; t$_R$=2.94 min.

Compound 82: (9H-fluoren-9-yl)methyl ((80S,83S)-84-methyl-80-((4-((((4-nitrophenoxy)-carbonyl)oxy)methyl)phenyl)carbamoyl)-74,82-dioxo-2,5,8,11,14,17,20,23,26,29,32,35,38,41,44,47,50,53,56,59,62,65,68,71-tetracosaoxa-75,81-diazapentaoctacontan-83-yl)carbamate To a solution of compound 81 (300 mg, 179.4 µmol) in DCM (10 mL) were added bis (4-nitrophenyl) carbonate (450 mg, 1.48 mmol) and DIEA (60 µL, 361.2 µmol). The reaction medium was stirred at RT overnight then was added bis (4-nitrophenyl) carbonate (80 mg, 263.1 µmol) and stirring carried on for 4 h. At that time was added bis (4-nitrophenyl) carbonate (80 mg, 263.1 µmol) and stirring carried on overnight. The reaction medium was concentrated in vacuo and purified by flash chromatography on 80 g of silica gel (gradient elution DCM/MeOH/H$_2$O) to give 325 mg of compound 82 as a white lacquer (98%).

RMN $^1$H (400 MHz, δ in ppm, DMSO-d6): 0.86 (d, J=7.0 Hz, 3H); 0.89 (d, J=7.0 Hz, 3H); 1.20 to 1.45 (m, 4H); 1.58 to 1.76 (m, 2H); 1.99 (m, 1H); 2.27 (t, J=6.8 Hz, 2H); 3.00 (m, 2H); 3.22 (s, 3H); 3.40 to 3.70 (m, 94H); 3.91 (dd, J=7.2 and 9.1 Hz, 1H); 4.19 to 4.32 (m, 3H); 4.39 (m, 1H); 5.24 (s, 2H); 7.31 (dt, J=1.2 and 7.8 Hz, 2H); 7.40 (m, 4H); 7.57 (d, J=9.2 Hz, 2H); 7.62 (d, J=8.6 Hz, 2H); 7.73 (m, 3H); 7.89 (d, J=7.8 Hz, 2H); 8.07 (d, J=7.8 Hz, 1H); 8.31 (d, J=9.2 Hz, 2H); 10.10 (s, 1H). LCMS (d): ES m/z=827; m/z=1836 [M+H]$^+$; $t_R$=3.38 min.

Compound 83: 4-((S)-80-((S)-2-amino-3-methylbutanamido)-74-oxo-2,5,8,11,14,17,20,23,26,29,32,35,38,41,47,50,53,56,59,62,65,68,71-tetracosaoxa-75-azahenoctacontanamido)-benzyl 4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl-carbamate To a solution of (E)-(3S,10R,16S)-16-{(S)-1-[(2R,3R)-3-(4-aminomethyl-phenyl)-oxiranyl]-ethyl}-10-(3-chloro-4-methoxy-benzyl)-3-isobutyl-6,6-dim ethyl-1,4-dioxa-8,11-diaza-cyclohexadec-13-ene-2,5,9,12-tetraone (the synthesis of which was described in WO2011001052, compound 77, 79 mg, 113.1 μmol) in DCM (5 mL) were added a solution of compound 82 (325 mg, 177.5 μmol) in DCM (5 mL) and DIEA (63 μL, 365.6 μmol). The reaction medium was stirred for 20 h at RT then was added compound 82 (34 mg, 18.6 μmol) and stirring carried on for 4 h. The reaction medium was concentrated in vacuo and purified by two consecutive flash chromatographies on 25 g of silica gel and 15 g of diol-modified silica gel (gradient elution DCM/MeOH) to give 152 mg of crude product that was purified by reverse phase chromatography on a 10 μm C18 column 250×40 mm (gradient elution MeCN/H$_2$O) to give 78 mg of the Fmoc-protected intermediate containing 16% of compound 83 as a white powder (29%).

RMN $^1$H (500 MHz, δ in ppm, DMSO-d6): 0.78 (d, J=6.8 Hz, 6H); 0.85 (d, J=7.0 Hz, 3H); 0.88 (d, J=7.0 Hz, 3H); 1.00 (s, 3H); 1.04 (d, J=7.1 Hz, 3H); 1.12 (s, 3H); 1.20 to 1.43 (m, 5H); 1.50 to 1.74 (m, 4H); 1.79 (m, 1H); 1.99 (m, 1H); 2.25 (m, 3H); 2.68 (m, 2H); 2.93 to 3.04 (m, 5H); 3.22 (s, 3H); 3.32 (masked m, 2H); 3.40 to 3.76 (m, 94H); 3.80 (s, 3H); 3.87 (d, J=2.0 Hz, 1H); 3.90 (dd, J=7.5 and 9.1 Hz, 1H); 4.19 (d, J=6.5 Hz, 2H); 4.20 to 4.33 (m, 4H); 4.39 (m, 1H); 4.90 (dd, J=3.9 and 9.9 Hz, 1H); 4.93 (s, 2H); 5.11 (m, 1H); 5.79 (dd, J=1.8 and 15.2 Hz, 1H); 6.47 (ddd, J=3.8, 11.4 et 15.2 Hz, 1H); 7.05 (d, J=8.6 Hz, 1H); 7.17 (dd, J=2.4 and 8.6 Hz, 1H); 7.20 to 7.36 (m, 10H); 7.41 (m, 3H); 7.48 (d, J=8.6 Hz, 2H); 7.70 to 7.80 (m, 5H); 7.89 (d, J=7.8 Hz, 2H); 8.08 (d, J=8.0 Hz, 1H); 8.35 (d, J=8.0 Hz, 1H); 10.04 (s, 1H).

To a solution of this intermediate (75 mg, 31.3 μmol) in DMF (5 mL) was added piperidine (25 μL, 253.2 μmol). The reaction medium was stirred for 1 h 30 at RT, concentrated in vacuo and purified by flash chromatography on 4 g of silica gel (gradient elution DCM/MeOH/H$_2$O) to give 58 mg of compound 83 as a white lacquer (85%).

RMN $^1$H (500 MHz, δ in ppm, DMSO-d6): 0.78 (d, J=6.9 Hz, 9H); 0.88 (d, J=7.0 Hz, 3H); 1.00 (s, 3H); 1.05 (d, J=7.1 Hz, 3H); 1.12 (s, 3H); 1.15 to 1.50 (m, 7H); 1.52 to 1.73 (m, 4H); 1.80 (m, 1H); 1.93 (m, 1H); 2.27 (m, 3H); 2.69 (m, 2H); 2.95 to 3.04 (m, 6H); 3.23 (s, 3H); 3.32 (m, 1H); 3.40 to 3.55 (m, 92H); 3.57 (t, J=6.8 Hz, 2H); 3.80 (s, 3H); 3.87 (d, J=2.2 Hz, 1H); 4.20 (d, J=6.5 Hz, 2H); 4.24 (ddd, J=3.9, 8.2 and 12.0 Hz, 1H); 4.42 (m, 1H); 4.90 (dd, J=3.8 and 9.8 Hz, 1H); 4.98 (s, 2H); 5.10 (m, 1H); 5.79 (d, J=15.8 Hz, 1H); 6.47 (ddd, J=3.8, 6.0 and 11.5 Hz, 1H); 7.05 (d, J=8.6 Hz, 1H); 7.16 (dd, J=2.4 and 8.6 Hz, 1H); 7.20 to 7.31 (m, 8H); 7.58 (d, J=8.6 Hz, 2H); 7.78 (m, 2H); 8.10 (d, J=8.6 Hz, 1H); 8.36 (d, J=8.1 Hz, 1H); 10.10 (s, 1H). LCMS (d): ES m/z=725; m/z=1087 [M+2H]$^{2+}$; $t_R$=1.07 min.

Example 38: (80S,83S)-80-((4-(((((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)oxy)methyl)-phenyl)carbamoyl)-83-isopropyl-74,82,85-trioxo-2,5,8,11,14,17,20,23,26,29,32,35,38,41,44,47,50,53,56,59,62,65,68,71-tetracosaoxa-75,81,84-triazanonaoctacontan-89-oic Acid To a solution of compound 83 (58 mg, 26.7 μmol) in DCM (2 mL) was added glutaric anhydride (5.5 mg, 48.2 μmol). The reaction medium was stirred for 3 h at RT, concentrated in vacuo and purified by two consecutive flash chromatographies on 4 g and 12 g of silica gel (gradient elution DCM/MeOH/H$_2$O) to give 37 mg of example 38 as a white lacquer (61%).

RMN $^1$H (500 MHz, δ in ppm, DMSO-d6): 0.79 (d, J=6.8 Hz, 6H); 0.93 (d, J=7.0 Hz, 3H); 0.97 (d, J=7.0 Hz, 3H); 1.00 (s, 3H); 1.04 (d, J=7.1 Hz, 3H); 1.12 (s, 3H); 1.20 to 1.45 (m, 5H); 1.51 to 1.75 (m, 6H); 1.80 (m, 1H); 2.00 (m, 1H); 2.13 to 2.33 (m, 7H); 2.69 (m, 2H); 2.95 to 3.05 (m, 5H); 3.23 (s, 3H); 3.32 (m, 1H); 3.40 to 3.58 (m, 94H); 3.80 (s, 3H); 3.87 (d, J=2.2 Hz, 1H); 4.15 to 4.38 (m, 4H); 4.32 (m, 1H); 4.90 (dd, J=3.8 and 9.8 Hz, 1H); 4.98 (s, 2H); 5.10 (m, 1H); 5.79 (d, J=15.2 Hz, 1H); 6.47 (ddd, J=3.8, 11.4 and 15.2 Hz, 1H); 7.05 (d, J=8.6 Hz, 1H); 7.16 (dd, J=2.4 and 8.6 Hz, 1H); 7.20 to 7.32 (m, 8H); 7.60 (d, J=8.6 Hz, 2H); 7.78 (t, J=6.5 Hz, 1H); 7.90 (broad d, J=8.6 Hz, 2H); 8.20 (m, 1H); 8.38 (d, J=8.6 Hz, 2H); 10.08 (m, 1H); 12.10 (m, 1H). LCMS (d): ES m/z=698; m/z=2287 [M+H]$^+$; $t_R$=3.13 min.

Example 39: (80S,83S)-2,5-dioxopyrrolidin-1-yl 80-((4-(((((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diaza-cyclohexadec-13-en-16-yl)ethyl)oxiran-2-yl)benzyl)carbamoyl)oxy)methyl)phenyl)carbamoyl)-83-isopropyl-74,82,85-trioxo2,5,8,11,14,17,20,23,26,29,32,35,38,41,44,47,50,53,56,59,62,65,68,71-tetracosaoxa-75,81,84-triazanonaoctacontan-89-oate To a solution of example 38 (29 mg, 12.7 μmol) in THF (3 mL) were added DSC (3.6 mg, 13.8 μmol) and DIEA (2.1 μL, 12.9 μmol). The reaction medium was stirred for 20 h at RT, concentrated in vacuo and purified by flash chromatography on 4 g of silica gel (gradient elution DCM/iPrOH) to give 6.9 mg of example 39 as a colorless lacquer (23%).

RMN $^1$H (500 MHz, δ in ppm, DMSO-d6): 0.79 (d, J=6.8 Hz, 6H); 0.93 (d, J=7.0 Hz, 3H); 0.97 (d, J=7.0 Hz, 3H); 1.00 (s, 3H); 1.04 (d, J=7.1 Hz, 3H); 1.11 (s, 3H); 1.13 to 1.42 (m, 5H); 1.52 to 1.88 (m, 7H); 1.98 (m, 1H); 2.28 (m, 5H); 2.53 to 2.72 (m, 4H); 2.80 (s, 4H); 2.96 to 3.05 (m, 5H); 3.23 (s, 3H); 3.32 (m, 1H); 3.60 to 3.65 (m, 94H); 3.80 (s, 3H); 3.87 (d, J=2.2 Hz, 1H); 4.15 to 4.28 (m, 4H); 4.33 (m, 1H); 4.90 (dd, J=3.8 and 9.8 Hz, 1H); 4.98 (s, 2H); 5.10 (m, 1H); 5.79 (d, J=15.8 Hz, 1H); 6.47 (ddd, J=3.8, 11.4 and 15.2 Hz, 1H); 7.05 (d, J=8.6 Hz, 1H); 7.17 (dd, J=2.4 and 8.6 Hz, 1H); 7.20 to 7.32 (m, 8H); 7.60 (d, J=8.6 Hz, 2H); 7.78 (m, 2H); 7.90 (d, J=8.5 Hz, 1H); 8.07 (m, 2H); 8.37 (d, J=8.5 Hz, 2H); 9.95 (s, 1H). LCMS (D): ES m/z=698; m/z=2384 [M+H]$^+$; $t_R$=3.19 min.

Synthesis of Examples 40 & 41:
DBCO-glutaryl-Val-PEG24Lys-PABA-C52
Benzylic Amine and Corresponding ADC

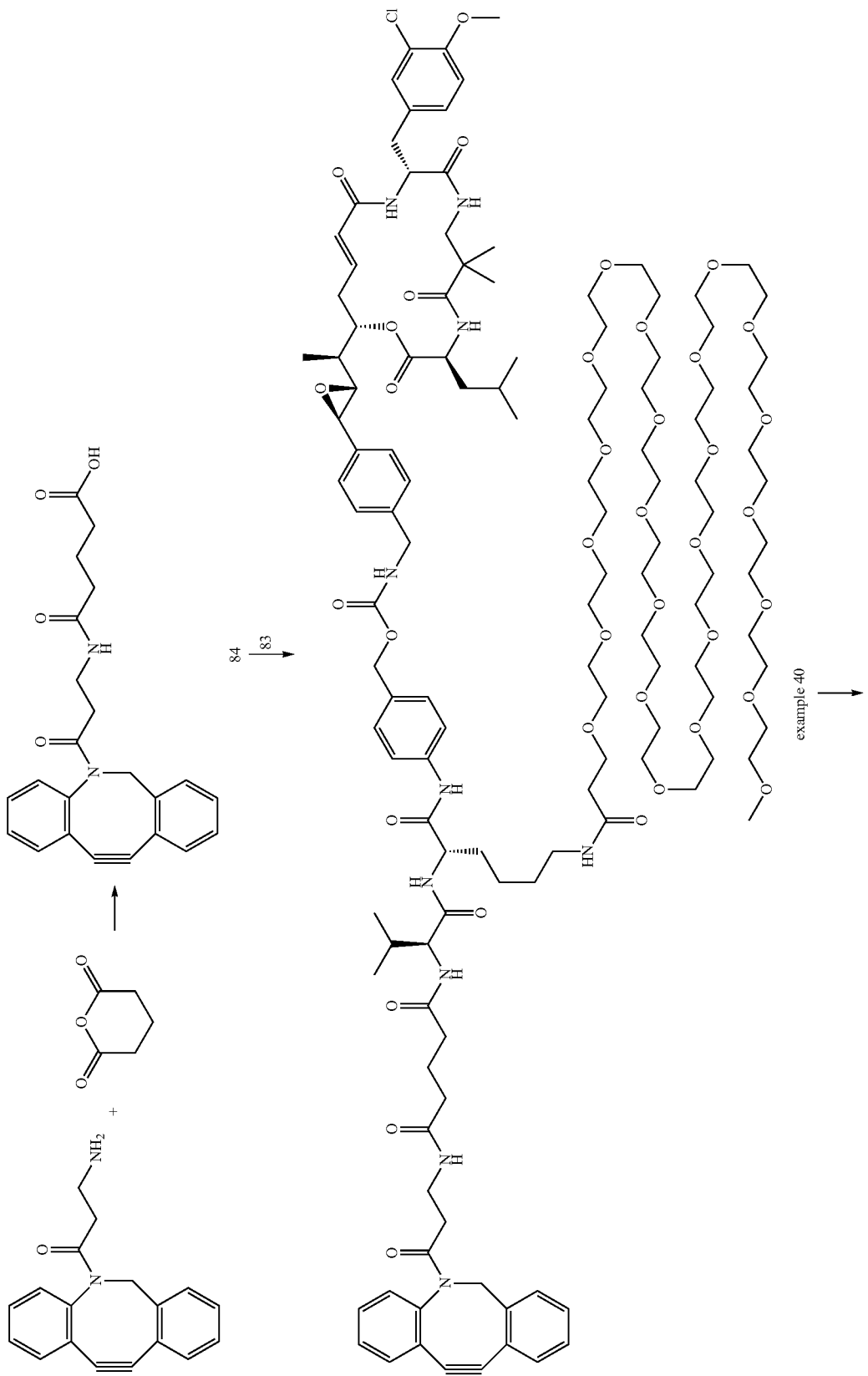

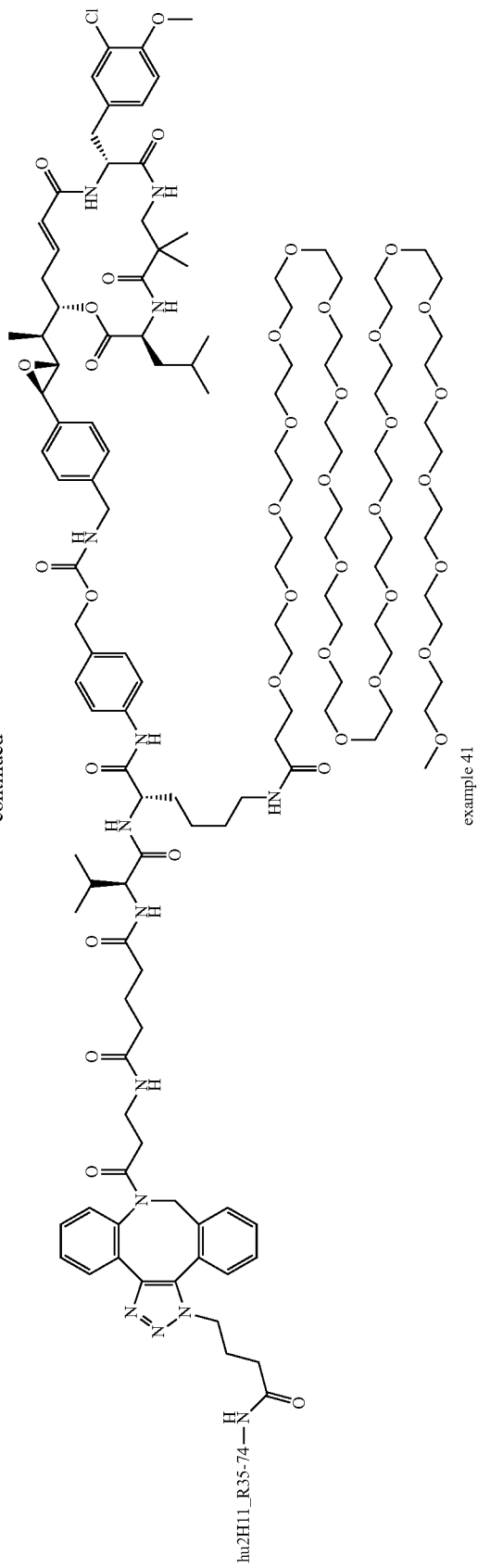

Compound 84: 5-[[3-(11,12-didehydrodibenz[b,f]azocin-5(6H)-yl)-3-oxopropyl]amino]-5-oxopentanoic Acid To a solution of DBCO-amine (50 mg, 180.9 μmol) in DCM (2 mL) was added glutaric anhydride (21.1 mg, 180.9 μmol). The reaction medium was stirred for 2 h at RT, concentrated in vacuo and purified by flash chromatography on 4 g of silica gel (gradient elution DCM/MeOH) to give 32.6 mg of compound 84 (45%).

RMN $^1$H (400 MHz, δ in ppm, DMSO-d6): 1.59 (m, 2H); 1.81 (m, 1H); 1.94 (t, J=7.4 Hz, 2H); 2.11 (t, J=7.4 Hz, 2H); 2.40 (m, 1H); 2.91 (m, 1H); 3.09 (m, 1H); 3.62 (d, J=14.2 Hz, 1H); 5.13 (d, J=14.2 Hz, 1H); 7.38 to 7.53 (m, 6H); 7.56 to 7.67 (m, 3H); 12.05 (broad m, 1H).

Example 40: DBCO-glutaryl-Val-PEG24Lys-PABA-C52 Benzylic Amine

To a solution of compound 83 (22 mg, 10.1 μmol) in DCM (2 mL) were added compound 84 (5.14 mg, 13.2 μmol), EDC (1.8 μL, 10.1 μmol) and HOBt (1.4 mg, 10.1 μmol). The reaction medium was stirred at RT overnight, concentrated in vacuo and purified by reverse phase chromatography on a C18-modified 5 μm column 150 mm×30 mm (gradient elution MeCN/0.2N ammonium acetate pH 5.6) to give 9.2 mg of example 40 as a white powder (36%).

RMN $^1$H (500 MHz, δ in ppm, DMSO-d6): 0.78 (d, J=6.8 Hz, 6H); 0.80 to 0.90 (m, 6H); 1.00 (s, 3H); 1.05 (d, J=7.1 Hz, 3H); 1.12 (s, 3H); 1.20 to 1.41 (m, 5H); 1.52 to 1.72 (m, 6H); 1.75 to 2.00 (m, 5H); 2.09 (m, 2H); 2.27 (m, 3H); 2.40 (m, 1H); 2.68 (m, 2H); 2.88 to 3.12 (m, 7H); 3.23 (s, 3H); 3.28 to 3.58 (partially masked m, 95H); 3.60 (d, J=11.0 Hz, 1H); 3.80 (s, 3H); 3.88 (d, J=2.0 Hz, 1H); 4.11 to 4.28 (m, 4H); 4.33 (m, 1H); 4.90 (dd, J=3.8 and 9.8 Hz, 1H); 4.97 (s, 2H); 5.04 (d, J=11.0 Hz, 1H); 5.11 (m, 1H); 5.80 (d, J=15.2 Hz, 1H); 6.47 (ddd, J=3.8, 11.4 and 15.2 Hz, 1H); 7.05 (d, J=8.6 Hz, 1H); 7.17 (dd, J=2.4 and 8.6 Hz, 1H); 7.20 to 7.31 (m, 6H); 7.32 to 7.50 (m, 6H); 7.53 to 7.70 (m, 4H); 7.80 (m, 3H); 8.08 (d, J=8.9 Hz, 1H); 8.36 (d, J=8.4 Hz, 1H); 9.95 (s, 1H). LCMS (D): ES m/z=849 [M+3H]$^{3+}$; m/z=1273 [M+2H]$^{2+}$; $t_R$=5.29 min.

Example 41: hu2H11_R35-74-Ex40

194 mg of hu2H11_R35-74 in buffer A were reacted with 627 μL of a solution of 2,5-dioxopyrrolidin-1-yl 4-azidobutanoate (CAS number [943858-70-6]) at 22.0 mM in DMA (10 eq.) such as the final antibody concentration was 10.5 mg/mL and the percentage of DMA in buffer A was 5%. After stirring for 2 h at RT, the mixture was purified by gel filtration using a a Sephadex™ G25 matrix (Hiprep 26/10 desalting column, GEHealthcare) pre-equilibrated in buffer A. The fractions containing the monomeric modified antibody were pooled and filtered through a Steriflip® filter unit (0.22 μm Durapore® PVDF membrane, Millipore) to provide 173 mg of modified antibody at a concentration of 5.75 mg/mL with a ratio of linker per antibody of 5.2 (HRMS), a monomeric purity of 97% and a global yield of 89%.

The general method described previously was used for the preparation of example 41. 45 mg of modified hu2H11_R35-74 were reacted with 604 μL of a 6.89 mM solution of example 40 in DMA (14 eq.) for 4 h 30 then were added 604 μL of a 10 mM solution of example 40 in DMA (14 eq.) and stirring was pursued overnight at RT. After purification on Superdex 200 pg in buffer B pH 6.5+20% NMP, concentration on Amicon Ultra-15, gel filtration on PD-10 in buffer B pH 6.5+5% NMP and filtration on 0.22 μm PVDF filter, 28 mg of example 41 were obtained as a colorless limpid solution at a concentration of 1.6 mg/mL with a DAR of 3.44 (HRMS), a monomeric purity of 99.6% and a yield of 62%.

SEC-HRMS: m/z=152041 (D1); m/z=154678 (D2); m/z=157332 (D3); m/z=159992 (D4); m/z=162648 (D5); m/z=165303 (D6); m/z=168004 (D7).

Synthesis of Example 42: sulfo-Val-PEG4Lys-C52 Benzylic Amine

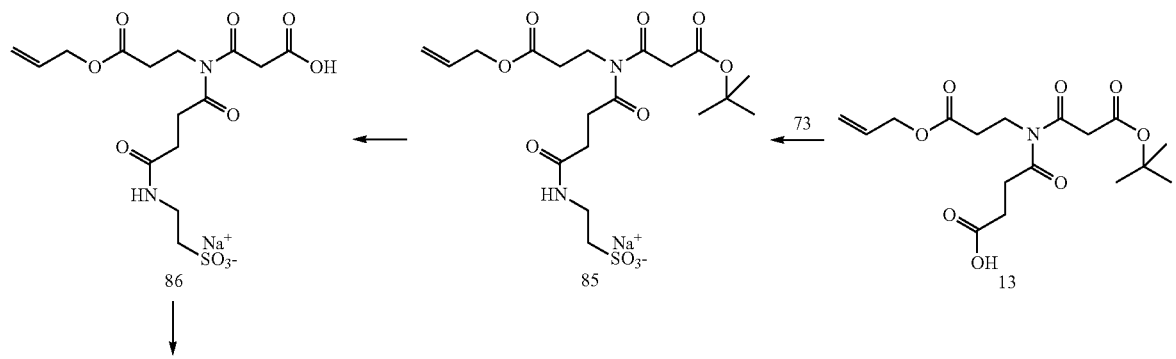

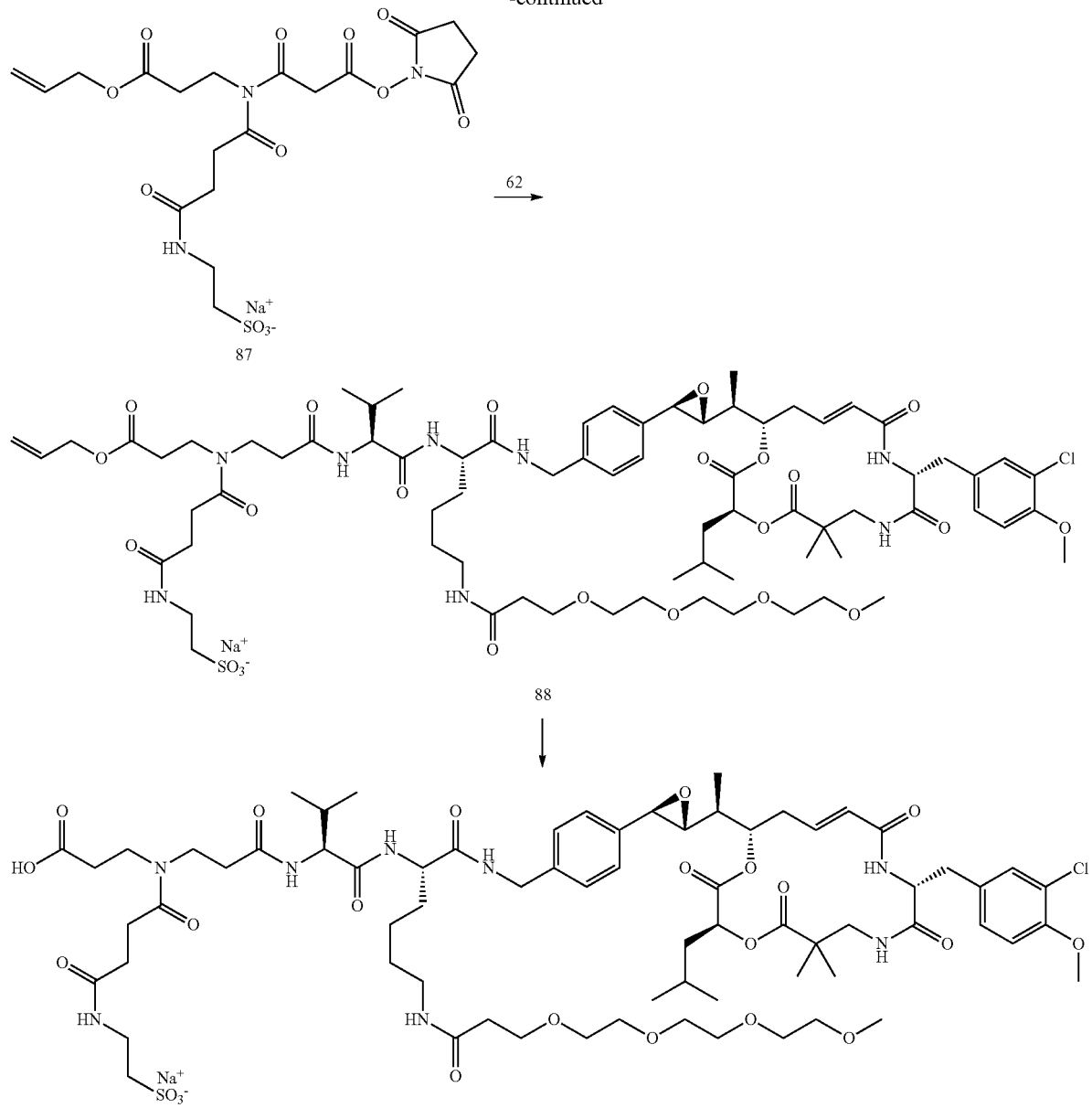

example 42

Compound 85: Sodium 2-(4-((3-(allyloxy)-3-oxopropyl)(3-(tert-butoxy)-3-oxopropyl)amino)-4-oxobutanamido)ethane-1-sulfonate To a solution of compound 13 (0.958 g, 2.68 mmol) in DMF (5 mL) were added NHS (390.3 mg, 3.32 mmol) and EDC (604.2 μL, 3.4 mmol). The reaction medium was stirred for 2 h at RT then stored 2 d at −20° C. After getting back at RT, the reaction medium was stirred for 2 h at RT then were added EDC (60 μL, 340 μmol) and a solution of NHS (20 mg, 170.3 μmol) in DMF (3 mL). The reaction medium was stirred at RT overnight then were added a solution of compound 73 (1.96 g, 13.3 mmol) in H$_2$O (10 mL) and sodium hydrogenocarbonate (225.2 mg, 2.68 mmol). The reaction medium was stirred for 1 h at RT, diluted with H$_2$O (6 mL), acidified to pH 3 with Amberlite IR-120 (H) (CAS number [78922-04-4]), filtered, concentrated in vacuo and purified by flash chromatography on silica gel (gradient elution DCM/MeOH/H$_2$O) to give 270 mg of compound 85 as a colorless foam (21%).

RMN $^1$H (400 MHz, δ in ppm, DMSO-d6): 50:50 conformer mixture; 1.39 (s, 4.5H); 1.40 (s, 4.5H); 2.27 (t, J=7.0 Hz, 4H); 2.38 (t, J=7.0 Hz, 2H); 3.53 (m, 3H); 2.68 (t, J=7.0 Hz, 1H); 3.25 to 3.61 (m, 6H); 4.55 to 4.58 (m, 2H); 5.18 to 5.36 (m, 2H); 5.90 (m, 1H); 7.70 (t, J=6.8 Hz, 1H); 10.53 (broad m, 1H). LCMS (A): ES m/z=409; m/z=463 [M−H]$^-$; m/z=465 [M+H]$^+$; t$_R$=1.13 min.

Compound 86: sodium 2-(4-((3-(allyloxy)-3-oxopropyl)(2-carboxyethyl)amino)-4-oxobutanamido)-ethane-1-sulfonate To a solution of compound 85 (60 mg, 123.3 μmol) in DCM (4 mL) was added TFA (100 μL, 1.25 mmol). The reaction medium was stirred for 2 h at RT then was added TFA (100 μL, 1.25 mmol) and stirring was carried on for 2 d at RT. Then was added TFA (50 μL, 0.625 mmol), the reaction medium was stirred at RT, concentrated in vacuo and co-evaporated with toluene (3×) to give 60 mg of compound 86 as a colorless lacquer (quant.).

Compound 87: Sodium 2-(4-((3-(allyloxy)-3-oxopropyl)(3-((2,5-dioxopyrrolidin-1-yl)oxy)-3-oxopropyl)amino)-4-oxobutanamido)ethane-1-sulfonate To a solution of compound 86 (52.94 mg, 123 μmol) in DCM (5 mL) were added EDAC (26.0 μL, 147.6 μmol), NHS (14.75 mg, 123 μmol) and DMF (0.5 mL). The reaction mixture was stirred for 4 h at RT then was added EDC (10 μL, 45.7 μmol) and stirring was carried on at RT overnight. The reaction medium was stored at −20° C. and used such as for the synthesis of compound 88.

Compound 88: sodium (20S,23S)-28-(2-allyloxy-2-carboxyethyl)-20-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)-23-isopropyl-14,22,25,29,32-pentaoxo-2,5,8,11-tetraoxa-15,21,24,28,33-pentaazapentatriacontane-35-sulfonate To a solution of compound 62 (50 mg, 43.7 μmol) in DCM (4 mL) was added, dropwise under Ar, the reaction medium containing compound 87 (23.06 mg, 43.7 μmol). The reaction medium was stirred at RT for 15 min, concentrated in vacuo and purified by flash chromatography on 15 g of silica gel (gradient elution DMC/MeOH/H2O) to give 26 mg of compound 88 as a white lacquer (38%).

Example 42: sodium (20S,23S)-28-(2-carboxyethyl)-20-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)-23-isopropyl-14,22,25,29,32-pentaoxo-2,5,8,11-tetraoxa-15,21,24,28,33-pentaazapentatriacontane-35-sulfonate To a solution of compound 88 (14 mg, 9 μmol) in THF were added dimedone (2.57 mg, 18.0 μmol) and tetrakis(triphenylphosphine)palladium (0) (5.3 mg, 4.5 μmol). The reaction medium was stirred for 1 h at RT then were added dimedone (2.57 mg, 18.0 μmol) and tetrakis(triphenyl-phosphine)palladium (0) (5.3 mg, 4.5 μmol) and stirring was carried on at RT overnight. At that time, were added dimedone (2.57 mg, 18.0 μmol) and tetrakis(triphenyl-phosphine) palladium (0) (5.3 mg, 4.5 μmol). The reaction medium was stirred for 4 h at RT, filtered, concentrated in vacuo and purified by flash chromatography on 4 g of silica gel (gradient elution DCM/MeOH/H₂O) to give 7 mg of example 42 as a white lacquer (51%).

RMN ¹H (500 MHz, δ in ppm, DMSO-d6): 50:50 conformer mixture; 0.78 (d, J=6.8 Hz, 6H); 0.81 (d, J=6.8 Hz, 6H); 0.86 (m, 6H); 1.00 (s, 3H); 1.04 (d, J=7.1 Hz, 3H); 1.11 (s, 3H); 1.15 to 1.41 (m, 5H); 1.53 to 1.70 (m, 4H); 1.80 (m, 1H); 2.00 (m, 1H); 2.11 to 2.58 (partially masked m, 13H); 2.70 (m, 2H); 2.92 to 3.05 (m, 5H); 3.23 (s, 3H); 3.25 to 3.58 (partially masked m, 23H); 3.81 (s, 3H); 3.88 (d, J=2.0 Hz, 1H); 4.10 to 4.32 (m, 5H); 4.91 (dd, J=3.8 and 9.9 Hz, 1H); 5.10 (m, 1H); 5.80 (d, J=15.2 Hz, 1H); 6.47 (ddd, J=3.8, 11.4 and 15.2 Hz, 1H); 7.06 (d, J=8.6 Hz, 1H); 7.18 (dd, J=2.4 and 8.6 Hz, 1H); 7.20 to 7.32 (m, 6H); 7.67 to 7.93 (m, 3H); 8.18 to 8.60 (m, 4H). LCMS (E): ES m/z=747.5 [M+2H]²⁺; m/z=1491 [M−H]⁻; m/z=1493 [M+H]⁺; $t_R$=4.74 min.

Synthesis of Example 43:
sulfo-Val-GlucoseGln-C52 Benzylic Amine

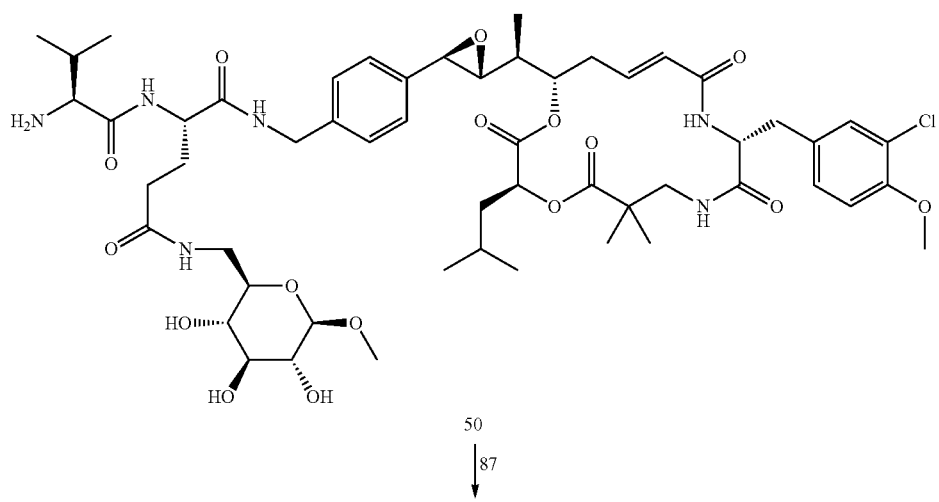

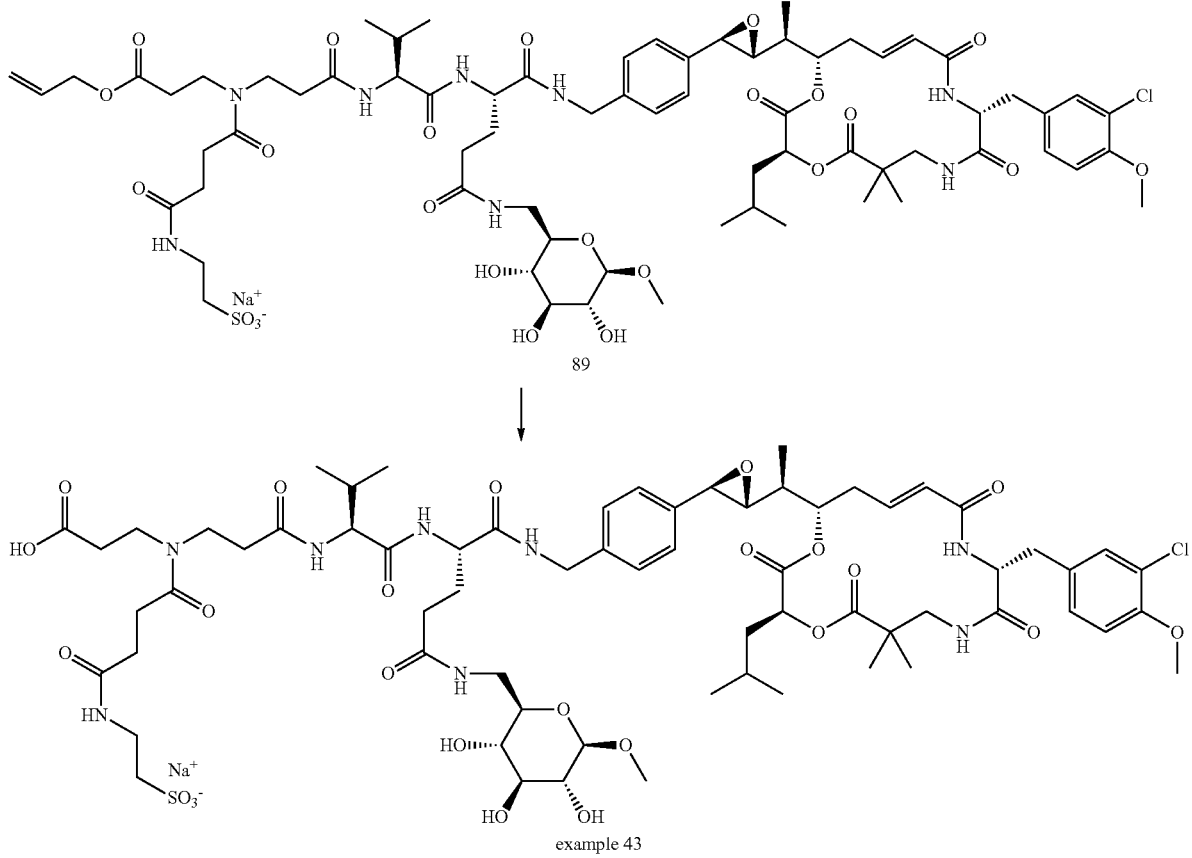

example 43

Compound 89: Sodium (6S,9S)-14-(3-(allyloxy)-3-oxopropyl)-6-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)-9-isopropyl-3,8,11,15,18-pentaoxo-1-((2R,3S,4S,5R,6R)-3,4,5-trihydroxy-6-methoxytetrahydro-2H-pyran-2-yl)-2,7,10,14,19-pentaazahenicosane-21-sulfonate To a solution of compound 50 (55 mg, 49.9 µmol) in DMF (3 mL) was added a a solution of compound 87 in DMF (1.66 mL at 30 mM, 49.9 µmol). The reaction medium was stirred for 18 h at RT, filtered over 0.45 µm, washed twice with DMF (0.8 mL) and purified by reverse phase chromatography on a 5 µm C18 column 30×150 mm (gradient elution MeCN/0.2N ammonium acetate pH 5.6) to give 19.8 mg of compound 89 as a white solid (26%).

RMN $^1$H (500 MHz, δ in ppm, DMSO-d6): 60:40 conformer mixture; 0.78 (d, J=6.8 Hz, 6H); 0.81 (d, J=6.8 Hz, 6H); 0.81 to 0.87 (m, 6H); 0.99 (s, 3H); 1.03 (d, J=7.1 Hz, 3H); 1.12 (s, 3H); 1.30 (m, 1H); 1.52 to 1.62 (m, 2H); 1.80 (m, 3H); 1.85 to 2.00 (m, 3H); 2.10 to 2.30 (m, 5H); 2.35 to 2.48 (m, 2H); 2.53 (m, 6H); 2.68 (m, 2H); 2.88 to 3.15 (m, 9H); 3.28 (m, 3H); 3.38 (m, 3H); 3.40 to 3.58 (m, 5H); 3.80 (s, 3H); 3.87 (d, J=2.3 Hz, 1H); 4.01 (d, J=8.0 Hz, 1H); 4.10 to 4.24 (m, 6H); 4.55 (m, 1.2H); 4.57 (0.8H); 4.91 (dd, J=3.8 et 9.9 Hz, 1H); 4.95 (d, J=5.0 Hz, 1H); 5.01 (d, J=5.0 Hz, 1H); 5.06 (d, J=5.0 Hz, 1H); 5.10 (m, 1H); 5.18 to 5.35 (m, 2H); 5.80 (dd, J=2.0 and 15.2 Hz, 1H); 5.92 (m, 1H); 6.47 (ddd, J=3.8, 11.4 and 15.2 Hz, 1H); 7.06 (d, J=8.6 Hz, 1H); 7.18 (dd, J=2.4 and 8.6 Hz, 1H); 7.23 (m, 5H); 7.29 (d, J=2.4 Hz, 1H); 7.69 (t, J=6.8 Hz, 1H); 7.88 (t, J=6.8 Hz, 1H); 7.98 (d, J=9.0 Hz, 0.4H); 8.04 (d, J=7.0 Hz, 0.4H); 8.08 (d, J=9.0 Hz, 0.6H); 8.14 (d, J=7.0 Hz, 0.6H); 8.32 (t, J=7.0 Hz, 1H); 8.38 (d, J=8.0 Hz, 1H). LCMS (A): ES m/z=746.5 [M+2H]$^{2+}$; m/z=1490 [M−H]$^-$; m/z=1492 [M+H]$^+$; $t_R$=1.4 min.

Example 43: sodium (6S,9S)-14-(2-carboxyethyl)-6-((4-((2R,3R)-3-((S)-1-((3S,10R,16S,E)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl)oxiran-2-yl)benzyl)carbamoyl)-9-isopropyl-3,8,11,15,18-pentaoxo-1-((2R,3S,4S,5R,6R)-3,4,5-trihydroxy-6-methoxytetrahydro-2H-pyran-2-yl)-2,7,10,14,19-pentaazahenicosane-21-sulfonate To a solution of compound 89 (19 mg, 12.6 µmol) in DMF (1 mL) were added barbituric acid (5.94 mg, 37.7 µmol) and a solution of tetrakis (triphenylphosphine)palladium(0) (0.74 mg, 0.63 µmol) in DMF (0.5 mL). The reaction medium was stirred for 3 h at RT then added barbituric acid (5.94 mg, 37.7 µmol) and a solution of tetrakis(triphenylphosphine)palladium(0) (0.74 mg, 0.63 µmol) in DMF (0.5 mL). The reaction medium was stirred at RT overnight, diluted with DMF, filtered over 0.45 µm and purified by two consecutive reverse phase chromatographies on a 5 µm C18 column 30×150 mm (gradient elution MeCN/0.2N ammonium acetate pH 5.6) to give 4.7 mg of example 43 as a white solid (25%).

RMN ¹H (500 MHz, δ in ppm, DMSO-d6): 0.80 (m, 6H); 0.85 (m, 6H); 0.99 (s, 3H); 1.03 (d, J=7.3 Hz, 3H); 1.11 (s, 3H); 1.33 (m, 1H); 1.58 (m, 2H); 1.78 (m, 2H); 1.90 (m, 2H); 2.03 to 2.55 (partially masked m, 11H); 2.70 (m, 2H); 2.90 to 3.58 (partially masked m, 19H); 3.18 (s, 3H); 3.81 (s, 3H); 3.88 (s, 1H); 4.00 to 4.40 (m, 8H); 4.90 (m, 1H); 4.99 (m, 1H); 5.80 (d, J=15.2 Hz, 1H); 6.46 (ddd, J=3.8, 11.4 and 15.2 Hz, 1H); 7.05 (d, J=8.6 Hz, 1H); 7.18 (dd, J=2.4 and 8.6 Hz, 1H); 7.22 (m, 4H); 7.29 (d, J=2.4 Hz, 1H); 7.31 (m, 1H); 8.30 to 8.70 (m, 5H). LCMS (A): ES m/z=1448 [M−H]⁻; m/z=1450 [M+H]⁺; $t_R$=1.58 min.

For illustrative purposes, two conjugates derived from WO2011/001052, ADC1 and ADC2 depicted below, and one conjugate described in PCT/EP2016/076603, ADC3 depicted below, were also tested.

sucrose pH6.5 and analyzed by HRMS and SEC HPLC to determine the DAR and the monomeric purity.

TABLE I

| | 5% NMP | | no NMP | | Δ % | | |
|---|---|---|---|---|---|---|---|
| | DAR | % monomer | DAR | % monomer | ΔDAR (%) | monomer (%) | protein recovery |
| ADC1 | 4.1 | 99 | 3.25 | 88.7 | −21% | −10% | quant. |
| ADC3 | 3.5 | 99.7 | 3.5 | 99.5 | 0% | −0.2% | n.d. |
| Ex.3 | 3.4 | 99.8 | 3.2 | 99.7 | −6% | −0.1% | 88% |
| Ex.6 | 4.05 | 99 | 3.4 | 99 | −16% | 0% | 75% |
| Ex.16* | 2.5 | 99.8 | 2.3 | 99.8 | −8% | 0% | 73% |

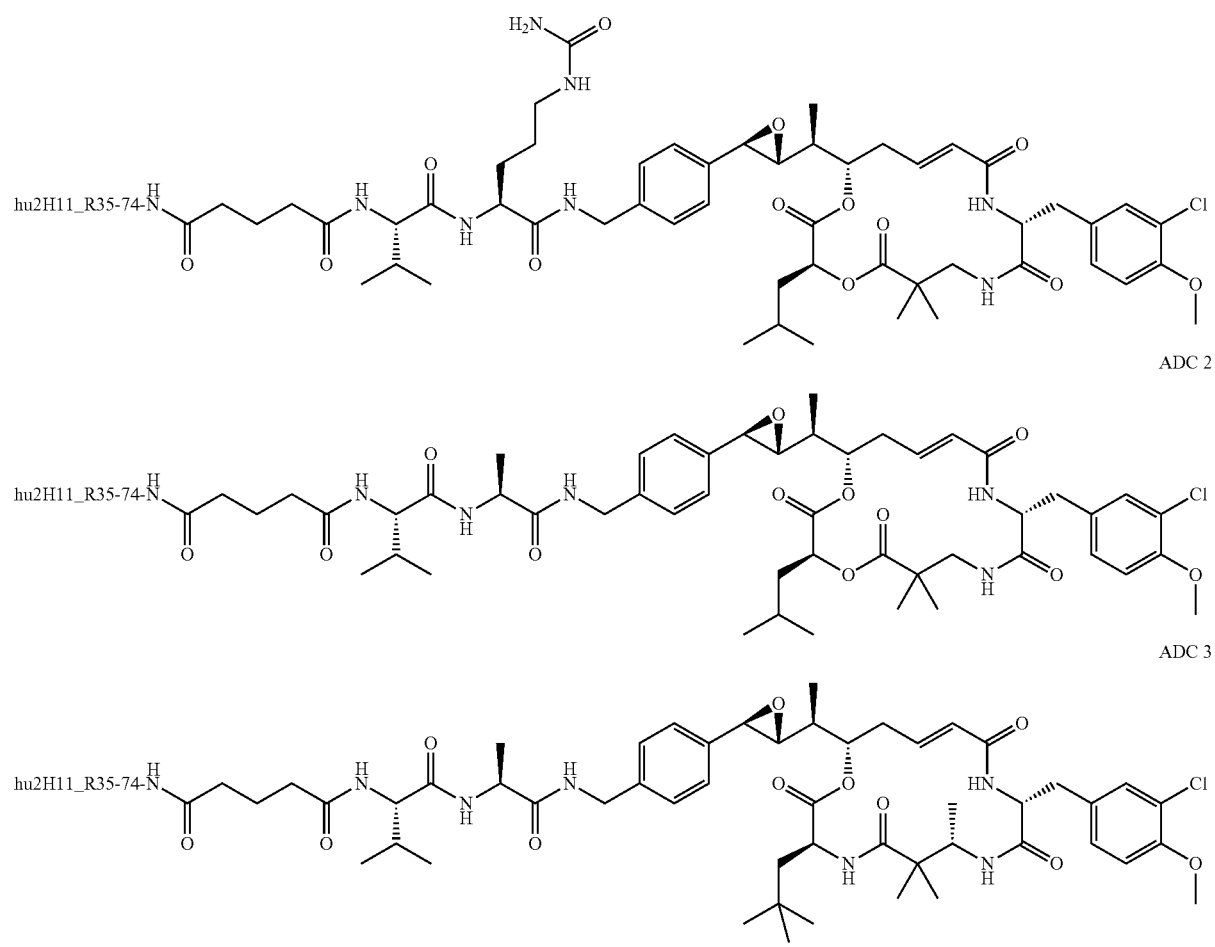

ADC 1

ADC 2

ADC 3

Physico-Chemical Results

The conjugates of formula (V) were subjected to stability studies evaluating aggregation (looking at monomeric purity) and loss of DAR upon removal of the organic co-solvent used in the formulation and under accelerated stress conditions (10 day heating at 40° C.).

Stability in the Absence of NMP

ADC stored in 10 mM phosphate 140 mM NaCl pH6.5 5% NMP were filtered on a SEC column to remove the NMP, formulated in 10 mM phosphate 70 mM NaCl 5%

TABLE I-continued

| | 5% NMP | | no NMP | | Δ % | | |
|---|---|---|---|---|---|---|---|
| | DAR | % monomer | DAR | % monomer | ΔDAR (%) | monomer (%) | protein recovery |
| Ex.19 | 2.8 | 97.9 | 2.4 | 97.8 | −14% | −0.1% | 72% |
| Ex.23* | 2.9 | 100 | 2.4 | 100 | −17% | 0% | 76% |
| Ex.26 | 3.9 | 100 | 3.9 | 100 | 0% | 0% | n.d. |

TABLE I-continued

|  | 5% NMP | | no NMP | | | Δ % | |
| --- | --- | --- | --- | --- | --- | --- | --- |
|  | DAR | % monomer | DAR | % monomer | ΔDAR (%) | monomer (%) | protein recovery |
| Ex.29 | 4 | 98.4 | 3.9 | 100 | −2.5% | 0% | 76% |
| Ex.32 | 2.8 | 95.1 | 2.9 | 94.1 | 0 | −11% | 82% |

*After 10 months at 4° C., significant aggregation was observerd for Ex.16 and Ex.23 (respectively −22% and −19% in terms of monomeric purity), therefore both batches were purified by gel filtration on Superdex 200 pg prior to performing stability studies.

Stability after 10 Days at 40° C. in Phosphate Buffer

ADC in 10 mM phosphate 70 mM NaCl 5% sucrose pH6.5 were heated at 40° C. during 10 days and analyzed by HRMS and SEC HPLC to determine the DAR and the monomeric purity.

TABLE 11

|  | At t0 | | After 10 d at 40° C. | | | Δ % | |
| --- | --- | --- | --- | --- | --- | --- | --- |
|  | DAR | % monomer | DAR | % monomer | ΔDAR (%) | monomer (%) | protein recovery |
| ADC1 | 3.25 | 88.7 | 3.0 | 85.7% | −8% | −3% | 56% |
| ADC3 | 3.5 | 99.5 | 3 | 85 | −14% | −15% | 46% |
| Ex.3 | 3.2 | 99.7 | 2.9 | 92 | −9% | −8% | 96% |
| Ex.6 | 3.4 | 99 | 3.3 | 97 | −3% | −2% | 91% |
| Ex.16 | 2.3 | 99.8 | 1.8 | 93.8 | −22% | −6% | 89% |
| Ex.19 | 2.4 | 97.8 | 1.8 | 92.9 | −25% | −5% | quant. |
| Ex.23 | 2.4 | 100 | 2.4 | 91.6 | 0% | −8% | 91% |
| Ex.26 | 3.9 | 100 | 3.6 | 100 | −8% | 0% | n.d. |
| Ex.29 | 3.9 | 100 | 3.9 | 98.7 | 0% | −1% | 97% |
| Ex.32 | 2.9 | 94.1 | 2.7 | 89.8 | −7% | −5% | 95% |
| Ex.41 | 3.3 | 97.9 | 3.05 | 75.3 | −7.5% | −23% | quant. |

Evaluation of Drug Release after Treatment of the Conjugates of Formula (V) by Cathepsin B Drug release by Cathepsin B was evaluated in vitro by incubating the ADC (1.5 μg/mL) in the presence of human Cathepsin B (Calbiochem #219362, 40 μg/mL) in acetate buffer pH 5 at 37° C. for 24 h and detecting the drug by UPLC-MS-SIR-DAD-ELSD. The slope was determined based on the kinetics over the 1$^{st}$ hour, the half-life on the 24 h kinetics.

TABLE III

|  | slope | $t_{1/2}$ (h) |
| --- | --- | --- |
| ADC1 | 34.3 | 2 |
| ADC2 | 14.1 | 15 |
| Ex.16 | 12.8 | >24 |
| Ex.19 | 22.3 | 3.5 |
| Ex.23 | 19.3 | 6 |
| Ex.32 | 33.5 | 2 |

Cryptophycin conjugates of formula (V) were cleaved by human Cathepsin B with a kinetics similar to the one of reference ADCs.

Pharmacological Results

The conjugates of formula (V) were subjected to pharmacological tests for determining their antitumoral effect.

Evaluation of the Inhibition of Proliferation of the MDA-MB-231 Cell Line by the Conjugates of Formula (V)

MDA-MB-231 cells in their exponential growth phase were trypsinized and resuspended in their culture medium (DMEM/F12 Gibco #21331, 10% FCS Gibco #10500-056, 2 nM glutamine Gibco #25030). The cell suspension was seeded in Cytostar 96-well culture plates (GE Healthcare Europe, #RPNQ0163) in the whole culture medium containing serum at a density of 5000 cells/well. After incubation for 4 h, successive dilutions of the ADC were added to the wells at concentrations decreasing from $10^{-7}$ to $10^{-12}$ M (in triplicate for each concentration). The cells were cultured at 37° C. in an atmosphere containing 5% $CO_2$ in the presence of the ADC for 3 d. On the 4$^{th}$ day, 10 μL of a $^{14}$C-thymidine solution (0.1 μCi/well, Perkin Elmer #NEC56825000) were added to each well. The incorporation of $^{14}$C-thymidine was measured 96 h after the start of the experiment with a microbeta radioactivity counter (Perkin Elmer). The data were expressed in the form of a percentage of survival by determining the ratio between the reduced count obtained with the cells treated with the ADC and the count obtained with the cells of the control wells (treated with the culture medium alone). In certain experiments, the naked antibody was added to the wells at a concentration of 1 μM at the start of the experiment and the inhibition of proliferation was measured as described previously.

TABLE IV

| | $IC_{50}$ (pM), MDA-MB-231 | | |
| --- | --- | --- | --- |
|  | ADC alone | in the presence of naked antibody | Selectivity ratio |
| ADC1 | 42 | 4571 | 109 |
| ADC2 | 46 | 9377 | 204 |
| Ex.3 | 19 | 5602 | 295 |
| Ex.6 | 22 | 7417 | 337 |
| Ex.16 | 39 | 13908 | 357 |
| Ex.19 | 29 | 18243 | 629 |
| Ex.23 | 37 | 9022 | 243 |
| Ex.26 | 27 | 33689 | 1248 |
| Ex.29 | 67 | >100000 | >1493 |
| Ex.32 | 25 | 7953 | 318 |
| Ex.35 | 25 | 11272 | 451 |
| Ex.41 | 34 | 5043 | 148 |

Cryptophycin conjugates of formula (V), as well as ADC1 and ADC2, were found to inhibit the proliferation of MDA-MB-231 cell line with $IC_{50}$ ranging from 19 μM to 67 μM and selectivity ratio ADC alone vs ADC+naked antibody between 109 and >1493.

Determination of the MTD of the Conjugates of Formula (V) Following Single i.v. Administration in SCID Mice MTD was determined as the maximal dose that does not induce 15% body weight loss during 3 consecutive days for an individual mouse or 20% body weight loss during 1 day or mortality. It was evaluated after a single intravenous (i.v.) bolus injection in 3 female SCID mice and during a period of 28 days post-treatment.

TABLE V

|  | MTD (mg/kg) |
| --- | --- |
| ADC1 | 20 |
| ADC2 | 30 |
| Ex.3 | 30 |
| Ex.6 | >40 |
| Ex.16 | n.d. |
| Ex.19 | n.d. |
| Ex.23 | n.d. |
| Ex.26 | 30 |
| Ex.29 | 40 |
| Ex.32 | n.d. |

TABLE V-continued

| | MTD (mg/kg) |
|---|---|
| Ex.35 | n.d. |
| Ex.41 | 30 |

Tested cryptophycin conjugates of formula (V) displayed MTD in SCID mice ranging from 30 mg/kg to ≥40 mg/kg.

Evaluation of the In Vivo Antitumor Activity of Conjugates of Formula (V) Against MDA-MB-231 in SCID Mice Following Single i.v. Administration In vivo antitumor activity was evaluated at 3 dose-levels against measurable breast MDA-MB-231 xenografts implanted s.c. in female SCID mice. Control groups were left untreated. Conjugates were administered by a single i.v. bolus injection, the day of the treatment was indicated on each graph by an arrow (▼).

For the evaluation of antitumor activity of conjugates, animals were weighed twice weekly and tumors were measured twice weekly by caliper. Animal body weights included the tumor weights. Tumor volume were calculated using the formula mass $(mm^3)$=[length (mm)×width $(mm)^2$]/2. The primary efficacy end points were $\Delta T/\Delta C$, percent median regression, partial and complete regressions (PR and CR). Changes in tumor volume for each treated (T) and control (C) were calculated for each tumor by subtracting the tumor volume on the day of first treatment (staging day) from the tumor volume on the specified observation day. The median $\Delta T$ was calculated for the treated group and the median $\Delta C$ was calculated for the control group. Then the ratio $\Delta T/\Delta C$ was calculated and expressed as a percentage: $\Delta T/\Delta C$=(delta T/delta C)×100.

The percentage of tumor regression was defined as the % of tumor volume decrease in the treated group at a specified observation day (t) compared to its volume on the first day of first treatment (t0). At a specific time point and for each animal, % regression was calculated. The median % regression was then calculated for the group. % regression (at t)=((Volume$_{t0}$−Volume$_t$)/Volume$_{t0}$)×100. Regressions were defined as partial (PR) if the tumor volume decreased to 50% of the tumor volume at the start of treatment and complete (CR) when tumor volume cannot be measured (0 $mm^3$). Tumor free survivor (TFS) was defined as the animals with undetectable tumors at the end of the study (>100 days post last treatment).

Evaluation of the In Vivo Antitumor Activity of Ex. 6 Against MDA-MB-231 in SCID Mice Following Single i.v. Administration

TABLE VI

| | Dose (mg/kg) | Median ΔT/ΔC in % (D36) | Median % of regression | Regressions | | |
|---|---|---|---|---|---|---|
| | | | | PR | CR | TFS |
| Control | — | — | — | — | — | — |
| ADC2 | 2.5 | 8 | — | 1 | 1 | 1 |
| Ex.6 | 5 | <0 | 100% | 5 | 4 | — |
| | 2.5 | <0 | 4% | 2 | 1 | — |
| | 1.25 | 33 | — | — | — | — |

Evaluation of the In Vivo Antitumor Activity of Ex. 16, Ex. 19, Ex. 23 and Ex. 32 Against MDA-MB-231 in SCID Mice Following Single i.v. Administration at 2.5 mg/kg

TABLE VII

| | Dose (mg/kg) | Median ΔT/ΔC in % (D59) | Median % of regression | Regressions | | |
|---|---|---|---|---|---|---|
| | | | | PR | CR | TFS |
| Control | — | — | — | — | — | — |
| ADC2 | 2.5 | <0 | 14% | — | — | — |
| Ex.16 | 2.5 | <0 | 92% | 6 | 3 | — |
| Ex.19 | 2.5 | <0 | 100% | 6 | 5 | 2 |
| Ex.23 | 2.5 | <0 | 100% | 6 | 6 | 1 |
| Ex.32 | 2.5 | <0 | 100% | 6 | 6 | 2 |

Evaluation of the In Vivo Antitumor Activity of Ex. 16, Ex. 19, Ex. 23 and Ex. 32 Against MDA-MB-231 in SCID Mice Following Single i.v. Administration at 1.25 mg/kg

TABLE VIII

| | Dose (mg/kg) | Median ΔT/ΔC in % (D50) | Median % of regression | Regressions | | |
|---|---|---|---|---|---|---|
| | | | | PR | CR | TFS |
| Control | — | — | — | — | — | — |
| ADC2 | 1.25 | 14 | — | — | — | — |
| Ex.16 | 1.25 | 7 | — | — | — | — |
| Ex.19 | 1.25 | 1 | — | 1 | 1 | — |
| Ex.23 | 1.25 | 0 | — | 1 | — | — |
| Ex.32 | 1.25 | 9 | — | 2 | 1 | — |

Evaluation of the In Vivo Antitumor Activity of Ex. 26 Against MDA-MB-231 in SCID Mice Following Single i.v. Administration

TABLE IX

| | Dose (mg/kg) | Median ΔT/ΔC in % (D36) | Median % of regression | Regressions | | |
|---|---|---|---|---|---|---|
| | | | | PR | CR | TFS |
| Control | — | — | — | — | — | — |
| ADC2 | 2.5 | 8 | — | 1 | — | 1 |
| Ex.26 | 5 | <0 | 100% | 6 | 6 | 2 |
| | 2.5 | <0 | 100% | 6 | 4 | 1 |
| | 1.25 | 10 | — | 1 | — | — |

Evaluation of the In Vivo Antitumor Activity of Ex. 29 Against MDA-MB-231 in SCID Mice Following Single i.v. Administration

TABLE X

| | Dose (mg/kg) | Median ΔT/ΔC in % (D27) | Median % of regression | Regressions | | |
|---|---|---|---|---|---|---|
| | | | | PR | CR | TFS |
| Control | — | — | — | — | — | — |
| Ex.29 | 4 | <0 | 100% | 6 | 6 | 6 |
| | 2 | <0 | 100% | 6 | 6 | 4 |
| | 1 | 0 | — | — | — | — |

Evaluation of the In Vivo Antitumor Activity of Ex. 35 Against MDA-MB-231 in SCID Mice Following Single i.v. Administration

TABLE XI

|  | Dose (mg/kg) | Median ΔT/ΔC in % (D27) | Median % of regression | Regressions PR | CR | TFS |
|---|---|---|---|---|---|---|
| Control | — | — | — | — | — | — |
| Ex.35 | 4 | <0 | 100% | 6 | 6 | 4 |
|  | 2 | <0 | 100% | 6 | 4 | 1 |
|  | 1 | 3 | — | — | — | — |

Evaluation of the In Vivo Antitumor Activity of Ex. 41 Against MDA-MB-231 in SCID Mice Following Single i.v. Administration

TABLE XII

|  | Dose (mg/kg) | Median ΔT/ΔC in % (D49) | Median % of regression | Regressions PR | CR | TFS |
|---|---|---|---|---|---|---|
| Control | — | — | — | — | — | — |
| Ex.26 | 4 | <0 | 100% | 6 | 6 | 6 |
|  | 2 | <0 | 100% | 6 | 6 | 4 |
|  | 1 | <0 | 51% | 3 | 2 | 1 |
| Ex.41 | 4 | <0 | 100% | 6 | 4 | 2 |
|  | 2 | <0 (D46) | 25% | 2 | — | — |
|  | 1 | 20 | — | — | — | — |

All tested cryptophycin ADC of the invention, as well as ADC2, displayed antitumor activity at doses ranging from 1 mg/kg to 5 mg/kg.

It is therefore apparent that the compounds (V) of the invention have an anticancer activity.

Accordingly, in another of its aspects, the invention also relates to the use of cryptophycin conjugates of formula (V) as anticancer agents.

Accordingly, in another of its aspects, the invention also relates to the use of cryptophycin conjugates of formula (V) for the preparation of a medicament for treating cancer, for instance breast cancer.

The present invention, according to another of its aspects, also provides conjugates of formula (V) according to the present invention for use in the treatment of cancer.

The present invention, according to another of its aspects, also provides medicaments which comprise at least one conjugate of formula (V).

These medicaments are employed therapeutically, especially in the treatment of cancer, for instance breast cancer.

According to another of its aspects, the present invention relates to pharmaceutical compositions comprising as active principle a conjugate of formula (V) according to the invention. These pharmaceutical compositions comprise an effective dose of at least one conjugate of formula (V) according to the invention and also at least one pharmaceutically acceptable excipient.

Thus, according to another aspect, the present invention relates to a pharmaceutical composition comprising at least one conjugate of formula (V) according to the present invention, and also at least one pharmaceutically acceptable excipient.

The said excipients are selected, in accordance with the pharmaceutical form and method of administration desired, from the customary excipients, which are known to a person skilled in the art.

The present invention, according to another of its aspects, also provides a method of treating the pathologies indicated above such as cancer, for instance breast cancer, which comprises administering to a patient an effective dose of a conjugate of formula (V) according to the invention.

The invention claimed is:

1. A compound of formula (V):

Ab—G—L—Y—[structure]  (V)

wherein:
- $R_1$ is $(C_1\text{-}C_6)$alkyl;
- $R_2$ is hydrogen or $(C_1\text{-}C_6)$alkyl;
- $R_3$ is hydrogen or $(C_1\text{-}C_6)$alkyl; or
- $R_2$ and $R_3$, together with the carbon atom to which they are attached, form $(C_3\text{-}C_6)$cycloalkyl or $(C_3\text{-}C_6)$heterocycloalkyl;
- $R_4$ is hydrogen, $(C_1\text{-}C_6)$alkyl, $(C_1\text{-}C_6)$alkylene-C(O)OH, $(C_1\text{-}C_6)$alkylene-NHR$_{12}$, $(C_1\text{-}C_6)$alkylene-OH, or $(C_1\text{-}C_6)$alkylene-SH;
- $R_5$ is hydrogen, $(C_1\text{-}C_6)$alkyl, $(C_1\text{-}C_6)$alkylene-C(O)OH, $(C_1\text{-}C_6)$alkylene-NHR$_{12}$, $(C_1\text{-}C_6)$alkylene-OH, or $(C_1\text{-}C_6)$alkylene-SH; or
- $R_4$ and $R_5$, together with the carbon atom to which they are attached, form $(C_3\text{-}C_6)$cycloalkyl or $(C_3\text{-}C_6)$heterocycloalkyl;
- $R_6$ is hydrogen or $(C_1\text{-}C_6)$alkyl;
- $R_7$ is hydrogen, $(C_1\text{-}C_6)$alkyl, $(C_1\text{-}C_6)$alkylene-C(O)OH, or $(C_1\text{-}C_6)$alkylene-N[$(C_1\text{-}C_6)$alkyl]$_2$;
- $R_8$ is hydrogen, $(C_1\text{-}C_6)$alkyl, $(C_1\text{-}C_6)$alkylene-C(O)OH, or $(C_1\text{-}C_6)$alkylene-N[$(C_1\text{-}C_6)$alkyl]$_2$;
- each $R_9$ is independently hydrogen, halogen, —NH$_2$, —NH$(C_1\text{-}C_6)$alkyl, N[$(C_1\text{-}C_6)$alkyl]$_2$, —NH$(C_3\text{-}C_6)$cycloalkyl, OH, O$(C_1\text{-}C_4)$alkyl, or $(C_3\text{-}C_6)$heterocycloalkyl;
- each $R_{10}$ is independently hydrogen or $(C_1\text{-}C_4)$alkyl;
- $R_{11}$ is hydrogen or $(C_1\text{-}C_6)$alkyl;
- $R_{12}$ is hydrogen or $(C_1\text{-}C_6)$alkyl;
- X is —O— or —NR$_6$—;
- Y is —NR$_{11}$—$(C_1\text{-}C_6)$alkylene-, wherein the $(C_1\text{-}C_6)$ alkylene is bonded to the phenyl ring and —NR$_{11}$— is bonded directly to L1 of formula (II);
- L is formula (I):

RCG1-L$_{linker}$-P    (I)

wherein:
- P is OH; or
- P is an activated O moiety selected from the group consisting of:

[structures of activated O moieties]

wherein:
- each G is independently selected from the group consisting of halogen and nitro; and
- M is Na$^+$, K$^+$, K$^+$, or Cs$^+$;

L$_{linker}$ is formula (II):

[structure]    (II)

wherein:
L1 is formula (III):

[structure]    (III)

wherein:
x is 0 or 1;
y is 0;
z is 0;
$J_1$ is $CA_1$ or N;
$J_2$ is $CA_1$ or N;
$J_3$ is $CA_1$ or N;
$J_4$ is $CA_1$ or N;
$A_1$ is hydrogen or $(C_1\text{-}C_6)$alkyl;
$A_2$ is hydrogen or $(C_1\text{-}C_6)$alkyl;
$A_3$ is hydrogen or $(C_1\text{-}C_6)$alkyl; and
$A_4$ is hydrogen or $(C_1\text{-}C_6)$alkyl;
wherein L1 is bonded directly to $-NR_{11}-$ of Y;
$(AA)_w$ is a sequence of w amino acids connected together via peptide bonds, wherein the amino acids, $(AA)_w$, are independently selected from the group consisting of a non-substituted amino acid, $(AA_{ns})$, and a substituted amino acid, $(AA_s)$;
w is 2, 3, 4, 5, 6, 7, 8, 9, 10, 11, or 12;
each $(AA_{ns})$ is a natural or non-natural amino acid independently selected from the group consisting of alanine, γ-aminobutyric acid, 2-amino-2-cyclohexylacetic acid, 2-amino-2-phenylacetic acid, arginine, asparagine, aspartic acid, citrulline, cysteine, α,α-dimethyl-γ-aminobutyric acid, 3,3-dimethyl-γ-aminobutyric acid, glutamine, glutamic acid, glycine, homocysteine, selenocysteine, homoselenocysteine, histidine, isoleucine, leucine, lysine, ε-(acetyl)-lysine, methionine, ornithine, phenylalanine, proline, serine, threonine, tryptophan, tyrosine, and valine;
each $(AA_s)$ is independently formula (VI):

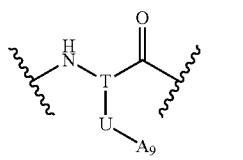

(VI)

wherein:
T is a trivalent $(C_1\text{-}C_8)$alkyl;
U is -a single bond-, $-C(O)-$, $-C(O)NH-$, $-C(O)N(alkyl)$-, $-C(O)O-$, $-NH-$, $-N(alkyl)$-, $-NHC(O)-$, $-N(alkyl)C(O)-$, $-NHC(NH)NH-$, $-NHC(O)NH-$, $-NHS(O)_2-$, $-N(alkyl)S(O)_2-$, $-O-$, $-OC(O)-$, $-OC(O)O-$, $-OP(O)-$, $-P(O)(OH)-$, $-P(O)(OH)O-$, $-OP(O)(OH)O-$, $-S-$, $-S(O)-$, $-S(O)_2-$, $-S(O)_2NH-$, $-S(O)_2N(alkyl)$-, or $-Se-$; and
$A_9$ is a straight, branched, saturated, or unsaturated $C_1\text{-}C_{160}$ hydrocarbon, wherein the $C_1\text{-}C_{160}$ hydrocarbon is optionally substituted by 1 or more substituents independently selected from the group consisting of halogen, alkyl, $NH_2$, NH(alkyl), $N(alkyl)_2$, OH, and O(alkyl), and further wherein 1 or more $-CH_2-$ units of the $C_1\text{-}C_{160}$ hydrocarbon are optionally and independently replaced by 1 or more atoms or groups independently selected from the group consisting of $-CHF-$, $-CF_2-$, $-CH(OH)-$, $-CH(Oalkyl)$-, $-CH(SO_3H)-$, $-CH(SO_3^-M^+)-$, $-C(O)-$, $-C(O)NH-$, $-C(O)N(alkyl)$-, $-C(O)O-$, $-NH-$, $-N^+H(alkyl)$-, $-N(alkyl)$-, $-N^+(alkyl)_2$-, $-NHC(O)-$, $-N(alkyl)C(O)-$, $-NHC(NH)NH-$, $-NHC(O)NH-$, $-NHS(O)_2-$, $-N(alkyl)S(O)_2-$, $-P(O)(OH)-$, $-P(O)(OH)O-$, $-O-$, $-OC(O)-$, $-OC(O)O-$, $-OP(O)-$, $-OP(O)(OH)-$, $-OP(O)(OH)O-$, $-S-$, $-S(O)-$, $-S(O)_2-$, $-S(O)_2NH-$, $-S(O)_2N(alkyl)$-, $-Se-$, and heterocycloalkyl, wherein the heterocycloalkyl is optionally substituted by 1 or more substituents independently selected from the group consisting of halogen, alkyl, $NH_2$, NH(alkyl), $N(alkyl)_2$, OH, and O(alkyl); and $M^+$ is an alkali metal;
wherein the $-C(O)-$ of one $(AA_s)$ of formula (VI) or the $-C(O)-$ of one $(AA_{ns})$ of $(AA)_w$ is bonded to $-NR_{11}-$ of Y or $-NA_4-$ of L1 and the $-NH-$ of one $(AA_s)$ of formula (VI) or the $-NH-$ of one $(AA_{ns})$ of $(AA)_w$ is bonded to the $-C(O)-$ attached to L2; and L2 is $-(C_1\text{-}C_{160})$alkylene-, wherein the $C_1\text{-}C_{160}$ alkylene is optionally substituted by 1 or more substituents independently selected from the group consisting of halogen, alkyl, $NH_2$, NH(alkyl), $N(alkyl)_2$, OH, O(alkyl), $SO_3H$, and $SO_3^-M^+$, and further wherein 1 or more $-CH_2-$ units of the $C_1\text{-}C_{160}$ alkylene are optionally and independently replaced by 1 or more atoms or groups independently selected from the group consisting of $-CHF-$, $-CF_2-$, $-CH(OH)-$, $-CH(Oalkyl)$-, $-CH(SO_3H)-$, $-CH(SO_3^-M^+)-$, $-C(O)-$, $-NA_7-$, $-NA_8-$, $-P(O)(OH)-$, $-P(O)(OH)O-$, $-O-$, $-OP(O)-$, $-S-$, $-S(O)-$, and $-S(O)_2-$;

$A_7$ is a straight, branched, saturated, or unsaturated $C_1\text{-}C_{160}$ hydrocarbon, wherein the $C_1\text{-}C_{160}$ hydrocarbon is optionally substituted by 1 or more substituents independently selected from the group consisting of halogen, alkyl, $NH_2$, NH(alkyl), $N(alkyl)_2$, OH, and O(alkyl), and further wherein 1 or more $-CH_2-$ units of the $C_1\text{-}C_{160}$ hydrocarbon are optionally and independently replaced by 1 or more atoms or groups independently selected from the group consisting of $-CH(OH)-$, $-CH(SO_3H)-$, $-CH(SO_3^-M^+)-$, $-C(O)-$, $-C(O)NH-$, $-C(O)N(alkyl)$-, $-C(O)O-$, $-NHC(O)-$, $-N(alkyl)C(O)-$, $-NHS(O)_2-$, $-N(alkyl)S(O)_2-$, $-P(O)(OH)-$, $-P(O)(OH)O-$, $-O-$, $-OC(O)-$, $-OC(O)O-$, $-OP(O)(OH)-$, $-OP(O)(OH)O-$, $-S(O)-$, $-S(O)_2-$, $-S(O)_2NH-$, $-S(O)_2N(alkyl)$-, and heterocycloalkyl, wherein the heterocycloalkyl is optionally substituted by 1 or more substituents independently selected from the group consisting of halogen, alkyl, $NH_2$, NH(alkyl), $N(alkyl)_2$, OH, and O(alkyl);

$A_8$ is hydrogen or $(C_1-C_6)$alkyl; and
$M^+$ is an alkali metal:
wherein L2 is bonded to RCG1; and
RCG1 is:
Cl, C≡CH, $NH_2$, $N_3$, OH, O(alkyl)-NHOH, SH, C≡CH, C(O)H, C(O)$C_1-C_6$ alkyl, C(O)$NH_2$, C(O)OH, $N_2$, $N_3$, SH,

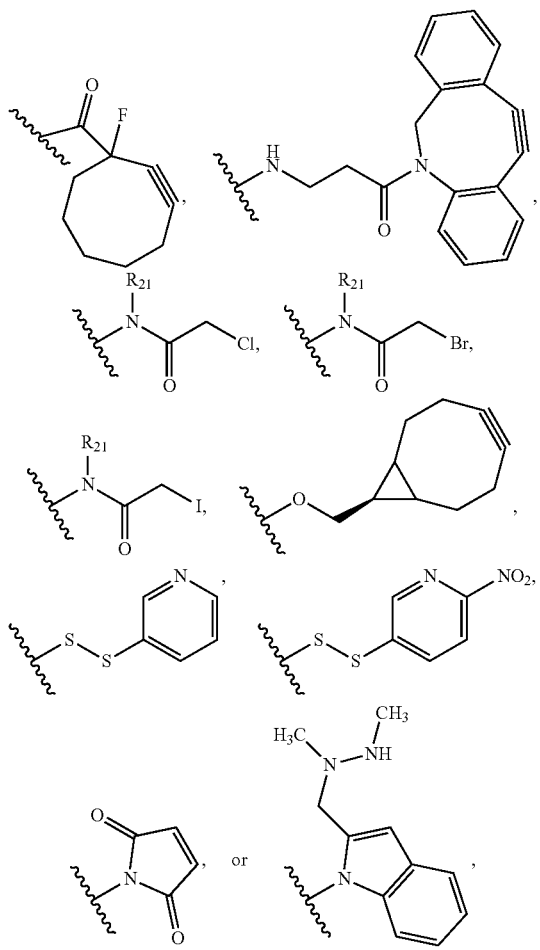

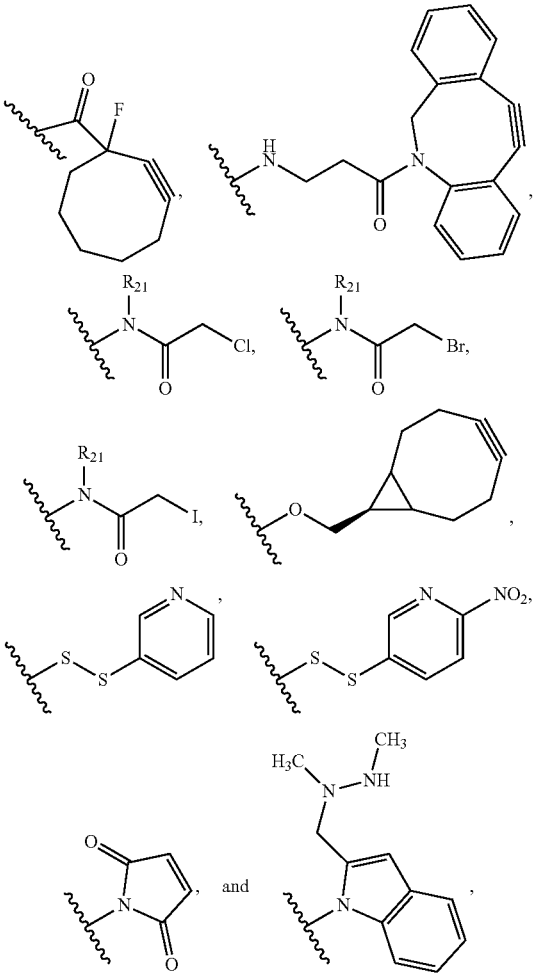

wherein:
$R_{21}$ is hydrogen or $(C_1-C_6)$ alkyl; and
the —CO—, —NH—, —$NR_{21}$—, —N=, —O—, or S is bonded to L2; or
RCG1 is:
$C(O)Z_aR_a$,
wherein:
$Z_a$ is a single bond, —NH—, or —O—; and
$R_a$ is hydrogen, $(C_1-C_6)$alkyl, alkenyl, $(C_3-C_7)$ cycloalkyl, $(C_3-C_7)$heterocycloalkyl, aryl, or heteroaryl, wherein the $(C_3-C_7)$heterocycloalkyl, aryl, or heteroaryl is optionally substituted by 1, 2, 3, 4, or 5 substituents independently selected from the group consisting of halogen, CN, $NO_2$, alkyl, OH, O(alkyl), and =O;
wherein —C(O)— is bonded to L2;
G is the product of a reaction between RCG1 and RCG2;
wherein RCG2 is an orthogonal reactive chemical group present on an antibody, Ab, and wherein for each RCG1, RCG2 is independently selected from the group consisting of:

wherein:
$R_{21}$ is hydrogen or $(C_1-C_6)$ alkyl; and
Ab is the antibody;
with the provisos that:

(1) if P is —OH, then x is 0, y is 0, and z is 0; and (2) if P is an activated 0 moiety, then x is 1, y is 0, and z is 0;

(3) at least one amino acid, $(AA)_w$, is a substituted amino acid, $(AA)_s$, of formula (VI); and (4) the substituted amino acid, $(AA)_s$, of formula (VI) is not selected from the group consisting of alanine, γ-aminobutyric acid, 2-amino-2-cyclohexylacetic acid, 2-amino-2-phenylacetic acid, arginine, asparagine, aspartic acid, citrulline, cysteine, α,α-dimethyl-γ-aminobutyric acid, 3,3-dimethyl-γ-aminobutyric acid, glutamine, glutamic acid, glycine, homocysteine, selenocysteine, homoselenocysteine, histidine, isoleucine, leucine, lysine, ε-(acetyl)-lysine, methionine, ornithine, phenylalanine, proline, serine, threonine, tryptophan, tyrosine, and valine.

2. The compound according to claim 1, wherein the compound has the following structure:

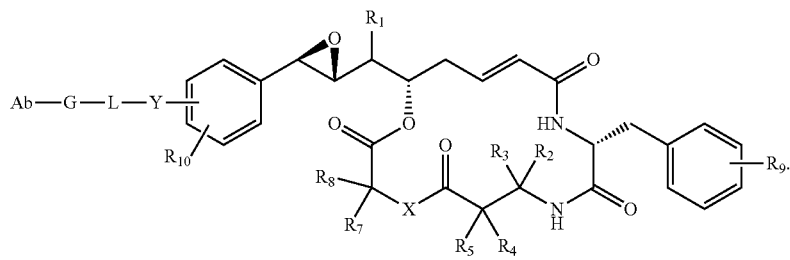

3. The compound according to claim 1, wherein:

Y is —NR$_{11}$—(CH$_2$)$_n$—; and n is 1, 2, 3, 4, 5, or 6;

wherein Y is bonded in an ortho, meta, or para position on the phenyl relative to where the oxirane moiety is bonded to the phenyl.

4. The compound according to claim 1, wherein:

U is -a single bond-, —C(O)—, —C(O)NH—, —C(O)N(alkyl)-, —NH—, —N(alkyl)-, —NHC(O)—, or —N(alkyl)C(O)—;

A$_9$ is a straight, branched, saturated, or unsaturated C$_1$-C$_{160}$ hydrocarbon, wherein 1 or more —CH$_2$— units of the C$_1$-C$_{160}$ hydrocarbon are optionally and independently replaced by 1 or more atoms or groups independently selected from the group consisting of —CH(OH)—, —CH(SO$_3$H)—, —CH(SO$_3^-$M$^+$)-, —C(O)—, —C(O)NH—, —C(O)N(alkyl)-, —NH—, —N(alkyl)-, —NHC(O)—, —N(alkyl)C(O)—, —O—, and heterocycloalkyl, wherein the heterocycloalkyl is optionally substituted by 1 or more substituents independently selected from the group consisting of halogen, alkyl, OH, and O(alkyl); and M$^+$ is an alkali metal.

5. The compound according to claim 1, wherein:

T is

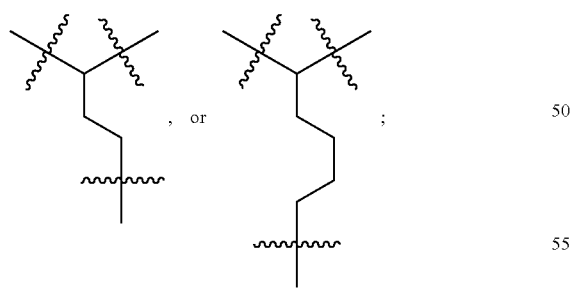

U is —C(O)NH— or —NHC(O)—;

A$_9$ is —[(CH$_2$)$_2$O]$_b$—CH$_3$; and b is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

6. The compound according to claim 1, wherein (AA)$_w$ is selected from the group consisting of:

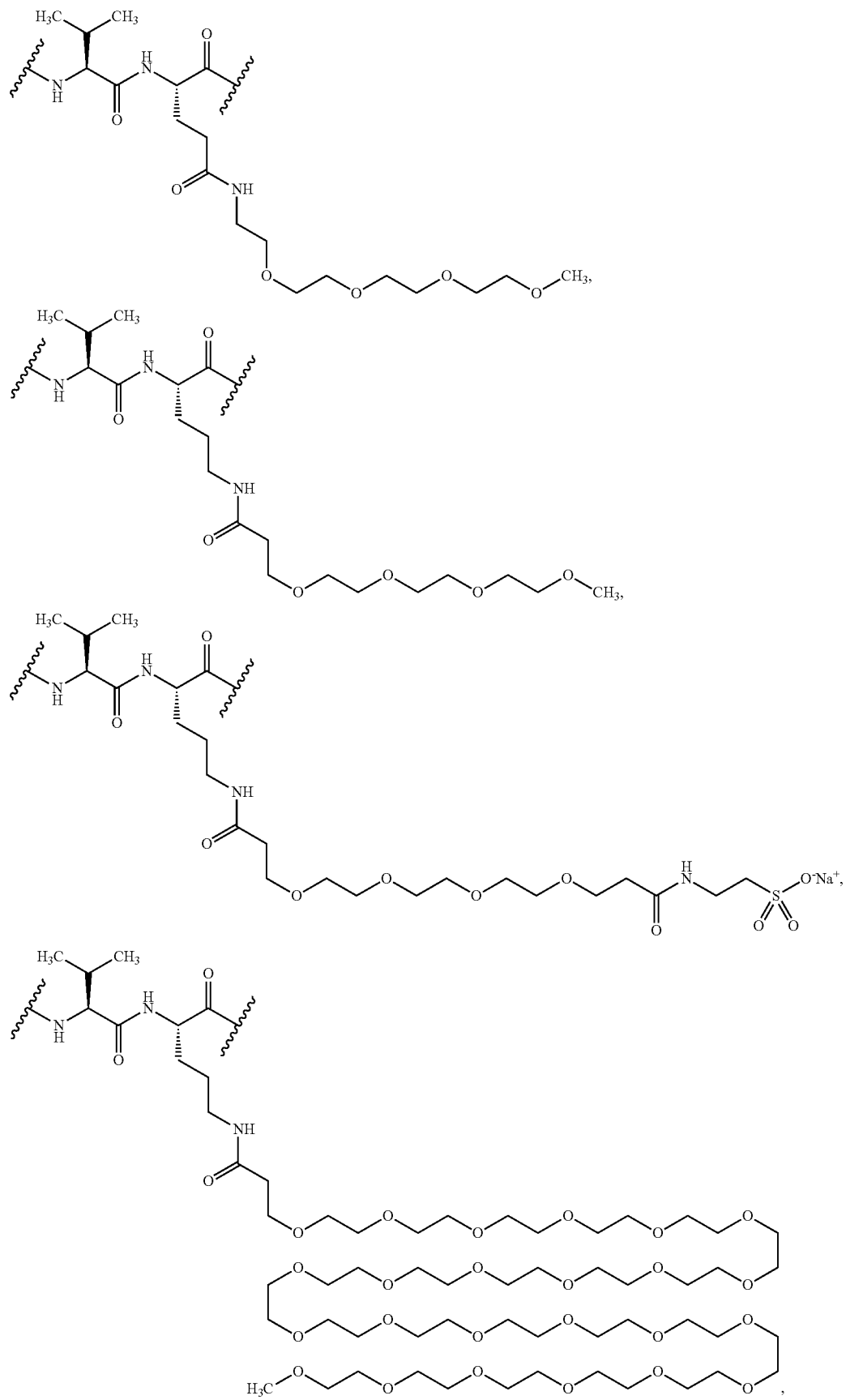

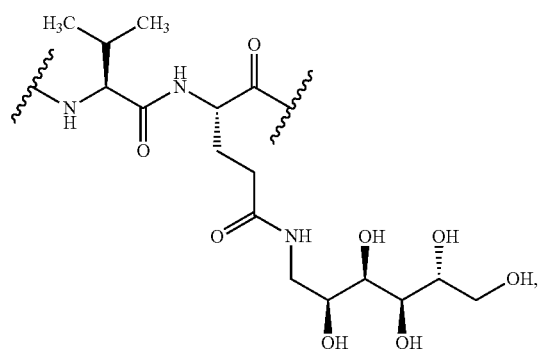

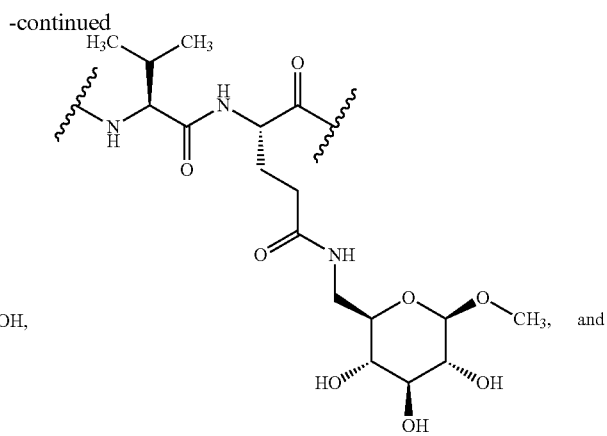

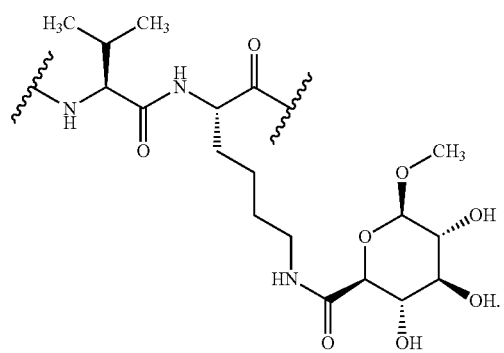

7. The compound according to claim 1, wherein:
$A_7$ is C(O)—[(CH$_2$)$_2$O]$_4$—CH$_3$, C(O)—[(CH$_2$)$_2$O]$_7$—CH$_3$, C(O)—[(CH$_2$)$_2$O]$_{24}$—CH$_3$, C(O)—(CH$_2$)$_2$C(O)NH(CH$_2$)$_2$—SO$_3$H, C(O)—(CH$_2$)$_2$C(O)NH(CH$_2$)$_2$—SO$_3^-$M$^+$, C(O)—(CH$_2$)$_2$C(O)NH—[(CH$_2$)$_2$O]$_4$(CH$_2$)$_2$C(O)NH(CH$_2$)$_2$—SO$_3$H, or C(O)—(CH$_2$)$_2$C(O)NH—[(CH$_2$)$_2$O]$_4$(CH$_2$)$_2$C(O)NH(CH$_2$)$_2$—SO$_3^-$M$^+$; and
M$^+$ is an alkali metal.

8. The compound according to claim 1, wherein:
L2 is —(C$_1$-C$_6$)alkylene-, —C(O)—(C$_1$-C$_6$)alkylene-, or —(C$_1$-C$_6$)alkylene-NAS-(C$_1$-C$_6$)alkylene-;
$A_7$ is —C(O)CH$_2$CH$_2$C(O)NHCH$_2$CH$_2$SO$_3$H or —C(O)CH$_2$CH$_2$C(O)NHCH$_2$CH$_2$SO$_3^-$M$^+$; and
M$^+$ is an alkali metal.

9. The compound according to claim 1, wherein L2 is selected from the group consisting of:

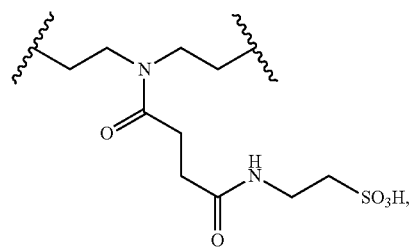

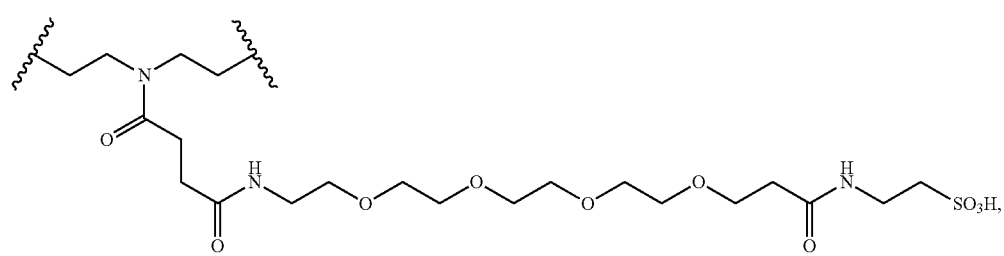

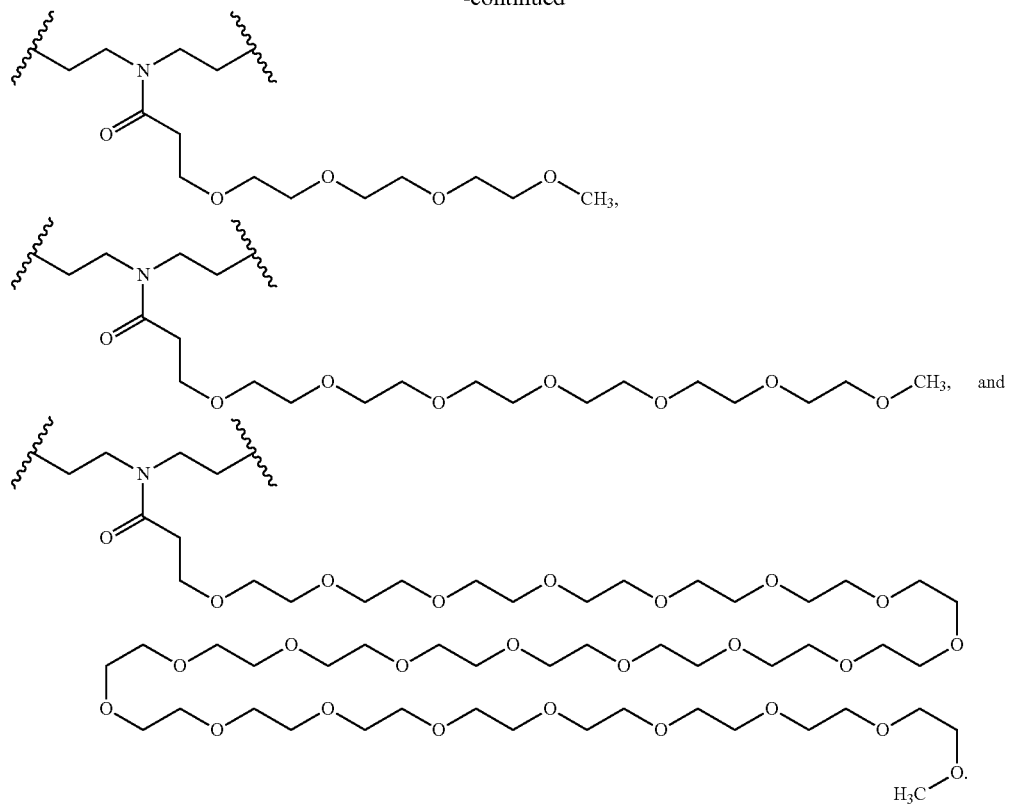
10. The compound according to claim 1, wherein L is selected from the group consisting of:
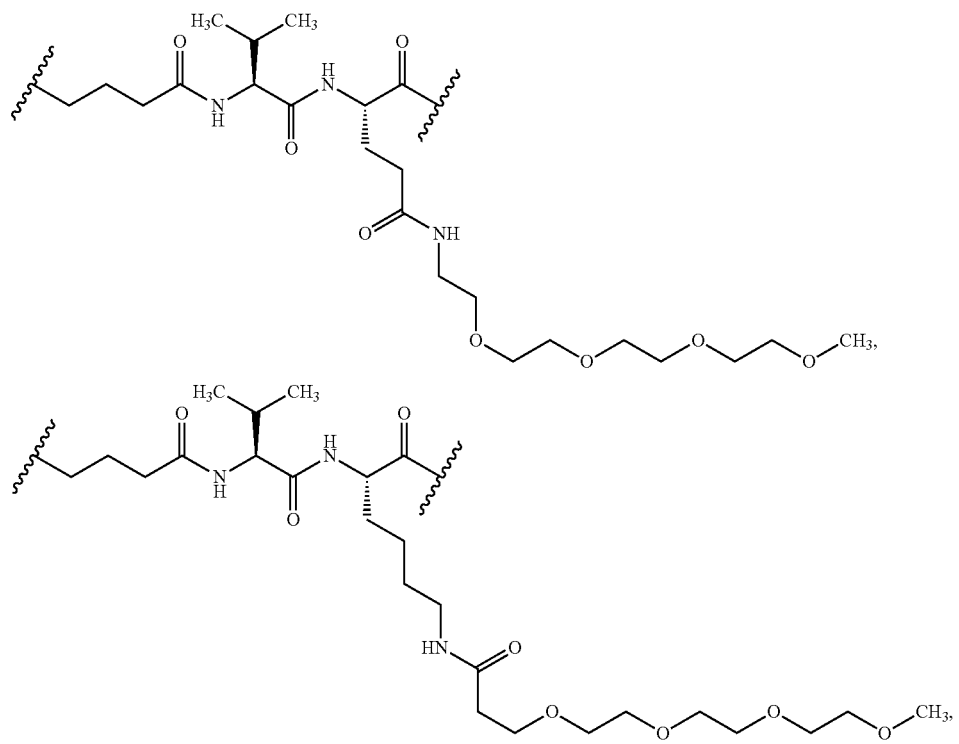

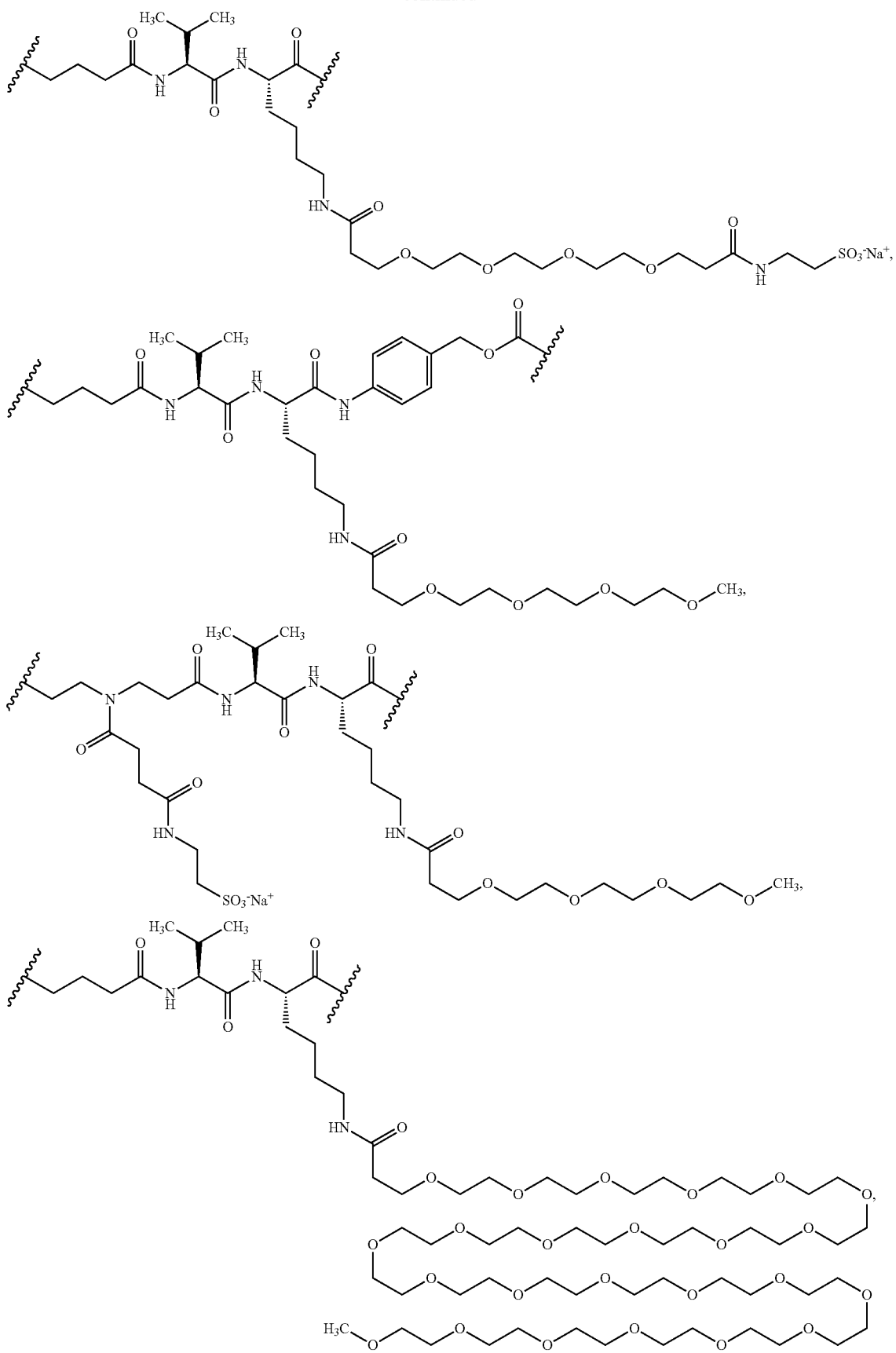

-continued
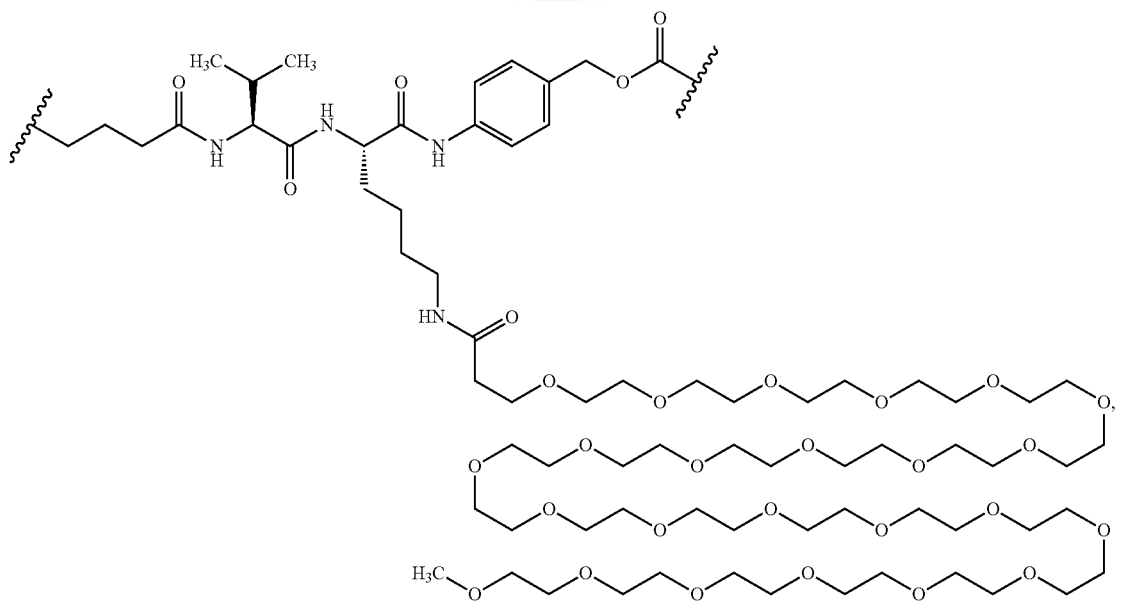
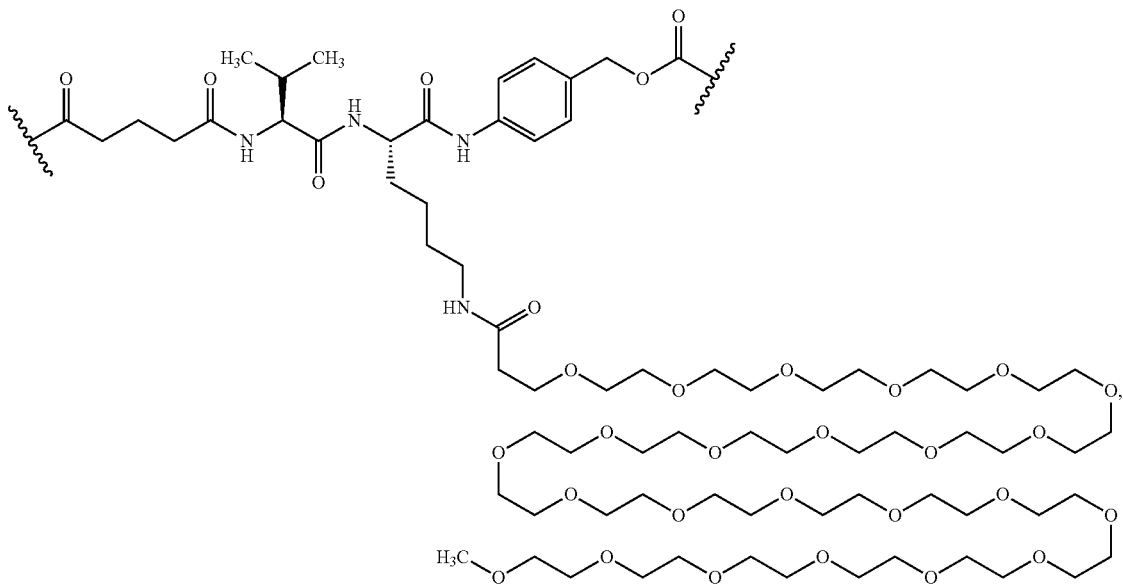
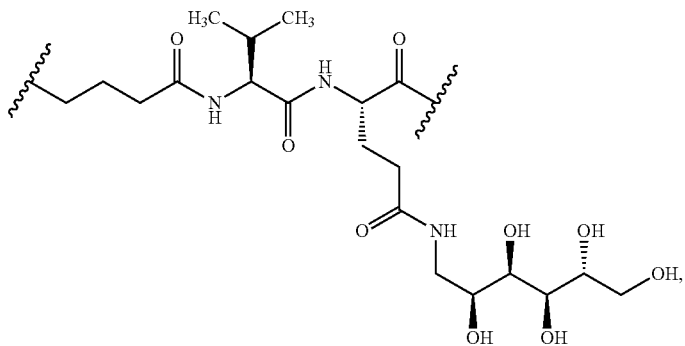

-continued

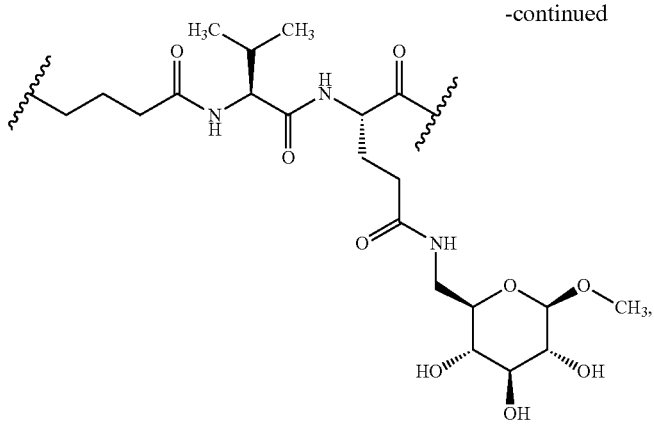

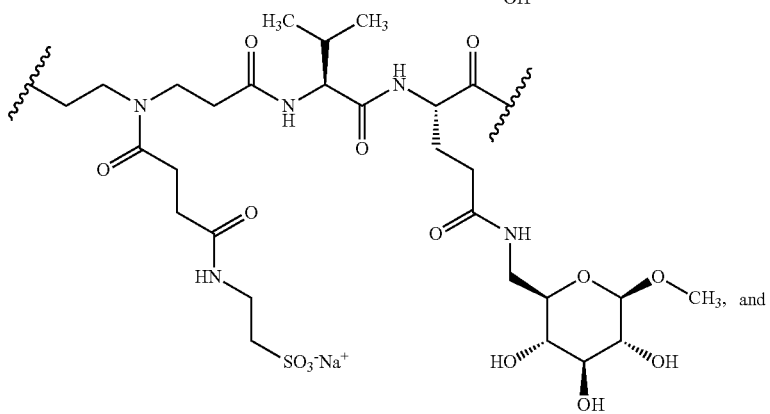

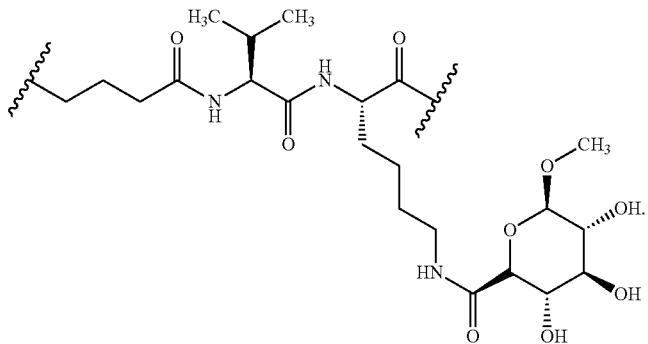

11. The compound according to claim 1, wherein RCG2 is selected from the group consisting of:
  (i) a C(O)H group of an engineered formylglycine residue of the antibody;
  (ii) a C(O)NH$_2$ group borne by the side chain of a glutamine residue that is present at the surface of the antibody;
  (iii) an α-NH$_2$ group of an N-terminal amino acid of a heavy chain or a light chain of the antibody;
  (iv) an ε-NH$_2$ group borne by the side chain of a lysine residue that is present at the surface of the antibody;
  (v) an SH of a cysteine residue generated by reducing an intra-chain disulfide bond of the antibody; and
  (vi) an SH of an engineered cysteine residue of the antibody.

12. The compound according to claim 1, wherein:
  (i) RCG1 is Cl,

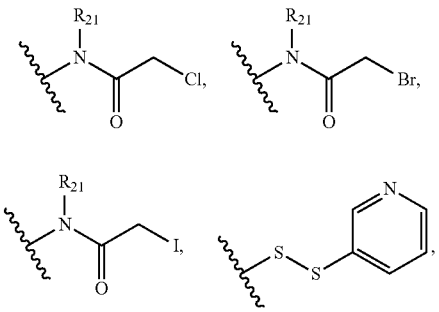

353
-continued
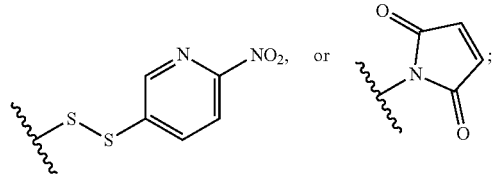
and
RCG2 is SH; or
(ii) RCG1 is C≡CH,
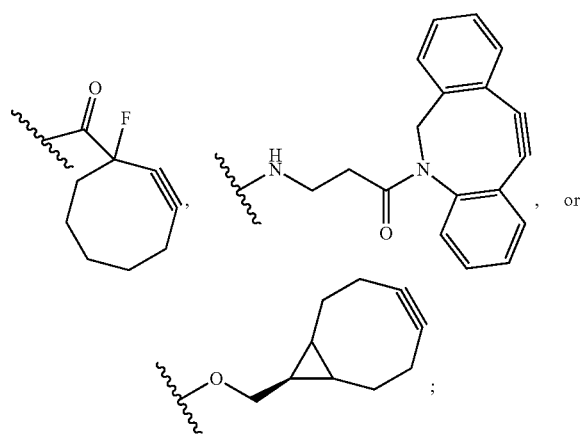
and
RCG2 is N₃; or
(iii) RCG1 is NH₂ or OH; and
RCG2 is C(O)NH₂ or C(O)OH; or
(iv) RCG1 is N₃; and
RCG2 is C≡CH,
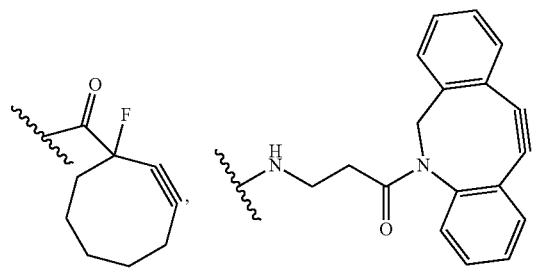
354
or
(v) RCG1 is O(alkyl)-NHOH or
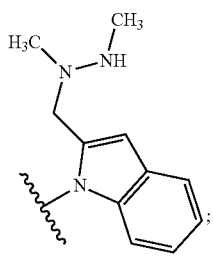 [SMILES: *n1c(CN(C)NC)cc2ccccc21]
and
RCG2 is C(O)H or C(O)C₁-C₆ alkyl; or
(vi) RCG1 is SH; and
RCG2 is
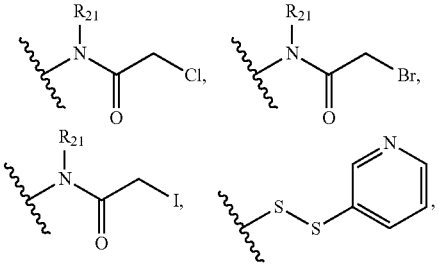
or
(vii) RCG1 is
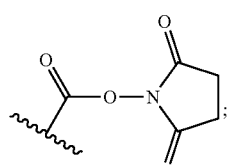
and
RCG2 is NH₂.
13. The compound according to claim 1, wherein G is the product of a reaction between RCG1 and RCG2 and is selected from the group consisting of:
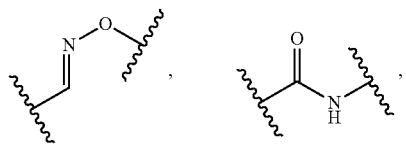

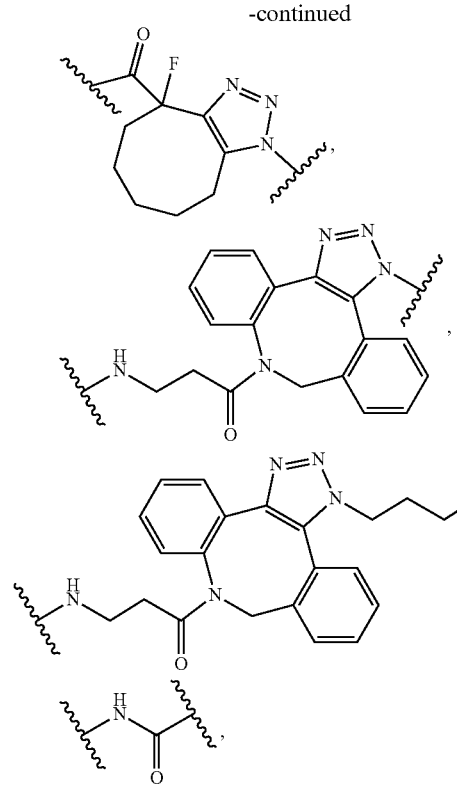
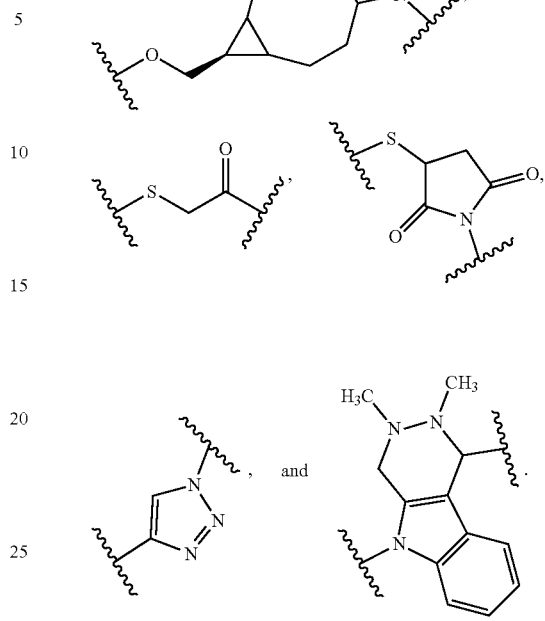
14. The compound according to claim 1, wherein the compound is selected from the group consisting of:
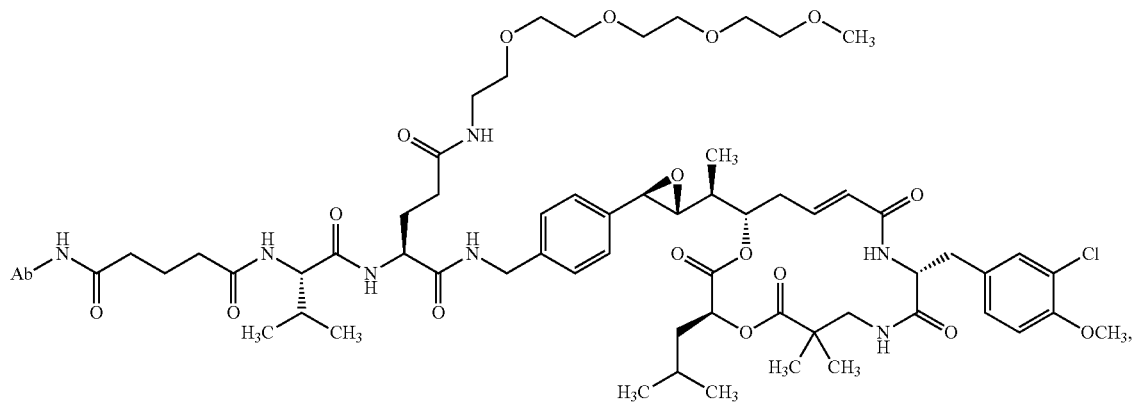
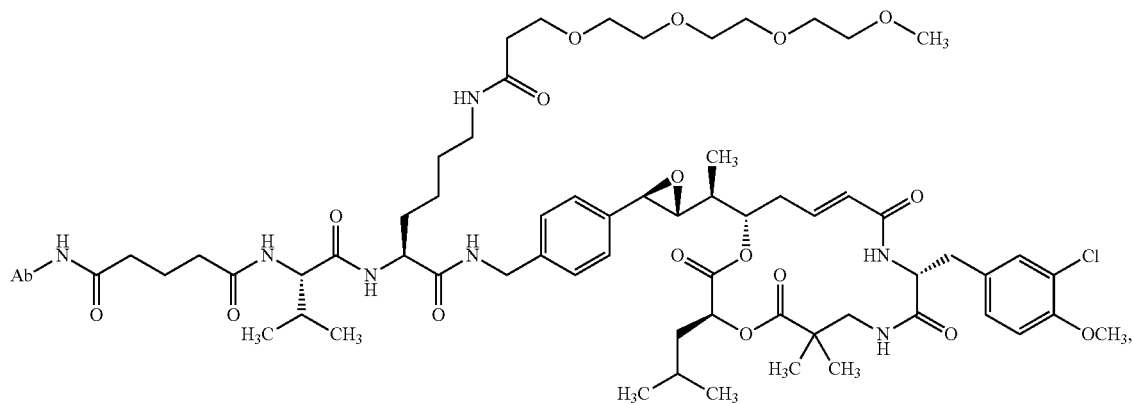

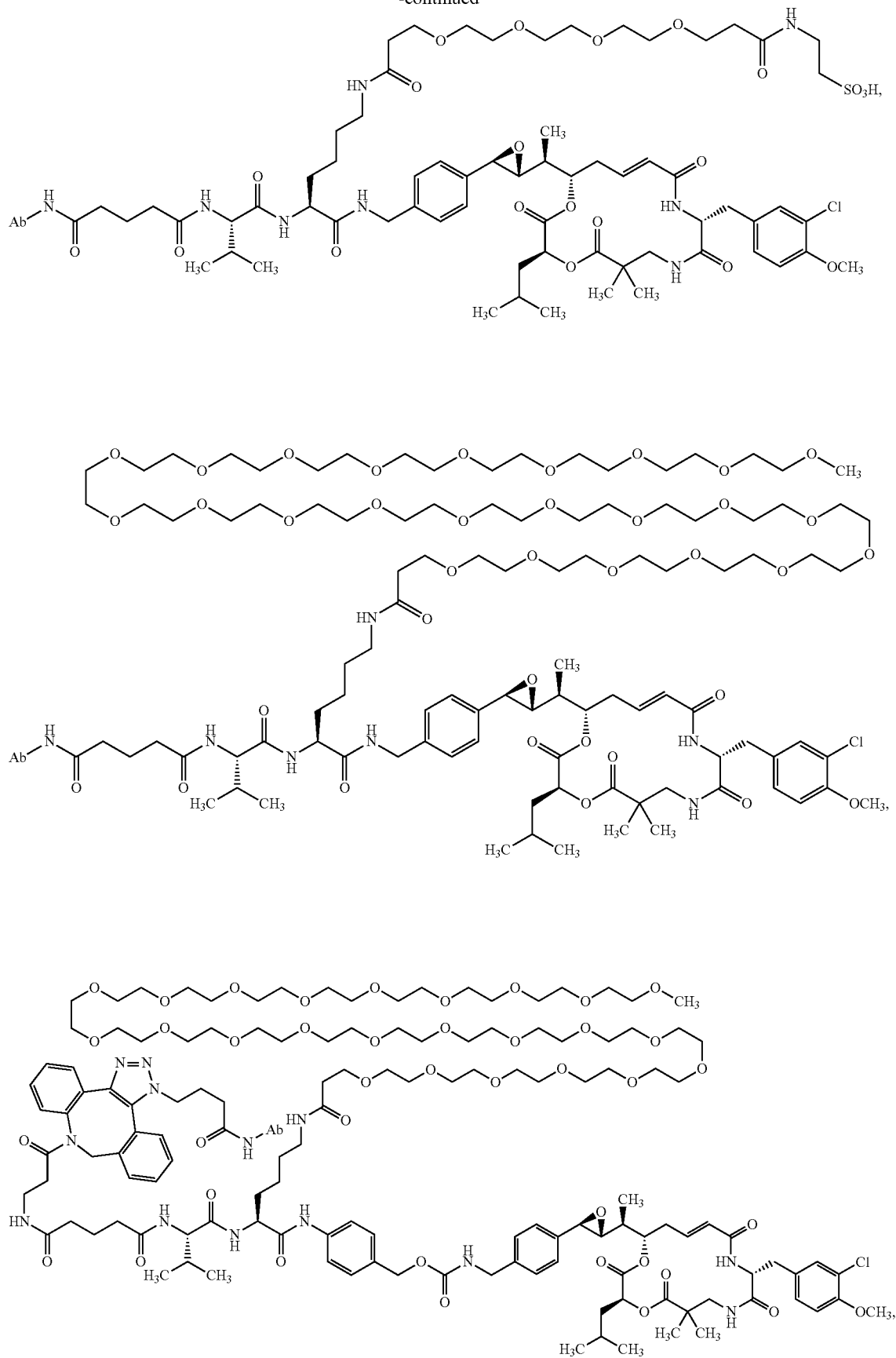

359 360
-continued
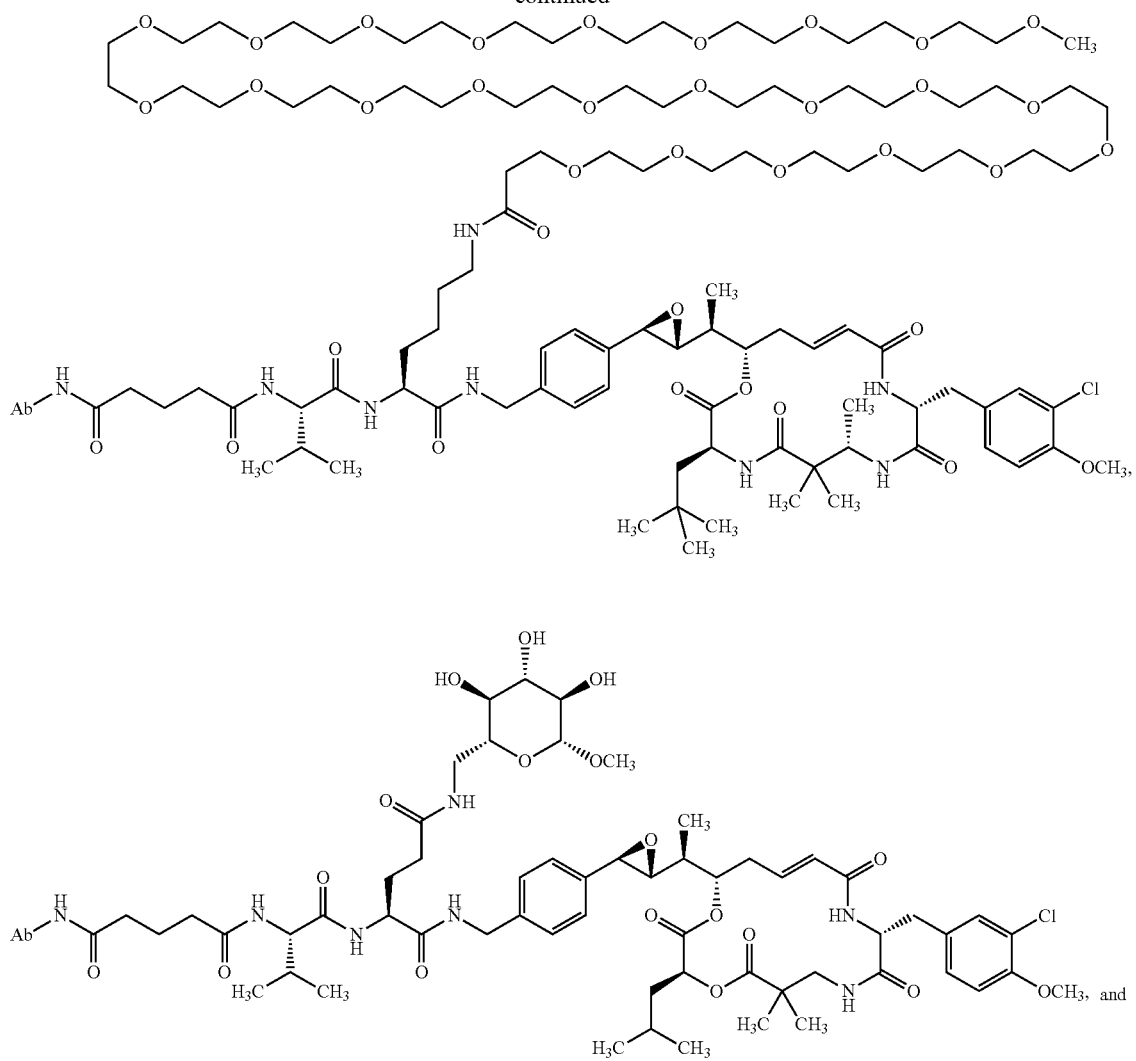
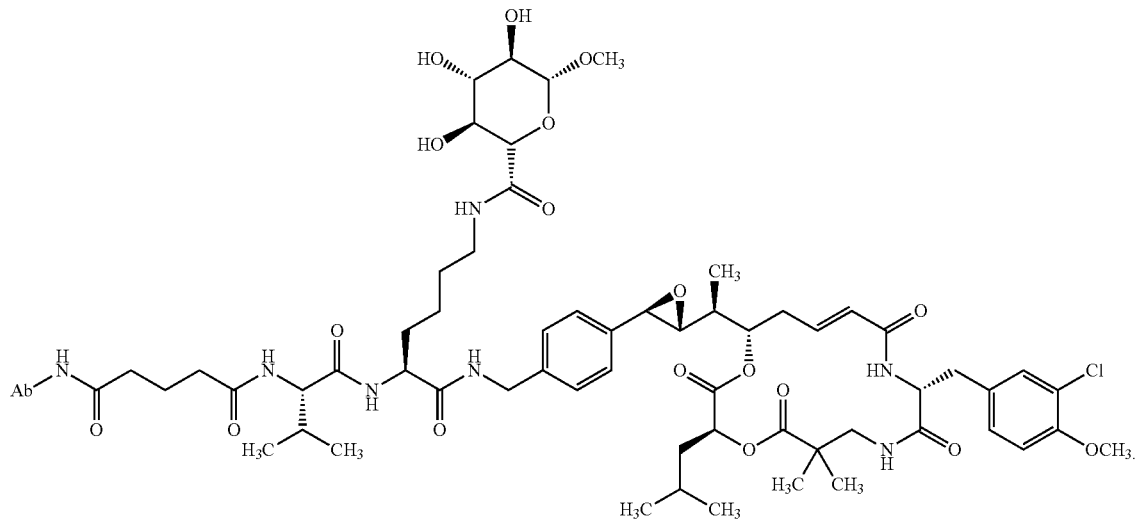

15. A pharmaceutical composition comprising a compound according to claim 1 and a pharmaceutically acceptable excipient.

16. The pharmaceutical composition according to claim 15, wherein:
U is -a single bond-, —C(O)—, —C(O)NH—, —C(O)N(alkyl)-, —NH—, —N(alkyl)-, —NHC(O)—, or —N(alkyl)C(O)—;
$A_9$ is a straight, branched, saturated, or unsaturated $C_1$-$C_{160}$ hydrocarbon, wherein 1 or more —$CH_2$— units of the $C_1$-$C_{160}$ hydrocarbon are optionally and independently replaced by 1 or more atoms or groups independently selected from the group consisting of —CH(OH)—, —CH($SO_3$H)—, —CH($SO_3^-M^+$)—, —C(O)—, —C(O)NH—, —C(O)N(alkyl)-, —NH—, —N(alkyl)-, —NHC(O)—, —N(alkyl)C(O)—, —O—, and heterocycloalkyl, wherein the heterocycloalkyl is optionally substituted by 1 or more substituents independently selected from the group consisting of halogen, alkyl, OH, and O(alkyl); and
$M^+$ is an alkali metal.

17. A method for treating cancer in a patient in need thereof, comprising administering to the patient a therapeutically effective amount of a compound according to claim 1.

18. The method according to claim 15, wherein:
U is -a single bond-, —C(O)—, —C(O)NH—, —C(O)N(alkyl)-, —NH—, —N(alkyl)-, —NHC(O)—, or —N(alkyl)C(O)—;
$A_9$ is a straight, branched, saturated, or unsaturated $C_1$-$C_{160}$ hydrocarbon, wherein 1 or more —$CH_2$— units of the $C_1$-$C_{160}$ hydrocarbon are optionally and independently replaced by 1 or more atoms or groups independently selected from the group consisting of —CH(OH)—, —CH($SO_3$H)—, —CH($SO_3^-M^+$)—, —C(O)—, —C(O)NH—, —C(O)N(alkyl)-, —NH—, —N(alkyl)-, —NHC(O)—, —N(alkyl)C(O)—, —O—, and heterocycloalkyl, wherein the heterocycloalkyl is optionally substituted by 1 or more substituents independently selected from the group consisting of halogen, alkyl, OH, and O(alkyl); and
$M^+$ is an alkali metal.

19. A process for preparing a compound of formula (V) according to claim 1:

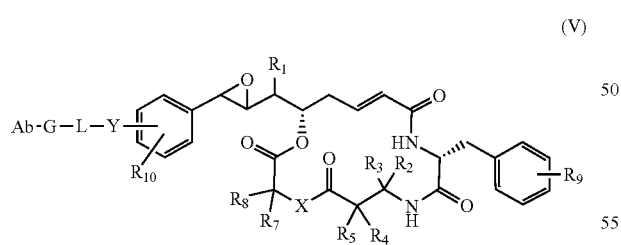

(V)

wherein:
$R_1$ is ($C_1$-$C_6$)alkyl;
$R_2$ is hydrogen or ($C_1$-$C_6$)alkyl;
$R_3$ is hydrogen or ($C_1$-$C_6$)alkyl; or
$R_2$ and $R_3$, together with the carbon atom to which they are attached, form ($C_3$-$C_6$)cycloalkyl or ($C_3$-$C_6$)heterocycloalkyl;
$R_4$ is hydrogen, ($C_1$-$C_6$)alkyl, ($C_1$-$C_6$)alkylene-C(O)OH, ($C_1$-$C_6$)alkylene-NH$R_{12}$, ($C_1$-$C_6$)alkylene-OH, or ($C_1$-$C_6$)alkylene-SH;

$R_5$ is hydrogen, ($C_1$-$C_6$)alkyl, ($C_1$-$C_6$)alkylene-C(O)OH, ($C_1$-$C_6$)alkylene-NH$R_{12}$, ($C_1$-$C_6$)alkylene-OH, or ($C_1$-$C_6$)alkylene-SH; or
$R_4$ and $R_5$, together with the carbon atom to which they are attached, form ($C_3$-$C_6$)cycloalkyl or ($C_3$-$C_6$)heterocycloalkyl;
$R_6$ is hydrogen or ($C_1$-$C_6$)alkyl;
$R_7$ is hydrogen, ($C_1$-$C_6$)alkyl, ($C_1$-$C_6$)alkylene-C(O)OH, or ($C_1$-$C_6$)alkylene-N[($C_1$-$C_6$)alkyl]$_2$;
$R_8$ is hydrogen, ($C_1$-$C_6$)alkyl, ($C_1$-$C_6$)alkylene-C(O)OH, or ($C_1$-$C_6$)alkylene-N[($C_1$-$C_6$)alkyl]$_2$;
each $R_9$ is independently hydrogen, halogen, —$NH_2$, —NH($C_1$-$C_6$)alkyl, N[($C_1$-$C_6$)alkyl]$_2$, —NH($C_3$-$C_6$)cycloalkyl, OH, O($C_1$-$C_4$)alkyl, or ($C_3$-$C_6$)heterocycloalkyl;
each $R_{10}$ is independently hydrogen or ($C_1$-$C_4$)alkyl;
$R_{11}$ is hydrogen or ($C_1$-$C_6$)alkyl;
$R_{12}$ is hydrogen or ($C_1$-$C_6$)alkyl;
X is —O— or —$NR_6$—;
Y is —$NR_{11}$—($C_1$-$C_6$)alkylene-, wherein the ($C_1$-$C_6$) alkylene is bonded to the phenyl ring and —$NR_{11}$— is bonded directly to L1 of formula (II);
L is formula (I):

RCG1-L$_{linker}$-P  (I)

wherein:
P is OH; or
P is an activated O moiety selected from the group consisting of:

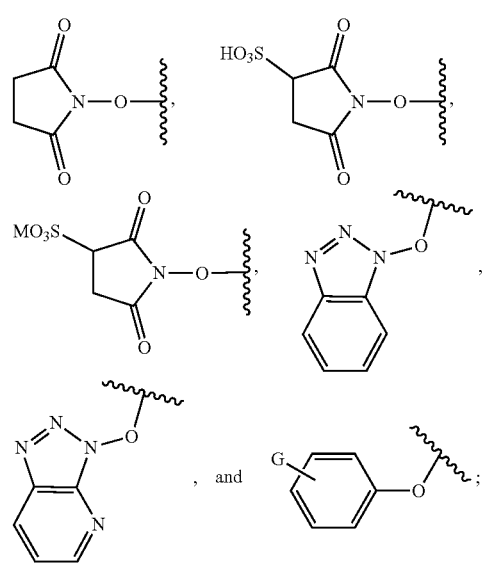

wherein:
each G is independently selected from the group consisting of halogen and nitro; and
M is $Na^+$, $K^+$, or $Cs^+$;
L$_{linker}$ is formula (II):

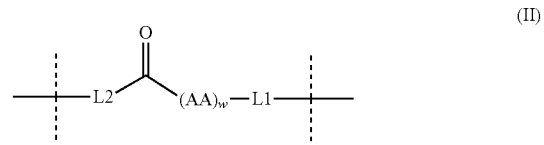

(II)

wherein:
L1 is formula (III):

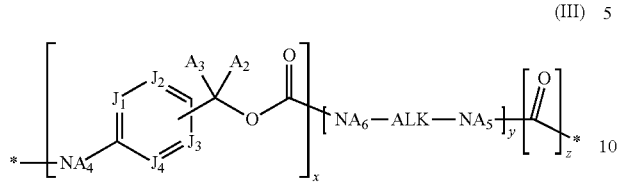

wherein:
x is 0 or 1;
y is 0;
z is 0;
$J_1$ is $CA_1$ or N;
$J_2$ is $CA_1$ or N;
$J_3$ is $CA_1$ or N;
$J_4$ is $CA_1$ or N;
$A_1$ is hydrogen or $(C_1-C_6)$alkyl;
$A_2$ is hydrogen or $(C_1-C_6)$alkyl;
$A_3$ is hydrogen or $(C_1-C_6)$alkyl; and
$A_4$ is hydrogen or $(C_1-C_6)$alkyl;
wherein L1 is bonded directly to $-NR_{11}-$ of Y;
$(AA)_w$ is a sequence of w amino acids connected together via peptide bonds, wherein the amino acids, $(AA)_w$, are independently selected from the group consisting of a non-substituted amino acid, $(AA_{ns})$, and a substituted amino acid, $(AA_s)$;
w is 2, 3, 4, 5, 6, 7, 8, 9, 10, 11, or 12;
each $(AA_{ns})$ is a natural or non-natural amino acid independently selected from the group consisting of alanine, γ-aminobutyric acid, 2-amino-2-cyclohexylacetic acid, 2-amino-2-phenylacetic acid, arginine, asparagine, aspartic acid, citrulline, cysteine, α,α-dimethyl-γ-aminobutyric acid, 3,3-dimethyl-γ-aminobutyric acid, glutamine, glutamic acid, glycine, homocysteine, selenocysteine, homoselenocysteine, histidine, isoleucine, leucine, lysine, ε-(acetyl)-lysine, methionine, ornithine, phenylalanine, proline, serine, threonine, tryptophan, tyrosine, and valine;
each $(AA_s)$ is independently formula (VI):

wherein:
T is a trivalent $(C_1-C_8)$alkyl;
U is -a single bond-, $-C(O)-$, $-C(O)NH-$, $-C(O)N(alkyl)-$, $-C(O)O-$, $-NH-$, $-N(alkyl)-$, $-NHC(O)-$, $-N(alkyl)C(O)-$, $-NHC(NH)NH-$, $-NHC(O)NH-$, $-NHS(O)_2-$, $-N(alkyl)S(O)_2-$, $-O-$, $-OC(O)-$, $-OC(O)O-$, $-OP(O)-$, $-P(O)(OH)-$, $-P(O)(OH)O-$, $-OP(O)(OH)O-$, $-S-$, $-S(O)-$, $-S(O)_2-$, $-S(O)_2NH-$, $-S(O)_2N(alkyl)-$, or $-Se-$; and $A_9$ is a straight, branched, saturated, or unsaturated $C_1-C_{160}$ hydrocarbon, wherein the $C_1-C_{160}$ hydrocarbon is optionally substituted by 1 or more substituents independently selected from the group consisting of halogen, alkyl, $NH_2$, NH(alkyl), N(alkyl)$_2$, OH, and O(alkyl), and further wherein 1 or more $-CH_2-$ units of the $C_1-C_{160}$ hydrocarbon are optionally and independently replaced by 1 or more atoms or groups independently selected from the group consisting of $-CHF-$, $-CF_2-$, $-CH(OH)-$, $-CH(Oalkyl)-$, $-CH(SO_3H)-$, $-CH(SO_3^-M^+)-$, $-C(O)-$, $-C(O)NH-$, $-C(O)N(alkyl)-$, $-C(O)O-$, $-NH-$, $-N^+H(alkyl)-$, $-N(alkyl)-$, $-N^+(alkyl)_2-$, $-NHC(O)-$, $-N(alkyl)C(O)-$, $-NHC(NH)NH-$, $-NHC(O)NH-$, $-NHS(O)_2-$, $-N(alkyl)S(O)_2-$, $-P(O)(OH)-$, $-P(O)(OH)O-$, $-O-$, $-OC(O)-$, $-OC(O)O-$, $-OP(O)-$, $-OP(O)(OH)-$, $-OP(O)(OH)O-$, $-S-$, $-S(O)-$, $-S(O)_2-$, $-S(O)_2NH-$, $-S(O)_2N(alkyl)-$, $-Se-$, and heterocycloalkyl, wherein the heterocycloalkyl is optionally substituted by 1 or more substituents independently selected from the group consisting of halogen, alkyl, $NH_2$, NH(alkyl), N(alkyl)$_2$, OH, and O(alkyl); and
$M^+$ is an alkali metal;
wherein the $-C(O)-$ of one $(AA_s)$ of formula (VI) or the $-C(O)-$ of one $(AA_{ns})$ of $(AA)_w$ is bonded to of Y or $-NR_{11}-$ of L1 and the $-NA_4-$ of one $(AA_s)$ of formula (VI) or the $-NH-$ of one $(AA_{ns})$ of $(AA)_w$ is bonded to the $-C(O)-$ attached to L2; and
L2 is $-(C_1-C_{160})$alkylene-, wherein the $C_1-C_{160}$ alkylene is optionally substituted by 1 or more substituents independently selected from the group consisting of halogen, alkyl, $NH_2$, NH(alkyl), N(alkyl)$_2$, OH, O(alkyl), $SO_3H$, and $SO_3^-M^+$, and further wherein 1 or more $-CH_2-$ units of the $C_1-C_{160}$ alkylene are optionally and independently replaced by 1 or more atoms or groups independently selected from the group consisting of $-CHF-$, $-CF_2-$, $-CH(OH)-$, $-CH(Oalkyl)-$, $-CH(SO_3H)-$, $-CH(SO_3^-M^+)-$, $-C(O)-$, $-NA_7-$, $-NA_8-$, $-P(O)(OH)-$, $-P(O)(OH)O-$, $-O-$, $-OP(O)-$, $-S-$, $-S(O)-$, and $-S(O)_2-$;
$A_7$ is a straight, branched, saturated, or unsaturated $C_1-C_{160}$ hydrocarbon, wherein the $C_1-C_{160}$ hydrocarbon is optionally substituted by 1 or more substituents independently selected from the group consisting of halogen, alkyl, $NH_2$, NH(alkyl), N(alkyl)$_2$, OH, and O(alkyl), and further wherein 1 or more $-CH_2-$ units of the $C_1-C_{160}$ hydrocarbon are optionally and independently replaced by 1 or more atoms or groups independently selected from the group consisting of $-CH(OH)-$, $-CH(SO_3H)-$, $-CH(SO_3^-M^+)-$, $-C(O)-$, $-C(O)NH-$, $-C(O)N(alkyl)-$, $-C(O)O-$, $-NHC(O)-$, $-N(alkyl)C(O)-$, $-NHS(O)_2-$, $-N(alkyl)S(O)_2-$, $-P(O)(OH)-$, $-P(O)(OH)O-$, $-O-$, $-OC(O)-$, $-OC(O)O-$, $-OP(O)(OH)-$, $-OP(O)(OH)O-$, $-S(O)-$, $-S(O)_2-$, $-S(O)_2NH-$, $-S(O)_2N(alkyl)-$, and heterocycloalkyl, wherein the heterocycloalkyl is optionally substituted by 1 or more substituents independently selected from the group consisting of halogen, alkyl, $NH_2$, $NH(alkyl)$, $N(alkyl)_2$, OH, and O(alkyl);

$A_8$ is hydrogen or $(C_1-C_6)$alkyl; and $M^+$ is an alkali metal:

wherein L2 is bonded to RCG1; and

RCG1 is:

Cl, C≡CH, $NH_2$, $N_3$, OH, O(alkyl)-NHOH, SH,

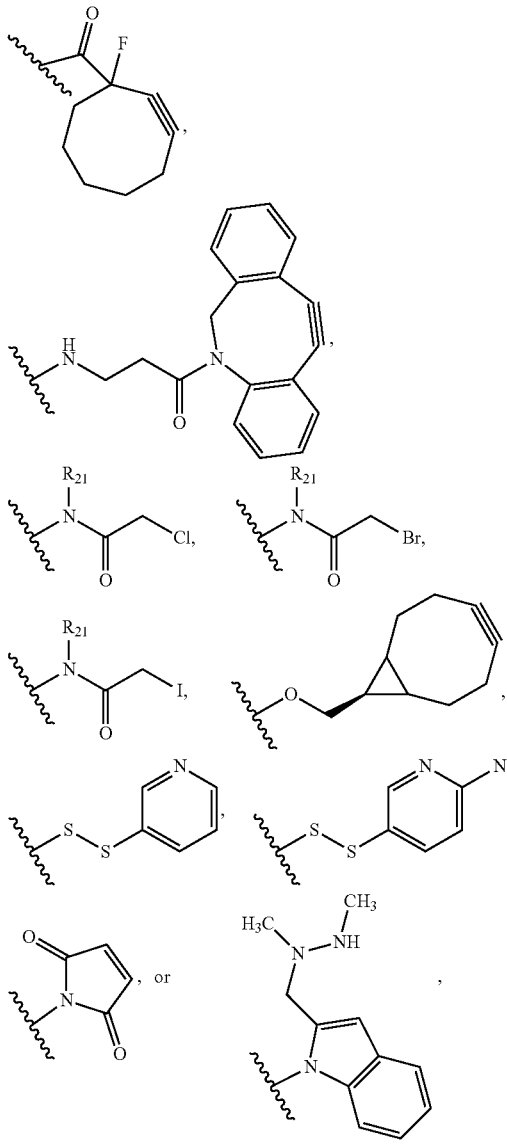

wherein:
  $R_{21}$ is hydrogen or $(C_1-C_6)$ alkyl; and
  the —CO—, —NH—, —$NR_{21}$—, —N=, —O—, or S is bonded to L2; or RCG1 is:

$C(O)Z_aR_a$, wherein:
  $Z_a$ is a single bond, —NH—, or —O—; and
  $R_a$ is hydrogen, $(C_1-C_6)$alkyl, alkenyl, $(C_3-C_7)$ cycloalkyl, $(C_3-C_7)$heterocycloalkyl, aryl, or heteroaryl, wherein the $(C_3-C_7)$heterocycloalkyl, aryl, or heteroaryl is optionally substituted by 1, 2, 3, 4, or 5 substituents independently selected from the group consisting of halogen, CN, $NO_2$, alkyl, OH, O(alkyl), and =O;
  wherein —C(O)— is bonded to L2;

G is the product of a reaction between RCG1 and RCG2;

wherein RCG2 is an orthogonal reactive chemical group present on an antibody, Ab, and wherein for each RCG1, RCG2 is independently selected from the group consisting of:

C≡CH, C(O)H, $C(O)C_1-C_6$ alkyl, $C(O)NH_2$, C(O)OH, $NH_2$, $N_3$, SH,

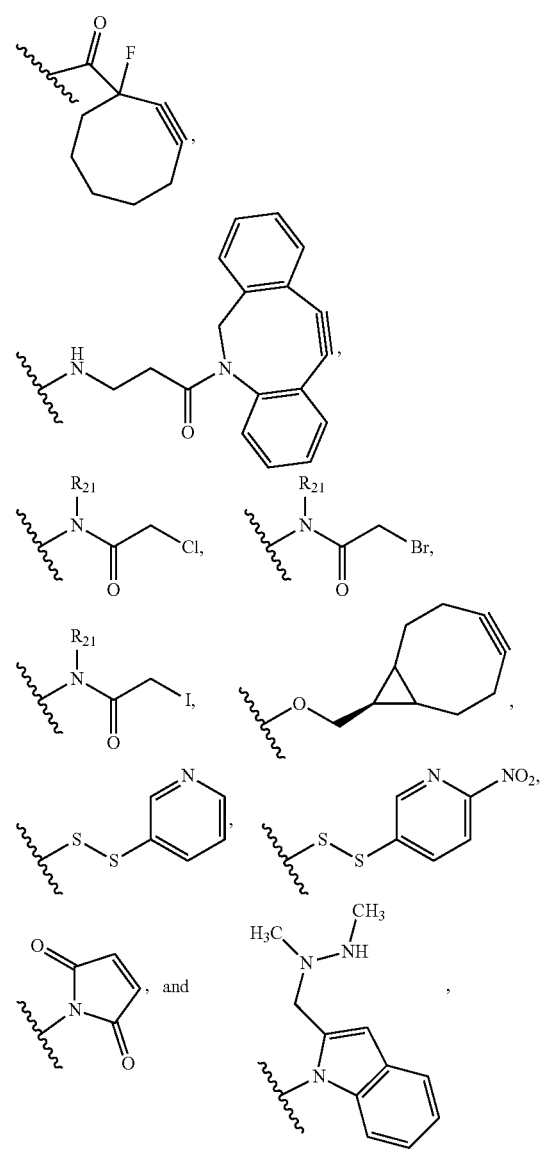

wherein:
  $R_{21}$ is hydrogen or $(C_1-C_6)$ alkyl; and
  Ab is the antibody;

with the provisos that:
(1) if P is —OH, then x is 0, y is 0, and z is 0; and
(2) if P is an activated 0 moiety, then x is 1, y is 0, and z is 0;
(3) at least one amino acid, $(AA)_w$, is a substituted amino acid, $(AA)_s$, of formula (VI); and (4) the substituted amino acid, $(AA)_s$, of formula (VI) is not selected from the group consisting of alanine, γ-aminobutyric acid, 2-amino-2-cyclohexylacetic acid, 2-amino-2-phenylacetic acid, arginine, asparagine, aspartic acid, citrulline, cysteine, α,α-dimethyl-γ-aminobutyric acid, 3,3-dimethyl-γ-aminobutyric acid, glutamine, glutamic acid, glycine, homocysteine, selenocysteine, homoselenocysteine, histidine, isoleucine, leucine, lysine, ε-(acetyl)-lysine, methionine, ornithine, phenylalanine, proline, serine, threonine, tryptophan, tyrosine, and valine;

wherein the process comprises the following steps:
(i) contacting and reacting a solution of a compound of formula (IV):

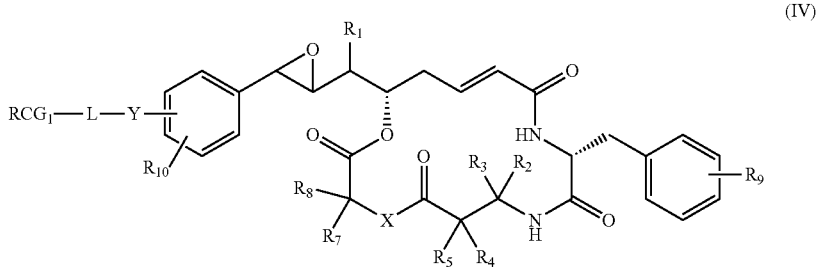

(IV)

wherein:
- $R_1$ is $(C_1-C_6)$alkyl;
- $R_2$ is hydrogen or $(C_1-C_6)$alkyl;
- $R_3$ is hydrogen or $(C_1-C_6)$alkyl; or
- $R_2$ and $R_3$, together with the carbon atom to which they are attached, form $(C_3-C_6)$cycloalkyl or $(C_3-C_6)$heterocycloalkyl;
- $R_4$ is hydrogen, $(C_1-C_6)$alkyl, $(C_1-C_6)$alkylene-C(O)OH, $(C_1-C_6)$alkylene-NHR$_{12}$, $(C_1-C_6)$alkylene-OH, or $(C_1-C_6)$alkylene-SH;
- $R_5$ is hydrogen, $(C_1-C_6)$alkyl, $(C_1-C_6)$alkylene-C(O)OH, $(C_1-C_6)$alkylene-NHR$_{12}$, $(C_1-C_6)$alkylene-OH, or $(C_1-C_6)$alkylene-SH; or
- $R_4$ and $R_5$, together with the carbon atom to which they are attached, form $(C_3-C_6)$cycloalkyl or $(C_3-C_6)$heterocycloalkyl;
- $R_6$ is hydrogen or $(C_1-C_6)$alkyl;
- $R_7$ is hydrogen, $(C_1-C_6)$alkyl, $(C_1-C_6)$alkylene-C(O)OH, or $(C_1-C_6)$alkylene-N[$(C_1-C_6)$alkyl]$_2$;
- $R_8$ is hydrogen, $(C_1-C_6)$alkyl, $(C_1-C_6)$alkylene-C(O)OH, or $(C_1-C_6)$alkylene-N[$(C_1-C_6)$alkyl]$_2$;
- each $R_9$ is independently hydrogen, halogen, —NH$_2$, —NH$(C_1-C_6)$alkyl, N[$(C_1-C_6)$alkyl]$_2$, —NH$(C_3-C_6)$cycloalkyl, OH, O$(C_1-C_4)$alkyl, or $(C_3-C_6)$heterocycloalkyl;
- each $R_{10}$ is independently hydrogen or $(C_1-C_4)$alkyl;
- $R_{11}$ is hydrogen or $(C_1-C_6)$alkyl;
- $R_{12}$ is hydrogen or $(C_1-C_6)$alkyl;
- X is —O— or —NR$_6$—;
- Y is —NR$_{11}$—$(C_1-C_6)$alkylene-, wherein the $(C_1-C_6)$alkylene is bonded to the phenyl ring and —NR$_{11}$— is bonded directly to L1 of formula (II);
- L is formula (I):

RCG1-L$_{linker}$-P   (I)

wherein:
P is OH; or
P is an activated O moiety selected from the group consisting of:

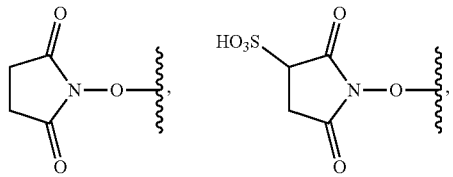

-continued

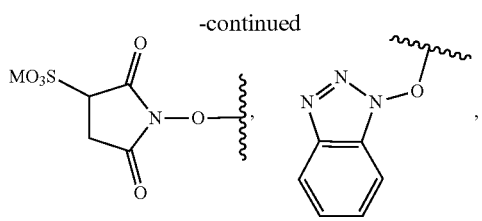

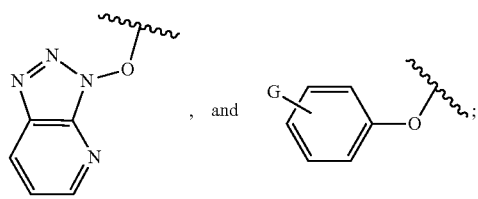

wherein:
each G is independently selected from the group consisting of halogen and nitro; and
M is Na$^+$, K$^+$, or Cs$^+$;

$L_{linker}$ is formula (II):

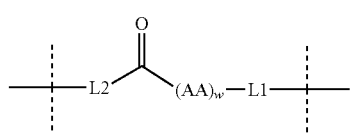

(II)

wherein:

L1 is formula (III):

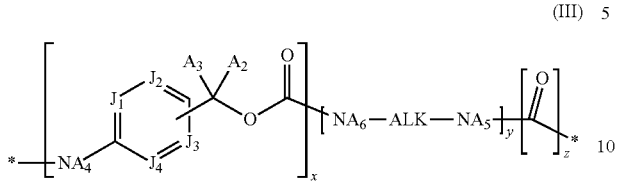

wherein:
x is 0 or 1;
y is 0;
z is 0;
$J_1$ is $CA_1$ or N;
$J_2$ is $CA_1$ or N;
$J_3$ is $CA_1$ or N;
$J_4$ is $CA_1$ or N;
$A_1$ is hydrogen or $(C_1-C_6)$alkyl;
$A_2$ is hydrogen or $(C_1-C_6)$alkyl;
$A_3$ is hydrogen or $(C_1-C_6)$alkyl; and
$A_4$ is hydrogen or $(C_1-C_6)$alkyl;
wherein L1 is bonded directly to $-NR_{11}-$ of Y;
$(AA)_w$ is a sequence of w amino acids connected together via peptide bonds, wherein the amino acids, $(AA)_w$, are independently selected from the group consisting of a non-substituted amino acid, $(AA_{ns})$, and a substituted amino acid, $(AA_s)$;
w is 2, 3, 4, 5, 6, 7, 8, 9, 10, 11, or 12;
each $(AA_{ns})$ is a natural or non-natural amino acid independently selected from the group consisting of alanine, γ-aminobutyric acid, 2-amino-2-cyclohexylacetic acid, 2-amino-2-phenylacetic acid, arginine, asparagine, aspartic acid, citrulline, cysteine, α,α-dimethyl-γ-aminobutyric acid, 3,3-dimethyl-γ-aminobutyric acid, glutamine, glutamic acid, glycine, homocysteine, selenocysteine, homoselenocysteine, histidine, isoleucine, leucine, lysine, ε-(acetyl)-lysine, methionine, ornithine, phenylalanine, proline, serine, threonine, tryptophan, tyrosine, and valine;
each $(AA_s)$ is independently formula (VI):

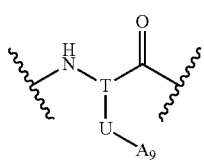

wherein:
T is a trivalent $(C_1-C_8)$alkyl;
U is -a single bond-, $-C(O)-$, $-C(O)NH-$, $-C(O)N(alkyl)-$, $-C(O)O-$, $-NH-$, $-N(alkyl)-$, $-NHC(O)-$, $-N(alkyl)C(O)-$, $-NHC(NH)NH-$, $-NHC(O)NH-$, $-NHS(O)_2-$, $-N(alkyl)S(O)_2-$, $-O-$, $-OC(O)-$, $-OC(O)O-$, $-OP(O)-$, $-P(O)(OH)-$, $-P(O)(OH)O-$, $-OP(O)(OH)O-$, $-S-$, $-S(O)-$, $-S(O)_2-$, $-S(O)_2NH-$, $-S(O)_2N(alkyl)-$, or $-Se-$; and $A_9$ is a straight, branched, saturated, or unsaturated $C_1-C_{160}$ hydrocarbon, wherein the $C_1-C_{160}$ hydrocarbon is optionally substituted by 1 or more substituents independently selected from the group consisting of halogen, alkyl, $NH_2$, NH(alkyl), $N(alkyl)_2$, OH, and O(alkyl), and further wherein 1 or more $-CH_2-$ units of the $C_1-C_{160}$ hydrocarbon are optionally and independently replaced by 1 or more atoms or groups independently selected from the group consisting of $-CHF-$, $-CF_2-$, $-CH(OH)-$, $-CH(Oalkyl)-$, $-CH(SO_3H)-$, $-CH(SO_3^-M^+)-$, $-C(O)-$, $-C(O)NH-$, $-C(O)N(alkyl)-$, $-C(O)O-$, $-NH-$, $-N^+H(alkyl)-$, $-N(alkyl)-$, $-N^+(alkyl)_2-$, $-NHC(O)-$, $-N(alkyl)C(O)-$, $-NHC(NH)NH-$, $-NHC(O)NH-$, $-NHS(O)_2-$, $-N(alkyl)S(O)_2-$, $-P(O)(OH)-$, $-P(O)(OH)O-$, $-O-$, $-OC(O)-$, $-OC(O)O-$, $-OP(O)-$, $-OP(O)(OH)-$, $-OP(O)(OH)O-$, $-S-$, $-S(O)-$, $-S(O)_2-$, $-S(O)_2NH-$, $-S(O)_2N(alkyl)-$, $-Se-$, and heterocycloalkyl, wherein the heterocycloalkyl is optionally substituted by 1 or more substituents independently selected from the group consisting of halogen, alkyl, $NH_2$, NH(alkyl), $N(alkyl)_2$, OH, and O(alkyl); and $M^+$ is an alkali metal;
wherein the $-C(O)-$ of one $(AA_s)$ of formula (VI) or the $-C(O)-$ of one $(AA_{ns})$ of $(AA)_w$ is bonded to $-NR_{11}-$ of Y or $-NA_4-$ of L1 and the $-NH-$ of one $(AA_s)$ of formula (VI) or the $-NH-$ of one $(AA_{ns})$ of $(AA)_w$ is bonded to the $-C(O)-$ attached to L2; and L2 is $-(C_1-C_{160})$alkylene-, wherein the $C_1-C_{160}$ alkylene is optionally substituted by 1 or more substituents independently selected from the group consisting of halogen, alkyl, $NH_2$, NH(alkyl), $N(alkyl)_2$, OH, O(alkyl), $SO_3H$, and $SO_3^-M^+$, and further wherein 1 or more $-CH_2-$ units of the $C_1-C_{160}$ alkylene are optionally and independently replaced by 1 or more atoms or groups independently selected from the group consisting of $-CHF-$, $-CF_2-$, $-CH(OH)-$, $-CH(Oalkyl)-$, $-CH(SO_3H)-$, $-CH(SO_3^-M^+)-$, $-C(O)-$, $-NA_7-$, $-NA_8-$, $-P(O)(OH)-$, $-P(O)(OH)O-$, $-O-$, $-OP(O)-$, $-S-$, $-S(O)-$, and $-S(O)_2-$;

$A_7$ is a straight, branched, saturated, or unsaturated $C_1-C_{160}$ hydrocarbon, wherein the $C_1-C_{160}$ hydrocarbon is optionally substituted by 1 or more substituents independently selected from the group consisting of halogen, alkyl, $NH_2$, NH(alkyl), $N(alkyl)_2$, OH, and O(alkyl), and further wherein 1 or more $-CH_2-$ units of the $C_1-C_{160}$ hydrocarbon are optionally and independently replaced by 1 or more atoms or groups independently selected from the group consisting of $-CH(OH)-$, $-CH(SO_3H)-$, $-CH(SO_3^-M^+)-$, $-C(O)-$, $-C(O)NH-$, $-C(O)N(alkyl)-$, $-C(O)O-$, $-NHC(O)-$, $-N(alkyl)C(O)-$, $-NHS(O)_2-$, $-N(alkyl)S(O)_2-$, $-P(O)(OH)-$, $-P(O)(OH)O-$, $-O-$, $-OC(O)-$, —OC(O)O—, —OP(O)(OH)—, —OP(O)(OH)O—, —S(O)—, —S(O)₂—, —S(O)₂NH—, —S(O)₂N(alkyl)-, and heterocycloalkyl, wherein the heterocycloalkyl is optionally substituted by 1 or more substituents independently selected from the group consisting of halogen, alkyl, NH₂, NH(alkyl), N(alkyl)₂, OH, and O(alkyl);

A₈ is hydrogen or (C₁-C₆)alkyl; and

M⁺ is an alkali metal:

wherein L2 is bonded to RCG1; and

RCG1 is:

Cl, C≡CH, NH₂, N₃, OH, O(alkyl)-NHOH, SH,

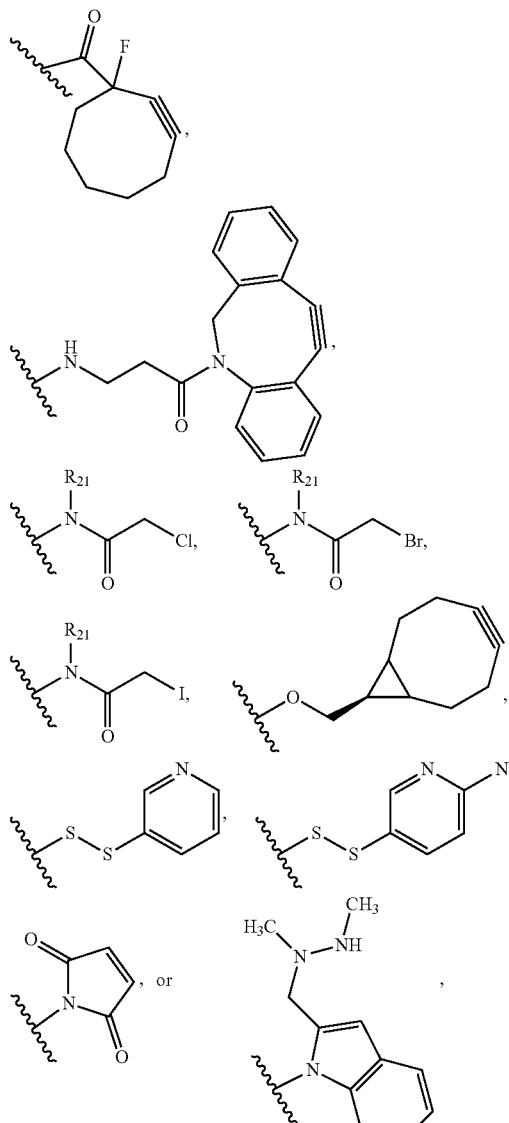

wherein:

R₂₁ is hydrogen or (C₁-C₆) alkyl; and the —CO—, —NH—, —NR₂₁—, —N=, —O—, or S is bonded to L₂; or RCG1 is:

C(O)Z$_a$R$_a$, wherein:

Z$_a$ is a single bond, —NH—, or —O—; and

R$_a$ is hydrogen, (C₁-C₆)alkyl, alkenyl, (C₃-C₇)cycloalkyl, (C₃-C₇)heterocycloalkyl, aryl, or heteroaryl, wherein the (C₃-C₇)heterocycloalkyl, aryl, or heteroaryl is optionally substituted by 1, 2, 3, 4, or 5 substituents independently selected from the group consisting of halogen, CN, NO₂, alkyl, OH, O(alkyl), and =O;

wherein —C(O)— is bonded to L2;

with the provisos that:

(1) if P is —OH, then x is 0, y is 0, and z is 0; and (2) if P is an activated 0 moiety, then x is 1, y is 0, and z is 0;

(3) at least one amino acid, (AA)$_w$, is a substituted amino acid, (AA)$_s$, of formula (VI); and (4) the substituted amino acid, (AA)$_s$ of formula (VI) is not selected from the group consisting of alanine, γ-aminobutyric acid, 2-amino-2-cyclohexylacetic acid, 2-amino-2-phenylacetic acid, arginine, asparagine, aspartic acid, citrulline, cysteine, α,α-dimethyl-γ-aminobutyric acid, 3,3-dimethyl-γ-aminobutyric acid, glutamine, glutamic acid, glycine, homocysteine, selenocysteine, homoselenocysteine, histidine, isoleucine, leucine, lysine, ε-(acetyl)-lysine, methionine, ornithine, phenylalanine, proline, serine, threonine, tryptophan, tyrosine, and valine;

with an optionally buffered aqueous solution of an antibody, Ab, containing an orthogonal reactive chemical group, RCG2, present on the antibody, wherein for each RCG1, RCG2 is independently selected from the group consisting of:

C≡CH, C(O)H, C(O)C₁-C₆ alkyl, C(O)NH₂, C(O)OH, NH₂, N₃, SH,

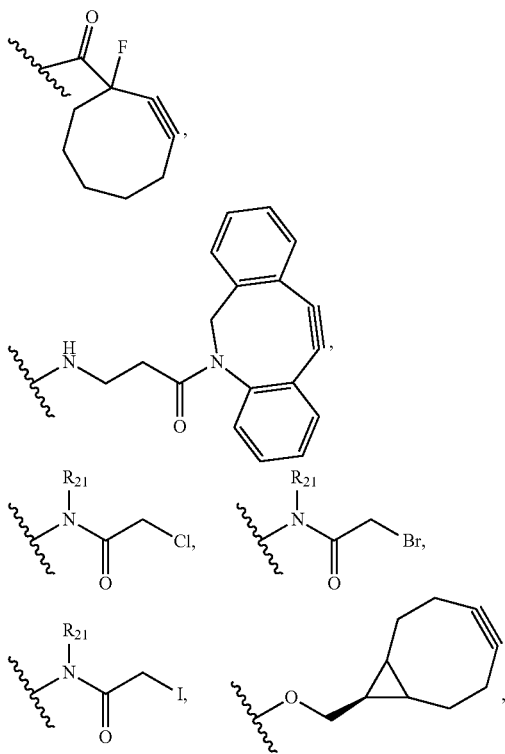

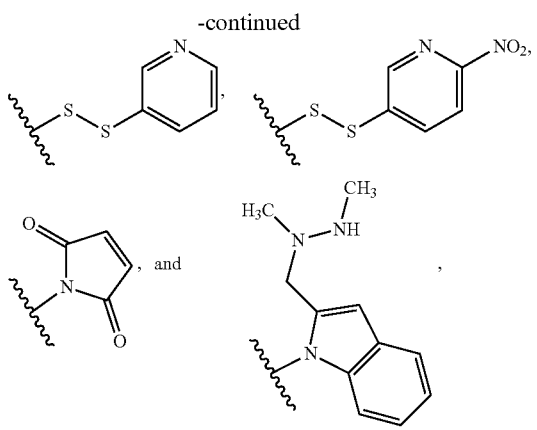

wherein:
R$_{21}$ is hydrogen or (C$_1$-C$_6$) alkyl; and
G is the product of a reaction between RCG1 and RCG2;
optionally in the presence of a modifying agent, to provide the compound of formula (V) above according to claim 1; and
(ii) optionally separating the compound of formula (V) provided in step (i) above from any unreacted compound of formula (IV) or unreacted antibody, Ab, or a combination thereof.

20. The process according to claim 19, wherein:
Y is —NR$_{11}$—(CH$_2$)$_n$—; and
n is 1, 2, 3, 4, 5, or 6;
wherein Y is bonded in an ortho, meta, or para position on the phenyl relative to where the oxirane moiety is bonded to the phenyl.

* * * * *

SEQUENCE LISTING

```
<160> NUMBER OF SEQ ID NOS: 5

<210> SEQ ID NO 1
<211> LENGTH: 238
<212> TYPE: PRT
<213> ORGANISM: Homo sapiens
<220> FEATURE:
<221> NAME/KEY: MISC_FEATURE
<223> OTHER INFORMATION: Light chain of antibody hu2H11_R35R74

<400> SEQUENCE: 1

Met Gly Trp Ser Cys Ile Ile Leu Phe Leu Val Ala Thr Ala Thr Gly
1               5                   10                  15

Val His Ser Asp Val Val Met Thr Gln Thr Pro Leu Ser Leu Ser Val
                20                  25                  30

Thr Leu Gly Gln Pro Ala Ser Ile Ser Cys Lys Ser Ser Gln Ser Leu
            35                  40                  45

Ile His Ser Asp Gly Arg Thr Tyr Leu Asn Trp Leu Leu Gln Arg Pro
        50                  55                  60

Gly Gln Ser Pro Lys Arg Leu Ile Tyr Leu Val Ser Arg Leu Asp Ser
65                  70                  75                  80

Gly Val Pro Asp Arg Phe Thr Gly Ser Gly Ala Gly Thr Asp Phe Thr
                85                  90                  95

Leu Lys Ile Ser Arg Val Glu Ala Glu Asp Leu Gly Val Tyr Tyr Cys
                100                 105                 110
```

```
Trp Gln Gly Ser His Phe Pro Arg Thr Phe Gly Gly Thr Lys Leu
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
                195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 2
<211> LENGTH: 467
<212> TYPE: PRT
<213> ORGANISM: Homo sapiens
<220> FEATURE:
<221> NAME/KEY: MISC_FEATURE
<223> OTHER INFORMATION: Heavy chain of antibody hu2H11_R35R74

<400> SEQUENCE: 2

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Val Lys
            20                  25                  30

Pro Gly Ala Ser Val Lys Ile Ser Cys Lys Ala Ser Gly Tyr Thr Phe
        35                  40                  45

Thr Ala Tyr Tyr Met His Trp Val Lys Gln Ser Pro Val Gln Ser Leu
    50                  55                  60

Glu Trp Ile Gly Leu Val Asn Pro Tyr Asn Gly Phe Ser Ser Tyr Asn
65                  70                  75                  80

Gln Lys Phe Gln Gly Lys Ala Ser Leu Thr Val Asp Arg Ser Ser Ser
                85                  90                  95

Thr Ala Tyr Met Glu Leu His Ser Leu Thr Ser Glu Asp Ser Ala Val
            100                 105                 110

Tyr Tyr Cys Ala Arg Glu Phe Tyr Gly Tyr Arg Tyr Phe Asp Val Trp
        115                 120                 125

Gly Gln Gly Thr Ala Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
```

```
            225                 230                 235                 240

Cys Asp Lys Thr His Thr Cys Pro Pro Cys Pro Ala Pro Glu Leu Leu
            245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly
465

<210> SEQ ID NO 3
<211> LENGTH: 4
<212> TYPE: PRT
<213> ORGANISM: Artificial Sequence
<220> FEATURE:
<223> OTHER INFORMATION: non-substituted amino acid
<220> FEATURE:
<221> NAME/KEY: MISC_FEATURE
<222> LOCATION: (4)..(4)
<223> OTHER INFORMATION: Xaa represents a citrulline

<400> SEQUENCE: 3

Gly Phe Leu Xaa
1

<210> SEQ ID NO 4
<211> LENGTH: 4
<212> TYPE: PRT
<213> ORGANISM: Artificial Sequence
<220> FEATURE:
<223> OTHER INFORMATION: non-substituted amino acid

<400> SEQUENCE: 4

Gly Phe Leu Gly
1

<210> SEQ ID NO 5
```

```
<211> LENGTH: 4
<212> TYPE: PRT
<213> ORGANISM: Artificial Sequence
<220> FEATURE:
<223> OTHER INFORMATION: non-substituted amino acid

<400> SEQUENCE: 5

Ala Leu Ala Leu
1
```